United States Patent
Machacek et al.

(10) Patent No.: US 12,173,026 B2
(45) Date of Patent: Dec. 24, 2024

(54) PRMT5 INHIBITORS

(71) Applicants: Merck Sharp & Dohme LLC, Rahway, NJ (US); MSD International GmbH, Lucerne (CH)

(72) Inventors: Michelle Machacek, Belmont, MA (US); David Witter, Norfolk, MA (US); Craig Gibeau, Northborough, MA (US); Chunhui Huang, Arlington, MA (US); Shuhei Kawamura, Cambridge, MA (US); David L. Sloman, Brookline, MA (US); Phieng Siliphaivanh, Newton, MA (US); Ryan Quiroz, Boston, MA (US); Murray Wan, Watertown, MA (US); Sebastian Schneider, Boston, MA (US); Charles S. Yeung, Dedham, MA (US); Michael H. Reutershan, Brighton, MA (US); Timothy J. Henderson, Beaulieu, MA (US); Jean-Laurent Paparin, Vendemian (FR); Houcine Rahali, Beaulieu (FR); Jonathan M. E. Hughes, Hoboken, NJ (US); Sulagna Sanyal, Belmont, MA (US); Yingchun Ye, Belmont, MA (US); David A. Candito, Wrentham, MA (US); Patrick S. Fier, Monroe Township, NJ (US); Steven M. Silverman, Jersey City, NJ (US)

(73) Assignees: Merck Sharp & Dohme LLC, Rahway, NJ (US); MSD International GmbH, Lucerne (CH)

( * ) Notice: Subject to any disclaimer, the term of this patent is extended or adjusted under 35 U.S.C. 154(b) by 814 days.

(21) Appl. No.: 17/266,521

(22) PCT Filed: Aug. 5, 2019

(86) PCT No.: PCT/US2019/045050
§ 371 (c)(1),
(2) Date: Feb. 5, 2021

(87) PCT Pub. No.: WO2020/033288
PCT Pub. Date: Feb. 13, 2020

(65) Prior Publication Data
US 2022/0363707 A1     Nov. 17, 2022

Related U.S. Application Data

(60) Provisional application No. 62/715,446, filed on Aug. 7, 2018, provisional application No. 62/792,623, filed on Jan. 15, 2019, provisional application No. 62/859,490, filed on Jun. 10, 2019.

(51) Int. Cl.
    *C07H 19/14*     (2006.01)
    *A61P 35/00*     (2006.01)
    *C07D 487/04*     (2006.01)

(52) U.S. Cl.
    CPC .............. *C07H 19/14* (2013.01); *A61P 35/00* (2018.01); *C07D 487/04* (2013.01)

(58) Field of Classification Search
    CPC .... C07H 19/14; C07D 487/04; C07D 519/00; A61P 35/00
    See application file for complete search history.

(56) References Cited

U.S. PATENT DOCUMENTS

| | | | |
|---|---|---|---|
| 2,789,118 A | 4/1957 | Seymour | |
| 2,990,401 A | 6/1961 | Seymour | |
| 3,048,581 A | 8/1962 | Josef | |
| 3,126,375 A | 3/1964 | Hensel et al. | |

(Continued)

FOREIGN PATENT DOCUMENTS

| | | |
|---|---|---|
| CN | 105837573 A | 8/2016 |
| CN | 105837573 B | 7/2018 |

(Continued)

OTHER PUBLICATIONS

Ludek et al., Synthesis, 2003, 13, p. 2101-2109. (Year: 2003).*
Chen et al., Tetrahedron, 2014, 70, p. 892-900. (Year: 2014).*
Belikov, V.G., Pharmaceutical Chemistry, Moscow MEDpress-inform, 2007, 27-29, 4th Edition.
Dyson, G. and May, P., Chemistry of Synthetic Medicinal Substances, M: World, 1964, 12-19, N/A.

(Continued)

*Primary Examiner* — Jonathan S Lau
(74) *Attorney, Agent, or Firm* — James T. Corcoran; Catherine D. Fitch

(57) ABSTRACT

The present invention provides a compound of Formula (I) and the pharmaceutically acceptable salts, esters, and prodrugs thereof, which are PRMT5 inhibitors. Also provided are methods of making compounds of Formula I, pharmaceutical compositions comprising compounds of Formula I, and methods of using these compounds to treat cancer, sickle cell, and hereditary persistence of foetal hemoglobin (HPFH) mutations.

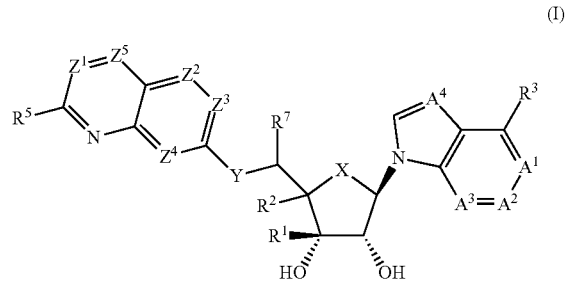

(I)

20 Claims, No Drawings

(56) References Cited

U.S. PATENT DOCUMENTS

| | | |
|---|---|---|
| 3,749,712 A | 7/1973 | Cavazza |
| 3,928,326 A | 12/1975 | Brattsand |
| 3,929,768 A | 12/1975 | Brattsand |
| 3,996,359 A | 12/1976 | Brattsand |
| 4,231,938 A | 11/1980 | Monaghan et al. |
| 4,294,926 A | 10/1981 | Monaghan et al. |
| 4,319,039 A | 3/1982 | Albers-schonberg |
| 4,346,227 A | 8/1982 | Terahara et al. |
| 4,410,629 A | 10/1983 | Terahara et al. |
| 4,444,784 A | 4/1984 | Hoffman et al. |
| 4,537,859 A | 8/1985 | Terahara et al. |
| 4,681,893 A | 7/1987 | Roth |
| 4,782,084 A | 11/1988 | Vyas et al. |
| 4,820,850 A | 4/1989 | Verhoeven et al. |
| 4,885,314 A | 12/1989 | Vyas |
| 4,911,165 A | 3/1990 | Lennard et al. |
| 4,916,239 A | 4/1990 | Treiber |
| 4,929,437 A | 5/1990 | Tobert |
| 5,030,447 A | 7/1991 | Joshi et al. |
| 5,118,853 A | 6/1992 | Lee et al. |
| 5,134,142 A | 7/1992 | Matsuo et al. |
| 5,162,339 A | 11/1992 | Lowe, III |
| 5,177,080 A | 1/1993 | Angerbauer et al. |
| 5,180,589 A | 1/1993 | Joshi et al. |
| 5,189,164 A | 2/1993 | Kapa et al. |
| 5,232,929 A | 8/1993 | Desai |
| 5,242,930 A | 9/1993 | Baker |
| 5,273,995 A | 12/1993 | Roth |
| 5,290,946 A | 3/1994 | Lee et al. |
| 5,342,952 A | 8/1994 | Butler et al. |
| 5,344,991 A | 9/1994 | Reitz et al. |
| 5,354,772 A | 10/1994 | Kathawala |
| 5,356,896 A | 10/1994 | Kabadi et al. |
| 5,373,003 A | 12/1994 | Lowe, III |
| 5,380,738 A | 1/1995 | Norman et al. |
| 5,387,595 A | 2/1995 | Mills |
| 5,393,790 A | 2/1995 | Reitz et al. |
| 5,409,944 A | 4/1995 | Black et al. |
| 5,420,245 A | 5/1995 | Brown |
| 5,436,265 A | 7/1995 | Black et al. |
| 5,459,270 A | 10/1995 | Williams |
| 5,466,823 A | 11/1995 | Talley et al. |
| 5,474,995 A | 12/1995 | Ducharme et al. |
| 5,489,691 A | 2/1996 | Butler et al. |
| 5,494,926 A | 2/1996 | Owens |
| 5,496,833 A | 3/1996 | Baker |
| 5,510,510 A | 4/1996 | Patel |
| 5,523,430 A | 6/1996 | Patel |
| 5,532,359 A | 7/1996 | Marsters, Jr. |
| 5,536,752 A | 7/1996 | Ducharme et al. |
| 5,550,142 A | 8/1996 | Ducharme et al. |
| 5,571,792 A | 11/1996 | Bolton |
| 5,589,485 A | 12/1996 | Hochlowski |
| 5,602,098 A | 2/1997 | Sebti |
| 5,604,260 A | 2/1997 | Guay et al. |
| 5,633,272 A | 5/1997 | Talley et al. |
| 5,637,699 A | 6/1997 | Dorn |
| 5,643,958 A | 7/1997 | Iwasawa |
| 5,661,152 A | 8/1997 | Bishop |
| 5,698,584 A | 12/1997 | Black et al. |
| 5,710,140 A | 1/1998 | Ducharme et al. |
| 5,719,147 A | 2/1998 | Dorn |
| 5,728,830 A | 3/1998 | Kanda |
| 5,750,567 A | 5/1998 | Baudoin |
| 5,789,647 A | 8/1998 | Heidlas |
| 5,856,439 A | 1/1999 | Clerc |
| 5,861,419 A | 1/1999 | Dube et al. |
| 5,889,053 A | 3/1999 | Baudoin |
| 5,919,786 A | 7/1999 | Iwasawa |
| 5,932,598 A | 8/1999 | Talley et al. |
| 5,936,097 A | 8/1999 | Commercon |
| 6,001,843 A | 12/1999 | Dube et al. |
| 6,020,343 A | 2/2000 | Belley et al. |
| 6,069,134 A | 5/2000 | Roth et al. |
| RE37,314 E | 8/2001 | Hirai et al. |
| 6,284,781 B1 | 9/2001 | Danishefsky et al. |
| 6,288,237 B1 | 9/2001 | Hoefle et al. |
| 7,199,127 B2 | 4/2007 | Jeong et al. |
| 2004/0102360 A1 | 5/2004 | Barnett et al. |
| 2004/0116432 A1 | 6/2004 | Carling et al. |
| 2005/0029941 A1 | 2/2005 | Kwon |
| 2005/0043361 A1 | 2/2005 | Colca |
| 2005/0044294 A1 | 2/2005 | Vo |
| 2005/0075320 A1 | 4/2005 | Nadin |
| 2005/0176776 A1 | 8/2005 | Coleman et al. |
| 2017/0240584 A1 | 8/2017 | Bourderioux et al. |
| 2019/0048014 A1* | 2/2019 | Lin ............... C07H 19/14 |
| 2020/0317686 A1 | 10/2020 | Vandyck et al. |

FOREIGN PATENT DOCUMENTS

| | | |
|---|---|---|
| EA | 027908 B1 | 9/2017 |
| EP | 0604181 A1 | 6/1994 |
| EP | 0618221 A2 | 10/1994 |
| EP | 0675112 A1 | 10/1995 |
| EP | 0696593 A2 | 2/1996 |
| WO | 1994015932 A1 | 7/1994 |
| WO | 1994019357 A1 | 9/1994 |
| WO | 1995008542 A1 | 3/1995 |
| WO | 1995010514 A1 | 4/1995 |
| WO | 1995010515 A1 | 4/1995 |
| WO | 1995010516 A1 | 4/1995 |
| WO | 1995011917 A1 | 5/1995 |
| WO | 1995012572 A1 | 5/1995 |
| WO | 1995012612 A1 | 5/1995 |
| WO | 1995024612 A1 | 9/1995 |
| WO | 1995025086 A1 | 9/1995 |
| WO | 1995032987 A1 | 12/1995 |
| WO | 1995034535 A1 | 12/1995 |
| WO | 1996000736 A1 | 1/1996 |
| WO | 1996005168 A1 | 2/1996 |
| WO | 1996005169 A1 | 2/1996 |
| WO | 1996005529 A1 | 2/1996 |
| WO | 1996006138 A1 | 2/1996 |
| WO | 1996006193 A1 | 2/1996 |
| WO | 1996016443 A1 | 5/1996 |
| WO | 1996017861 A1 | 6/1996 |
| WO | 1996021456 A1 | 7/1996 |
| WO | 1996021701 A2 | 7/1996 |
| WO | 1996022278 A1 | 7/1996 |
| WO | 1996024611 A1 | 8/1996 |
| WO | 1996024612 A1 | 8/1996 |
| WO | 1996030017 A1 | 10/1996 |
| WO | 1996030018 A1 | 10/1996 |
| WO | 1996030343 A1 | 10/1996 |
| WO | 1996030362 A1 | 10/1996 |
| WO | 1996030363 A1 | 10/1996 |
| WO | 1996031111 A1 | 10/1996 |
| WO | 1996031477 A1 | 10/1996 |
| WO | 1996031478 A1 | 10/1996 |
| WO | 1996031501 A1 | 10/1996 |
| WO | 1996033159 A1 | 10/1996 |
| WO | 1996034850 A1 | 11/1996 |
| WO | 1996034851 A1 | 11/1996 |
| WO | 1997000252 A1 | 1/1997 |
| WO | 1997002920 A1 | 1/1997 |
| WO | 1997003047 A1 | 1/1997 |
| WO | 1997003050 A1 | 1/1997 |
| WO | 1997004785 A1 | 2/1997 |
| WO | 1997017070 A1 | 5/1997 |
| WO | 1997018813 A1 | 5/1997 |
| WO | 1997021701 A1 | 6/1997 |
| WO | 1997023478 A1 | 7/1997 |
| WO | 1997026246 A1 | 7/1997 |
| WO | 1997030053 A1 | 8/1997 |
| WO | 1997038665 A2 | 10/1997 |
| WO | 1997044350 A1 | 11/1997 |
| WO | 1998002436 A1 | 1/1998 |
| WO | 1998028980 A1 | 7/1998 |
| WO | 1998029119 A1 | 7/1998 |
| WO | 0050032 A1 | 8/2000 |
| WO | 200044777 A1 | 8/2000 |
| WO | 200061186 A1 | 10/2000 |
| WO | 2001070677 A1 | 9/2001 |

(56) References Cited

FOREIGN PATENT DOCUMENTS

| | | |
|---|---|---|
| WO | 2001090084 A1 | 11/2001 |
| WO | 2002030912 A1 | 4/2002 |
| WO | 2002036555 A1 | 5/2002 |
| WO | 2002047671 A2 | 6/2002 |
| WO | 2002081433 A1 | 10/2002 |
| WO | 2002081435 A1 | 10/2002 |
| WO | 2002083064 A2 | 10/2002 |
| WO | 2002083138 A1 | 10/2002 |
| WO | 2002083139 A1 | 10/2002 |
| WO | 2002083140 A1 | 10/2002 |
| WO | 2003013506 A1 | 2/2003 |
| WO | 2003018543 A1 | 3/2003 |
| WO | 2003039460 A2 | 5/2003 |
| WO | 2003049527 A2 | 6/2003 |
| WO | 2003049678 A2 | 6/2003 |
| WO | 2003049679 A2 | 6/2003 |
| WO | 2003050064 A2 | 6/2003 |
| WO | 2003050122 A2 | 6/2003 |
| WO | 2003079973 A2 | 10/2003 |
| WO | 2003084473 A2 | 10/2003 |
| WO | 2003086279 A2 | 10/2003 |
| WO | 2003086394 A1 | 10/2003 |
| WO | 2003086403 A1 | 10/2003 |
| WO | 2003086404 A1 | 10/2003 |
| WO | 2003093251 A1 | 11/2003 |
| WO | 2003093252 A1 | 11/2003 |
| WO | 2003093253 A1 | 11/2003 |
| WO | 2003093264 A1 | 11/2003 |
| WO | 2003099211 A2 | 12/2003 |
| WO | 2003105855 A1 | 12/2003 |
| WO | 2003106417 A1 | 12/2003 |
| WO | 2004031137 A1 | 4/2004 |
| WO | 2004031138 A1 | 4/2004 |
| WO | 2004031139 A1 | 4/2004 |
| WO | 2004037171 A2 | 5/2004 |
| WO | 2004039370 A1 | 5/2004 |
| WO | 2004039774 A2 | 5/2004 |
| WO | 2004039800 A1 | 5/2004 |
| WO | 2004041162 A2 | 5/2004 |
| WO | 2004058148 A2 | 7/2004 |
| WO | 2004058700 A2 | 7/2004 |
| WO | 2004089911 A1 | 10/2004 |
| WO | 2004096129 A2 | 11/2004 |
| WO | 2004096130 A2 | 11/2004 |
| WO | 2004096131 A2 | 11/2004 |
| WO | 2004096135 A2 | 11/2004 |
| WO | 2004101538 A1 | 11/2004 |
| WO | 2004101539 A1 | 11/2004 |
| WO | 2005014553 A1 | 2/2005 |
| WO | 2005017190 A2 | 2/2005 |
| WO | 2005018547 A2 | 3/2005 |
| WO | 2005018638 A1 | 3/2005 |
| WO | 2005019205 A1 | 3/2005 |
| WO | 2005019206 A1 | 3/2005 |
| WO | 2005030731 A1 | 4/2005 |
| WO | 2005100344 A1 | 10/2005 |
| WO | 2005100356 A1 | 10/2005 |
| WO | 2012170347 A1 | 12/2012 |
| WO | 2014100719 A2 | 6/2014 |
| WO | 2015200680 A2 | 12/2015 |
| WO | 2017032840 A1 | 3/2017 |
| WO | 2018065365 A1 | 4/2018 |
| WO | 2019032859 A1 | 2/2019 |

OTHER PUBLICATIONS

Hulpia, Fabian et al., Synthesis of a 3'-C-ethynyl-beta-d-ribofuranose purine nucleoside library: Discovery of C7-deazapurine analogs as potent antiproliferative nucleosides, European Journal of Medicinal Chemistry, 2018, 248-267, 157.
Ben-Av et al., Induction of Vascular Endothielial Growth Factor Expression in Synovial fibroblasts by Prostaglandin E and Interleukin-1: A Potential mechanism for Inflammatory Angiogenesis, FEBS Letters, 372, 83-87, 1995.
Benezra et al., In Vivo Angiogenic Activity of Interleukins, Arch Ophthalmol, 108, 573-576, 1990.
Blume-Jensen, Peter et al., Oncogenic kinase signalling, Nature, 411, 355-365, 2001.
Bouma et al., Thrombin Activable Fibrinolysis Inhibitor (TAFI, Plasma Procarboxypeptidedase B, Procarboxypeptidase R, Procarboxypeptidase U), Thrombosis Research, 101, 329-354, 2001.
Brower, Tumor Angiogenesis New Drugs on the Block, Nature America, 17, 963-968, 1999.
Chakraborty et al., Developmental Expression of the Cyclo-Oxygenase-1 and Cyclo-oxygenase-2 genes in the Peri-implantation Mouse Uterus and their differential regulation by the blastocyst and ovarian steroids, J. Mol Endocrinol, 16, 107-122, 1996.
Chiang, Kelly et al., PRMT5 Is a Critical Regulator of Breast Cancer Stem Cell Function via Histone Methylation and FOXP1 Expression, Cell Reports, 21, 3498-3513, 2017.
Chiarugi et al., Cox-2, iNOS and p53 as play-makers of tumor angiogenesis (Review), International J. of Molecular Medicine, 2, 715-719, 1998.
Clarke, Thomas L. et al., PRMT5-Dependent Methylation of the TIP60 Coactivator RUVBL1 Is a Key Regulator of Homologous Recombination, Molecular Cell, 65, 900-916, e1-e7, 2017.
Diaz-Flores et al., Intense Vascular Sprouting From Rat Femoral Vein Induced by Prostaglandins E1 and E2, The Anatomical Record, 238, 68-76, 1994.
Fathallah-Shaykh et al., Gene Transfer of IFN-y into Established Brain Tumors Represses Grwoth by Antiangiogenesis, J. of Immunology, 164, 217-222, 2000.
Fernandez et al., Neovascularization Produced by Angiotensin II, Clinical Mediicne, 105, 141-145, 1985.
Gerhart, Sarah V. et al., Activation of the p53-MDM4 regulatory axis defines the antitumour response to PRMT5 inhibition through its role in regulating cellular splicing, Scientific Reports, 8:9711, 1-15, 2018.
Gralinkski et al., Effects of Troglitazone and Pioglitazone on Cytokine-Mediated Endothelial Cell Proliferation in Vitro, J. of Cardiovascular Pharmacology, 31, 909-913, 1998.
Gu et al., Effect of Novel CAAX Peptidomimetic Farnesyltransferase Inhibitor on Angiogenesis In Vitro and In Vivo, European J. of Cancer, 35, 1394-1401, 1999.
Hall et al., The Promise and Reality of Cancer Gene Therapy, Am. J. Hum. Genet, 61, 785-789, 1997.
Hamard, Pierre-Jacques et al., PRMT5 Regulates DNA Repair by Controlling the Alternative Splicing of Histone-Modifying Enzymes, Cell Reports, 24, 2643-2657, 2018.
Harada et al., Expression and Regulation of Vascular Endothelial Growth Factor in Osteoblasts, Clinical Ortho, 313, 76-80, 1995.
Hla et al., Human Cyclooxygenase-2 cDNA, Proc. Natl. Acad. Sci., 89, 7384-7388, 1992.
Kim et al., Inhibition of Endothelial Growth Factor-Induced Angiogenesis Suppreses Tumour Growth in Vivo, Nature, 362, 841-844, 1993.
Korte et al., Changes of the Coagulation and Fibrinolysis System n Malignancy: Their possible Impact on Future Diagnostic And Therapeutic Procedures, Clin Chem Lab Med, 38 (8), 679-692, 2000, 38.
Kufe et al., Principles of Gene Therapy, Cancer Medicine, 5th Ed., pp. 876-889, 2000.
Li et al., Adenovirus-Mediated Delivery of a uPA/uPAR Antagonist Suppresses Angiogenesis-Dependent Tumor Growth and Dissemination in Mice, Gene Therapy, 5, 1105-1113, 1998.
Majima et al., Significant Roles of Inducible Cyclooxygenase (COX)-2 in Angiogenesis in Rat Sponge Implants, Jpn. J. Pharmacol., 75, 105-114, 1997.
Mao, Ruifeng et al., Potent, Selective, and Cell Active Protein Arginine Methyltransferase 5 (PRMT5) Inhibitor Developed by Structure-Based Virtual Screening and Hit Optimization, Journal of Medicinal Chemistry, 60, 6289-6304, 2017.
Miller et al., Histone Deacetylase Inhibitors, J. of Medicinal Chemistry, 46, 5097-5116, 2003.
Murata et al., Peroxisome Proliferator-Activated Receptor-y Ligands Inhibit Choroidal Neovascularization, Inestigative Ophthalmology & visual Science, 41, 2309-2317, 2000.

(56) References Cited

OTHER PUBLICATIONS

Murata et al., Response of Experimental Retinal Neovascularization to Thiazolidinediones, Arch Ophthamol, 119, 709-717, 2001.

Seed et al., The Inhibition of Colon-26 Adenocarcinoma Development and Angiogenesis by Topical Diclofenac in 2.5% Hyaluronan, Cancer Research, 57, 1625-1629, 1997.

Still et al., Rapid Chromatographic Technique for Preparative Separations with Moderate Resolution, J. Org. Chem., 43, 2923-2925, 1978.

Tsujii et al., Cyclooxgenase Regulates Angiogenesis Induced by Colon Cancer Cells, Cell, 93, 705-716, 1998.

Xin et al., Peroxisome Proliferator Activated Receptor γ Ligands are Potent Inhibitors of Angiogenesis in Vitro and in Vivo, J. Biol Chem,, 13, 9116-9121, 1999.

Yalpani et al., Coronary Heart Disease is the most Serious Threat to life in the Western World, but Progress is Being Made in Finding Ways to Reduce the Risks of Suffering Such a Fate, Chemistry & Industry, 85-89, 1996.

Zacharski et al., Heparin and Cancer, Thromb Haemost, 80, 10-23, 1998.

Ziche et al., Role of Prostaglandin E, and Copper in Angiogenesis, JNCI, 69, 475-482, 1982.

\* cited by examiner ced adult γ-globin gene expression (in the setting of
PRMT5 INHIBITORS

CROSS REFERENCE TO RELATED APPLICATIONS

This application is a U.S. National Phase application under 35 U.S.C. § 371 of PCT Application No. PCT/US2019/045050 filed Aug. 5, 2019, which claims priority to U.S. Ser. No. 62/715,446 filed Aug. 7, 2018, 62/792,623 filed Jan. 15, 2019, and 62/859,490 filed Jun. 10, 2019, the contents of which are hereby incorporated by reference in their entireties.

BACKGROUND OF THE INVENTION

PRMT5 (aka JBP1, SKB1, IBP72, SKB1his and HRM-TIL5) is a Type II arginine methyltransferase, and was first identified in a two-hybrid search for proteins interacting with the Janus tyrosine kinase (Jak2) (Pollack et al., 1999). PRMT5 plays a significant role in control and modulation of gene transcription. Inter alia, PRMT5 is known to symmetrically methylate histone H3 at Arg-8 (a site distinct from that methylated by PRMT4) and histone H4 at Arg-3 (the same site methylated by PRMT1). PRMT5 has been reported to perform diverse roles including but not limited to impacting cell viability, stemness, DNA damage repair and RNA splicing (Clarke et al., Mol Cell (2017), Chiang et al., Cell Rep (2017), Gerhart et al., Sci Rep (2018)). Specifically, inhibition of PRMT5 induces alternative splicing of the negative regulator of p53, MDM4 resulting in increased expression of the short isoform of MDM4 (MDM4-S), decreased expression of the full-length isoform (MDM4-FL) and increased p53 activity (Gerhart el al Sci Rep (2018)). Most of the physiological functions of p53 are attributable to its role as a transcriptional activator, responding to agents that damage DNA. p53 status is wild type in approximately half of human cancer cases. These include 94% in cervix, 87% in blood malignancies, 85% in bones and endocrine glands, and 75% of primary breast cancer. Restoration of p53 in cancer cells harboring wild type p53, by way of inhibiting mechanisms that suppress its function leads to growth arrest and apoptosis and is regarded as a potentially effective means of tumor suppression.

In response to DNA damage caused by a variety of agents, including doxorubicin, camptothecin and UV light, and also in response to treatment with Nutlin-3, knockdown of PRMT5 results in an increase in sub-G1 population and concomitant reduction in G1 cells and, in the presence of p53, a significant increase in apoptosis. Knockdown of PRMT5 also resulted in an increased level of p21, a key p53 target gene that regulates cell cycle arrest during the p53 response and MDM2, a p53 E3 ubiquitin ligase, but not PUMA, NOXA, AIP1 & APAF1, p53 target genes linked to apoptosis.

Knockdown of PRMT5 (but not PRMT1 or CARM1/PRMT4) results in decreased p53 stabilization, decreased basal p53 levels, decreased p53 oligomerisation, and also decreased expression of eIF4E a major component of translational machinery involved in ribosome binding to mRNA. Indeed, eIF4E is a potent oncogene, which has been shown to promote malignant transformation in vitro and human cancer formation.

The role of PRMT5 in the DNA damage response has been explored with groups reporting a role for PRMT5 in regulating high fidelity homologous recombination mediated DNA repair in both solid (Clarke et al., Mol Cell (2017)) and hematological tumor models (Hamard et al., Cell Rep (2018)).

PRMT5 is aberrantly expressed in around half of human cancer cases, further linking this mechanism to cancers. PRMT5 overexpression has been observed in patient tissue samples and cell lines of Prostate cancer (Gu et al., 2012). Lung cancer (Zhongping et al., 2012), Melanoma cancer (Nicholas et al., 2012), Breast cancer (Powers et al., 2011), Colorectal cancer (Cho et al., 2012), Gastric cancer (Kim et al., 2005), Esophagus and Lung carcinoma (Aggarwal et al., 2010) and B-Cell lymphomas and leukemia (Wang, 2008). Moreover, elevated expression of PRMT5 in Melanoma, Breast and Colorectal cancers has been demonstrated to correlate with a poor prognosis.

Lymphoid malignancies including chronic lymphocytic leukemia (CLL) are associated with over-expression of PRMT5. PRMT5 is over-expressed (at the protein level) in the nucleus and cytosol in a number of patient derived Burkitt's lymphoma; mantle cell lymphoma (MCL); in vitro EBV-transformed lymphoma; leukemia cell lines; and B-CLL cell lines, relative to normal CD19+ B lymphocytes (Pal et al., 2007; Wang et al., 2008). Intriguingly, despite elevated levels of PRMT5 protein in these tumor cells, the levels of PRMT5 mRNA are reduced (by a factor of 2-5). Translation of PRMT5 mRNA is, however, enhanced in lymphoma cells, resulting in increased levels of PRMT5 (Pal et al., 2007; Wang et al., 2008).

In addition to genomic changes, CLL, like almost all cancers, has aberrant epigenetic abnormalities characterised by global hypomethylation and hot-spots of repressive hypermethylation of promoters including tumor suppressor genes. While the role of epigenetics in the origin and progression of CLL remains unclear, epigenetic changes appear to occur early in the disease and specific patterns of DNA methylation are associated with worse prognosis (Chen et al., 2009; Kanduri et al., 2010). Global symmetric methylation of histones H3R8 and H4R3 is increased in transformed lymphoid cell lines and MCL clinical samples (Pal et al., 2007), correlating with the overexpression of PRMT5 observed in a wide variety of lymphoid cancer cell lines and MCL clinical samples.

PRMT5 is therefore a target for the identification of novel cancer therapeutics.

Hemoglobin is a major protein in red blood cells and is essential for the transport of oxygen from the lungs to the tissues. In adult humans, the most common hemoglobin type is a tetramer called hemoglobin A, consisting of two α and two β subunits. In human infants, the hemoglobin molecule is made up of two α and two γ chains. The gamma chains are gradually replaced by β subunits as the infant grows. The developmental switch in human ß-like globin gene subtype from foetal (γ) to adult (ß) that begins at birth heralds the onset of the hemoglobinopathies ß-thalassemia or sickle cell disease (SCD). In ß-thalassemia the adult chains are not produced. In SCD, a point mutation in the coding sequence in the ß globin gene leads to the production of a protein with altered polymerisation properties. The observation that increased adult γ-globin gene expression (in the setting of hereditary persistence of foetal hemoglobin (HPFH) mutations) significantly ameliorates the clinical severity of ß-thalassemia and SCD has prompted the search for therapeutic strategies to reverse γ-globin gene silencing. To date, this has been achieved through pharmacological induction, using compounds that broadly influence epigenetic modifications, including DNA methylation and histone deacetylation. The development of more targeted therapies is dependent on the identification of the molecular mechanisms underpinning foetal globin gene silencing. These mechanisms have remained elusive, despite exhaustive study of the HPFH mutations, and considerable progress in many other aspects of globin gene regulation.

PRMT5 plays a critical role in triggering coordinated repressive epigenetic events that initiate with dimethylation of histone H4 Arginine 3 (H4R3me2s), and culminate in DNA methylation and transcriptional silencing of the γ-genes (Rank et al., 2010). Integral to the synchronous establishment of the repressive markers is the assembly of a PRMT5-dependent complex containing the DNA methyltransferase DNMT3A, and other repressor proteins (Rank et al., 2010). DNMT3A is directly recruited to bind to the PRMT5-induced H4R3me2s mark, and loss of this mark through shRNA-mediated knock-down of PRMT5, or enforced expression of a mutant form of PRMT5 lacking methyltransferase activity leads to marked upregulation of γ-gene expression, and complete abrogation of DNA methylation at the γ-promoter. Treatment of human erythroid progenitors with non-specific methyltransferase inhibitors (Adox and MTA) also resulted in upregulation of γ-gene expression (He Y, 2013). Inhibitors of PRMT5 thus have potential as therapeutics for hemoglobinopathies such as ß-thalassemia or Sickle Cell Disease (SCD).

The present inventors have developed compounds that inhibit the activity of PRMT5 and therefore may be of use in treating conditions ameliorated by the inhibition of the activity of PRMT5.

SUMMARY OF THE INVENTION

Compounds of Formula I

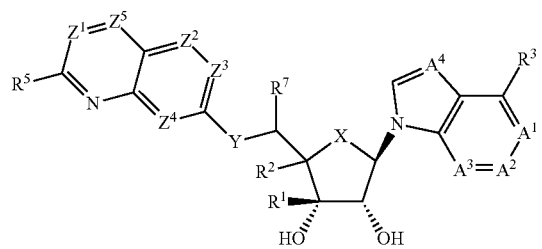

(I)

and the pharmaceutically acceptable salts, esters, and prodrugs thereof, which are PRMT5 inhibitors. Also provided are methods of making compounds of formula I, pharmaceutical compositions comprising compounds of formula I, and methods of using these compounds to treat cancer, sickle cell, and hereditary persistence of foetal hemoglobin (HPFH) mutations.

DETAILED DESCRIPTION OF THE INVENTION

The invention is a compound of the formula

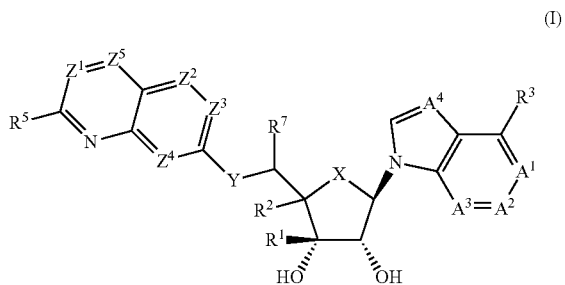

(I)

or pharmaceutically acceptable salts thereof, wherein
X is $CH_2$ or O;
Y is $CH_2$, NH, or O;
$Z^1$ is $CR^4$ or N;
$Z^2$, $Z^3$, $Z^4$, and $Z^5$ are independently selected from N or $CR^9$;
$A^1$ is CH or N;
$A^2$ is $CR^{10}$ or N;
$A^3$ is CH or N;
$A^4$ is CR or N;
$R^1$, $R^2$ and $R^7$ are:
  i) $R^1$ is H, CCH, or $C_{1-3}$alkyl optionally substituted with 1 to 2 halogens; and $R^2$ is H, halogen, OH, $CH_3$, $NH_2$, $NHCH_3$, $CH_2OH$, $CH_2F$, or $CHF_2$, and $R^7$ is H, provided that $R^1$ and $R^2$ cannot simultaneously be H; or
  ii) $R^1$ and $R^7$ taken together to form a five membered carbon ring optionally substituted with 1-3 halogens or a five membered heterocycloalkyl ring comprising one O atom,
    and $R^2$ is H, OH $CH_3$, $CHF_2$, or F;
$R^3$ is H, halogen, $NH_2$, $NHCH_3$, CN, OH, $OCH_3$, $C_{1-4}$alkyl optionally substituted with 1-3 halogen or OH, or $C_{3-5}$cycloalkyl optionally substituted with 1-3 halogens or OH;
$R^5$ is H, $NH_2$, or $NHR^6$; and $R^4$, when present, is H, halogen, $CH_3$, $CHF_2$, or $CF_3$; or
$R^4$ and $R^5$ taken together with the carbon atoms to which they are attached, join to form a 5 membered heterocycloalkyl comprising one N atom, wherein the heterocycloalkyl is optionally substituted with one to four substituents independently selected from halogen, $CH_3$, $CF_3$, or $CF_2H$;
$R^6$, when present, is $CH_3$, $C_2H_5$, $CH_2CH_2CH_3$, $CH(CH_3)_2$, $CH_2CHF_2$, $CH_2CF_3$, or $CH_2$-cyclopropyl;
$R^8$, when present, is H, halogen, $C_{1-4}$alkyl optionally substituted with 1-3 halogens, $C_{3-5}$cycloalkyl optionally substituted with 1-3 halogens, or aryl optionally substituted with 1-3 halogens;
each $R^9$, when present, is independently selected from H or halogen; and
$R^{10}$, when present, is H, $C_{1-6}$alkyl, $NH_2$, or halogen.

An embodiment of the invention of the compound of formula (I), or a pharmaceutically acceptable salt thereof, is the compound of formula (Ia);

(Ia)

or pharmaceutically acceptable salts thereof, wherein
X is CH$_2$ or O;
Y is CH$_2$, NH, or O;
Z$^1$ is CR$^4$ or N;
Z$^2$ is CH or N;
Z$^3$ is CH or N;
Z$^4$ is CH or N;
A$^1$ is CH or N;
A$^2$ is CH, N, CNH$_2$ or CCH$_3$;
A$^3$ is CH or N;
A$^4$ is CR$^8$ or N;
R$^1$, R$^2$ and R$^7$ are:
  i) R$^1$ is H, CCH, or C$_{1-3}$alkyl optionally substituted with 1 to 2 halogens; and R$^2$ is H, halogen, OH, CH$_3$, NH$_2$, NHCH$_3$, CH$_2$OH, CH$_2$F, or CHF$_2$, and R$^7$ is H, provided that R$^1$ and R$^2$ cannot simultaneously be H; or
  ii) R$^1$ and R$^7$ taken together to form a five membered ring and R is H, OH, CH$_3$, CHF$_2$, or F;
R$^3$ is H, halogen, CH$_3$, C$_2$H$_5$, cyclopropyl, NH$_2$, NHCH$_3$, CN, CF$_3$, OH, OCH$_3$, or CHF$_2$;
R$^4$, when present, is H, halogen, CH$_3$, CHF$_2$, or CF$_3$; and R is H, NH$_2$, or NHR$^6$; or
R$^4$ and R$^5$ taken together with the carbon atoms to which they are attached, join to form a 5 membered heterocycloalkyl comprising one N atom, wherein the heterocycloalkyl is optionally substituted with one to four substituents independently selected from halogen, CH$_3$, CF$_3$, or CF$_2$H;
R$^6$, when present, is CH$_3$, C$_2$H$_5$, CH$_2$CH$_2$CH$_3$, CH(CH$_3$)$_2$, CH$_2$CHF$_2$, CH$_2$CF$_3$, or CH$_2$-cyclopropyl; and
R$^8$ when present, is H, C$_{1-4}$alkyl, or halogen.

An embodiment of the invention of the compound of formula (I), or a pharmaceutically acceptable salt thereof, is the compound of formula (Ib);

(Ib)

In a subembodiment of the invention of formula Ib, X is CH$_2$ or O.

In a further subembodiment of the invention of formula Ib, X is CH$_2$.

In a further subembodiment of the invention of formula Ib, X is O.

In a subembodiment of the invention of formula Ib, Y is CH$_2$, NH, or O.

In a further subembodiment of the invention of formula Ib, Y is CH$_2$.

In a further subembodiment of the invention of formula Ib, Y is O.

In a subembodiment of the invention of formula Ib, W is CR$^{11}$R$^{11}$ or O.

In a subembodiment of the invention of formula Ib, W is O, CHF, CF$_2$, or CH$_2$.

In a subembodiment of the invention of formula Ib, W is CHF.

In a subembodiment of the invention of formula Ib, W is CF$_2$.

In a further subembodiment of the invention of formula Ib, W is O.

In a further subembodiment of the invention of formula Ib, W is CH$_2$.

In a subembodiment of the invention of formula Ib, Z$^2$, Z$^3$, Z$^4$, and Z$^5$ are independently selected from N or CR$^9$.

In a subembodiment of the invention of formula Ib, A$^2$ is CR$^{10}$ or N.

In a further subembodiment of the invention of formula Ib, A$^2$ is N, CH, CNH$_2$, CF, CCl, or CCH$_3$.

In a further subembodiment of the invention of formula Ib, A$^2$ is CH, CCl, or CF.

In a subembodiment of the invention of formula Ib, R$^2$ is H, OH, CH$_3$, CHF$_2$, or F.

In a further subembodiment of the invention of formula Ib, R$^2$ is H.

In a subembodiment of the invention, R$^3$ is H, halogen, NH$_2$, NHCH$_3$, CN, OH, OCH$_3$, C$_{1-4}$alkyl optionally substituted with 1-3 halogen or OH, or C$_{3-5}$cycloalkyl optionally substituted with 1-3 halogens or OH.

In a further subembodiment of the invention of formula Ib, R$^3$ is NH$_2$, Cl, OCH$_3$, or CH$_3$.

In a further subembodiment of the invention of formula Ib, R$^3$ is NH$_2$ or CH$_3$.

In a subembodiment of the invention of formula Ib, R$^4$ is H, halogen, CH$_3$, CHF$_2$, or CF$_3$.

In a further subembodiment of the invention of formula Ib, R$^4$ is H.

In a further subembodiment of the invention of formula Ib, R$^4$ is halogen.

In a further subembodiment of the invention of formula Ib, R$^4$ is H, Cl, F or Br.

In a subembodiment of the invention of formula Ib, R$^5$ is H, NH$_2$, or NHR$^6$.

In a subembodiment of the invention of formula Ib, R$^6$, when present, is CH$_3$, C$_2$H$_5$, CH$_2$CH$_2$CH$_3$, CH(CH$_3$)$_2$, CH$_2$CHF$_2$, CH$_2$CF$_3$, or CH$_2$-cyclopropyl.

In a subembodiment of the invention of formula Ib, each R$^{11}$, when present, is independently selected from H or halogen.

In a further subembodiment of the invention of formula Ib, R$^5$ is H.

In a further subembodiment of the invention of formula Ib, R$^5$ is NH$_2$.

In a subembodiment of the invention of formula Ib, R$^8$ is H, halogen, C$_{1-4}$alkyl optionally substituted with 1-3 halogens, C$_{3-5}$cycloalkyl optionally substituted with 1-3 halogens, or aryl optionally substituted with 1-3 halogens.

In a further subembodiment of the invention of formula Ib, R$^8$ is H, CH$_3$, or F.

In a subembodiment of the invention of formula Ib, each $R^9$, when present, is independently selected from H or halogen.

In a subembodiment of the invention of formula Ib, each $R^9$, when present, is independently selected from H, F, or Cl.

In a further subembodiment of the invention of formula Ib, $R^9$, when present, is H.

In a further subembodiment of the invention of formula Ib, $R^9$, when present, is F.

In a further subembodiment of the invention of formula Ib, $R^9$, when present, is Cl.

In a subembodiment of the invention of formula Ib, $R^{10}$, when present, is H, $NH_2$, $C_{1-6}$alkyl, or halogen.

In a further subembodiment of the invention of formula Ib, $R^{10}$ is H.

In a further subembodiment of the invention of formula Ib, $R^{10}$ is $CH_3$.

In a further subembodiment of the invention of formula Ib, $R^{10}$ is F.

An embodiment of the invention of the compound of formula (I), or a pharmaceutically acceptable salt thereof, is the compound of formula (Ic);

(Ic)

In a subembodiment of the invention of formula Ic, X is $CH_2$ or O.

In a subembodiment of the invention of formula Ic, Y is $CH_2$, NH, or O.

In a subembodiment of the invention of formula Ic, W is $CH_2$ or O.

In a subembodiment of the invention of formula Ic, $R^2$ is H, OH, $CH_3$, $CHF_2$, or F.

In a further subembodiment of the invention of formula Ic, $R^2$ is H.

In a subembodiment of the invention of formula Ic, $R^3$ is H, halogen, $CH_3$, $C_2H_5$, cyclopropyl, $NH_2$, $NHCH_3$, CN, $CF_3$, OH, $OCH_3$, or $CHF_2$.

In a further subembodiment of the invention of formula Ic, $R^3$ is $CH_3$, Cl, $NH_2$, or $OCH_3$.

In a subembodiment of the invention of formula Ic, $R^4$ is H, halogen, $CH_3$, $CHF_2$, or $CF_3$.

In a further subembodiment of the invention of formula Ic, $R^4$ is H or halogen.

In a further subembodiment of the invention of formula Ic, $R^4$ is H or Br.

In a subembodiment of the invention of formula Ic, $R^5$ is H, $NH_2$, or $NHR^6$.

In a further subembodiment of the invention of formula Ic, $R^5$ is H or $NH_2$.

In a further subembodiment of the invention of formula Ic, $R^5$ is $NH_2$.

In a subembodiment of the invention for formula Ic, $R^4$ and $R^5$ taken together with the carbon atoms to which they are attached, join to form a 5 membered heterocycloalkyl comprising one N atom, wherein the heterocycloalkyl is optionally substituted with one to four substituents independently selected from halogen, $CH_3$, $CF_3$, or $CF_2H$.

In a subembodiment of the invention of formula Ic, $R^6$, when present, is $CH_3$, $C_2H_5$, $CH_2CH_2CH_3$, $CH(CH_3)_2$, $CH_2CHF_2$, $CH_2CF_3$, or $CH_2$-cyclopropyl.

In a further subembodiment of the invention of formula Ic, $R^6$, when present, is $CH_3$.

In a subembodiment of the invention of formula Ic, $R^8$ is H, $C_{1-4}$alkyl, or halogen.

In a subembodiment of the invention of formula Ic, $R^8$ is H.

A subembodiment of the invention of the compound of formula (I), or a pharmaceutically acceptable salt thereof, is the compound of formula (Id);

(Id)

In a subembodiment of the invention of formula Id, X is $CH_2$ or O.

In a subembodiment of the invention of formula Id, Y is $CH_2$, NH, or O.

In a subembodiment of the invention of formula Id, $R^1$ is H, CCH, or $C_{1-3}$alkyl optionally substituted with 1 to 2 halogens, and $R^2$ is H, halogen, OH, $CH_3$, $NH_2$, $NHCH_3$, $CH_2OH$, $CH_2F$, or $CHF_2$, where $R^1$ and $R^2$ cannot simultaneously be H.

In a further subembodiment of the invention of formula Id, $R^1$ is H, $CH_3$, CCH, $CH_2F$, or $CHF_2$, and $R^2$ is H or $CH_3$, where $R^1$ and $R^2$ cannot simultaneously be H.

In a further subembodiment of the invention of formula Id, $R^1$ is H, $CH_3$ or CCH, where $R^1$ and $R^2$ cannot simultaneously be H.

In a further subembodiment of the invention of formula Id, $R^2$ is H or $CH_3$, where $R^1$ and $R^2$ cannot simultaneously be H.

In a subembodiment of the invention of formula Id, $R^3$ is H, halogen, $CH_3$, $C_2H_5$, cyclopropyl, $NH_2$, $NHCH_3$, CN, $CF_3$, OH, $OCH_3$, or $CHF_2$.

In a further subembodiment of the invention of formula Id, $R^3$ is H, $CH_3$, $NH_2$, Cl, OH, or $OCH_3$.

In a further subembodiment of the invention of formula Id, $R^3$ is $CH_3$, Cl, $OCH_3$, or $NH_2$.

In a subembodiment of the invention of formula Id, $R^4$ is H, halogen, $CH_3$, $CHF_2$, or $CF_3$.

In a further subembodiment of the invention of formula Id, $R^4$ is H or halogen.

In a further subembodiment of the invention of formula Id, $R^4$ is H or Br.

In a subembodiment of the invention of formula Id, $R^5$ is H, $NH_2$, or $NHR^6$.

In a further subembodiment of the invention of formula Id, $R^5$ is H or $NH_2$.

In a further subembodiment of the invention of formula Id, $R^5$ is $NH_2$.

In a subembodiment of the invention of formula Id, $R^6$, when present, is $CH_3$, $C_2H_5$, $CH_2CH_2CH_3$, $CH(CH_3)_2$, $CH_2CHF_2$, $CH_2CF_3$, or $CH_2$-cyclopropyl.

In a further subembodiment of the invention of formula Id, $R^6$ is $CH_3$.

In a subembodiment of the invention of formula Id, $R^8$ is H, $C_{1-4}$alkyl, or halogen.

In a further subembodiment of the invention of formula Id, $R^8$ is H.

In an embodiment of the invention, the compound of formula I is:

(1R,2S,3R,5R)-5-(((2-amino-3-bromoquinolin-7-yl)oxy)methyl)-3-(4-chloro-7H-pyrrolo[2,3-d]pyrimidin-7-yl)-1-methylcyclopentane-1,2-diol, (1R,2S,3R,5R)-5-(((2-amino-3-bromoquinolin-7-yl)oxy)methyl)-3-(4-amino-7H-pyrrolo[2,3-d]pyrimidin-7-yl)-1-methylcyclopentane-1,2-diol, (2R,3S,4R,5R)-2-(((2-amino-3-bromoquinolin-7-yl)oxy)methyl)-5-(4-amino-7H-pyrrolo[2,3-d]pyrimidin-7-yl)-3-ethynyltetrahydrofuran-3,4-diol, (2R,3S,4R,5R)-2-(2-(2-amino-3-bromoquinolin-7-yl)ethyl)-5-(4-amino-7H-pyrrolo[2,3-d]pyrimidin-7-yl)-2,3-dimethyltetrahydrofuran-3,4-diol, (2R,3R,3aS,6S,6aR)-6-((2-amino-3-bromoquinolin-7-yl)oxy)-2-(4-chloro-7H-pyrrolo[2,3-d]pyrimidin-7-yl)hexahydro-2H-cyclopenta[b]furan-3,3a-diol, (2R,3R,3aS,6S,6aR)-6-((2-amino-3-bromoquinolin-7-yl)oxy)-2-(4-amino-7H-pyrrolo[2,3-d]pyrimidin-7-yl)hexahydro-2H-cyclopenta[b]furan-3,3a-diol, (2R,3R,3aS,6S,6aR)-6-((2-amino-3-bromoquinolin-7-yl)oxy)-2-(4-methyl-7H-pyrrolo[2,3-d]pyrimidin-7-yl)hexahydro-2H-cyclopenta[b]furan-3,3a-diol, (2R,3R,3aS,6S,6aR)-6-((2-amino-3-bromoquinolin-7-yl)methyl)-2-(4-methyl-7H-pyrrolo[2,3-d]pyrimidin-7-yl)hexahydro-2H-cyclopenta[b]furan-3,3a-diol, (2R,3R,3aS,6S,6aR)-6-((2-amino-3-bromoquinolin-7-vi)methyl)-2-(4-amino-7H-pyrrolo[2,3-d]pyrimidin-7-yl)hexahydro-2H-cyclopenta[b]furan-3,3a-diol, (2R,3S,4R,5R)-2-(((2-amino-3-bromoquinolin-7-yl)oxy)methyl)-5-(4-amino-7H-pyrrolo[2,3-d]pyrimidin-7-yl)-3-methyltetrahydrofuran-3,4-diol, (2R,3S,4R,5R)-2-{[(2-amino-3-bromoquinolin-7-yl)oxy]methyl}-5-(4-chloro-7H-pyrrolo[2,3-d]pyrimidin-7-yl)-3-methyltetrahydrofuran-3,4-diol, (2R,3S,4R,5R)-2-(((2-amino-3-bromoquinolin-7-yl)oxy)methyl)-5-(4-methoxy-7H-pyrrolo[2,3-d]pyrimidin-7-yl)-2-methyltetrahydrofuran-3,4-diol, (2R,3S,4R,5R)-2-(((2-amino-3-bromoquinolin-7-yl)oxy)methyl)-5-(4-amino-7H-pyrrolo[2,3-d]pyrimidin-7-yl)-2-methyltetrahydrofuran-3,4-diol, (2R,3S,4R,5R)-2-(((2-amino-3-bromoquinolin-7-yl)oxy)methyl)-5-(4-amino-7H-pyrrolo[2,3-d]pyrimidin-7-yl)-3-methyltetrahydrofuran-3,4-diol, (1S,2R,3S,5R)-3-[2-(2-amino-3-bromo-7-quinolinyl)ethyl]-5-(4-amino-7H-pyrrolo[2,3-d]pyrimidin-7-yl)-3-methyl-1,2-cyclopentanediol, (1S,2R,3aR,4S,6aR)-4-((2-amino-3-fluoroquinolin-7-yl)methyl)-2-(4-methyl-7H-pyrrolo[2,3-d]pyrimidin-7-yl)hexahydropentalene-1,6a(1H)-diol, (1S,2R,3 aR,4S,6aR)-4-((2-amino-3-chloroquinolin-7-yl)methyl)-2-(4-methyl-7H-pyrrolo[2,3-d]pyrimidin-7-yl)hexahydropentalene-1,6a(1H)-diol, (1S,2R,3aR,4R,6aR)-4-((2-amino-3-fluoroquinolin-7-yl)methyl)-2-(4-methyl-7H-pyrrolo[2,3-d]pyrimidin-7-yl)hexahydropentalene-1,6a(1H)-diol, (1S,2R,3aR,4S,6aR)-4-((2-amino-3-bromoquinolin-7-yl)methy)-2-(4-methyl-7H-pyrrolo[2,3-d]pyrimidin-7-yl)hexahydropentalene-1,6a(1H)-diol, (2R,3R,3aS,6S,6aR)-6-[(2-amino-3,8-difluoroquinolin-7-yl)methyl]-2-(4-amino-7H-pyrrolo[2,3-d]pyrimidin-7-yl)hexahydro-3aH-cyclopenta[b]furan-3,3a-diol, (2R,3R,3aS,6S,6aR)-6-[(2-amino-3-chloro-5-fluoroquinolin-7-yl)methyl]-2-(4-amino-7H-pyrrolo[2,3-d]pyrimidin-7-yl)hexahydro-3aH-cyclopenta[b]furan-3,3a-diol, (2R,3R,3aS,6S,6aR)-6-[(2-amino-3-chloro-8-fluoroquinolin-7-yl)methyl]-2-(4-methyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-(difluoromethyl)quinolin-7-yl)methyl)-2-(4-methyl-7H-pyrrolo[2,3-d]pyrimidin-7-yl)hexahydro-3aH-cyclopenta[b]furan-3,3a-diol, (2R,3R,3aS,6S,6aR)-6-((2-amino-3,5-difluoroquinolin-7-yl)methyl)-2-(4-amino-5-fluoro-7H-pyrrolo[2,3-d]pyrimidin-7-yl)hexahydro-3aH-cyclopenta[b]furan-3,3a-diol, (2R,3R,3aS,6S,6aR)-6-((6-amino-7-fluoro-1,5-naphthyridin-3-yl)methyl)-2-(4-methyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-chloro-8-fluoroquinolin-7-yl)methyl)-2-(4-amino-7H-pyrrolo[2,3-d]pyrimidin-7-yl)hexahydro-3aH-cyclopenta[b]furan-3,3a-diol, (2R,3R,3aS,6S,6aR)-6-[(2-amino-3,6-difluoroquinolin-7-yl)methyl]-2-(4-amino-7H-pyrrolo[2,3-d]pyrimidin-7-yl)hexahydro-3aH-cyclopenta[b]furan-3,3a-diol, (2R,3R,3aS,6S,6aR)-6-((7-amino-6-chloro-1,8-naphthyridin-2-yl)methyl)-2-(4-amino-7H-pyrrolo[2,3-d]pyrimidin-7-yl)hexahydro-3aH-cyclopenta[b]furan-3,3a-diol, (2R,3R,3aS,6S,6aR)-6-[(2-amino-3,5-difluoroquinolin-7-yl)methyl]-2-(4-amino-7H-pyrrolo[2,3-d]pyrimidin-7-yl)hexahydro-3aH-cyclopenta[b]furan-3,3a-diol, (1S,2R,3aR,4S,6aR)-4-((2-amino-3-fluoroquinolin-7-yl)methyl)-2-(4-methyl-7H-pyrrolo[2,3-d]pyrimidin-7-yl)hexahydropentalene-1,6a(1H)-diol, (1S,2R,3aR,4S,6aR)-2-(4-amino-2-methyl-7H-pyrrolo[2,3-d]pyrimidin-7-yl)-4-((2-amino-3-chloroquinolin-7-yl)methyl)hexahydropentalene-1,6a(1H)-diol, (1S,2R,3aR,4S,6aR)-2-(4-amino-2-methyl-7H-pyrrolo[2,3-d]pyrimidin-7-yl)-4-((2-amino-3-fluoroquinolin-7-yl)methyl)hexahydropentalene-1,6a(1H)-diol, (1S,2R,3aR,4S,6aR)-4-((2-amino-3-fluoroquinolin-7-yl)methyl)-2-(4-amino-5-fluoro-7H-pyrrolo[2,3-d]pyrimidin-7-yl)hexahydropentalene-1,6a(1H)-diol, (1S,2R,3aR,4S,6aR)-4-((2-amino-3-chloroquinolin-7-yl)methyl)-2-(4-amino-5-fluoro-7H-pyrrolo[2,3-d]pyrimidin-7-yl)hexahydropentalene-1,6a(1H)-diol, (1S,2R,3aR,4S,6aR)-4-[(2-amino-3,5-difluoroquinolin-7-yl)methyl]-2-(4-amino-5-methyl-7H-pyrrolo[2,3-d]pyrimidin-7-yl)hexahydropentalene-1,6a(1H)-diol, (1S,2R,3aR,4S,6aR)-4-[(2-amino-3-chloro-5-fluoroquinolin-7-yl)methyl]-2-(4-amino-5-methyl-7H-pyrrolo[2,3-d]pyrimidin-7-yl)hexahydropentalene-1,6a(1H)-diol, (1S,2R,3aR,4S,6aR)-2-(4-amino-2-methyl-7H-pyrrolo[2,3-d]pyrimidin-7-yl)-4-((2-amino-3-bromoquinolin-7-yl)methyl)hexahydropentalene-1,6a(1H)-diol, (1S,2R,3aR,4S,6aR)-4-((2-amino-3-fluoroquinolin-7-yl)methyl)-2-(4-amino-5-methyl-7H-pyrrolo[2,3-d]pyrimidin-7-yl)hexahydropentalene-1,6a(1H)-diol, (1S,2R,3aR,4S,6aR)-4-((2-amino-3-chloroquinolin-7-yl)methyl)-2-(4-amino-5-methyl-7H-pyrrolo[2,3-d]pyrimidin-7-yl)hexahydropentalene-1,6a(1H)-diol, (1S,2R,3aR,4S,6aR)-4-((2-amino-3-bromoquinolin-7-yl)methyl)-2-(4-amino-5-methyl-7H-pyrrolo[2,3-d]pyrimidin-7-yl)hexahydropentalene-1,6a(1H)-diol, (1S,2R,3aR,4S,6aR)-4-((2-amino-3-bromoquinolin-7-yl)methyl)-2-(4-amino-7H-pyrrolo[2,3-d]pyrimidin-7-yl)hexahydropentalene-1,6a(1H)-diol, (1S,2R,3aR,4S,6aR)-4-((2-amino-3-bromoquinolin-7-yl)methyl)-2-(4-amino-5-fluoro-7H-pyrrolo[2,3-d]pyrimidin-7-yl)hexahydropentalene-1,6a(1H)-diol, (2R,3R,3aS,6S,6aR)-6-[(2-amino-3-bromoquinolin-7-yl)methyl]-2-[4-amino-5-(difluoromethyl)-7H-pyrrolo[2,3-d]pyrimidin-7-yl]hexahydro-3aH-cyclopenta[b]furan-3,3a-diol, (2R,3R,3aS,6S,6aR)-6-((2-amino-3-fluoroquinolin-7-yl)methyl)-2-(4-amino-5-fluoro-2-methyl-7H-pyrrolo[2,3-d]pyrimidin-7-yl)hexahydro-3aH-cyclopenta[b]furan-3,3a-diol, (2R,3R,3aS,6S,6aR)-2-(4-amino-2-fluoro-7H-pyrrolo[2,3-d]pyrimidin-7-yl)-6-((2-amino-3-fluoroquinolin-7-yl)methyl)hexahydro-3aH-cyclopenta[b]furan-3,3a-diol, (2R,3R,3aS,6S,6aR)-6-((2-amino-3-bromoquinolin-7-yl)oxy)-2-(2-amino-7H-pyrrolo[2,3-d]pyrimidin-7-yl)hexahydro-3aH-cyclopenta[b]furan-3,3a-diol dihydrochloride, (2R,3R,3aS,6S,6aR)-2-(4-amino-2-chloro-7H-pyrrolo[2,3-d]pyrimidin-7-yl)-6-[(2-amino-3-chloroquinolin-7-yl)methyl]hexahydro-3aH-cyclopenta[b]furan-3,3a-diol, (2R,3R,3aS,6S,6aR)-2-(4-amino-2-chloro-7H-pyrrolo[2,3-d]pyrimidin-7-yl)-6-[(2-amino-3-fluoroquinolin-7-yl)methyl]hexahydro-3aH-cyclopenta[b]furan-3,3a-diol, (2R,3R,3aS,6S,6aR)-6-[(2-amino-3-bromoquinolin-7-yl)oxy]-2-(4-amino-5-phenyl-7H-pyrrolo[2,3-d]pyrimidin-7-yl)hexahydro-3aH-cyclopenta[b]furan-3,3a-diol, (2R,3R,3aS,6S,6aR)-2-(4-amino-5-cyclopropyl-7H-pyrrolo[2,3-d]pyrimidin-7-yl)-6-[(2-amino-3-fluoroquinolin-7-yl)methyl]hexahydro-3aH-cyclopenta[b]furan-3,3a-diol, (2R,3R,3aS,6S,6aR)-2-[4-amino-5-(difluoromethyl)-7H-pyrrolo[2,3-d]pyrimidin-7-yl)-6-(2-amino-3-fluoroquinolin-7-yl)methyl]hexahydro-3aH-cyclopenta[b]furan-3,3a-diol, (2R,3R,3aS,6S,6aR)-6-[(2-amino-3-bromoquinolin-7-yl)oxy]-2-(4-amino-5-cyclopropyl-7H-pyrrolo[2,3-d]pyrimidin-7-yl)hexahydro-3aH-cyclopenta[b]furan-3,3a-diol, (2R,3R,3aS,6S,6aR)-6-[(2-amino-3-fluoroquinolin-7-yl)methyl]-2-(4-amino-7H-pyrrolo[2,3-d]pyrimidin-7-yl)-5,5-difluorohexahydro-3aH-cyclopenta[b]furan-3,3a-diol, (2R,3R,3aS,5S,6S,6aR)-6-[(2-amino-3-fluoroquinolin-7-yl)methyl]-2-(4-amino-7H-pyrrolo[2,3-d]pyrimidin-7-yl)-5-fluorohexahydro-3aH-cyclopenta[b]furan-3,3a-diol, (2R,3R,3aS,5S,6S,6aR)-2-(4-amino-5-fluoro-7H-pyrrolo[2,3-d]pyrimidin-7-yl)-6-[(2-amino-3-fluoroquinolin-7-yl)methyl]-5-fluorohexahydro-3aH-cyclopenta[b]furan-3,3a-diol, (2R,3R,3aS,6S,6aR)-6-((2-amino-3-bromoquinolin-7-yl)oxy)-2-(4-amino-5-fluoro-7H-pyrrolo[2,3-d]pyrimidin-7-yl)hexahydro-3aH-cyclopenta[b]furan-3,3a-diol, (2R,3R,3aS,6S,6aR)-2-(4-amino-7H-pyrrolo[2,3-d]pyrimidin-7-yl)-6-((2-((2,2,2-trifluoroethyl)amino)quinolin-7-yl)oxy)hexahydro-3aH-cyclopenta[b]furan-3,3a-diol, (2R,3R,3aS,6S,6aR)-2-(4-amino-7H-pyrrolo[2,3-d]pyrimidin-7-yl)-6-((2-((cyclopropylmethyl)amino)quinolin-7-yl)oxy)hexahydro-3aH-cyclopenta[b]furan-3,3a-diol, (2R,3R,3aS,6S,6aR)-6-((2-amino-3-fluoroquinolin-7-yl)methyl)-2-(4-amino-5-fluoro-7H-pyrrolo[2,3-d]pyrimidin-7-yl)hexahydro-3aH-cyclopenta[b]furan-3,3a-diol, (2R,3R,3aS,6S,6aR)-6-((2-amino-3-bromoquinolin-7-yl)oxy)-2-(4-amino-5-methyl-7H-pyrrolo[2,3-d]pyrimidin-7-yl)hexahydro-3aH-cyclopenta[b]furan-3,3a-diol, (2R,3R,3aS,6S,6aR)-2-(4-amino-2-methyl-7H-pyrrolo[2,3-d]pyrimidin-7-yl)-6-((2-amino-3-bromoquinolin-7-yl)methyl)hexahydro-3aH-cyclopenta[b]furan-3,3a-diol, (2R,3R,3aS,6S,6aR)-6-((2-amino-3-fluoroquinolin-7-yl)methyl)-2-(4-amino-5-methyl-7H-pyrrolo[2,3-d]pyrimidin-7-yl)hexahydro-3aH-cyclopenta[b]furan-3,3a-diol, (2R,3R,3aS,6S,6aR)-2-(4-amino-2-methyl-7H-pyrrolo[2,3-d]pyrimidin-7-yl)-6-((2-amino-3-bromoquinolin-7-yl)oxy)hexahydro-3aH-cyclopenta[b]furan-3,3a-diol, (2R,3R,3aS,6S,6aR)-6-((2-amino-3-chloroquinolin-7-yl)oxy)-2-(4-amino-5-methyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-fluoroquinolin-7-yl)oxy)-2-(4-amino-5-methyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-chloroquinolin-7-yl)methyl)-2-(4-amino-5-methyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-chloroquinolin-7-yl)methyl)-2-(4-amino-7H-pyrrolo[2,3-d]pyrimidin-7-yl)hexahydro-3aH-cyclopenta[b]furan-3,3a-diol, (2R,3R,3aS,6S,6aR)-6-((2-amino-3-chloroquinolin-7-yl)methyl)-2-(4-amino-5-fluoro-7H-pyrrolo[2,3-d]pyrimidin-7-yl)hexahydro-3aH-cyclopenta[b]furan-3,3a-diol, (2R,3R,3aS,6S,6aR)-6-((2-amino-3-bromoquinolin-7-yl)oxy)-2-(4-amino-5-ethyl-7H-pyrrolo[2,3-d]pyrimidin-7-yl)hexahydro-3aH-1-cyclopenta[b]furan-3,3a-diol, (2R,3R,3aS,6S,6aR)-6-((2-amino-3-bromoquinolin-7-yl)methyl)-2-(4-amino-5-methyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-fluoroquinolin-7-yl)oxy)-2-(4-amino-7H-pyrrolo[2,3-d]pyrimidin-7-yl)hexahydro-3aH-cyclopenta[b]furan-3,3a-diol, (2R,3R,3aS,6S,6aR)-6-((2-amino-3-chloroquinolin-7-yl)oxy)-2-(4-amino-7H-pyrrolo[2,3-d]pyrimidin-7-yl)hexahydro-3aH-cyclopenta[b]furan-3,3a-diol, (2R,3R,3aS,6S,6aR)-6-((2-amino-3-fluoroquinolin-7-yl)oxy)-2-(4-amino-5-fluoro-7H-pyrrolo[2,3-d]pyrimidin-7-yl)hexahydro-3aH-cyclopenta[b]furan-3,3a-diol, (2R,3R,3aS,6S,6aR)-6-((2-amino-3-chloroquinolin-7-yl)oxy)-2-(4-amino-5-fluoro-7H-pyrrolo[2,3-d]pyrimidin-7-yl)hexahydro-3aH-cyclopenta[b]furan-3,3a-diol, (2R,3R,3aS,6S,6aR)-2-(4-amino-7H-pyrrolo[2,3-d]pyrimidin-7-yl)-6-((2,3-dihydro-1-pyrrolo[2,3-b]quinolin-7-yl)oxy)hexahydro-3aH-cyclopenta[b]furan-3,3a-diol, (2R,3R,3aS,6S,6aR)-6-((2-amino-3-(trifluoromethyl)quinolin-7-yl)methyl)-2-(4-amino-7H-pyrrolo[2,3-d]pyrimidin-7-yl)hexahydro-3aH-cyclopenta[b]furan-3,3a-diol, (2R,3R,3aS,6S,6aR)-6-[(2-amino-3-bromoquinolin-7-yl)oxy]-2-[4-(hydroxymethyl)-7H-pyrrolo[2,3-d]pyrimidin-7-yl]hexahydro-3aH-cyclopenta[b]furan-3,3a-diol, (2R,3R,3aS,6S,6aR)-6-[(2-amino-3-bromoquinolin-7-yl)oxy]-2-[4-(2-hydroxypropan-2-yl)-7H-pyrrolo[2,3-d]pyrimidin-7-yl]hexahydro-3aH-cyclopenta[b]furan-3,3a-diol, (2R,3R,3aS,6S,6aR)-6-((2-amino-3-bromoquinolin-7-yl)oxy)-2-(4-(difluoromethyl)-7H-pyrrolo[2,3-d]pyrimidin-7-yl)hexahydro-3aH-cyclopenta[b]furan-3,3a-diol, (2R,3R,3aS,6S,6aR)-6-((2-amino-3-bromoquinolin-7-yl)oxy)-2-(2,4-dimethyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-bromoquinolin-7-yl)methyl)-2-(2,4-dimethyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-bromoquinolin-7-yl)oxy)-2-(4-amino-5-ethyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-bromoquinolin-7-yl)methyl)-2-(4-isopropyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-bromoquinolin-7-yl)methyl)-2-(5-fluoro-4-methyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-bromoquinolin-7-yl)oxy)-2-(7H-pyrrolo[2,3-d]pyrimidin-7H-yl)hexahydro-3aH-cyclopenta[b]furan-3,3a-diol, (2R,3R,3aS,6S,6aR)-6-((2-amino-3-fluoroquinolin-7-yl)oxy)-2-(4-methyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-bromoquinolin-7-yl)methyl)-2-(4-cyclopropyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-(trifluoromethyl)quinolin-7-yl)methyl)-2-(4-methyl-7H-pyrrolo[2,3-d]pyrimidin-7-yl)hexahydro-3aH-cyclopenta[b]furan-3,3a-diol, (2R,3R,3aS,6S,6aR)-6-((2,3-dihydro-1H-pyrrolo[2,3-b]quinolin-7-yl)oxy)-2-(4-methyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-fluoroquinolin-7-yl)methyl)-2-(2,4-dimethyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-chloroquinolin-7-yl)methyl)-2-(2,4-dimethyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-bromoquinolin-7-yl)methyl)-2-(4-(methylamino)-7H-pyrrolo[2,3-d]pyrimidin-7-yl)hexahydro-3aH-cyclopenta[b]furan-3,3a-diol, (1R,2S,3R,5R)-5-(((2-amino-3-bromoquinolin-7-yl)oxy)methyl)-1-methyl-3-(4-(methylamino)-7H-pyrrolo[2,3-d]pyrimidin-7-yl)cyclopentane-1,2-diol, (2R,3R,3aS,6S,6aR)-6-((2-amino-3-bromoquinolin-7-yl)oxy)-2-(4-(methylamino)-7H-pyrrolo[2,3-d]pyrimidin-7-yl)hexahydro-3aH-cyclopenta[b]furan-3,3a-diol, (2R,3R,3aS,6S,6aR)-6-((2-amino-3-fluoroquinolin-7-yl)methyl)-2-(4-(methylamino)-7H-pyrrolo[2,3-d]pyrimidin-7-yl)hexahydro-3aH-cyclopenta[b]furan-3,3a-diol, (2R,3R,3aS,6S,6aR)-6-((2-amino-3-bromoquinolin-7-yl)methyl)-2-(5-fluoro-4-(methylamino)-7H-pyrrolo[2,3-d]pyrimidin-7-yl)hexahydro-3aH-cyclopenta[b]furan-3,3a-diol, (1S,2R,3aR,4S,6aR)-4-((2-amino-3-bromoquinolin-7-yl)methyl)-2-(4-(methylamino)-7-pyrrolo[2,3-d]pyrimidin-7-yl)hexahydropentalene-1,6a(1H)-diol, (2R,3S,4R,5R)-5-(4-amino-7H-pyrrolo[2,3-d]pyrimidin-7-yl)-2-methyl-2-((quinolin-7-yloxy)methyl)tetrahydrofuran-3,4-diol, (2R,3S,4R,5R)-5-(4-amino-7H-pyrrolo[2,3-d]pyrimidin-7-yl)-3-methyl-2-((quinolin-7-yloxy)methyl)tetrahydrofuran-3,4-diol, (1S,2R,3R,5R)-3-(((2-amino-3-bromoquinolin-7-yl)oxy)methyl)-5-(4-amino-7H-pyrrolo[2,3-d]pyrimidin-7-yl)-3-methylcyclopentan-1,2-diol, (1S,2R,3R,5R)-5-(4-amino-7H-pyrrolo[2,3-d]pyrimidin-7-yl)-3-(((2-aminoquinolin-7-yl)oxy)methyl)-3-methylcyclopentane-1,2-diol, (1S,2R,5R)-3-(2-(2-amino-3-bromoquinolin-7-yl)ethyl)-5-(4-amino-7H-pyrrolo[2,3-d]pyrimidin-7-yl)-3-(fluoromethyl)cyclopentane-1,2-diol, (1R,2S,3R,5S)-5-(2-(2-amino-3-bromoquinolin-7-yl)ethyl)-3-(4-amino-7H-pyrrolo[2,3-d]pyrimidin-7-yl)-1-methylcyclopentane-1,2-diol, (2R,3R,3aS,6S,6aR)-2-(4-amino-7H-pyrrolo[2,3-d]pyrimidin-7-yl)-6-((2-aminoquinolin-7-yl)oxy)hexahydro-2H-cyclopenta[b]furan-3,3a-diol, (1R,2S,3R,5R)-5-(((2-aminoquinolin-7-yl)oxy)methyl)-1-methyl-3-(7H-pyrrolo[2,3-d]pyrimidin-7-yl)cyclopentane-1,2-diol, (1R,2S,3R,5R)-5-(((2-amino-3-methylquinolin-7-yl)oxy)methyl)-1-methyl-3-(4-methyl-7H-pyrrolo[2,3-d]pyrimidin-7-yl)cyclopentane-1,2-diol, (2R,3R,3aS,6S,6aR)-6-((2-aminoquinolin-7-yl)methyl)-2-(4-methyl-7H-pyrrolo[2,3-d]pyrimidin-7-yl)hexahydro-2H-cyclopenta[b]furan-3,3a-diol, (2R,3R,3aS,6S,6aR)-6-((2-amino-3-bromoquinolin-7-yl)methyl)-2-(4-amino-5-fluoro-7H-pyrrolo[2,3-d]pyrimidin-7-yl)hexahydro-2H-cyclopenta[b]furan-3,3a-diol, (1S,2R,3S,5R)-3-(2-(2-amino-3-bromoquinolin-7-yl)ethyl)-3-methyl-5-(4-methyl-7H-pyrrolo[2,3-d]pyrimidin-7-yl)cyclopentane-1,2-diol, (1S,2R,3S,5R)-3-(2-(2,3-dihydro-1H-pyrrolo[2,3-b]quinolin-7-yl)ethyl)-3-methyl-5-(4-methyl-7H-pyrrolo[2,3-d]pyrimidin-7-yl)cyclopentane-1,2-diol, (1R,2S,3R,5R)-5-(((2-amino-3-bromoquinolin-7-yl)oxy)methyl)-3-(4-amino-7H-pyrrolo[2,3-d]pyrimidin-7-yl)-1,5-dimethylcyclopentane-1,2-diol, (2R,3R,3aS,6S,6aR)-6-((2-amino-3-chloroquinolin-7-yl)oxy)-2-(4-methyl-7H-pyrrolo[2,3-d]pyrimidin-7-yl)hexahydro-2H-cyclopenta[b]furan-3,3a-diol, (2R,3R,3aS,6S,6aR)-6-((2-aminoquinolin-7-yl)oxy)-2-(4-methyl-7H-pyrrolo[2,3-d]pyrimidin-7-yl)hexahydro-2H-cyclopenta[b]furan-3,3a-diol, (2R,3R,3aS,6S,6aR)-6-((2-amino-3-bromoquinolin-7-yl)oxy)-2-(2-amino-4-methyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-(difluoromethyl)quinolin-7-yl)oxy)-2-(4-methyl-7H-pyrrolo[2,3-d]pyrimidin-7-yl)hexahydro-3aH-cyclopenta[b]furan-3,3a-diol, (1S,2R,3R,5R)-3-(2-(2-amino-3-fluoroquinolin-7-yl)ethyl)-5-(4-amino-7H-pyrrolo[2,3-d]pyrimidin-7-yl)-3-methyl-cyclopentane-1,2-diol, (1R,2S,3R,5S)-5-(2-(2-amino-3-bromoquinolin-7-yl)ethyl)-3-(4-amino-7H-pyrrolo[2,3-d]pyrimidin-7-yl)-1,5-dimethylcyclopentane-1,2-diol, (1R,2S,3S,4R)-1-(2-(2-amino-3-bromoquinolin-7-yl)ethyl)-4-(4-amino-7H-pyrrolo[2,3-d]pyrimidin-7-yl)-2-methylcyclopentane-1,2,3-triol, (1S,2R,3aR,4S,6aR)-4-((2-amino-3-bromoquinolin-7-yl)oxy)-2-(4-amino-7H-pyrrolo[2,3-d]pyrimidin-7-yl)hexahydropentalene-1,6a(1H)-diol, (2R,3R,3aS,6S,6aR)-6-((2-am no-3-fluoroquinolin-7-yl)amino)-2-(4-methyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-fluoroquinolin-7-yl)methyl)-2-(4-amino-7H-pyrrolo[2,3-d]pyrimidin-7-yl)-6a-methylhexahydro-3aH-cyclopenta[b]furan-3,3a-diol, (2R,3R,3aS,6S,6aR)-6-((2-amino-3-chloroquinolin-7-yl)methyl)-2-(4-methyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-fluoroquinolin-7-yl)methyl)-2-(4-methyl-7H-pyrrolo[2,3-d]pyrimidin-7-yl)hexahydro-3aH-cyclopenta[b]furan-3,3a-diol, (2R,3R,3aS,6S,6aR)-6-((2-amino-3-fluoroquinolin-7-yl)methyl)-2-(4-amino-7H-pyrrolo[2,3-d]pyrimidin-7-yl)hexahydro-3aH-cyclopenta[b]furan-3,3a-diol, (2R,3R,3aS,6S,6aR)-6-((2-amino-3-methylquinolin-7-yl)methyl)-2-(4-amino-7H-pyrrolo[2,3-d]pyrimidin-7-yl)hexahydro-3aH-cyclopenta[b]furan-3,3a-diol, (1S,2R,3S,5R)-5-(4-amino-7H-pyrrolo[2,3-d]pyrimidin-7-yl)-3-(2-(2,3-dihydro-1H-pyrrolo[2,3-b]quinolin-7-yl)ethyl)-3-methylcyclopentane-1,2-diol, (2R,3R,3aS,6S,6aR)-6-((2-amino-3-bromoquinolin-7-yl)
methyl)-2-(2-amino-4-methyl-7H-pyrrolo[2,3-d]pyrimi-
din-7-yl)hexahydro-3aH-cyclopenta[b]furan-3,3a-diol,
(2R,3R,3aS,6S,6aR)-6-((2-amino-3-(difluoromethyl)quino-
lin-7-yl)oxy)-2-(4-amino-7H-pyrrolo[2,3-d]pyrimidin-7-
yl)hexahydro-3aH-cyclopenta[b]furan-3,3a-diol,
(2R,3R,3aS,6R,6aR)-6-((2-amino-3-bromoquinolin-7-yl)
oxy)-2-(4-methyl-7H-pyrrolo[2,3-d]pyrimidin-7-yl)hexa-
hydro-3aH-cyclopenta[b]furan-3,3a-diol,
(2R,3R,3aS,6S,6aR)-6-((2-amino-3-bromoquinolin-7-yl)
oxy)-2-(2-amino-5-fluoro-7H-pyrrolo[2,3-d]pyrimidin-7-
yl)hexahydro-3aH-cyclopenta[b]furan-3,3a-diol,
(2R,3R,3aS,6R,6aR)-6-((2-amino-3-chloroquinolin-7-yl)
methyl)-2-(4-methyl-7H-pyrrolo[2,3-d]pyrimidin-7-yl)
hexahydro-3aH-cyclopenta[b]furan-3,3a-diol,
(3aS,4S,5R)-1-((2-amino-3-bromoquinolin-7-yl)methyl)-5-
(4-amino-7H-pyrrolo[2,3-d]pyrimidin-7-yl)tetrahydro-
1H-cyclopenta[c]furan-3a,4(3H)-diol,
(2R,3R,3aS,6S,6aR)-6-((2-amino-3-bromoquinolin-7-yl)
methyl)-2-(4-methyl-7H-pyrrolo[2,3-d]pyrimidin-7-yl)
tetrahydrofuro[3,4-b]furan-3,3a(4H)-diol,
(2R,3R,3aS,6R,6aR)-6-((2-amino-3-bromoquinolin-7-yl)
methyl)-2-(4-methyl-7H-pyrrolo[2,3-d]pyrimidin-7-yl)
tetrahydrofuro[3,4-b]furan-3,3a(4H)-diol,
(2R,3R,3aS,6S,6aR)-6-((2-amino-3-bromoquinolin-7-yl)
methyl)-2-(4-amino-5-methyl-7H-pyrrolo[2,3-d]pyrimi-
din-7-yl)tetrahydrofuro[3,4-b]furan-3,3a(4H)-diol,
(2R,3R,3aS,6S,6aR)-6-((2-amino-3-bromoquinolin-7-yl)
methyl)-2-(4-amino-7H-pyrrolo[2,3-d]pyrimidin-7-yl)
tetrahydrofuro[3,4-b]furan-3,3a(4H)-diol, or
(2R,3R,3aS,6S,6aR)-6-((2-amino-3-(difluoromethyl)quino-
lin-7-yl)methyl)-2-(4-amino-7H-pyrrolo[2,3-d]pyrimi-
din-7-yl)hexahydro-2H-cyclopenta[b]furan-3,3a-diol,
or a pharmaceutically acceptable salt thereof.

Reference to compounds of formula I encompasses reference formula Ia, Ib, Ic, or Id, and all subembodiments thereof, in the following.

In one embodiment, the present invention is a composition for treating cancer comprising a compound of formula I, Ia, Ib, Ic, or Id, or a pharmaceutically acceptable salt thereof.

In one embodiment, the present invention is a composition for treating cancer comprising a compound of formula I, Ia, Ib, Ic, or Id, or a pharmaceutically acceptable salt thereof, and a pharmaceutically acceptable carrier.

In one embodiment, the present invention is a composition for treating hemoglobinopathies such as ß-thalassemia or Sickle Cell Disease (SCD), comprising a compound of formula I, Ia, Ib, Ic, or Id, or a pharmaceutically acceptable salt thereof.

In one embodiment, the present invention is a composition for treating hemoglobinopathies such as ß-thalassemia or Sickle Cell Disease (SCD), comprising a compound of formula I, Ia, Ib, Ic, or Id, or a pharmaceutically acceptable salt thereof, and a pharmaceutically acceptable carrier.

In another embodiment, the present invention is a method of treating cancer comprising administering to a patient in need thereof a compound of formula I, Ia, Ib, Ic, or Id, or a pharmaceutically acceptable salt thereof.

In another embodiment, the present invention includes a method of treating hemoglobinopathies such as ß-thalassemia or Sickle Cell Disease (SCD), comprising administering to a patient in need thereof a compound of formula I, Ia, Ib, Ic, or Id, or a pharmaceutically acceptable salt thereof.

In another embodiment, the present invention is a method of treating cancer comprising administering to a patient in need thereof a compound of formula I, Ia, Ib, Ic, or Id, or a pharmaceutically acceptable salt thereof.

In another embodiment, the present invention is a method of treating cancer comprising administering to a patient in need thereof a compound of formula I, Ia, Ib, Ic, or Id, or a pharmaceutically acceptable salt thereof, and a pharmaceutically acceptable carrier.

In another embodiment, the present invention is a method of treating hemoglobinopathies such as ß-thalassemia or Sickle Cell Disease (SCD), comprising administering to a patient in need thereof a compound of formula I, Ia, Ib, Ic, or Id, or a pharmaceutically acceptable salt thereof.

In another embodiment, the present invention is a method of treating hemoglobinopathies such as ß-thalassemia or Sickle Cell Disease (SCD), comprising administering to a patient in need thereof a compound of formula I, Ia, Ib, Ic, or Id, or a pharmaceutically acceptable salt thereof, and a pharmaceutically acceptable carrier.

In another embodiment, the present invention is a method of treating cancer comprising administering to a patient in need thereof, a composition comprising a compound of formula I, Ia, Ib, Ic, or Id, or a pharmaceutically acceptable salt thereof, and a pharmaceutically acceptable carrier.

In another embodiment, the present invention is a method of treating hemoglobinopathies such as ß-thalassemia or Sickle Cell Disease (SCD), comprising administering to a patient in need thereof, a composition comprising a compound of formula I, Ia, Ib, Ic, or Id, or a pharmaceutically acceptable salt thereof, and a pharmaceutically acceptable carrier.

In another embodiment, the present invention is the use of a compound of formula I, Ia, Ib, Ic, or Id, or a pharmaceutically acceptable salt thereof, in the manufacture of a medicament for treating cancer.

In another embodiment of the present invention is the use of a compound of formula I, Ia, Ib, Ic, or Id, or a pharmaceutically acceptable salt thereof, in the manufacture of a medicament for treating hemoglobinopathies such as ß-thalassemia or Sickle Cell Disease (SCD).

In another embodiment, the present invention includes the use of compounds of formula I, Ia, Ib, Ic, or Id, for the preparation of a medicament for the treatment of cancer, or hemoglobinopathies such as ß-thalassemia or Sickle Cell Disease (SCD).

In another embodiment, the use of compounds of formula I, Ia, Ib, Ic, or Id, for the preparation of a medicament for the treatment of cancer. In another embodiment, the use of compounds of formula I, Ia, Ib, Ic, or Id, for the preparation of a medicament for the treatment of hemoglobinopathies such as ß-thalassemia or Sickle Cell Disease (SCD). In a subembodiment, the cancer is cardiac cancer, lung cancer, gastrointestinal cancer, genitourinary tract cancer, liver cancer, bone cancer, nervous system cancer, gynecological cancer, hematological cancer, skin cancer, or adrenal cancer.

In another embodiment, the present invention includes compounds of formula I, Ia, Ib, Ic, or Id, for use in the treatment of cancer or hemoglobinopathies such as ß-thalassemia or Sickle Cell Disease (SCD). In another embodiment, the present invention includes compounds of formula I, Ia, Ib, Ic, or Id, for use in the treatment of cardiac cancer, lung cancer, gastrointestinal cancer, genitourinary tract cancer, liver cancer, bone cancer, nervous system cancer, gynecological cancer, hematological cancer, skin cancer, or adrenal cancer.

In one embodiment, the compound disclosed herein is selected from the group consisting of the compounds exemplified herein, for example, in Examples 1-137, or a pharmaceutically acceptable salt thereof.

The term "composition" is intended to encompass a product comprising the specified ingredients in the specified amounts, as well as any product which results, directly or indirectly, from combination of the specified ingredients in the specified amounts. The term "anti-cancer agent" means a drug (medicament or pharmaceutically active ingredient) for treating cancer. The term "antineoplastic agent" means a drug (medicament or pharmaceutically active ingredient) for treating cancer (i.e. a chemotherapeutic agent). The term "at least one" means one or more than one. The meaning of "at least one" with reference to the number of compounds of the invention is independent of the meaning with reference to the number of chemotherapeutic agents. The term "chemotherapeutic agent" means a drug (medicament or pharmaceutically active ingredient) for treating cancer (i.e., an antineoplastic agent). The term "compound" with reference to the antineoplastic agents, includes the agents that are antibodies. The term "consecutively" means one following the other. The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician. Thus, for example, in the methods of treating cancer described herein "effective amount" (or "therapeutically effective amount") means, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, an effective amount, or a therapeutically effective amount of the PRMT5 inhibitor (i.e. a compound of the invention) is that amount which results in the reduction in PRMT5 activity. The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

The invention also provides a pharmaceutical composition comprising an effective amount of at least one compound of formula I, Ia, Ib, Ic, or Id, and a pharmaceutically acceptable carrier. The invention also provides a pharmaceutical composition comprising an effective amount of at least one compound of formula I, Ia, Ib, Ic, or Id, and an effective amount of at least one other pharmaceutically active ingredient (such as, for example, a chemotherapeutic agent), and a pharmaceutically acceptable carrier.

The invention also provides a method of inhibiting PRMT5 in a patient in need of such treatment comprising administering to said patient an effective amount of at least one compound of formula I, Ia, Ib, Ic, or Id. The invention also provides a method for treating cancer in a patient in need of such treatment, said method comprising administering to said patient an effective amount of at least one compound of formula I, Ia, Ib, Ic, or Id. The invention also provides a method for treating cancer in a patient in need of such treatment, said method comprising administering to said patient an effective amount of at least one compound of formula I, Ia, Ib, Ic, or Id, in combination with an effective amount of at least one chemotherapeutic agent. The methods of the invention include the administration of a pharmaceutical composition comprising at least one compound of the invention and a pharmaceutically acceptable carrier. The invention also provides any of the above methods of treating cancer wherein the cancer is colorectal. The invention also provides any of the above methods of treating cancer wherein the cancer is melanoma. The methods of treating cancers described herein can optionally include the administration of an effective amount of radiation (i.e., the methods of treating cancers described herein optionally include the administration of radiation therapy).

The methods of treating cancer described herein include methods of treating cancer that comprise administering a therapeutically effective amount of a compound of the instant invention in combination with radiation therapy and/or in combination with a second compound selected from: an estrogen receptor modulator, an androgen receptor modulator, a retinoid receptor modulator, a cytotoxicytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed herein.

In any of the methods of treating cancer described herein, unless stated otherwise, the methods can optionally include the administration of an effective amount of radiation therapy. For radiation therapy, γ-radiation is preferred.

Thus, another example of the invention is directed to a method of treating cancer in a patient in need of such treatment, said method comprising administering an effective amount of a compound of formula I, Ia, Ib, Ic, or Id. Another example of the invention is directed to a method of treating cancer in a patient in need of such treatment, said method comprising administering to said patient an effective amount of a compound of formula I, Ia, Ib, Ic, or Id, and an effective amount of at least one chemotherapeutic agent.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, NJ 07645-1742, USA), the Physicians' Desk Reference, 56$^{th}$ Edition, 2002 (published by Medical Economics company, Inc. Montvale, NJ 07645-1742), the Physicians' Desk Reference, 57$^{th}$ Edition, 2003 (published by Thompson PDR, Montvale, NJ 07645-1742), the Physicians' Desk Reference, 60 Edition, 2006 (published by Thompson PDR, Montvale, NJ 07645-1742), and the Physicians' Desk Reference, 64$^{th}$ Edition, 2010 (published by PDR Network, LLC at Montvale, NJ 07645-1725), presently accessible through www.pdr.net; the disclosures of which are incorporated herein by reference thereto.

If the patient is responding, or is stable, after completion of the therapy cycle, the therapy cycle can be repeated according to the judgment of the skilled clinician. Upon completion of the therapy cycles, the patient can be continued on the compounds of the invention at the same dose that was administered in the treatment protocol. This maintenance dose can be continued until the patient progresses or can no longer tolerate the dose (in which case the dose can be reduced, and the patient can be continued on the reduced dose).

Those skilled in the art will recognize that the actual dosages and protocols for administration employed in the methods of the invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula (1) and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether growth of the tumor has been retarded or even reversed. Relief of disease-related symptoms such as pain, and improvement in overall condition can also be used to help judge effectiveness of treatment.

The compounds, compositions and methods provided herein are useful for the treatment of cancer. Cancers that may be treated by the compounds, compositions and methods disclosed herein include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans) meninges (meningioma, meningiosarcoma, gliomatosis), brain (astrocytoma, medulloblastoma, gliona, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

In the treatment of breast cancer (e.g., postmenopausal and premenopausal breast cancer, e.g., hormone-dependent breast cancer) the compound of formula (1) may be used with an effective amount of at least one antihormonal agent selected from the group consisting of: (a) aromatase inhibitors, (b) antiestrogens, and (c) LHRH analogues; and optionally an effective amount of at least one chemotherapeutic agent. Examples of aromatase inhibitors include but are not limited to: Anastrozole (e.g., Arimidex), Letrozole (e.g., Femara), Exemestane (Aromasin), Fadrozole and Formestane (e.g., Lentaron). Examples of antiestrogens include but are not limited to: Tamoxifen (e.g., Nolvadex), Fulvestrant (e.g., Faslodex), Raloxifene (e.g., Evista), and Acolbifene. Examples of LHRH analogues include but are not limited to: Goserelin (e.g., Zoladex) and Leuprolide (e.g., Leuprolide Acetate, such as Lupron or Lupron Depot). Examples of chemotherapeutic agents include but are not limited to: Trastuzumab (e.g., Herceptin), Gefitinib (e.g., Tressa), Erlotinib (e.g., Erlotinib HCl, such as Tarceva), Bevacizumab (e.g., Avastin), Cetuximab (e.g., Erbitux), and Bortezomib (e.g., Velcade).

In one example of the invention the cancer treated is colo-rectal cancer (such as, for example, colon adenocarcinoma and colon adenoma). Thus, another example of the invention is directed to a method of treating colo-rectal cancer in a patient in need of such treatment, said method comprising administering an effective of a compound of formula I, Ia, Ib, Ic, or Id, or a pharmaceutically acceptable salt thereof, to said patient. Another example of the invention is directed to a method of treating colo-rectal cancer in a patient in need of such treatment, said method comprising administering to said patient an effective amount of a compound of formula I, Ia, Ib, Ic, or Id, or a pharmaceutically acceptable salt thereof, and an effective amount of at least one chemotherapeutic agent.

In one example of the invention the cancer treated is melanoma. Thus, another example of the invention is directed to a method of treating melanoma in a patient in need of such treatment, said method comprising administering an effective amount of a compound of formula I, Ia, Ib, Ic, or Id, or a pharmaceutically acceptable salt thereof, to said patient. Another example of the invention is directed to a method of treating melanoma in a patient in need of such treatment, said method comprising administering to said patient an effective amount of a compound of formula I, Ia, Ib, Ic, or Id, or a pharmaceutically acceptable salt thereof, and an effective amount of at least one chemotherapeutic agent.

The compounds of the invention are also useful in preparing a medicament that is useful in treating cancer.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in (*Cancer Principles and Practice of Oncology* by V. T. Devita and S. Hellman (editors), 9$^{th}$ edition (May 16, 2011). Lippincott Williams & Wilkins Publishers. A person of ordinary skill in the art would be able to discern which combinations of agents would be useful based on the particular characteristics of the drugs and the cancer involved. Such agents include the following: estrogen receptor modulators, programmed cell death protein 1 (PD-1) inhibitors, programmed death-ligand 1 (PD-L1) inhibitors, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

PD-1 inhibitors include pembrolizumab (lambrolizumab), nivolumab and MPDL3280A. PDL-1 inhibitors include atezolizumab, avelumab, and durvalumab.

"Androgen receptor modulators" refers to compounds which interfere or inhibit the binding of androgens to the receptor, regardless of mechanism. Examples of androgen receptor modulators include finasteride and other 5a-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibrorodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN-10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, TDX258, the epothilones (see for example U.S. Pat. Nos. 6,284,781 and 6,288,237) and BMS188797. In an example the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreuasin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydr0xy-3,5-dimethoxyphenyl]-5,5a,6,8,8a,9-hexahydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethyl]amino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527. WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an example inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680 (tozasertib).

"Antiproliferative agents" includes antisense RNA and DNA oligonucleotides such as G3139, ODN698, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl) sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356.896), atorvastatin (LIPITOR®; see U.S. Pat. Nos. 5,273,995, 4,681,893, 5,489,691 and 5,342,952), rosuvastatin (CRESTOR® U.S. Reissue Patent RE37,314) and cerivastatin (also known as rivastatin and BAYCHOL®; see U.S. Pat. No. 5,177,080). The structural formulas of these and additional HMG-CoAreductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of the invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, and 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 9606193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); *JNCI*, Vol. 69, p. 475 (1982); *Arch. Opthalmol.*, Vol. 108, p. 573 (1990); *Anal. Rec.*, Vol. 238, p. 68 (1994); *FEBS Letters*, Vol. 372, p. 83 (1995); *Clin. Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); Cell, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101: 329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK1 and CHK2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of the specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of the specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272 and 5,932,598, all of which are hereby incorporated by reference.

Inhibitors of COX-2 that are particularly useful in the instant method of treatment are: 3-phenyl-4-(4-(methylsulfonyl)phenyl)-2-(0.57)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: rofecoxib, etoricoxib, parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl) phenyl]methyl]-1H-1,2,3-triazole-4-carboxamide, CM101, squalamine, combretastatin, RP14610, NX31838, sulfated mannopentaose phosphate, 7,7-(carbonyl-bis[imino-N-methyl-4,2-pyrrolocarbonylimino[N-methyl-4,2-pyrrole]- carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylindenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, ST1571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another example of the instant invention is the use of the presently disclosed compounds in combination with gene therapy for the treatment of cancer. For an overview of genetic strategies to treating cancer see Hall et al., (*Am. J. Hum. Genet.* 61:785-789, 1997) and Kufe et al., (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another example, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 9201688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an example, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, Cl1033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with the following therapeutic agents: pembrolizumab (Keytruda®), abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdAr®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estranustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gertuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®,9); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); mechlorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®) methotrexate (Methotrexate®); methoxsalen (Uvadex®) mitomycin C (Mutamycin®); mitotane (Lysodren®); mitoxantrone (Novantrone®); nandrolone phenpropionate (Durabolin-50R); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); penetrexed disodium (Alimta®)); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukinel®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositurmomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®).

In an example, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyanidotriazole, combretastatin A-4, squalamine, 6-O-chloroacetyl-carbonyl)-fumagillol, thalidomide, angiostatin, troponin-1, or an antibody to VEGF. In an example, the estrogen receptor modulator is tamoxifen or raloxifene.

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxic cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another example of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The therapeutic combination disclosed herein may be used in combination with one or more other active agents, including but not limited to, other anti-cancer agents that are used in the prevention, treatment, control, amelioration, or reduction of risk of a particular disease or condition (e.g., cell-proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, prior to, contemporaneously, or sequentially with a compound of the present disclosure.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

When any variable occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is bicyclic, it is intended that the bond be attached to any of the suitable atoms on either ring of the bicyclic moiety.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. Also, "optionally substituted" means optional substitution with the specified groups, radicals or moieties.

The present invention includes compounds of structural formula I, Ia, Ib, Ic, or Id as well as the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of the invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, 4-bromobenzenesulfonate, butyrate, camphorate, camphorsulfonate, camsylate, carbonate, chloride, clavulanate, citrate, cyclohexylamidosulfonate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glucuonate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate lactobionate, laurate, malate, maleate, mandelate, mesylate, methylbromide, methylnitrate, methylsulfate, methanesulfonate, mucate, 2-naphthalenesulfonate napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, trifluoromethylsulfonate, p-toluenesulfonate, undeconate, valerate and the like.

Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts.

With basic reagents such as hydroxides, carbonates, hydrogencarbonates, alkoxides and ammonia, organic bases or alternatively basic amino acids the compounds of the formula I, Ia, Ib, Ic, or Id form stable alkali metal, alkaline earth metal or optionally substituted ammonium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethanolamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, ornithine, piperazine, piperidine, polyamine resins, procaine, purines, theobromine, triethanolamine, triethylamine, trimethylamine, tripropylamine, trometamol, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The preparation of pharmacologically acceptable salts from compounds of the formula I, Ia, Ib, Ic, or Id capable of salt formation, including their stereoisomeric forms is carried out known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of formula I, Ia, Ib, Ic, or Id. Centers of asymmetry that are present in the compounds of formula I, Ia, Ib, Ic, or Id can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formulas. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of the invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of formula I, Ia, Ib, Ic, or Id, or it can be done on a final racemic product. Absolute stereochemistry may be determined by X-ray crystallography of crystalline products or crystalline intermediates which are derivatized, if necessary, with a reagent containing a stereogenic center of known configuration. Where compounds of the invention are capable of tautomerization, all individual tautomers as well as mixtures thereof are included in the scope of the invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Furthermore, compounds of the present invention may exist in amorphous form and/or one or more crystalline forms, and as such all amorphous and crystalline forms and mixtures thereof of the compounds of formula I, Ia, Ib, Ic, or Id are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of the invention, along with un-solvated and anhydrous forms.

The present invention includes compounds of structural formula I, Ia, Ib, Ic, or Id, or any other generic structural formula or specific compound described or claimed herein, and is intended to encompass the specific compound or compounds falling within the scope of the formula or embodiment.

The present invention includes compounds of structural formula I, Ia, Ib, Ic, or Id as well as salts thereof, particularly pharmaceutically acceptable salts, solvates of such compounds and solvated salt forms thereof, where such forms are possible unless specified otherwise.

Except where noted herein, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or CH$_3$ or a symbol that is an extended bond as the terminal group, e.g. "$\vdash$—", ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-4}$ alkyl" (or "C$_1$-C$_4$ alkyl") for example, means linear or branched chain alkyl groups, including all isomers, having the specified number of carbon atoms. For example, the structures

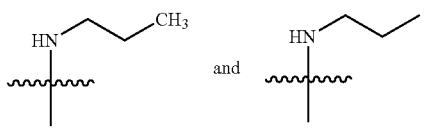

have equivalent meanings. C$_{1-4}$ alkyl includes n-, iso-, sec- and t-butyl, n- and isopropyl, ethyl and methyl. If no number is specified, 1-4 carbon atoms are intended for linear or branched alkyl groups.

"CCH" refers to carbon atom triple bonded to CH.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

"Celite®" (Fluka) diatomite is diatomaceous earth, and can be referred to as "celite".

"Cycloalkyl" refers to a non-aromatic ring system comprising from about 3 to about 5 ring carbon atoms. Non-limiting examples of monocyclic cycloalkyls include cyclopropyl, cyclobutyl, cyclopentyl.

"Heterocycle" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

"Heterocycloalkyl" refers to a stable cyclic group having carbon atoms and 1 to 3 heteroatoms independently selected from S, N, or O. The term "heterocycloalkyl" is intended to include both substituted and unsubstituted heterocycloalkyl groups. Heterocycloalkyl groups can be substituted with 1 to 4 groups such as halogen, CH$_3$, CF$_3$, or CF$_2$H. Embraced within the term "heterocycloalkyl" are 5 membered rings having one carbon-carbon or one carbon-nitrogen double bond in the ring (e.g., 2-pyrrolinyl, 3-pyrrolinyl, etc.).

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl and naphthyl. Multicyclic rings include, but are not limited to, naphthyl and bicyclic rings wherein phenyl is fused to a C$_{5-7}$cycloalkyl or C$_{5-7}$cycloalkenyl ring. Aryl groups may be optionally substituted with one or more substituents as defined herein. Bonding can be through any of the carbon atoms of any ring.

"Heteroaryl" refers to a aromatic monocyclic or multicyclic ring moiety comprising ring carbon atoms and 1-4 ring heteroatoms provided in the aromatic ring system, wherein each heteroatom is independently selected from S, N, or O. Heteroaryl bicyclic ring systems can include one or more heteroatoms in one or both rings.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms independently selected from nitrogen, oxygen, and sulfur. In some embodiments, the 5-6 membered heteroaryl has 1-2 ring heteroatoms independently selected from nitrogen, oxygen, and sulfur. In some embodiments, the 5-6 membered heteroaryl has 1 ring heteroatom selected from nitrogen, oxygen, and sulfur. In certain embodiments, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

The term "substituted" means that one or more hydrogens on the atoms of the designated are replaced with a selection from the indicated group, provided that the atoms' normal valencies under the existing, circumstances are not exceeded, and that the substitution results in a stable compound. Combinations of substituents and/or variables are permissible only if such combinations result in stable compounds.

If the compounds of formula I, Ia, Ib, Ic, or Id simultaneously contain acidic and basic groups in the molecule the invention also includes, in addition to the salt forms mentioned, inner salts or betaines (zwitterions). Salts can be obtained from the compounds of formula I, Ia, Ib, Ic, or Id by customary methods which are known to the person skilled in the art, for example by combination with an organic or inorganic acid or base in a solvent or dispersant, or by anion exchange or cation exchange from other salts. The present invention also includes all salts of the compounds of formula I, Ia, Ib, Ic, or Id which, owing to low physiological compatibility, are not directly suitable for use in pharmaceuticals but which can be used, for example, as intermediates for chemical reactions or for the preparation of physiologically acceptable salts.

The invention also includes derivatives of the compound of formula I, Ia, Ib, Ic, or Id, acting as prodrugs and solvates. Any pharmaceutically acceptable pro-drug modification of a compound of the invention which results in conversion in vivo to a compound within the scope of the invention is also within the scope of the invention. Prodrugs, following administration to the patient, are converted in the body by normal metabolic or chemical processes, such as through hydrolysis in the blood, to the compound of formula I, Ia, Ib, Ic, or Id. Such prodrugs include those that demonstrate enhanced bioavailability, tissue specificity, and/or cellular delivery, to improve drug absorption of the compound of formula I, Ia, Ib, Ic, or Id. The effect of such prodrugs may result from modification of physicochemical properties such as lipophilicity, molecular weight, charge, and other physicochemical properties that determine the permeation properties of the drug. For example, esters can optionally be made by esterification of an available carboxylic acid group or by formation of an ester on an available hydroxy group in a compound. Similarly, labile amides can be made. Pharmaceutically acceptable esters or amides of the compounds of the invention may be prepared to act as pro-drugs which can be hydrolyzed back to an acid (or —COO— depending on the pH of the fluid or tissue where conversion takes place) or hydroxy form particularly in vivo and as such are encompassed within the scope of the invention. Examples of pharmaceutically acceptable pro-drug modifications include, but are not limited to, —$C_{1-6}$alkyl esters and —$C_{1-6}$alkyl substituted with phenyl esters.

When any variable occurs more than one time in any constituent or in formula I, its definition on each occurrence is independent of its definition at every other occurrence. Also, combinations of substituents and/or variables are permissible only if such combinations result in stable compounds.

Except where noted, the ter "halogen" means fluorine, chlorine, bromine or iodine.

Where ring atoms are represented by variables such as "X", e.g,

the variables are defined by indicating the atom located at the variable ring position without depicting the ring bonds associated with the atom. For example, when X in the above ring is nitrogen, the definition will show "N" and will not depict the bonds associated with it, e.g., will not show "=N—". Likewise, when X is a carbon atom that is substituted with bromide, the definition will show "C—Br" and will not depict the bonds associated with it, e.g., will not show

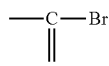

The invention also includes derivatives of the compound of formula I, Ia, Ib, Ic, or Id acting as prodrugs and solvates. Prodrugs, following administration to the patient, are converted in the body by normal metabolic or chemical processes, such as through hydrolysis in the blood, to the compound of formula I, Ia, Ib, or Ic. Such prodrugs include those that demonstrate enhanced bioavailability, tissue specificity, and/or cellular delivery, to improve drug absorption of the compound of formula I, Ia, Ib, or Ic. The effect of such prodrugs may result from modification of physicochemical properties such as lipophilicity, molecular weight, charge, and other physicochemical properties that determine the permeation properties of the drug.

The invention also relates to medicaments containing at least one compound of the formula I, Ia, Ib, Ic, or Id and/or of a pharmaceutically acceptable salt of the compound of the formula I, Ia, Ib, Ic, or Id and/or an optionally stereoisomeric form of the compound of the formula I, Ia, Ib, Ic, or Id or a pharmaceutically acceptable salt of the stereoisomeric form of the compound of formula I, Ia, Ib, Ic, or Id, together with a pharmaceutically acceptable vehicle, additive and/or other active substances and auxiliaries.

The medicaments according to the invention can be administered by oral, inhalative, rectal or transdermal administration or by subcutaneous, intraarticular, intraperitoneal or intravenous injection. Oral administration is preferred. Coating of stents with compounds of the formula I, Ia, Ib, Ic, or Id and other surfaces which come into contact with blood in the body is possible.

The invention also relates to a process for the production of a medicament, which comprises bringing at least one compound of the formula I, Ia, Ib, Ic, or Id into a suitable administration form using a pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the compounds may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver about 0.01 mg per kg of body weight per day (mg/kg/day) to about 30 mg/kg/day, preferably 0.025-7.5 mg/kg/day, more preferably 0.1-2.5 mg/kg/day, and even more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

The compounds of the invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of formula I, Ia, Ib, Ic, or Id hereinabove.

Methods for Making the Compounds of Present Invention
General Methods

The compounds of the present invention can be readily produced from known compounds or commercially available compounds by, for example, known processes described in published documents, and produced by production processes described below. The present invention is not limited to the production processes described below. The invention also includes processes for the preparation of compounds of the invention.

It should be noted that, when a compound of structural formula I, Ia, Ib, Ic, or Id has a reactive group such as hydroxy group, amino group, carboxyl group, or thiol group as its substituent, such group may be adequately protected with a protective group in each reaction step and the protective group may be removed at an adequate stage. The process of such introduction and removal of the protective group may be adequately determined depending on the group to be protected and the type of the protective group, and such introduction and removal are conducted, for example, by the process described in the review section of Greene, T. W., et. al., "*Protective Groups in Organic Synthesis*", 2007, 4th Ed., Wiley, New York, or Kocienski, P., "*Protecting Groups*" 1994, Thieme.

It should be noted that, if a discrepancy between the chemical name and structure exists, the structure is understood to dominate.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

All solvents used were commercially available and were used without further purification. Reactions were typically run using anhydrous solvents under an inert atmosphere of nitrogen.

Starting materials used were either available from commercial sources or prepared according to literature procedures and had experimental data in accordance with those reported.

Abbreviations used are those conventional in the art of the following.

ACN acetonitrile
AcOH acetic acid
ADDP 1,1-(azodicarbonyl)dipiperidine
AIBN α,α'-azoisobutyronitrile
Ar aryl
Atm atmosphere
Aq. Aqueous
9-BBN 9-Borabicyclo(3.3.1)nonane
BBN Borabicyclo(3.3.1)nonane
BnBr Benzyl bromide
BOC Butyloxycarbonyl
BSA bovine serum albumin
Bz benzoyl
° C. degree Celsius
conc. concentration
$CDCl_3$ deuterated chloroform
$CD_3OD$ deuterated methanol
CO carbon monoxide
$Cs_2CO_3$ cesium carbonate
$CuBrMe_2S$ Copper bromide dimethyl sulfide
DAST Diethylaminosulfur trifluoride
DBU 1,8-diazabicyclo[5.4.0]undec-7-ene
DCA dichloroacetic acid
DCE 1,2-dichloroethane
DCM dichloromethane
DDQ 2,3-dichloro-5,6-dicyano-p-benzoquinone
DIAD Diisopropyl azodicarboxylate
DIEA N,N-diisopropylethylamine
DEAD di-tert-butylazodicarboxylate
DMAP 4-(dimethylamino)pyridine
DMF N,N-dimethylformamide
DMSO dimethylsulfoxide
DMP Dess-Martin periodinane
DMTr 4,4'-dimethoxytrityl
dppf 1,1-bis(diphenylphosphino)ferrocene
DTT dithiothreitol
eq equivalent (molar)
EDC N-(3-dimethylaminopropyl)-N'-ethylcarbodiimide
EtOAc ethyl acetate
EtOH ethanol
g gram
h hour(s)
HATU N-[(Dimethylamino)-1H-1,2,3-triazolo-[4,5-b]pyridin-1-ylmethylene]-N-methylmethanaminium hexafluorophosphate N-oxide
HCl hydrochloric acid
HMPA Hexamethylphosphoramide
HPLC high pressure liquid chromatography
IBX 2-iodoxybenzoic acid
Im imidazole
LCMS liquid chromatography and mass spectrometry
LiHMDS lithium bis(trimethylsilyl)amide
M molar
m-CPBA meta-chloroperoxybenzoic acid
MeCN acetonitrile
MeOH methanol
$MePPh_3Br$ Methyltriphenylphosphonium bromide
MS mass spectrometry
MTBE methyl tert-butyl ether
mmol millimole
mg milligram
min minutes
mL milliliter(s)
N normal
$NaBH_4$ sodium borohydride
NaH sodium hydride
$NaHCO_3$ sodium bicarbonate
NaOH sodium hydroxide
$Na_2SO_4$ Sodium sulfate
$NH_4HCO_3$ ammonium bicarbonate
$NH_4Cl$ ammonium chloride
nM nanomolar
NMO N-methylmorpholine-N-oxide
NMP N-methyl-2-pyrrolidone
NMR nuclear magnetic resonance
OTIPS Triisopropylsilyl ether
$P(n-Bu)_3$ Triphenyl phosphine
PDC Pyridinium Dichromate
$PdCl_2(dppf)$ [1,1-bis(diphenylphosphine)ferrocene]dichloropalladium(II)
$Pd(PPh_3)_4$ tetrakis(triphenylphosphine)palladium (0)
Ph Phenyl
$Ph_3P$/PPh3 Triphenylphosphine
PMP P-methoxybenzyl
$POCl_3$ phosphorus(V) oxychloride
Pol polymer-bound
psi pound per square inch
pTsOH p-toluenesulfonic acid py pyridine
rt room temperature
Rh(nbd)₂BF₄ Bis(norbornadiene)rhodium(I) tetrafluoroborate
RuPhos Pd G3(2-Dicyclohexylphosphino-2',6'-diisopropoxy-1,1'-biphenyl)[2-(2'-amino-1,1'-biphenyl)]palladium(II) methanesulfonate
sat. saturated
SFC supercritical fluid chromatography
SM starting material
SOCl₂ thionyl chloride
t-BuOK Potassium t-butoxide
TBAF tetrabutylammonium fluoride
TBAI tetrabutylammonium iodide
TBDPS tert-butyldiphenylsilyl
TBDPSO tert-butyldiphenylsilyl ether
TBDPSCl tert-butyl(chloro)diphenylsilane
TBHP tert-butyl hydroperoxide
TEA triethylamine
Tf triflyl
TFA trifluoroacetic acid
THF tetrahydrofuran
TIPS Triisopropylsilyl
TIPSOTf Triisopropylsilyl trifluoromethanesulfonate
TLC thin layer chromatography
TMS trimethylsilyl
TMSOTf Trimethylsilyl trifluoromethanesulfonate
TsCl Toluenesulfonyl chloride
TsOH p-toluenesulfonic acid
Prep-TLC preparative TLC
μL microliter
Xantphos Pd G3 Methanesulfonato[4,5-Bis(diphenylphosphino)-9,9-dimethylxanthene](2'-amino-1,1'-biphenyl-2-yl)palladium(II)
vol volume General Synthetic Schemes While the present invention has been described in conjunction with the specific examples set forth above, many alternatives, modifications and variations thereof will be apparent to those of ordinary skill in the art. In some cases, the order of carrying out the steps of the reaction schemes may be varied to facilitate the reaction or to avoid unwanted reaction products. All such alternatives, modifications and variations are intended to fall within the spirit and scope of the present invention. Starting materials and intermediates are purchased from commercial sources, made from known procedures, or are otherwise illustrated.

Unless otherwise indicated, all variables are as previously defined. In all general schemes, Ar implies either aryl or heteroaryl.

Scheme 1:

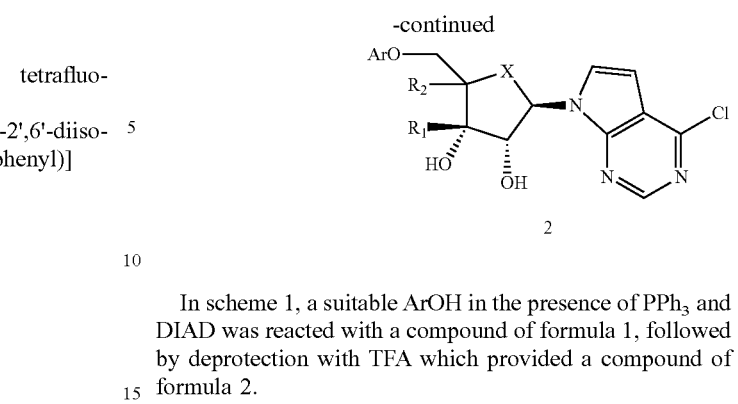

In scheme 1, a suitable ArOH in the presence of PPh₃ and DIAD was reacted with a compound of formula 1, followed by deprotection with TFA which provided a compound of formula 2.

Scheme 2

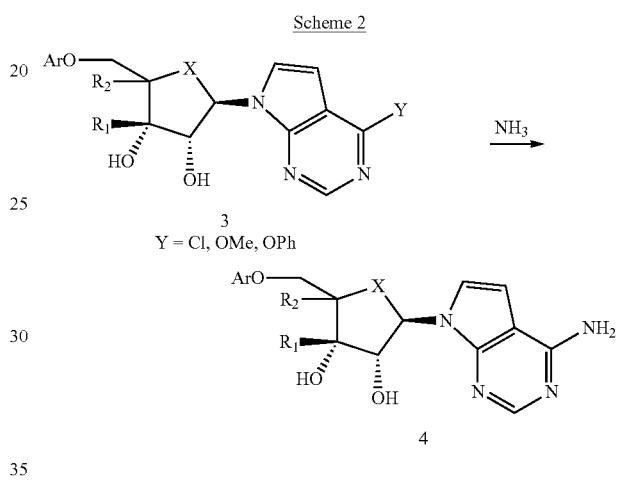

In scheme 2, the leaving group on the nucleobase is displaced with an ammonia source which provided a compound of formula 4.

Scheme 3:

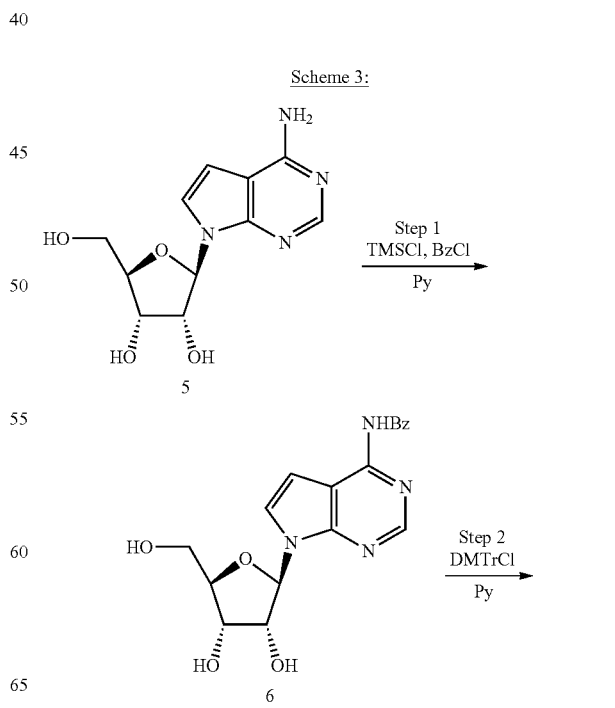

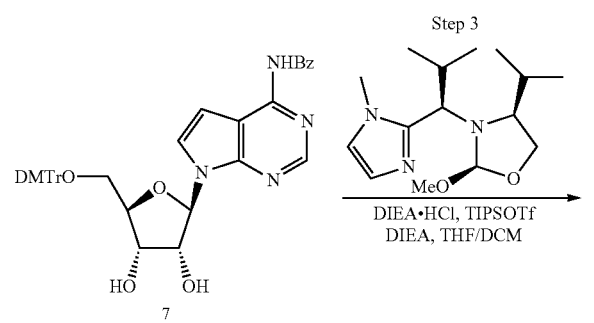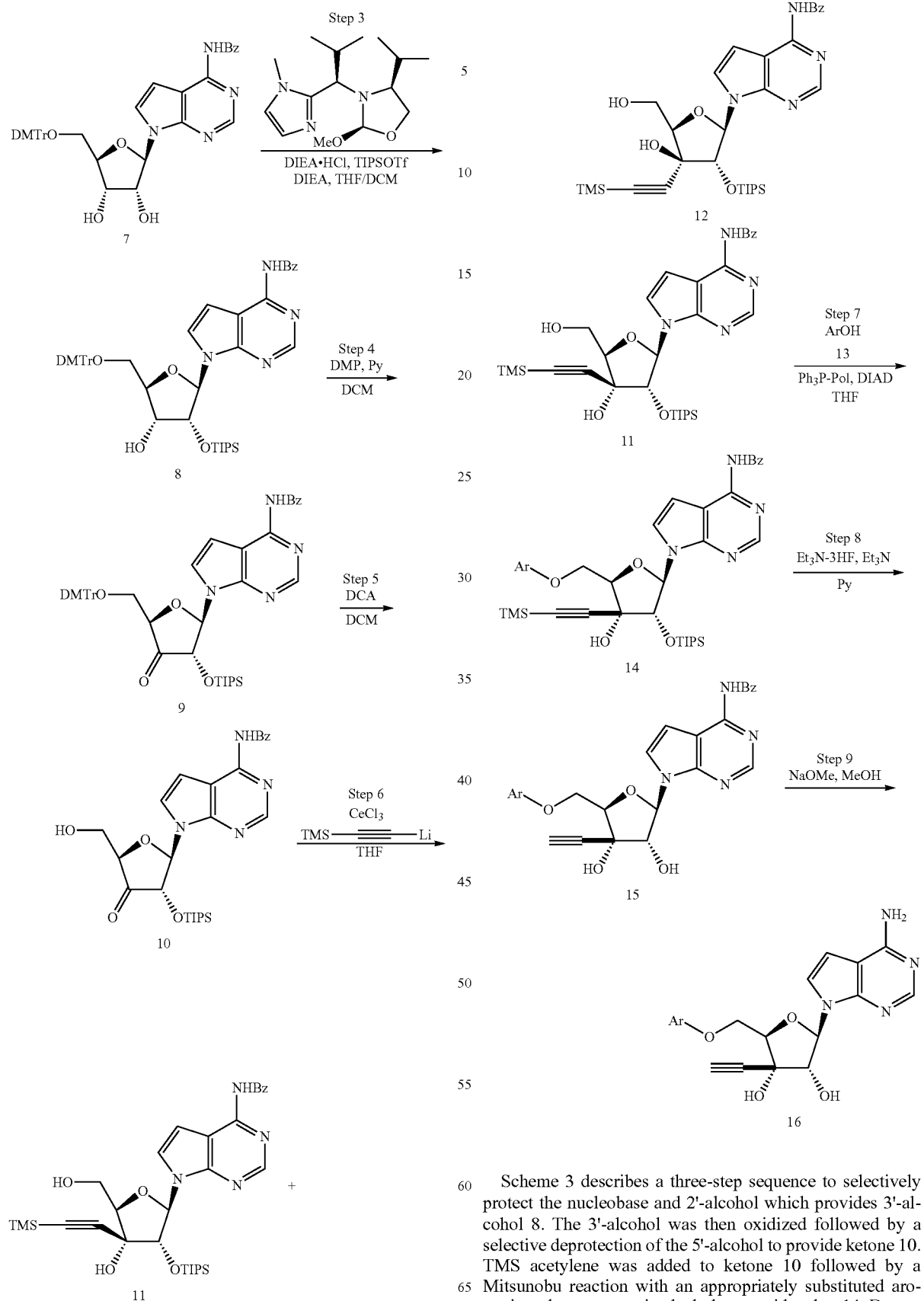

Scheme 3 describes a three-step sequence to selectively protect the nucleobase and 2'-alcohol which provides 3'-alcohol 8. The 3'-alcohol was then oxidized followed by a selective deprotection of the 5'-alcohol to provide ketone 10. TMS acetylene was added to ketone 10 followed by a Mitsunobu reaction with an appropriately substituted aromatic or heteroaromatic alcohol to provide ether 14. Deprotection in steps 8 and 9 provided a compound of formula 16.

Scheme 4:
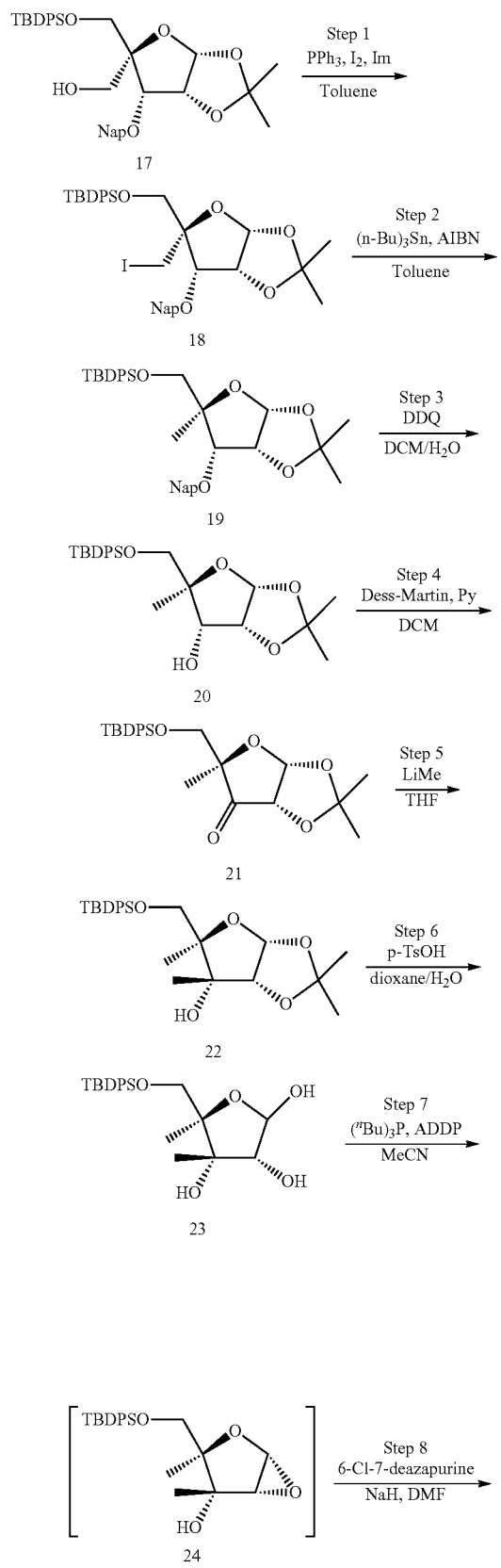
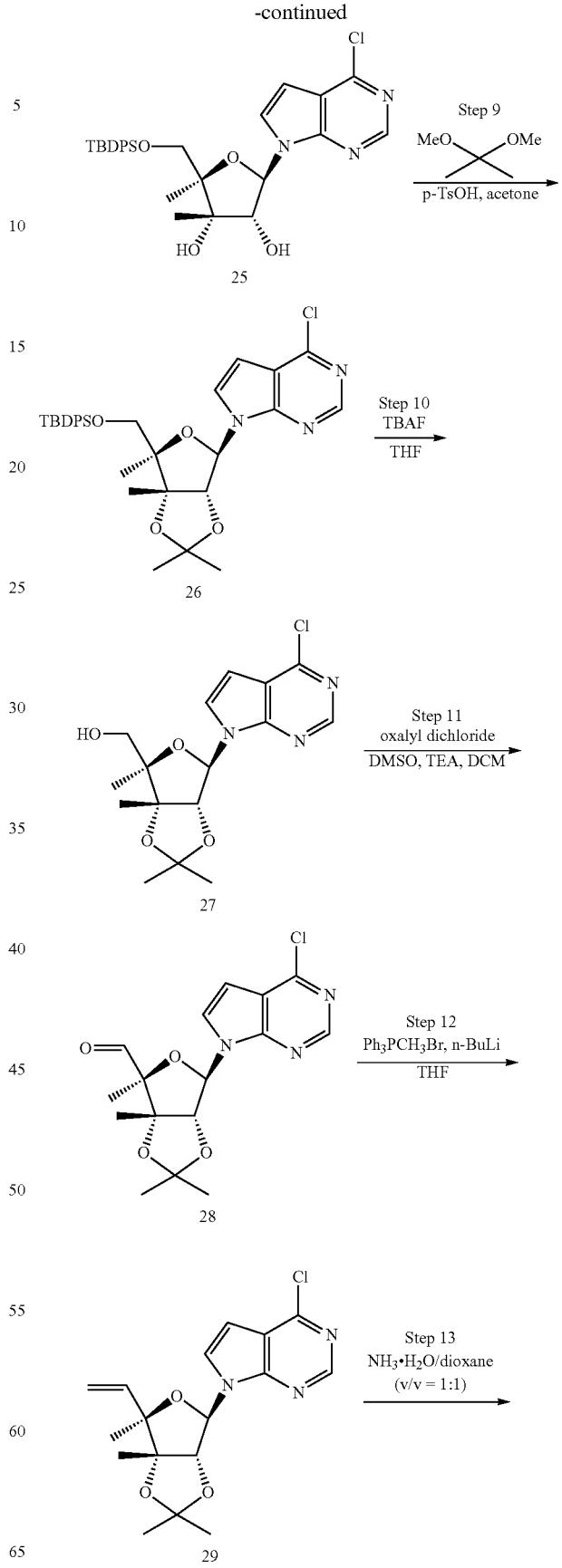

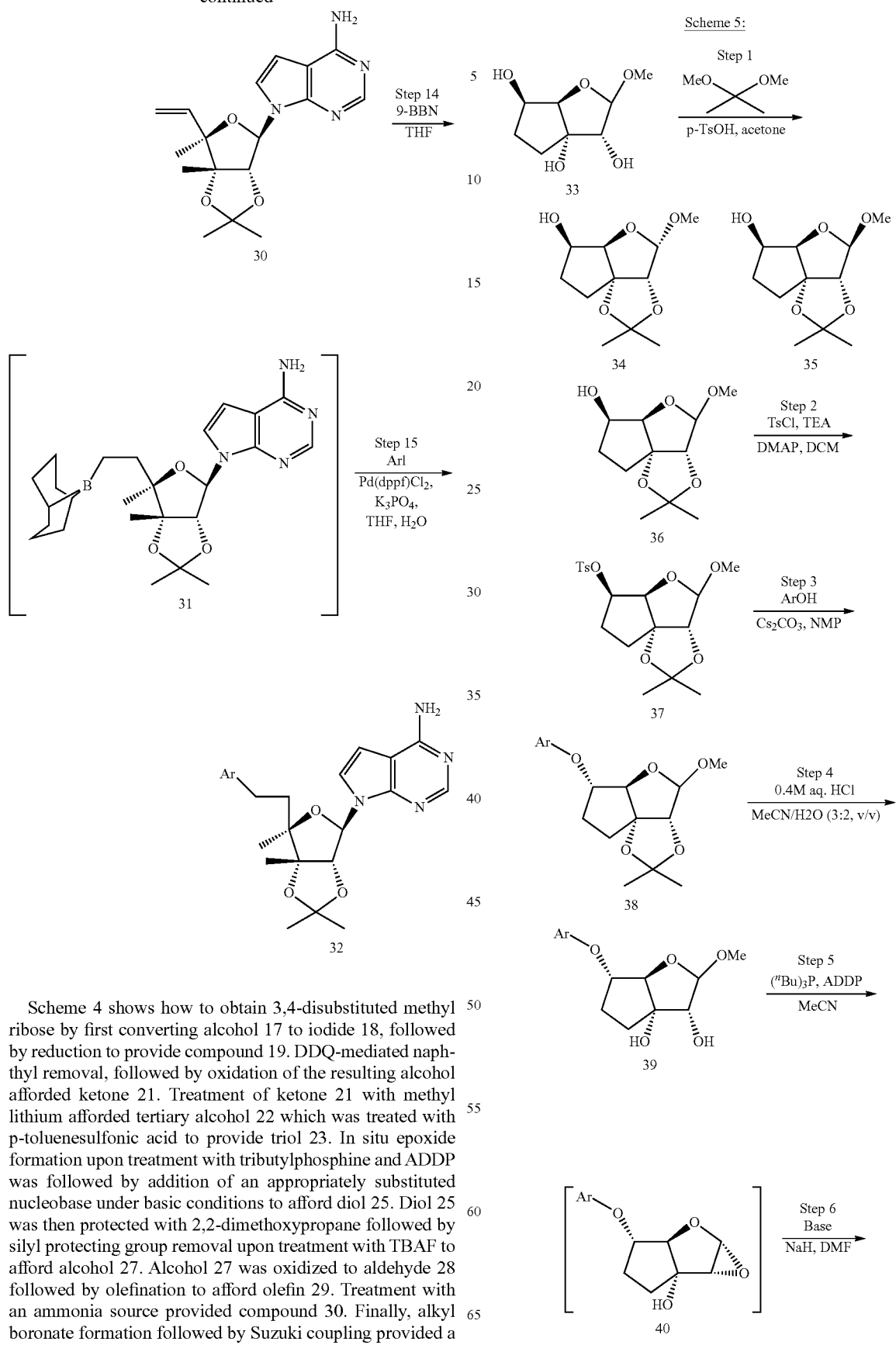

Scheme 4 shows how to obtain 3,4-disubstituted methyl ribose by first converting alcohol 17 to iodide 18, followed by reduction to provide compound 19. DDQ-mediated naphthyl removal, followed by oxidation of the resulting alcohol afforded ketone 21. Treatment of ketone 21 with methyl lithium afforded tertiary alcohol 22 which was treated with p-toluenesulfonic acid to provide triol 23. In situ epoxide formation upon treatment with tributylphosphine and ADDP was followed by addition of an appropriately substituted nucleobase under basic conditions to afford diol 25. Diol 25 was then protected with 2,2-dimethoxypropane followed by silyl protecting group removal upon treatment with TBAF to afford alcohol 27. Alcohol 27 was oxidized to aldehyde 28 followed by olefination to afford olefin 29. Treatment with an ammonia source provided compound 30. Finally, alkyl boronate formation followed by Suzuki coupling provided a compound of formula 32.

-continued

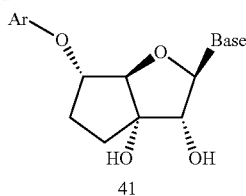

41

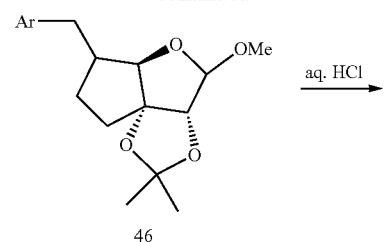

46

In scheme 5, acetonide formation in the presence of 2,2-dimethoxypropane and p-toluenesulfonic acid is followed by tosylate formation under basic conditions to provide tosylate 37. Displacement of the tosylate with an appropriately substituted aryl or heteroaryl alcohol afforded ether 38, which was deprotected under acidic conditions to provide triol 39. In situ epoxide formation upon treatment with tributylphosphine and ADDP was followed by addition of an appropriately substituted nucleobase (Base) under basic conditions to provide a compound of formula 41.

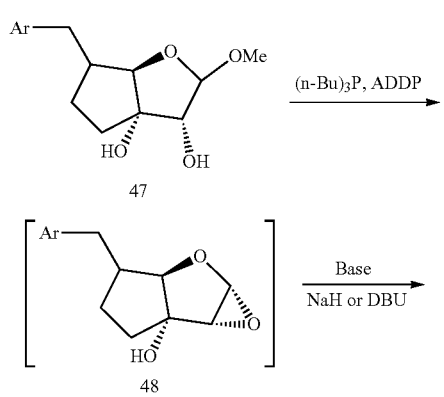

Scheme 6:

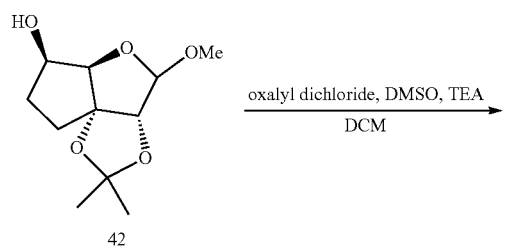

42

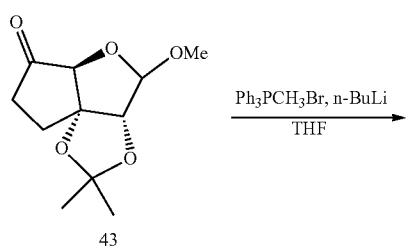

43

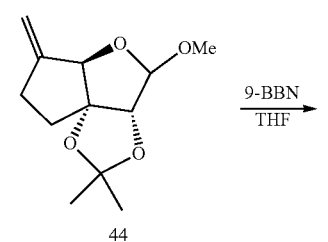

44

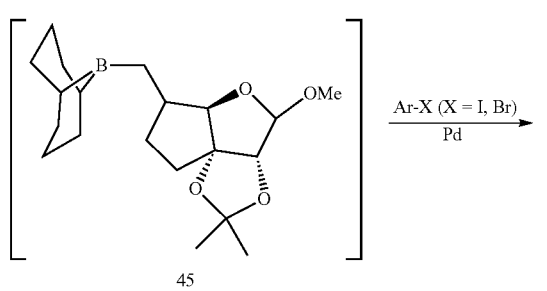

45

In scheme 6, alcohol 42 was oxidized to ketone 43, olefination, alkylboronate formation, followed by palladium catalyzed coupling with an appropriately substituted aryl or heteroaryl iodide provided compound 46. Acid mediated deprotection, in situ epoxide formation, and then addition of an appropriately substituted nucleobase (Base) under basic conditions provided a compound of formula 49.

Scheme 7:

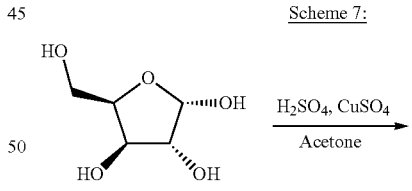

50

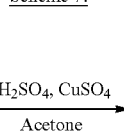

51

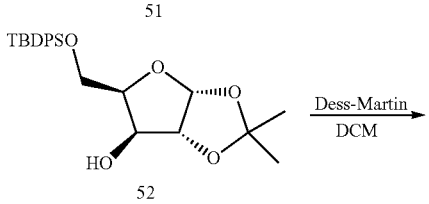

52

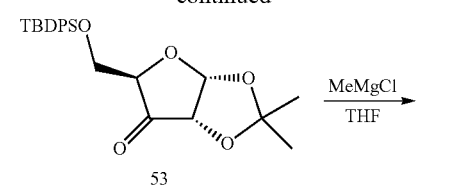

53

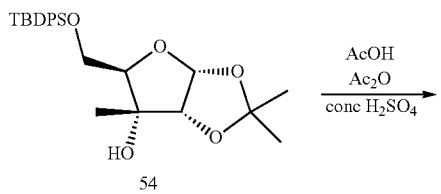

54

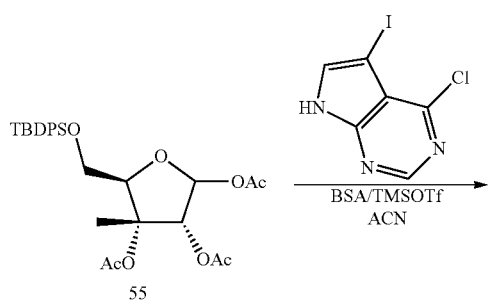

55

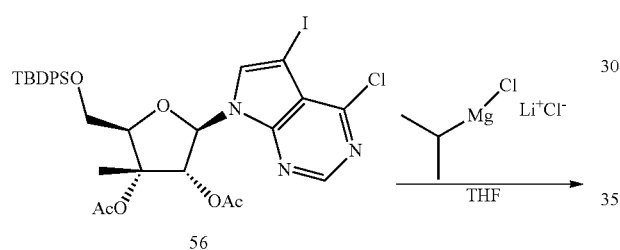

56

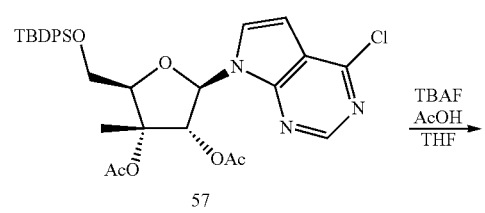

57

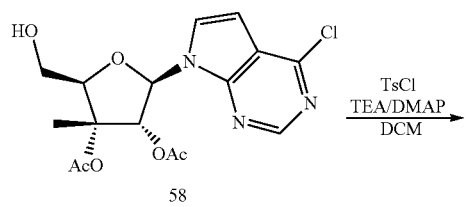

58

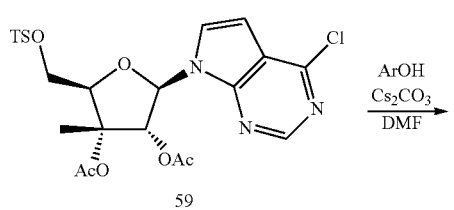

59

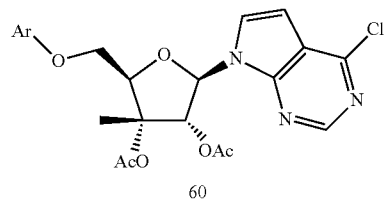

60

In scheme 7, acetonide and silyl ether formation provided alcohol 52. Oxidation and addition of methyl magnesium bromide was followed by a one one-pot acid mediated acetonide deprotection and acetate formation to provide compound 55. Lewis acid catalyzed addition of an appropriately substituted nucleobase provided compound 56. Reduction of the iodide followed by deprotection of the silyl group provided compound 58. Activation of the alcohol as a tosylate leaving group followed by displacement with an appropriately substituted aryl or heteroaryl alcohol provided a compound of formula 60.

Scheme 8:

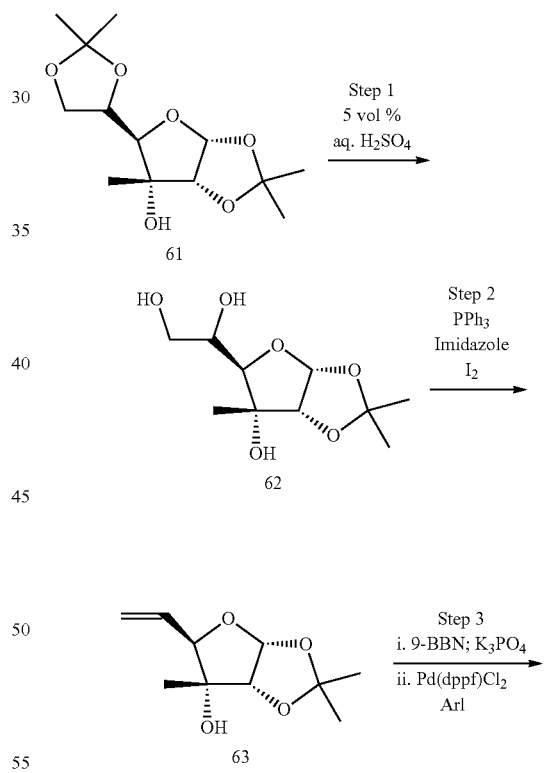

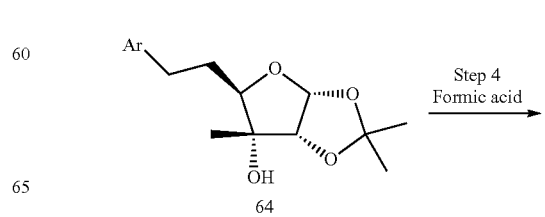

64

-continued

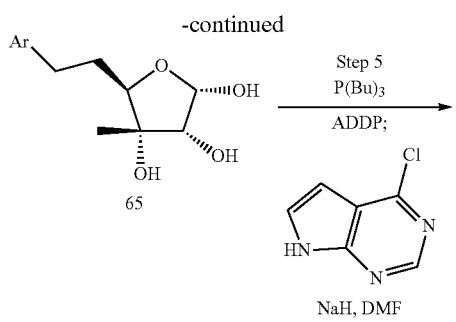

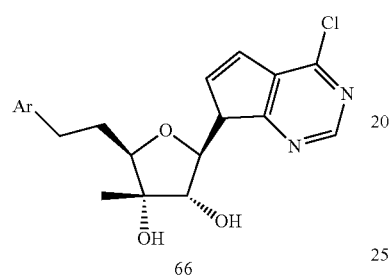

In scheme 8, one of the ketals in compound 61 was selectively deprotected, and then converted to olefin 63. Alkyl boronate formation, palladium catalyzed coupling with an appropriately substituted aryl or heteroaryl iodide, deprotection of the remaining ketal, followed by addition of an appropriately substituted nucleobase provided a compound of formula 66.

Compounds of formulas 68 and 69 can be formed in the following sequence (Scheme 9). Compound 68 is generated from 67 via aminolysis with ammonia, and compound 69 is generated from 67 via aminolysis with methylamine.

Scheme 10:

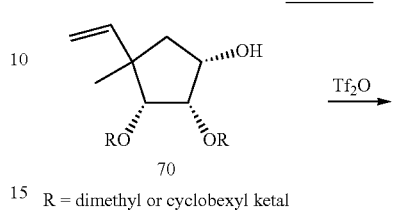

R = dimethyl or cyclohexyl ketal

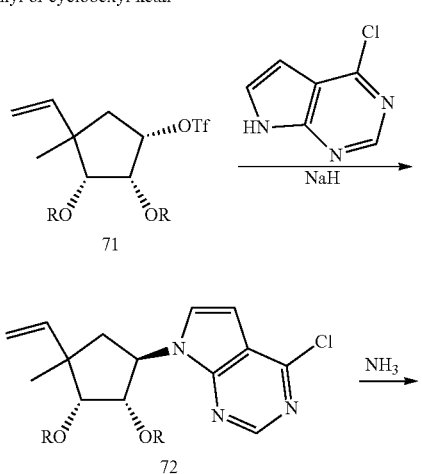

Scheme 9:

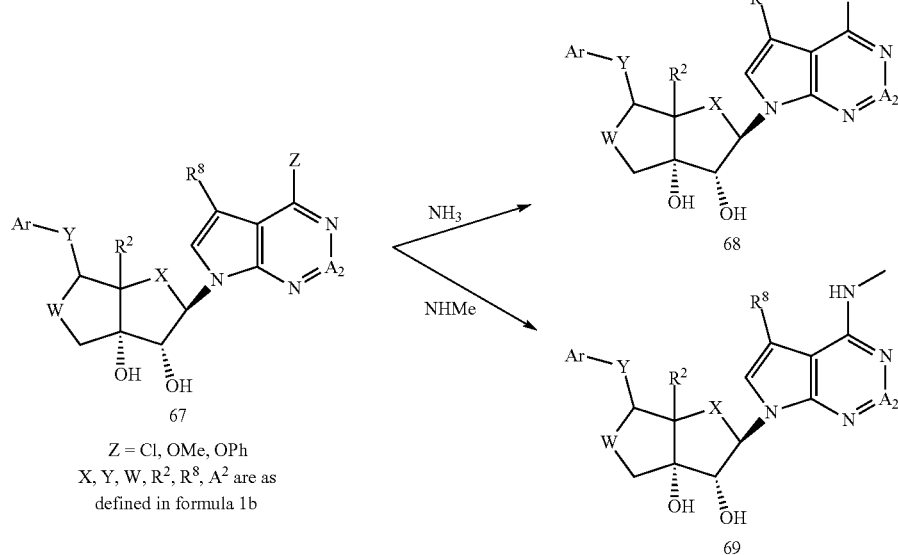

Z = Cl, OMe, OPh
X, Y, W, R², R⁸, A² are as defined in formula 1b

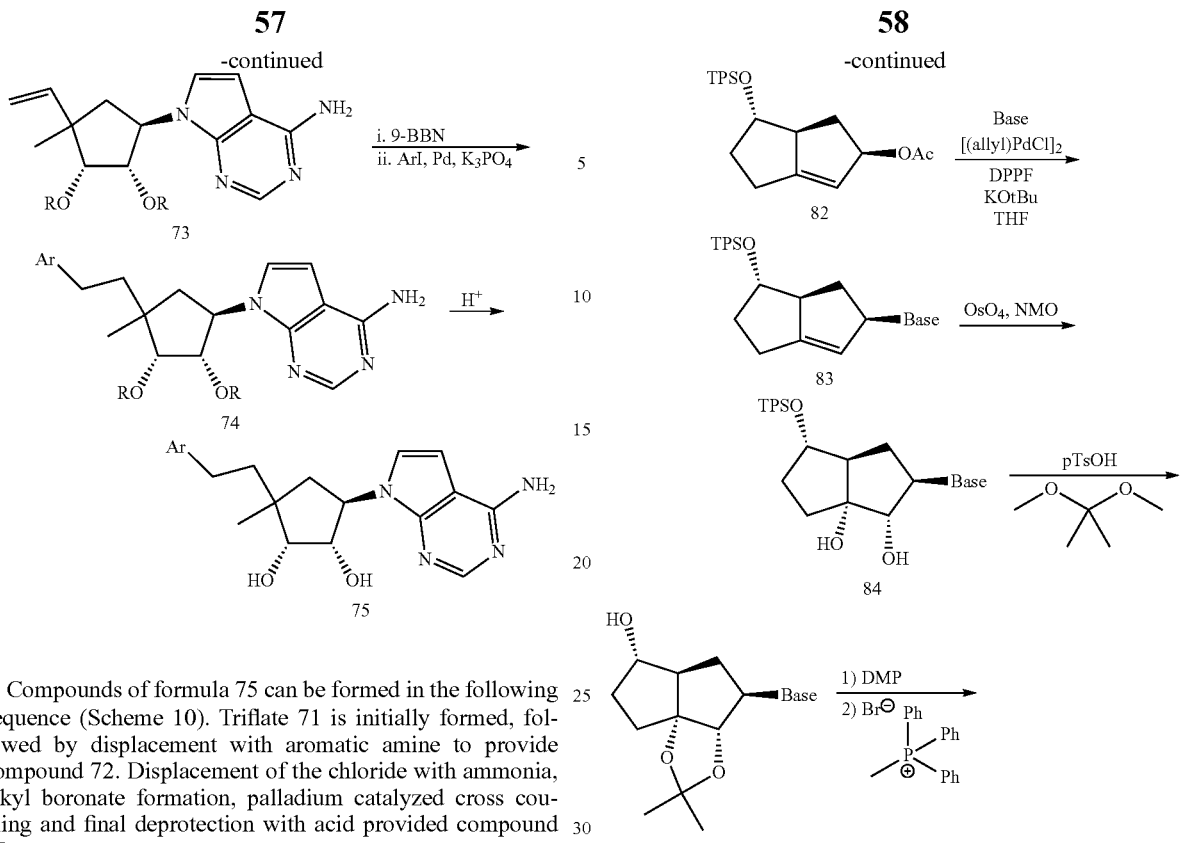

Compounds of formula 75 can be formed in the following sequence (Scheme 10). Triflate 71 is initially formed, followed by displacement with aromatic amine to provide compound 72. Displacement of the chloride with ammonia, alkyl boronate formation, palladium catalyzed cross coupling and final deprotection with acid provided compound 75.

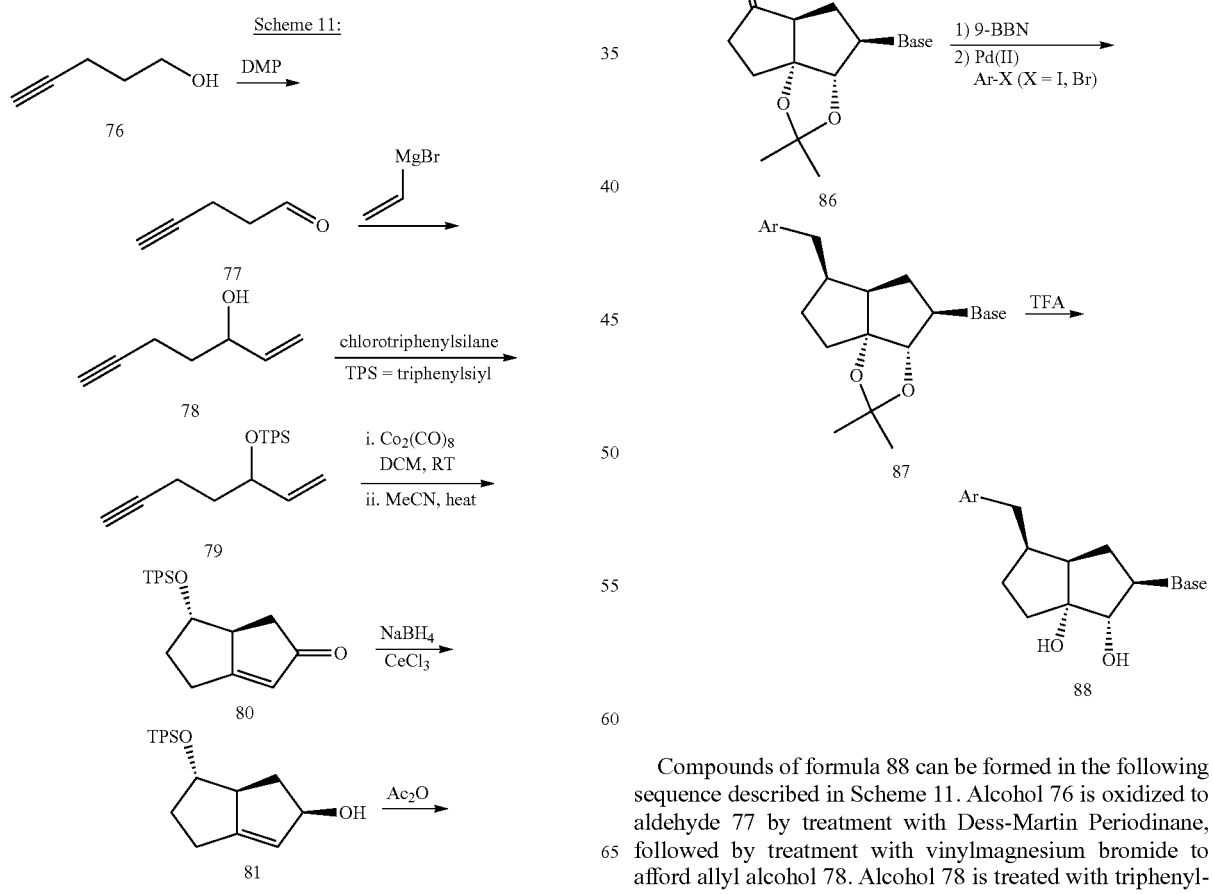

Compounds of formula 88 can be formed in the following sequence described in Scheme 11. Alcohol 76 is oxidized to aldehyde 77 by treatment with Dess-Martin Periodinane, followed by treatment with vinylmagnesium bromide to afford allyl alcohol 78. Alcohol 78 is treated with triphenylsilylchloride, followed by cobalt catalyzed Pauson-Khand conditions to form bicyclic enone 80. Enone 80 is reduced with sodium borohydride and treated with acetic anhydride to form allylacetate 82. Allyl acetate 82 is subjected to palladium-catalyzed allylic alkylation conditions in the presence of an appropriately substituted nucleobase (Base) to afford compound 83. The resulting olefin is dihydroxylated with osmium tetroxide to afford 84. Deprotection of the silyl ether and acetonide formation is followed by oxidation with Dess-Martin Periodinane and olefination to afford exocyclic olefin 86. Alkyl boronate formation followed by palladium-catalyzed cross coupling with an aryl or heteroarylhalide provided compound 87. Deprotection of the acetonide with acid provided compound 88.

Scheme 12

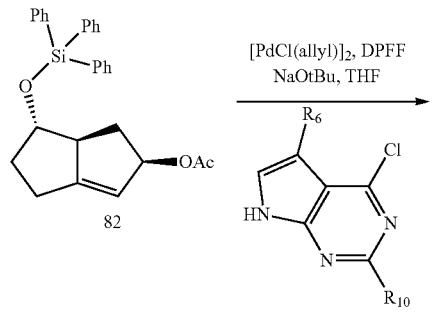

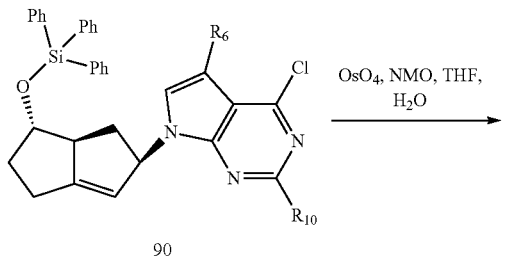

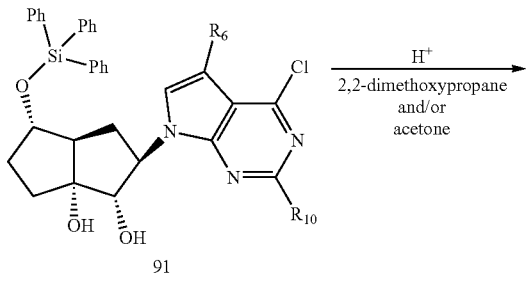

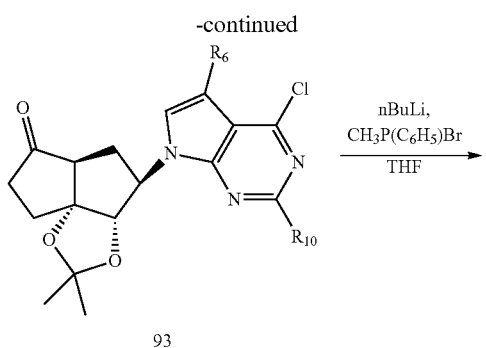

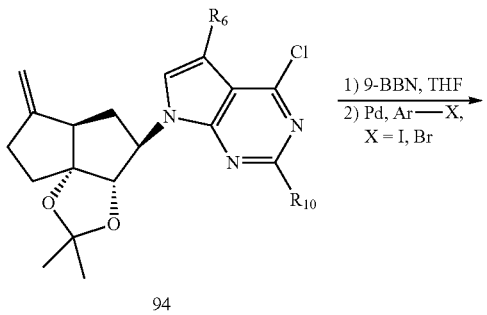

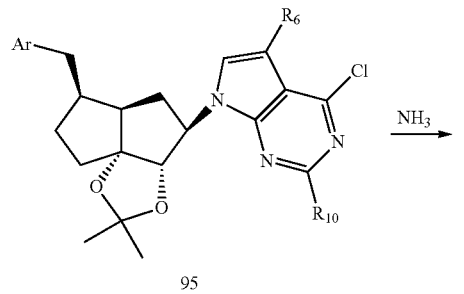

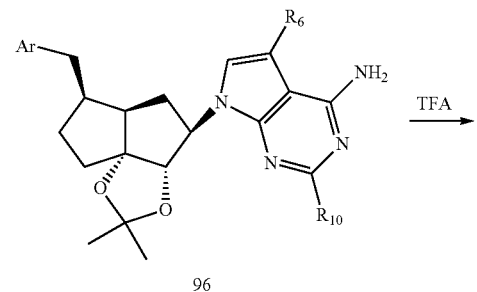

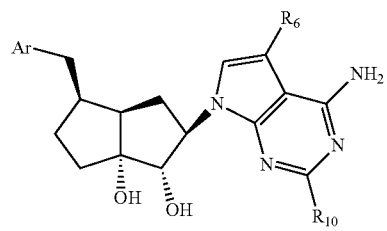

Compounds of formula 97 can be formed in the following sequence described in Scheme 12. Allyl acetate 82 was subjected to palladium-catalyzed allylic alkylation conditions in the presence of an appropriately substituted nucleobase (89) to afford compound 90. The resulting olefin is dihydroxylated with osmium tetroxide to afford 91. Deprotection of the silyl ether and acetonide formation is followed by oxidation with Dess-Martin Periodinane and olefination to afford exocyclic olefin 94. Alkyl boronate formation followed by palladium-catalyzed cross coupling with an aryl or heteroarylbromide provided compound 95. Displacement of the chloride with ammonia followed by deprotection of the acetonide with acid provided compound 97.

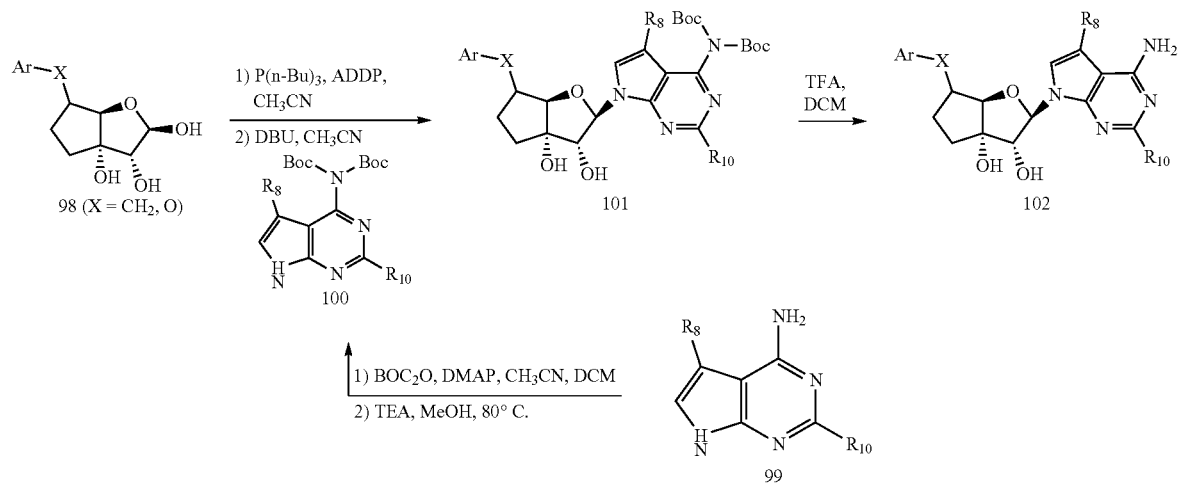

Scheme 13

Compounds of formula 102 can be formed in the following sequence described in Scheme 13. Substituted aminonucleobase compound 99 was BOC-protected. Compound 98 was subjected to Mitsunobu conditions to introduce the protected nucleobase (100) to form compound 101. Acid mediated deprotection provided compound 102.

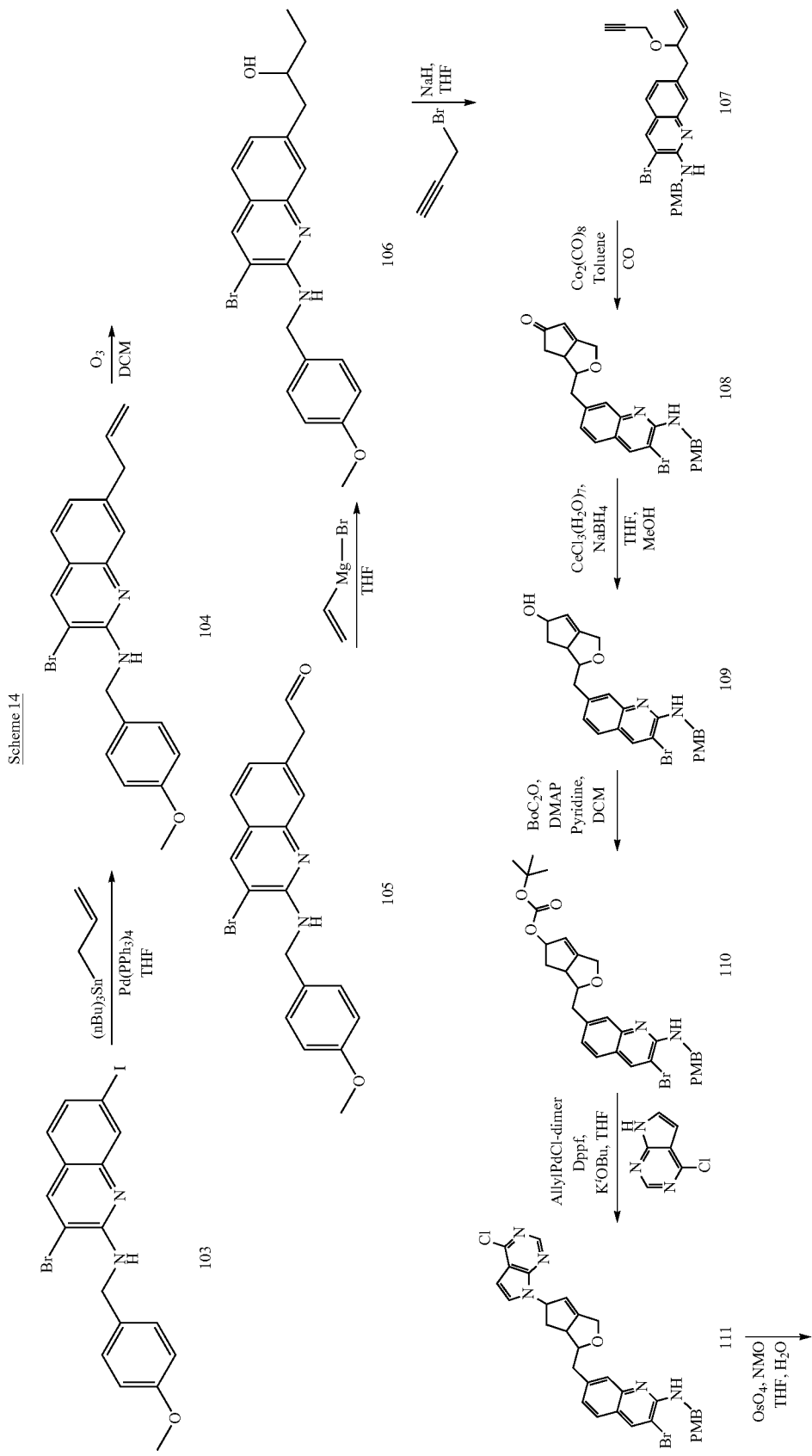
Scheme 14

-continued
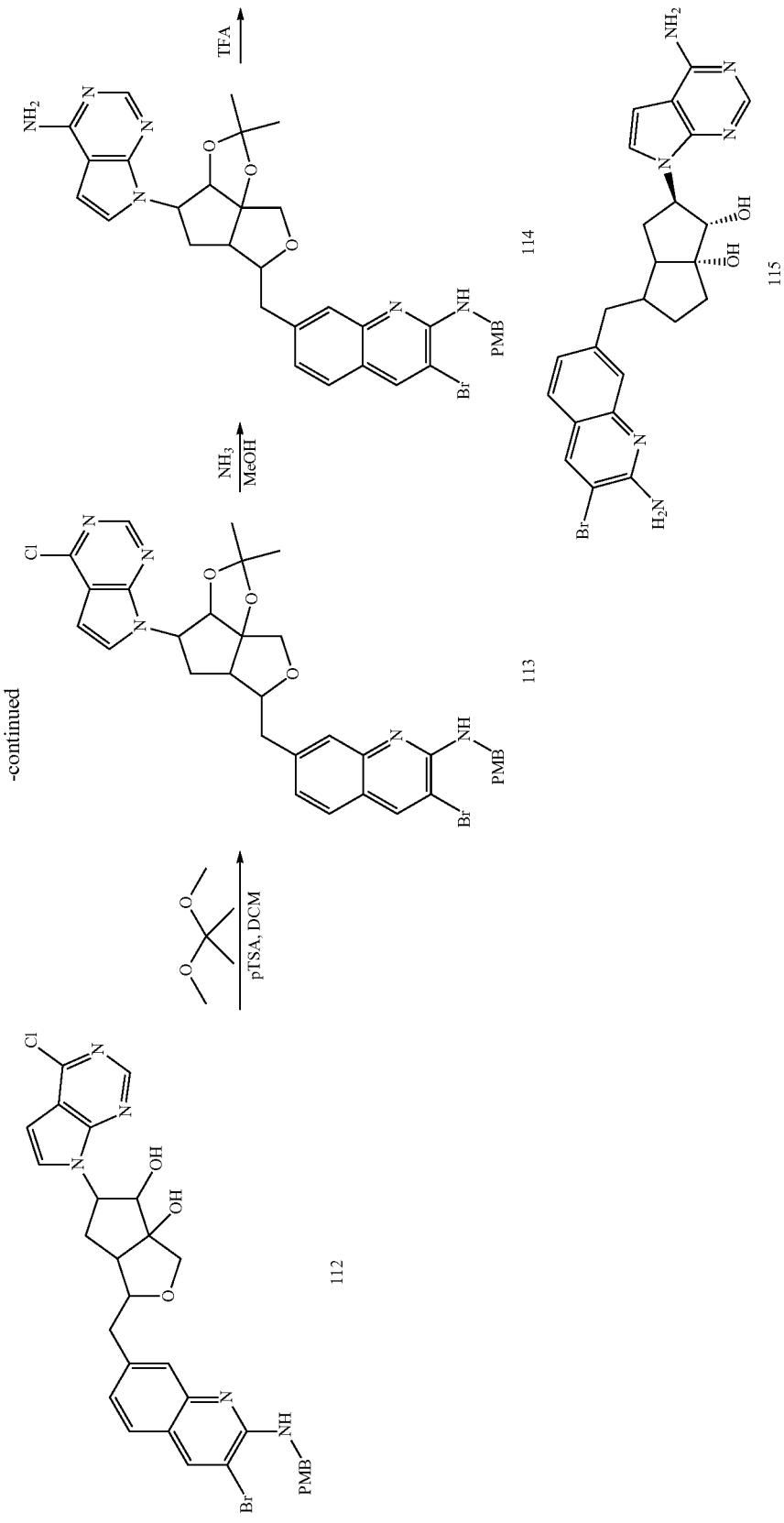

Compounds of formula 115 can be formed in the following sequence described in Scheme 14. Quinoline iodide 103 was subjected to Stille conditions to afford olefin 104. Subsequent ozonolysis and vinyl Grignard addition afforded alcohol 106. Alkylation afforded en-yne 107, which were subjected to cobalt-catalyzed Pauson-Khand conditions to afford enone 108. Reduction and carbonate formation provided carbonate 110. Palladium-catalyzed allylic alkylation conditions afforded bicycle 111. Olefin dihydroxylation and acetonide protection yielded ketal 113. Subsequent chloride displacement with ammonia and acid deprotection provided compound 115.

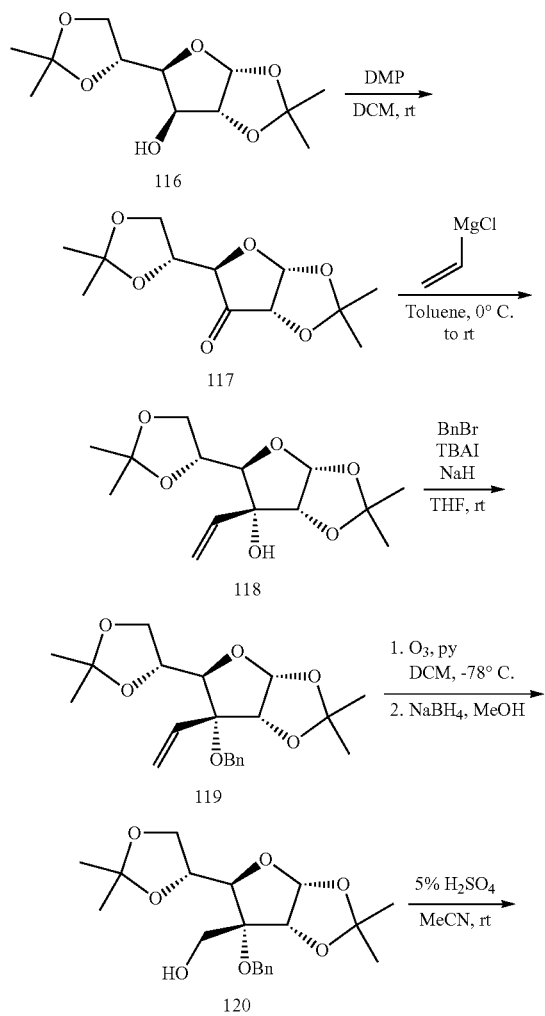

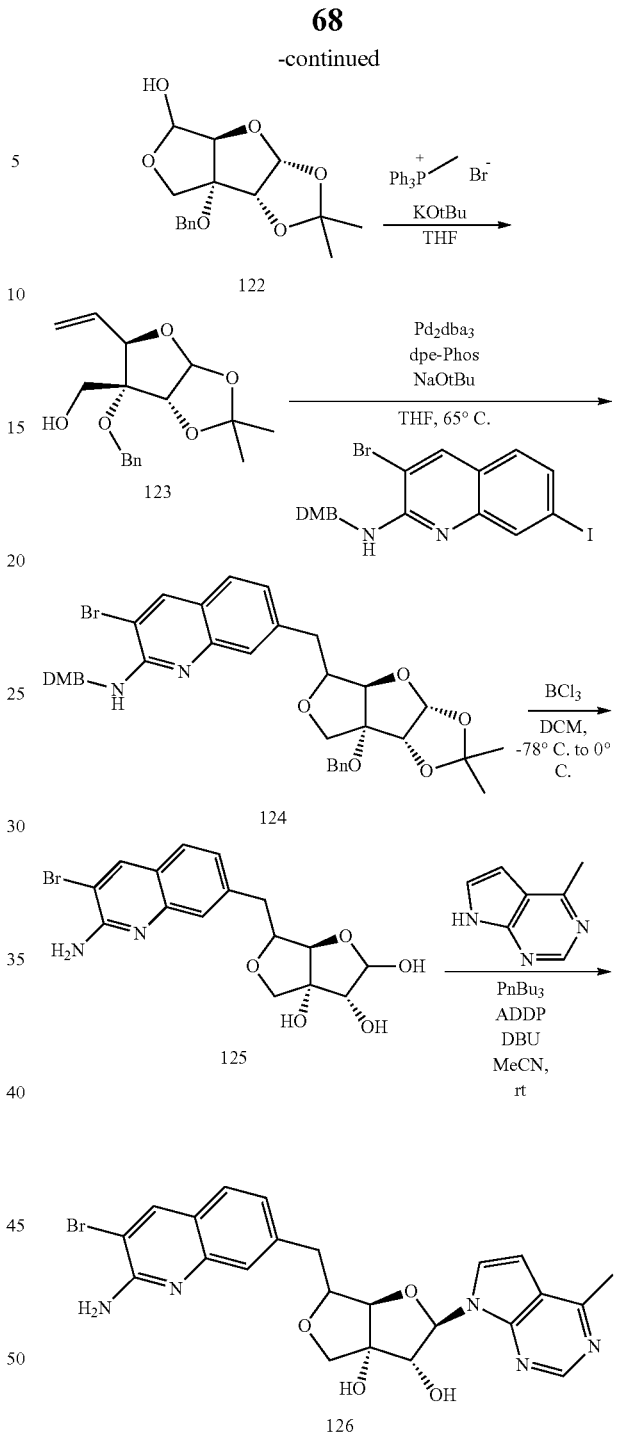

Compounds of formula 126 can be formed in the following sequence described in Scheme 15. Sugar 116 was oxidized with Dess-Martin Periodinane to afford ketone 117. Vinyl Grignard addition followed by benzyl protection afford olefin 119, which was subsequently ozonolyzed and reduced to afford alcohol 120. Selective acetonide deprotection afforded triol 121, which was oxidatively cleaved and cyclized to afford lactol 122. Wittig homologation yielded olefin 123, which was then subjected to a palladium-catalyzed cyclization/arylation to afford bicycle 124. Global deprotection with $BCl_3$ followed by nucleobase installation provided compound 126.

Scheme 16

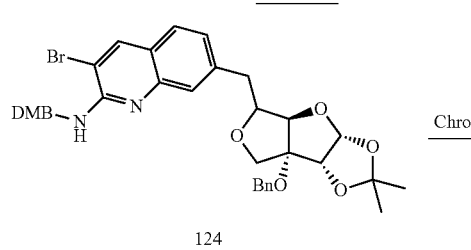
124

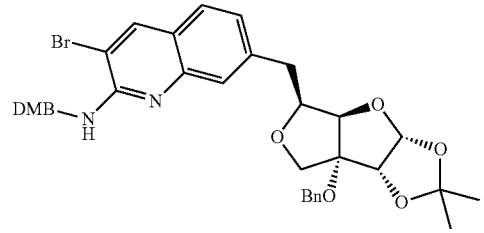
127

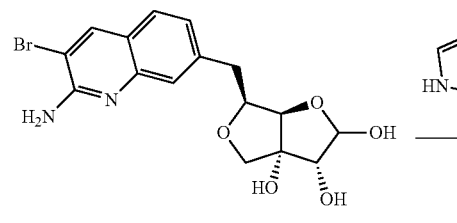
128

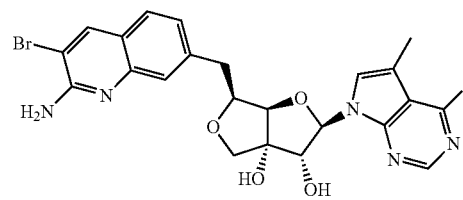
129

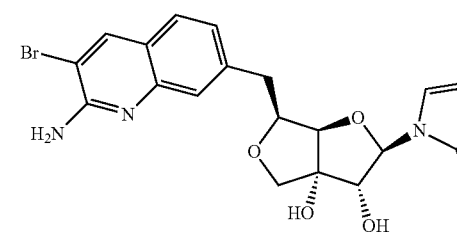
130

Compounds of formula 130 can be formed in the following sequence described in Scheme 16. Chromatographic purification of compound 124 yielded bicycle 127. Global deprotection with BCl$_3$ followed by nucleobase installation afforded compound 129. Chloride displacement with ammonia provided compound 130.

Synthesis of Intermediates

Synthetic Scheme of Intermediate 1

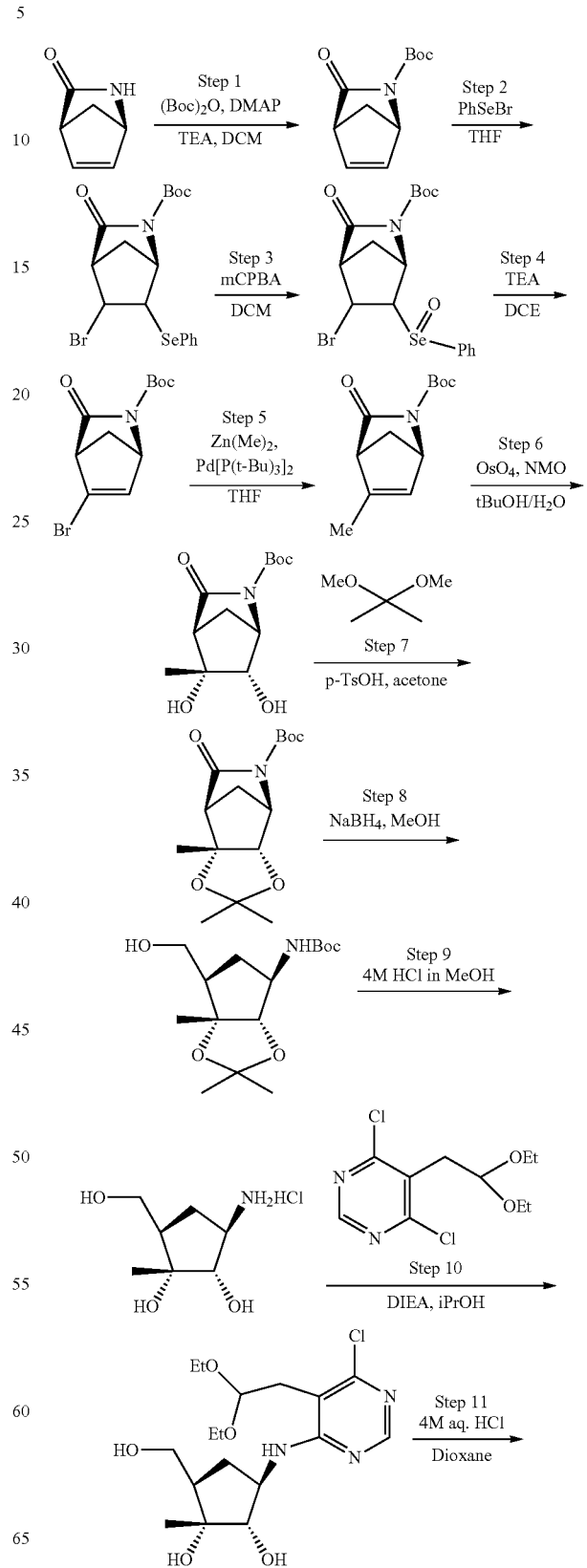

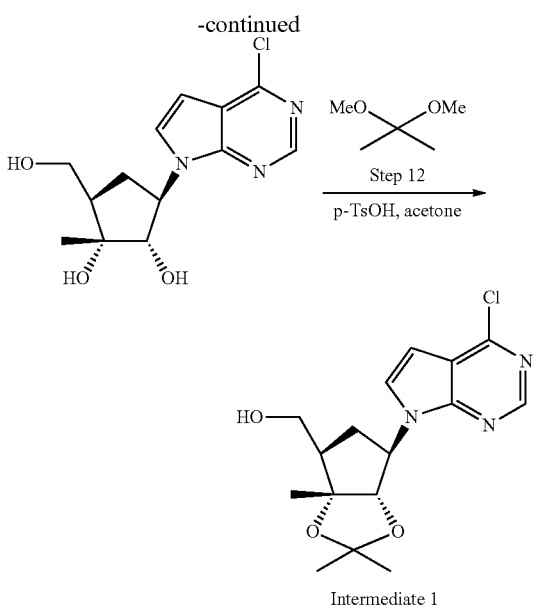

Intermediate 1: ((3aR,4R,6R,6aS)-6-(4-chloro-7H-pyrrolo[2,3-d]pyrimidin-7-yl)-2,2,3a-trimethyltetrahydro-3aH-cyclopenta[d][1,3]dioxol-4-yl)methanol

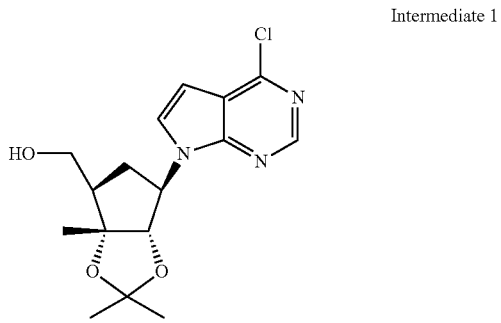 [SMILES: CC1(C)O[C@H]2[C@H](n3ccc4c(Cl)ncnc43)C[C@H](CO)[C@@]2(C)O1]

Step 1: To a mixture of (1R,4S)-2-azabicyclo[2.2.1]hept-5-en-3-one (50 g, 458 mmol), di-tert-butyl dicarbonate (120 g, 550 mmol) and N,N-dimethylpyridin-4-amine (5.6 g, 45.8 mmol) in DCM (500 mL) was added triethylamine (69.5 g, 687 mmol) at 25° C. The reaction mixture was stirred for 2 hours at 25° C. The reaction was quenched by saturated aqueous NaHCO₃ (1500 mL) and extracted with EtOAc (2000 mL×3). The combined organic layers were dried over anhydrous Na₂SO₄ and filtered. The filtrate was concentrated under reduced pressure. The residue was purified by a silica gel column chromatography and eluted with 0-20% of ethyl acetate in petroleum ether to afford (1R,4S)-tert-butyl-3-oxo-2-azabicyclo[2.2.1]hept-5-ene-2-carboxylate. MS: 154 (M−55).

Step 2: To a solution of (1R,4S)-tert-butyl 3-oxo-2-azabicyclo[2.2.1]hept-5-ene-2-carboxylate (40 g, 191 mmol) in THF (400 mL) was added phenyl hypobromoselenoite (49.6 g, 210 mmol) in THF (1.0 L) dropwise at −78° C. under an argon atmosphere. The mixture was stirred for 2 hours at −78° C., and then the temperature was warmed to 25° C. slowly. The reaction mixture was stirred at 25° C. for 16 hours. The reaction was quenched by saturated aqueous NaHCO₃ (500 mL) and extracted with DCM (500 mL×3). The combined organic layers were dried over anhydrous Na₂SO₄ and filtered. The filtrate was concentrated under reduced pressure. The residue was purified by silica gel column chromatography and eluted with 1%-20% of ethyl acetate in petroleum ether to afford (1R,4R)-tert-butyl 5-bromo-3-oxo-6-(phenylselanyl)-2-azabicyclo[2.2.1]heptane-2-carboxylate (mixture of two isomers). MS: 390/392 (M−55/M−53). ¹H NMR (400 MHz, DMSO-d₆) isomer 1: δ 7.73-7.59 (m, 2H), 7.44-7.26 (m, 3H), 4.65 (t, J=4.0 Hz, 1H), 4.38 (s, 1H), 3.55 (t, J=3.4 Hz, 1H), 3.05 (q, J=1.8 Hz, 1H), 2.29-2.16 (m, 1H), 2.04 (dt, J=11.1, 1.4 Hz, 1H), 1.31 (s, 9H). isomer 2: δ 7.73-7.59 (m, 2H), 7.44-7.26 (m, 3H), 4.73 (t, J=2.0 Hz, 1H), 4.33 (dd, J=3.6, 2.0 Hz, 1H), 4.24 (t, J=3.1 Hz, 1H), 3.05 (q, J=1.8 Hz, 1H), 2.42 (dq, J=10.7, 1.9 Hz, 1H), 2.29-216 (m, 1H), 1.36 (s, 9H).

Step 3: To a solution of (1R,4R)-tert-butyl 5-bromo-3-oxo-6-(phenylselanyl)-2-azabicyclo[2.2.1]heptane-2-carboxylate (33 g, 74.1 mmol) in DCM (150 mL) was added 3-chloroperbenzoic acid (20.1 g, 82 mmol) in several portions at −78° C. under an argon atmosphere. The resulting mixture was stirred for 2 hours at −78° C. The reaction was quenched by saturated aqueous NaHCO₃ (100 mL) and extracted with DCM (300 mL×3). The combined organic layers were dried over anhydrous Na₂SO₄ and filtered. The filtrate was concentrated under reduced pressure to afford the crude product (1R,4R)-tert-butyl 5-bromo-3-oxo-6-(phenylseleninyl)-2-azabicyclo[2.2.1]heptane-2-carboxylate. MS: 462/464 (M+1/M+3).

Step 4: To a stirred mixture of (1R,4R)-tert-butyl 5-bromo-3-oxo-6-(phenylseleninyl)-2-azabicyclo[2.2.1]heptane-2-carboxylate (127 g, 274 mmol) in DCE (1000 mL) was added triethylamine (76 mL, 549 mmol) at 25° C. The resulting mixture was stirred for 6 hours at 80° C. The reaction was cooled to room temperature and quenched with water (500 mL). The organic layers were separated, washed with brine (100 ml×2), dried over anhydrous sodium sulfate, and filtered. The filtrate was concentrated to dryness. The residue was purified by silica gel column chromatography, eluted with 0-10% of ethyl acetate in petroleum ether to afford (1R,4R)-tert-butyl 5-bromo-3-oxo-2-azabicyclo[2.2.1]hept-5-ene-2-carboxylate. ¹H NMR (400 MHz, DMSO-d₆) δ 7.20 7.20 (d, J=2.6 Hz, 1H), 4.96 (t, J=2.6 Hz, 1H), 3.42 (t, J=2.8 Hz, 1H), 2.40 (t, J=1.8 Hz, 2H), 1.44 (s, 9H).

Step 5 (method A): To a stirred solution of (1R,4R)-tert-butyl 5-bromo-3-oxo-2-azabicyclo[2.2.1]hept-5-ene-2-carboxylate (15 g, 52.1 mmol) in toluene (50 mL) were added Pd(PPh₃)₄ (6.0 g, 5.2 mmol) and tetramethylstannane (28.9 mL, 208 mmol) at 25° C. The mixture was stirred for 6 hours at 100° C. in a sealed tube. The reaction mixture was quenched by saturated NaHCO₃ solution (200 mL) and extracted with EtOAc (300 mL×3). The combined organic layers were dried over anhydrous Na₂SO₄, filtered, and the filtrate was concentrated to dryness. The residue was purified by silica gel column chromatography, eluted with 0-3% EtOAc in a mixture of petroleum ether/DCM (v:v, 5/1) to afford (1R,4S)-tert-butyl 5-methyl-3-oxo-2-azabicyclo[2.2.1]hept-5-ene-2-carboxylate. ¹H NMR (300 MHz, DMSO-d₆) δ 6.51-6.42 (m, 1H), 4.78 (p, J=2.2 Hz, 1H), 3.12 (d, J=2.8 Hz, 1H), 2.25 (d, J=8.4 Hz, 1H), 2.12-2.10 (m, 1H), 1.87 (s, 3H), 1.40 (s, 9H).

Step 5 (method B): To a stirred solution of (1R,4R)-tert-butyl 5-bromo-3-oxo-2-azabicyclo[2.2.1]hept-5-ene-2-carboxylate (26 g, 90 mmol) in THF (250 mL) were added dimethylzinc (1 M in toluene, 180 mL, 180 mmol) dropwise and bis(tri-tert-butylphosphine)palladium(0) (0.92 g, 1.8 mmol) at 0° C. The resulting mixture was stirred for 16 hours at 20° C. The reaction was quenched by saturated aqueous NH₄Cl (400 mL) and extracted with DCM (500 mL×2). The combined organic layers were dried over anhydrous Na₂SO₄ and filtered. The filtrate was concentrated under reduced pressure. The residue was purified by silica gel column chromatography, eluted with 0-3% EtOAc in a mixture of petroleum ether and DCM (v/v=5:1) to afford (1R,4S)-tert-butyl 5-methyl-3-oxo-2-azabicyclo[2.2.1]hept-5-ene-2-carboxylate. ¹H NMR (400 MHz, DMSO-d₆) δ 6.53-6.47 (m, 1H), 4.82-4.80 (m, 1H), 3.16-3.14 (m, 1H), 2.28 (dt, 1=8.4, 1.8 Hz, 1H), 2.12-2.10 (m, 1H), 1.90 (s, 3H), 1.43 (s, 9H).

Step 6: To a solution of (1R,4S)-tert-butyl 5-methyl-3-oxo-2-azabicyclo[2.2.1]hept-5-ene-2-carboxylate (5 g, 22.4 mmol) in tBuOH (25 mL)/water (25 mL) was added 4-methylmorpholine 4-oxide (5.25 g, 44.8 mmol) at 0° C. under argon atmosphere. This was followed by the addition of osmium (VIII) oxide (18.5 mL, 22.4 mmol, 4% in water) dropwise at 0° C., The mixture was stirred for 16 hours at room temperature. The reaction was quenched by the addition of saturated aqueous Na₂S₂O₃ (30 mL), then extracted with EtOAc (30 mL×4). The combined organic layers were washed with brine (30 mL), dried over anhydrous Na₂SO₄ and filtered. The filtrate was concentrated to dryness. The residue was purified by silica gel column chromatography and eluted with 0-70% ethyl acetate in petroleum ether. The fractions containing the desired product were combined and concentrated under reduced pressure to afford (1R,4S,5R,6S)-tert-butyl 5,6-dihydroxy-5-methyl-3-oxo-2-azabicyclo[2.2.1]heptane-2-carboxylate. ¹H NMR (300 MHz, DMSO-d₆) δ 5.54 (d, J=5.7 Hz, 1H), 4.96 (s, 1H), 4.04 (s, 1H), 3.49-3.37 (m, 1H), 2.37 (d, J=2.4 Hz, 1H), 2.11 (dd, J=10.5, 1.8 Hz, 1H), 1.98-1.80 (m, 1H), 1.45 (s, 9H), 1.21 (s, 3H).

Step 7: (1R,4S,5R,6S)-tert-butyl-5,6-dihydroxy-5-methyl-3-oxo-2-azabicyclo[2.2.1]heptane-2-carboxylate (1.4 g, 5.4 mmol) was co-evaporated with dry toluene (10 mL×3) and then re-dissolved in acetone (10 mL). To this solution was added 4-methylbenzenesulfonic acid (0.094 g, 0.5 mmol), followed by the addition of 2,2-dimethoxypropane (2.83 g, 27.2 mmol) at room temperature. The resulting mixture was stirred at ambient temperature for 1 hour. The mixture was neutralized with saturated aqueous NaHCO₃ to pH 7. The mixture was concentrated to dryness. The crude product was purified by silica gel column chromatography and eluted with 10-50% ethyl acetate in petroleum ether to give (3aS,4R,7S,7aR)-tert-butyl 2,2,7a-trimethyl-6-oxotetrahydro-4,7-methano[1,3]dioxolo[4,5-c]pyridine-5(6H)-carboxylate. ¹H NMR (400 MHz, Chloroform-d) δ 4.39 (t, J=1.6 Hz, 1H), 4.21 (d, J=1.5 Hz, 1H), 2.71 (q, J=1.6 Hz, 1H), 2.23-2.19 (m, 1H), 2.07-2.00 (m, 1H), 1.61 (s, 3H), 1.53 (s, 91H), 1.49 (s, 3H), 1.48 (s, 3H).

Step 8: To a solution of (3aS,4R,7S,7aR)-tert-butyl 2,2,7a-trimethyl-6-oxotetrahydro-4,7-methano[1,3]dioxolo[4,5-c]pyridine-5(6H)-carboxylate (2.9 g, 9.8 mmol) in MeOH (58 mL) was added NaBH₄ (0.74 g, 19.5 mmol) at 0° C. The mixture was stirred for 2 hours at 0° C. The reaction mixture was quenched by saturated aqueous NH₄Cl (50 mL) and extracted with ethyl acetate (60 mL×3). The combined organic layers were concentrated to dryness. The residue was purified by column chromatography on silica gel and eluted with 0-40% of EtOAc in petroleum ether. The collected fractions were combined and concentrated under vacuum to give tert-butyl ((3aS,4R,6R,6aR)-6-(hydroxymethyl)-2,2,6a-trimethyltetrahydro-3aH-cyclopenta[d][1,3]dioxol-4-yl)carbamate. ¹H NMR (300 MHz, DMSO-d₆) 7.05 (br s, 1H), 4.49 (t, J=5.0 Hz, 1H), 3.86 (d, J=2.8 Hz, 1H), 3.77-3.74 (m, 1H), 3.55-3.44 (m, 1H), 3.31-3.25 (m, 1H), 2.07-1.97 (m, 1H), 2.21-2.14 (m, 1H), 1.40 (s, 9H), 1.40-1.39 (m, 1H), 1.38 (s, 3H), 1.25 (s, 3H), 1.23 (s, 3H).

Step 9: Tert-butyl ((3aS,4R,6R,6aR)-6-(hydroxymethyl)-2,2,6a-trimethyltetrahydro-3aH-cyclopenta[d][1,3]dioxol-4-yl)carbamate (3.5 g, 11.6 mmol) was dissolved in HCl (30 mL, 4 M in methanol). The resulting solution was stirred at ambient temperature for 2 h. The solution was concentrated to give the crude product of (1R,2S,3R,5R)-3-amino-5-(hydroxymethyl)-1 methylcyclopentane-1,2-diol hydrochloride. ¹H NMR (300 MHz, DMSO-d₆) δ 8.21 (br s, 3H), 5.21 (br s, 1H), 4.60-4.31 (m, 2H), 3.52 (d, J=9.0 Hz, 1H), 3.44 (dd, J=105, 5.1 Hz, 1H), 3.32-3.19 (m, 2H), 2.18-2.07 (m, 1H), 2.00-1.76 (m, 1H), 1.46-1.36 (m, 1H), 1.10 (s, 3H).

Step 10: To a stirred mixture of (1R,2S,3R,5R)-3-amino-5-(hydroxymethyl)-1-methylcyclopentane-1,2-diol hydrochloride (1.85 g, 9.4 mmol) and 4,6-dichloro-5-(2,2-diethoxyethyl)pyrimidine (2.73 g, 10.3 mmol) in 2-propanol (40 mL) was added N-ethyl-N-isopropylpropan-2-amine (2.42 g, 18.7 mmol) at 25° C. The reaction mixture was stirred for 16 hours at 100° C. The reaction mixture was cooled to room temperature and concentrated to dryness. The residue was purified by silica gel column chromatography (0-15% MeOH in DCM) to afford (1R,2S,3R,5R)-3-((6-chloro-5-(2,2-diethoxyethyl)pyrimidin-4-yl)amino)-5-(hydroxymethyl)-1-methylcyclopentane-1,2-diol. MS: 390 (M+1). ¹H NMR (400 MHz, DMSO-d₆) δ 8.15 (s, 1H), 6.79 (d, J=7.5 Hz, 1H), 4.68-4.56 (m, 2H), 4.50-4.40 (m, 1H), 4.37-4.30 (m, 1H), 4.01 (s, 1H), 3.76-3.58 (m, 2H), 3.50-3.39 (m, 4H), 3.35-3.25 (m, 1H), 2.92-2.90 (m, 2H), 2.25-2.18 (m, 1H), 1.94-1.85 (m, 1H), 1.31-1.24 (m, 1H), 1.21-1.02 (m, 9H).

Step 11: To a stirred solution of (1R,2S,3R,5R)-3-((6-chloro-5-(2,2-diethoxyethyl)pyrimidin-4-yl)amino)-5-(hydroxymethyl)-1-methylcyclopentane-1,2-diol (10 g, 25.6 mmol) in 1,4-dioxane (80 mL) was added dropwise aqueous HCl (20 mL, 80 mmol, 4 M in water) at room temperature. The resulting mixture was stirred for 0.5 hours at 50° C. Then the mixture was cooled to 0° C. with an ice bath and neutralized with saturated aqueous NaHCO₃ to pH~8 to 9. The resulting mixture was concentrated to dryness and the residue was purified by silica gel column chromatography, eluting with 0-10% of MeOH in DCM to afford (1R,2S,3R,5R)-3-(4-chloro-7H-pyrrolo[2,3-d]pyrimidin-7-yl)-5-(hydroxymethyl)-1-methylcyclopentane-1,2-diol MS: 298 (M+1). ¹H NMR (400 MHz, DMSO-d₆) δ 8.62 (s, 1H), 7.89 (d, J=3.6 Hz, 1H), 6.71 (d, J=3.6 Hz, 1H), 5.10 (q, J=9.6 Hz, 1H), 4.86 (d, J=7.2 Hz, 1H), 4.73 (t, J=4.8 Hz, 1H), 4.27 (s, 1H), 4.05 (dd, J=9.6, 7.2 Hz, 1H), 3.54-3.51 (m, 2H) 2.41-2.33 (m, 1H), 2.05-1.95 (m, 1H), 1.73-1.66 (m, 1H), 1.21 (s, 3H).

Step 12: (1R,2S,3R,5R)-3-(4-chloro-7H-pyrrolo[2,3-d]pyrimidin-7-yl)-5-(hydroxymethyl)-1-methylcyclopentane-1,2-diol (2.03 g, 6.8 mmol) was co-evaporated with dry toluene (10 mL×3) and then re-dissolved in acetone (20 mL). To this solution were added 4-methylbenzenesulfonic acid (0.12 g, 0.68 mmol), followed by 2,2-dimethoxypropane (3.55 g, 34.1 mmol). The resulting mixture was stirred at 25° C. for 1 hour. Then the solution was neutralized with saturated aqueous NaHCO₃ to pH~7 to 8. The resulting mixture was extracted with EtOAc (30 mL×3). The combined organic layers were washed with brine (50 mL), dried over anhydrous sodium sulfate, and filtered. The filtrate was concentrated under reduced pressure. The residue was purified by silica gel column chromatography and eluted with 0-70% ethyl acetate in petroleum ether to afford ((3aR,4R, 6R,6aS)-6-(4-chloro-7H-pyrrolo[2,3-d]pyrimidin-7-yl)-2,2, 3a-trimethyltetrahydro-3aH-cyclopenta[d][1,3]dioxol-4-yl)methanol. MS: 338 (M+1). ¹H NMR (400 MHz, DMSO-d₆) δ 8.67 (s, 1H), 7.94 (d, J=3.6 Hz, 1H), 6.74 (d, J=3.6 Hz, 1H), 5.20-5.10 (m, 1H), 4.56 (t, J=5.2 Hz, 1H), 4.41 (d, J=4.4 Hz, 1H), 3.64 (dt, J=10.5, 5.2 Hz, 1H), 3.54-3.35 (m, 1H), 2.44-2.26 (m, 2H), 2.28-2.11 (m, 1H), 1.49 (s, 6H), 1.26 (s, 3H).

Synthetic Scheme of Intermediate 2

Intermediate 2: (3,3aS,6R,6aR)-2-methoxyhexahydro-3aH-cyclopenta[b]furan-3,3a,6-triol

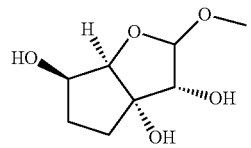

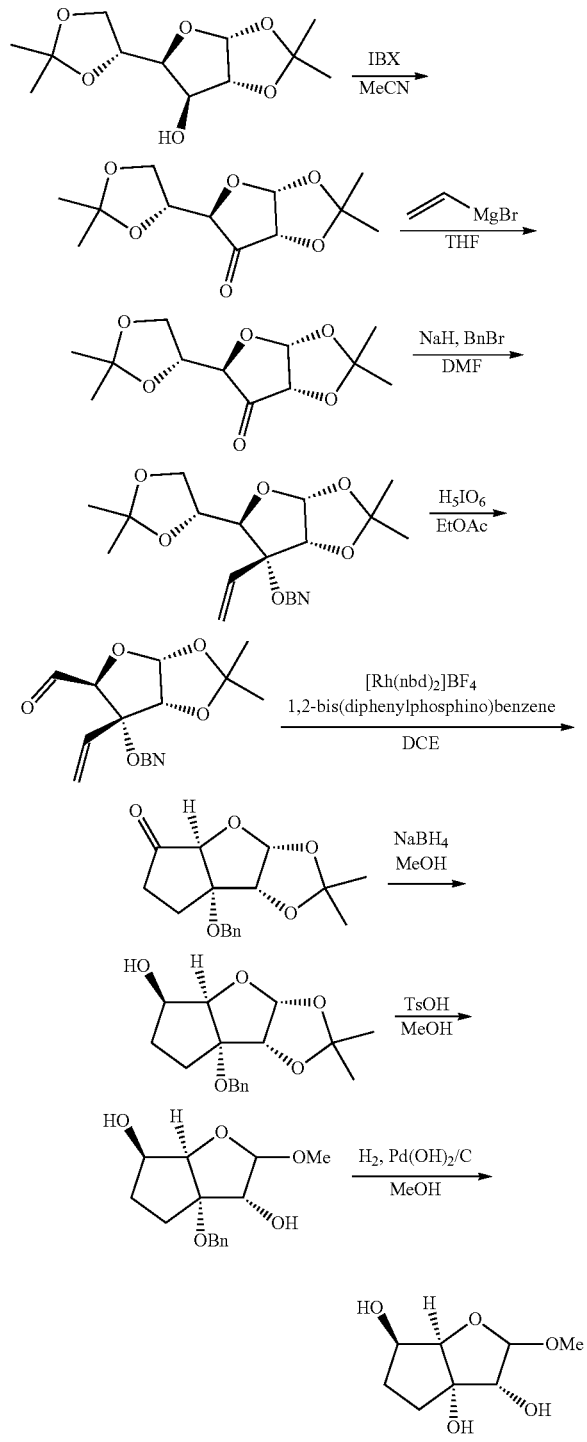

Step 1: To a solution of (3aR,5S,6S,6aR)-5-((R)-2,2-dimethyl-1,3-dioxolan-4-yl)-2,2-dimethyltetrahydrofuro[2,3-d][1,3]dioxol-6-ol (500 g, 1.92 mol) in MeCN (2.50 L) at 25° C. was added slowly IBX (807 g, 2.88 mol) at 20~25° C. The reaction mixture was stirred at 85~90° C. for 3 hours. The mixture was filtered and concentrated. The crude product (3aR,5R,6aS)-5-((R)-2,2-dimethyl-1,3-dioxolan-4-yl)-2,2-dimethyldihydrofuro[2,3-d][1,3]dioxol-6(5H)-one was used in the next step without further purification. ¹H NMR (400 MHz, CDCl₃) δ: 6.14 (d, J=4.4 Hz, 1H), 4.31-4.45 (m, 3H), 4.00-4.06 (m, 2H), 1.46 (s, 3H), 1.43 (s, 3H), 1.34 (s, 6H).

Step 2: To a solution of (3aR,5R,6aS)-5-((R)-2,2-dimethyl-1,3-dioxolan-4-yl)-2,2-dimethyldihydrofuro[2,3-d][1,3]dioxol-6(5H)-one (500 g, 1.94 mol) in dry THF (2.50 L) cool to 0~5° C. was added vinyl magnesium bromide (1 M, 3.87 L) maintaining the temperature at 0~5° C. The reaction was warmed to 15~20° C. and stirred for 0.5 hours. The reaction mixture was quenched by pouring into aqueous NH₄Cl (10 L) at 0~5° C. The aqueous phase was extracted with MTBE (3 L×3). The combined organic phase was washed with brine (2 L), dried with anhydrous Na₂SO₄, filtered, and concentrated under reduced pressure. The residue was purified by column chromatography (silica, petroleum ether/ethyl acetate=1/0 to 5/1) to give (3aR,5R,6aR)-5-((R)-2,2-dimethyl-1,3-dioxolan-4-yl)-2,2-dimethyl-6-vinyltetrahydrofuro[2,3-d][1,3]dioxol-6-ol.

Step 3: To a solution of NaH (105 g, 2.62 mol, 60% dispersion in mineral oil) in DMF (2.75 L) at 15~20° C. was added (3aR,5R,6aR)-5-((R)-2,2-dimethyl-1,3-dioxolan-4-yl)-2,2-dimethyl-6-vinyltetrahydrofuro[2,3-d][1,3]dioxol-6-ol (375 g, 1.31 mol) in DMF (1 L) dropwise at 15~20° C. The reaction mixture was stirred at 55~60° C. for 1 h, then BnBr (336 g, 1.96 mol, 233 mL) was added. The reaction mixture was stirred at 15~20° C. for another 5 hours. The reaction was quenched by pouring the mixture into ice water (1.5 L). The resultant mixture was extracted with ethyl acetate (2 L×3). The combined organic phase was washed with aqueous NaHCO₃ (1.5 L), dried with anhydrous Na₂SO₄, filtered, and concentrated under reduced pressure. The crude product (3aR,5R,6R,6aR)-6-(benzyloxy)-5-((R)-2,2-dimethyl-1,3-dioxolan-4-yl)-2,2-dimethyl-6-vinyltetrahydrofuro[2,3-d][1,3]dioxole was used without further purification.

Step 4: To a solution of (3aR,5R,6R,6aR)-6-(benzyloxy)-5-((R)-2,2-dimethyl-1,3-dioxolan-4-yl)-2,2-dimethyl-6-vinyltetrahydrofuro[2,3-d][1,3]dioxole (400 g, 1.06 mol) in EtOAc (2 L) at 15~20° C. was added periodic acid (250 g, 1.09 mol) and the resultant mixture was stirred for 1 hour. The reaction was filtered, and the filtrate was concentrated under reduced pressure. The residue was purified by column chromatography (silica, petroleum ether/ethyl acetate=20/1 to 0/1) to afford (3aR,5S,6R,6aR)-6-(benzyloxy)-2,2-dimethyl-6-vinyltetrahydrofuro[2,3-d][1,3]dioxole-5-carbaldehyde. ¹H NMR (400 MHz, CDCl₃) δ: 9.58 (s, 1H), 7.26-7.43

(m, 5H), 5.97 (d, J=3.20 Hz, 1H), 5.78-5.76 (m, 1H), 5.38-5.54 (m, 2H), 4.59-4.73 (m, 4H), 1.62 (s, 3H), 1.40 (s, 3H)

Step 5: To a suspension of [Rh(nbd)$_2$]BF$_4$ (6.14 g, 16.4 mmol) in DCE (60 mL) at 15~20° C. under N$_2$ was added 1,2-bis(diphenylphosphino)benzene (6.10 g, 13.7 mmol). The suspension was degassed under reduced pressure, purged with 112 three times, and the 112 was bubbled through the solution for 0.25 hours. The reaction mixture was flushed again with N$_2$ for 0.25 hours to remove H$_2$. (3aR,5S,6R,6aR)-6-(benzyloxy)-2,2-dimethyl-6-vinyltetrahydrofuro[2,3-d][1,3]dioxole-5-carbaldehyde (50.0 g, 164 mmol) in DCE (60 mL) was added dropwise to the above solution at 15~20° C. under N2. The mixture was stirred at 75~80° C. for 12 hours. The mixture was filtered and solvent was removed to give crude (3aR,4aS,7aS,7bR)-7a-(benzyloxy)-2,2-dimethylhexahydro-5H-cyclopenta[4,5]furo[2,3-d][1,3]dioxol-5-one. $^1$H NMR: (400 MHz, CDCl$_3$) δ: 7.5-7.25 (m, 5H), 5.94 (m, 1H), 4.69 (m, 1H), 4.63-4.57 (m, 2H), 4.18 (s, 1H), 2.40-2.56 (m, 3H), 1.68-1.74 (m, 1H), 1.61 (s, 3H), 1.40 (s, 3H)

Step 6: NaBH$_4$ (37.3 g, 986 mmol) was added to a mixture of (3aR,4aS,7aS,7bR)-7a-(benzyloxy)-2,2-dimethylhexahydro-5H-cyclopenta[4,5]furo[2,3-d][1,3]dioxol-5-one (150 g, 493 mmol) in MeOH (750 mL) at 0~5° C. The mixture was stirred at 0~-5° C. for 1 hour. The residue was poured into ice-water (250 mL) and the aqueous phase was extracted with ethyl acetate (250 mL×3). The combined organic phases were washed with brine (125 mL), dried with anhydrous Na$_2$SO$_4$, filtered, and concentrated under reduced pressure. The residue was purified by column chromatography (silica, petrol urn ether/ethyl acetate=20/1 to 0/1) to afford (3aR,4aR,5R,7aR,7bR)-7a-(benzyloxy)-2,2-dimethylhexahydro-5H-cyclopenta[4,5]furo[2,3-d][1,3]dioxol-5-ol. $^1$H NMR: (400 MHz, CDCl$_3$) δ: 7.33-7.40 (m, 5H), 5.88 (d, J=3.6 Hz, 1H), 4.65 (d, J=10.8 Hz, 1H), 4.56 (d, J=3.2 Hz, 1H), 4.45-4.51 (m, 2H), 4.18-4.29 (m, 1H), 2.06-2.26 (m, 3H), 1.66-1.77 (m, 1H), 1.66-1.77 (m, 1H), 1.62 (s, 3H), 1.41 (s, 3H)

Step 7: To a solution of TsOH (10.8 g, 62.7 mmol) in MeOH (150 mL) at 15~20° C. was added 3aR,4aR,5R,7aR,7bR)-7a-(benzyloxy)-2,2-dimethylhexahydro-5H-cyclopenta[4,5]furo[2,3-d][1,3]dioxol-5-ol (30.0 g, 97.9 mmol). The mixture was stirred at 15-20° C. for 12 hours. The reaction was poured into ice water (16 mL) and neutralized with aqueous Na$_2$CO$_3$ (25 mL). The aqueous phase was extracted with ethyl acetate (100 mL×4). The combined organic fractions were washed with brine (100 mL), dried with anhydrous Na$_2$SO$_4$, filtered, and concentrated under reduced pressure. The residue was purified by column chromatography (silica, petroleum ether/ethyl acetate=20/1 to 0/1) to give (3R,3aS,6R,6aR)-3a-(benzyloxy)-2-methoxyhexahydro-2H-cyclopenta[b]furan-3,6-diol. $^1$H NMR: (400 MHz, CDCl$_3$) δ: 7.26-7.40 (m, 5H), 4.93-5.03 (m, 1H), 4.52-4.76 (m, 1H), 4.33-4.45 (m, 1H), 4.00-4.19 (m, 1H), 3.78-3.97 (m, 1H), 3.46 (d, J=7.6 Hz, 3H), 2.98-3.04 (m, 1H), 2.20-2.34 (m, 1H), 1.82-2.12 (m, 4H).

Step 8: Pd(OH)$_2$/C (1.70 g, 2.42 mmol, 20 wt. % loading) was added to (3R,3aS,6R,6aR)-3a-(benzyloxy)-2-methoxyhexahydro-2H-cyclopenta[b]furan-3,6-diol (17.0 g, 60.7 mmol) in MeOH (150 mL) at 15~20° C. under N2 followed by addition of acetic acid (2.98 g, 49.5 mmol, 2.83 mL). The suspension was degassed under reduced pressure and purged with H$_2$ several times. The mixture was then stirred under H$_2$ (50 psi) at 50~55° C. for 12 hours. The reaction mixture was filtered and concentrated under reduced pressure to afford (3R,3aS,6R,6aR)-2-methoxyhexahydro-3aH-cyclopenta[b]furan-3,3a,6-triol. $^1$H NMR: (400 MHz, CDCl$_3$) δ: 5.00 (d, J=4.0 Hz, 1H), 4.94 (d, J=2.0 Hz, 1H), 4.22-4.18 (m, 1H), 4.16-4.13 (m, 2H), 3.76-3.83 (m, 1H), 3.47 (d, J=13.8 Hz, 3H), 2.14-1.96 (m, 2H), 1.81-1.62 (m, 2H).

Synthetic Scheme of Intermediate 3

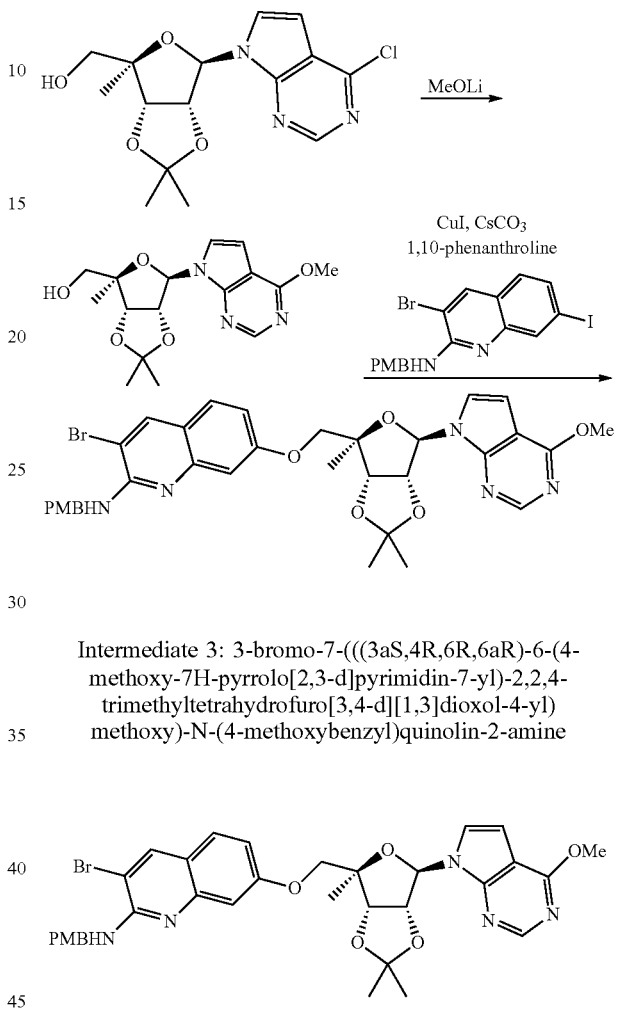

Intermediate 3: 3-bromo-7-(((3aS,4R,6R,6aR)-6-(4-methoxy-7H-pyrrolo[2,3-d]pyrimidin-7-yl)-2,2,4-trimethyltetrahydrofuro[3,4-d][1,3]dioxol-4-yl)methoxy)-N-(4-methoxybenzyl)quinolin-2-amine

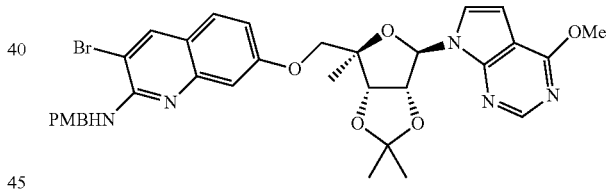

Step 1: To a solution of ((3aS,4R,6R,6aR)-6-(4-chloro-7H-pyrrolo[2,3-d]pyrimidin-7-yl)-2,2,4-trimethyltetrahydrofuro[3,4-d][1,3]dioxol-4-yl)methanol (95.0 mg, 0.280 mmol) in methanol (1.0 mL) was added LiOMe (106 mg, 2.80 mmol). The reaction mixture was stirred at room temperature for 20 minutes and then diluted with water (10 mL). The resulting mixture was extracted with DCM (10 mL) and organic layers were dried over Na$_2$SO$_4$. The organic solvent was removed under reduced pressure to yield ((3aS,4R,6R,6aR)-6-(4-methoxy-7H-pyrrolo[2,3-d]pyrimidin-7-yl)-2,2,4-trimethyltetrahydrofuro[3,4-d][1,3]dioxol-4-yl)methanol. The product was used for the next step without further purification. MS: 336 (M+1). 1H NMR (500 MHz, CDCl$_3$) 8.43 (s, 1H), 7.07 (d, J=3.6 Hz, 1H), 6.89 (dd, J=12.1, 1.7 Hz, 1H), 6.51 (d, J=3.6 Hz, 1H), 5.74 (d, J=5.7 Hz, 1H), 5.35 (t, J=5.8 Hz, 1H), 5.01 (d, J=5.9 Hz, 1H), 4.12 (s, 3H), 3.80 (dd, J=12.2, 1.7 Hz, 1H), 3.63 (t, J=12.2 Hz, 1H), 1.65 (s, 3H), 1.37 (s, 3H), 1.35 (s, 3H).

Step 2: To a solution of ((3aS,4R,6R,6aR)-6-(4-methoxy-7H-pyrrolo[2,3-d]pyrimidin-7-yl)-2,2,4-trimethyltetrahydrofuro[3,4-d][1,3]dioxol-4-yl)methanol (94.0 mg, 0.280 mmol), 3-bromo-7-iodo-N-(4-methoxybenzyl)quinolin-2-amine (75.0 mg, 0.160 mmol), copper iodide (3.05 mg, 0.0160 mmol) and 1,10-phenanthroline (5.77 mg, 0.0320 mmol) in dioxanes (0.250 mL) was added cesium carbonate (78.0 mg, 0.240 mmol). The resulting mixture was stirred at 110° C. for 23 hours. The reaction mixture was directly purified by flash column chromatography (EtOAc in hexanes, 0-25%) to yield 3-bromo-7-(((3aS,4R,6R,6aR)-6-(4-methoxy-7H-pyrrolo[2,3-d]pyrimidin-7-yl)-2,2,4-trimethyltetrahydrofuro[3,4-d][1,3]dioxol-4-yl)methoxy)-N-(4-methoxybenzyl)quinolin-2-amine as a solid. MS: 676/678 (M+1/M+3). $^{1}$H-NMR (500 MHz, Chloroform-d) δ 8.51 (s, 1H), 8.01 (s, 1H), 7.42 (d, J=8.8 Hz, 1H), 7.36 (d, J=8.6 Hz, 2H), 7.32 (d, J=3.7 Hz, 1H), 7.06 (d, J=2.4 Hz, 1H), 6.90 (d, J=8.7 Hz, 2H), 6.81 (dd, J=8.8, 2.5 Hz, 1H), 6.49 (d, J=3.7 Hz, 1H), 6.44 (d, J=3.7 Hz, 1H), 5.56 (t, J=5.1 Hz, 1H), 5.44 (dd, J=6.1, 3.8 Hz, 1H), 5.00 (d, J=6.2 Hz, 1H), 4.72 (d, J=5.1 Hz, 2H), 4.21 (d, J=9.7 Hz, 1H), 4.09 (s, 3H), 4.05 (d, J=9.7 Hz, 1H), 3.81 (s, 3H), 1.71 (s, 3H), 1.55 (s, 3H), 1.42 (s, 3H).

Synthetic Scheme of Intermediate 4

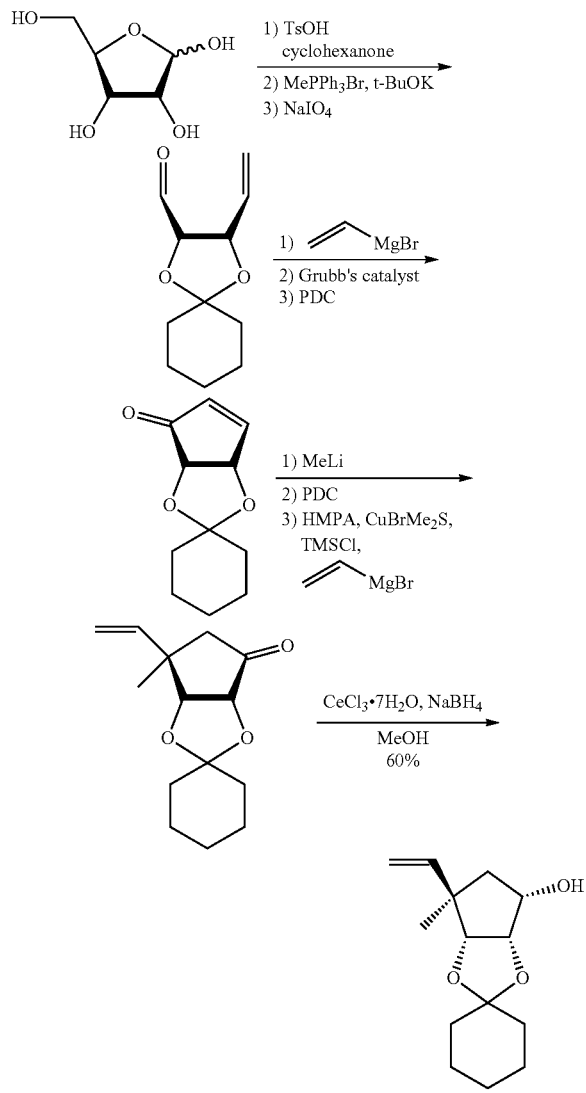

Intermediate 4: (3a'R,4'R,6'S,6a'S)-4'-methyl-4'-vinyltetrahydro-4'H-spiro[cyclohexane-1,2'-cyclopenta[d][1,3]dioxol]-6'-ol

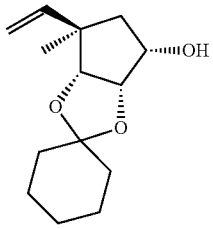 [SMILES: C=C[C@@]1(C)C[C@H](O)[C@@H]2OC3(CCCCC3)O[C@@H]21]

Step 1: Into a 10-L 4-necked round-bottom flask, purged and maintained with an inert atmosphere of nitrogen were placed D-ribofuranose (970 g, 6.46 mol), cyclohexanone (6.4 L), and 4-methylbenzene-1-sulfonic acid (22.8 g, 132 mmol). The resulting solution was stirred overnight at 25° C. The resulting solution was extracted with 5 L of ethyl acetate and the organic layers combined. The organic layers were washed with 5 L of saturated aqueous NaHCO$_3$ solution and 5 L of H$_2$O. The organic layers were dried over sodium sulfate. The resulting mixture was concentrated under reduced pressure. The residue was purified by silica gel column chromatography (EtOAc/petroleum ether (1:1)) to afford 2,3-O-1,1-cyclohexanediyl-D-ribofuranose.

Step 2: Into a 20-L 4-necked round-bottom flask, purged and maintained with an inert atmosphere of nitrogen were placed MePPh$_3$Br (1.83 kg, 5.13 mol) and tetrahydrofuran (12.7 L). This was followed by the addition of t-BuOK (657 g, 5.86 mol) at 0° C. in 15 min. To this mixture was added 2,3-O-1,1-cyclohexanediyl-D-ribofuranose (422 g, 1.83 mol) at 0° C. The resulting solution was stirred for 1 hours at 25° C. The reaction was quenched by the addition of 20 L of water. The resulting solution was extracted with 20 L of ethyl acetate, and the organic layers were combined and dried over sodium sulfate. The resulting mixture was filtered and concentrated under reduced pressure. The residue was purified by column chromatography on silica (EtOAc/petroleum ether (1:3)) to afford (R)-1-((2R,3S)-3-vinyl-1,4-dioxaspiro[4.5]decan-2-yl)ethane-1,2-diol.

Step 3: Into a 20-L 4-necked round-bottom flask, purged and maintained with an inert atmosphere of nitrogen were placed (R)-1-((2R,3S)-3-vinyl-1,4-dioxaspiro[4.5]decan-2-yl)ethane-1,2-diol (630 g, 2.76 mol) and dichloromethane (8.19 L). This was followed by the dropwise addition of a solution of sodium periodate (588 g, 275 mol) in water (4.41 L). The resulting mixture was stirred for 30 minutes at 25° C. The solids were filtered off and the filtrate was concentrated under reduced pressure. The residue was purified via a silica gel column with ethyl acetate/petroleum ether (1:10). The product containing fractions were combined and concentrated under reduced pressure to afford (2S,3S)-3-vinyl-1,4-dioxaspiro[4.5]decane-2-carbaldehyde.

Step 4: Into a 20-L 4-necked round-bottom flask, purged and maintained with an inert atmosphere of nitrogen were placed (2S,3S)-3-vinyl-1,4-dioxaspiro[4.5]decane-2-carbaldehyde (637 g, 3.25 mol) and tetrahydrofuran (7.96 L). This was followed by the dropwise addition of bromo(ethenyl)magnesium (4.88 L, 1 M in THF) with stirring at 0° C. The resulting mixture was stirred for 10 minutes at 0° C., and then warmed to room temperature and allowed to stir for an additional 1 hour at 25° C. The reaction was quenched by the addition of 7 L of saturated aqueous NH$_4$Cl solution. The resulting solution was extracted with 7 L of ethyl acetate, and the combined organic layers were dried over sodium sulfate, filtered, and concentrated under reduced pressure. The residue was purified via a silica gel column with ethyl acetate/petroleum ether (1:50) to afford (R)-1-((2S,3R)-3-vinyl-1,4-dioxaspiro[4.5]decan-2-yl)prop-2-en-1-ol.

Step 5: Into a 20-L 4-necked round-bottom flask, purged and maintained with an inert atmosphere of nitrogen were placed (R)-1-((2S,3R)-3-vinyl-1,4-dioxaspiro[4.5]decan-2-yl)prop-2-en-1-ol (400 g, 1.78 mol), dichloromethane (12.8 L), and Grubbs catalyst (24.3 g). The mixture was stirred for 24 hours at 25° C. To the mixture were added PDC (1.34 kg, 3.57 mol) and 4 Å molecular sieves (400 g). The resulting mixture was stirred for 4 hours at 25° C. The solids were filtered off, and the filtrate was concentrated under reduced pressure. The residue was purified by column chromatography on silica (EtOAc/petroleum ether (1:40)) to afford (3a'S,6a'S)-3a',6a'-dihydro-4'H-spiro[cyclohexane-1,2'-cyclopenta[d][1,3]dioxol]-4'-one.

Step 6: Into a 10-L 4-necked round-bottom flask, purged and maintained with an inert atmosphere of nitrogen, were placed (3a'S,6a'S)-3a',6a'-dihydro-4'H-spiro[cyclohexane-1,2'-cyclopenta[d][1,3]dioxol]-4'-one (246 g, 1.27 mol) and tetrahydrofuran (3.44 L). To this stirring mixture at −78° C. was added methyllithium (1.74 L, 2.79 mol, 1.6 M in diethyl ether) dropwise. The mixture was stirred for 30 minutes at −78° C., then allowed to warm to room temperature and continued to stir for an additional 1 hours at 25° C. The reaction was quenched by the addition of 3 L of saturated aqueous NH₄Cl solution. The resulting solution was extracted with 3 L of ethyl acetate and the organic layers were combined and dried over sodium sulfate, filtered, and concentrated under reduced pressure. The residue was purified by column chromatography on silica (EtOAc/petroleum ether (1:20)) to afford (3a'S,4'R,6a'S)-4'-methyl-4',6a'-dihydro-3a'H-spiro[cyclohexane-1,2'-cyclopenta[d][1,3]dioxol]-4'-ol.

Step 7: Into a 10-L 3-necked round-bottom flask, purged and maintained with an inert atmosphere of nitrogen were placed (3a'S,4'R,6a'S)-4'-methyl-4',6a'-dihydro-3a'H-spiro[cyclohexane-1,2'-cyclopenta[d][1,3]dioxol]-4'-ol (192 g, 913 mmol), dichloromethane (3.84 L), 4 Å molecular sieves (192 g), PDC (688 g, 1.83 mol), and acetic anhydride (747 g, 7.3 mol). The mixture was stirred overnight at 25° C. The reaction was quenched by the addition of 1 L of saturated aqueous Na₂CO₃ solution. The resulting solution was extracted with 1 L of dichloromethane and the combined organic layers were dried over sodium sulfate, filtered, and concentrated under reduced pressure. The residue was purified by column chromatography on silica (EtOAc/petroleum ether (1:50)) to afford (3a'R,6a'R)-6'-methyl-3a',6a'-dihydro-4'H-spiro[cyclohexane-1,2'-cyclopenta[d][1,3]dioxol]-4'-one.

Step 8: Into a 2-L 3-necked round-bottom flask, purged and maintained with an inert atmosphere of nitrogen, was placed CuBrMe₂S (8.43 g, 41.1 mmol) and tetrahydrofuran (627 mL). This was followed by the dropwise addition of bromo(ethenyl)magnesium (548 mL, 2 M in THF, 548 mmol) with stirring at −78° C. To this mixture was added HMPA (294 g, 1.64 mol) at −78° C., then (3a'R,6a'R)-6'-methyl-3a',6a'-dihydro-4'-spiro[cyclohexane-1,2'-cyclopenta[d][1,3]dioxol]-4'-one (57.0 g, 274 mmol) and chlorotrimethylsilane (148 g, 1.36 mol). The resulting mixture was stirred for 3 hours at −78° C. The reaction was quenched by the addition of 500 mL of saturated aqueous NH₄Cl solution. The resultant mixture was extracted with 1 L of ethyl acetate the combined organic layers were dried over sodium sulfate, filtered, and concentrated under reduced pressure. The residue was purified by column chromatography on silica (EtOAc/petroleum ether (1:100)) to afford (3a'R,6'R,6a'R)-6'-methyl-6'-vinyltetrahydro-4'R-spiro[cyclohexane-1,2'-cyclopenta[d][1,3]dioxol]-4'-one.

Step 9: Into a 2-L 3-necked round-bottom flask, purged and maintained with an inert atmosphere of nitrogen were placed (3a'R,6'R,6a'R)-6'-methyl-6'-vinyltetrahydro-4'H-spiro[cyclohexane-1,2'-cyclopenta[d][1,3]dioxol]-4'-one (322 g, 136 mmol) and methanol (966 mL). To this mixture was added CeCl₃.7H₂O (50.8 g) at −30° C., then NaBH₄ (10.3 g, 273 mmol). The resulting mixture was stirred for 15 minutes at −30° C., then allowed to warm to room temperature, and the stirring was continued for an additional 30 minutes at 25° C. The reaction was quenched by the addition of 1 L ethyl acetate/petroleum ether (1:1). The solids were filtered off. The filtrate was concentrated under reduced pressure. The residue was purified by column chromatography on silica (EtOAc/petroleum ether (1:70)) to afford (3a'R,4'R,6'S,6a'S)-4'-methyl-4'-vinyltetrahydro-4'H-spiro [cyclohexane-1,2'-cyclopenta[d][1,3]dioxol]-6'-ol. ¹H NMR (300 MHz, CDCl₃) δ 5.72-5.66 (m, 1H), 5.03-4.99 (m, 2H), 4.45 (t, J=6.0 Hz, 1H), 4.32 (d, J=5.5 Hz, 1H), 4.03-3.99 (m, 1H), 2.51 (d, J=10.0 Hz, 1H), 1.98-1.94 (m, 1H), 1.72-1.52 (m, 9H), 1.43-1.38 (m, 2H), 1.12 (s, 3H).

Synthetic Scheme of Intermediate 5

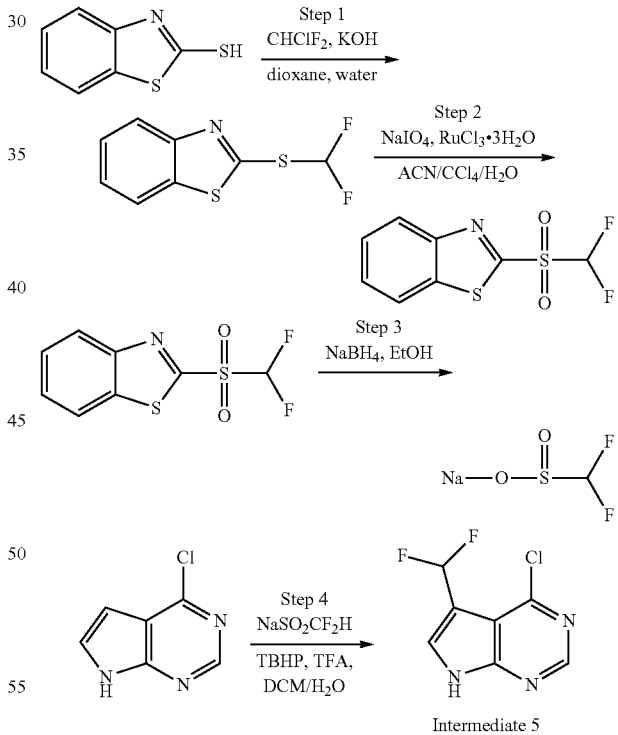

Intermediate 5: 4-chloro-5-(difluoromethyl)-7H-pyrrolo[2,3-d]pyrimidine

Step 1: To a solution of benzo[d]thiazole-2-thiol (50 g, 300 mmol) in 1,4-dioxane (125 mL) and water (125 mL) was added potassium hydroxide (30 g, 540 mmol) at 0° C. Excess chlorodifluoromethane was bubbled through the resulting mixture over 5 h. The reactor was sealed, and the mixture was stirred at room temperature for 8 h before being concentrated under reduced pressure. The residue was purified by column chromatography on silica (neutralized with triethylamine) (0-30% ethyl acetate/hexanes) to give 2-((difluoromethyl)thio)benzo[d]thiazole. MS: 218 (M+1). $^1$H-NMR (300 MHz, Chloroform-d) δ 8.05-8.02 (m, 1H), 7.89-7.86 (m, 1H), 7.67-7.41 (m, 3H). $^{19}$F-NMR (282 MHz, Chloroform-d) δ−93.20 (s, CF$_2$H).

Step 2: To a solution of 2-((difluoromethyl)thio)benzo[d]thiazole (11.1 g, 51 mmol) in a mixture of ACN/CCl$_4$/water (v:v:v=1:1:2, 222 mL) were added sodium periodate (34.2 g, 160 mmol) and ruthenium(III) chloride trihydrate (33 mg, 0.13 mmol) portion wise. The resulting solution was stirred at room temperature for 3 h. The mixture was diluted with water (800 mL) and extracted with DCM (1500 mL). The organic phase was washed with brine (800 mL), dried over anhydrous sodium sulfate, and filtered. The filtrate was concentrated under reduced pressure, and the residue was purified by column chromatography on silica (0-20% ethyl acetate/DCM) to give 2-((difluoromethyl)sulfonyl)benzo[d]thiazole. MS: 250 (M+1). $^1$H-NMR (400 MHz, Chloroform-d) δ 8.38-8.33 (m, 1H), 8.15-8.06 (m, 1H), 7.76-7.69 (m, 2H), 6.62 (t, J=52 Hz, 1H). $^{19}$F-NMR (376 MHz, Chloroform-d) δ−121.39 (s, CF$_2$H).

Step 3: To a solution of 2-((difluoromethyl)sulfonyl) benzo[d]thiazole (116.5 g, 467 mmol) in ethanol (700 mL) was added sodium borohydride (26.5 g, 700 mmol) portion wise at room temperature under argon atmosphere. The mixture was stirred at room temperature for 2 h. The reaction mixture was concentrated under reduced pressure. The crude material was triturated with hexane (600 mL×3) at room temperature to afford sodium difluoromethanesulfinate. $^1$H-NMR (400 MHz, Methanol-d$_4$) δ 5.14 (1, J=56 Hz, 1H). $^{19}$F-NMR (376 MHz, Methanol-d$_4$) δ−128.92 (s, CF$_2$H).

Step 4: To a solution of 4-chloro-7H-pyrrolo[2,3-d]pyrimidine (10 g, 65.1 mmol) in DCM (150 mL) and water (60 mL) were added sodium difluoromethanesulfinate (27 g, 195 mmol) and TFA (10.0 mL, 130 mmol) portion wise at 0° C. To this mixture was dropwise added tert-butyl hydroperoxide (5.5M in decane, 59 mL, 330 mmol) and the resulting mixture was stirred at room temperature for 5 days before being quenched with sodium bicarbonate (2 M aq, 110 mL). The mixture was extracted with DC M (200 mL×3). The combined organic layers were washed with brine (200 mL×3), dried over anhydrous sodium sulfate, filtered, and the filtrate was concentrated under reduced pressure. The product was purified by column chromatography (0-20% ethyl acetate/hexanes) to give 4-chloro-5-(difluoromethyl)-7H-pyrrolo[2,3-d]pyrimidine. MS: 204 (M+1). $^1$H-NMR (400 MHz, DMSO-d$_6$) δ 13.40 (br s, 1H), 8.73 (s, 1H), 7.31 (t, J=54 Hz, 1H), 7.00-7.00 (m, 1H). $^{19}$F-NMR (376 MHz, DMSO-d$_6$) δ−112.14 (s, CF$_2$H).

Synthetic Scheme of Intermediate 6

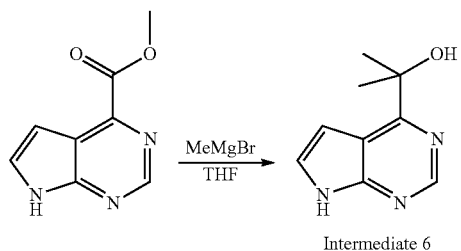

Intermediate 6

Intermediate 6: 2-(7H-pyrrolo[2,3-d]pyrimidin-4-yl) propan-2-ol

Methyl 7H-pyrrolo[2,3-d]pyrimidine-4-carboxylate (0.52 g, 2.9 mmol) dissolved in tetrahydrofuran (12 mL) was purged with nitrogen and cooled to −78° C. To the solution was added methylmagnesium bromide (1.4 M, 4.6 mL, 6.5 mmol), and the reaction was warmed to room temperature and stirred for 1 h. After 2 hours additional methylmagnesium bromide (1.4 M, 4.6 mL, 6.5 mmol) was added at −78° C., and the reaction stirred for 18 h and warmed to room temperature. The reaction was quenched with saturated aq. ammonium chloride and stirred for 1 h. at room temperature. The organics were separated, washed with brine, dried over sodium sulfate, and the solvents were removed under reduced pressure to afford 2-(7H-pyrrolo[2,3-d]pyrimidin-4-yl)propan-2-ol, which was used without further purification. MS: 178 (M+1).

Synthetic Scheme of Intermediate 7

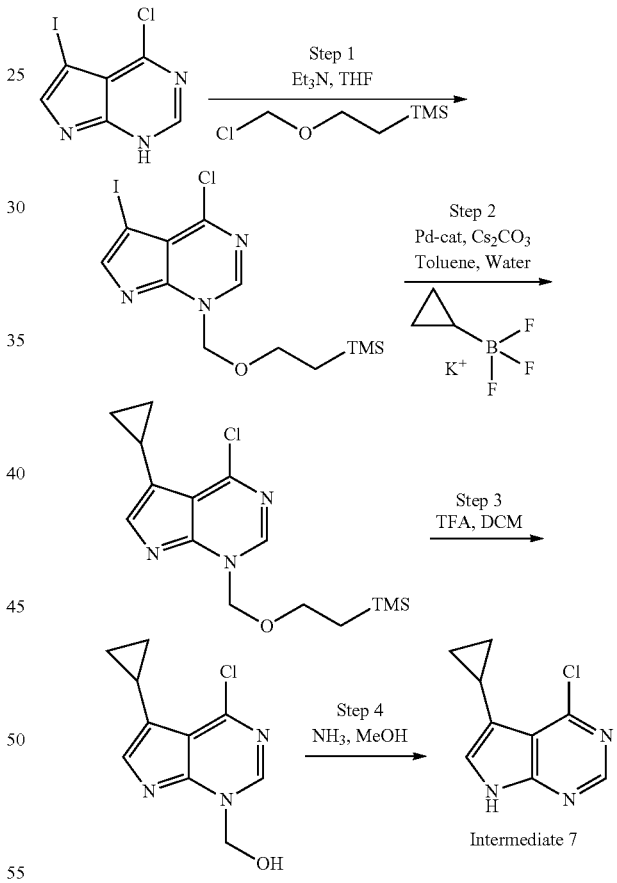

Intermediate 7

Intermediate 7: 4-Chloro-5-cyclopropyl-1H-pyrrolo [2,3-d]pyrimidine

Step 1: To a stirred mixture of 4-chloro-5-iodo-1H-pyrrolo[2,3-d]pyrimidine (10.0 g, 35.8 mmol) in THF (119 mL) was added triethylamine (12.5 mL, 89.0 mmol) and (2-(chloromethoxy)ethyl)trimethylsilane (7.60 mL, 42.9 mmol) at 0° C. The mixture was warmed to room temperature and stirred overnight. The mixture was treated with water and extracted with EtOAc. The combined organics were washed with brine, dried over sodium sulfate, concentrated under reduced pressure, and purified by column chromatography on silica (0-10% EtOAc/DCM) to afford 4-chloro-5-iodo-7-{[2-(trimethylsilyl)ethoxy]methyl}-7H-pyrrolo[2,3-d]pyrimidine. MS: 410 (M+1). $^1$H NMR (500 MHz, DMSO-$d_6$) δ 8.69 (s, 1H), 8.13 (s, 1H), 5.60 (s, 2H), 3.57-3.45 (m, 2H), 0.87-0.75 (m, 2H), −0.10 (s, 9H).

Step 2: A mixture of 4-chloro-5-iodo-7-{[2-(trimethylsilyl)ethoxy]methyl}-7H-pyrrolo[2,3-d]pyrimidine (12.2 g, 29.8 mmol), potassium cyclopropyltrifluoroborate (5.29 g, 35.7 mmol), cesium carbonate (291 g, 89.0 mmol), and [(di(1-adamantyl)-butylphosphine)-2-(2'-amino-1,1'-biphenyl)]palladium(II) methanesulfonate (2.17 g, 2.98 mmol) in toluene (135 mL)/water (13.5 mL) was purged with nitrogen and then stirred at 100° C. for 10 h. The mixture was cooled to room temperature, diluted with EtOAc, and washed with water and brine. The organic layer was dried over sodium sulfate, concentrated, and purified by column chromatography on silica (0-20% EtOAc/DCM) to afford 4-chloro-5-cyclopropyl-7-{[2-(trimethylsilyl)ethoxy]methyl}-7H-pyrrolo[2,3-d]pyrimidine. MS: 324 (M+1).

Step 3: To a stirred solution of 4-chloro-5-cyclopropyl-7-{[2-(trimethylsilyl)ethoxy]methyl}-7H-pyrrolo[2,3-d]pyrimidine (7.35 g, 22.7 mmol) in DCM (91 mL) was added TFA (14.0 mL, 182 mmol). The mixture was stirred at 32° C. overnight. The mixture was cooled to room temperature, concentrated, diluted with EtOAc, and washed with saturated sodium bicarbonate solution. The organic layer was dried over sodium sulfate, concentrated, and purified by silica gel chromatography (0-100% EtOAc in DCM) to afford (4-chloro-5-cyclopropyl-7H-pyrrolo[2,3-d]pyrimidin-7-yl)methanol. MS: 224 (M+1). $^1$H NMR (500 MHz, DMSO-$d_6$) δ 8.59 (s, 1H), 7.49-7.38 (m, 1H), 6.73-6.59 (m, 1H), 5.53 (d, J=4.6 Hz, 2H), 2.20-2.09 (m, 1H), 1.00-0.85 (m, 2H), 0.71-0.59 (m, 2H).

Step 4: To (4-chloro-5-cyclopropyl-7H-pyrrolo[2,3-d]pyrimidin-7-yl)methanol (3.40 g, 15.2 mmol) was added ammonia (7 N in MeOH, 58.6 mL, 410 mmol). The solution was left to stir for 10 min, concentrated, and purified by column chromatography on silica (0-100% EtOAc/DCM) to afford 4-chloro-5-cyclopropyl-1H-pyrrolo[2,3-d]pyrimidine. MS: 194 (M+1). $^1$H NMR (600 MHz, DMSO-$d_6$) δ 12.23 (s, 1H), 8.51 (s, 1H), 7.34 (d, J=0.8 Hz, 1H), 2.17-2.09 (m, 1H), 0.91-0.86 (m, 2H), 0.68-0.62 (m, 2H).

Synthetic Scheme of Intermediate 8.

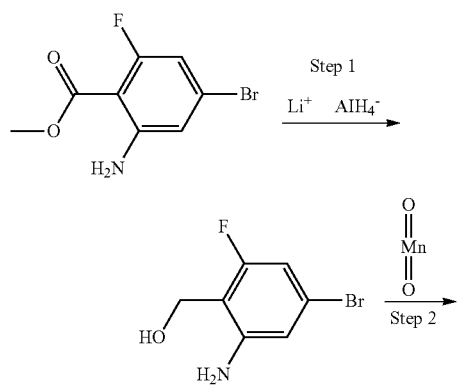

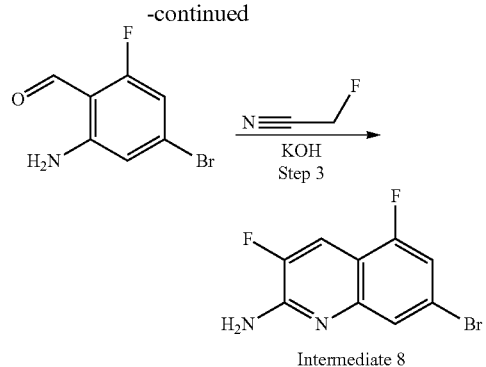

Intermediate 8:
7-bromo-3,5-difluoroquinolin-2-amine

Step 1: Methyl 2-amino-4-bromo-6-fluorobenzoate (5.0 g, 20 mmol) was dissolved in THF (40 mL) under an atmosphere of nitrogen and cooled to 0° C. Lithium Aluminum Hydride (1M in THF 40.3 mL, 40.3 mmol) was added dropwise to the stirring solution. The reaction was stirred for 3 h and cooled to 0° C. The reaction was quenched with sequential dropwise additions of water (2 mL), sodium hydroxide (1N in water, 3 mL), and water (6 mL). Magnesium sulfate w as then added and stirred for 30 minutes. The solution was filtered through a pad of Celite® and the solvent removed under reduced pressure. The residue was purified by column chromatography on silica (0-30% DCM/3:1 EtOAc/EtOH) to afford (2-amino-4-bromo-6-fluorophenyl)methanol. MS: 202/204 (M−18/M−16).

Step 2: Manganese(IV) Oxide (4.27 g, 49.1 mmol) was added to a stirring solution of (2-amino-4-bromo-6-fluorophenyl)methanol (2.7 g, 12.27 mmol) in DCM (61 mL). The reaction was stirred for 18 h at 40° C. The reaction was filtered through a pad of Celite® and rinsed with EtOAc, and the solvent removed to afford 2-amino-4-bromo-6-fluorobenzaldehyde, which was used without further purification. MS: 218/220 (M+1/M+3).

Step 3: 2-Amino-4-bromo-6-fluorobenzaldehyde (1.20 g, 5.50 mmol) was dissolved in DMSO (11 mL). To the stirring solution was added 2-fluoroacetonitrile (1.2 mL, 22 mmol) and potassium hydroxide (0.055 mL, 0.83 mmol). The reaction mixture was then stirred at 80° C. for 18 h. The reaction was then diluted with EtOAc, added to water, and let stir for several minutes. The aqueous layer was separated and washed with EtOAc. The combined organic layers were dried over sodium sulfate, filtered, and the solvent removed under reduced pressure. The material was purified by column chromatography on silica (0-100% EtOAc/Hexanes) to afford 7-bromo-3,5-difluoroquinolin-2-amine. MS: 259/261 (M+1/1+3). $^1$H NMR (DMSO-d6) δ: 7.89 (d, J=11 Hz, 1H), 7.52 (s, 1H), 7.32 (dd, J=10, 1 Hz, 1H), 7.28 (s, 2H)

Intermediates 9-10: Intermediates 9-10 (as shown in Table 1) were synthesized using the protocol described with intermediate 8 making the appropriate substitution for the aryl-ester in step 1 or the benzylic alcohol in step 2 or the aryl-aldehyde in step 3. The substituted reagents and starting material were commercially acquired, synthesized as reported above, or synthesized through known routes reported in the literature.

TABLE 1

| Intermediate | Structure | Name | MS |
|---|---|---|---|
| 9 | 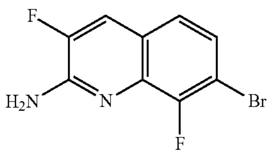 [SMILES: Nc1nc2c(F)c(Br)ccc2cc1F] | 7-bromo-3,8-difluoroquinolin-2-amine | 259/261 (M + 1/M + 3) |
| 10 | 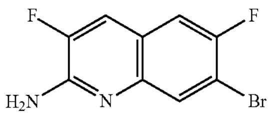 | 7-bromo-3,6-difluoroquinolin-2-amine | 259/261 (M + 1/M + 3) |

Synthetic Scheme of Intermediate 11

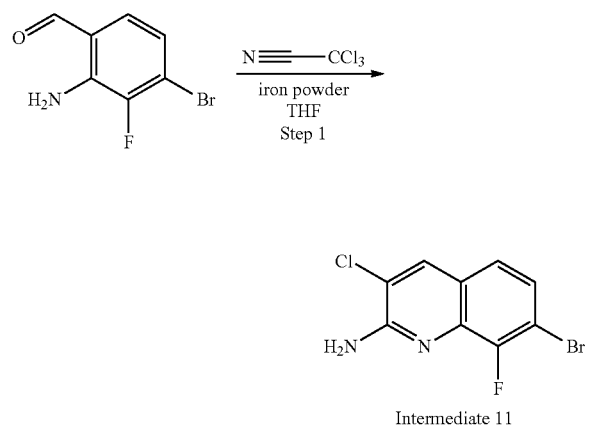

TABLE 2

| Intermediate | Structure | Name | MS |
|---|---|---|---|
| 12 | 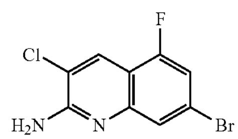 | 7-bromo-3-chloro-5-fluoroquinolin-2-amine | 275/277 (M + 1/M + 3) |

Synthetic Scheme of Intermediate 13

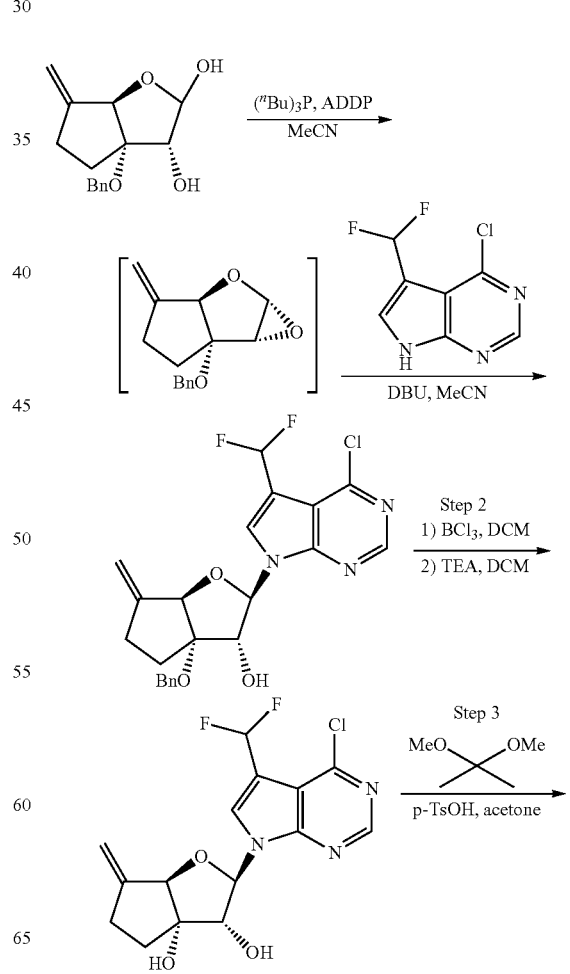

Intermediate 11:
7-bromo-3-chloro-8-fluoroquinolin-2-amine

A flask containing 2-amino-4-bromo-3-fluorobenzaldehyde (1.8 g, 8.3 mmol) and iron powder (4.6 g, 80 mmol) was purged with nitrogen, charged with THF (16.5 mL), trichloroacetonitrile (1.2 mL, 12 mmol) and heated to 65° C. overnight. The reaction was cooled to room temperature, filtered, and washed with EtOAc. The organics were concentrated under reduced pressure, and the residue was purified by column chromatography on silica (0-100% EtOAc/DCM). The product containing fractions were concentrated under reduced pressure. The residue was dissolved in THF (50 mL), charged with N-propyldiethanolamine-functionalized silica gel (0.84 mmol/g) and allowed to stir overnight. The silica was filtered off through a pad of Celite® and washed with THF (50 mL). The organics were concentrated under reduced pressure to yield 7-bromo-3-chloro-8-fluoroquinolin-2-amine. MS: 275/277 (M+1/M+3). $^1$H NMR (500 MHz, DMSO-d6) δ 8.32 (s, 1H), 7.48-7.45 (m, 1H), 7.41 (m, 1H), 7.26 (br s, 2H).

Intermediate 12: Intermediate 12 in Table 2 was synthesized using the protocol described in intermediate II making the appropriate substitution for the aryl-aldehyde. The substituted starting material was commercially acquired, synthesized as reported above, or synthesized through known routes reported in the literature.

-continued

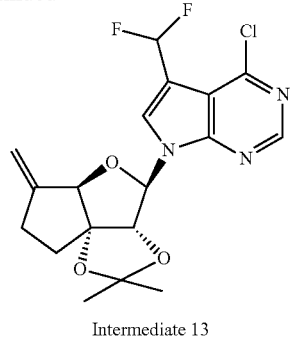

Intermediate 13

Intermediate 13: 4-chloro-5-(difluoromethyl)-7-(3aR,4R,5aR,8aR)-dimethyl-6-methylenehexahydro-cyclopenta[2,3]furo[3,4-d][1,3]dioxol-4-yl)-7H-pyrrolo[2,3-d]pyrimidine Step 1: To a stirred solution of (3R,3aS,6aR)-3a-(benzyloxy)-6-methylenehexaydro-2H-cyclopenta[b]furan-2,3-diol (1.0 g, 3.8 mmol) in dry acetonitrile (60 mL) was dropwise added (E)-diazene-1,2-diylbis(piperidin-1-yl-methanone) (1.54 g, 6.1 mmol) at 0° C. under the atmosphere of argon, followed by tributylphosphine (1.4 mL, 5.7 mmol). The resulting mixture was stirred at 35° C. for 1 h. In a separate container, DBU (0.86 mL, 5.7 mmol) was added to a stirring solution of 4-chloro-5-(difluoromethyl)-7H-pyrrolo[2,3-d]pyrimidine (1.1 g, 5.3 mmol) in dry acetonitrile (25 mL) under the atmosphere of argon at room temperature. The resultant mixture was stirred at room temperature for 30 min. The DBU solution was transferred to the above epoxide containing solution by means of a syringe. The final mixture was stirred at 35° C. for 16 h. The reaction mixture was quenched by adding saturated aqueous ammonium chloride (150 mL) and extracted with ethyl acetate (100 mL×3). The combined organics was washed with brine (100 mL), dried over anhydrous sodium sulfate, and filtered. The filtrate was concentrated under reduced pressure. The product was purified by column chromatography on silica (0-30% ethyl acetate/petroleum ether) to give (2R,3R,3aS,6aR)-3a-(benzyloxy)-2-(4-chloro-5-(difluoromethyl)-7H-pyrrolo[2,3-d]pyrimidin-7-yl)-6-methylenehexahydro-2H-cyclopenta[b]furan-3-ol. MS: 448(M+1). $^1$H NMR (300 MHz, DMSO-$d_6$) δ 8.84 (s, 1H), 7.61-7.21 (m, 7H), 6.16 (d, J=8.1 Hz, 1H), 5.77 (d, J=6.3 Hz, 1H), 5.21-5.14 (m, 3H), 4.94 (d, J=12.0 Hz, 1H), 4.72-4.66 (m, 2H), 2.85-2.75 (m, 1H), 2.59-2.54 (m, 1H), 2.28-2.25 (m, 1H), 2.07-2.00 (m, 1H). $^{19}$F NMR (282 MHz, DMSO-$d_6$) δ −109.36 (d, 1F), −114.08 (d, 1F).

Step 2: To a solution of (2R,3R,3aS,6aR)-3a-(benzyloxy)-2-(4-chloro-5-(difluoromethyl)-7H-pyrrolo[2,3-d]pyrimidin-7-yl)-6-methylenehexahydro-2H-cyclopenta[b]furan-3-ol (1.79 g, 4.00 mmol) in DCM (20 mL) was added boron trichloride (1M in DCM, 8.0 mL, 8.0 mmol) at −78° C. under argon atmosphere. The mixture was then stirred at −78° C. for 2 h. Triethylamine (2.2 mL, 16 mmol) was carefully added at −78° C. to quench the reaction and the mixture was stirred at −78° C. for 0.5 h. The mixture was poured into saturated aqueous sodium bicarbonate (100 mL) at 0° C. The mixture was extracted with 200 mL of ethyl acetate. The organic phase was washed with water (30 mL) and brine (60 mL), dried over anhydrous sodium sulfate, and filtered. The filtrate was concentrated under reduced pressure, and the residue was purified by column chromatography on silica (0-50% ethyl acetate/petroleum ether) to give (2R,3R,3aS,6aR)-2-(4-chloro-5-(difluoromethyl)-7H-pyrrolo[2,3-d]pyrimidin-7-yl)-6-methylenehexahydro-2H-cyclopenta[b]furan-3,3a-diol. MS: 358(M+1). $^1$H NMR (400 Hz, DMSO-$d_6$) δ 8.81 (s, 1H), 7.59-7.09 (m, 2H), 6.07-6.04 (m, 1H), 5.50-5.47 (m, 1H), 5.31 (d, J=4.4 Hz, 1H), 5.14-5.09 (m, 2H), 4.94-4.89 (m, 1H), 4.40 (d, J=4.0 Hz, 1H), 2.80-2.67 (m, 1H), 2.51-2.41 (n 1H), 2.13-2.06 (m, 1H), 1.71-1.65 (m, 1H). $^{19}$F NMR (376 MHz, DMSO-$d_6$) δ−108.88 (d, 1F), −114.52 (d, 1F).

Step 3: To a mixture of (2R,3R,3aS,6aR)-2-(4-chloro-5-(difluoromethyl)-7H-pyrrolo[2,3-d]pyrimidin-7-yl)-6-methylenehexahydro-2H-cyclopenta[b]furan-3,3a-diol (670 mg, 1.87 mmol) in acetone (12 mL) was added 2,2-dimethoxypropane (1.2 mL, 9.4 mmol) and 4-methylbenzenesulfonic acid (32 mg, 0.19 mmol) portion wise at ambient temperature. The reaction mixture was stirred at ambient temperature for 16 h. The mixture was concentrated under reduced pressure, and the residue was purified by column chromatography on silica (0-30% ethyl acetate/petroleum ether) to give 4-chloro-5-(difluoromethyl)-7-((3aR,4R,5aR,8aR)-2,2-dimethyl-6-methylenehexahydrocyclopenta[2,3]furo[3,4-d][1,3]dioxol-4-yl)-7H-pyrrolo[2,3-d]pyrimidine. MS: 398 (M+1). $^1$H NMR (300 MHz, Methanol-$d_4$) δ 8.74 (s, 1H), 7.40-7.05 (m, 2H), 6.27 (d, J=4.5 Hz, 1H), 5.76 (d, J=4.2 Hz, 1H), 5.09-5.06 (m, 2H), 4.63 (s, 1H), 2.94-2.72 (m, 2H), 2.57-2.50 (m, 1H), 2.19-2.08 (m, 1H), 1.62 (s, 3H), 1.44 (s, 3H). $^{19}$F NMR (282 MHz Methanol-$d_4$) δ−112.94 (d, 1F), −115.23 (d, 1F).

Synthetic Scheme of Intermediate 14

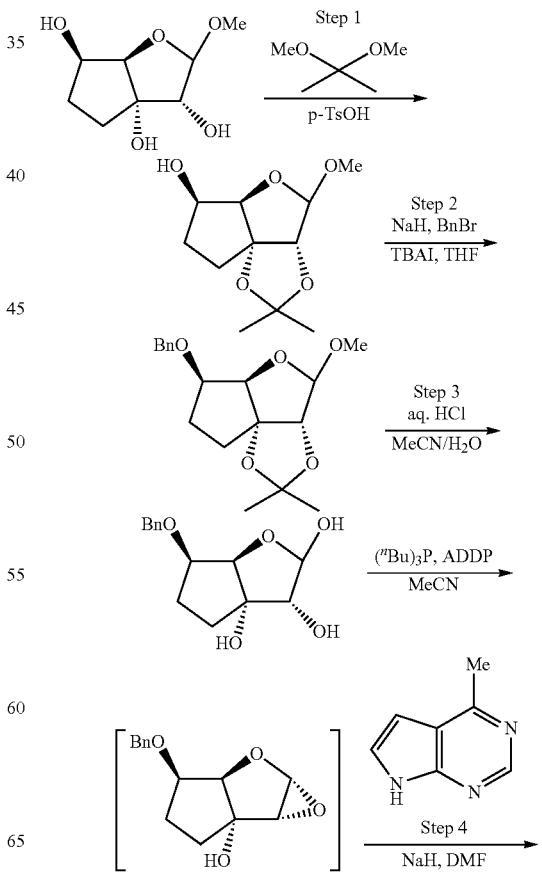

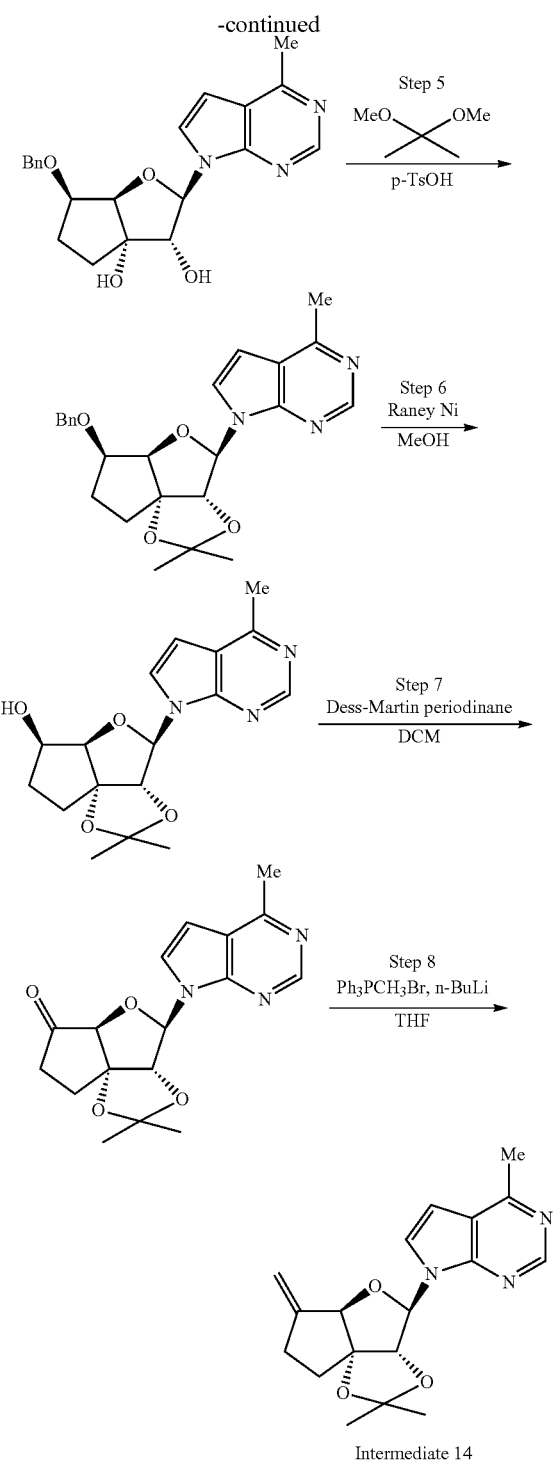

Intermediate 14: 7-((3aR,4R,5aR,8aR)-2,2-dimethyl-6-methylenehexahydrocyclopenta[2,3]furo[3,4-d]dioxol-4-yl)-4-methyl-7H-pyrrolo[2,3-d]pyrimidine Step 1: (3R,3aS,6R,6aR)-2-methoxyhexahydro-2H-cyclopenta[b]furan-3,3a,6-triol (2 g, 10 mmol) was co-evaporated with dry toluene (5 mL×3) and then re-dissolved in acetone (50 mL). To this solution was added 4-methylbenzenesulfonic acid (0.091 g, 0.53 mmol), followed by 2,2-dimethoxypropane (2.74 g, 26.3 mmol). The resulting mixture was stirred at ambient temperature for 1 h. The pH of the resulting solution was adjusted to 8 with saturated aqueous NaHCO$_3$ (50 mL) at 0° C. The resulting mixture was extracted with EtOAc (150 mL×3). The combined organic layers were washed with brine (100 mL), dried over anhydrous Na$_2$SO$_4$, filtered, and the filtrate was concentrated under reduced pressure. The residue was purified by column chromatography on silica (EtOAc/pet. ether) to afford (3aR,5aR,6R,8aR)-4-methoxy-2,2-dimethylhexahydrocyclopenta[2,3]furo[3,4-d][1,3]dioxol-6-ol. MS: 248.20 (M+NH$_4$). $^1$H NMR (300 MHz, DMSO-d$_6$) δ 4.96 (s, 1H), 4.41 (d, J=5.1 Hz, 1H), 4.17 (s, 1H), 4.10 (d, J=6.0 Hz, 1H), 3.88-3.79 (m, 1H), 3.33 (s, 3H), 2.04-1.92 (m, 1H), 1.76-1.62 (m, 3H), 1.39 (s, 3H), 1.31 (s, 3H). The column was further eluted with 45-50% of EtOAc in petroleum ether to afford (3aR,5aR,6R,8aR)-4-methoxy-2,2-dimethylhexahydrocyclopenta[2,3]furo[3,4-d][1,3]dioxol-6-ol. MS: 248 (M+NH$_4$). $^1$H NMR (300 MHz, DMSO-d$_6$) δ 4.92 (d, J=4.2 Hz, 1H), 4.72 (d, J=6.0 Hz, 1H), 4.35 (d, J=4.2 Hz, 1H), 4.00 (d, J=(5.4 Hz, 1H), 3.91-3.82 (m, 1H), 3.35 (s, 3H), 2.09-1.97 (m, 1H), 1.83-1.62 (m, 2H), 1.52-1.43 (m, 1H), 1.40 (s, 3H), 1.31 (s, 3H).

Step 2: To a mixture of sodium hydride (60% wt. dispersed in mineral oil, 0.88 g, 22 mmol) in anhydrous THF (20 mL) was added tetrabutylammonium iodide (0.67 g, 1.8 mmol) at ambient temperature under argon atmosphere. The mixture was cooled to 0° C., and a solution of (3aR,5aR,6R,8aR)-4-methoxy-2,2-dimethylhexahydrocyclopenta[2,3]furo[3,4-d][1,3]dioxol-6-ol (4.2 g, 18 mmol) in THF (15 mL) was added. The mixture was stirred for 0.5 h at ambient temperature. A solution of (bromomethyl)benzene (2.6 mL, 22 mmol) in THF (5 mL) was added to the mixture at 0° C. The resulting mixture was stirred at ambient temperature for 12 h. The reaction mixture was quenched with saturated aqueous NH$_4$Cl (100 mL) at 0° C. The resulting mixture was extracted with EtOAc (2×300 mL). The combined organic layers were washed with saturated aqueous NaHCO$_3$ (100 mL) and brine (100 mL). The organic layer was dried over anhydrous Na$_2$SO$_4$, filtered, and the filtrate was concentrated under reduced pressure. The crude product was purified by column chromatography on silica (0%-10% EtOAc/petroleum ether) to afford (3aR,4S,5aR,6R,8aR)-6-(benzyloxy)-4-methoxy-2,2-dimethylhexahydrocyclopenta[2,3]furo[3,4-d][1,3]dioxole. MS: 343(M+Na). $^1$H NMR (300 MHz, DMSO-d$_6$) δ 7.33-7.25 (m, 5H), 4.96-4.94 (m, 1H), 4.59 (d, J=11.7 Hz, 1H), 4.42 (d, J=11.7 Hz, 1H), 4.34 (d, J=6.0 Hz, 1H), 4.19-417 (m, 1H), 3.77-3.70 (m, 1H), 3.24 (s, 3H), 2.04-1.97 (m, 1H), 1.85-1.64 (m, 3H), 1.38 (s, 3H), 1.29 (s, 3H).

Step 3: To a solution of (3aR,4S,5aR,6R,8aR)-6-(benzyloxy)-4-methoxy-2,2-dimethylhexahydro cyclopenta[2,3]furo[3,4-d][1,3]dioxole (5.7 g, 18 mmol) in acetonitrile (150 mL) and water (100 mL) was added concentrated aq. hydrochloric acid (8.6 mL, 103 mmol) dropwise at ambient temperature. The reaction mixture was stirred at 90° C. for 1 h. The pH value of the resulting solution was adjusted to 7 with 1 M aq. NaOH at 0° C. The mixture was concentrated under reduced pressure. The residue was purified by column chromatography on silica (0-10% Methanol/DCM) to give (3R,3a'S,6R,6aR)-6-(benzyloxy)hexahydro-2-cyclopenta[b]furan-2,3,3a-triol. MS: 284 (M+NH$_4$).

Step 4: To a stirred mixture of (3R,3aS,6R,6aR)-6-(benzyloxy)hexahydro-2H-cyclopenta[b]furan-2,3,3a-triol (1.7 g, 6.4 mmol) in dry acetonitrile (100 mL) was added tributylphosphine (2.55 mL, 10 mmol) under argon atmosphere, followed by (E)-diazene-1,2-diylbis(piperidin-1-ylmethanone) (2.4 g, 9.6 mmol) at room temperature. The resulting mixture was stirred at room temperature for 30 min. The resulting epoxide containing solution was used directly without any further processing. A separate round bottom flask was charged with a solution of 4-methyl-7H-pyrrolo[2,3-d]pyrimidine (1.7 g, 13 mmol) in dry DMF (25 mL). To this was added sodium hydride (60 wt. % dispersed in mineral oil) (0.77 g, 19 mmol) at 0° C. under argon atmosphere. The suspension was stirred at room temperature for 30 min, and then it was transferred to the previous obtained epoxide containing solution by means of a syringe. The resulting mixture was stirred at room temperature for 1 h. The reaction was quenched by the addition of saturated aqueous ammonium chloride (100 mL) and extracted with EtOAc (3×100 mL). The combined organic layers were washed with brine (100 mL), dried over anhydrous sodium sulfate, and filtered. The filtrate was concentrated under reduced pressure. The residue was purified by reverse-phase column chromatography on C18 (0-95% 5 mM aq. $NH_4HCO_3$/ACN) to give (2R,3R,3aS,6R,6aR)-6-(benzyloxy)-2-(4-methyl-7H-pyrrolo[2,3-d]pyrimidin-7-yl)hexahydro-2H-cyclopenta[b]furan-3,3a-diol. MS: 382(M+1). $^1$H-NMR (300 MHz, DMSO-$d_6$) δ 8.69 (s, 1H), 7.74 (d, J=3.6 Hz, 1H), 7.36-7.25 (m, 5H), 6.73 (d, J=3.9 Hz, 1H), 6.16 (d, J=8.4 Hz, 1H), 5.41 (d, J=6.9 Hz, 1H), 5.24 (s, 1H), 4.55-4.50 (m, 2H), 4.27-4.19 (m, 2H), 3.92-3.86 (m, 1H), 2.67 (s, 3H), 2.02-1.98 (m, 3H), 1.60-1.52 (m, 1H).

Step 5: To a mixture of (2R,3R,3aS,6R,6aR)-6-(benzyloxy)-2-(4-methyl-7H-pyrrolo[2,3-d]pyrimidin-7-yl)hexahydro-2H-cyclopenta[b]furan-3,3a-diol (2.4 g, 6.3 mmol) in 2,2-dimethoxypropane (50 mL) under argon atmosphere was added 4-methylbenzenesulfonic acid (0.11 g, 0.63 mmol) at ambient temperature. The mixture was stirred at 70° C. for 48 h. The mixture was quenched with saturated aqueous $NaHCO_3$ (50 mL), and then extracted with DCM (100 mL×3). The combined organic layers were dried over anhydrous $Na_2SO_4$, filtered, and the filtrate was concentrated under reduced pressure. The residue was purified by column chromatography on silica (0-60% EtOAc/Petroleum ether) to give 7-((3aR,4R,5aR,6R,8aR)-6-(benzyloxy)-2,2-dimethylhexahydrocyclopenta[2,3]furo[3,4-d][1,3]dioxol-4-yl)-4-methyl-7H-pyrrolo[2,3-d]pyrimidine. MS: 422(M+1). $^1$H-NMR (400 MHz, DMSO-$d_6$) δ 8.71 (s, 1H), 7.79 (d, J=4.0 Hz, 1H), 7.33-723 (m, 5H), 6.81 (d, J=3.6 Hz, 1H), 6.32 (d, J=4.4 Hz, 1H), 5.15 (d, J=4.8 Hz, 1H), 4.51 (q, J=12.0 Hz, 2H), 4.42 (d, J=4.4 Hz, 1H), 3.93-3.87 (m, 1H), 2.67 (s, 3H), 2.47-2.41 (m, 1H), 2.03-1.99 (m, 1H), 1.95-1.83 (m, 2H), 1.55 (s, 3H), 1.36 (s, 3H).

Step 6: To a solution of 7-((3aR,4R,5aR,6R,8aR)-6-(benzyloxy)-2,2-dimethylhexahydrocyclopenta[2,3]furo[3,4-d][1,3]dioxol-4-yl)-4-methyl-7H-pyrrolo[2,3-d]pyrimidine (1.2 g, 2.9 mmol) in anhydrous MeOH (35 mL) under argon atmosphere was added wet Raney Ni (8 g, 50 wt. % in water) at ambient temperature. The resulting mixture was stirred at 60° C. for 5 h. The resulting mixture was filtered, and the filtrate was concentrated under reduced pressure. The product was purified by column chromatography on silica (0-100% EtOAc/petroleum ether) to give (3aR,4R,5aR,6R,8aR)-2,2-dimethyl-4-(4-methyl-7H-pyrrolo[2,3-d]pyrimidin-7-yl)hexahydrocyclopenta[2,3]furo[3,4-d][1,3]dioxol-6-ol. MS: 332(M+1). $^1$H-NMR (400 MHz, DMSO-$d_6$) δ 8.70 (s, 1H), 7.83 (d, J=4.0 Hz, 1H), 6.83 (d, J=4.0 Hz, 1H), 6.29 (d, J=4.4 Hz, 1H), 5.10 (d, J=4.8 Hz, 1H), 4.92 (d, J=6.0 Hz, 1H), 4.15 (d, J=4.8 Hz, 1H), 3.98-3.94 (m, 1H), 2.68 (s, 3H), 2.43-2.35 (m, 1H), 1.90-1.84 (m, 3H), 1.55 (s, 3H) 1.36 (s, 3H).

Step 7: To a mixture of (3aR,4R,5aR,6R,8aR)-2,2-dimethyl-4-(4-methyl-7H-pyrrolo[2,3-d]pyrimidin-7-yl)hexahydrocyclopenta[2,3]furo[3,4-d][1,3]dioxol-6-ol (2.0 g, 6.04 mmol) in DCM (60 mL) was added Dess-Martin Periodinane (4.6 g, 11 mmol) at 25° C. under argon atmosphere. The resulting mixture was stirred at 25° C. for 1.5 h. The mixture was quenched by the addition of saturated aqueous $NaHCO_3$ (150 mL) and extracted with EtOAc (3×250 mL). The combined organic layers were dried over anhydrous $Na_2SO_4$, filtered, and the filtrate was concentrated under reduced pressure. The residue was purified by column chromatography on silica (0-100% EtOAc/Petroleum ether to give (3aR,4R,5aS,8aS)-2,2-dimethyl-4-(4-methyl-7H-pyrrolo[2,3-d]pyrimidin-7-yl)tetrahydrocyclopenta[2,3]furo[3,4-d][1,3]dioxol-6(5aH)-one. MS: 330 (M+1). $^1$H-NMR (400 MHz, DMSO-$d_6$) δ 8.67 (s, 1H), 7.63 (d, J=3.6 Hz, 1H), 6.75 (d, J=3.6 Hz, 1H), 6.36 (d, J=2.4 Hz, 1H), 5.51 (d, J=2.8 Hz, 1H), 4.56 (s, 1H), 2.96-2.82 (m, 1H), 2.78-2.59 (m, 5H), 2.42-2.34 (m, 1H), 1.57 (s, 3H), 1.46 (s, 3H).

Step 8: To a mixture of bromo(methyl)triphenylphosphorane (5.8, 16 mmol) in THF (30 mL) was added n-butyllithium (2.5 M in hexane, 6 mL, 15 mmol) at −10° C. under argon atmosphere. The resulting mixture was stirred at −10° C. for 0.5 h. To this was added dropwise a solution of (3aR,4R,5aS,8aS)-2,2-dimethyl-4-(4-methyl-7H-pyrrolo[2,3-d]pyrimidin-7-yl)tetrahydrocyclopenta[2,3]furo[3,4-d][1,3]dioxol-6(5aH)-one (1.9 g, 5.8 mmol) in THF (30 mL) at −10° C. The resulting mixture was stirred at −10° C. for 1 h. The mixture was quenched by the addition of saturated aqueous $NH_4Cl$ (150 mL) then extracted with DCM (3×200 mL). The combined organic layers were dried over anhydrous $Na_2SO_4$, filtered, and the filtrate was concentrated under reduced pressure. The residue was purified by column chromatography on silica (0-60% EtOAc/Petroleum ether) to give 7-((3aR,4R,5aR,8aR)-2,2-dimethyl-6-methylenehexahydrocyclopenta[2,3]furo[3,4-d][1,3]dioxol-4-yl)-4-methyl-7H-pyrrolo[2,3-d]pyrimidine. 328(M+1). $^1$H-NMR (400 MHz, DMSO-$d_6$) δ 8.70 (s, 1H), 7.68 (d, J=3.6 Hz, 1H), 6.80 (d, J=3.6 Hz, 1H), 6.32 (d, J=4.0 Hz, 1H), 5.27 (d, J=4.0 Hz, 1H), 5.13-5.11 (m, 2H), 4.61 (s, 1H), 2.67 (s, 3H), 2.61-2.40 (m, 3H), 2.05-1.95 (m, 1H), 1.56 (s, 3H), 1.38 (s, 3H).

Synthetic Scheme of Intermediate 15

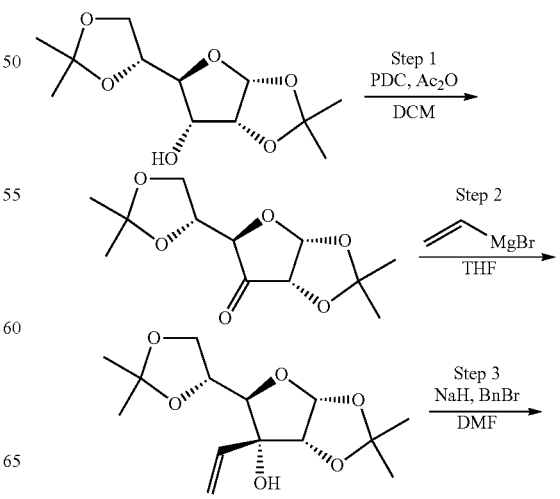

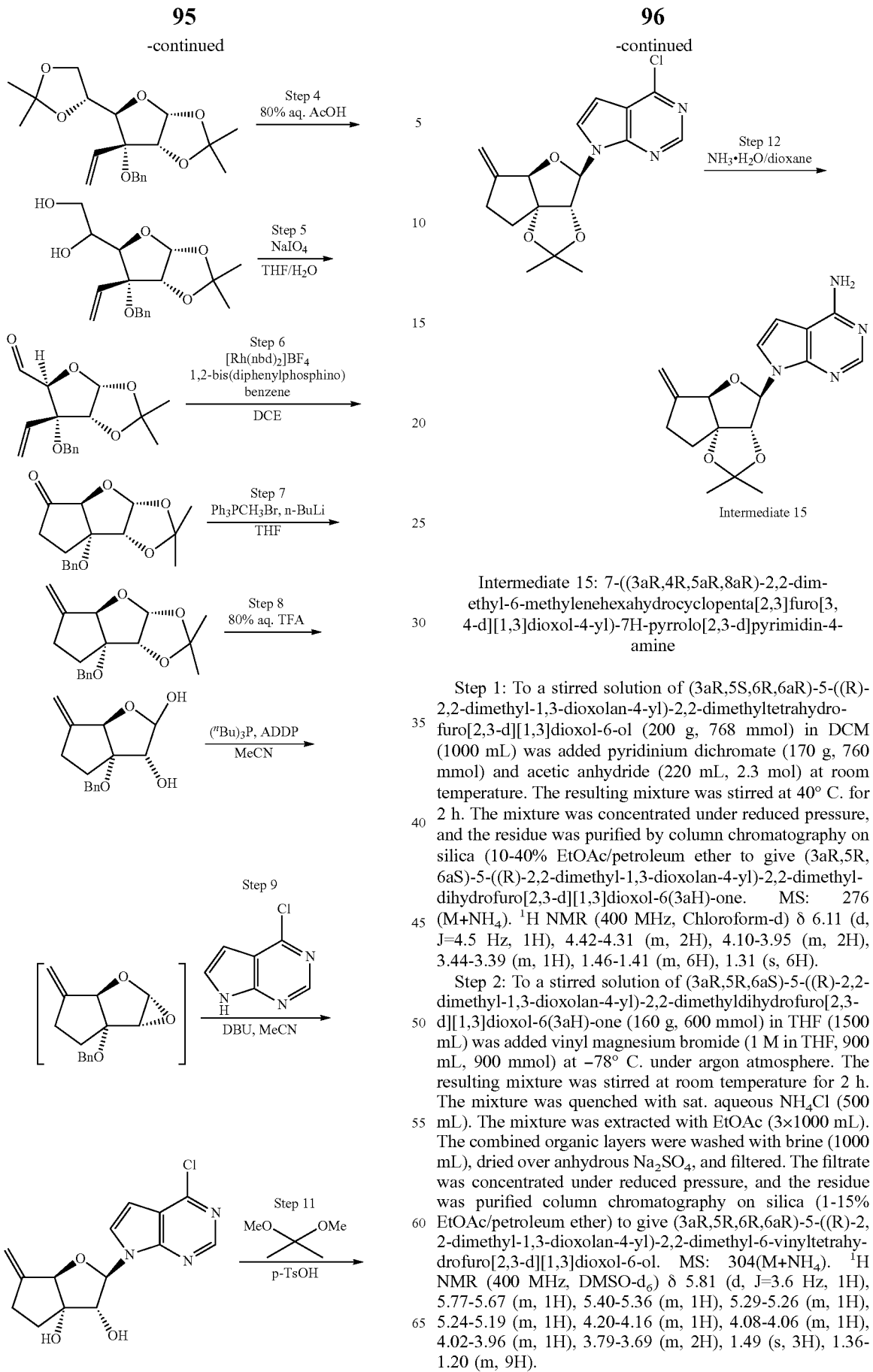

Intermediate 15: 7-((3aR,4R,5aR,8aR)-2,2-dimethyl-6-methylenehexahydrocyclopenta[2,3]furo[3,4-d][1,3]dioxol-4-yl)-7H-pyrrolo[2,3-d]pyrimidin-4-amine Step 1: To a stirred solution of (3aR,5S,6R,6aR)-5-((R)-2,2-dimethyl-1,3-dioxolan-4-yl)-2,2-dimethyltetrahydrofuro[2,3-d][1,3]dioxol-6-ol (200 g, 768 mmol) in DCM (1000 mL) was added pyridinium dichromate (170 g, 760 mmol) and acetic anhydride (220 mL, 2.3 mol) at room temperature. The resulting mixture was stirred at 40° C. for 2 h. The mixture was concentrated under reduced pressure, and the residue was purified by column chromatography on silica (10-40% EtOAc/petroleum ether to give (3aR,5R,6aS)-5-((R)-2,2-dimethyl-1,3-dioxolan-4-yl)-2,2-dimethyl-dihydrofuro[2,3-d][1,3]dioxol-6(3aH)-one. MS: 276 (M+NH$_4$). $^1$H NMR (400 MHz, Chloroform-d) δ 6.11 (d, J=4.5 Hz, 1H), 4.42-4.31 (m, 2H), 4.10-3.95 (m, 2H), 3.44-3.39 (m, 1H), 1.46-1.41 (m, 6H), 1.31 (s, 6H).

Step 2: To a stirred solution of (3aR,5R,6aS)-5-((R)-2,2-dimethyl-1,3-dioxolan-4-yl)-2,2-dimethyldihydrofuro[2,3-d][1,3]dioxol-6(3aH)-one (160 g, 600 mmol) in THF (1500 mL) was added vinyl magnesium bromide (1 M in THF, 900 mL, 900 mmol) at −78° C. under argon atmosphere. The resulting mixture was stirred at room temperature for 2 h. The mixture was quenched with sat. aqueous NH$_4$Cl (500 mL). The mixture was extracted with EtOAc (3×1000 mL). The combined organic layers were washed with brine (1000 mL), dried over anhydrous Na$_2$SO$_4$, and filtered. The filtrate was concentrated under reduced pressure, and the residue was purified column chromatography on silica (1-15% EtOAc/petroleum ether) to give (3aR,5R,6R,6aR)-5-((R)-2,2-dimethyl-1,3-dioxolan-4-yl)-2,2-dimethyl-6-vinyltetrahydrofuro[2,3-d][1,3]dioxol-6-ol. MS: 304(M+NH$_4$). $^1$H NMR (400 MHz, DMSO-d$_6$) δ 5.81 (d, J=3.6 Hz, 1H), 5.77-5.67 (m, 1H), 5.40-5.36 (m, 1H), 5.29-5.26 (m, 1H), 5.24-5.19 (m, 1H), 4.20-4.16 (m, 1H), 4.08-4.06 (m, 1H), 4.02-3.96 (m, 1H), 3.79-3.69 (m, 2H), 1.49 (s, 3H), 1.36-1.20 (m, 9H).

Step 3: Sodium hydride (60 wt. % dispersed in mineral oil, 28 g, 700 mmol) was suspended in anhydrous DMF (1000 mL) under argon atmosphere, and the mixture was cooled to 0° C. A solution of (3aR,5R,6R,6aR)-5-((R)-2,2-dimethyl-1,3-dioxolan-4-yl)-2,2-dimethyl-6-vinyltetrahydrofuro[2,3-d][1,3]dioxol-6-ol (133 g, 465 mmol) in anhydrous DMF (300 mL) was added dropwise over a period of 45 min. The mixture was stirred at 50° C. for 1 h then cooled to 0° C. Bromomethyl benzene (160 g, 930 mmol) was added dropwise, and the reaction mixture was stirred at room temperature for 3 h. The reaction mixture was quenched with sat. aqueous $NH_4Cl$ (1300 mL) and extracted with EtOAc (3×1000 mL). The combined organic layers were washed with brine (2000 mL), dried over anhydrous $Na_2SO_4$, filtered, and the filtrate was concentrated under reduced pressure. The residue was purified by column chromatography on silica (1-20% EtOAc/petroleum ether) to give (3aR,5R,6R,6aR)-6-(benzyloxy)-5-((R)-2,2-dimethyl-1,3-dioxolan-4-yl)-2,2-dimethyl-6-vinyltetrahydrofuro[2,3-d][1,3]dioxole. MS: 394(M+$NH_4$). $^1$H NMR (300 MHz, DMSO-$d_6$) δ 7.40-7.24 (m, 5H), 5.89 (d, J=3.3 Hz, 1H), 5.86-5.76 (m, 1H), 5.49-5.36 (m, 2H), 4.79 (d, J=3.6 Hz, 1H), 4.55-4.46 (m, 2H), 4.14-4.02 (m, 2H), 3.90-3.85 (m, 1H), 3.74-3.69 (m, 1H), 1.50 (s, 3H), 1.30 (s, 3H), 1.27 (s, 3H), 1.24 (s, 3H).

Step 4: (3aR,5R,6R,6aR)-6-(benzyloxy)-5-((R)-2,2-dimethyl-1,3-dioxolan-4-yl)-2,2-dimethyl-6-vinyltetrahydrofuro[2,3-d][1,3]dioxole (130 g, 350 mmol) was dissolved in 80% aq. acetic acid (900 mL) and the reaction mixture was stirred at 50° C. for 2 h. The reaction mixture was concentrated under reduced pressure and co-evaporated with toluene (2×300 mL). The residue was partitioned between EtOAc (1000 ml) and sat. aqueous $NaHCO_3$ (900 mL). The organic phase was combined and concentrated under reduced pressure to give 1-((3aR,5lR,6R,6aR)-6-(benzyloxy)-2,2-dimethyl-6-vinyltetrahydrofuro[2,3-d][1,3]dioxol-5-yl)ethane-1,2-diol. The product was used without further purification. MS: 354 (M+$NH_4$).

Step 5: To a stirred solution of 1-((3aR,5R,6R,6aR)-6-(benzyloxy)-2,2-dimethyl-6-vinyl tetrahydrofuro[2,3-d][1,3]dioxol-5-v)ethane-1,2-diol (60 g, 180 mmol) in THF (100 mL) was added a solution of sodium periodate (60 g, 270 mmol) in water (100 mL). The reaction was stirred at room temperature for 1 h. Water (200 mL) was added and the resulting mixture was extracted with DCM (3×300 mL). The combined organic layers were washed with brine (800 mL), dried over anhydrous sodium sulfate, and filtered. The filtrate was concentrated under reduced pressure, and the residue was purified by column chromatography on silica (10-30% EtOAc/petroleum ether to give (3aR,5S,6R,6aR)-6-(benzyloxy)-2,2-dimethyl-6-vinyltetrahydrofuro[2,3-d][1,3]dioxole-5-carbaldehyde. MS: 322(M+$NH_4$). $^1$H NMR (400 MHz, Chloroform-d) δ 9.58 (s, 1H), 7.42-7.28 (m, 5H), 6.01-5.97 (m, 1H), 5.81-5.74 (m, 1H), 5.55-5.41 (m, 2H), 4.75-4.62 (m, 4H), 1.62 (s, 3H), 1.41 (s, 3H).

Step 6: Bis(norbornadiene) rhodium (I) tetrafluoroborate (0.74 g, 2.0 mmol) and 1,2-bis(diphenylphosphino)benzene (1.1 g, 2.4 mmol) were suspended in DCE (70 mL). The mixture was stirred at room temperature under an atmosphere of argon for 10 min. Then hydrogen was bubbled through the solution for 10 min, followed by flushing again with argon for 20 min. (3aR,5S,6R,6aR)-6-(benzyloxy)-2,2-dimethyl-6-vinyltetrahydrofuro[2,3-d][1,3]dioxole-5-carbaldehyde (6 g, 20 mmol) in DCE (120 mL) was added dropwise to the above solution, and the mixture was stirred for 20 h at 75° C. The reaction mixture was concentrated under reduced pressure, and the residue was purified by column chromatography on silica (1-15% EtOAc/petroleum ether) to give (3aR,4aS,7aS,7bR)-7a-(benzyloxy)-2,2-dimethyltetrahydro-3aH-cyclopenta[4,5]furo[2,3-d][1,3]dioxol-5(4aH)-one. MS: 322(M+$NH_4$). $^1$H NMR (300 MHz, Chloroform-d) δ 7.40-7.31 (m 5H), 5.96 (d, J=3.6 Hz, 1H), 4.77 (d, J=10.8 Hz, 1H), 4.67-4.61 (m, 2H), 4.19 (s, 1H), 2.58-2.43 (m, 3H), 1.82-1.68 (m, 1H), 1.66 (s, 3H), 1.42 (s, 3H).

Step 7: To a stirred mixture of bromo(methyl)triphenylphosphorane (28.3 g, 79 mmol) in THF (109 mL) was added n-butyllithium (2.5 M in hexane, 28 mL, 71 mmol) dropwise at −60° C. under argon atmosphere. The resulting mixture was stirred at room temperature for 0.5 h. (3aR,4aS,7aS,7bR)-7a-(benzyloxy)-2,2-dimethyltetrahydro-3aH-cyclopenta[4,5]furo[2,3-d][1,3]dioxol-5(4aH)-one (8.6 g, 28.3 mmol) in THF (110 mL) was then added dropwise to the above solution by syringe at −60° C. The reaction mixture was stirred at room temperature for 2 h. The mixture was quenched with saturated aqueous brine (200 mL) at 0° C. The mixture was extracted with EtOAc (3×300 mL). The combined organic layers were dried over anhydrous sodium sulfate and filtered. The filtrate was concentrated under reduced pressure. The residue was purified by column chromatography on silica (0-30% EtOAc/petroleum ether) to afford (3aR,4aR,7aR,7bR)-7a-(benzyloxy)-2,2-dimethyl-5-methylenehexahydro-5H-cyclopenta[4,5]furo[2,3-d][1,3]dioxole. $^1$H-NMR (400 MHz, DMSO-$d_6$) δ 7.34-7.25 (m, 5H), 5.87 (d, J=4.0 Hz, 1H), 5.23-5.22 (m, 1H), 5.10-5.09 (m, 1H), 4.68 (d, J=3.6 Hz, 1H), 4.59 (d, J=11.2 Hz, 1H), 4.51 (d, J=11.2 Hz, 1H), 4.44 (s, 1H), 2.49-2.39 (m, 2H), 2.22-2.16 (m, 1H), 1.63-1.55 (m, 1H), 1.51 (s, 3H), 1.32 (s, 3H).

Step 8: To (3aR,4aR,7aR,7bR)-7a-(benzyloxy)-2,2-dimethyl-5-methylenehexahydro-5H-cyclopenta[4,5]furo[2,3-d][1,3]dioxole (6.8 g, 22 mmol) was added a solution of TFA (45 mL) in water (11 mL) at 0° C. The resulting mixture was stirred at room temperature for 0.25 h. The mixture was neutralized with 2 M aq. NaOH then extracted with EtOAc (4×200 mL). The combined organic layers were dried over anhydrous sodium sulfate and filtered. The filtrate was concentrated under reduced pressure. The residue was purified by silica gel column chromatography (0-70% EtOAc in petroleum ether) to afford (3R,3aS,6aR)-3a-(benzyloxy)-6-methylenehexahydro-2H-cyclopenta[b]furan-2,3-diol as a mixture of two diastereomers at the anomeric center in 5:4 ratio. $^1$H-NMR (400 MHz, DMSO-$d_6$) δ 7.37-7.24 (m, 5H), 6.51-6.06 (m, 1H), 5.25-4.87 (m, 4H), 4.68-4.36 (m, 3H), 3.87-3.76 (m, 1H), 2.57-2.33 (m, 2H), 2.10-1.72 (m, 2H).

Step 9: To a stirred solution of (3R,3aS,6aR)-3a-(benzyloxy)-6-methylenehexahydro-2H-cyclopenta[b]furan-2,3-diol (5.0 g, 19 mmol) in dry acetonitrile (63 mL) under the atmosphere of argon was added dropwise (E)-diazene-1,2-diylbis(piperidin-1-ylmethanone) (7.2 g, 29 mmol) in acetonitrile (63 mL) via syringe over 0.5 min at room temperature. Tributylphosphine (7.6 mL, 31 mmol) was added via syringe over 5 min at room temperature. The reaction solution was stirred at room temperature for about 5 min. The reaction mixture was stirred at 46° C. for 3 h. The resultant epoxide mixture was used directly. In parallel, a separate round bottom flask was charged with a solution of 4-chloro-7H-pyrrolo[2,3-d]pyrimidine (5.6 g, 36 mmol) in dry acetonitrile (30 mL) and DBU (5.2 mL, 34 mmol) at room temperature under an atmosphere of argon. The resulting mixture was stirred at room temperature for 30 min. Then the DBU containing solution was transferred to the above mixture containing the epoxide intermediate by means of a syringe at room temperature under argon atmosphere. The resulting mixture was stirred at 46° C. for 2 h, and then concentrated under reduced pressure. The residue was purified by column chromatography on silica (0-30% EtOAc/petroleum ether) to afford (2R,3R,3aS,6aR)-3a-(benzyloxy)-2-(4-chloro-7H-pyrrolo[2,3-d]pyrimidin-7-yl)-6-methylenehexahydro-2H-cyclopenta[b]furan-3-ol. MS: 398 (M+1). ¹H-NMR (400 MHz, DMSO-d₆) δ 8.71 (s, 1H), 7.96 (d, J=4.0 Hz, 1H), 7.45-7.28 (m, 5H), 6.80 (d, J=3.6 Hz, 1H), 6.30 (d, J=8.0 Hz, 1H), 5.83 (d, J 6.8 Hz, 1H), 5.14 (d, J=16.0 Hz, 2H), 4.92 (d, J=12.0 Hz, 1H), 4.71 (d, J=11.6 Hz, 1H), 4.67 (s, 1H), 4.61-4.58 (m, 1H), 2.84-2.78 (m, 1H), 2.56-2.51 (m, 1H), 2.19-2.13 (m, 1H), 2.09-2.04 (m, 1H).

Step 10: To a solution of (2R,3R,3aS,6aR)-3a-(benzyloxy)-2-(4-chlor-7H-pyrrolo[2,3-d]pyrimidin-7-yl)-6-methylenehexahydro-2H-cyclopenta[b]furan-3-ol (690 mg, 1.7 mmol) in DCM (10 mL) was added dropwise trichloroborane (1 M in DCM, 3.5 mL, 3.5 mmol) at −78° C. under argon atmosphere. The resulting solution was stirred at −78° C. for 3 h. The reaction mixture was quenched by the addition of TEA (1.0 mL, 7.0 mmol) then stirred at −78° C. for 0.5 h. The reaction solution was poured into saturated aqueous NaHCO₃ (150 mL) at 0° C. with vigorous stirring. The mixture was extracted by EtOAc (3×200 mL). The organic layers were dried over anhydrous sodium sulfate and filtered. The filtrate was concentrated under reduced pressure. The crude residue was purified by column chromatography on silica (0-10% MeOH/DCM) to afford (2R,3R,3aS, 6aR)-2-(4-chloro-7H-pyrrolo[2,3-d]pyrimidin-7-yl)-6-methylenehexahydro-2H-cyclopenta[b]furan-3,3a-diol. MS: 308(M+1). ¹H-NMR (400 MHz, DMSO-d₆) δ 8.72 (s, 1H), 7.95 (d, J=4.0 Hz, 1H), 6.78 (d, J=4.0 Hz, 1H), 6.21 (d, J=8.0 Hz, 1H), 5.52 (d, J=7.2 Hz, 1H), 5.38 (s, 1H), 5.12-5.07 (m, 2H), 4.44-4.34 (m, 2H), 2.78-2.69 (m, 1H), 2.51-2.42 (m, 1H), 2.08-2.03 (m, 1H), 1.72-1.64 (m, 1H).

Step 11: To a mixture of (2R,3R,3aS,6aR)-2-(4-chloro-7H-pyrrolo[2,3-d]pyrimidin-7-yl)-6-methylenehexahydro-2H-cyclopenta[b]furan-3,3a-diol (720 ng, 2.3 mmol) in 2,2-dimethoxypropane (2 mL) was added 4-methylbenzenesulfonic acid (40 mg, 0.23 mmol) at ambient temperature. The mixture was stirred for 16 h at ambient temperature. The reaction mixture was quenched with NaHCO₃ (200 mg) at ambient temperature. The reaction mixture was concentrated under reduced pressure. The residue was purified by column chromatography on silica (0-30% EtOAc/petroleum ether) to give 4-chloro-7-((3aR, 4R,5aR,8aR)-2,2-dimethyl-6-methylenehexahydrocyclopenta[2,3]furo[3,4-d][1,3]dioxol-4-yl)-7H-pyrrolo[2,3-d]pyrimidine. MS: 348 (M+1). ¹H-NMR (400 MHz, DMSO-d₆) δ 8.72 (s, 1H), 7.87 (d, J=4.0 Hz, 1H), 6.79 (d, J=4.0 Hz, 1H), 6.36 (d, J=3.6 Hz, 1H), 5.30 (d, J=3.6 Hz, 1H), 5.15-5.14 (m, 2H), 4.68 (s, 1H), 2.58-2.41 (m, 3H), 2.04-1.93 (m, 1H), 1.57 (s, 3H), 1.39 (s, 3H).

Step 12: To 4-chloro-7-((3aR,4R,5aR,8aR)-2,2-dimethyl-6-methylenehexahydrocyclopenta[2,3]furo[3,4-d][1,3]dioxol-4-yl)-7H-pyrrolo[2,3-d]pyrimidine (2.7 g, 7.76 mmol) was added 1,4-dioxane (18 mL) and concentrated aqueous ammonia (28 wt. %, 18 mL) at room temperature. The reaction container was sealed and stirred at 90° C. for 16 h. The mixture was concentrated under reduced pressure. The residue was purified by column chromatography on silica (0-10% MeOH/DCM) to give 7-((3aR,4R,5aR,8aR)-2,2-dimethyl-6-methylenehexahydrocyclopenta[2,3]furo[3,4-d][1,3]dioxol-4-yl)-7H-pyrrolo[2,3-d]pyrimidin-4-amine. MS: 329 (M+1). ¹H-NMR (400 MHz, DMSO-d₆) δ 8.09 (s, 1H), 7.29 (d, J=3.6 Hz, 1H), 7.10 (s, 2H), 6.64 (d, J=3.6 Hz, 1H), 6.20 (d, J=4.4 Hz, 1H), 5.19 (d, J=4.0 Hz, 1H), 5.13-5.11 (m, 2H), 4.55 (s, 1H), 2.63-2.42 (m, 3H), 2.01-1.96 (m, 1H), 1.55 (s, 3H), 1.38 (s, 3H).

Synthetic Scheme of Intermediate 16:

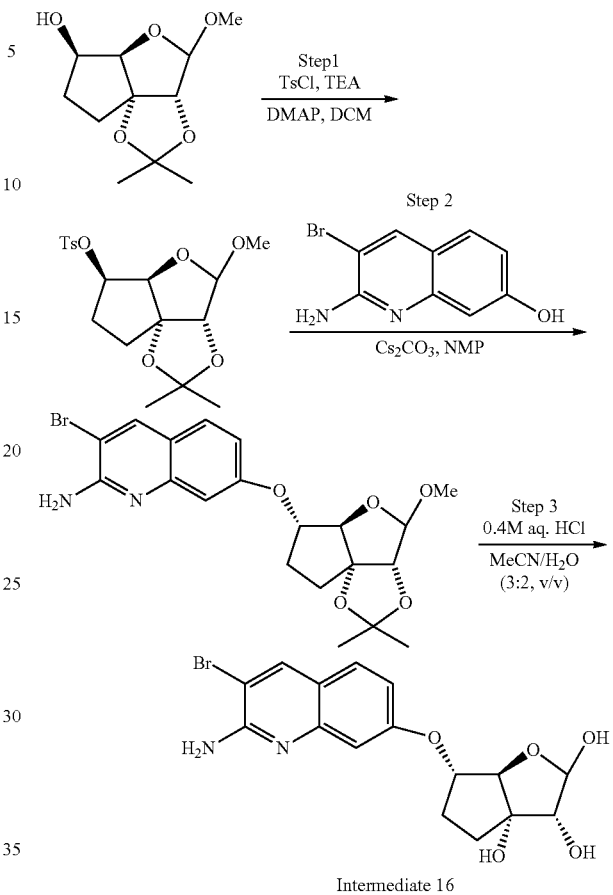

Intermediate 16: (3R,3aS,6S,6aR)-6-((2-amino-3-bromoquinolin-7-yl)oxy)hexahydro-3aH-cyclopenta[b]furan-2,3,3a-triol Step 1: To a solution of (3aR,5aR,6R,8aR)-4-methoxy-2,2-dimethylhexahydrocyclopenta[2,3]furo[3,4-d][1,3]dioxol-6-ol (5.0 g, 22 mmol) in DCM (40 mL) was added 4-dimethylaminopyridine (2.9 g, 24 mmol) at room temperature. To the mixture was added dropwise triethylamine (2.4 g, 24 mmol) followed by p-toluenesulfonyl chloride (6.2 g, 33 mmol). The reaction mixture was stirred at 25° C. for 16 h. The resulting mixture was quenched with saturated aqueous NH₄Cl (100 mL) and extracted with DCM (100 mL×3). The combined organic layers were washed with brine (100 mL) and dried over anhydrous sodium sulfate. After filtration, the filtrate was concentrated under reduced pressure. The residue was purified by column chromatography on silica (0-27% ethyl acetate/petroleum ether) to give (3aR,5aR,6R,8aR)-4-methoxy-2,2-dimethylhexahydrocyclopenta[2,3]furo[3,4-d][1,3]dioxol-6-yl 4-methylbenzenesulfonate. MS: 402 (M+NH₄). ¹H-NMR (400 MHz, DMSO-d₆) δ 7.84-7.82 (m, 2H), 7.52-7.49 (m, 2H), 4.87 (d, J=4.0 Hz, 1H), 4.77-4.72 (m, 1H), 4.40 (d, J=4.0 Hz, 1H), 3.93 (d, J=5.2 Hz, 1H), 3.24 (s, 3H), 2.44 (s, 3H), 2.13-2.08 (m, 1H), 1.91-1.86 (m, 1H), 1.78-1.57 (m, 2H), 1.36 (s, 3H), 1.28 (s, 3H).

Step 2: A mixture of 2-amino-3-bromoquinolin-7-ol (2.0 g, 8.2 mmol) and (3aR,5aR,6R,8aR)-4-methoxy-2,2-dimethylhexahydrocyclopenta[2,3]furo[3,4-d][1,3]dioxol-6-yl 4-methylbenzenesulfonate (3.0 g, 7.8 mmol) was co-evaporated with dry toluene (10 mL each, three times) and re-dissolved in NMP (10 mL). To this solution was added cesium carbonate (7.6 g, 23 mmol) at ambient temperature. The resulting mixture was stirred at 90° C. for 1.5 h. The reaction mixture was filtered, and the filtrate was purified by reversed-phase column chromatography on C18 (0-95% 5 mM aq. NH$_4$HCO$_3$/MeCN) to give 3-bromo-7-(((3aR,5aR,6S,8aR)-4-methoxy-2,2-dimethylhexahydrocyclopenta[2,3]furo[3,4-d][1,3]dioxol-6-yl)oxy)quinolin-2-amine. MS: 451/453 (M+1/M+3). $^1$H-NMR (400 MHz, DMSO-d$_6$) δ 8.30 (s, 1H), 7.60 (d, J=8.4 Hz, 1H), 6.91-6.86 (m, 2H), 6.62 (s, 2H), 4.95 (d, J=4.4 Hz, 1H), 4.66 (d, J=4.0 Hz, 1H), 4.54 (d, J=4.4 Hz, 1H), 4.19-4.18 (m, 1H), 3.37 (s, 3H), 2.26-1.98 (m, 4H), 1.36 (s, 3H), 1.28 (s, 3H).

Step 3: 3-bromo-7-(((3aR,5aR,6S,8aR)-4-methoxy-2,2-dimethylhexahydrocyclopenta[2,3]furo[3,4-d][1,3]dioxol-6-yl)oxy)quinolin-2-amine (4.9 g, 11 mmol) was dissolved in 0.4 M aq. HCl in MeCN/H$_2$O (3:2, v/v) (120 mL) at 0° C. The resulting mixture was stirred at 90° C. for 3 h in a sealed tube. The reaction mixture was cooled to 0° C. The pH value of the solution was adjusted to 7~8 with 2 M aq. NaOH. The resulting mixture was concentrated under reduced pressure, and the residue was purified by reverse-phase column chromatograph on AQ-C18 (0-95% 5 mM aq. NH$_4$HCO$_3$/MeCN) to give (3R,3aS,6S,6aR)-6-((2-amino-3-bromoquinolin-7-yl)oxy)hexahydro-3aH-cyclopenta[b]furan-2,3,3a-triol. MS: 397/399 (M+1/M+3). $^1$H NMR (400 MHz, Methanol-d$_4$) δ 8.22-8.21 (m, 1H), 7.57-7.54 (m, 1H), 7.12-7.03 (m, 1H), 6.98-6.94 (m, 1H), 5.35-5.20 (m, 1H), 4.94-4.64 (m, 1H), 4.36-4.18 (m, 1H), 3.80-3.62 (m, 1H), 2.36-2.02 (m, 4H).

Intermediates 17-21: Intermediates 17-21 in Table 3 were synthesized using the protocol described in intermediate 16 (Synthetic Scheme of Intermediate 16) making the appropriate substitution for the 2-amino-3-bromoquinolin-7-ol in step 2. The substituted starting material was commercially acquired, synthesized as reported above or synthesized through known routes reported in the literature.

TABLE 3

| Intermediate | Structure | Name | MS |
| --- | --- | --- | --- |
| 17 | 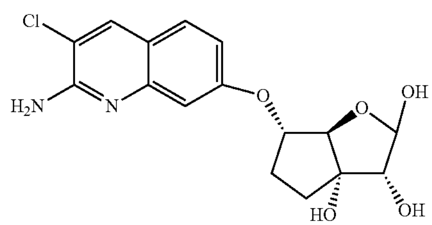 | (3R,3aS,6S,6aR)-6-[(2-amino-3-chloroquinolin-7-yl)oxy]hexahydro-3aH-cyclopenta[b]furan-2,3,3a-triol | 353 (M + 1) |
| 18 | 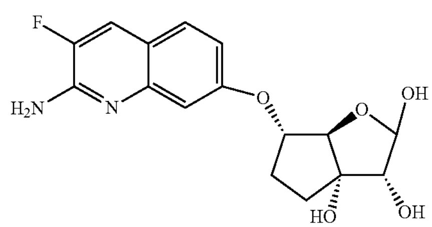 | (3R,3aS,6S,6aR)-6-[(2-amino-3-fluoroquinolin-7-yl)oxy]hexahydro-3aH-cyclopenta[b]furan-2,3,3a-triol | 337 (M + 1) |
| 19 | 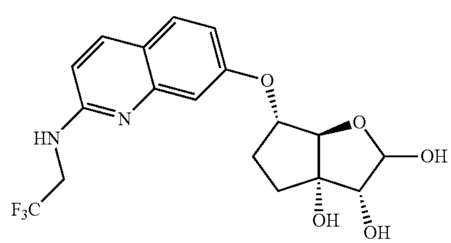 | (3R,3aS,6S,6aR)-6-((2-((2,2,2-trifluoroethyl)amino)quinolin-7-yl)oxy)hexahydro-3aH-cyclopenta[b]furan-2,3,3a-triol | 401 (M + 1) |
| 20 | 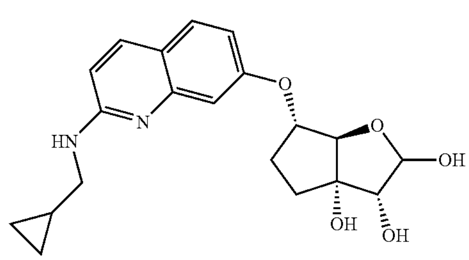 | (3R,3aS,6S,6aR)-6-((2-((cyclopropylmethyl)amino)quinolin-7-yl)oxy)hexahydro-3aH-cyclopenta[b]furan-2,3,3a-triol | 373 (M + 1) |

TABLE 3-continued

| Intermediate | Structure | Name | MS |
|---|---|---|---|
| 21 | 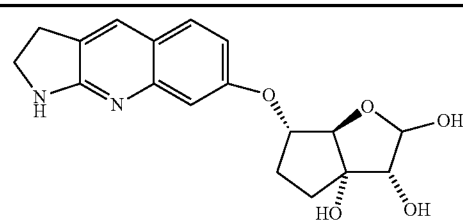 | (3R,3aS,6S,6aR)-6-((2,3-dihydro-1H-pyrrolo[2,3-b]quinolin-7-yl)oxy)hexahydro-3aH-cyclopenta[b]furan-2,3,3a-triol | 345 (M + 1) |

Synthetic Scheme of Intermediate 22

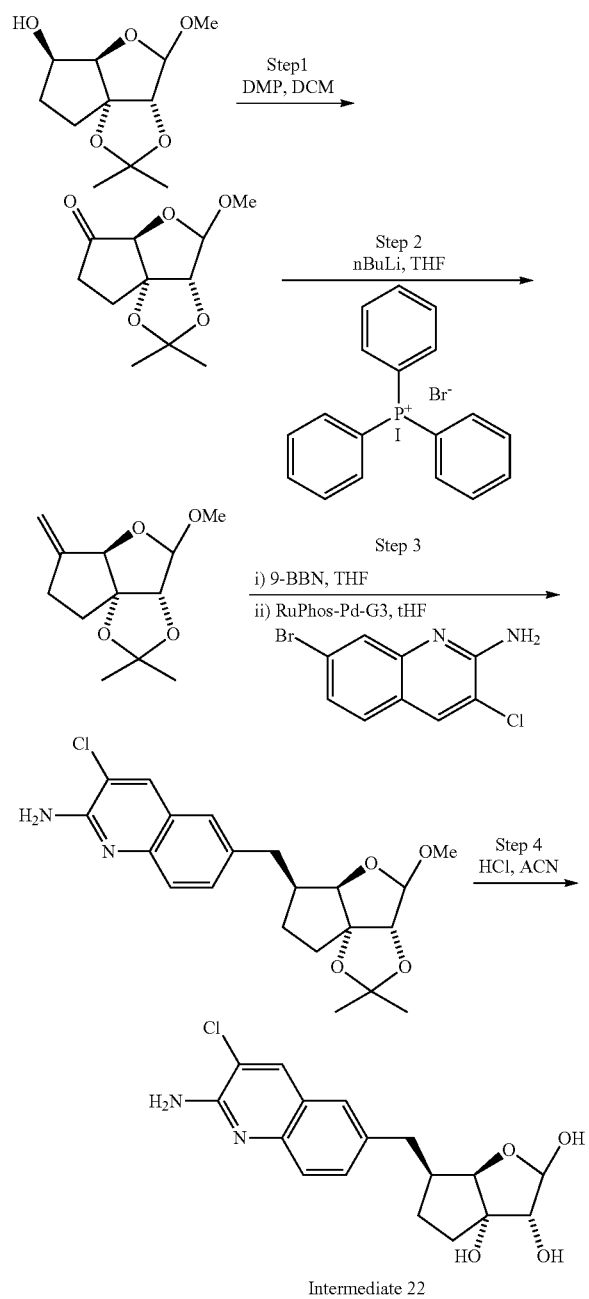

Intermediate 22

Intermediate 22: (3R,3aS,6S,6aR)-6-[(2-amino-3-chloroquinolin-7-yl)methyl]hexahydro-3aH-cyclopenta[b]furan-2,3,3a-triol Step 1: To a solution of (3aR,5aR,6R,8aR)-4-methoxy-2,2-dimethylhexahydrocyclopenta[2,3]furo[3,4-d][1,3]dioxol-6-ol (2.0 g, 8.7 mmol) in anhydrous DCM (43 mL) at 0° C. under nitrogen atmosphere was added DMP (4.4 g, 10 mmol) in one portion. The mixture was stirred at room temperature overnight. The mixture was diluted with DCM (40 mL) and treated with saturated aqueous sodium bicarbonate (80 mL) and sodium thiosulfate (10 g, 63 mmol). The resulting mixture was stirred for 10 minutes at room temperature. The organic layer was separated, and the aqueous phase was extracted with DCM (40 mL×3). The combined organic layers were washed with brine (80 mL), dried with anhydrous sodium sulfate, filtered, and concentrated under reduced pressure. The residue was purified by column chromatography on silica (0-60% EtOAc/hexanes) to afford (3aR,5aS,8aS)-4-methoxy-2,2-dimethyltetrahydrocyclopenta[2,3]furo[3,4-d][1,3]dioxol-6(5aH)-one. $^1$H NMR (600 MHz, DMSO-$d_6$) δ 4.97 (s, 1H), 4.39 (s, 1H), 4.15 (s, 1H), 3.09 (s, 3H), 2.50-2.46 (m, 1H), 2.46-2.40 (m, 1H), 2.40-2.29 (m, 2H), 1.38 (s, 3H), 1.36 (s, 3H).

Step 2: To a solution of methyltriphenylphosphonium bromide (5.26 g, 14.7 mmol) in anhydrous TH-F (23 mL) at −78° C. under an argon atmosphere was added n-butyllithium (5.52 mL, 2.5 M in hexanes, 13.8 mmol) dropwise. The mixture was stirred at room temperature for 0.5 h. A solution of (3aR,5aS,8aS)-4-methoxy-2,2-dimethyltetrahydrocyclopenta[2,3]furo[3,4-d][1,3]dioxol-6(5aH)-one (1.05 g, 4.6 mmol) dissolved in anhydrous THF (23 mL) was added dropwise at −78° C. The reaction was stirred at room temperature for 1 h. The reaction was quenched with saturated aqueous ammonium chloride (50 mL) at 0° C. The mixture was extracted with EtOAc (2×30 mL), and the combined organic layers were washed with brine, dried over anhydrous sodium sulfate, filtered, and concentrated under reduced pressure. The residue was purified by column chromatography on silica (0-40% EtOAc/hexanes) to afford (3aR,4S,5aR,8aR)-4-methoxy-2,2-dimethyl-6-methylidenehexahydrocyclopenta[2,3]furo[3,4-d][1,3]dioxole.

Step 3: To an oven-dried flask containing (3aR,4S,5aR,8aR)-4-methoxy-2,2-dimethyl-6-methylidenehexahydrocyclopenta[2,3]furo[3,4-d][1,3]dioxole (533 mg, 2.4 mmol) dissolved in THF (6 mL) at 0° C. under an atmosphere of argon was added 9-BBN (24 mL, 0.5 M in THF, 12 mmol) dropwise. The reaction was warmed to room temperature and stirred overnight. The mixture was cooled to 0° C. and treated with potassium phosphate tribasic (12 mL, 1 M in water, 12 mmol). The mixture was then stirred for 30 min at room temperature. In a separate vial, a mixture of 7-bromo-3-chloroquinolin-2-amine (910 mg, 3.5 mmol). THF (18 mL), and (2-dicyclohexylphosphino-2',6'-diisopropoxy-1,1'-biphenyl)[2-(2'-amino-1,1'-biphenyl)]palladium(II) methanesulfonate (200 mg, 0.24 mmol), was purged with nitrogen for 5 min. The stirring quinoline mixture was added to the vial containing the boronate. This reaction was heated at 50° C. for 1.5 h. The mixture was cooled to room temperature and partitioned between brine and EtOAc. The aqueous phase was extracted with EtOAc. The combined organic layers were dried over anhydrous sodium sulfate, filtered, and concentrated under reduced pressure. The residue was purified by column chromatography on silica (0-50% EtOAc/hexanes) to afford 3-chloro-6-{[(3aR,5aR,6S,8aR)-4-methoxy-2,2-dimethylhexahydrocyclopenta[2,3]furo[3,4-d][1,3]dioxol-6-yl]methyl}quinolin-2-amine. MS: 405 (M+1).

Step 4: To a vial containing 3-chloro-6-{[(3aR,5aR,6S,8aR)-4-methoxy-2,2-dimethylhexahydrocyclopenta[2,3]furo[3,4-d][1,3]dioxol-6-yl]methyl}quinolin-2-amine (600 mg, 1.48 mmol) dissolved in acetonitrile (6 mL) were added water (4 mL) and HCl (355 µL, 37% in water, 4.33 mmol). The mixture was heated at 80° C. for 2.5 h, and then stirred overnight at room temperature. The mixture was cooled to 0° C. and quenched with saturated aqueous sodium bicarbonate (364 mg, 4.3 mmol). The aqueous layer was extracted with EtOAc, and the combined organic layers were washed with brine, dried over anhydrous sodium sulfate, filtered, and concentrated under reduced pressure to afford (3R,3aS,6S,6aR)-6-[(2-amino-3-chloroquinolin-7-yl)methyl]hexahydro-3aH-cyclopenta[b]furan-2,3,3a-triol. MS: 351 (M+1). $^1$H NMR (DMSO-d6) δ: 8.14 (s, 1H), 7.57 (d, J=8.2 Hz, 1H), 7.34 (s, 1H), 7.13 (dd, J=8.2, 1.4 Hz, 1H), 6.65 (s, 2H), 5.96 (d, J=6.6 Hz, 1H), 5.16 (dd, J=6.6, 4.0 Hz, 1H), 4.66 (d, J=7.6 Hz, 1H), 4.46 (s, 1H), 3.92 (d, J=4.6 Hz, 1H), 3.48 (dd, J=7.5, 4.0 Hz, 1H), 2.82 (dd, J=13.4, 8.4 Hz, 1H), 2.66 (dd, J=13.4, 6.7 Hz, 1H), 2.26-2.12 (m, 1H), 1.83-1.73 (m, 1H), 1.62 (dt, J=12.6, 6.6 Hz, 1H), 1.57-1.46 (m, 1H), 1.31 (qd, J=12.1, 7.1 Hz, 1H).

Intermediates 23-25: Intermediates 23-25 in Table 4 were synthesized using the protocol described in intermediate 22 making the appropriate substitution for the 7-bromo-3-chloroquinolin-2-amine in step 3. The substituted starting material was commercially acquired, synthesized as reported above, or synthesized through known routes reported in the literature.

TABLE 4

| Intermediate | Structure | Name | MS |
|---|---|---|---|
| 23 | 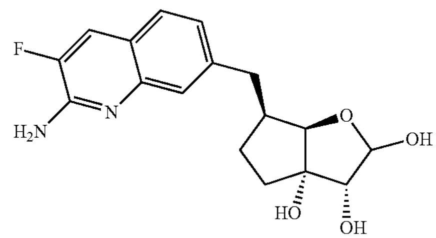 | (3R,3aS,6S,6aR)-6-[(2-amino-3-fluoroquinolin-7-yl)methyl]hexahydro-3aH-cyclopenta[b]furan-2,3,3a-triol | 335 (M + 1) |
| 24 | 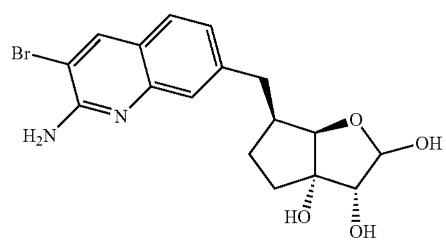 | (3R,3aS,6S,6aR)-6-[(2-amino-3-bromoquinolin-7-yl)methyl]hexahydro-3aH-cyclopenta[b]furan-2,3,3a-triol | 395/397 (M + 1/M + 3) |
| 25 | 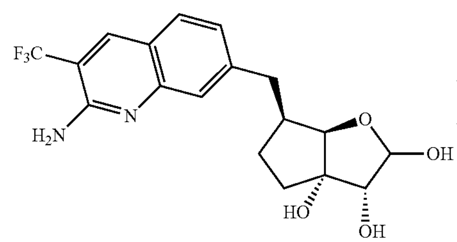 | (3R,3aS,6S,6aR)-6-((2-amino-3-(trifluoromethyl)quinolin-7-yl)methyl]hexahydro-3aH-cyclopenta[b]furan-2,3,3a-triol | 385 (M + 1) |

Synthetic Scheme of Intermediate 26

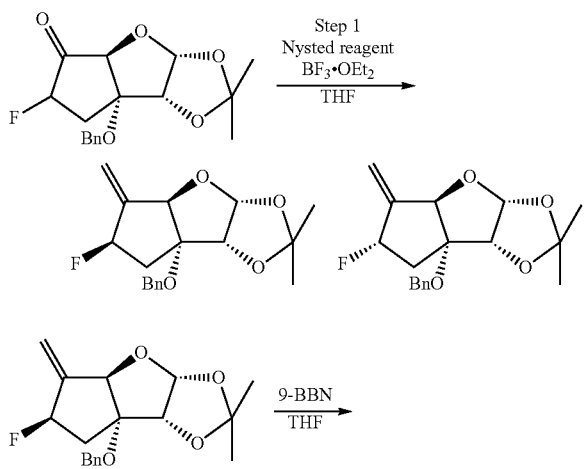

-continued

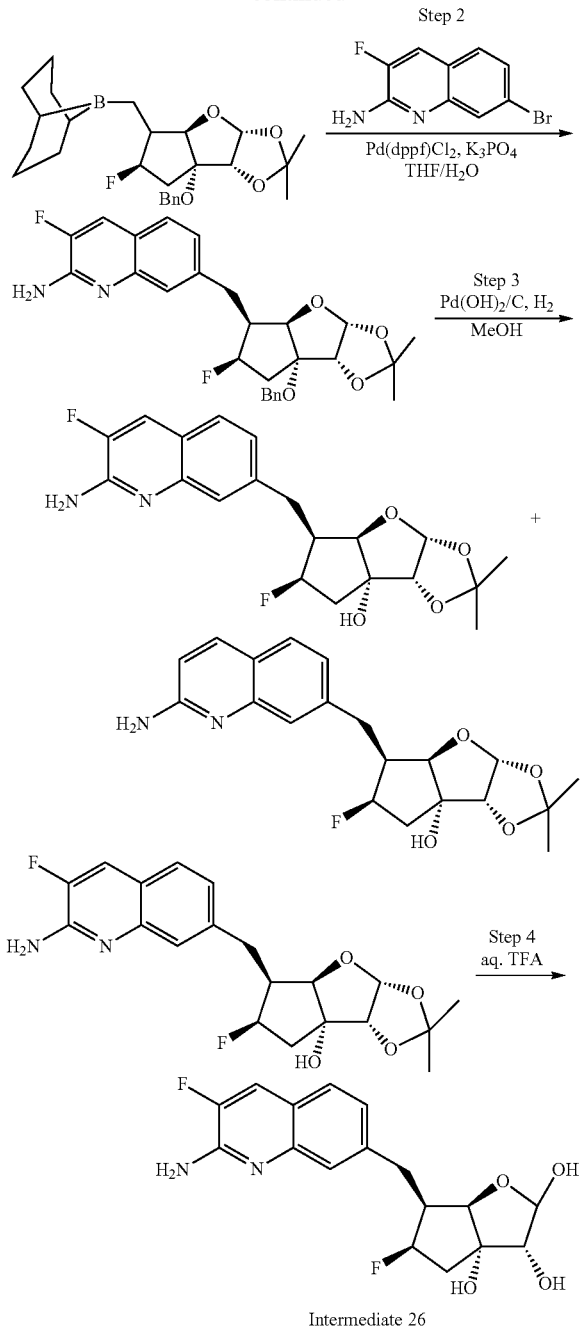

Intermediate 26: (3R,3aS,5R,6S,6aR)-6-((2-amino-3-fluoroquinolin-7-yl)methyl)-5-fluorohexahydro-2H-cyclopenta[b]furan-2,3,3a-triol Step 1: To a mixture of Nysted Reagent (6.37 g, 14.0 mmol) in anhydrous THF (40 mL) was added dropwise boron trifluoride diethyl etherate (1.8 mL, 14.0 mmol) at 0° C. under argon atmosphere. The mixture was stirred at 0° C. for 5 minutes. A solution of (3aR,4aS,7aS,7bR)-7a-(benzyloxy)-6-fluoro-2,2-dimethyltetrahydro-3aH-cyclopenta[4,5]furo[2,3-d][1,3]dioxol-5(4aH)-one (1.5 g, 4.7 mmol) in anhydrous THF (35 mL) was added at 0° C. The resulting mixture was stirred at ambient temperature for 15 h. The reaction mixture was quenched by adding saturated aqueous NaHCO₃ (40 mL) at 0° C., and then it was partitioned between EtOAc/H₂O (250 mL/50 mL). The organic layer was separated and the aqueous layer was re-extracted with EtOAc (100 mL). The combined organic layers were washed with water (150 mL) and brine (2×100 mL). The organic layer was dried over anhydrous Na₂SO₄, filtered, and the filtrate was concentrated under reduced pressure. The residue was purified by column chromatography on silica (0-10% EtOAc/petroleum ether) to afford (3aR,4aR,6R,7aR,7bR)-7a-(benzyloxy)-6-fluoro-2,2-dimethyl-5-methylenehexahydro-3aH-cyclopenta[4,5]furo[2,3-d][1,3]dioxole. ¹H-NMR (400 MHz, CDCl₃) δ 7.38-7.29 (m, 5H), 5.99 (d, J=3.6 Hz, 1H), 5.68-5.64 (m, 2H), 5.57-5.39 (m, 1H), 4.78 (s, 1H), 4.72 (d, J=10.8 Hz, 1H), 4.64 (d, J=4.0 Hz, 1H), 4.57 (d, J=10.8 Hz, 1H), 2.79-2.72 (m, 1H), 1.96-1.85 (m, 1H), 1.67 (s, 3H), 1.43 (s, 3H). ¹⁹F-NMR (376 MHz, CDCl₃) δ −169.53 (s, 1F). The chromatography step also afforded (3aR,4aR,6S,7aR,7bR)-7a-(benzyloxy)-6-fluoro-2,2-dimethyl-5-methylenehexahydro-3aH-cyclopenta[4,5]furo[2,3-d][1,3]dioxole. ¹H-NMR (400 MHz, CDCl₃) δ 7.45-7.44 (m, 2H), 7.44-7.27 (m, 3H), 5.87 (d, J=3.6 Hz, 1H), 5.72 (dd, J=44, 1.6 Hz, 2H), 5.58-5.42 (m, 1H), 4.85 (s, 1H), 4.66 (dd, J=17.2, 10.4 Hz, 2H), 4.61 (d, J=4.0 Hz, 1H), 2.67-2.56 (m, 1H), 2.02-1.89 (m, 1H), 1.66 (s, 3H), 1.42 (s, 3H). ¹⁹F-NMR (376 MHz, CDCl₃) δ −164.53 (s, 1F).

Step 2: To a solution of (3aR,4aR,6R,7aR,7bR)-7a-(benzyloxy)-6-fluoro-2,2-dimethyl-5-methylenehexahydro-3aH-cyclopenta[4,5]furo[2,3-d][1,3]dioxole (180 mg, 0.562 mmol) in anhydrous THF (0.5 mL) was added dropwise 9-BBN in THF (0.5 M, 6.7 mL, 3.4 mmol) at 0° C. under argon atmosphere, and the mixture was stirred at 70° C. for 1.5 h. The mixture was cooled to 0° C., and a solution of K₃PO₄ (1M in water, 716 ng, 3.37 mmol) was added. The resultant mixture was stirred for 0.5 h at ambient temperature. Then, a solution of 7-bromo-3-fluoroquinolin-2-amine (122 mug, 0.51 mmol) in 3.5 mL of anhydrous THF and Pd(dppf)Cl₂ (41.1 mg, 0.056 mmol) were added to the mixture. The mixture was heated to 80° C. in a microwave reactor for 3.0 h. The organic layer was separated, and the aqueous layer was extracted with EtOAc (150 mL×2). The combined organic layers were washed with water (50 mL) and brine (80 mL). The organic layer was dried over anhydrous Na₂SO₄, filtered, and the filtrate was concentrated under reduced pressure. The residue was purified by column chromatography on silica (0-25% EtOAc/petroleum ether) to afford 7-(((3aR,4aR,5S,6R,7aR,7bR)-7a-(benzyloxy)-6-fluoro-2,2-dimethylhexahydro-3aH-cyclopenta[4,5]furo[2,3-d][1,3]dioxol-5-yl)methyl)-3-fluoroquinolin-2-amine. MS 483 (M+1). ¹H-NMR (400 MHz, Chloroform-d) δ 7.62-7.54 (m, 3H), 7.35-7.33 (m, 4H), 7.31-7.28 (m, 2H), 6.02 (d, J=3.6 Hz, 1H), 5.51 (s, 2H), 5.09-4.93 (m, 1H), 4.72-4.67 (m, 2H), 4.54 (d, J=4.0 Hz, 1H), 4.45 (d, J=10.8 Hz, 1H), 3.14-3.11 (m, 2H), 2.60-2.41 (m, 2H), 2.20-2.07 (m, 1H), 1.62 (s, 3H), 1.44 (s, 3H). ¹⁹F-NMR (376 MHz, Chloroform-d) δ −137.96 (s, 1F), −182.37 (s, 1F).

Step 3: To a mixture of 7-(((3aR,4aR,5S,6R,7aR,7bR)-7a-(benzyloxy)-6-fluoro-2,2-dimethylhexahydro-3aH-cyclopenta[4,5]furo[2,3-d][1,3]dioxol-5-yl)methyl)-3-fluoroquinolin-2-amine (180 mg, 0.37 mmol) in MeOH (16 mL) and THF (2 mL) was added Pd(OH)₂/C (20 wt. %, 500 mg, 0.71 mmol) at ambient temperature under argon atmosphere. The suspension was degassed under vacuum and purged with H₂ several times, and then it was stirred under 1 atm of H₂ at ambient temperature for 6 h. The mixture was filtered, and the filter cake was washed with MeOH/concentrated aqueous ammonia (10:1) three times (each 10 mL). The filtrate was concentrated under reduced pressure. The residue was purified by column chromatography on silica (0-10% MeOH/DCM) to afford (3aR,4aR,5S,6R,7aR,7bR)-5-((2-amino-3-fluoroquinolin-7-yl)methyl)-6-fluoro-2,2-dimethylhexahydro-3aH-cyclopenta[4,5]furo[2,3-d][1,3]dioxol-7a-ol. MS: 393(M+1).

Step 4: (3aR,4aR,5S,6,7aR,7bR)-5-((2-amino-3-fluoroquinolin-7-yl)methyl)-6-fluoro-2,2-dimethylhexahydro-3aH-cyclopenta[4,5]furo[2,3-d][1,3]dioxol-7a-ol (40 mg, 0.10 mmol) was dissolved in TFA and 1-120 (2.0 mL, TFA/H$_2$O=1:1) at 0° C. and the mixture was stirred at ambient temperature for 1.0 h. The mixture was co-evaporated with toluene (3×15.0 mL) to dryness. The obtained residue was purified by reverse-phase column chromatograph on C18 (0-95% 5 mM aq. NH$_4$HCO$_3$/ACN) to afford (3R,3aS,5R,6S,6aR)-6-((2-amino-3-fluoroquinolin-7-yl)methyl)-5-fluorohexahydro-2H-cyclopenta[b]furan-2,3,3a-triol. MS: 353(M+1). $^1$H-NMR (300 MHz, CD$_3$OD) δ 7.70 (d, J=11.4 Hz, 1H), 7.60-7.52 (m, 2H), 7.29 (d, J=8.1 Hz, 1H), 5.37 (d, J=4.2 Hz, 1H), 5.08-4.95 (m, 1H), 4.31-3.71 (m, 2H), 3.10-2.98 (m, 2H), 2.45-2.29 (m, 2H), 2.08-1.93 (m, 1H). $^{19}$F-NMR (282 MHz, CD$_3$OD) δ −139.28 to −139.34 (m, 1F), −186.24 to −189.90 (m, 1F).

Synthetic Scheme for Intermediate 27

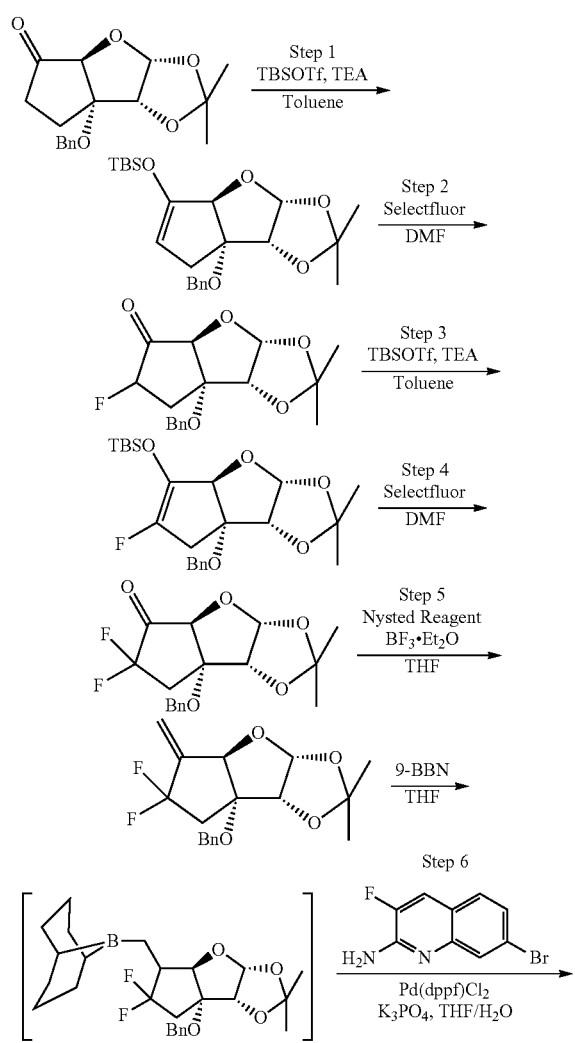

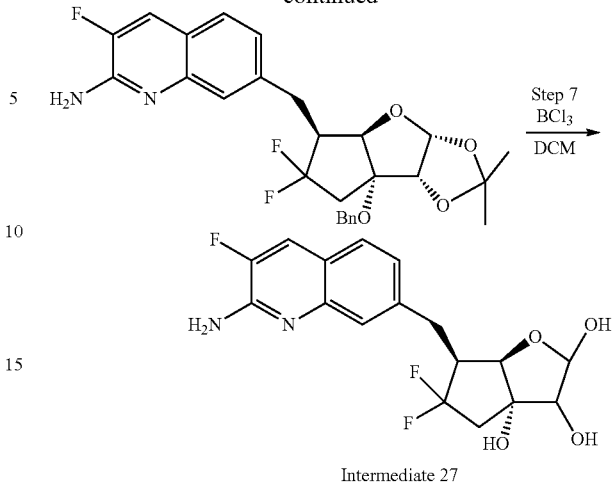

Intermediate 27: (3R,3aS,6S,6aR)-6-((2-amino-3-fluoroquinolin-7-yl)methyl)-5,5-difluorohexahydro-2H-cyclopenta[b]furan-2,3,3a-triol Step 1: To a mixture of (3aR,4aS,7aS,7bR)-7a-(benzyloxy)-2,2-dimethylhexahydro-5H-cyclopenta[4,5]furo[2,3-d][1,3]dioxol-5-one (3.0 g, 9.9 mmol) in toluene (40 mL) was added triethylamine (46.6 mL, 340 mmol) at ambient temperature under argon atmosphere. The reaction mixture was heated to 100° C. then treated with tert-butyldimethylsilyl trifluoromethanesulfonate (5.21 g, 20. mmol). The resulting mixture was stirred at 100° C. for 30 min. After completion of the reaction, the mixture was cooled to room temperature, diluted with toluene (300 mL), and washed with saturated aqueous NaHCO$_3$ (300 mL). The organic layer was dried over anhydrous Na$_2$SO$_4$ and filtered. The filtrate was concentrated under reduced pressure. The residue was purified by column chromatography on silica (0-15% EtOAc/petroleum ether) to afford (((3aR,4aS,7R,7bR)-7a-(benzyloxy)-2,2-dimethyl-4a,7,7a,7b-tetrahydro-3aH-cyclopenta[4,5]furo[2,3-d][1,3]dioxol-5-yl)oxy)(tert-butyl)dimethylsilane. $^1$H-NMR (300 MHz, DMSO-d$_6$) δ 7.36-7.26 (m, 5H), 5.85 (d, J=3.3 Hz, 1H), 4.81-4.79 (m, 1H), 4.64-4.56 (m, 3H), 4.46 (s, 1H), 2.70-2.64 (m, 1H), 2.37-2.31 (m, 1H), 1.51 (s, 3H), 1.35 (s, 3H), 0.91 (s, 9H), 0.18 (s, 6H).

Step 2: To a mixture of (((3aR,4aS,7aR,7bR)-7a-(benzyloxy)-2,2-dimethyl-4a,7,7a,7b-tetrahydro-3aH-cyclopenta[4,5]furo[2,3-d][1,3]dioxol-5-yl)oxy)(tert-butyl)dimethylsilane (4.0 g, 9.6 mmol) in anhydrous DMF (70 mL) was added 1-(chloromethyl)-4-fluoro-1,4-diazabicyclo[2.2.2]octane-1,4-diium tetrafluoroborate (3.72 g, 10.5 mmol) at ambient temperature under argon atmosphere. The resulting mixture was stirred at ambient temperature for 2 h. The reaction mixture was diluted with toluene (200 mL) and washed with water (3×50 mL). The combined organic layer was dried over anhydrous Na$_2$SO$_4$ and filtered. The filtrate was concentrated under reduced pressure. The residue was purified by column chromatography on silica (0-60% EtOAc/petroleum ether) to afford (3aR,4aS,7aS,7bR)-7a-(benzyloxy)-6-fluoro-2,2-dimethyltetrahydro-3aH-cyclopenta[4,5]furo[2,3-d][1,3]dioxol-5(4aH)-one. $^1$H NMR (400 MHz, DMSO-d$_6$) δ 7.20-7.05 (m, 51H), 5.88-5.67 (m, 1H), 4.62-4.49 (m, 1H), 4.44-4.40 (m, 3H), 3.85-3.83 (m, 1H), 2.13-1.94 (m, 2H), 1.28-1.26 (m, 3H), 1.16-1.14 (m, 3H).

Step 3: To a mixture of (3aR,4aS,7aS,7bR)-7a-(benzyloxy)-6-fluoro-2,2-dimethyltetrahydro-3aH-cyclopenta[4,5]furo[2,3-d][1,3]dioxol-5(4aH)-one (2.0 g, 6.2 mmol) in toluene (10 mL) was added triethylamine (21.4 g, 210 mmol) at ambient temperature under argon atmosphere. The reaction mixture was heated to 100° C. then treated with tert-butyldimethylsilyl trifluoromethanesulfonate (3.28 g, 12.4 mmol). The resulting mixture was stirred at 100° C. for 30 min. After completion of the reaction, the mixture was cooled to room temperature, diluted with water (150 mL), and extracted with EtOAc (3×150 mL). The combined organic layers were dried over anhydrous $Na_2SO_4$ and filtered. The filtrate was concentrated under reduced pressure. The residue was purified by column chromatography on silica (0-10% EtOAc/petroleum ether) to afford (((3aR,4aS,7aR,7bR)-7a-(benzyloxy)-6-fluoro-2,2-dimethyl-4a,7,7a,7b-tetrahydro-3aH-cyclopenta[4,5]furo[2,3-d][1,3]dioxol-5-yl)oxy)(tert-butyl)dimethylsilane. $^1$H-NMR (400 MHz, DMSO-$d_6$) δ 7.17-7.07 (m, 5H), 5.70-5.56 (m, 1H), 4.52-4.42 (m, 3H), 4.39-4.32 (m, 1H), 2.68 (d, J=16.0 Hz, 1H), 2.51 (d, J=16.4 Hz, 1H), 1.30-1.29 (m, 3H), 1.16-1.15 (m, 3H), 0.72 (s, 9H), −0.04 (s, 6H).

Step 4: To a mixture of (((3aR,4aS,7aR,7bR)-7a-(benzyloxy)-6-fluoro-2,2-dimethyl-4a,7,7a 7b-tetrahydro-3aH-cyclopenta[4,5]furo[2,3-d][1,3]dioxol-5-yl)oxy)(tert-butyl)dimethylsilane (2.6 g, 6.0 mmol) in anhydrous DMF (60 mL) was added 1-(chloromethyl)-4-fluoro-1,4-diazabicyclo[2.2.2]octane-1,4-diium tetrafluoroborate (2.53 g, 7.2 mmol) at 25° C. under argon atmosphere. The resulting mixture was stirred at 25° C. for 2 h. The reaction mixture was diluted with water (300 mL) and extracted with EtOAc (3×300 mL). The combined organic layers were dried over anhydrous $Na_2SO_4$ and filtered. The filtrate was concentrated under reduced pressure. The residue was purified by column chromatography on silica (0-50% EtOAc/petroleum ether) to afford (3aR,4aS,7bR)-7a-(benzyloxy)-6,6-difluoro-2,2-dimethyltetrahydro-3aH-cyclopenta[4,5]furo[2,3-d][1,3]dioxol-5(4aH)-one. $^1$H-NMR (400 MHz, Chloroform-d) δ 7.42-7.34 (m, 5H), 5.96 (d, J=3.6 Hz, 1H), 4.78 (d, J=10.4 Hz, 1H), 4.62 (d, J=3.6 Hz, 1H), 4.54 (d, J=10.8 Hz, 1H), 4.38 (d, J=4.8 Hz, 1H), 2.90-2.77 (m, 1H), 2.47-2.38 (m, 1H), 1.61 (s, 3H), 1.46 (s, 3H).

Step 5: To a stirred solution of Nysted Reagent (36.9 g, 16.2 mmol, 20 wt. % in THF) in THF (22 mL) was added boron trifluoride diethyl etherate (2.29 g, 16.2 mmol) at 0° C. under argon atmosphere. The mixture was stirred at 0° C. for 5 minutes. A solution of (3aR,4aS,7aS,7R)-7a-(benzyloxy)-6,6-difluoro-2,2-dimethyltetrahydro-3aH-cyclopenta[4,5]furo[2,3-d][1,3]dioxol-5(4aH)-one (1.1 g, 3.2 mmol) in anhydrous THF (33 mL) was added dropwise into the mixture at 0° C. The resulting mixture was stirred at ambient temperature for 4 h. The reaction mixture was quenched with saturated aqueous $NaHCO_3$ (50 mL) at 0° C. The resulting mixture was extracted with EtOAc (2×100 mL). The combined organic layers were washed with brine (50 mL), dried over anhydrous $Na_2SO_4$, filtered, and the filtrate was concentrated under reduced pressure. The residue was purified by Prep-TLC (EtOAc:petroleum ether=1:3) to give (3aR,4aR,7aR,7bR)-7a-(benzyloxy)-6,6-difluoro-2,2-dimethyl-5-methylenehexahydro-3aH-cyclopenta[4,5]furo[2,3-d][1,3]dioxole. $^1$H-NMR (400 MHz, DMSO-$d_6$) δ 7.37-7.26 (m, 5H), 5.97 (d, J=3.6 Hz, 1H). 5.87-5.84 (m, 2H), 4.77 (d, J=4.0 Hz, 1H), 4.70-4.69 (m, 1H), 4.63 (d, J=11.2 Hz, 1H), 4.53 (d, J=11.2 Hz, 1H), 2.98 (t, J=16.0 Hz, 2H), 2.35-2.23 (m, 1H), 1.53 (s, 3H), 1.34 (s, 3H).

Step 6: (3aR,4aR,7aR,7bR)-7a-(benzyloxy)-6,6-difluoro-2,2-dimethyl-5-methylenehexahydro-3aH-cyclopenta[4,5]furo[2,3-d][1,3]dioxole (170 mg, 0.50 mmol) was dissolved in 9-BBN (6.029 mL, 3.01 mmol, 0.5 M in THF) at ambient temperature under argon atmosphere. The resulting solution was stirred at 50° C. for 1 h. The mixture was cooled to 0° C. and treated with a solution of $K_3PO_4$ (533 mg, 2.50 mmol) in 3.5 mL water. The mixture was stirred for 0.5 h at ambient temperature, then a solution of 7-bromo-3-fluoroquinolin-2-amine (97 mg, 0.40 mmol) in 5.0 mL anhydrous THF and Pd(dppf)$Cl_2$ (37 mg, 0.05 mmol) were added to the mixture. The mixture was heated to 80° C. in a microwave reactor for 3 h. The mixture was cooled to room temperature, diluted with water (40 mL) and extracted with EtOAc (3×80 mL). The combined organic layers were dried over anhydrous $Na_2SO_4$, filtered, and the filtrate was concentrated under reduced pressure. The residue was purified by Prep-TLC (EtOAc:petroleum ether==1:2) to give 7-(((3aR,4aR,5S,7aR,7bR)-7a-(benzyloxy)-6,6-difluoro-2,2-dimethylhexahydro-3aH-cyclopenta[4,5]furo[2,3-d][1,3]dioxol-5-yl)methyl)-3-fluoroquinolin-2-amine. MS: 501 (M+1). $^1$H-NMR (400 MHz, Chloroform-d) δ 7.61 (s, 1H), 7.55 (d, J=3.6 Hz, 1H), 7.52 (s, 1H), 7.36-7.25 (m, 6H), 5.99 (d, J=3.6 Hz, 1H), 5.61 (s, 2H), 4.68 (d, J=10.4 Hz, 1H), 4.62 (d, J=3.6 Hz, 1H), 4.48 (d, J=10.8 Hz, 1H), 4.39 (dd, J=6.4 Hz, 3.2 Hz, 1H), 3.16-3.05 (m, 2H), 2.87-2.74 (m, 2H), 2.32-2.21 (m, 1H), 1.56 (s, 3H), 1.42 (s, 3H).

Step 7: To a solution of 7-(((aR,4aR,5S,7aR,7bR)-7a-(benzyloxy)-6,6-difluoro-2,2-dimethylhexahydro-3aH-cyclopenta[4,5]furo[2,3-d][1,3]dioxol-5-yl)methyl)-3-fluoroquinolin-2-amine (290 mg, 0.58 mmol) in anhydrous DCM (6.0 mL) was added dropwise $BCl_3$ (1 M in DCM, 1.7 mL, 1.74 mmol) at −78° C. under argon atmosphere. The resulting mixture was stirred at −78° C. for 2 h. The reaction mixture was quenched by the addition of triethylamine (0.32 mL, 2.3 mmol), and the resulting mixture was kept at −78° C. for 0.5 h. Then the reaction mixture was poured into saturated aqueous $NaHCO_3$ (30 mL) at 0° C., and the resulting mixture was stirred at 0° C. for another 0.5 h. The final mixture was extracted with EtOAc (3×200 mL). The combined organic layers were dried over anhydrous $Na_2SO_4$ and filtered. The filtrate was concentrated under reduced pressure. The residue was purified by reverse-phase column chromatography on C18 (0-95% 5 mM aq. $NH_4HCO_3$/MeCN) to afford (3R,3aS,6S,6aR)-6-((2-amino-3-fluoroquinolin-7-yl)methyl)-5,5-difluorohexahydro-2H-cyclopenta[b]furan-2,3,3a-triol. MS: 371 (M+1). $^1$H-NMR (300 MHz, DMSO-$d_6$) δ 7.81 (d, J=12.0 Hz, 1H), 7.61 (d, J=8.1 Hz, 1H), 7.41 (s, 1H), 7.19 (d, J=8.1 Hz, 1H), 6.81-6.75 (m, 2H), 6.21 (d, J=7.2 Hz, 1H), 5.26-5.22 (m, 1H), 5.01-4.95 (m, 2H), 4.00-3.99 (m, 1H), 3.66-3.62 (m, 1H), 2.97-2.66 (m, 3H), 2.42-2.09 (m, 2H).

Synthetic Scheme for Intermediate 28

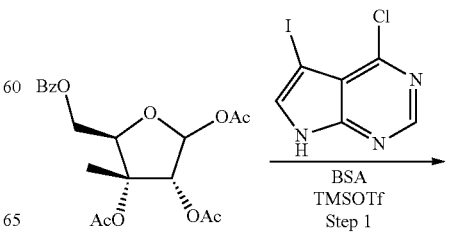

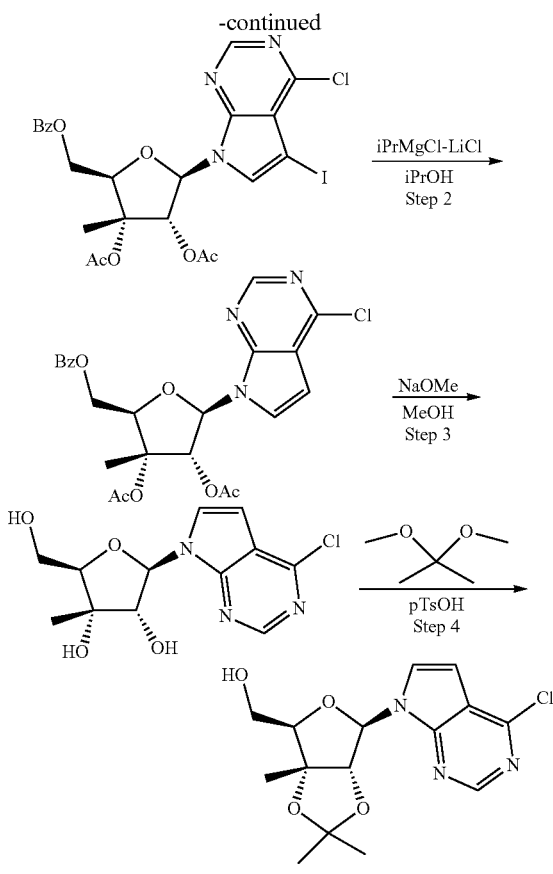

Intermediate 28: ((3aR,4R,6R,6aR)-6-(4-chloro-7H-pyrrolo[2,3-d]pyrimidin-7-yl)-2,2,3a-trimethyltetrahydrofuro[3,4-d][1,3]dioxol-4-yl)methanol Step 1: A solution of 4-chloro-5iodo-7H-pyrrolo[2,3-d]pyrimidine (1.417 g, 5.07 mmol) in dry ACN (10 mL) was stirred with BSA (1.25 mL, 5.07 mmol) at room temperature for 15 minutes. (3R,4R,5R)-5-((benzoyloxy)methyl)-4-methyltetrahydrofuran-2,3,4-triyl triacetate (2 g, 5.07 mmol) in ACN (20 mL) was added followed by TMSOTf (1.84 mL, 10.1 mmol) and the reaction mixture was stirred for a further 10 minutes at room temperature, followed by 3 h at 80° C. The reaction mixture was cooled to room temperature and diluted with EtOAc (40 mL). The reaction mixture was then washed with saturated aqueous NaHCO₃ (2×30 mL) and brine (2×30 mL), and dried. The residue was purified by column chromatography on silica gel (PE/Et₂O) to afford (2R,3R,4R,5R)-2-((benzoyloxy)methyl)-5-(4-chloro-5-iodo-7H-pyrrolo[2,3-d]pyrimidin-7-yl)-3-methyltetrahydrofuran-3,4-diyl diacetate. MS: 614 (M+1)

Step 2: To a stirred solution of (2R,3R,4R,5R)-2-((benzoyloxy)methyl)-5-(4-chloro-3-iodo-1H-indol-1-yl)-3-methyltetrahydrofuran-3,4-diyl diacetate (4.6 g, 7.5 mmol) in dry THF (45 mL) was dropwise added isopropylmagnesium chloride-lithium chloride complex (7.21 mL, 9.37 mmol) over a period of 5 minutes at −78° C. The mixture was stirred at −78° C. for 20 minutes, and then quenched with dropwise addition of i-PrOH (0.808 mL, 10.5 mmol) at −78° C. The reaction mixture was poured into a mixture of ice and saturated aqueous NH₄Cl, and extracted with DCM. The organic layers were combined, dried, and concentrated under reduced pressure to afford (2R,3R,4R,5R)-2-((benzoyloxy)methyl)-5-(4-chloro-7H-pyrrolo[2,3-d]pyrimidin-7-yl)-3-methyltetrahydrofuran-3,4-diyl diacetate as an oil. MS: 489 (M+1)

Step 3: At 0° C., sodium methoxide (7.75 mL, 387 mmol) was added to a stirred solution of (2R,3R,4R,5R)-2-((benzoyloxy)methyl)-5-(4-chloro-1H-indol-1-yl)-3-methyltetrahydrofuran-3,4-diyl diacetate (3.15 g, 6.46 mmol) in MeOH (100 mL). The mixture was stirred at 0° C. for 1 h and then at room temperature for 2 h. The reaction mixture was quenched with Dowex until pH:=6. The reaction mixture was concentrated under reduced pressure, and the residue was purified by column chromatography on silica gel (0-10% MeOH/DCM) to afford (2R,3S,4R,5R)-5-(4-chloro-7H-pyrrolo[2,3-d]pyrimidin-7-yl)-2-(hydroxymethyl)-3-methyltetrahydrofuran-3,4-diol as a foam. MS: 300 (M+1)

Step 4: A mixture of (2R,3S,4R,5R)-5-(4-chloro-1H-indol-1-yl)-2-(hydroxymethyl)-3-methyltetrahydrofuran-3,4-diol (443 mg, 1.48 mmol), p-toluenesulfonic acid monohydrate (562 ng, 2.96 mmol) and 2,2-dimethoxypropane (1.844 µl, 14.78 mmol) in acetone (35 mL) was stirred at 65° C. overnight. The reaction mixture was extracted with DCM and the organic phase was washed with saturated aqueous NaHCO₃. The organic phase was dried, concentrated under reduced pressure, and the residue was purified by reverse phase HPLC (C18, ACN/water) to afford ((3aR,4R,6R,6aR)-6-(4-chloro-7H-pyrrolo[2,3-d]pyrimidin-7-yl)-2,2,3a-trimethyltetrahydrofuro[3,4-d][1,3]dioxol-4-yl)methanol as a foam. MS: 363 (M+24)

Synthetic Scheme for Intermediate 29

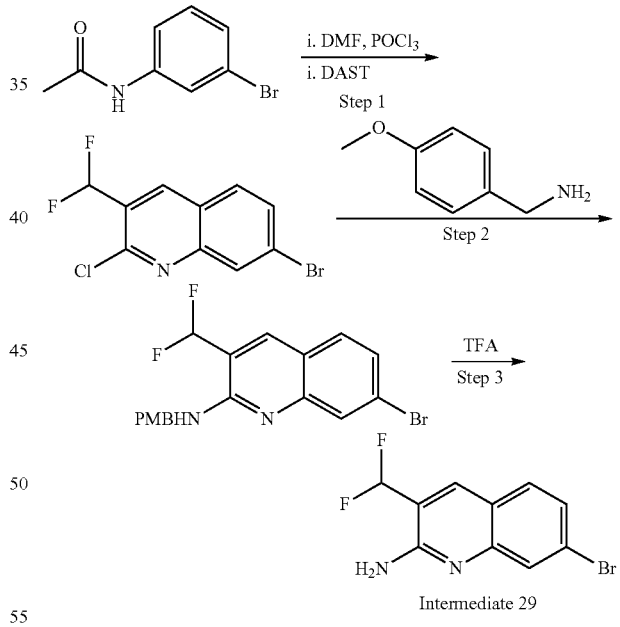

Intermediate 29:
7-bromo-3-(difluoromethyl)quinolin-2-anine

Step 1: To DMF (16 mL) was added POCl₃ (48.8 mL, 523 mmol) dropwise via cannula over 30 minutes at 0° C., and the reaction mixture was stirred for another 30 minutes at this temperature. Then, N-(3-bromophenyl)acetamide (16 g, 75 mmol) was added to the mixture and the reaction was stirred at 80° C. for 2 h. The solvent was then removed under reduced pressure to afford crude residue which was diluted with 200 mL of saturated aqueous NaHCO₃ and extracted with 1000 mL of EtOAc. The organic phase was washed with water (600 mL), brine (300 mL), dried over anhydrous sodium sulfate, filtered, and the filtrate was concentrated under reduced pressure. The resulting residue was purified by silica gel column chromatography (eluted with 20% EtOAc/PE) to afford 7-bromo-2-chloroquinoline-3-carbaldehyde as a solid. Then, 7-bromo-2-chloroquinoline-3-carbaldehyde (1.8 g, 6.65 mmol) was co-evaporated with toluene (5 mL) three times. To a solution of 7-bromo-2-chloroquinoline-3-carbaldehyde (1.8 g, 6.65 mmol) in DCM (27 mL) was added DAST (1.76 mL, 13.31 mmol) at 0° C., and the mixture was then stirred at 50° C. for 1.5 h. The reaction was diluted with 50 mL of saturated aqueous NaHCO₃ at 0° C. and extracted with 250 mL EtOAc. The organic phase was washed with water (100 mL), brine (100 ml), dried over anhydrous sodium sulfate, filtered, and the filtrate was concentrated under reduced pressure. The resulting residue was purified by silica gel column chromatography (eluted with 30% DCM/PE) to afford 7-bromo-2-chloro-3-(difluoromethyl)quinoline as a solid. MS: 292/294 (M+1/M+3).

Step 2: A solution of 7-bromo-2-chloro-3-(difluoromethyl)quinoline (960 mg, 3.28 mmol) and (4-methoxyphenyl)methanamine (2.144 mL, 16.41 mmol) in 1,4-dioxane (10 mL) was stirred at room temperature in a sealed tube. Then the reaction mixture was heated at 90° C. for 16 h. The reaction was concentrated under reduced pressure, and the resulting residue was purified by silica gel column chromatography (eluted with 20% EtOAc/PE) to afford 7-bromo-3-(difluoromethyl)-N-(4-methoxybenzyl)quinolin-2-amine as a solid. MS: 393/395 (M+1/M+3).

Step 3: A solution of 7-bromo-3-(difluoromethyl)-N-(4-methoxybenzyl)quinolin-2-amine (200 mg, 0.509 mmol) in TFA (15 mL) was stirred at 50° C. under argon for 3 h. The reaction was then diluted with 100 mL of saturated aqueous NaHCO₃ at 0° C. and extracted with 200 mL of EtOAc. The organic phase was washed with water (50 mL), brine (50 mL), dried over anhydrous sodium sulfate, filtered, and the filtrate was concentrated under reduced pressure. The resulting residue was purified by silica gel column chromatography (eluted with 20% EtOAc/PE) to afford 7-bromo-3-(difluoromethyl)quinolin-2-anine as a solid. MS: 273/275 (M+1/M+3).

Synthetic Scheme for Intermediate 30

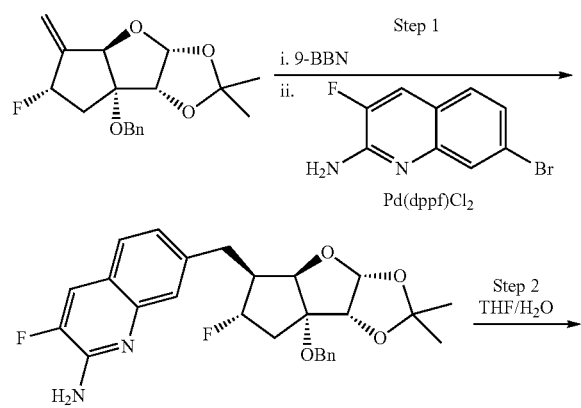

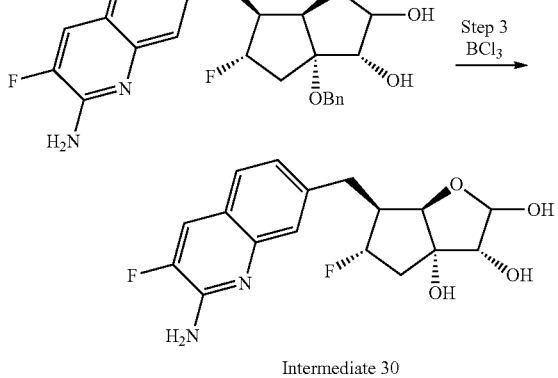

Intermediate 30

Intermediate 30: (3R,3aS,5S,6S)-6-((2-amino-3-fluoroquinolin-7-yl)methyl)-5-fluorohexahydro-2H-cyclopenta[b]furan-2,3,3a-triol Step 1: To a solution of (3aR,4aR,6S,7aR,7bR)-7a-(benzyloxy)-6-fluoro-2,2-dimethyl-5-methylenehexahydro-3aH-cyclopenta[4,5]furo[2,3-d][1,3]dioxole (190 mg, 0.593 mmol) in anhydrous THF (0.5 mL) was added 9-BBN (7.12 mL, 0.5M in THF, 3.56 mmol) dropwise at room temperature under argon. The mixture was stirred at 70° C. for 1.5 h. Then, the mixture was cooled to 0° C., and a solution of K₃PO₄ (755 mg, 3.56 mmol) in 2.5 mL of H₂O was added. The resultant mixture was stirred for another 0.5 h at room temperature. Then, a solution of 7-bromo-3-fluoroquinolin-2-amine (129 mg, 0.534 mmol) in anhydrous THF (3 mL) and Pd(dppf)Cl₂ (43.4 mg, 0.059 mmol) were added to the mixture. The final reaction mixture was irradiated with microwave radiation at 80° C. for 3 h. The organic layer was then separated, and the aqueous layer was re-extracted with EtOAc (60 mL×2). The combined organic layers were washed with H₂O (60 mL) and brine (60 mL), dried over anhydrous Na₂SO₄, filtered, and the filtrate was concentrated under reduced pressure. The resulting residue was purified by silica gel flash chromatography (eluted with 0-25% EtOAc/PE) to afford 7-(((3aR,4aR,5S,6S,7aR,7bR)-7a-(benzyloxy)-6-fluoro-2,2-dimethylhexahydro-3aH-cyclopenta[4,5]furo[2,3-d][1,3]dioxol-5-yl)methyl)-3-fluoroquinolin-2-amine as a solid. MS: 483 (M+1). ¹H-NMR (300 MHz, DMSO-d₆) δ 7.81 (d, J=11.7 Hz, 1H), 7.61 (d, J=8.1 Hz, 1H), 7.47-7.36 (m, 5H), 7.34-7.29 (m, 1H), 7.15-7.12 (m, 1H), 6.76 (br s, 2H5.86 (d, J=3.9 Hz, 1H), 5.42-5.34 (m, 1H), 4.68-4.65 (m, 2H), 4.57 (d, J=11.1 Hz, 1H), 4.22 (s, 1H), 3.02 (dd, J=14.1, 6.9 Hz, 1H), 2.86-2.78 (m, 1H), 2.70-2.64 (m, 2H), 2.08-1.90 (m, 1H), 1.40 (s, 3H), 1.30 (s, 3H).

Step 2: 7-(((3aR,4aR,5S,6S,7aR,7bR)-7a-(benzyloxy)-6-fluoro-2,2-dimethylhexahydro-3aH-b cyclopenta[4,5]furo[2,3-d][1,3]dioxol-5-yl)methyl)-3-fluoroquinolin-2-amine (750 mg, 1.55 mmol) was dissolved in TFA and H₂O (12.0 mL, 1:1 TFA/H₂O) at 0° C. and the mixture was then stirred at room temperature for 1 h. The mixture was co-evaporated with toluene (3×20 mL) under reduced pressure. The residue was purified by silica gel column chromatography (eluted with 1-10% MeOH/DCM) to afford (3R,3aS,5S,6S)-6-((2-amino-3-fluoroquinolin-7-yl)methyl)-3a-(benzyloxy)-5-fluorohexahydro-2H-cyclopenta[b]furan-2,3-diol as a solid. MS: 443 (M+1).

Step 3: To a solution of (3R,3aS,5S,6S)-6-((2-amino-3-fluoroquinolin-7-yl)methyl)-3a-(benzyloxy)-5-fluorohexahydro-2H-cyclopenta[b]furan-2,3-diol (650 mg, 1.47 mmol) in anhydrous DCM (20 mL) was added BCl₃ (4.41 mL, IM in DCM, 4.41 mmol) dropwise at −78° C. under argon. The resulting solution was stirred at −78° C. for 1 h. The reaction was then quenched with triethylamine (0.819 mL, 5.88 mmol) and stirred at −78° C. for 0.5 h. The reaction mixture was poured into ice-cold saturated aqueous NaHCO₃ (50 mL) at 0° C. and stirring continued for 0.5 h. The mixture was then extracted with EtOAc (3×200 mL). The combined organic layers were dried over anhydrous Na₂SO₄ and filtered. The filtrate was concentrated under reduced pressure and the resulting residue and all of the aqueous phase were purified by RP-Combi-Flash at room temperature (ACN/water with 5 mM NH₄CO₃ modifier) to afford (3R, 3aS,5S,6S)-6-((2-amino-3-fluoroquinolin-7-yl)methyl)-5-fluorohexahydro-2H-cyclopenta[b]furan-2,3,3a-triol as a solid. MS: 353 (M+1). ¹H NMR (300 MHz, CD₃OD) δ 7.71 (d, J=11.4 Hz. 1H), 7.61 (d, J=8.1 Hz, 1H), 7.50 (s, 1H), 7.25 (d, J=8.1 Hz, 1H), 5.29-5.21 (m, 1H), 5.03-4.97 (m, 1H), 4.39-4.20 (m, 1H), 3.82-3.67 (m, 1H), 3.06-2.99 (m, 2H), 2.68-2.40 (m, 1H), 2.33-2.05 (m, 2H).

Synthetic Scheme for Intermediate 31

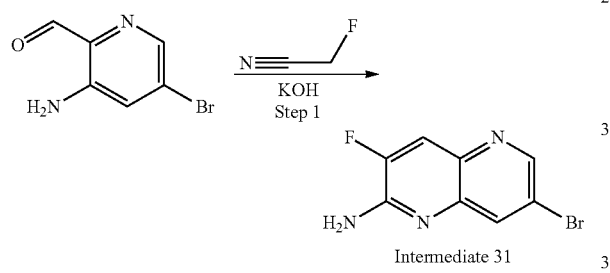

Intermediate 31

Intermediate 31: 7-bromo-3-fluoro-1,5-naphthyridin-2-amine

Step 1: 3-amino-5-bromopicolinaldehyde (1000 mg, 4.97 mmol) was dissolved in DMSO (10 mL), charged with 2-fluoroacetonitrile (1108 μL, 19.9 mmol), 15M potassium hydroxide (100 μL, 1.49 mmol) and heated to 80° C. for 2 h. The reaction was poured into 10 mL water, diluted with EtOAc (30 mL) and filtered through Celite. The organic layer was washed with brine, dried over sodium sulfate, filtered, and concentrated under reduced pressure. The residue was purified by column chromatography on silica (0-100% EtOAc/CH₂Cl₂ to afford 7-bromo-3-fluoro-1,5-naphthyridin-2-amine as a solid. MS: 242/244 (M+1/3).

Synthetic Scheme for Intermediate 32

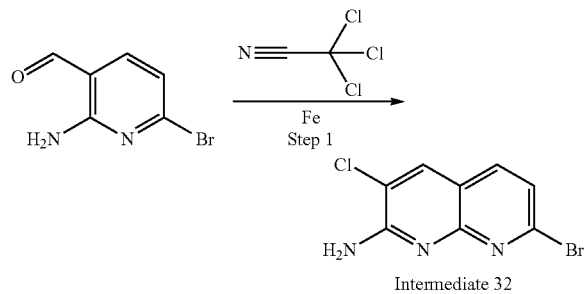

Intermediate 32

Intermediate 32: 7-bromo-3-chloro-1,8-naphthyridin-2-amine

Step 1: A mixture of 2-amino-6-bromonicotinaldehyde (2.6 g, 12.9 mmol), and iron powder (7.22 g, 129 mmol) was degassed under nitrogen, and then charged with THF (26 mL). Trichloroacetonitrile (1.95 mL, 19.4 mmol) was added and the mixture was stirred for 2 h at room temperature. The reaction was refluxed at 65° C. overnight. The reaction was cooled to room temperature and filtered through Celite charged with 10 g of silica gel. The mixture was concentrated under reduced pressure, and the residue was purified by column chromatography on silica (0-50% 3:1 EtOAc: EtOH/Hexanes with 1% aqueous NH₄OH modifier). The resulting solid was washed with 2×10 mL cold Et₂O to afford 7-bromo-3-chloro-1,8-naphthyridin-2-amine as a solid used without further purification MS: 258/260 (M+1/3).

Synthetic Scheme for Intermediate 33

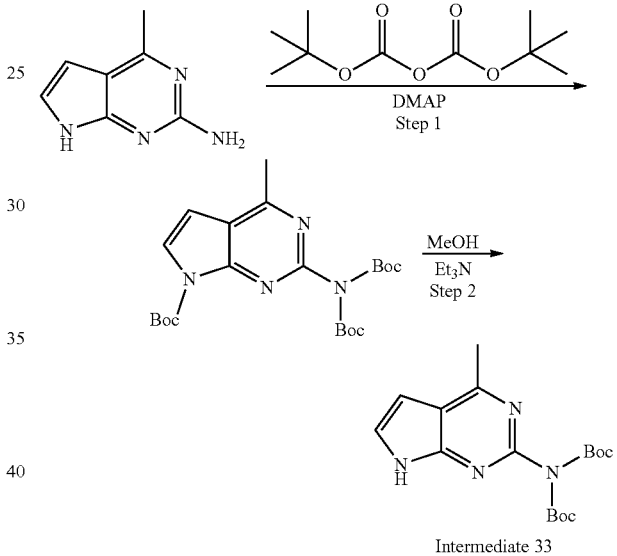

Intermediate 33

Intermediate 33: di-tert-butyl (4-methyl-7H-pyrrolo[2,3-d]pyrimidin-2-yl)imidodicarbonate Step 1: To a solution of 4-methyl-7H-pyrrolo[2,3-d]pyrimidin-2-amine (0.5 g, 3.4 mmol) in acetonitrile (8.5 mL)/DCM (8.5 mL) was added di-tert-butyl dicarbonate (2.6 g, 12 mmol) and 4-dimethylaminopyridine (0.082 g, 0.68 mmol). The solution was stirred for 18 h at room temperature. The reaction was concentrated and purified by column chromatography on silica (0-60% EtOAc/hexanes) to afford tert-butyl 2-[bis(tert-butoxycarbonyl)amino]-4-methyl-7H-pyrrolo[2,3-d]pyrimidine-7-carboxylate as a solid. MS: 449 (M+1).

Step 2 To a solution of tert-butyl 2-[bis(tert-butoxycarbonyl)amino]-4-methyl-7H-pyrrolo[2,3-d]pyrimidine-7-carboxylate (0.6 g, 1.34 mmol) in MeOH (2.2 mL) was added triethylamine (187 mL, 13.4 mmol) at room temperature. The reaction was then heated to 60° C. and stirred for 18 h. The mixture was cooled to room temperature and concentrated under reduced pressure. The residue was purified by column chromatography on silica (0-100% EtOAc/

Hexanes) to afford di-tert-butyl (4-methyl-7H-pyrrolo[2,3-d]pyrimidin-2-yl)imidodicarbonate. MS: 349 (M+1).
Synthetic Scheme for Intermediate 34

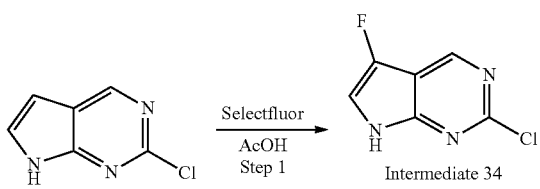 [SMILES: Clc1ncc2cc[nH]c2n1 ; Fc1c[nH]c2nc(Cl)ncc12]

Intermediate 34: 2-chloro-5-fluoro-1H-pyrrolo[2,3-d]pyrimidine

To 2-chloro-1H-pyrrolo[2,3-d]pyrimidine (335 mg, 2.18 mmol) in acetonitrile (11 mL) was added Selectfluor (1.16 g, 3.27 mmol) and AcOH (1.1 mL). The mixture was heated at 70° C. overnight. The mixture was cooled to room temperature and concentrated under reduced pressure. The residue was diluted with EtOAc and washed with water (2×). The solution was dried over sodium sulfate, filtered, and concentrated under reduced pressure. The residue was purified by chromatography on silica (20-50% EtOAc/Hexanes) to afford 2-chloro-5-fluoro-1H-pyrrolo[2,3-d]pyrimidine. MS: 172 (M+1).

Synthetic Scheme for Intermediate 35

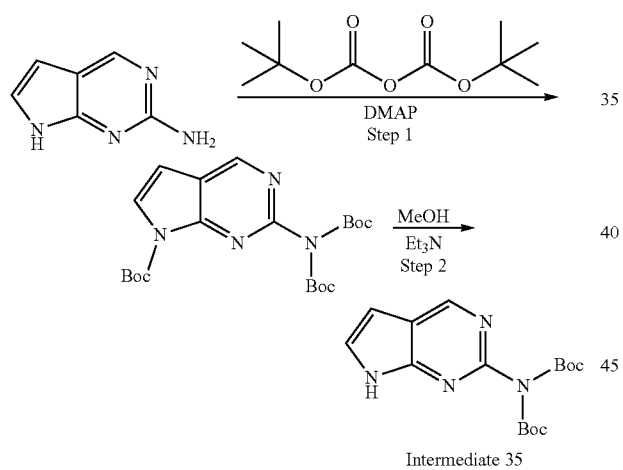

Intermediate 35: bis(2-methyl-2-propanyl) 7H-pyrrolo[2,3-d]pyrimidin-2-ylimidodicarbonate Step 1: To a stirred solution of 7H-pyrrolo[2,3-d]pyrimidin-2-amine (500 mg, 3.73 mmol) in acetonitrile (9 mL) and dichloromethane (9 mL) was added Boc-anhydride (2.85 g, 13.1 mmol) and DMAP (91 mg, 0.75 mmol). The reaction mixture was stirred overnight. The mixture was concentrated under reduced pressure, and the residue was purified by column chromatography on silica (0-40% EtOAc in Hex) to afford 2-methyl-2-propanyl 2-(bis{[(2-methyl-2-propanyl)oxy]carbonyl}amino)-7H-pyrrolo[2,3-d]pyrimidine-7-carboxylate. MS: 435 (M+1).

Step 2: To a stirred solution of 2-methyl-2-propanyl 2-(bis{[(2-methyl-2-propanyl)oxy]carbonyl}amino)-7H-pyrrolo[2,3-d]pyrimidine-7-carboxylate (1.52 g, 3.50 mmol) in MeOH (17.5 mL) was added TEA (4.88 mL, 35.0 mmol). The solution was heated at reflux for 2.5 h. The mixture was cooled to room temperature, concentrated under reduced pressure, and purified by silica gel chromatography (0-60%. EtOAc in Hex) to afford bis(2-methyl-2-propanyl) 7H-pyrrolo[2,3-d]pyrimidin-2-ylimidodicarbonate. MS: 335 (M+1). $^1$H NMR (500 MHz, DMSO-$d_6$) δ 12.23 (s, 1H), 8.98 (s, 1H), 7.62 (d, J=3.5 Hz, 1H), 6.63 (d, J=3.5 Hz, 1H), 1.38 (s, 18H).

Synthetic Scheme for Intermediate 36

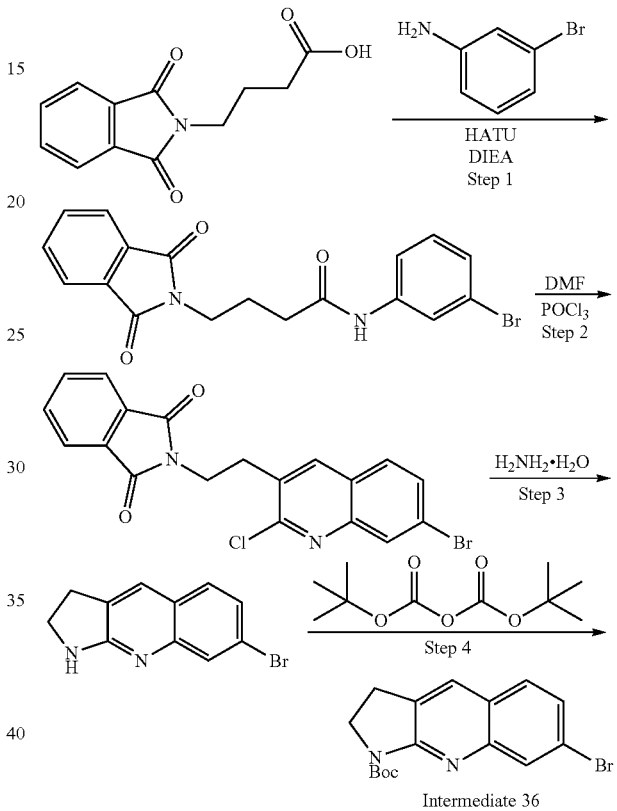

Intermediate 36: tert-butyl 7-bromo-2,3-dihydro-1H-pyrrolo[2,3-b]quinoline-1-carboxylate Step 1: To a solution of 4-(1,3-dioxoisoindolin-2-yl)butanoic acid (7.73 g, 33.1 mmol), HATU (15.1 g, 39.8 mmol) and DIEA (17.4 mL, 99 mmol) in DMF (50 mL) was added 3-bromoaniline (5.7 g, 33.1 mmol) at 15° C. The mixture was stirred for 0.5 h. Water (500 mL) was added and the mixture was extracted with EtOAc (200 mL×3). The combined organic layers were washed with brine (200 mL) and concentrated under reduced pressure. The residue was purified by filtering with EtOAc to afford N-(3-bromophenyl)-4-(1,3-dioxoisoindolin-2-yl)butanamide as a solid. MS:387/389 (M+1/M+3)

Step 2: DMF (2.70 ml, 34.9 mmol) was added dropwise to POCl$_3$ (19.02 mL, 204 mmol) at 5° C. (temperature kept within 5-15° C.), and the reaction mixture was stirred for 15 minutes. N-(3-bromophenyl)-4-(1,3-dioxoisoindolin-2-yl) butanamide (9 g, 23.24 mmol) was added to the reaction mixture and heated to 80° C. for 12 hours. The mixture was cooled to room temperature and poured into water (200 mL), and the pH was adjusted to 9. The mixture was extracted with EtOAc (100 mL×3), and the combined organic layers were concentrated under reduced pressure. The residue was purified by filtering with EtOAc to afford 2-(2-(7-bromo-2-chloroquinolin-3-yl)ethyl)isoindoline-1,3-dione as a solid. MS: 415/417 (M+1/M+3)

Step 3: Hydrazine hydrate (0.905 mL, 18.2 mmol) was added dropwise to 2-(2-(7-bromo-2-chloroquinolin-3-yl)ethyl)isoindoline-1,3-dione (6.3 g, 15.2 mmol) in butan-1-ol (60 mL) at 80° C. The reaction mixture was stirred at 100° C. for 12 h. The reaction was concentrated under reduced pressure to afford 7-bromo-2,3-dihydro-1H-pyrrolo[2,3-b]quinoline as a solid. MS: 249/251 (M+1/M+3)

Step 4: Into a 5 L 4-necked round bottom flask purged and maintained with an inert atmosphere of nitrogen was added 7-bromo-2,3-dihydro-1H-pyrrolo[2,3-b]quinoline (100 g, 0.401 mol) and di-tert-butyl dicarbonate (400 g, 1.83 mol). The resulting solution was stirred for 12 h at 100° C. The mixture was cooled to room temperature and concentrated under reduced pressure. The residue was purified by column chromatography on silica (1:10 ethyl acetate/petroleum ether) to afford tert-butyl 7-bromo-2,3-dihydro-1H-pyrrolo[2,3-b]quinoline-1-carboxylate as a solid. MS: 349/351 (M+1/M+3).

Synthetic Scheme for Intermediate 37

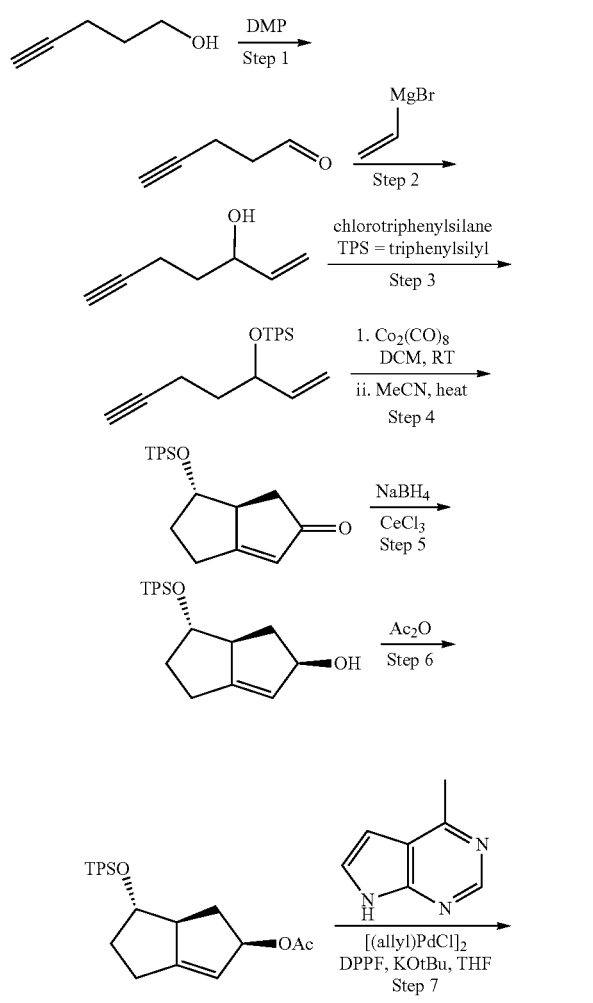

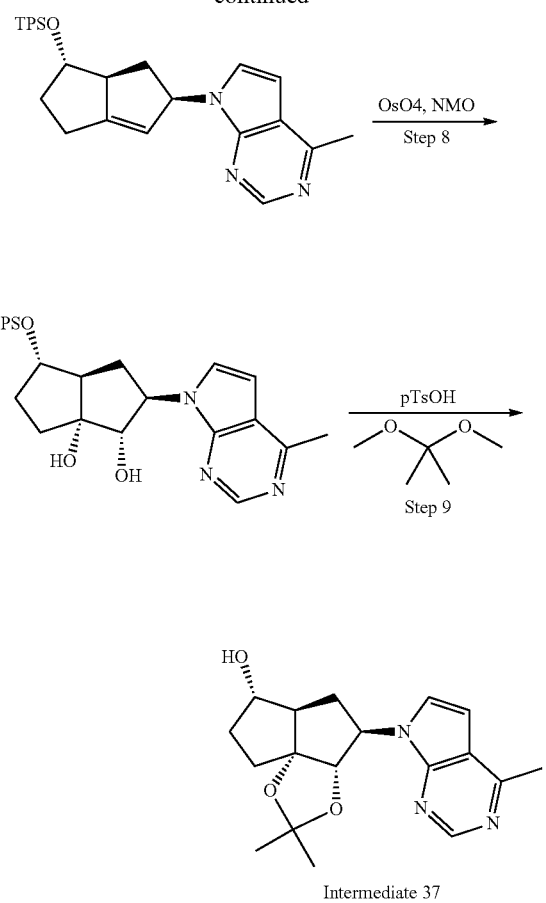

Intermediate 37: (3aS,4R,5aR,6S,8aR)-2,2-dimethyl-4-(4-methyl-7H-pyrrolo[2,3-d]pyrimidin-7-yl)hexahydro-5H-pentaleno[1,6a-d][1,3]dioxol-6-ol Step 1: To a flask containing a solution of pent-4-yn-1-ol (2.4 mL, 25 mmol) in DCM 1(200 mL) was added Dess-Martin Periodinane (14 g, 33 mmol). The reaction was stirred at room temperature overnight. The reaction was slowly poured into a beaker containing a stirring solution of both saturated aqueous sodium bicarbonate and saturated aqueous sodium thiosulfate. The mixture was poured into a separatory funnel and extracted. The organic layers were combined, dried over magnesium sulfate, filtered through a plug of Celite®, and concentrated under reduced pressure to afford pent-4-ynal which was used in the next step without further purification.

Step 2: To a flask containing the crude pent-4-ynal was added THF (200 mL). The reaction was cooled to 0° C. under an atmosphere of argon. Vinyl magnesium bromide (50 mL, 1M, 50 mmol) was added and the reaction was stirred at 0° C. for 70 minutes. The reaction was then poured into a separatory funnel containing saturated aqueous ammonium chloride and extracted with EtOAc. The organic layers were combined, dried over magnesium sulfate, filtered, and concentrated under reduced pressure to afford hept-a-en-6-yn-3-ol which was used in the next step without further purification.

Step 3: To a flask containing the crude hept-1-en-6-yn-3-ol in DCM (200 mL), was added pyridine (6.0 mL, 74 mmol), DMAP (4.58 g, 37.5 mmol), and triphenylchlorosilane (11.5 g 37.5 mmol). The reaction was stirred at room temperature overnight. The reaction was then poured into a separatory funnel containing saturated aqueous ammonium chloride and extracted. The organic layers were combined, dried over magnesium sulfate, filtered, and concentrated under reduced pressure. The residue was then purified by column chromatography on silica (0-10% EtOAc/hexanes) to afford (hept-1-en-6-yn-3-yloxy)triphenylsilane. $^1$H NMR (600 MHz, CDCl$_3$) δ 7.65-7.61 (m, 6H), 7.45-7.41 (m, 3H), 7.39-7.35 (m, 6H), 5.85-5.78 (m, 1H), 5.06-499 (m, 2H), 4.42 (q, J=6.2 Hz, 1H), 2.27-2.15 (m, 2H), 1.87-1.78 (m, 2H), 1.77-1.70 (m, 1H).

Step 4: To a flask containing a solution of (hept-1-en-6-yn-3-yloxy)triphenylsilane (4.72 g, 12.8 mmol) in DCM (250 mL) was added dicobalt octacarbonyl (5.25 g, 14.6 mmol), under an atmosphere of argon. The reaction was stirred at room temperature for 2 h. The reaction was then concentrated under reduced pressure, and the residue was dissolved in acetonitrile (500 mL). The reaction was then heated to 83° C. under an atmosphere of argon for overnight. The reaction was then concentrated under reduced pressure, triturated with ether, filtered over a plug of Celite®, and then the filtrate was concentrated under reduced pressure. The residue was purified by column chromatography on silica (10-30% EtOAc/hexanes) followed by chiral SFC (R,R'-Welk-O1 column, 20% MeOH w/0.1% NH$_4$OH in CO$_2$) to afford (6R,6aR)-6-((triphenylsilyl)oxy)-4,5,6,6a-tetrahydropentalen-2(1H)-one. $^1$H NMR (600 MHz, CDCl$_3$) δ 7.65-7.61 (m, 6H), 7.47-7.43 (m, 3H), 7.42-7.37 (m, 6H), 5.80-5.78 (m, 1H), 3.93 (q, J=8.8 Hz, 1H), 3.18-3.12 (m, 1H), 2.83-2.74 (m, 1H), 2.49-2.41 (m, 1H), 2.37 (dd, J=18.1, 6.2 Hz, 1H), 2.21-210 (m, 2H), 1.73 (dd, J=18.1, 3.1 Hz, 1H).

Step 5: To a flask containing (6R,6aR)-6-((triphenylsilyl)oxy)-4,5,6,6a-tetrahydropentalen-2(1H)-one (7.13 g, 18 mmol) was added THF (100 mL) and methanol (80 mL). The solution was cooled in a dry ice/MeCN bath, and then cerium(III) chloride heptahydrate (6.70 g, 18.0 mmol) was added. The reaction was stirred in the bath for 20 minutes before sodium borohydride (0.817 g, 22 mmol) was added. The reaction was stirred in the cold bath for another 20 minutes before being brought out of the bath. After 5 minutes, the reaction was then poured into a separatory funnel containing EtOAc and 3:2:1 saturated ammonium chloride:water:brine (200 mL). The aqueous layer was separated and washed twice more with EtOAc. The combined organic layers were then dried over sodium sulfate, filtered over Celite®, and concentrated under reduced pressure. The crude (2R,6S,6aS)-6-((triphenylsilyl)oxy)-1,2,4,5,6,6a-hexahydropentalen-2-ol was taken directly to the next step.

Step 6: To a flask containing the crude (2R,6S,6aS)-6-((triphenylsilyl)oxy)-1,2,4,5,6,6a-hexahydropentalen-2-ol in DCM (120 mL) was added pyridine (2.9 mL, 36 mmol), DMAP (2.86 g, 23.4 mmol), and acetic anhydride (2.2 mL, 23 mmol). The reaction was stirred at room temperature for three day s. The reaction was then quenched with saturated aqueous ammonium chloride (80 mL). The organic layer was separated by a Phase Separator, concentrated under reduced pressure, and purified by column chromatography on silica (0-10% EtOAc/hexanes) to afford (2R,6S,6aS)-6-((triphenylsilyl)oxy)-1,2,4,5,6,6a-hexahydropentalen-2-yl acetate. $^1$H NMR (600 MHz, CDCl$_3$) δ 7.66-7.62 (m, 6H), 7.46-7.42 (m, 3H), 7.41-7.37 (m, 6H), 5.82-5.77 (m, 1H), 5.24-5.20 (m, 1H), 3.93 (q, J=8.0 Hz, 1H), 2.98-2.91 (m, 1H), 2.49-2.43 (m, 1H), 2.40-2.32 (m, 1H), 2.20-2.12 (m, 1H), 2.09-2.04 (m, 2H), 1.99 (s, 3H), 1.14-1.08 (m, 1H).

Step 7: To a flask containing allyl palladium(II) chloride dimer (1.66 g, 4.45 mmol), dppf (6.36 g, 11.1 mmol), 4-methyl-7H-pyrrolo[2,3-d]pyrimidine (4.44 g, 33.4 mmol), and potassium tert-butoxide (3.74 g, 33.4 mmol) was added THF (100 mL) under an atmosphere of argon. The solution was stirred at room temperature for 10 minutes. Then, a solution of (2R,6S,6aS)-6-((triphenylsilyl)oxy)-1,2,4,5,6,6a-hexahydropentalen-2-yl acetate (9.8 g, 22 mmol) in THF (100 mL) was added, and the reaction was heated to 40° C. overnight. The reaction was then cooled to room temperature, filtered through Celite®, and concentrated under reduced pressure. The residue was subjected to column chromatography on silica (10-50% EtOAc/hexanes) to afford 4-methyl-7-((2R,6S,6aS)-6-((triphenylsilyl)oxy)-1,2,4,5,6,6a-hexahydropentalen-2-yl)-7H-pyrrolo[2,3-d]pyrimidine. MS: 514 (M+1). $^1$H NMR (600 MHz, CDCl$_3$) δ 8.75 (s, 1H), 7.65-7.58 (m, 6H), 7.43-7.38 (m, 3H), 7.38-7.31 (m, 6H), 7.05 (d, J=3.7 Hz, 1H), 6.54 (d, J=3.6 Hz, 1H), 6.15 (s, 1H), 5.23-5.19 (m, 1H), 3.99 (q, J=7.9 Hz, 1H), 3.17-3.11 (m, 1H), 2.78 (s, 3H), 2.63-2.58 (m, 1H), 2.49-2.42 (m, 1H), 2.29-2.22 (m, 1H), 2.20-2.12 (m, 2H), 1.22-1.15 (m, 1H).

Step 8: To a flask containing a solution of 4-methyl-7-((2R,6S,6aS)-6-((triphenylsilyl)oxy)-1,2,4,5,6,6a-hexahydropentalen-2-yl)-7H-pyrrolo[2,3-d]pyrimidine (13.2 g, 25.7 mmol) in TH-F (300 mL) was added water (150 mL). The solution was cooled to 0° C., then NMO (6.02 g, 51.4 mmol) was added, followed by Osmium (VIII) oxide (7.8 mL, 4% in water, 1.3 mmol). The reaction was stirred overnight, and the bath was allowed to expire naturally. The reaction was quenched with saturated aqueous sodium sulfite (60 mL), and stirring was continued at room temperature for 30 minutes. The reaction was then poured into a separatory funnel containing water and 25% IPA/chloroform. The aqueous layer was separated and washed twice more with 25% IPA/chloroform. The combined organic layers were dried over sodium sulfite, filtered over Celite®, and concentrated under reduced pressure to afford crude (1S,2R,3aR,4S,6aR)-2-(4-methyl-7H-pyrrolo[2,3-d]pyrimidin-7-yl)-4-((triphenylsilyl)oxy)hexahydropentalene-1,6a(1H)-diol. This crude product was used directly in the next step.

Step 9: To a flask containing the crude (1S,2R,3aR,4S,6aR)-2-(4-methyl-7H-pyrrolo[2,3-d]pyrimidin-7-yl)-4-((triphenylsilyl)oxy)hexahydropentalene-1,6a(1H)-diol was added DCM (200 mL), followed by 2,2-dimethoxypropane (35 mL, 290 mmol) and p-toluenesulfonic acid monohydrate (17.1 g, 90 mmol). The reaction was stirred at room temperature for 1 h. The reaction was quenched with saturated aqueous sodium bicarbonate (100 mL). The organic layer was separated by Phase Separator and concentrated under reduced pressure. The residue was purified by column chromatography on silica (50-100% EtOAc/hexanes to 100% 3:1 EtOAc:EtOH)) to afford (3aS,4R,5aR,6S,8aR)-2,2-dimethyl-4-(4-methyl-7H-pyrrolo[2,3-d]pyrimidin-7-yl)hexahydro-5H-pentaleno[1,6a-d][1,3]dioxol-6-ol. MS: 330 (M+1).

Intermediate 38: Intermediate 38 in Table 5 was synthesized using the protocol described in intermediate 37, making the appropriate substitution for 4-methyl-7H-pyrrolo[2,3-d]pyrimidine in step 7. The substituted starting material was commercially acquired, synthesized as reported above, or synthesized through known routes reported in the literature.

TABLE 5

| Intermediate | Structure | Name | MS |
|---|---|---|---|
| 38 | 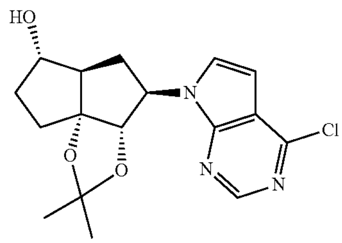 [SMILES: CC1(C)O[C@H]2[C@H](n3ccc4c(Cl)ncnc43)C[C@@H]3[C@@H](O)CC[C@@]32O1] | (3aS,4R,5aR,6S,8aR)-4-(4-chloro-7H-pyrrolo[2,3-d]pyrimidin-7-yl)-2,2-dimethylhexahydro-5H-pentaleno[1,6a-d][1,3]dioxol-6-ol | 350 (M + 1) |

Intermediate 39: Intermediate 39 in Table 6 was synthesized using the protocol described in intermediate 13, making the appropriate substitution for 4-chloro-5-(difluoromethyl)-7H-pyrrolo[2,3-d]pyrimidine in step 1. The substituted starting material was commercially acquired, synthesized as reported above, or synthesized through known routes reported in the literature.

TABLE 6

| Intermediate | Structure | Name | MS |
|---|---|---|---|
| 39 | 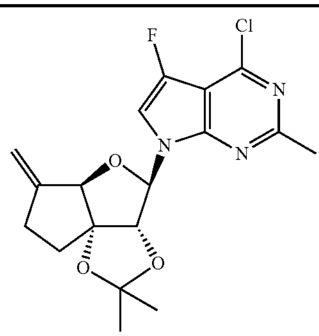 | 4-chloro-7-(3aR,4R,5aR,8aR)-2,2-dimethyl-6-methylenehexahydrocyclopenta[2,3]furo[3,4-d][1,3]dioxol-4-yl)-5-fluoro-2-methyl-7H-pyrrolo[2,3-d]pyrimidine | 380 (M + 1) |

EXAMPLES

The following experimental procedures detail the preparation of specific examples of the instant disclosure. The examples are for illustrative purposes only and are not intended to limit the scope of the instant disclosure in any way.

Example 1

(1R,2S,3R,5R)-5-((2-amino-3-bromoquinolin-7-yl)oxy)methyl)-3-(4-chloro-7H-pyrrolo[2,3-d]pyrimidin-7-yl)-1-methylcyclopentane-1,2-diol

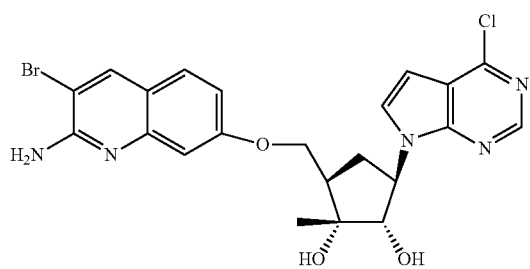 [SMILES: C[C@@]1(O)[C@@H](COc2ccc3cc(Br)c(N)nc3c2)C[C@@H](n2ccc3c(Cl)ncnc32)[C@@H]1O]

Step 1: A mixture of ((3aR,4R,6R,6aS)-6-(4-chloro-7H-pyrrolo[2,3-d]pyrimidin-7-yl)-2,2,3a-trimethyltetrahydro-3aH-cyclopenta[d][1,3]dioxol-4-yl)methanol (1.2 g, 3.6 mmol), 2-amino-3-bromoquinolin-7-ol (0.934 g, 3.91 mmol) and triphenylphosphine (1.86 g, 7.10 mmol) was co-evaporated with dry toluene (three times, 10 mL each) and then re-dissolved in anhydrous THF (20 mL). The reaction mixture was cooled to 0° C., and (E)-diisopropyl diazene-1,2-dicarboxylate (144 g, 7.10 mmol) was added dropwise at 0° C. The mixture was warmed to room temperature naturally, and the mixture was stirred at room temperature for 2 hours. The reaction mixture was concentrated under reduced pressure. The residue was purified by silica gel column chromatography (0-10% MeOH in DCM). The fractions containing the desired product were combined and concentrated under reduced pressure to afford a crude solid. The crude material was further purified by reverse-phase column chromatography (0-100% 5 mM aqueous NH$_4$HCO$_3$/acetonitrile) to afford 3-bromo-7-(((3aR,4R,6R,6aS)-6-(4-chloro-7H-pyrrolo[2,3-d]pyrimidin-7-yl)-2,2,3a-trimethyltetrahydro-3aH-cyclopenta[d][1,3]dioxol-4-yl)methoxy)quinolin-2-amine. MS 558, 560 (M+1, M+3). TH NMR (400 MHz, DMSO-d$_6$) δ 8.68 (d, J=1.2 Hz, 1H), 8.28 (s, 1H), 7.96 (d, J=3.6 Hz, 1H), 7.58 (d, J=8.8 Hz, 1H), 6.98 (d, J=2.4 Hz, 1H), 6.90 (dd, J=9.2, 2.4 Hz, 1H), 6.76 (d, J=3.6 Hz, 1H), 6.53 (s, 2H), 5.40-5.13 (m, 1H), 4.51 (d, J=4.0 Hz, 1H), 4.27 (dd, J=10.0, 6.0 Hz, 1H), 4.12 (t, J=8.8 Hz, 1H), 2.72-2.66 (m, 1H), 2.49-2.45 (m, 1H), 2.42-2.36 (m, 1H), 1.60 (s, 3H), 1.51 (s, 3H), 1.30 (s, 3H).

Step 2: To a solution of 3-bromo-7-(((3aR,4R,6R,6aS)-6-(4-chloro-7H-pyrrolo[2,3-d]pyrimidin-7-yl)-2,2,3a-trimethyltetrahydro-3aH-cyclopenta[d][1,3]dioxol-4-yl)methoxy)quinolin-2-amine (430 mg, 0.769 mmol) in water (8 mL) was added TFA (8 mL) at room temperature. The reaction was stirred at 25° C. for 4 h. The reaction was cooled to 0° C. The pH was adjusted to pH 7-8 with saturated aqueous sodium bicarbonate (50 mL). The resultant mixture was extracted with EtOAc (50 mL×5) and the combined organic layers were dried over anhydrous sodium sulfate, filtered, and concentrated under reduced pressure. The residue was purified by silica gel column chromatography (0-15% of MeOH in DCM) to afford (1R,2S,3R,5R)-5-(((2-amino-3-bromoquinolin-7-yl)oxy)methyl)-3-(4-chloro-7H-pyrrolo[2,3-d]pyrimidin-7-yl)-1-methylcyclopentane-1,2-diol. MS 518, 520 (M+1, M+3). $^1$H NMR (400 MHz, DMSO-$d_6$) δ 8.60 (s, 1H), 8.28 (s, 1H), 7.93 (d, J=4.0 Hz, 1H), 7.58 (d, J=8.8 Hz, 1H), 6.97 (s, 1H), 6.93 (d, J=8.8 Hz, 1H), 6.71 (d, J=3.6 Hz, 1H), 6.51 (br s, 2H), 5.13 (q, J=9.2 Hz, 1H), 4.99 (d, J=7.2 Hz, 1H), 4.51 (s, 1H), 4.21-4.11 (m, 3H), 2.47-2.39 (m, 2H), 1.82-1.75 (m, 1H), 1.26 (s, 3H).

Example 2

(1R,2S,3R,5R)-5-((2-amino-3-bromoquinolin-7-yl)oxy)methyl)-3-(4-amino-7H-pyrrolo[2,3-d]pyrimidin-7-yl)-1-methylcyclopentane-1,2-diol

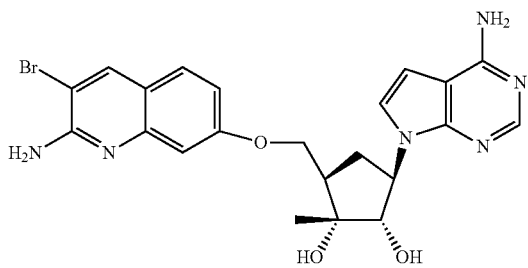 [SMILES: C[C@@]1(O)[C@@H](COc2ccc3cc(Br)c(N)nc3c2)C[C@@H](n2ccc3c(N)ncnc32)[C@@H]1O]

To a sealed tube (10 mL) was added (1R,2S,3R,5R)-5-(((2-amino-3-bromoquinolin-7-yl)oxy)methyl)-3-(4-chloro-7H-pyrrolo[2,3-d]pyrimidin-7-yl)-1-methylcyclopentane-1,2-diol (350 mg, 0.675 mmol), 1,4-dioxane (3 mL) and NH$_3$·H$_2$O (5 mL; 25%-28% w/w) at room temperature. The reaction mixture was sealed tightly and then stirred at 90° C. for 16 hours. The reaction mixture was concentrated under reduced pressure. The residue was purified by reverse phase HPLC (0-45% acetonitrile/water) to afford (1R,2S,3R,5R)-5-(((2-amino-3-bromoquinolin-7-yl)oxy)methyl)-3-(4-amino-7H-pyrrolo[2,3-d]pyrimidin-7-yl)-1-methylcyclopentane-1,2-diol. MS 499, 501 (M+1, M+3). $^1$H NMR (400 MHz, DMSO-$d_6$) δ 8.28 (s, 1H), 8.02 (s, 1H), 7.58 (d, J=8.7 Hz, 1H), 7.30 (d, J=3.6 Hz, 1H), 6.96-6.89 (m, 4H), 6.57-6.53 (m, 3H), 4.97-4.91 (m, 2H), 4.41 (s, 1H), 4.19-4.10 (m, 3H), 2.45-2.37 (m, 2H), 1.72-1.66 (m, 1H), 1.24 (s, 3H).

Example 3

(2R,3S,4R,5R)-2-(((2-amino-3-bromoquinolin-7-yl)oxy)methyl)-5-(4-amino-7H-pyrrolo[2,3-d]pyrimidin-7-yl)-3-ethynyltetrahydrofuran-3,4-diol

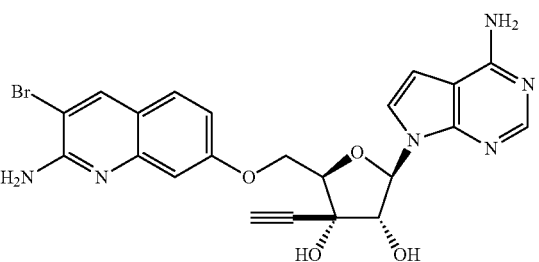 [SMILES: C#C[C@@]1(O)[C@@H](COc2ccc3cc(Br)c(N)nc3c2)O[C@@H](n2ccc3c(N)ncnc32)[C@@H]1O]

Step 1: (2R,3R,4S,5R)-2-(4-amino-7H-pyrrolo[2,3-d]pyrimidin-7-yl)-5-(hydroxymethyl)tetrahydrofuran-3,4-diol (2 g 7.5 mmol) was co-evaporated with dry pyridine (10 mL×3) and then re-suspended in dry pyridine (30 mL) at ambient temperature under an argon atmosphere. To this suspension was added chlorotrimethylsilane (5.71 g, 52.6 mmol) in one portion at 0° C., and the mixture was maintained at ambient temperature for 1 hour. Then to the mixture was added benzoyl chloride (1.58 g, 11.3 mmol) at 0° C. After stirring at ambient temperature for 2 h, the resulting mixture was quenched with H$_2$O (8 mL) at 0° C. Then aqueous NH$_3$ solution (15 mL, 25-28% wt) was added drop wise at 0° C. followed by stirring at ambient temperature for 30 min. The reaction mixture was concentrated under reduced pressure, and the residue was purified by column chromatography on silica (6% MeOH in DCM) to afford N-(7-((2R,3R,4S,5R)-3,4-dihydroxy-5-(hydroxymethyl)tetrahydrofuran-2-yl)-7H-pyrrolo[2,3-d]pyrimidin-4-yl)benzamide. MS: 371 (M+1). $^1$H NMR (300 MHz, DMSO-$d_6$) δ 11.12 (s, 1H), 8.59 (s, 1H), 8.10-8.00 (m, 2H), 7.71 (d, J=3.8 Hz, 1H), 7.63 (t, J=7.3 Hz, 1H), 7.53 (dd, J=8.3, 6.6 Hz, 2H), 6.67 (d, J=3.8 Hz, 1H), 6.22 (d, J=6.1 Hz, 1H), 5.35 (d, J=6.4 Hz, 1H), 5.15 (d, J=4.8 Hz, 1H), 5.06 (t, J=5.4 Hz, 1H), 4.41 (dd, J=5.9 Hz, 1H), 4.10 (dd, J=4.5 Hz, 1H), 3.91 (d, J=3.7 Hz, 1H), 3.69-3.47 (m, 2H).

Step 2: N-(7-((2R,3R,4S,5R)-3,4-dihydroxy-5-(hydroxymethyl)tetrahydrofuran-2-yl)-7H-pyrrolo[2,3-d]pyrimidin-4-yl)benzamide (2.1 g, 5.7 mmol) was co-evaporated with dry pyridine (10 mL×3) and then re-suspended in dry pyridine (15 mL) at ambient temperature under an argon atmosphere. To this suspension was added 4,4'-(chloro(phenyl)methylene)bis(methoxybenzene) (2.11 g, 6.24 mmol) in one portion at ambient temperature, and the mixture was maintained at ambient temperature for 2 hours. The reaction mixture was concentrated under reduced pressure, and the residue was purified by column chromatography on silica (EtOAc in petroleum ether) to give N-(7-((2R,3R,4S,5R)-5-((bis(4-methoxyphenyl)(phenyl)methoxy)methyl)-3,4-dihydroxytetrahydrofuran-2-yl)-7H-pyrrolo[2,3-d]pyrimidin-4-yl)benzamide as a solid. MS: 673 (M+1). $^1$H-NMR (300 MHz, DMSO-$d_6$) δ 11.13 (s, 1H), 8.59 (s, 1H), 8.15-7.94 (m, 2H), 7.68-7.48 (m, 4H), 7.37 (d, J=7.6 Hz, 2H), 7.31-7.15 (m, 7H), 6.84 (dd, J=8.7, 1.6 Hz, 4H), 6.65 (d, J=3.7 Hz, 1H), 6.25 (d, J=5.0 Hz, 1H) 5.47 (d, J=5.9 Hz, 1H), 5.19 (d, J=5.6 Hz, 1H), 4.46 (dd, J=5.5 Hz, 1H), 4.20 (dd, J=5.2 Hz, 1H), 3.99 (d, J=7.1 Hz, 1H), 3.71 (s, 6H), 3.23-3.19 (m, 2H).

Step 3: N-(7-((2R,3R,4S,5R)-5-((bis(4-methoxyphenyl)(phenyl)methoxy)methyl)-3,4-dihydroxytetrahydrofuran-2- yl)-7H-pyrrolo[2,3-d]pyrimidin-4-yl)benzamide (2.36 g, 3.51 mmol), (2R,4S)-4-isopropyl-2-methoxy-3-((R)-2-methyl-1-(1-methyl-1H-imidazol-2-yl)propyl)oxazolidine (0.20 g, 0.70 mmol) and N-ethyl-N-isopropylpropan-2-amine hydrochloride (0.017 g, 0.105 mmol) were co-evaporated with dry toluene (10 mL×3) and then re-suspended in dry THF (21 mL) under an argon atmosphere. To the suspension was added N-ethyl-N-isopropylpropan-2-amine (2.13 g, 16.5 mmol) in one portion at 0° C. This was followed by addition of triisopropylsilyl trifluoromethanesulfonate (4.62 g, 15.1 mmol) in DCM (10 mL) at 0° C. The reaction was stirred at ambient temperature for 40 min. The reaction mixture was then quenched with water (10 mL) and extracted with EtOAc (2×100 mL). The combined organic layers were washed with saturated aqueous NaHCO$_3$ (50 mL) and brine (2×50 mL), dried over anhydrous sodium sulfate, and filtered. The filtrate was concentrated under reduced pressure, and the residue was purified by column chromatography on silica (25% EtOAc in petroleum ether) to afford N-(7-((2R,3R,4R,5R)-5-((bis(4-methoxyphenyl)(phenyl)methoxy)methyl)-4-hydroxy-3-((triisopropylsilyl)oxy)tetrahydrofuran-2-yl)-7H-pyrrolo[2,3-d]pyrimidin-4-yl)benzamide. MS: 829 (M+1). $^1$H NMR (300 MHz, DMSO-d$_6$) δ 11.10 (s, 1H), 8.55 (s, 1H), 8.19-7.95 (m, 2H), 7.68-7.48 (m, 4H), 7.45-7.35 (m, 2H), 7.25 (dd, J=7.2, 5.4 Hz, 7H), 6.89-6.80 (m, 4H), 6.68 (d, J=3.7 Hz, 1H), 6.32 (d, J=5.6 Hz, 1H), 5.11 (d, J=6.1 Hz, 1H), 4.77 (t, J=5.4 Hz, 1H), 4.26-4.06 (m, 2H), 3.71 (s, 6H), 3.28-3.17 (m, 2H), 0.98-0.87 (m, 12H), 0.82 (d, J=6.4 Hz, 9H).

Step 4: N-(7-((2R,3R,4R,5R)-5-((bis(4-methoxyphenyl)(phenyl)methoxy)methyl)-4-hydroxy-3-((triisopropylsilyl)oxy)tetrahydrofuran-2-yl)-7H-pyrrolo[2,3-d]pyrimidin-4-yl)benzamide (1.95 g, 2.35 mmol) was co-evaporated with dry pyridine (10 mL×3) and then re-suspended in dry DCM (30 mL) at ambient temperature under an argon atmosphere. To this suspension was added Dess-Martin periodinane (2.49 g, 5.88 mmol) and pyridine (0.65 g, 8.2 mmol) at ambient temperature. The resulting mixture was then stirred at 0° C. for 2 hours. The reaction mixture was quenched with saturated aqueous NaHCO$_3$(10 mL) and then extracted with EtOAc (100 mL×2). The combined organic layers were washed with brine (100 mL), dried over anhydrous sodium sulfate, and filtered. The filtrate was concentrated under reduced pressure to give crude N-(7-((2R,3S,5R)-5-((bis(4-methoxyphenyl)(phenyl)methoxy)methyl)-4-oxo-3-((triisopropylsilyl)oxy)tetrahydrofuran-2-yl)-7H-pyrrolo[2,3-d]pyrimidin-4-yl)benzamide, which was used directly in the next step. MS: 827 (M+1).

Step 5: To a solution of N-(7-((2R,3S,5R)-5-((bis(4-methoxyphenyl)(phenyl)methoxy)methyl)-4-oxo-3-((triisopropylsilyl)oxy)tetrahydrofuran-2-yl)-7l-pyrrolo[2,3-d]pyrimidin-4-yl)benzamide (2.27 g, 2.74 mmol) in DCM (40 mL) was added 2,2-dichloroacetic acid (3.18 g, 24.7 mmol) at ambient temperature and then stirred for 30 minutes. Triethylsilane (31.9 g, 274 mmol) was added to this suspension. After stirring for an additional 10 minutes, pyridine (1.5 mL) was added to the mixture. Then the mixture was concentrated under reduced pressure, and the residue was purified by column chromatography on silica (30% EtOAc in petroleum ether) to afford V-(7-((2R,3S,5R)-5-(hydroxymethyl)-4-oxo-3-((triisopropylsilyl)oxy)tetrahydrofuran-2-yl)-7H-pyrrolo[2,3-d]pyrimidin-4-yl)benzamide. MS: 525 (M+1). $^1$H NMR (400 MHz, DMSO-d$_6$) δ 11.20 (s, 1H), 8.65 (s, 1H), 8.14-8.04 (m, 2H) 7.89 (d, J=3.8 Hz, 1H), 7.71-7.62 (m, 1H), 7.61-7.53 (m, 2H), 6.84 (d, J=3.8 Hz, 1H), 6.53 (d, J=8.3 Hz, 1H), 5.39 (br, 1H), 5.00 (d, J=8.3 Hz, 1H), 4.44 (t, J=2.8 Hz, 1H), 3.74-3.70 (m, 2H), 0.91-0.87 (m, 12H), 0.78-0.73 (m, 9H).

Step 6: Cerium (III) chloride (3.04 g, 12.4 mmol) was dried at 140° C. under reduced pressure for 1 h. The resulting powder was cooled under argon. Anhydrous THF (20 mL) was added. The resulting mixture was cooled to −78° C., and ((trimethylsilyl)ethynyl)lithium (24.7 mL, 12.4 mmol) was added. The reaction mixture was stirred for 1 h at −78° C. Then a cooled solution (−78° C.) of N-(7-((2R,3S,5R)-5-(hydroxymethyl)-4-oxo-3-((triisopropylsilyl)oxy)tetrahydrofuran-2-yl)-7H-pyrrolo[2,3-d]pyrimidin-4-yl)benzamide (1.08 g, 2.06 mmol) in anhydrous THF (20 mL) was rapidly added, and the stirring was continued for 2 h. The reaction was quenched with saturated aqueous ammonium chloride solution (40 mL). The mixture was diluted with EtOAc (300 mL) and washed with water (100 mL×2). The organic fraction was dried over anhydrous sodium sulfate and filtered. The filtrate was concentrated under reduced pressure, and the residue was purified by reverse phase HPLC (0-95% 5 mM aqueous NH$_4$HCO$_3$/acetonitrile) to afford N-(7-((2R,3R,4R,5R)-4-hydroxy-5-(hydroxymethyl)-3-((triisopropylsilyl)oxy)-4-((trimethylsilyl)ethynyl)tetrahydrofuran-2-yl)-7-f-pyrrolo[2,3-d]pyrimidin-4-yl)benzamide. MS: 623 (M+1). $^1$H NMR (300 MHz, DMSO-d$_6$) δ 11.08 (s, 1H), 8.56 (s, 1H), 8.06-8.03 (m, 2H), 7.80 (d, J=3.8 Hz, 1H), 7.69-7.41 (m, 3H), 6.71 (d, J=3.7 Hz, 1H), 6.29 (d, J=7.1 Hz, 1H), 5.80 (s, 1H), 5.18 (t, J=4.6 Hz, 1H), 4.98 (d, J=7.2 Hz, 1H), 3.98 (t, J=3.2 Hz, 1H), 3.87-3.60 (m, 2H), 0.85-0.70 (m, 2H), 0.14 (s, 9H).

Step 7: To a mixture of N-(7-((2R,3R,4R,5R)-4-hydroxy-5-(hydroxymethyl)-3-((triisopropylsilyl)oxy)-4-((trimethylsilyl)ethynyl)tetrahydrofuran-2-yl)-7H-pyrrolo[2,3-d]pyrimidin-4-yl)benzamide (250 mg, 0.401 mmol) in THF (8 mL) was added 2-amino-3-bromoquinolin-7-ol (115 mg, 0.482 mmol) and triphenylphosphine (368 mg, 1.41 mmol) under an argon atmosphere. Then (E)-diisopropyl diazene-1,2-dicarboxylate (203 mg, 1.00 mmol) was added dropwise at 0° C. The mixture was stirred at ambient temperature for 12 h. The reaction mixture was filtered, and the filtrate was concentrated under reduced pressure. The residue was purified by column chromatography on silica (50% EtOAc in petroleum ether) to afford N-(7-((2R,3R,4R,5R)-5-(((2-amino-3-bromoquinolin-7-yl)oxy)methyl)-4-hydroxy-3-((triisopropylsilyl)oxy)-4-((trimethylsilyl)ethynyl)tetrahydrofuran-2-yl)-7H-pyrrolo[2,3-d]pyrimidin-4-yl)benzamide. MS: 843/845 (M+1/M+3).

Step 8: To a mixture of N-(7-((2R,3R,4R,5R)-5-(((2-amino-3-bromoquinolin-7-yl)oxy) methyl)-4-hydroxy-3-((triisopropylsilyl)oxy)-4-((trimethylsilyl)ethynyl)tetrahydrofuran-2-yl)-7H-pyrrolo[2,3-d]pyrimidin-4-yl)benzamide (90 mg, 0.11 mmol) in pyridine (3 mL) was added triethylamine (1.08 g, 10.7 mmol) and triethylamine trihydrofluoride (860 mg, 5.33 mmol) at ambient temperature. Stirring was then continued at ambient temperature for 1 h. The reaction mixture was concentrated under reduced pressure, and the residue was purified by column chromatography on silica (90% EtOAc in petroleum ether) to afford N-(7-((2R,3R,4S,5R)-5-(((2-amino-3-bromoquinolin-7-yl)oxy)methyl)-4-ethynyl-3,4-dihydroxytetrahydrofuran-2-yl)-7H-pyrrolo[2,3-d]pyrimidin-4-yl)benzamide. MS: 615/617 (M+1/M+3). $^1$H NMR (300 MHz, CD$_3$OD) δ 8.57 (s, 1H), 8.21 (s, 1H), 8.06-8.00 (m, 2H), 7.73 (d, J=3.8 Hz, 1H), 7.68-7.60 (m, 1H), 7.58 (d, J=4.2 Hz, 1H), 7.56-7.53 (m, 1H), 7.52-7.32 (m, 1H), 7.10-7.00 (m, 2H), 6.88 (d, J=3.8 Hz, 1H), 6.50 (d, J=7.4 Hz, 1H), 4.94 (d, J=7.4 Hz, 1H), 4.54-4.41 (m, 3H), 3.15 (s, 1H).

Step 9: To a mixture of N-(7-((2R,3R,4S,5R)-5-(((2-amino-3-bromoquinolin-7-yl)oxy)methyl)-4-ethynyl-3,4-dihydroxytetrahydrofuran-2-yl)-7H-pyrrolo[2,3-d]pyrimidin-4-yl)benzamide (40 mg, 0.065 mmol) in MeOH (2 mL) was added sodium methanolate (17.6 mg, 0.325 mmol) at ambient temperature. Stirring was then continued at ambient temperature for 16 h. The reaction mixture was concentrated under reduced pressure, and the residue was purified by reverse phase column chromatography (ACN/water with 5 mM aqueous $NH_4HCO_3$ modifier) to afford (2R,3S,4R,5R)-2-(((2-amino-3-bromoquinolin-7-yl)oxy)methyl)-5-(4-amino-7H-pyrrolo[2,3-d]pyrimidin-7-yl)-3-ethynyltetrahydrofuran-3,4-diol. MS: 511/513 (M+1/M+3). $^1$H NMR (300 MHz, DMSO-$d_6$) δ 8.30 (s, 1H), 8.10 (s, 1H), 7.60 (d, J=9.5 Hz, 1H), 7.45 (d, J=3.7 Hz, 1H), 7.22 (br s, 2H), 6.95-6.93 (m, 2H), 6.76-6.60 (m, 3H), 6.22 (s, 1H), 6.16 (d, J=7.5 Hz, 1H), 5.95 (d, J=7.3 Hz, 1H), 4.74 (t, J=7.3 Hz, 1H), 4.35-4.29 (m, 3H), 3.61 (s, 1H).

Example 4

(2R,3S,4R,5R)-2-(2-(2-amino-3-bromoquinolin-7-yl)ethyl)-5-(4-amino-7H-pyrrolo[2,3-d]pyrimidin-7-yl)-2,3-dimethyltetrahydrofuran-3,4-diol

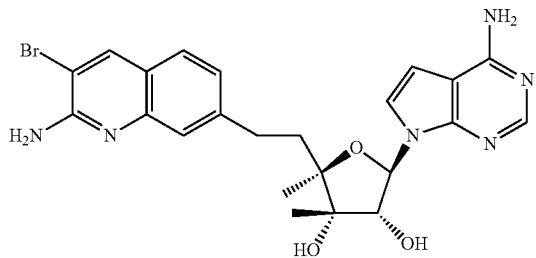 [SMILES: C[C@]1(O)[C@@H](O)[C@H](n2ccc3c(N)ncnc32)O[C@@]1(C)CCc1ccc2cc(Br)c(N)nc2c1]

Step 1: To a stirred solution of ((3aR,5R,6S,6aR)-5-((tert-butyldiphenylsilyloxy)methyl)-2,2-dimethyl-6-(naphthalen-2-ylmethoxy)-tetrahydrofuro[3,2-d][1,3]dioxol-5-yl)methanol (12 g, 20 mmol) and imidazole (5.44 g, 80 mmol) in toluene (240 mL) was added $PPh_3$ (21 g, 80 mmol) at 25° C. under an argon atmosphere. Then $I_2$ (10.1 g, 40 mmol) was added in portions to the mixture at 60° C. The resulting mixture was stirred at 80° C. for 14 h. The reaction mixture was cooled to 0° C., quenched with saturated aqueous $Na_2S_2O_3$ (200 mL) and diluted with EtOAc (300 mL). The organic layer was washed with $H_2O$ (150 mL), saturated aqueous $NaHCO_3$ (150 mL×2) and brine (150 mL). The organic layer was dried over anhydrous $Na_2SO_4$, filtered, and the filtrate was concentrated under reduced pressure. The residue was purified by silica gel column chromatography (10-40% EtOAc/pet. ether) to afford tert-butyl(((3aR,5R,6S,6aR)-5-(iodomethyl)-2,2-dimethyl-6-(naphthalen-2-ylmethoxy)-tetrahydrofuro[3,2-d][1,3]dioxol-5-yl)methoxy)diphenylsilane. MS: 726 (M+$NH_4$). $^1$H NMR (300 MHz, DMSO-$d_6$): δ 7.92-7.68 (m, 4H), 7.60-7.25 (m, 13H), 5.68 (d, J=3.6 Hz, 1H), 4.98-4.82 (m, 2H), 4.71 (d, J=12.3 Hz, 1H), 4.41 (d, J=2.4 Hz, 1H), 3.87 (d, J=12.0 Hz, 1H), 3.71-3.50 (m, 3H), 1.50 (s, 3H), 1.27 (s, 3H), 0.81 (s, 9H).

Step 2: Tert-butyl (((3aR,5R,6S,6aR)-5-(iodomethyl)-2,2-dimethyl-6(naphthalen-2-ylmethoxy)-tetrahydrofuro[3,2-d][1,3]dioxol-5-yl)methoxy)diphenylsilane (10.6 g, 14.6 mmol) (co-evaporated with freshly distilled toluene (10 mL×3)) was dissolved in 200 mL of toluene. (Z)-3,3'-(diazene-1,2-diyl)bis(2,2-dimethyl-3-oxopropanenitrile) (615 mg, 3.85 mmol) and (n-Bu)$_3$SnH (11 g, 37 mmol) were added at 60° C. under an argon atmosphere in one portion; then the temperature was increased to 120° C., and the reaction was stirred at this temperature for 3 h. The reaction mixture was cooled to room temperature and diluted with EtOAc (300 mL). The organic layer was washed with $H_2O$ (150 mL), saturated aqueous $NaHCO_3$ (150 mL×2) and brine (150 mL). The organic layer was dried over anhydrous $Na_2SO_4$, filtered, and the filtrate was concentrated under the reduced pressure. The residue was purified by silica gel column chromatography (14% EtOAc/pet. ether) to afford tert-butyldiphenyl(((3aR,5R,6S,6aR)-2,2,5-trimethyl-6-(naphthalen-2-ylmethoxy)-tetrahydrofuro[3,2-d][1,3]dioxol-5-yl)methoxy)silane. MS: 600 (M+$NH_4$). $^1$H NMR (300 MHz, DMSO-$d_6$): δ 7.91-7.84 (m, 4H), 7.56-7.49 (m, 7H), 7.45-7.34 (m, 6H), 5.70 (d, J=3.9 Hz, 1H), 4.94-4.83 (m, 2H), 4.67 (d, J=12.3 Hz, 1H), 4.16 (d, J=5.1 Hz, 1H), 3.41 (dd, J=21.0, 9.0 Hz, 2H), 1.52 (s, 3H), 1.30 (s, 3H), 1.26 (s, 3H), 0.82 (s, 9H).

Step 3: To a solution of tert-butyldiphenyl(((3aR,5R,6S,6aR)-2,2,5-trimethyl-6-(naphthalen-2-ylmethoxy)tetrahydrofuro[2,3-d][1,3]dioxol-5-yl)methoxy)silane (5 g, 8.6 mmol) in DCM (50 mL) and water (12.5 mL) was added DDQ (3.90 g, 17.2 mmol) at ambient temperature. The resulting mixture was stirred at room temperature for 2 h. The reaction mixture was quenched with saturated aqueous $NaHCO_3$ (100 mL) and extracted with DCM (100 mL×3). The combined organic layers were washed with saturated aqueous $NaHCO_3$ (150 mL), dried over anhydrous $Na_2SO_4$, and filtered. The filtrate was concentrated under reduced pressure, and the residue was purified by silica gel chromatography (1-20% EtOAc/pet. ether) to afford (3aR,5R,6S,6aR)-5-(((tert-butyldiphenylsilyl)oxy)methyl)-2,2,5-trimethyltetrahydrofuro[2,3-d][1,3]dioxol-6-ol. MS: 460 (M+$NH_4$). $^1$H NMR (300 MHz, DMSO-$d_6$) δ 7.61-7.42 (m, 10H), 5.65 (d, J=3.6 Hz, 1H), 5.11 (d, J=6.6 Hz, 1H), 4.57 (t, J=4.8 Hz, 1H), 4.16 (t, J=6.0 Hz, 1H), 3.49-3.40 (m, 2H), 1.48 (s, 3H), 1.25 (s, 3H), 1.14 (s, 3H), 0.99 (s, 9H).

Step 4: To a stirred solution of (3aR,5R,6S,6aR)-5-(((tert-butyldiphenylsilyl)oxy)methyl)-2,2,5-trimethyltetrahydrofuro[2,3-d][1,3]dioxol-6-ol (3.5 g, 7.91 mmol) in DCM (80 mL) was added pyridine (2.24 mL, 27.7 mmol) and Dess Martin Periodinane (6.71 g, 15.8 mmol) at 0° C. The resulting mixture was stirred at room temperature for 2 h. The reaction mixture was quenched with saturated aqueous $NaHCO_3$ (50 mL) and extracted with EtOAc (80 mL×3). The combined organic layers were washed with saturated aqueous $NaHCO_3$(80 mL) and brine (100 mL), dried over anhydrous sodium sulfate, and filtered. The filtrate was concentrated under reduced pressure, and the residue was purified by silica gel column chromatography (1-24% EtOAc/pet. ether) to afford (3aR,5R,6aS)-5-(((tert-butyldiphenylsilyl)oxy)methyl)-2,2,5-trimethyldihydrofuro[2,3-d][1,3]dioxol-6(3aH)-one. MS: 458 (M+$NH_4$). $^1$H NMR (300 MHz, Chloroform-d) δ 7.68-7.65 (m, 2H), 7.59-7.56 (m, 2H), 7.45-7.36 (m, 6H), 6.27 (d, J=4.5 Hz, 1H), 4.53 (d, J=4.5 Hz, 1H), 3.66-3.55 (m, 2H), 1.51 (s, 3H), 1.44 (s, 3H), 1.26 (s, 3H), 1.00 (s, 9H).

Step 5: To a stirred solution of (3aR,5R,6aS)-5-(((tert-butyldiphenylsilyl)oxy)methyl)-2,2,5-trimethyldihydrofuro[2,3-d][1,3]dioxol-6(3aH)-one (3 g, 6.8 mmol) in THF (25 mL) was added methyllithium (1.6 M in $Et_2O$, 10.6 mL, 17.0 mmol) dropwise at −78° C. The resulting mixture was stirred at −78° C. for 2 hours. The reaction mixture was quenched with saturated aqueous $NH_4Cl$ (50 mL) and extracted with diethylether (100 mL×3). The combined organic layers were washed with brine (50 mL), dried over anhydrous sodium sulfate, and filtered. The filtrate was concentrated under reduced pressure, and the residue was purified by silica gel column chromatography (1-14% EtOAc/pet. ether) to afford (3aR,5R,6S,6aR)-5-(((tert-butyldiphenylsilyl)oxy)methyl)-2,2,5,6-tetramethyltetrahydrofuro[2,3-d][1,3]dioxol-6-ol. MS: 479 (M+Na). $^1$H NMR (400 MHz, DMSO-d$_6$) δ 7.64-7.43 (m, 10H), 5.71 (d, J=4.4 Hz, 1H), 4.58 (s, 1H), 4.26 (d, J=4.4 Hz, 1H), 3.55-3.44 (m, 2H), 1.49 (s, 3H), 1.29 (s, 3H), 1.24 (s, 3H), 1.12 (s, 3H), 1.00 (s, 9H).

Step 6: To a solution of (3aR,5R,6S,6aR)-5-(((tert-butyldiphenylsilyl)oxy)methyl)-2,2,5,6-tetramethyltetrahydrofuro[2,3-d][1,3]dioxol-6-ol (2.3 g, 5.04 mmol) in 1,4-Dioxane (40 mL) and water (10 mL) was added 4-methylbenzenesulfonic acid (0.173 g, 1.01 mmol) at room temperature. The resulting mixture was stirred at 80° C. for 2 hours. The reaction mixture was cooled to room temperature and quenched with saturated aqueous NaHCO$_3$ (50 mL) and extracted with EtOAc (50 mL×3). The combined organic layers were washed with saturated aqueous NaHCO$_3$ (50 mL), dried over anhydrous sodium sulfate, and filtered. The filtrate was concentrated under reduced pressure, and the residue was purified by silica gel column chromatography (10-40% EtOAc/pet. ether) to afford (3R,4S,5R)-5-(((tert-butyldiphenylsilyl)oxy)methyl)-4,5-dimethyltetrahydrofuran-2,3,4-triol. MS: 439 (M+Na). $^1$H NMR (400 MHz, DMSO-d$_6$) δ 7.75-7.39 (m, 10H), 5.65 (d, J=7.6 Hz, 1H), 5.04-5.01 (m, 1H), 4.66 (d, J=8.8 Hz, 1H), 4.35 (s, 1H), 4.06-4.01 (m, 2H), 3.40 (s, 1H), 1.22 (s, 3H), 1.04 (s, 3H), 0.98 (s, 9H).

Step 7: To a stirred solution of (3R,4S,5R)-5-(((tert-butyldiphenylsilyl)oxy)methyl)-4,5-dimethyltetrahydrofuran-2,3,4-triol (1.45 g, 3.5 mmol) (co-evaporated with dry MeCN 6 mL×3) in acetonitrile (20 mL) was added tributylphosphine (1.13 g, 5.6 mmol) and (E)-diazene-1,2-diylbis(piperidin-1-ylmethanone) (1.41 g, 5.6 mmol) at ambient temperature under an argon atmosphere. The reaction mixture was stirred for 1 h at room temperature. The resulting mixture containing (1S,3R,4S,5R)-3-(((tert-butyldiphenylsilyl)oxy)methyl)-3,4-dimethyl-2,6-dioxabicyclo[3.1.0]hexan-4-ol was used in the next step directly without work-up or purification.

Step 8: To a stirred solution of 4-chloro-7H-pyrrolo[2,3-d]pyrimidine (1.07 g, 6.96 mmol) in DMF (4 mL) was added NaH (418 mg, 10.4 mmol) at 0° C. The reaction mixture was stirred at room temperature for 0.5 h. A solution of (1S,3R,4S,5R)-3-(((tert-butyldiphenylsilyl)oxy)methyl)-3,4-dimethyl-2,6-dioxabicyclo[3.1.0]hexan-4-ol (~3.5 mmol) in MeCN (20 mL) (from the previous step) was added to the above system at room temperature. The resulting mixture was stirred at room temperature for 0.5 h. The reaction mixture was quenched with saturated aqueous NaHCO$_3$ (35 mL) and extracted with EtOAc (50 mL×3). The combined organic layers were washed with water (100 mL) and brine (50 mL), dried over anhydrous sodium sulfate, and filtered. The filtrate was concentrated under reduced pressure, and the residue was purified by silica gel column chromatography (1-24% EtOAc/pet. ether) to afford (2R,3S,4R,5R)-2-(((tert-butyldiphenylsilyl)oxy)methyl)-5-(4-chloro-7H-pyrrolo[2,3-d]pyrimidin-7-yl)-2,3-dimethyltetrahydrofuran-3,4-diol. MS: 552 (M+1). $^1$H NMR (300 MHz, DMSO-d$_6$) δ 8.58 (s, 1H), 7.68-7.34 (m, 1H), 6.51 (d, J=3.6 Hz, 1H), 6.15 (d, J=8.4 Hz, 1H), 5.44 (d, J=7.2 Hz, 1H), 4.87 (s, 1H), 4.65-4.60 (m, 1H), 3.82 (d, J=10.8 Hz, 1H), 3.57 (d, J=11.1 Hz, 1H), 1.34 (s, 3H), 1.18 (s, 3H), 1.06 (s, 9H).

Step 9: To a solution of (2R,3S,4R,5R)-2-(((tert-butyldiphenylsilyl)oxy)methyl)-5-(4-chloro-7-pyrrolo[2,3-d]pyrimidin-7-yl)-2,3-dimethyltetrahydrofuran-3,4-diol (600 mg, 1.09 mmol) in acetone (50 mL) were added 2,2-dimethoxypropane (1.13 g, 10.9 mmol) and 4-methylbenzenesulfonic acid (19 mg, 0.11 mmol) at room temperature. The reaction mixture was stirred at 40° C. for 5 h. The reaction mixture was quenched with saturated aqueous NaHCO$_3$ (40 mL), and the acetone was removed under reduced pressure. The aqueous phase was extracted with EtOAc (50 mL×3). The combined organic layers were washed with brine (50 mL), dried over anhydrous Na$_2$SO$_4$, and filtered. The filtrate was concentrated under reduced pressure, and the residue was purified by silica gel column chromatography (0-40% EtOAc/pet. ether) to afford 7-((3aR,4R,6R,6aS)-6-(((tert-butyldiphenylsilyl)oxy)methyl)-2,2,6,6a-tetramethyltetrahydrofuro[3,4-d][1,3]dioxol-4-yl)-4-chloro-7H-pyrrolo[2,3-d]pyrimidine. MS: 592 (M+1). $^1$H NMR (400 MHz, CDCl$_3$) δ 8.66 (s, 1H), 7.65-7.53 (m, 5H), 7.55-7.45 (m, 1H), 7.49-7.28 (m, 5H), 6.48 (d, J=3.7 Hz, 1H), 6.30 (d, J=2.7 Hz, 1H), 5.15 (d, J=2.8 Hz, 1H), 3.64 (d, J=10.8 Hz, 1H), 3.54 (d, J=10.8 Hz, 1H), 1.66 (s, 3H), 1.53 (s, 6H), 1.46 (s, 3H), 1.08 (s, 9H).

Step 10: To a solution of 7-((3aR,4R,6R,6a S)-6-(((tert-butyldiphenylsilyl)oxy)methyl)-2,2,6,6a-tetramethyltetrahydrofuro[3,4-d][1,3]dioxol-4-yl)-4-chloro-7H-pyrrolo[2,3-d]pyrimidine (416 mg, 0.702 mmol) in tetrahydrofuran (5 mL) under an argon atmosphere was added tetrabutylammonium fluoride (1 M in THF, 2.11 mL, 2.11 mmol) at room temperature. The reaction solution was stirred at room temperature for 3 h. The solvent was removed under reduced pressure. The residue was purified by silica gel column chromatography (0-20% MeOH/DCM) to afford ((3aS,4R,6R,6aR)-6-(4-chloro-7H-pyrrolo[2,3-d]pyrimidin-7-yl)-2,2,3a,4-tetramethyltetrahydrofuro[3,4-d][1,3]dioxol-4-yl) methanol. MS: 354 (M+1). $^1$H NMR (400 MHz, CDCl$_3$) δ 8.69 (s, 1H), 7.41 (d, J=3.7 Hz, 1H), 6.67 (d, J=3.7 Hz, 1H), 6.10 (d, J=5.1 Hz, 1H), 5.14 (d, J=5.1 Hz, 1H), 4.84 (dd, J=8.9, 3.8 Hz, 1H), 3.74-3.55 (m, 2H), 1.71 (s, 6H), 1.59 (s, 3H), 1.38 (s, 3H).

Step 11: To a solution of oxalyl dichloride (201 mg, 1.6 mmol) in anhydrous DCM (5 mL) was added DMSO (309 mg, 3.96 mmol) dropwise at −78° C. under an argon atmosphere. The resulting solution was stirred at −78° C. for 0.5 h. Then a solution of ((3aS,4R,6R,6aR)-6-(4-chloro-7H-pyrrolo[2,3-d]pyrimidin-7-yl)-2,2,3a,4-tetramethyltetrahydrofuro[3,4-d][1,3]dioxol-4-yl)methanol (140 mg, 0.40 mmol) in anhydrous DCM (5 mL) was added dropwise to the above reaction system at −78° C. The resulting solution was stirred at −78° C. for another 0.5 h. This was followed by the addition of TEA (400 mg, 4 mmol) at −78° C. The resulting solution was stirred for 0.5 h at −78° C. The reaction solution was quenched with H$_2$O (5 mL) at 0° C., and diluted with DCM (30 mL). The organic layer was washed with saturated aqueous NaHCO$_3$ (40 mL), brine (30 mL), dried over anhydrous Na$_2$SO$_4$ and filtered. The filtrate was concentrated under reduced pressure to afford (3aS,4S,6R,6aR)-6-(4-chloro-7H-pyrrolo[2,3-d]pyrimidin-7-yl)-2,2,3a,4-tetramethyltetrahydrofuro[3,4-d][1,3]dioxole-4-carbaldehyde, which was used in next step directly without further purification. MS: 352 (M+1). $^1$H NMR (400 MHz, CDCl$_3$) δ 9.52 (s, 1H), 8.68 (s, 1H), 7.46 (d, J=3.7 Hz, 1H), 6.73 (d, J=3.7 Hz, 1H), 6.34 (d, J=23 Hz, 1H), 5.29 (d, J=2.3 Hz, 1H), 1.73 (s, 3H), 1.67 (s, 3H), 1.51 (s, 3H), 1.49 (s, 3H).

Step 12: To a solution of methyltriphenylphosphonium bromide (395 mg, 1.11 mmol) in anhydrous tetrahydrofuran (5 mL) was added n-BuLi (2.5 M in THF, 0.411 mL, 1.03 mmol) dropwise at −10° C. under an argon atmosphere. The reaction mixture was stirred at room temperature for 0.5 h. Then a solution of (3aS,4S,6R,6aR)-6-(4-chloro-7H-pyrrolo

[2,3-d]pyrimidin-7-yl)-2,2,3a,4-tetramethyltetrahydrofuro[3,4-d][1,3]dioxole-4-carbaldehyde (139 mg, 0.396 mmol) in anhydrous tetrahydrofuran (8 mL) was added dropwise to the above reaction system at −10° C. The reaction mixture was stirred for 1 h at room temperature. The reaction mixture was quenched with saturated aqueous NH₄Cl (20 mL) at 0° C. The reaction solution was diluted with EtOAc (100 mL), washed with H₂O (20 mL) and brine (30 mL), dried over anhydrous Na₂SO₄, and filtered. The filtrate was concentrated under reduced pressure. The residue was purified by silica gel column chromatography (0-30% EtOAc/pet. ether) to afford 4-chloro-7-((3aR,4R,6R,6aS)-2,2,6,6a-tetramethyl-6-vinyltetrahydrofuro[3,4-d][1,3]dioxol-4-yl)-7H-pyrrolo[2,3-d]pyrimidine. MS: 350 (MI). ¹H NMR (400 MHz, CDCl₃) δ 8.72 (s, 1H), 7.42 (d, J=3.7 Hz, 1H), 6.70 (d, J=3.7 Hz, 1H), 6.50 (d, J=2.5 Hz, 1H), 5.88 (dd, J=17.3, 11.0 Hz, 1H), 5.21 (dd, J=17.3, 1.3 Hz, 1H), 5.13 (dd, J=11.0, 1.3 Hz, 1H), 4.89 (d, J=2.5 Hz, 1H), 1.66 (s, 3H), 1.58 (s, 3H), 1.55 (s, 3H), 1.47 (s, 3H).

Step 13: To a sealed tube (20 mL) was added 4-chloro-7-((3aR,4R,6R,6aS)-2,2,6,6a-tetramethyl-6-vinyltetrahydrofuro[3,4-d][1,3]dioxol-4-yl)-7H-pyrrolo[2,3-d]pyrimidine (50 mg, 0.143 mmol), 1,4-dioxane (8 mL) and NH₃H₂O (8 mL, 25%-28% wt) at room temperature. The mixture was sealed tightly and then stirred at 90° C. for 16 hours. The reaction mixture was cooled to room temperature and concentrated under reduced pressure. The residue was purified by silica gel column chromatography (0-10% MeOH/DCM) to afford 7-((3aR,4R,6R,6aS)-2,2,6,6a-tetramethyl-6-vinyltetrahydrofuro[3,4-d][1,3]dioxol-4-yl)-7H-pyrrolo[2,3-d]pyrimidin-4-amine. MS: 331 (M+1). ¹H NMR (400 MHz, CDCl₃) δ 8.38 (s, 1H), 7.15 (d, J=3.7 Hz, 1H), 6.49 (d, J=2.6 Hz, 1H), 6.46 (d, J=3.7 Hz, 1H), 5.89 (dd, J=17.3, 11.0 Hz, 1H), 5.33 (s, 2H), 5.23 (dd, J=17.3, 1.4 Hz, 1H), 5.12 (dd, J=11.0, 1.4 Hz, 1H), 4.82 (d, J=2.5 Hz, 1H), 1.65 (s, 3H), 1.57 (s, 3H), 1.54 (s, 3H), 1.45 (s, 3H).

Step 14: To a solution of 7-((3aR,4R,6R,6aS)-2,2,6,6a-tetramethyl-6-vinyltetrahydrofuro[3,4-d][1,3]dioxol-4-yl)-7H-pyrrolo[2,3-d]pyrimidin-4-amine (20 mg, 0.061 mmol) in anhydrous THF (1.0 mL) was added 9-BBN in THF (0.605 mL, 0.303 mmol, 0.5 M) dropwise at 0° C. under an argon atmosphere. The reaction solution was stirred at 50° C. for 1 h. The resulting solution was used in next step directly.

Step 15: To the above solution was added potassium phosphate tribasic (64.3 mg, 0.303 mmol) in water (0.2 mL) dropwise at 0° C. under an atmosphere of argon. The reaction solution was stirred at room temperature for 0.5 h. 3-bromo-7-iodo-N-(4-methoxybenzyl)quinolin-2-amine (31.3 mg, 0.067 mmol) in tetrahydrofuran (0.3 mL) and 1,1-bis(diphenylphosphino)ferrocene-palladium (II) dichloride dichloromethane complex (4.95 mg, 6.06 μmol) were added to the above reaction system respectively at room temperature. The reaction mixture was heated at 70° C. for 2 h under microwave irradiation. The reaction mixture was then cooled to room temperature, diluted with water (5 mL) and extracted with EtOAc (2×20 mL). The combined organic layers were dried over anhydrous sodium sulfate and filtered. The filtrate was concentrated under reduced pressure. The residue was purified by Prep-TLC (developed by 10% MeOH in DCM) to afford 7-(2-((3aS,4R,6R,6aR)-6-(4-amino-7H-pyrrolo[2,3-d]pyrimidin-7-yl)-2,2,3a,4-tetramethyltetrahydrofuro[3,4-d][1,3]dioxol-4-yl)ethyl)-3-bromo-N-(4-methoxybenzyl)quinolin-2-amine. MS: 673/675 (M+1/M+3). ¹H NMR (400 MHz, CDCl₃) δ 8.35 (s, 1H), 8.05 (s, 1H), 7.43-7.29 (m, 4H), 7.19 (d, J=3.7 Hz, 1H), 6.93 (d, J=8.6 Hz, 2H), 6.74 (d, J=8.1 Hz, 1H), 6.47 (d, J=3.7 Hz, 1H), 6.34 (d, J=2.4 Hz, 1H), 5.65-5.54 (m, 1H), 5.40-5.29 (m, 2H), 4.77 (d, J=5.0 Hz, 2H), 3.84 (s, 3H), 2.76-2.68 (m, 1H), 2.55-2.45 (m, 1H), 2.05-1.93 (m, 1H), 1.87-1.76 (m, 1H), 1.66 (s, 3H), 1.63 (s, 3H), 1.54 (s, 3H), 1.51 (s, 3H).

Step 16: A solution of 7-(2-((3aS,4R,6R,6aR)-6-(4-amino-7H-pyrrolo[2,3-d]pyrimidin-7-yl)-2,2,3a,4-tetramethyltetrahydrofuro[3,4-d][1,3]dioxol-4-yl)ethyl)-3-bromo-N-(4-methoxybenzyl)quinolin-2-amine (40 mg, 0.059 mmol) in TFA (2 mL, 26.0 mmol) was stirred at 60° C. for 1 h. The reaction was cooled to room temperature and concentrated under reduced pressure to afford the crude product N-(7-(2-((2R,3S,4R,5R)-5-(4-amino-7H-pyrrolo[2,3-d]pyrimidin-7-yl)-3,4-dihydroxy-2,3-dimethyltetrahydrofuran-2-yl)ethyl)-3-bromoquinolin-2-yl)-2,2,2-trifluoroacetamide, which was used in next step directly without further purification.

Step 17: To a solution of the crude N-(7-(2-((2R,3S,4R,5R)-5-(4-amino-7H-pyrrolo[2,3-d]pyrimidin-7-yl)-3,4-dihydroxy-2,3-dimethyltetrahydrofuran-2-yl)ethyl)-3-bromoquinolin-2-yl)-2,2,2-trifluoroacetamide (calculated as 0.059 mmol) in methanol (3 mL) was added K₂CO₃ (24.6 mg, 0.178 mmol) at room temperature. The reaction mixture was stirred at 60° C. for 1 h. The solid was filtered and washed with MeOH (0.5 mL). The filtrate was concentrated under reduced pressure, and the residue was purified by reverse phase column chromatography (ACN/water with 5 mM NH₄HCO₃ modifier) to afford (2R,3S,4R,5R)-2-(2-(2-amino-3-bromoquinolin-7-yl)ethyl)-5-(4-amino-7H-pyrrolo[2,3-d]pyrimidin-7-yl)-2,3-dimethyltetrahydrofuran-3,4-diol as solid. MS: 513/515 (M+1/M+3). ¹H NMR (400 MHz, DMSO-d₆) δ 8.33 (s, 1H), 8.06 (s, 1H), 7.58 (d, J=8.0 Hz, 1H), 7.38 (d, J=4.0 Hz, 1H), 7.30 (s, 1H), 7.08 (d, J=8.4 Hz, 1H), 7.01 (br s, 2H), 6.64 (d, J=3.6 Hz, 1H), 6.58 (br s, 2H), 6.03 (d, J=8.0 Hz, 1H), 5.29 (br s, 1H), 4.79-4.77 (m, 1H), 4.72 (s, 1H), 2.66-2.59 (m, 2H), 2.20-2.15 (m, 1H), 1.70-1.63 (m, 1H), 1.25 (s, 3H), 1.17 (s, 3H).

Example 5

(2R,3R,3aS,6S,6aR)-6-((2-amino-3-bromoquinolin-7-yl)oxy)-2-(4-chloro-7H-pyrrolo[2,3-d]pyrimidin-7-yl)hexahydro-2H-cyclopenta[b]furan-3,3a-diol

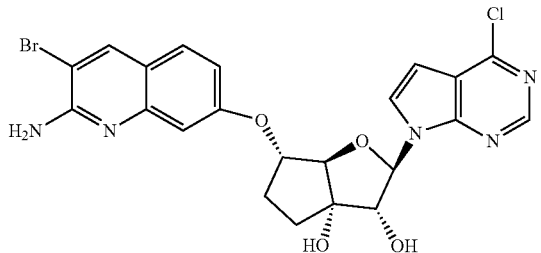 [SMILES: Nc1nc2cc(O[C@H]3CC[C@@]4(O)[C@@H]3O[C@@H](n3ccc5c(Cl)ncnc53)[C@@H]4O)ccc2cc1Br]

Step 1: (3R,3aS,6R,6aR)-2-methoxyhexahydro-2H-cyclopenta[b]furan-3,3a,6-triol (2 g, 10 mmol) was co-evaporated with dry toluene (5 mL×3) and then re-dissolved in acetone (50 mL). To this solution was added 4-methylbenzenesulfonic acid (0.091 g, 0.53 mmol), followed by 2,2-dimethoxypropane (2.74 g, 26.3 mmol). The resulting mixture was stirred at ambient temperature for 1 h. The pH of the resulting solution was adjusted to 8 with saturated aqueous NaHCO₃ (50 mL) at 0° C. The resulting mixture was extracted with EtOAc (150 mL×3). The combined organic layers were washed with brine (100 mL), dried over anhydrous Na₂SO₄, filtered, and the filtrate was concentrated under reduced pressure. The residue was purified by column chromatography on silica (EtOAc/pet. ether) to afford (3aR,5aR,6R,8aR)-4-methoxy-2,2-dimethylhexahydrocyclopenta[2,3]furo[3,4-d][1,3]dioxol-6-ol. MS: 248.20 (M+NH₄). ¹H NMR (300 MHz, DMSO-d₆) δ 4.96 (s, 1H), 4.41 (d, J=5.1 Hz, 1H), 4.17 (s, 1H), 4.10 (d, J=6.0 Hz, 1H), 3.88-3.79 (m, 1H), 3.33 (s, 3H), 2.04-1.92 (m, 1H), 1.76-1.62 (m, 3H), 1.39 (s, 3H), 1.31 (s, 3H). The column was further eluted with 45-50% of EtOAc in petroleum ether to afford (3aR,5aR,6R,8aR)-4-methoxy-2,2-dimethylhexahydrocyclopenta[2,3]furo[3,4-d][1,3]dioxol-6-ol. MS: 248 (M+NH₄). ¹H NMR (300 MHz, DMSO-d₆) δ 4.92 (d, J=4.2 Hz, 1H), 4.72 (d, J=6.0 Hz, 1H), 4.35 (d, J=4.2 Hz, 1H), 4.00 (d, J=(5.4 Hz, 1H), 3.91-3.82 (m, 1H), 3.35 (s, 3H), 2.09-1.97 (m, 1H), 1.83-1.62 (m, 2H), 1.52-1.43 (m, 1H), 1.40 (s, 3H), 1.31 (s, 3H).

Step 2: To a solution of (3aR,5aR,6R,8aR)-4-methoxy-2,2-dimethylhexahydrocyclopenta[2,3]furo[3,4-d][1,3]dioxol-6-ol (748 mg, 3.25 mmol) in DCM (30 mL) was added N,N-dimethylpyridin-4-amine (437 mg, 3.57 mmol) at room temperature. Then triethylamine (362 mg, 3.57 mmol) was added, followed by 4-methylbenzene-1-sulfonyl chloride (929 mg, 4.87 mmol). The reaction mixture was stirred for 16 h at 25° C. The resulting mixture was quenched with saturated aqueous NH₄Cl (200 mL) and extracted with DCM (100 mL×3). The combined organic layers were washed with brine (200 mL) and dried over anhydrous sodium sulfate. After filtration, the filtrate was concentrated under reduced pressure, and the residue was purified by column chromatography on silica (EtOAc/pet. ether) to afford (3aR,5aR,6R,8aR)-4-methoxy-2,2-dimethylhexahydrocyclopenta[2,3]furo[3,4-d][1,3]dioxol-6-yl 4-methylbenzenesulfonate. MS: 402 (M+NH₄). ¹H NMR (300 MHz, Chloroform-d) δ 7.85-7.81 (m, 2H), 7.35-7.32 (m, 2H), 4.94 (d, J=4.2 Hz, 1H), 4.74-4.67 (m, 1H), 4.35 (d, J=4.2 Hz, 1H), 4.15 (d, J=5.1 Hz, 1H), 3.38 (s, 3H), 2.44 (s, 3H), 2.18-1.75 (m, 4H), 1.49 (s, 3H), 1.37 (s, 3H).

Step 3: To a solution of (3aR,5aR,6R,8aR)-4-methoxy-2,2-dimethylhexahydrocyclopenta[2,3]furo[3,4-d][1,3]dioxol-6-yl 4-methylbenzenesulfonate (400 ng 1.04 mmol) and 2-amino-3-bromoquinolin-7-ol (249 mg, 1.04 mmol) (azeotroped with toluene 2 mL×3) in NMP (5 mL) was added Cs₂CO₃ (1.02 g, 3.12 mmol). The reaction mixture was stirred at 90° C. for 2 h under an argon atmosphere. The reaction mixture was cooled to room temperature and quenched with saturated aqueous NH₄Cl (60 mL) and extracted with DCM (60 mL×3). The combined organic layers were washed with brine (60 mL) and dried over anhydrous Na₂SO₄. After filtration, the filtrate was concentrated under reduced pressure. The residue was purified by column chromatography on silica (EtOAc/pet. Ether). The product was further purified by reverse phase HPLC (ACN/water) to afford 3-bromo-7-(((3aR,5aR,6S,8aR)-4-methoxy-2,2-dimethylhexahydrocyclopenta[2,3]furo[3,4-d][1,3]dioxol-6-yl)oxy)quinolin-2-amine. MS: 451/453 (M+1/M+3). ¹H NMR (300 MHz, Chloroform-d) δ 8.06 (s, 1H), 7.46 (d, J=9.0 Hz, 1H), 7.06 (d, J=2.4 Hz, 1H), 6.95 (dd, J=8.7, 2.4 Hz, 1H), 5.28 (s, 2H), 4.93 (d, J=4.2 Hz, 1H), 4.66 (d, J=4.2 Hz, 1H), 4.63-4.50 (m, 2H), 3.49 (s, 3H), 2.45-2.33 (m, 1H), 2.26-2.14 (m, 2H), 2.01-1.88 (m, 1H), 1.55 (s, 3H), 1.44 (s, 3H).

Step 4: A solution of 3-bromo-7-(((3aR,5aR,6S,8aR)-4-methoxy-2,2-dimethylhexahydrocyclopenta[2,3]furo[3,4-d][1,3]dioxol-6-yl)oxy)quinolin-2-amine (315 mg, 0.698 mmol) in HCl (10 mL, 4.00 mmol, 0.4 M in MeCN/H₂O=3:2 (v/v)) was stirred at 90° C. for 2 h. The reaction mixture was quenched with saturated aqueous NaHCO₃ (50 mL) and extracted with DCM (50 mL×3). The combined organic layers were washed with brine (50 mL), dried over anhydrous Na₂SO₄, and filtered. The filtrate was concentrated under reduced pressure. The combined residue was purified by reverse phase HPLC (ACN/water) to afford (3R,3aS,6S,6aR)-6-((2-amino-3-bromoquinolin-7-yl)oxy)hexahydro-2H-cyclopenta[b]furan-2,3,3a-triol. MS: 397/399 (M+1/M+3). ¹H NMR (300 MHz, Methanol-d₄) δ 8.20 (s, 1H), 7.56-7.52 (m, 1H), 7.11 (d, J=2.4 Hz, 1H), 7.02 (d, J=2.4 Hz, 1H), 6.97-6.92 (m, 1H), 5.34 (d, J=4.2 Hz, 1H), 5.20 (d, J=3.0 Hz, 1H), 4.76-4.74 (m, 1H), 4.64-4.62 (m, 1H), 4.36 (s, 1H), 4.18 (s, 1H), 3.79 (d, J=4.2 Hz, 1H), 3.63 (d, J=3.3 Hz, 1H), 2.46-1.81 (m, 4H).

Step 5: To a stirred solution of (3R,3aS,6S,6aR)-6-((2-amino-3-bromoquinolin-7-yl)oxy)hexahydro-2H-cyclopenta[b]furan-2,3,3a-triol (240 mg, 0.604 mmol) in anhydrous MeCN (10 mL) was added tributylphosphine (0.241 mL, 0.967 mmol), followed by (E)-diazene-1,2-diylbis(piperidin-1-ylmethanone) (229 mg, 0.906 mmol) at room temperature. The reaction mixture was stirred at ambient temperature for 20 minutes, and the solution containing crude (1aS,2aR,3S,5aR,5bR)-3-((2-amino-3-bromoquinolin-7-yl)oxy)hexahydro-5aH-cyclopenta[b]oxireno[2,3-d]furan-5a-ol was concentrated under reduced pressure. The product was used in next step without purification.

Step 6: To a stirred solution of 4-chloro-7H-pyrrolo[2,3-d]pyrimidine (184 mg, 1.20 mmol) in dry DMF (4 mL) was added sodium hydride (72 mg, 1.8 mmol) at 0° C. The suspension was stirred at room temperature for 30 minutes, then the suspension was transferred to a solution containing crude (1aS,2aR,3S,5aR,5bR)-3-((2-amino-3-bromoquinolin-7-yl)oxy)hexahydro-5aH-cyclopenta[b]oxireno[2,3-d]furan-5a-ol in ACN (4 mL) via syringe. The resulting mixture was stirred at room temperature for 2 h. The reaction mixture was quenched with saturated aqueous NH₄Cl (50 mL) and extracted with DCM (50 mL×3). The combined organic layers were washed with brine (50 mL), dried over anhydrous Na₂SO₄, and filtered. The filtrate was concentrated under reduced pressure, and the residue was purified by reverse phase HPLC (ACN/water with 5 mM aqueous ammonium bicarbonate). The crude product was further purified by Prep-TLC, developed by DCM:MeOH=10:1 (v:v) (rf=0.6) to afford (2R,3R,3aS,6S,6aR)-6-((2-amino-3-bromoquinolin-7-yl)oxy)-2-(4-chloro-7H-pyrrolo[2,3-d]pyrimidin-7-yl)hexahydro-2H-cyclopenta[b]furan-3,3a-diol. MS: 532/534 (M+1/M+3). ¹H NMR (300 MHz, DMSO-d₆) δ 8.72 (s, 1H), 8.27 (s, 1H), 8.18 (d, J=3.9 Hz, 1H), 7.57 (d, J=8.7 Hz, 1H), 6.88-6.83 (m, 3H), 6.61 (br s, 2H), 6.17 (d, J=8.4 Hz, 1H), 5.53 (d, J=7.2 Hz, 1H), 5.44 (s, 1H), 4.67 (d, J=4.8 Hz, 1H), 4.48 (t, J=7.8 Hz, 1H), 4.15 (s, 1H), 2.51-2.50 (m, 1H), 2.10-1.95 (m, 3H).

Example 6

(2R,3R,3aS,6S,6aR)-6-((2-amino-3-bromoquinolin-7-yl)oxy)-2-(4-amino-7H-pyrrolo[2,3-d]pyrimidin-7-yl)hexahydro-2H-cyclopenta[b]furan-3,3a-diol

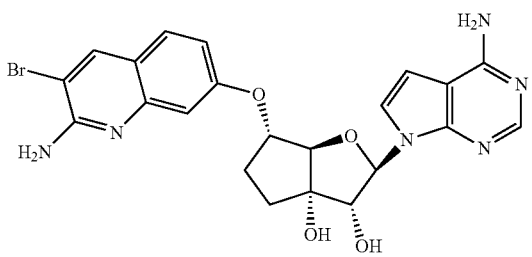 [SMILES: Nc1nc2cc(O[C@H]3CC[C@@]4(O)[C@@H]3O[C@@H](n3ccc5c(N)ncnc53)[C@@H]4O)ccc2cc1Br]

Step 1: A solution of (2R,3R,3aS,6S,6aR)-6-((2-amino-3-bromoquinolin-7-yl)oxy)-2-(4-chloro-7H-pyrrolo[2,3-d]pyrimidin-7-yl)hexahydro-2H-cyclopenta[b]furan-3,3a-diol (55 mg, 0.10 mmol), 1,4-dioxane (15 mL) and NH$_3$·H$_2$O (15 mL) was stirred in a sealed tube at 90° C. for 10 h. The reaction mixture was concentrated under reduced pressure, and the residue was diluted with saturated aqueous NH$_4$Cl (30 mL). The mixture was extracted with DCM (25 mL×5). The combined organic layers were washed with brine (50 mL), dried over anhydrous sodium sulfate, and filtered. The filtrate was concentrated under reduced pressure, and the residue was purified by column chromatography on silica (MeOH/DCM) to afford (2R,3R,3aS,6S,6aR)-6-((2-amino-3-bromoquinolin-7-yl)oxy)-2-(4-amino-7H-pyrrolo[2,3-d]pyrimidin-7-yl)hexahydro-2H-cyclopenta[b]furan-3,3a-diol. MS: 513/515 (M+1/M+3). $^1$H NMR (400 MHz, DMSO-d$_6$) δ 8.26 (s, 1H), 8.09 (s, 1H), 7.57 (d, J=8.8 Hz, 1H), 7.50 (d, J=3.6 Hz, 1H), 7.05 (br s, 2H), 6.87-6.83 (m, 2H), 6.66 (d, J=4.0 Hz, 1H), 6.53 (br s, 2H), 6.02 (d, J=8.8 Hz, 1H), 5.36 (d, J=7.2 Hz, 1H), 5.31 (s, 1H), 4.60 (d, J=4.8 Hz, 1H), 4.40 (t, J=7.6 Hz, 1H), 4.08 (s, 1H), 2.52-2.50 (m, 1H), 2.07-1.99 (m, 3H).

Example 7

(2R,3R,3aS,6S,6aR)-6-((2-amino-3-bromoquinolin-7-yl)oxy)-2-(4-methyl-7H-pyrrolo[2,3-d]pyrimidin-7-yl)hexahydro-2H-cyclopenta[b]furan-3,3a-diol

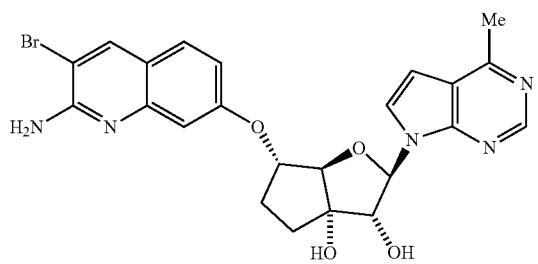 [SMILES: Cc1ncnc2c1ccn2[C@@H]1O[C@@H]2[C@@H](Oc3ccc4cc(Br)c(N)nc4c3)CC[C@]2(O)[C@H]1O]

Step 1: To a stirred solution of (3R,3aS,6S,6aR)-6-((2-amino-3-bromoquinolin-7-yl)oxy)hexahydro-2H-cyclopenta[b]furan-2,3,3a-triol (1.0 g, 2.5 mmol) in dry MeCN (30 mL) under an argon atmosphere was added (E)-diazene-1,2-diylbis(piperidin-1-ylmethanone) (1.13 g, 4.53 mmol) and tributylphosphine (1.20 mL, 4.78 mmol) at 25° C. The resulting mixture was stirred at 25° C. for 40 minutes. This solution was used in the next step without isolation and characterization.

Step 2: To a stirred solution of 4-methyl-7H-pyrrolo[2,3-d]pyrimidine (0.671 g, 5.04 mmol) (co-evaporated with dry toluene 10 mL×3 before being used) in anhydrous DMF (12 mL) was added sodium hydride (0.302 g, 7.56 mmol) at 0° C. The suspension was stirred at room temperature for 30 minutes. The suspension was transferred via a syringe at ambient temperature into the solution from the previous step, which contained (1aS,2aR,3S,5aR,5bR)-3-((2-amino-3-bromoquinolin-7-yl)oxy)hexahydro-1aH-cyclopenta[b]oxireno[2,3-d]furan-5a-ol (calculated as ~2.52 mmol). The resulting mixture was stirred at room temperature for 30 minutes. The reaction was quenched with saturated aqueous NH$_4$Cl (40 mL) and concentrated under reduced pressure. The residue was purified by reverse-phase HPLC (0-100% acetonitrile/water with 5 mM ammonium bicarbonate modifier) to afford (2R,3R,3aS,6S,6aR)-6-((2-amino-3-bromoquinolin-7-yl)oxy)-2-(4-methyl-7H-pyrrolo[2,3-d]pyrimidin-7-yl)hexahydro-2H-cyclopenta[b]furan-3,3a-diol as a solid. MS: 512/514 (M+1/M+3). $^1$H NMR (400 MHz, DMSO-d$_6$) δ 8.70 (s, 1H), 8.26 (s, 1H), 7.95 (d, J=4.0 Hz, 1H), 7.57 (d, J=8.8 Hz, 1H), 6.88-6.83 (m, 3H), 6.52 (br s, 2H), 6.15 (d, J=8.4 Hz, 1H), 5.45 (d, J=7.2 Hz, 1H), 5.39 (s, 1H), 4.64 (d, J=4.8 Hz, 1H), 4.48 (t, 3=8.0 Hz, 1H), 4.14 (s, 1H), 2.69 (s, 3H), 2.56-2.50 (m, 1H), 2.10-1.99 (m, 3H).

Example 8

(2R,3R,3aS,6S,6aR)-6-((2-amino-3-bromoquinolin-7-yl)methyl)-2-(4-methyl-7H-pyrrolo[2,3-d]pyrimidin-7-yl)hexahydro-2H-cyclopenta[b]furan-3,3a-diol

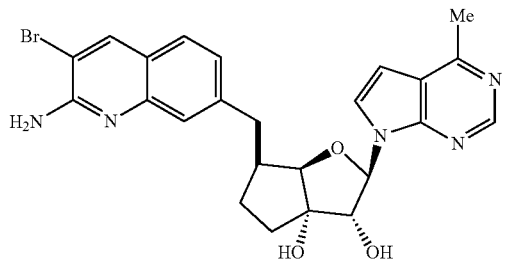

Step 1: To a solution of oxalyl dichloride (1.47 mL, 17.4 mmol) in anhydrous DCM (20 mL) was added DMSO (3.08 mL, 43.4 mmol) in anhydrous DCM (2 mL) at −78° C. under argon atmosphere. The reaction was stirred at −65° C. for 0.5 h. A solution of (3aR,5aR,6R,8aR)-4-methoxy-2,2-dimethylhexahydrocyclopenta[2,3]furo[3,4-d][1,3]dioxol-6-ol (1.0 g, 4.34 mmol) in anhydrous DCM (10 mL) was added to the above solution at −65° C. The solution was stirred for another 0.5 h at −65° C. Under this temperature, TEA (6.05 mL, 43.4 mmol) was added to the reaction mixture. The resulting solution was stirred for 0.5 h at −65° C. The reaction was quenched with H$_2$O (50 mL) at 0° C. and extracted with DCM (100 mL×3). The combined organic layers were washed with saturated aqueous NaHCO$_3$ (40 mL) and brine (30 mL), dried over anhydrous Na$_2$SO$_4$, and filtered. The filtrate was concentrated under reduced pressure to give (3aR,5aS,8aS)-4-methoxy-2,2-dimethyltetrahydrocyclopenta[2,3]furo[3,4-d][1,3]dioxol-6(5aH)-one, which was azeotroped with toluene (10 mL×3) and used directly in the next step without purification. $^1$H NMR (400

MHz, DMSO-$d_6$) δ 5.77 (d, J=1.6 Hz, 1H), 4.98 (d, J=1.6 Hz, 1H), 4.40 (d, J=1.6 Hz, 1H), 4.16 (s, 1H), 3.10 (s, 3H), 2.50-2.30 (m, 3H), 1.39 (s, 3H), 1.37 (s, 3H).

Step 2: To a solution of methyltriphenylphosphonium bromide (4.34 g, 12.2 mmol) in anhydrous THF (20 mL) was added n-BuLi (2.5 M in THF) (4.52 mL, 11.3 mmol) dropwise at −60° C. under an argon atmosphere. The reaction mixture was stirred at room temperature for 0.5 h. Then a solution of (3aR,5aS,8aS)-4-methoxy-2,2-dimethyltetrahydrocyclopenta[2,3]furo[3,4-d][1,3]dioxol-6(5aH)-one (1.8 g crude, 4.3 mmol) in anhydrous THF (20 mL) was added dropwise at −60° C. The reaction mixture was stirred at room temperature for 1 h. The reaction was quenched with saturated aqueous NH$_4$Cl (50 mL) at 0° C. The mixture was extracted with EtOAc (200 mL×2), and the combined organic layers were washed with brine (50 mL), dried over anhydrous Na$_2$SO$_4$, and filtered. The filtrate was concentrated under reduced pressure. The residue was purified by silica gel column chromatography (EtOAc/pet. ether) to afford (3aR,5aR,8aR)-4-methoxy-2,2-dimethyl-6-methylenehexahydrocyclopenta[2,3]furo[3,4-d][1,3]dioxole. $^1$H NMR (400 MHz, Chloroform-d) δ 5.17 (s, 1H), 5.07 (s, 1H), 5.02 (t, J=1.1 Hz, 1H), 4.64 (s, 1H), 4.30 (t, J=1.1 Hz, 1H), 3.29 (s, 3H), 2.75-2.59 (m, 1H), 2.44-2.33 (m, 1H), 2.23-2.09 (m, 1H), 2.15-2.05 (m, 1H), 1.51 (s, 3H), 1.41 (s, 3H).

Step 3: To a solution of (3aR,5aR,8aR)-4-methoxy-2,2-dimethyl-6-methylenehexahydrocyclopenta[2,3]furo[3,4-d][1,3]dioxole (300 mg, 1 mmol) in anhydrous THF (3 mL) was added 9-BBN (0.5 M in THF, 13.3 mL, 6.63 mmol) dropwise at 0° C. under an argon atmosphere. The reaction mixture was stirred at 50° C. for 1 h. This solution was used in the next step without characterization.

Step 4: To the solution containing the borane intermediate from the previous step was added a solution of potassium phosphate tribasic (1.41 g, 6.63 mmol) in water (3 mL) at 0° C. under an argon atmosphere. The reaction mixture was stirred at room temperature for 0.5 h. A solution of 3-bromo-7-iodo-N-(4-methoxybenzyl)quinolin-2-amine (684 mg, 1.46 mmol) and 1,1'-bis(diphenylphosphino)ferrocene-palladium(II)dichloridedichhloromethane complex (108 mg, 0.133 mmol) in THF (5 mL) was added at room temperature. The reaction mixture was stirred at 50° C. for 1.5 h. The reaction mixture was cooled to room temperature and partitioned between brine (80 mL) and EtOAc (100 mL). The aqueous phase was back-extracted with EtOAc (100 mL×2). The combined organic layers were dried over anhydrous sodium sulfate, filtered, and the filtrate was concentrated under reduced pressure. The residue was purified by column chromatography on silica (EtOAc/pet. ether) to afford 3-bromo-7-(((3aR,5aR,8aR)-4-methoxy-2,2-dimethylhexahydrocyclopenta[2,3]furo[3,4-d][1,3]dioxol-6-yl)methyl)-N-(4-methoxybenzyl)quinolin-2-amine. The crude product was used in next step directly without further purification. MS: 569/571 (M+1/M+3).

Step 5: A solution of 3-bromo-7-(((3aR,5aR,8aR)-4-methoxy-2,2-dimethylhexahydrocyclopenta[2,3]furo[3,4-d][1,3]dioxol-6-yl)methyl)-N-(4-methoxybenzyl)quinolin-2-amine (890 mg crude, 1.33 mmol) in HC (0.4 M in MeCN/H$_2$O (3:2, v/v), 10 mL, 4 mmol) was stirred at 90° C. for 1 h. The reaction was cooled to 0° C. and quenched with saturated aqueous Na$_2$CO$_3$ (60 mL) and extracted with EtOAc (100 mL×3). The combined organic layers were washed with brine (60 mL), dried over anhydrous sodium sulfate, filtered, and the filtrate was concentrated under reduced pressure. The residue was purified by silica gel column chromatography (MeOH/DCM) to afford (3R,3aS,6aR)-6-((3-bromo-2-((4-methoxybenzyl)amino)quinolin-7-yl)methyl)hexahydro-2H-cyclopenta[b]furan-2,3,3a-triol. MS: 515/517 (M+1/M+3). $^1$H NMR (400 MHz, DMSO-$d_6$) δ 8.33 (s, 1H), 7.57 (d, J=8.3 Hz, 1H), 7.35 (d, J=8.4 Hz, 3H), 7.13 (d, J=7.5 Hz, 2H), 6.88 (d, J=8.2 Hz, 2H), 5.93 (d, J=6.5 Hz, 1H), 5.20-5.12 (m, 1H), 4.64 (t, J=8.1 Hz, 3H), 4.46 (d, J=8.1 Hz, 1H), 3.93 (d, J=4.7 Hz, 1H), 3.72 (d, J=1.1 Hz, 3H), 3.49 (dd, J=7.5, 4.1 Hz, 1H), 2.87-2.76 (m, 1H), 2.65 (dd, J=13.6, 7.0 Hz, 1H), 2.20-1.19 (m, 5H).

Step 6: To a stirred solution of (3R,3aS,6aR)-6-((3-bromo-2-((4-methoxybenzyl)amino)quinolin-7-yl)methyl)hexahydro-2H-cyclopenta[b]furan-2,3,3a-triol (250 mg, 0.486 mmol) in dry MeCN (9 mL) was added tributylphosphine (176 mg, 0.869 mmol), followed by (E)-diazene-1,2-diylbis(piperidin-1-ylmethanone) (206 mg, 0.815 mmol) at room temperature. The reaction mixture was stirred at room temperature for 1 h, and the solution was used directly in the next step without characterization.

Step 7: To a stirred solution of 4-methyl-7H-pyrrolo[2,3-d]pyrimidine (129 mg, 0.970 mmol) in dry DMF (6 mL) was added sodium hydride (60% dispersion in mineral oil) (58.2 mg, 1.46 mmol) at 0° C. The suspension was stirred at room temperature for 30 minutes. The suspension was transferred to the solution from the previous step containing the epoxide intermediate via syringe, and the resulting mixture was stirred at room temperature for 2 h. The reaction mixture was quenched with saturated aqueous ammonium chloride (30 mL) and extracted with EtOAc (40 mL×3). The combined organic layers were washed with brine (40 mL), dried over anhydrous sodium sulfate and filtered. The filtrate was concentrated under reduced pressure. The residue was purified by Preparative TLC (MeOH/DCM) to afford (2R,3R,3aS,6aR)-6-((3-bromo-2-((4-methoxybenzyl)amino)quinolin-7-yl)methyl)-2-(4-methyl-7H-pyrrolo[2,3-d]pyrimidin-7-yl)hexahydro-3aH-cyclopenta[b]furan-3,3a-diol. MS: 630/632 (M+1/M+3). $^1$H NMR (400 MHz, DMSO-$d_6$) δ 8.69 (s, 1H), 8.32 (d, J=6.0 Hz, 1H), 8.02 (s, 1H), 7.54 (d, J=8.2 Hz, 1H), 7.33 (d, J=8.4 Hz, 2H), 7.14-7.04 (m, 3H), 6.91-6.80 (m, 4H), 6.03 (d, J=8.1 Hz, 1H), 5.30 (d, J=7.0 Hz, 1H), 5.12 (s, 1H), 4.61 (d, J=6.2 Hz, 2H), 4.22 (t, J=7.6 Hz, 1H), 4.04 (d, J=6.6 Hz, 1H), 3.72 (s, 3H), 2.83 (dd, J=13.7, 7.2 Hz, 1H), 2.69 (s, 3H), 2.65 (s, 1H), 2.37-2.22 (m, 1H), 1.99-1.93 (m, 1H), 1.55 (d, J=6.5 Hz, 2H).

Step 8: A solution of (2R,3R,3aS,6aR)-6-((3-bromo-2-((4-methoxybenzyl)amino)quinolin-7-yl)methyl)-2-(4-methyl-7H-pyrrolo[2,3-d]pyrimidin-7-yl)hexahydro-3aH-cyclopenta[b]furan-3,3a-diol (150 mg, 0.21 mmol) in TFA (2 mL) was stirred at 60° C. for 1 h. The reaction mixture was quenched with saturated aqueous NaHCO$_3$ (50 mL) and extracted with EtOAc (50 mL×3). The combined organic layers were washed with brine (50 mL), dried over anhydrous sodium sulfate, and filtered. The filtrate was concentrated under reduced pressure. The residue was purified by preparative TLC on silica (MeOH/DCM) to afford crude product as a solid. The crude product was further purified by reverse phase HPLC (ACN/water with 5 mM ammonium bicarbonate modifier) to afford (2R,3R,3aS,6S,6aR)-6-((2-amino-3-bromoquinolin-7-yl)methyl)-2-(4-methyl-7H-pyrrolo[2,3-d]pyrimidin-7-yl)hexahydro-2H-cyclopenta[b]furan-3,3a-diol. MS: 510/512 (M+1/M+3). $^1$H NMR (400 MHz, DMSO-$d_6$) δ 8.69 (s, 1H), 8.30 (s, 1H), 7.87 (d, J=3.6 Hz, 1H), 7.54 (d, J=8.4 Hz, 1H), 7.27 (s, 1H), 7.08 (dd, 3=8.4, 1.6 Hz, 1H), 6.82 (d, J=3.6 Hz, 1H), 6.53 (br s, 2H), 6.01 (d, J=8.0 Hz, 1H), 5.30 (d, J=6.8 Hz, 1H), 5.11 (s, 1H), 4.22 (t, J=7.6 Hz, 1H), 4.00 (d, J=5.6 Hz, 1H), 2.83 (dd, J=13.6, 7.8 Hz, 1H), 2.70 (s, 3H), 2.64 (dd, J=13.6, 7.6 Hz, 1H), 2.35-2.24 (m, 1H), 1.97 (dd, J=12.4, 5.6 Hz, 1H), 1.79-1.68 (m, 2H), 1.55 (dt, =12.4, 6.4 Hz, 1H).

Example 9

(2R,3R,3aS,6S,6aR)-6-((2-amino-3-bromoquinolin-7-yl)methyl)-2-(4-amino-7H-pyrrolo[2,3-d]pyrimidin-7-yl)hexahydro-2H-cyclopenta[b]furan-3,3a-diol

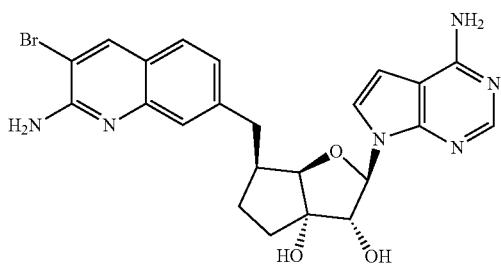 [SMILES: Nc1nc2cc(C[C@@H]3CC[C@@]4(O)[C@@H]3O[C@@H](n3ccc5c(N)ncnc53)[C@@H]4O)ccc2cc1Br]

Step 1: To a stirred solution of (3R,3aS,6aR)-6-((3-bromo-2-((4-methoxybenzyl)amino)quinolin-7-yl)methyl)hexahydro-2H-cyclopenta[b]furan-2,3,3a-triol (70 mg, 0.14 mmol) in dry MeCN (3 mL) was added (E)-diazene-1,2-diylbis(piperidin-1-ylmethanone) (51.4 mg, 0.204 mmol) in MeCN (0.3 mL) dropwise at 0° C. under an atmosphere of argon. This was followed by the addition of tributylphosphine (0.054 mL, 0.22 mmol) dropwise at 0° C. Then the reaction was stirred at 35° C. for 1 h. The resulting solution was used directly in the next step without further purification.

Step 2: To a stirred suspension of 4-chloro-7H-pyrrolo[2,3-d]pyrimidine (39.0 mg, 0.254 mmol) in dry ACN (3 mL) was added DBU (0.039 mL, 0.26 mmol) at room temperature under an argon atmosphere. The resultant solution was stirred at room temperature for 30 minutes. Then the solution from the previous step was transferred via syringe at room temperature under an argon atmosphere. The resulting mixture was stirred at 35° C. for 2 h. The reaction was quenched with brine (20 mL) and extracted with EtOAc (50 mL×3). The combined organic layers were dried over anhydrous sodium sulfate and filtered. The filtrate was concentrated under reduced pressure. The residue was purified by column chromatography on silica (MeOH/DCM) to afford (2R,3R,3aS,6S,6aR)-6-((3-bromo-2-((4-methoxybenzyl)amino)quinolin-7-yl)methyl)-2-(4-chloro-7H-pyrrolo[2,3-d]pyrimidin-7-yl)hexahydro-2H-cyclopenta[b]furan-3,3a-diol. MS: 650/652 (M+1/M+3). $^1$H NMR (400 MHz, DMSO-$d_6$) δ 8.71 (d, J=1.6 Hz, 1H), 8.32 (s, 1H), 8.12 (d, J=4.0 Hz, 1H), 7.55 (d, J=8.3 Hz, 1H), 7.37-7.29 (m, 4H), 7.10-7.05 (m, 1H), 6.86 (d, J=8.2 Hz, 2H), 6.84-6.79 (m, 1H), 6.04 (d, J=8.0 Hz, 1H), 5.37 (brs, 1H), 4.61 (d, J=6.0 Hz, 2H), 4.22 (d, J=8.0 Hz, 1H), 4.08-4.01 (m, 1H), 3.72 (s, 3H), 2.83 (dd, J=136, 7.6 Hz, 1H), 2.64 (dd, J=14.6, 7.6 Hz, 1H), 2.37-2.26 (m, 2H), 1.96 (dd, J=12.4, 6.0 Hz, 1H), 1.85-1.75 (m, 1H), 1.71-1.63 (m, 1H), 1.56-1.50 (m, 1H).

Step 3: A solution of (2R,3R,3aS,6S,6aR)-6-((3-bromo-2-((4-methoxybenzyl)amino)quinolin-7-yl)methyl)-2-(4-chloro-7H-pyrrolo[2,3-d]pyrimidin-7-yl)hexahydro-2H-cyclopenta[b]furan-3,3a-diol (60 ng, 0.09 mmol) in TFA (2 mL, 30 mmol) was stirred at 60° C. for 1 h. The mixture was cooled to room temperature and concentrated under reduced pressure. The residue was diluted with EtOAc (100 mL) and washed with saturated aqueous NaHCO$_3$ (20 mL). The organic layer was dried over anhydrous sodium sulfate and filtered. The filtrate was concentrated under reduced pressure. The residue was purified by column chromatography on silica (MeOH/DCM) to afford (2R,3R,3aS,6S,6aR)-6-((2-amino-3-bromoquinolin-7-yl)methyl)-2-(4-chloro-7H-pyrrolo[2,3-d]pyrimidin-7-yl)hexahydro-2H-cyclopenta[b]furan-3,3a-diol. MS. 530/532 (M+1/M+3). $^1$H NMR (400 MHz, DMSO-$d_6$) δ 8.72 (s, 1H), 8.31 (s, 1H), 8.11 (d, J=4.0 Hz, 1H), 7.55 (d, J=8.4 Hz, 1H), 7.29 (s, 1H), 7.10 (dd, J=8.4, 1.6 Hz, 1H), 6.83 (d, J=4.0 Hz, 1H), 6.57-6.51 (m, 3H), 6.03 (d, J=8.0 Hz, 1H), 5.39 (d, J=6.8 Hz, 1H), 5.17 (s, 1H), 4.24 (t, J=7.6 Hz, 1H), 4.05 (d, J=5.6 Hz, 1H), 2.84 (dd, J=13.6, 8.0 Hz, 1H), 2.71-2.60 (m, 1H), 2.37-2.15 (m, 1H), 2.03-1.92 (m, 1H), 1.88-1.63 (m, 1H), 1.62-1.49 (m, 1H).

Step 4: To a sealed tube (20 mL) was added (2R,3R,3aS,6S,6aR)-6-((2-amino-3-bromoquinolin-7-yl)methyl)-2-(4-chloro-7H-pyrrolo[2,3-d]pyrimidin-7-yl)hexahydro-2H-cyclopenta[b]furan-3,3a-diol (30 mg, 0.06 mmol), 1,4-dioxane (5 mL) and NH$_3$·H$_2$O (9 mL) at room temperature. The vial was sealed, and the reaction was stirred at 90° C. for 16 h. The reaction mixture was cooled to room temperature and concentrated under reduced pressure. The residue was purified by reverse phase HPLC (ACN/water with 5 mM ammonium bicarbonate modifier) to afford (2R,3R,3aS,6S,6aR)-6-((2-amino-3-bromoquinolin-7-yl)methyl)-2-(4-amino-7H-pyrrolo[2,3-d]pyrimidin-7-yl)hexahydro-2-cyclopenta[b]furan-3,3a-diol. MS: 511/513 (M+1/M+3). $^1$H NMR (400 MHz, DMSO-$d_6$) δ 8.30 (s, 1H), 8.09 (s, 1H), 7.54 (d, J=8.4 Hz, 1H), 7.43 (d, J=4.0 Hz, 1H), 7.28 (s, 1H), 7.09 (d, J=8.4 Hz, 1H), 7.03 (br s, 2H), 6.67 (d, J=3.6 Hz, 1H), 6.54 (br s, 2H), 5.88 (d, J=8.0 Hz, 1H), 5.23 (d, J=7.2 Hz, 1H), 5.04 (s, 1H), 4.13 (t, J=7.6 Hz, 1H), 3.95 (d, J=6.0 Hz, 1H), 2.82 (dd, J=13.2, 8.0 Hz, 1H), 2.62 (dd, J=14.4, 7.2 Hz, 1H), 2.24-2.22 (m, 1H), 1.96-1.92 (m, 1H), 1.70-1.68 (m, 2H), 1.57-1.51 (m, 1H).

Example 10 and 11

(2R,3S,4R,5R)-2-(((2-amino-3-bromoquinolin-7-yl)oxy)methyl)-5-(4-amino-7H-pyrrolo[2,3-d]pyrimidin-7-yl)-3-methyltetrahydrofuran-3,4-diol (Example 10) And (2R,3S,4R,5R)-2-{[(2-amino-3-bromoquinolin-7-yl)oxy]methyl}-5-(4-chloro-7H-pyrrolo[2,3-d]pyrimidin-7-yl)-3-methyltetrahydrofuran-3,4-diol (Example 11)

Example 10

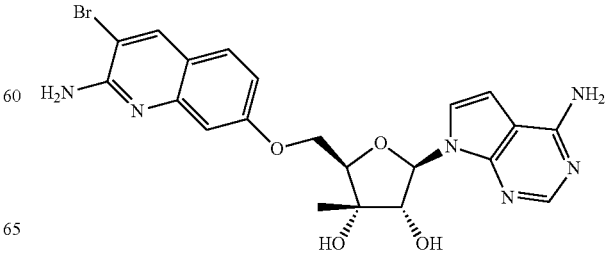

Example 11

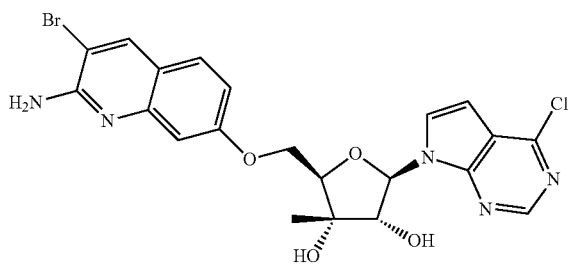

Step 1: Into a 10-L 4-necked round-bottom flask purged and maintained with an inert atmosphere of nitrogen was placed a solution of (5R,6S)-5-(hydroxymethyl)-2,2-dimethyltetrahydrofuro[2,3-d][1,3]dioxol-6-ol (951 g, 5 mol) in pyridine (7 L) and tert-butyl(chloro)diphenylsilane (1.4 kg, 5.1 mol). The resulting solution was stirred overnight at room temperature. The mixture was diluted with MeOH (600 mL) and then concentrated under reduced pressure. The residue was diluted with EtOAc, washed with HCl (0.5 M in water), saturated sodium bicarbonate, and brine. The organic layer was dried over sodium sulfate, filtered, and concentrated under reduced pressure to afford (5R,6S)-5-(((tert-butyldiphenylsilyl)oxy)methyl)-2,2-dimethyltetrahydrofuro[2,3-d][1,3]dioxol-6-ol as an oil, which was used in the next step without further purification.

Step 2: Into a 20-L 4-necked round-bottom flask purged and maintained with an inert atmosphere of nitrogen was placed a solution of (5R,6S)-5-(((tert-butyldiphenylsilyl)oxy)methyl)-2,2-dimethyltetrahydrofuro[2,3-d][1,3]dioxol-6-ol 1 (2.1 kg, 5 mol) in DCM (15 L) and Dess-Martin periodinane (3.18 kg, 7.50 mol). The resulting solution was stirred overnight at room temperature. The reaction was quenched by the addition of saturated aqueous sodium bicarbonate, and the solution was concentrated under reduced pressure. The residue was diluted with diethyl ether, and the mixture was filtered. The filtrate was concentrated under reduced pressure to afford (5R)-5-(((tert-butyldiphenylsilyl)oxy)methyl)-2,2-dimethyldihydrofuro[2,3-d][1,3]dioxol-6(5H)-one as an oil which was used in the next step without further purification.

Step 3: Into a 20-L 4-necked round-bottom flask purged and maintained with an inert atmosphere of nitrogen was placed a solution of (5R)-5-(((tert-butyldiphenylsilyl)oxy)methyl)-2,2-dimethyldihydrofuro[2,3-d][1,3]dioxol-6(5H)-one (2.1 kg, 5 mol) in THF (10 L). To this mixture was added methylmagnesium chloride (1.84 L, 3.0 M in THF) dropwise with stirring at 0° C. The resulting solution was stirred for 1 h at room temperature. The reaction was then quenched by the addition of saturated aqueous ammonium chloride. The organic layer was washed with brine, dried over anhydrous sodium sulfate, filtered, and concentrated under reduced pressure to afford (5R,6R)-5-(((tert-butyldiphenylsilyl)oxy)methyl)-2,2,6-trimethyltetrahydrofuro[2,3-d][1,3]dioxol-6-ol as an oil, which was used in the next step without further purification. $^1$H NMR (500 MHz, CDCl$_3$) δ 7.73-7.70 (m, 4H), 7.46-7.39 (m, 61H), 5.79 (d, J=3.8 Hz, 1H), 4.16-4.10 (m, 2H), 3.92 (dd, J=6.4, 4.5 Hz, 1H), 3.85-3.84 (m, 2H), 2.56 (s, 1H), 2.07 (s, 1H), 1.38 (s, 3H), 1.28 (t, J=7.1 Hz, 2H), 1.14 (s, 3H), 1.09 (s, 8H).

Step 4: Into a 20-L 4-necked round-bottom flask purged and maintained with an inert atmosphere of nitrogen was placed a solution of (5R,6R)-5-(((tert-butyldiphenylsilyl)oxy)methyl)-2,2,6-trimethyltetrahydrofuro[2,3-d][1,3]dioxol-6-ol (2.2 kg, 5 mol) in AcOH (10 L). To this mixture was added sulfuric acid (49.2 g, 502 mmol) dropwise with stirring at 10° C., followed by acetic anhydride (2.04 kg, 20.0 mol) dropwise with stirring at 10° C. The resulting solution was stirred for 3 h at room temperature. The mixture was concentrated under reduced pressure and then diluted with EtOAc. The resulting mixture was washed with saturated aqueous sodium bicarbonate and then brine. The organic layer was dried over anhydrous sodium sulfate, filtered, and concentrated under reduced pressure. The residue was purified by column chromatography on silica (eluting with 1:1 ethyl acetate/petroleum ether) to afford (3R,4R,5R)-5-(((tert-butyldiphenylsilyl)oxy)methyl)-4-methyltetrahydrofuran-2,3,4-triyl triacetate as an oil.

Step 5: Into a 5 L 4-necked round-bottom flask purged and maintained with an inert atmosphere of nitrogen was placed 4-chloro-5-iodo-7H-pyrrolo[2,3-d]pyrimidine (420 g, 1503 mmol), BSA (305 g, 7.11 mol), a solution of (3R,4R,5R)-5-(((tert-butyldiphenylsilyl)oxy)methyl)-4-methyltetrahydrofuran-2,3,4-triyl triacetate (795 g, 1.50 mol) in MeCN (7 L), and trimethylsilyl trifluoromethanesulfonate (668 g, 3.00 mol). The resulting solution was stirred for 6 h at 80° C. The mixture was cooled to room temperature, concentrated under reduced pressure, and diluted with EtOAc. The resulting mixture was washed with saturated aqueous sodium bicarbonate and brine. The organic layer was dried over anhydrous sodium sulfate, filtered, and concentrated under reduced pressure. The residue was purified by column chromatography on silica (EtOAc/pet. ether) to afford (2R,3R,4R,5R)-2-(((tert-butyldiphenylsilyl)oxy)methyl)-5-(4-chloro-5-iodo-7H-pyrrolo[2,3-d]pyrimidin-7-yl)-3-methyltetrahydrofuran-3,4-diyl diacetate as an oil. MS: 748 (M+1).

Step 6: Into a 5-L 4-necked round-bottom flask purged and maintained with an inert atmosphere of nitrogen was placed a solution of (2R,3R,4R,5R)-2-(((tert-butyldiphenylsilyl)oxy)methyl)-5-(4-chloro-5-iodo-7H-pyrrolo[2,3-d]pyrimidin-7-yl)-3-methyltetrahydrofuran-3,4-diyl diacetate (225 g, 300 mmol) in tetrahydrofuran (2.2 L). The solution was cooled to −78° C. and isopropylmagnesium chloride-lithium chloride complex (54.6 g, 376 mmol) was added dropwise, and the solution was stirred for 2 h at −78° C. The mixture was quenched with dropwise addition of iPrOH (25.2 g, 420 mmol) at −78° C. This cold reaction mixture was poured into a mixture of ice and saturated aqueous ammonium chloride. The mixture was extracted with DCM (2×) and the combined organic layers were dried over sodium sulfate, filtered, and concentrated under reduced pressure to afford (2R,3R,4R,5R)-2-(((tert-butyldiphenylsilyl)oxy)methyl)-5-(4-chloro-7H-pyrrolo[2,3-d]pyrimidin-7-yl)-3-methyltetrahydrofuran-3,4-diyl diacetate as an oil which was used as is without further purification.

Step 7: Into a 5-L 3-necked round-bottom flask purged and maintained with an inert atmosphere of nitrogen was placed a solution of (2R,3R,4R,5R)-2-(((tert-butyldiphenylsilyl)oxy)methyl)-5-(4-chloro-7H-pyrrolo[2,3-d]pyrimidin-7-yl)-3-methyltetrahydrofuran-3,4-diyl diacetate (186 g, 299 mmol) in THF (1.8 L) and AcOH (90 g, 1.5 mol). TBAF (600 mL, 2.00 equiv, 1.0 M in THF) was added dropwise with stirring at room temperature, and the solution was stirred for 2 h at room temperature. The reaction mixture was concentrated under reduced pressure, and the residue was purified by column chromatography on silica (MeOH/DCM) to afford (2R,3R,4R,5R)-5-(4-chloro-7H-pyrrolo[2,3-d]pyrimidin-7-yl)-2-(hydroxymethyl)-3-methyltetrahydrofuran-3,4-diyl diacetate as a solid. MS: 384 (M+1).

Step 8: A mixture of (2R,3R,4R,5R)-5-(4-chloro-7H-pyrrolo[2,3-d]pyrimidin-7-yl)-2-(hydroxymethyl)-3-methyltetrahydrofuran-3,4-diyl diacetate (542 mg, 1.41 mmol), TEA (0.59 mL, 4.2 mmol), and DMAP (34.5 mg, 0.28 mmol) was dissolved in DCM (11 mL). 4-Toluenesulfonyl chloride (538 mg, 2.8 mmol) was added at 0° C. and the reaction was stirred at room temperature overnight. The mixture was diluted with DCM and washed with water. The aqueous layer was extracted with DCM (2×). The combined organic layers were dried over sodium sulfate, filtered, and concentrated under reduced pressure. The residue was purified by column chromatography on silica (EtOAc/Hexanes) to afford (2R,3R,4R,5R)-5-(4-chloro-7H-pyrrolo[2,3-d]pyrimidin-7-yl)-3-methyl-2-((tosyloxy)methyl)tetrahydrofuran-3,4-diyl diacetate which was used as is without further purification. MS: 538 (M+1).

Step 9: To a solution of (2R,3R,4R,5R)-5-(4-chloro-7H-pyrrolo[2,3-d]pyrimidin-7-yl)-3-methyl-2-((tosyloxy)methyl)tetrahydrofuran-3,4-diyl diacetate (380 mg, 0.71 mmol) and 2-amino-3-bromoquinolin-7-ol (169 mg, 0.71 mmol) in DMF (5 mL) at 0° C. was added cesium carbonate (460 mg, 1.4 mmol). The mixture was stirred at room temperature overnight and then quenched with water. The precipitate was collected by filtration, rinsed with water, and dried under reduced pressure to afford (2R,3R,4R,5R)-2-{[(2-amino-3-bromoquinolin-7-yl)oxy]methyl}-5-(4-chloro-7H-pyrrolo[2,3-d]pyrimidin-7-yl)-3-methyltetrahydrofuran-3,4-diyl diacetate as a solid. MS: 604/606 (M+1/M+3).

Step 10: To a solution of (2R,3R,4R,5R)-2-{[(2-amino-3-bromoquinolin-7-yl)oxy]methyl}-5-(4-chloro-.7H-pyrrolo[2,3-d]pyrimidin-7-yl)-3-methyltetrahydrofuran-3,4-diyl diacetate (372 mg, 0.62 mmol) dissolved in dioxane (4 mL) was added ammonium hydroxide (4 mL, 51.8 mmol, 30% in water). The mixture was heated at 85° C. overnight. The mixture was cooled to room temperature and the reaction mixture was concentrated under reduced pressure. The residue was purified by mass triggered reverse phase HPLC (ACN/water with 0.1% TFA modifier) to afford:

Example 10

(2R,3S,4R,5R)-2-4((2-amino-3-bromoquinolin-7-yl)oxy)methyl)-5-(4-amino-7H-pyrrolo[2,3-d]pyrimidin-7-yl)-3-methyltetrahydrofuran-3,4-diol MS: 501/503 (M+1/M+3). $^1$H NMR (600 MHz, DMSO-d$_6$) δ 8.72-8.34 (m, 3H), 8.03-7.40 (m, 3H), 7.15-7.03 (m, 2H), 6.94 (d, J=3.0 Hz, 1H), 6.16 (d, J=7.9 Hz, 1H), 5.65-4.96 (m, 2H), 4.40-4.35 (m, 1H), 4.29-4.18 (m, 4H), 1.27 (s, 3H).

Example 11

(2R,3S,4R,5R)-2-{[(2-amino-3-bromoquinolin-7-yl)oxy]methyl}-5-(4-chloro-7H-pyrrolo[2,3-d]pyrimidin-7-yl)-3-methyltetrahydrofuran-3,4-diol MS: 520/522 (M+1/M+3). $^1$H NMR (600 MHz, DMSO-d$_6$) δ 8.73-8.62 (m, 2H), 8.13 (s, 1H), 7.93 (d, J=3.4 Hz, 1H), 7.76 (d, J=8.7 Hz, 1H), 7.18-7.11 (m, 2H), 6.73 (d, J=3.5 Hz, 1H), 6.25 (d, J=8.0 Hz, 1H), 4.51-4.44 (m, 2H), 4.33-4.20 (m, 5H), 1.28 (s, 3H).

Example 12

(2R,3S,4R,5R)-2-(((2-amino-3-bromoquinolin-7-yl)oxy)methyl)-5-(4-methoxy-7H-pyrrolo[2,3-d]pyrimidin-7-yl)-2-methyltetrahydrofuran-3,4-diol

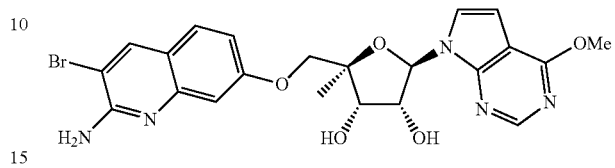

A solution of 3-bromo-7-(((3aS,4R,6R,6aR)-6-(4-methoxy-7H-pyrrolo[2,3-d]pyrimidin-7-yl)-2,2,4-trimethyl-tetrahydrofuro[3,4-d][1,3]dioxol-4-yl)methoxy)-N-(4-methoxybenzyl)quinolin-2-amine (30 ng, 0.04 mmol) in TFA (1.0 mL) was stirred at 40° C. for 3 days. The reaction mixture was concentrated in vacuum and the residue was purified by reverse-phase HPLC (ACN/water with 0.1% TFA modifier) to afford (2R,3S,4R,5R)-2-(((2-amino-3-bromoquinolin-7-yl)oxy)methyl)-5-(4-methoxy-7H-pyrrolo[2,3-d]pyrimidin-7-yl)-2-methyltetrahydrofuran-3,4-diol, TFA salt as a solid. MS: 516/518 (M+1/M+3). $^1$H-NMR (600 MHz, DMSO-d$_6$) δ 8.66 (br, 1H), 8.43 (s, 1H), 7.75 (d, J=8.2 Hz, 1H), 7.63-7.59 (m, 1H), 7.16-7.09 (m, 2H), 6.59-6.54 (m, 1H), 6.23 (d, J=6.6 Hz, 1H), 4.88-4.81 (m, 1H), 4.27-4.19 (m, 2H), 4.11 (d, J=9.9 Hz, 1H), 4.03 (s, 3H), 1.36 (s, 3H).

Example 13

(2R,3S,4R,5R)-2-(((2-amino-3-bromoquinolin-7-yl)oxy)methyl)-5-(4-amino-7H-pyrrolo[2,3-d]pyrimidin-7-yl)-2-methyltetrahydrofuran-3,4-diol

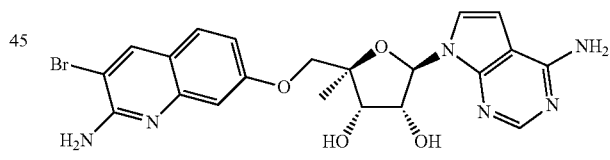

A solution of (2R,3S,4R,5R)-2-(((2-amino-3-bromoquinolin-7-yl)oxy)methyl)-5-(4-methoxy-7H-pyrrolo[2,3-d]pyrimidin-7-yl)-2-methyltetrahydrofuran-3,4-diol, TFA salt (10 ng, 0.019 mmol) in 30% ammonia in water (3 mL) was stirred at 150° C. for 4 h in a microwave reactor. The reaction mixture was concentrated under reduced pressure, and the residue was purified by chiral SFC (DIOL column, 35%/65% methanol/CO$_2$) to afford (2R,3S,4R,5R)-2-(((2-amino-3-bromoquinolin-7-yl)oxy)methyl)-5-(4-amino-7H-pyrrolo[2,3-d]pyrimidin-7-yl)-2-methyltetrahydrofuran-3,4-diol as a solid. MS: 501/503 (M+1/M+3). $^1$H-NMR (500 MHz, CD$_3$OD) δ 8.22 (s, 1H), 8.09 (s, 1H), 7.58 (d, J=9.0 Hz, 1H), 7.35 (d, J=3.7 Hz, 1H), 7.06-6.98 (m, 2H), 6.60 (d, J=3.3 Hz, 1H), 6.27 (d, J=6.7 Hz, 1H), 4.87-4.82 (m, 1H), 4.39 (d, J=5.4 Hz, 1H), 4.20 (d, J=10.2 Hz, 1H), 4.12 (d, J=10.2 Hz, 1H), 1.48 (s, 3H).

Example 14

(2R,3S,4R,5R)-2-(((2-amino-3-bromoquinolin-7-yl)oxy)methyl)-5-(4-amino-7H-pyrrolo[2,3-d]pyrimidin-7-yl)-3-methyltetrahydrofuran-3,4-diol

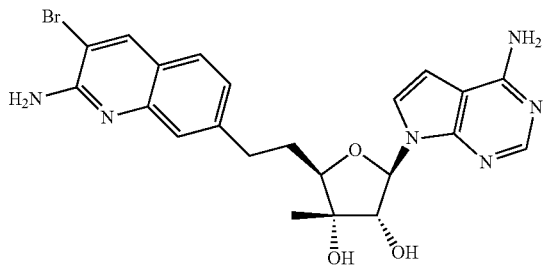 [SMILES: C[C@@]1(O)[C@@H](CCc2ccc3cc(Br)c(N)nc3c2)O[C@@H](n2ccc3c(N)ncnc32)[C@@H]1O]

Step 1: A 500 mL round bottom flask was charged with (3aR,5R,6aR)-5-((R)-2,2-dimethyl-1,3-dioxolan-4-yl)-2,2-dimethyltetrahydrofuro[2,3-d][1,3]dioxol-6-ol (10.0 g, 38.4 mol), which was then dissolved in DCM (100 mL). Then, Dess-Martin Periodinane (32.6 g, 77 mmol) was added portion-wise, and the cloudy white reaction was stirred at room temperature for 80 min. DCM (100 mL) was added, and the reaction was stirred at room temperature overnight. The reaction was quenched with saturated aqueous sodium bicarbonate and saturated aqueous sodium thiosulfate. After 1 h with stirring, the layers were extracted, and the organic layer was dried over magnesium sulfate, filtered, and concentrated under reduced pressure to afford crude (3aR,5S,6aS)-5-((R)-2,2-dimethyl-1,3-dioxolan-4-yl)-2,2-dimethyldihydrofuro[2,3-d][1,3]dioxol-6(3aH)-one as an oil, which was used directly in the next step without further purification. $^1$H NMR (600 MHz, CDCl$_3$) δ 6.14 (d, J=4.5 Hz, 1H), 4.39-4.38 (m, 1H), 4.38-4.34 (m, 2H), 4.04-4.01 (m, 2H), 1.46 (s, 3H), 1.43 (s, 3H), 1.35-1.32 (m, 6H).

Step 2: A flask was charged with crude (3aR,5R,6aS)-5-((S')-2,2-dimethyl-1,3-dioxolan-4-yl)-2,2-dimethyldihydrofuro[2,3-d][1,3]dioxol-6(3aH)-one (7.42 g, max 28.7 mmol), backfilled with argon, and then toluene (100 mL) was added. The solution was cooled to 0° C., and then methyl magnesium chloride (3.0 M in THF, 14.4 mL, 43.2 mmol) was added dropwise under an argon atmosphere. After 5 minutes, the reaction was removed from the ice bath and allowed to warm to room temperature, stirring overnight. The reaction was poured into a separatory funnel containing saturated ammonium chloride and extracted with EtOAc. The organic layers were combined and washed with brine, dried over magnesium sulfate, filtered, and concentrated under reduced pressure to afford (3aR,5R,6R,6aR)-5-((S)-2,2-dimethyl-1,3-dioxolan-4-yl)-2,2,6-trimethyltetrahydrofuro[2,3-d][1,3]dioxol-6-ol as a solid, which was used in the next step without further purification. $^1$H-NMR (600 MHz, CDCl$_3$) δ 5.70 (d, J=3.6 Hz, 1H), 4.17 (d, J=3.7 Hz, 1H), 4.12-4.08 (m, 2H), 3.95-3.91 (m, 1H), 3.78 (d, J=7.4 Hz, 1H), 2.67 (s, 1H), 1.59 (s, 3H), 1.45 (s, 3H), 1.36 (s, 3H), 1.35 (s, 3H), 1.28 (s, 3H).

Step 3: To flask charged with (3aR,5R,6R,6aR)-5-((S)-2,2-dimethyl-1,3-dioxolan-4-yl)-2,2,6-trimethyltetrahydrofuro[2,3-d][1,3]dioxol-6-ol (5.82 g, 21.2 mmol) was added acetonitrile (100 mL). Then, sulfuric acid (10 mL, 188 mmol) as a 5 vol % in water solution was added, and the reaction was stirred at room temperature for 4.5 h. The reaction was poured into a separatory funnel containing saturated sodium bicarbonate and extracted with EtOAc. The organic layers were combined and washed with brine, dried over sodium sulfate, filtered, and concentrated under reduced pressure to afford (S)-1-((3aR,5R,6R,6aR)-6-hydroxy-2,2,6-trimethyltetrahydrofuro[2,3-d][1,3]dioxol-5-yl)ethane-1,2-diol as a solid, which was used in the next reaction without further purification. $^1$H-NMR (600 MHz, CDCl$_3$) δ 5.73 (d, J=3.7 Hz, 1H), 4.16 (d, J=3.7 Hz, 1H), 3.85-3.81 (m, 2H), 3.75 (d, J=8.4 Hz, 1H), 3.72-3.68 (m, 1H), 2.87 (s, 1H), 2.53 (s, 1H), 2.02 (s, 1H), 1.59 (s, 3H), 1.36 (s, 3H), 1.33 (s, 3H).

Step 4: To a flask containing a solution of crude (S)-1-((3aR,5R,6R,6aR)-6-hydroxy-2,2,6-trimethyltetrahydrofuro[2,3-d][1,3]dioxol-5-yl)ethane-1,2-diol (1.24 g, 5.30 mmol) in toluene (100 mL) was sequentially added imidazole (1.44 g, 21.2 mmol) and triphenylphosphine (5.56 g, 21.2 mmol). The flask was cooled to 0° C., and then iodine (4.04 g, 15.9 mmol) was added. The ice bath was allowed to naturally expire, and the solution was then stirred at room temperature under an atmosphere of argon for four days. The reaction was poured into a separatory funnel containing 1M NaOH and extracted with EtOAc. The organic layers were combined and washed with brine, dried over magnesium sulfate, filtered, and concentrated under reduced pressure. The residue was purified by column chromatography on silica (0-10-20-30% EtOAc/hexanes) to afford (3aR,5R,6R,6aR)-2,2,6-trimethyl-5-vinyltetrahydrofuro[2,3-d][1,3]dioxol-6-ol as a solid. $^1$H-NMR (600 MHz, CDCl$_3$) δ 5.84-5.76 (2H), 5.40 (dt, J=17.3, 1.5 Hz, 1H), 5.29 (dt, J=10.7, 1.4 Hz, 1H), 4.21 (d, J=5.9 Hz, 1H), 4.17 (d, J=3.9 Hz, 1H), 2.63 (s, 1H), 1.59 (s, 3H), 1.37 (s, 3H), 1.12 (s, 3H).

Step 5: A vial charged with (3aR,5R,6R,6aR)-2,2,6-trimethyl-5-vinyltetrahydrofuro[2,3-d][1,3]dioxol-6-ol (200 mg, 0.999 mmol) and 9-BBN (0.5M in THF, 6 mL, 3.00 mmol) was stirred at 50° C. for 2 h under an atmosphere of argon. The reaction was cooled to room temperature, and tripotassium phosphate (2M in water, 2.5 mL, 5.00 mmol) was added. The mixture was stirred vigorously at room temperature for 30 minutes, and then a solution of 3-bromo-7-iodo-N-(4-methoxybenzyl)quinolin-2-amine (609 mg, 1.298 mmol) and 1,1'-bis(diphenylphosphino)ferrocene-palladium (II)dichloride dichloromethane complex (82 mg. 0.100 mmol) in THF (3 mL) was added. The vial headspace was purged with argon, and the reaction was stirred at 50° C. overnight. The reaction was then diluted with DCM and water and passed through a phase separator. The organic layers were combined and concentrated under reduced pressure. The residue was purified by column chromatography on silica (0-60% EtOAc/hexanes) to afford (3aR,5R,6R,6aR)-5-(2-(3-bromo-2-((4-methoxybenzyl)amino)quinolin-7-yl)ethyl)-2,2,6-trimethyltetrahydrofuro[2,3-d][1,3]dioxol-6-ol as a solid. MS: 543/545 (M+1/M+3).

Step 6: To a vial containing (3aR,5R,6R,6aR)-5-(2-(3-bromo-2-((4-methoxybenzyl)amino)quinolin-7-yl)ethyl)-2,2,6-trimethyltetrahydrofuro[2,3-d][1,3]dioxol-6-ol (353.2 mg, 0.650 mmol) was added water (5 mL), followed by neat formic acid (5 mL, 130 mmol). The resulting solution was heated at 50° C. overnight. The reaction was cooled to room temperature, and then poured into a separatory funnel containing water and extracted with 25% isopropanol/chloroform. The organic layers were combined and dried over sodium sulfate, filtered, and concentrated under reduced pressure to afford (2S,3R,4S,5R)-5-(2-(3-bromo-2-((4-methoxybenzyl)amino)quinolin-7-yl)ethyl)-4-methyltetrahydrofuran-2,3,4-triol as a solid, which was used in the next step without further purification. MS: 503/505 (M+1/M+3).

Step 7: In a vial, 4-chloro-7H-pyrrolo[2,3-d]pyrimidine (405 mg, 2.64 mmol) was dissolved in DMF (8 mL). Then, sodium hydride (106 mg, 2.64 mmol) was added. The mixture was stirred at room temperature under an atmosphere of argon for 75 minutes. Concurrently, to another vial was added al solution of crude (3R,4S,5R)-5-(2-(3-bromo-2-((4-methoxybenzyl)amino)quinolin-7-yl)ethyl)-4-methyltetrahydrofuran-2,3,4-triol (532 mg, 1.06 mmol) in acetonitrile (18 mL). Then, tri-n-butylphosphine (0.45 mL, 1.80 mmol) was added, followed by 1,1'-(azodicarbonyl)dipiperidine (400 mg, 1.58 mmol). The reaction was stirred at room temperature for 25 minutes before additional 1,1'-(azodicarbonyl)dipiperidine (130 mg) was added. 20 minutes later, more tri-n-butylphosphine (0.5 mL) was added. This mixture was stirred at room temperature for another 15 min. Then, the solution containing 4-chloro-7H-pyrrolo[2,3-d]pyrimidine and sodium hydride was taken up by syringe and added to the solution initially containing (3R,4S,5R)-5-(2-(3-bromo-2-((4-methoxybenzil)amino)quinolin-7-yl) ethyl)-4-methyltetrahydrofuran-2,3,4-triol. This combined reaction was stirred at room temperature under an atmosphere of argon overnight. The reaction was then poured into a separatory funnel containing water and extracted with EtOAc. The organic layers were combined, washed with water twice and then brine, dried over magnesium sulfate, filtered, and concentrated under reduced pressure. The residue was purified by column chromatography on silica (20-90% EtOAc/hexanes) to afford (2R,3S,4R,5R)-2-(2-(3-bromo-2-((4-methoxybenzyl)amino)quinolin-7-yl)ethyl)-5-(4-chloro-7H-pyrrolo[2,3-d]pyrimidin-7-yl)-3-methyltetrahydrofuran-3,4-diol as a solid, which was used directly in the next step. MS: 638/640 (M+1/M+3).

Step 8: To a vial was added a solution of (2R,3S,4R,5R)-2-(2-(3-bromo-2-((4-methoxybenzyl)amino)quinolin-7-yl)ethyl)-5-(4-chloro-7H-pyrrolo[2,3-d]pyrimidin-7-yl)-3-methyltetrahydrofuran-3,4-diol (114 mg, 0.178 mmol) in ammonia (7 M in MeOH, 10 mL, 70.0 mmol) and dioxane (2 mL). This solution was heated at 130° C. for 4 h in a microwave reactor. The entire solution was then concentrated under reduced pressure to afford (2R,3S,4R,5R)-5-(4-amino-7H-pyrrolo[2,3-d]pyrimidin-7-yl)-2-(2-(3-bromo-2-((4-methoxybenzyl)amino)quinolin-7-yl)ethyl)-3-methyltetrahydrofuran-3,4-diol, which was used in the next step without further purification. MS: 619/621 (M+1/M+3).

Step 9: To a flask containing crude (2R,3S,4R,5R)-5-(4-amino-7H-pyrrolo[2,3-d]pyrimidin-7-yl)-2-(2-(3-bromo-2-((4-methoxybenzyl)amino)quinolin-7-yl)ethyl)-3-methyltetrahydrofuran-3,4-diol (110 mg, 0.178 mmol) was added DCM (9 mL). Then, trifluoroacetic acid (1 mL, 12.98 mmol) was added, and the reaction was stirred at room temperature overnight. TFA (5 mL) was added, and the reaction was stirred at room temperature for another 1 h. TFA (2 mL) was added, and the reaction was refluxed for 7 h. The reaction was cooled to room temperature, concentrated under reduced pressure. The residue was purified by mass-triggered reverse phase HPLC (ACN/water with 0.1% TFA modifier) to afford (2R,3S,4R,5R)-2-(2-(2-amino-3-bromo-quinolin-7-yl)ethyl)-5-(4-amino-7H-pyrrolo[2,3-d]pyrimidin-7-yl)-3-methyltetrahydrofuran-3,4-diol as a solid TFA salt. MS: 499/501 (M+1/M+3). $^1$H-NMR (600 MHz, DMSO-d$_6$) δ 8.64 (s, 1H), 8.39 (s, 1H), 7.74 (d, J=3.7 Hz, 1H), 7.71 (d, J=8.2 Hz, 1H), 7.39 (s, 1H), 7.25 (d, J=8.0 Hz, 1H), 7.00 (d, J=3.7 Hz, 1H), 6.10 (d, J=7.7 Hz, 1H), 4.31 (d, J=7.7 Hz, 1H), 3.81 (dd, J=11.4, 2.9 Hz, 1H), 2.81 (ddd, J=13.8, 9.2, 4.7 Hz, 1H), 2.67 (dt J=13.8, 8.1 Hz 1H), 2.07-1.99 (m, 1H), 1.88-1.81 (m, 1H), 1.20 (s, 3H).

Example 15

(1S,2R,3S,5R)-3-[2-(2-amino-3-bromo-7-quinolinyl) ethyl]-5-(4-amino-7H-pyrrolo[2,3-d]pyrimidin-7-yl)-3-methyl-1,2-cyclopentanediol

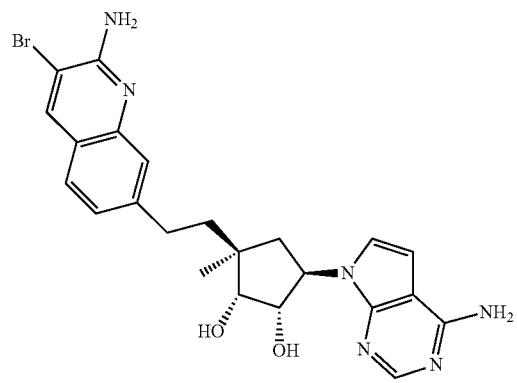 [SMILES: C[C@]1(CCc2ccc3cc(Br)c(N)nc3c2)C[C@@H](n2ccc3c(N)ncnc32)[C@H](O)[C@@H]1O]

Step 1: To a stirred solution of (3a'R,4'R,6'S,6a'S)-4'-methyl-4'-vinyltetrahydro-4'H-spiro[cyclohexane-1,2'-cyclopenta[d][1,3]dioxol]-6'-ol (3.8 g, 16 mmol) in DCM (80 mL) was added pyridine (6.45 mL, 80 mmol). The mixture was cooled to 0° C. and treated with trifluoromethanesulfonic anhydride in DCM (23.92 mL, 23.92 mmol) over 10 min. The mixture was stirred at 0° C. for 30 minutes and treated with water (5 mL). The organic layers were separated and washed with brine. The organic layers were combined, dried over sodium sulfate and concentrated under reduced pressure. Toluene (10 mL) was added to the residue and concentrated to afford (3a'R,4'S,6'R,6a'R)-6'-methyl-6'-vinyltetrahydro-3a'H-spiro[cyclohexane-1,2'-cyclopenta[d][1,3]dioxol]-4'-yl trifluoromethanesulfonate as an oil. The residue was used in the next step without further purification.

Step 2: To a stirred solution of 4-chloro-7H-pyrrolo[2,3-d]pyrimidine (2.94 g, 19.1 mmol) in DMF (35 mL) at 0° C. was added sodium hydride (0.893 g, 22.3 mmol). The mixture was stirred at that temperature for 30 minutes. In a separate flask, (3a'R,4'S,6'R,6a'R)-6'-methyl-6'-vinyltetrahydro-3a'H-spiro[cyclohexane-1,2'-cyclopenta[d][1,3]dioxol]-4'-yl trifluoromethanesulfonate (5.90 g, 15.9 mol) was dissolved in DMF (10 mL). The solution was added to the solution of the sodium salt slowly over 10 minutes. The resultant mixture was warmed to room temperature and stirred overnight. The mixture was cooled to 0° C. and treated with water. The mixture was diluted with EtOAc (500 mL) and washed with water (3×) and brine. The organic layer was dried over sodium sulfate, concentrated, and purified by column chromatography on silica (0-20%

EtOAc/DCM) to afford 4-chloro-7-((3a'R,4'R,6'R,6a'S)-4'-methyl-4'-vinyltetrahydro-4'H-spiro[cyclohexane-1,2'-cyclopenta[d][1,3]dioxol]-6'-yl)-7H-pyrrolo[2,3-d]pyrimidine. MS: 374 (MI). $^1$H-NMR (500 MHz, DMSO-d$_6$) δ 8.66 (s, 1H), 8.03 (d, J=3.2 Hz, 1H), 6.73 (d, J=3.2 Hz, 1H), 6.00 (dd, J=17.4, 10.7 Hz, 1H), 5.32-5.26 (m, 1H), 5.10-4.99 (m, 3H), 4.63 (d, J=7.5 Hz, 1H), 2.46 (m, 1H), 2.08 (dd, J=127, 7.2 Hz, 1H), 1.75-1.71 (m, 2H), 1.63-1.28 (m, 8H), 1.17 (s, 3H).

Step 3: To a stirred solution of 4-chloro-7-((3a'R,4'R,6'R,6a'S)-4'-methyl-4'-vinyltetrahydro-4'H-spiro[cyclohexane-1,2'-cyclopenta[d][1,3]dioxol]-6'-yl)-7H-pyrrolo[2,3-d]pyrimidine (910 mg, 2.43 mmol) in 1,4-dioxane (4 mL) was added ammonium hydroxide (28%, 4 mL) in a microwave vial. The reaction was heated to 160° C. for 5 h in a microwave reactor. The mixture was cooled to room temperature and diluted with EtOAc and water. The aqueous layer was extracted with EtOAc. The organic layers were combined and washed with brine, dried over sodium sulfate, and concentrated under reduced pressure to afford 7-((3a'R,4'R,6'R,6a'S)-4'-methyl-4'-vinyltetrahydro-4'H-spiro[cyclohexane-1,2'-cyclopenta[d][1,3]dioxol]-6'-yl)-7H-pyrrolo[2,3-d]pyrimidin-4-imine. The crude product was used in the next step without further purification. MS: 355 (M+1). $^1$H NMR (500 MHz, DMSO-d$_6$) δ 8.06 (s, 1H), 7.37 (d, J=2.8 Hz, 1H), 6.99 (s, 2H), 6.57 (d, J=2.8 Hz, 1H), 5.98 (dd, J=17.4, 10.7 Hz, 1H), 5.18-4.93 (m, 4H), 4.59 (d, J=7.6 Hz, 1H), 2.37 (dd, J=12.3 Hz, 1H), 2.00-1.95 (m, 1H), 1.74-1.28 (m, 10H), 1.14 (s, 3H).

Step 4: To 7-((3a'R,4'R,6'R,6a'S)-4'-methyl-4'-vinyltetrahydro-4'H-spiro[cyclohexane-1,2'-cyclopenta[d][1,3]dioxol]-6'-yl)-7H-pyrrolo[2,3-d]pyrimidin-4-amine (300 mg, 0.846 mmol) was added 9-BBN (0.5 M in THF, 6.77 mL, 3.39 mmol). The mixture was heated to 50° C. for 1 h, cooled to room temperature, treated with potassium phosphate tribasic (898 mg, 4.23 mmol) and water (0.9 mL), and left to stir for 30 minutes. The mixture was treated with THF (1 mL), 3-bromo-7-iodoquinolin-2-amine (266 mg, 0.762 mol), and PdCl$_2$(dppf) (61.9 mg, 0.085 mmol), purged with nitrogen for 5 minutes, and heated to 50° C. for 3 h. The mixture was cooled to room temperature, diluted with EtOAc, and washed with water and brine. The organic layers were combined and dried over sodium sulfate, concentrated, and purified by column chromatography on silica (0-10% MeOH/DCM) to afford 7-(2-((3a'S,4'R,6'S,6a'R)-4'-(4-imino-7H-pyrrolo[2,3-d]pyrimidin-7-yl)-6'-methyltetrahydro-4'H-spiro[cyclohexane-1,2'-cyclopenta[d][1,3]dioxol]-6'-yl)ethyl)-3-bromoquinolin-2-anine as a solid. MS: 577/579 (M+1/M+3). $^1$H-NMR (500 MHz, DMSO-d$_6$) δ 8.32 (s, 1H), 8.06 (s, 1H), 7.57 (d, J=8.1 Hz, 1H), 7.38 (s, 1H), 7.32 (s, 1H), 7.12 (d, J=8.1 Hz, 1H), 6.99 (s, 2H), 6.57 (s, 3H), 5.14-5.07 (m, 1H), 4.98-4.94 (m, 1H), 4.52 (d, J=7.5 Hz, 1H), 2.75-2.65 (m, 2H), 2.20 (dd J=12.4 Hz, 1H), 2.05-2.00 (m, 1H), 1.78-1.28 (m, 12H), 1.14 (s, 3H).

Step 5: To 7-(2-((3a'S,4'R,6'S,6a'R)-4'-(4-amino-7H-pyrrolo[2,3-d]pyrimidin-7-yl)-6'-methyltetrahydro-4'H-spiro[cyclohexane-1,2'-cyclopenta[d][1,3]dioxol]-6'-yl)ethyl)-3-bromoquinolin-2-amine (320 mg, 0.399 mmol) was added HCl (4M in MeOH, 10 mL). The mixture was stirred overnight, and then heated at 50° C. for 5 h. The reaction mixture was cooled to room temperature, concentrated under reduced pressure, and purified by reverse phase column chromatography (ACN/water with 0.1% TFA modifier) to afford (1S,2R,3S,5R)-3-[2-(2-amino-3-bromo-7-quinolinyl)ethyl]-5-(4-amino-7H-pyrrolo[2,3-d]pyrimidin-7-yl)-3-methyl-1,2-cyclopentanediol as the TFA salt. MS: 497/499 (M+1/M+3). $^1$H NMR (500 MHz, DMSO-d$_6$) δ 9.17 (brs, 1H), 8.72 (s, 1H), 8.65 (br s, 1H), 8.37 (s, 1H), 8.27 (brs, 2H), 7.76 (d, J=8.1 Hz, 1H), 7.70 (d, J=3.2 Hz, 1H), 7.46 (s, 1H), 7.34 (d, J=8.1 Hz, 1H), 6.94 (d, J=3.1 Hz, 1H), 5.00 (dd J=8.8 Hz, 1H), 4.89 (brs, 2H), 4.39-4.34 (m, 1H), 3.79 (d, J=5.9 Hz, 1H), 2.85-2.68 (m, 2H), 1.96-1.70 (m, 4H), 1.12 (s, 3H).

Example 16

(1S,2R,3aR,4S,6aR)-4-((2-amino-fluoroquinolin-7-yl)methyl)-2-(4-methyl-7H-pyrrolo[2,3-d]pyrimidin-7-yl)hexahydropentalene-1,6a(1H)-diol

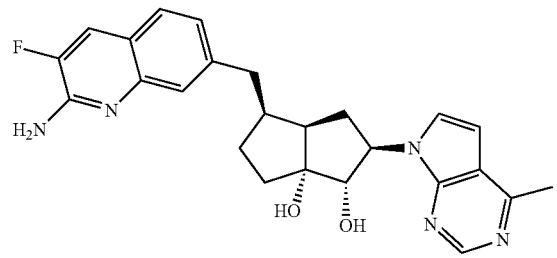 [SMILES: Cc1ncnc2c1ccn2[C@@H]1C[C@@H]2[C@H](Cc3ccc4cc(F)c(N)nc4c3)CC[C@]2(O)[C@H]1O]

Step 1: To a flask containing (3aS,4R,5aR,6S,8aR)-2,2-dimethyl-4-(4-methyl-7H-pyrrolo[2,3-d]pyrimidin-7-yl)hexahydro-5H-pentaleno[1,6a-d][1,3]dioxol-6-ol (6.0 g, 18 mmol) was added DCM (200 mL), followed by Dess-Martin Periodinane (10.25 g, 23.68 mmol). The reaction was stirred at room temperature overnight. The reaction was quenched with 1:1 saturated aqueous sodium bicarbonate:saturated aqueous sodium thiosulfate (160 ml) with vigorous stirring. The organic layer was separated by Phase Separator and concentrated under reduced pressure. The crude (3aS,4R,5aS,8aR)-2,2-dimethyl-4-(4-methyl-7H-pyrrolo[2,3-d]pyrimidin-7-yl)hexahydro-6H-pentaleno[1,6a-d][1,3]dioxol-6-one was used directly in the next reaction.

Step 2: To a flask was added methyltriphenylphosphonium bromide (21.91 g, 60.1 mmol), followed by THF (100 mL) under an atmosphere of argon. The mixture was cooled to 0° C., and then nBuLi (22 mL, 2.5M, 55 mmol) was added. The reaction was brought out of the cold bath and allowed to vigorously stir at room temperature under argon for 30 minutes. Then, the reaction was cooled back down to 0° C., and a solution of (3aS,4R,5aS,8aR)-2,2-dimethyl-4-(4-methyl-7H-pyrrolo[2,3-d]pyrimidin-7-yl)hexahydro-6H-pentaleno[1,6a-d][1,3]dioxol-6-one (5.96 g, 18.2 mmol) in THF (100 mL) was added. After addition, the reaction was brought out of the cold bath and allowed to stir at room temperature for 70 min. The reaction was poured into a separatory funnel containing EtOAc and saturated ammonium chloride. The aqueous layer was separated and washed twice with EtOAc. The organic layers were combined, dried over magnesium sulfate, filtered over Celite®, and concentrated under reduced pressure. The crude material was subjected to column chromatography on silica (10-100% EtOAc/hexanes) to afford 7-((3aS,4R,5aR,8aR)-2,2-dimethyl-6-methylenehexahydro-5H-pentaleno[1,6a-d][1,3]dioxol-4-yl)-4-methyl-7H-pyrrolo[2,3-d]pyrimidine. MS: 326 (M+1). $^1$H NMR (600 MHz, CDCl$_3$) δ 8.76 (s, 1H), 7.24 (d, J=3.4 Hz, 1H), 6.55 (d, J=3.4 Hz, 1H), 5.16-5.10 (m, 1H), 5.00-4.97 (m, 1H), 4.87 (s, 1H), 4.80 (d, J=5.3 Hz, 1H), 3.08 (1, J=9.1 Hz, 1H), 2.73 (s, 3H), 2.71-2.61 (m, 2H), 2.58-2.51 (m, 1H), 2.32-2.24 (m, 2H), 2.15-2.08 (m, 1H), 1.58 (s, 3H), 1.36 (s, 3H).

Step 3: To a flask containing 7-((3aS,4R,5aR,8aR)-2,2-dimethyl-6-methylenehexahydro-5H-pentaleno[1,6a-d][1,3]dioxol-4-yl)-4-methyl-7H-pyrrolo[2,3-d]pyrimidine (1.22 g, 3.7 mmol) was added THF (20 ml). Then, 9-BBN (23.0 mL, 0.5M in THF 11.5 mmol) solution was added under an atmosphere of argon. The reaction was then stirred at room temperature under argon for overnight. Then, tripotassium phosphate (9.5 mL, 2M in water, 19 mmol) was added, and the reaction was stirred at room temperature for 30 minutes. Then, a solution of 7-bromo-3-fluoroquinolin-2-amine (1.345 g, 5.60 mmol) and methanesulfonato(2-dicyclohexylphosphino-2',6'-diisopropoxy-1,1'-biphenyl)(2'-methylamino-1,1'-biphenyl-2-yl)palladium(II) (0.312 g, 0.373 mmol) in THF (10 mL) was added, and the reaction was heated to 50° C. for 2 h. The reaction was cooled to room temperature, and then concentrated under reduced pressure. The crude material was purified by column chromatography on silica (80-100% EtOAc, hexanes to 100% 3:1 EtOAc:EtOH) followed by chiral SFC (OJ-H column, 30% MeOH w/0.1% NH$_4$OH in CO$_2$) to afford 7-(((3aS,4R,5aR,6S,8aR)-2,2-dimethyl-4-(4-methyl-7H-pyrrolo[2,3-d]pyrimidin-7-yl)hexahydro-5H-pentaleno[1,6a-d][1,3]dioxol-6-yl)methyl)-3-fluoroquinolin-2-amine. MS: 488 (M+1).

Step 4: To a flask containing 7-(((3aS,4R,5aR,6S,8aR)-2,2-dimethyl-4-(4-methyl-7H-pyrrolo[2,3-d]pyrimidin-7-yl)hexahydro-5H-pentaleno[1,6a-d][1,3]dioxol-6-yl)methyl)-3-fluoroquinolin-2-amine (2.03 g, 4.17 mmol) were added DCM (50 mL), water (16 mL), and trifluoroacetic acid (40 mL, 520 mmol). The reaction was stirred at room temperature overnight. The reaction was then concentrated under reduced pressure and purified by mass-triggered reverse phase HPLC (ACN/water with 0.1% NH$_4$OH modifier) to afford (1S,2R,3aR,4S,6aR)-4-((2-amino-3-fluoroquinolin-7-yl)methyl)-2-(4-methyl-7H-pyrrolo[2,3-d]pyrimidin-7-yl)hexahydropentalene-1,6a(1H)-diol. MS: 448 (M+1). $^1$H NMR (600 MHz, DMSO) δ 8.60 (s, 1H), 7.82 (d, J=3.6 Hz, 1H), 7.75 (d, J=11.8 Hz, 1H), 7.55 (d, J=8.2 Hz, 1H), 7.29 (s, 1H), 7.10 (d, J=8.6 Hz, 1H), 6.71 (d, J=3.6 Hz, 1H), 6.67 (s, 2H), 4.84-4.74 (m, 2H), 4.67 (s, 1H), 3.95 (dd, J=10.2, 7.4 Hz, 1H), 2.76-2.66 (m, 2H), 2.65 (s, 3H), 2.49-2.42 (m, 1H), 2.18 (q, J=9.4 Hz, 1H) 1.88-1.78 (m, 3H), 1.71-1.64 (m, 1H), 1.64-1.55 (m, 1H), 1.49-1.43 (m, 1H).

Examples 17-18: Examples 17-18 in Table 7 were synthesized in an analogous fashion as described in example 16 by substituting 7-bromo-3-fluoroquinolin-2-amine with an appropriate aryl-halide in step 3. The substituted reagents and starting material were commercially acquired, synthesized as reported above, or synthesized through known routes reported in the literature.

TABLE 7

| Ex | Structure | Name | MS |
|---|---|---|---|
| 17 | 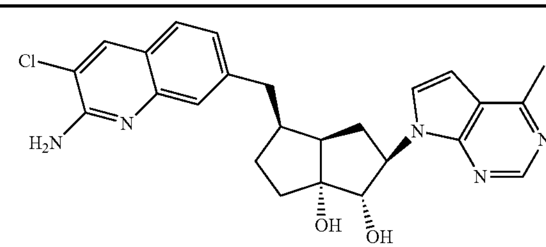 | (1S,2R,3aR,4S,6aR)-4-((2-amino-3-chloroquinolin-7-yl)methyl)-2-(4-methyl-7H-pyrrolo[2,3-d]pyrimidin-7-yl)hexahydropentalene-1,6a(1H)-diol | 464 (M + 1) |
| 18 | 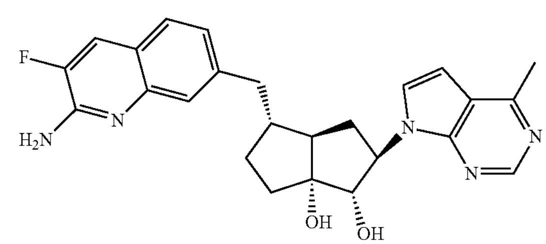 [SMILES: Cc1ncnc2c1ccn2[C@@H]1C[C@@H]2[C@@H](Cc3ccc4cc(F)c(N)nc4c3)CC[C@]2(O)[C@H]1O] | (1S,2R,3aR,4R,6aR)-4-((2-amino-3-fluoroquinolin-7-yl)methyl)-2-(4-methyl-7H-pyrrolo[2,3-d]pyrimidin-7-yl)hexahydropentalene-1,6a(1H)-diol | 448 (M + 1) |

Examples 19: Example 19 in Table 8 was synthesized in an analogous fashion as described in example 16 by substituting step 3 with step 1 in example 25, and substituting 7-bromo-3,5-difluoroquinolin-2-amine with an appropriate aryl-halide. The substituted reagents and starting material were commercially acquired, synthesized as reported above, or synthesized through known routes reported in the literature.

TABLE 8

| Ex | Structure | Name | MS |
|----|-----------|------|-----|
| 19 | 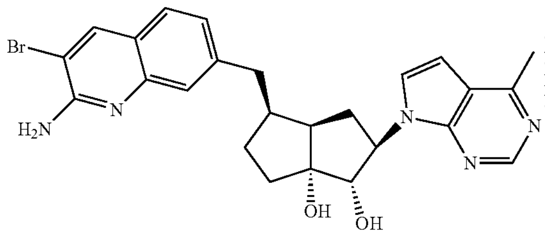 | (1S,2R,3aR,4S,6aR)-4-((2-amino-3-bromoquinolin-7-yl)methyl)-2-(4-methyl-7H-pyrrolo[2,3-d]pyrimidin-7-yl)hexahydropentalene-1,6a(1H)-diol | 508/510 (M + 1/M + 3) |

Examples 20-24: Examples 20-24 in Table 9 were synthesized in an analogous fashion as described in steps 3-4 of Example 16 by substituting the 7-((3aS,4R,5aR,8aR)-2,2-dimethyl-6-methylenehexahydro-5H-pentaleno[1,6a-d][1,3]dioxol-4-yl)-4-methyl-7H-pyrrolo[2,3-d]pyrimidine with an appropriate exo-olefin and 7-bromo-3-fluoroquinolin-2-amine with an appropriate aryl-halide and followed by chiral resolution by SFC if needed based on the substituted exo-olefin. The substituted reagents and starting material were commercially acquired, synthesized as reported above, or synthesized through known routes reported in the literature.

TABLE 9

| Ex | Structure | Name | MS |
|----|-----------|------|-----|
| 20 | 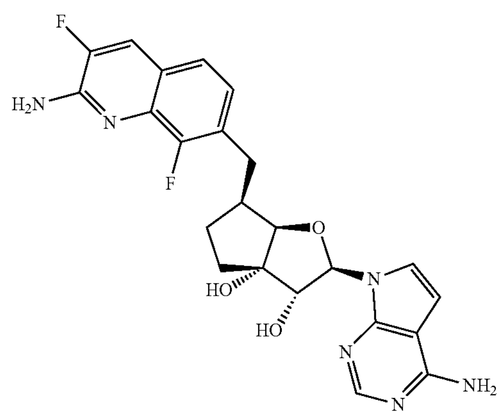 [SMILES: Nc1nc2c(F)c(C[C@@H]3CC[C@@]4(O)[C@@H]3O[C@@H](n3ccc5c(N)ncnc53)[C@@H]4O)ccc2cc1F] | (2R,3R,3aS,6S,6aR)-6-[(2-amino-3,8-difluoroquinolin-7-yl)methyl]-2-(4-amino-7H-pyrrolo[2,3-d]pyrimidin-7-yl)hexahydro-3aH-cyclopenta[b]furan-3,3a-diol | 469 (M + 1) |
| 21 | 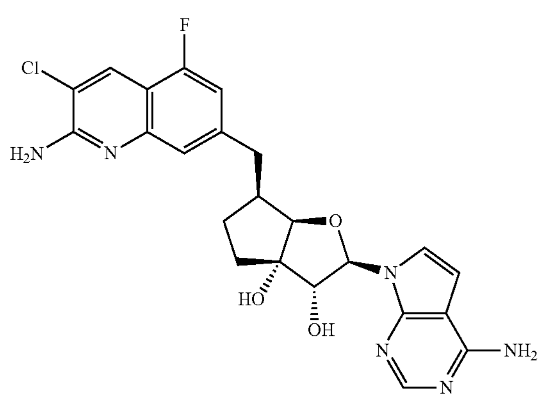 [SMILES: Nc1nc2cc(C[C@@H]3CC[C@@]4(O)[C@@H]3O[C@@H](n3ccc5c(N)ncnc53)[C@@H]4O)cc(F)c2cc1Cl] | (2R,3R,3aS,6S,6aR)-6-[(2-amino-3-chloro-5-fluoroquinolin-7-yl)methyl]-2-(4-amino-7H-pyrrolo[2,3-d]pyrimidin-7-yl)hexahydro-3aH-cyclopenta[b]furan-3,3a-diol | 485 (M + 1) |

TABLE 9-continued

| Ex | Structure | Name | MS |
|---|---|---|---|
| 22 | 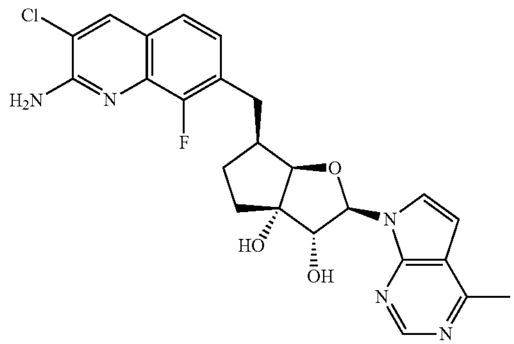 [SMILES: Cc1ncnc2c1ccn2[C@@H]1O[C@@H]2[C@H](Cc3ccc4cc(Cl)c(N)nc4c3F)CC[C@]2(O)[C@H]1O] | (2R,3R,3aS,6S,6aR)-6-[(2-amino-3-chloro-8-fluoroquinolin-7-yl)methyl]-2-(4-methyl-7H-pyrrolo[2,3-d]pyrimidin-7-yl)hexahydro-3aH-cyclopenta[b]furan-3,3a-diol | 484 (M + 1) |
| 23 | 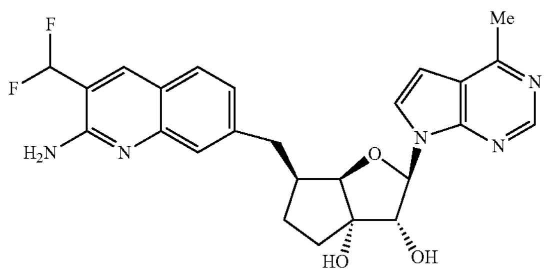 [SMILES: Cc1ncnc2c1ccn2[C@@H]1O[C@@H]2[C@H](Cc3ccc4cc(C(F)F)c(N)nc4c3)CC[C@]2(O)[C@H]1O] | (2R,3R,3aS,6S,6aR)-6-((2-amino-3-(difluoromethyl)quinolin-7-yl)methyl)-2-(4-methyl-7H-pyrrolo[2,3-d]pyrimidin-7-yl)hexahydro-3aH-cyclopenta[b]furan-3,3a-diol | 482 (M + 1) |
| 24 | 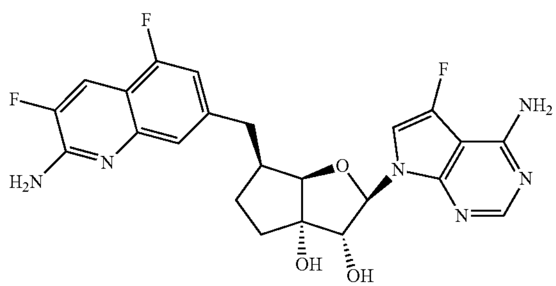 [SMILES: Nc1nc2cc(C[C@@H]3CC[C@@]4(O)[C@@H]3O[C@@H](n3cc(F)c5c(N)ncnc53)[C@@H]4O)cc(F)c2cc1F] | (2R,3R,3aS,6S,6aR)-6-((2-amino-3,5-difluoroquinolin-7-yl)methyl)-2-(4-amino-5-fluoro-7H-pyrrolo[2,3-d]pyrimidin-7-yl)hexahydro-3aH-cyclopenta[b]furan-3,3a-diol | 487 (M + 1) |

Example 25

(2R,3R,3aS,6S,6aR)-6-(((6-amino-7-fluoro-1,5-naphthyridin-3-yl)methyl)-2-(4-methyl-7H-pyrrolo[2,3-d]pyrimidin-7-yl)hexahydro-3aH-cyclopenta[b]furan-3,3a-diol, 3HCl

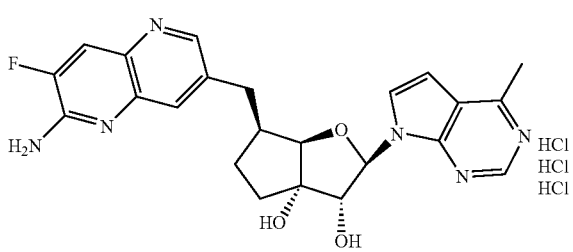 [SMILES: Cc1ncnc2c1ccn2[C@@H]1O[C@@H]2[C@H](Cc3cnc4cc(F)c(N)nc4c3)CC[C@]2(O)[C@H]1O]

Step 1: To a vial containing 7-((3aR,4R,5aR,8aR)-2,2-dimethyl-6-methylenehexahydrocyclopenta[2,3]furo[3,4-d][1,3]dioxol-4-yl)-4-methyl-7H-pyrrolo[2,3-d]pyrimidine (0.070 g, 0.214 mmol) was added THF (2.047 mL), followed by 9-BBN (0.5 M in THF, 1.37 mL, 0.684 mmol). The reaction was stirred at room temperature, under an argon atmosphere, overnight. Then, aqueous tripotassium phosphate (1 M, 1.155 mL, 1.155 mmol) was added, and the reaction was vigorously stirred at room temperature for 1 h. Then, a solution of 7-bromo-3-fluoro-1,5-naphthyridin-2-amine (0.078 g, 0.321 mmol) and [1,1'-bis(diphenylphosphino)ferrocene]dichloropalladium(II) (0.016 g, 0.021 mmol) in THF (1.01 mL) was added, and the reaction was heated to 50° C. for 2 h. The reaction was cooled to room temperature and poured into a separatory funnel containing water and EtOAc. After extraction, the aqueous layer was washed with EtOAc (×2). The organic layers were combined, dried over Na₂SO₄, filtered, and concentrated under reduced pressure. The material was purified by mass triggered reverse phase HPLC (ACN/water with 0.1% TFA for the modifier) to afford 7-(((3aR,4R,5aR,6S,8aR)-2,2-dimethyl-4-(4-methyl-7H-pyrrolo[2,3-d]pyrimidin-7-yl)hexahydrocyclopenta[2,3]furo[3,4-d][1,3]dioxol-6-yl)methyl)-3-fluoro-1,5-naphthyridin-2-amine as the TFA salt. MS: 491 (M+1).

Step 2: To a solution of 7-(((3aR,4R,5aR,6S,8aR)-2,2-dimethyl-4-(4-methyl-7H-pyrrolo[2,3-d]pyrimidin-7-yl)hexahydrocyclopenta[2,3]furo[3,4-d][1,3]dioxol-6-yl)methyl)-3-fluoro-1,5-naphthyridin-2-amine (0.117 g, 0.239 mmol) in MeOH (11.9 mL) was added dropwise hydrochloric acid (2 M, 11.9 mL, 23.9 mmol). The reaction was stirred for 90 minutes at room temperature. The temperature was increased to 40° C. and allowed to stir for 18 h. The reaction was split in two separate vials and concentrated under reduced pressure to afford (2R,3R,3aS,6S,6aR)-6-((6-amino-7-fluoro-1,5-naphthyridin-3-yl)methyl)-2-(4-methyl-7H-pyrrolo[2,3-d]pyrimidin-7-yl)hexahydro-3aH-cyclopenta[b]furan-3,3a-diol, 3HCL. MS: 451 (M+1). $^1$H NMR (499 MHz, DMSO-d$_6$) δ 9.19 (s, 1H), 8.66 (d, J=1.4 Hz, 1H), 8.34 (d, J=3.8 Hz, 1H), 8.20 (d, J=10.8 Hz, 1H), 8.10 (s, 1H), 7.32 (d, J=3.8 Hz, 1H), 6.12 (d, J=8.2 Hz, 1H), 4.21 (d, J=8.2 Hz, 1H), 4.10 (d, J=5.9 Hz, 1H), 3.02-2.91 (m, 3H), 2.87-2.80 (m, 1H), 2.45-2.35 (m, 1H), 2.05-1.95 (m, 1H), 1.89-1.79 (m, 1H), 1.78-1.70 (m, 1H), 1.62-1.52 (m, 1H).

Examples 26-29: Examples 26-29 in Table 10 were synthesized in an analogous fashion as described in steps 1-2 of Example 25 by substituting the 7-((3aS,4R,5aR,8aR)-2,2-dimethyl-6-methylenehexahydro-5H-pentaleno[1,6a-d][1,3]dioxol-4-yl)-4-methyl-7H-pyrrolo[2,3-d]pyrimidine with an appropriate exo-olefin and 7-bromo-3-fluoroquinolin-2-amine with an appropriate aryl-halide and followed by chiral resolution by SFC if needed based on the substituted exo-olefin. The substituted reagents and starting material were commercially acquired, synthesized as reported above, or synthesized through known routes reported in the literature.

TABLE 10

| Ex | Structure | Name | MS |
|---|---|---|---|
| 26 | 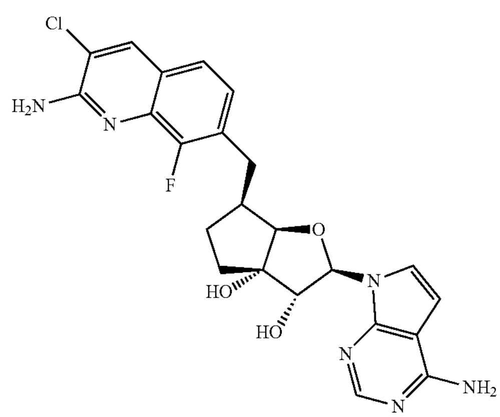 [SMILES: Nc1nc2c(F)c(C[C@@H]3CC[C@@]4(O)[C@@H]3O[C@@H](n3ccc5c(N)ncnc53)[C@@H]4O)ccc2cc1Cl] | (2R,3R,3aS,6S,6aR)-6-((2-amino-3-chloro-8-fluoroquinolin-7-yl)methyl)-2-(4-amino-7H-pyrrolo[2,3-d]pyrimidin-7-yl)hexahydro-3aH-cyclopenta[b]furan-3,3a-diol | 485 (M + 1) |
| 27 | 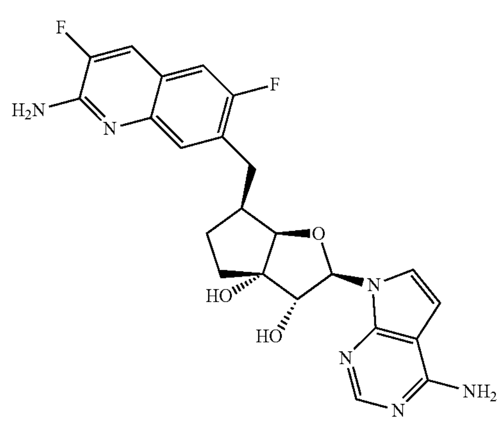 [SMILES: Nc1nc2cc(C[C@@H]3CC[C@@]4(O)[C@@H]3O[C@@H](n3ccc5c(N)ncnc53)[C@@H]4O)c(F)cc2cc1F] | (2R,3R,3aS,6S,6aR)-6-(2-amino-3,6-difluoroquinolin-7-yl)methyl]-2-(4-amino-7H-pyrrolo[2,3-d]pyrimidin-7-yl)hexahydro-3aH-cyclopenta[b]furan-3,3a-diol | 469 (M + 1) |

TABLE 10-continued

| Ex | Structure | Name | MS |
|---|---|---|---|
| 28 | 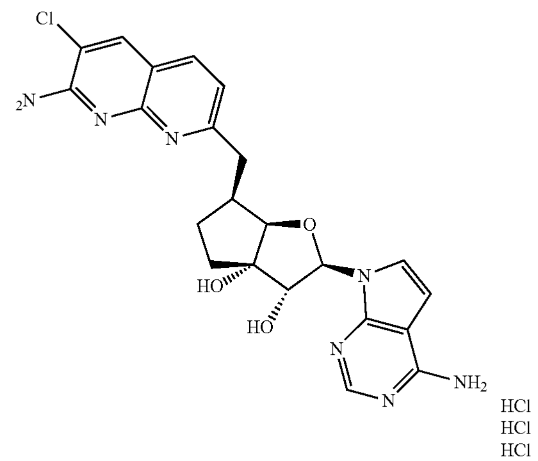 | (2R,3R,3aS,6S,6aR)-6-(7-amino-6-chloro-1,8-naphthyridin-2-yl)methyl)-2-(4-amino-7H-pyrrolo[2,3-d]pyrimidin-7-yl)hexahydro-3aH-cyclopenta[b]furan-3,3a-diol trihydrochloride | 468 (M + 1) |
| 29 | 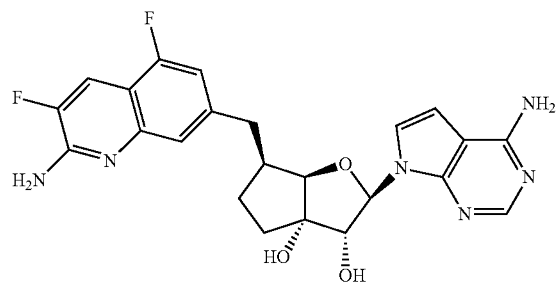 [SMILES: Nc1nc2cc(C[C@@H]3CC[C@@]4(O)[C@@H]3O[C@@H](n3ccc5c(N)ncnc53)[C@@H]4O)cc(F)c2cc1F] | (2R,3R,3aS,6S,6aR)-6-[(2-amino-3,5-difluoroquinolin-7-yl)methyl]-2-(4-amino-7H-pyrrolo[2,3-d]pyrimidin-7-yl)hexahydro-3aH-cyclopenta[b]furan-3,3a-diol | 469 (M + 1) |

Example 30

(1S,2R,3aR,4S,6aR)-4-((2-amino-3-fluoroquinolin-7-yl)methyl-2-(4-methyl-7H-pyrrolo[2,3-d]pyrimidin-7-yl)hexahydropentalene-1,6a(1H)-diol

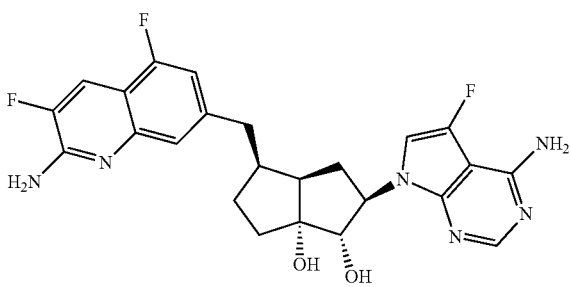 [SMILES: Nc1nc2cc(C[C@@H]3CC[C@@]4(O)[C@@H]3C[C@@H](n3cc(F)c5c(N)ncnc53)[C@@H]4O)cc(F)c2cc1F]

Step 1: To a flask containing 1,1'-bis(diphenylphosphino) ferrocene (1.6 g, 2.8 mmol), sodium tert-butoxide (0.96 g, 8.4 mmol), 4-chloro-5-fluoro-7H-pyrrolo[2,3-d]pyrimidine (1.4 g, 8.4 mmol), and allyl palladium chloride dimer (0.42 g, 1.1 mmol) was added argon-degassed THF (55 mL). This mixture was stirred at room temperature for 15 minutes. Then, a solution of (2R,6S,6aS)-6-((triphenylsilyl)oxy)-1,2,4,5,6,6a-hexahydropentalen-2-yl acetate (2.47 g, 5.61 mmol) in degassed THF (23 mL) was added. The reaction was stirred under an argon atmosphere at 40° C. for 3 ht. The mixture was quenched with water and extracted with EtOAc (2×). The combined organic layers were washed with brine, dried over anhydrous sodium sulfate, filtered, and concentrated under reduced pressure. The residue was purified by column chromatography on silica (0-15% EtOAc/hexanes) to afford 4-chloro-5-fluoro-7-((2R,6S,6aS)-6-((triphenylsilyl)oxy)-1,2,4,5,6,6a-hexahydropentalen-2-yl)-7H-pyrrolo[2,3-d]pyrimidine. MS: 552 (M+1).

Step 2: To a flask containing a solution of 4-chloro-5-fluoro-7-((2R,6S,6aS)-6-((triphenylsilyl)oxy)-1,2,4,5,6,6a-hexahydropentalen-2-yl)-7H-pyrrolo[2,3-d]pyrimidine (1.36 g, 2.46 mmol) in THF (59 mL) was added water (29 mL). The solution was cooled to 0° C., and NMO (0.58 g, 4.9 mmol) and osmium (VIII) oxide (0.75 mL, 4% NO in water, 0.12 mmol) were added. The ice bath was allowed to naturally expire as the reaction was stirred overnight. The reaction was quenched with saturated aqueous sodium sulfite (40 mL), and the mixture was stirred at room temperature for 15 minutes. The reaction was poured into a separatory funnel containing water and EtOAc. After separation, the aqueous layer was washed twice with EtOAc and then once with 3:1 chloroform:IPA. The combined organic layers were dried over anhydrous sodium sulfate, filtered, and concentrated under reduced pressure to afford (1S,2R,3aR,4S,6aR)-2-(4-chloro-5-fluoro-7H-pyrrolo[2,3-d]pyrimidin-7-yl)-4-((triphenylsilyl)oxy)hexahydropentalene-1,6a(1H)-diol. The material was used crude directly in the next step without further purification.

Step 3: To a flask containing (1S,2R,3aR,4S,6aR)-2-(4-chloro-5-fluoro-7H-pyrrolo[2,3-d]pyrimidin-7-yl)-4-((triphenylsilyl)oxy)hexahydropentalene-1,6a(1H)-diol (1.4 g, 2.4 mmol) dissolved in acetone (24 mL) under an argon atmosphere was added sulfuric acid (0.126 mL, 2.36 mmol). The mixture was stirred at room temperature for 4 h. The reaction was then cooled to 0° C. and quenched with sodium hydroxide (0.3 mL, 10 M in water, 3 mmol). The material was diluted with water (20 mL) and extracted with EtOAc (3×), and the combined organic layers were dried over anhydrous sodium sulfate, filtered, and concentrated under reduced pressure. The residue was purified by column chromatography on silica (50% EtOAc/hexanes) to afford (3aS,4R,5aR,6S,8aR)-4-(4-chloro-5-fluoro-7H-pyrrolo[2,3-d]pyrimidin-7-yl)-2,2-dimethylhexahydro-5H-pentaleno[1,6a-d][1,3]dioxol-6-ol. MS: 368 (M+1). $^1$H NMR (600 MHz, CDCl$_3$) δ 8.60 (s, 1H), 7.05 (d, J=2.6 Hz, 1H), 4.91-4.85 (m, 1H), 4.70 (d, J=7.2 Hz, 1H), 4.11-4.08 (m, 1H), 2.59-2.52 (m, 2H), 2.41-2.34 (m, 1H), 2.25-2.19 (m, 1H), 2.13-2.06 (m, 1H), 2.06-1.93 (m, 2H), 1.59 (s, 3H), 1.38 (s, 3H).

Step 4: To a solution of (3aS,4R,5aR,6S,8aR)-4-(4-chloro-5-fluoro-7H-pyrrolo[2,3-d]pyrimidin-7-yl)-2,2-dimethylhexahydro-5H-pentaleno[1,6a-d][1,3]dioxol-6-ol (270 mg, 0.734 mmol) in anhydrous DCM (5 mL) at 0° C. under a nitrogen atmosphere was added Dess-Martin Periodinane (374 mg, 0.881 mmol) in one portion. The mixture was stirred at room temperature overnight. The reaction was quenched with saturated aqueous sodium bicarbonate (10 mL) and 1 g of Na$_2$S$_2$O$_3$. The resulting mixture was stirred for 10 minutes at room temperature. The organic layer was separated, and the aqueous phase was extracted with DCM (10 mL×3). The combined organic layers were washed with brine (10 mL), dried with anhydrous sodium sulfate, filtered, and concentrated under reduced pressure. The residue was purified by column chromatography on silica (0-60% EtOAc/hexanes) to afford (3aS,4R,5aS,8aR)-4-(4-chloro-5-fluoro-7H-pyrrolo[2,3-d]pyrimidin-7-yl)-2,2-dimethylhexahydro-6H-pentaleno[1,6a-d][1,3]dioxol-6-one. MS: 366 (M+1).

Step 5: To a vial was added methyltriphenylphosphonium bromide (781 mg, 2.14 mmol), followed by THF (3.3 mL) under an argon atmosphere. The mixture was cooled to 0° C., and then nBuLi (650 µl, 2.5 M, 1.624 mmol) was added dropwise. The reaction was brought out of the ice bath and allowed to vigorously stir at room temperature for 30 minutes. Then, the reaction was cooled back down to 0° C., and a solution of (3aS,4R,5aS,8aR)-4-(4-chloro-5-fluoro-7H-pyrrolo[2,3-d]pyrimidin-7-yl)-2,2-dimethylhexahydro-6H-pentaleno[1,6a-d][1,3]dioxol-6-one (238 mg, 0.650 mmol) in THF (3.3 mL) was added dropwise. The reaction was brought out of the bath and allowed to stir at room temperature for 70 minutes. The reaction was quenched with saturated aqueous ammonium chloride (10 mL) at 0° C. The mixture was extracted with EtOAc (2×10 mL), and the combined organic layers were washed with brine, dried over anhydrous sodium sulfate, filtered, and concentrated under reduced pressure. The residue was purified by column chromatography on silica (0-50% EtOAc/hexanes) to afford 4-chloro-7-((3aS,4R,5aR,8aR)-2,2-dimethyl-6-methylenehexahydro-5H-pentaleno[1,6a-d][1,3]dioxol-4-yl)-5-fluoro-7H-pyrrolo[2,3-d]pyrimidine. MS: 364 (M+1).

Step 6: To an argon-purged vial containing 4-chloro-7-((3aS,4R,5aR,8aR)-2,2-dimethyl-6-methylenehexahydro-5H-pentaleno[1,6a-d][1,3]dioxol-4-yl)-5-fluoro-7H-pyrrolo[2,3-d]pyrimidine (201.6 mg, 0.554 mmol) was added THF (4 ml). Then, 9-BBN (3.4 ml, 1.700 mmol, 0.5 M in THF) solution was added. The reaction was stirred overnight at room temperature under a balloon of argon. Then, tripotassium phosphate (1.4 ml, 2.80 mmol, 2 M aqueous) was added, and the reaction was vigorously stirred for ~35 min. Then, potassium tert-butoxide (0.1 ml, 0.100 mmol) was added, followed quickly by a solution of chloro[di(i-adamantyl)-N-butylphosphine)-2-(2-aminobiphenyl)]palladium (II) (60 mg, 0.085 mmol) and 7-bromo-3,5-difluoroquinolin-2-amine (215 mg, 0.831 mmol) in THF (4 ml). The reaction was heated to 50 degrees under argon for 4 hrs. 40 min. The reaction was cooled to room temperature and diluted with DCM and water. The mixture was passed through a phase separator. The organic layer was concentrated under reduced pressure, and the crude material was subjected to silica gel flash chromatography (20-40-60% EtOAc/hexanes) followed by chiral SFC (OJ-H column, 15% MeOH w/0.1% NH$_4$OH modifier in CO2) to afford 7-(((3aS,4R,5aR,6S,8aR)-4-(4-chloro-5-fluoro-7H-pyrrolo[2,3-d]pyrimidin-7-yl)-2,2-dimethylhexahydro-5H-pentaleno[1,6a-d][1,3]dioxol-6-yl)methyl)-3,5-difluoroquinolin-2-amine as a foam.

Step 7: To a vial containing 7-(((3aS,4R,5aR,6S,8aR)-4-(4-chloro-5-fluoro-7H-pyrrolo[2,3-d]pyrimidin-7-yl)-2,2-dimethylhexahydro-5H-pentaleno[1,6a-d][1,3]dioxol-6-yl)methyl)-3,5-difluoroquinolin-2-amine (21.4 mg, 0.039 mmol) was added ammonia (I mL, 7 M in MeOH, 7 mmol). The vial was capped, and the reaction was heated at 140° C. in a microwave reactor for 5 h. The mixture was then concentrated under reduced pressure to give 7-(((3aS,4R,5aR,6S,8aR)-4-(4-amino-5-fluoro-7H-pyrrolo[2,3-d]pyrimidin-7-yl)-2,2-dimethylhexahydro-5H-pentaleno[1,6a-d][1,3]dioxol-6-yl)methyl)-3,5-difluoroquinolin-2-amine, which was used crude without further purification in the next reaction.

Step 8: To a vial containing 7-(((3aS,4R,5aR,6S,8aR)-4-(4-amino-5-fluoro-7H-pyrrolo[2,3-d]pyrimidin-7-yl)-2,2-dimethylhexahydro-5H-pentaleno[1,6a-d][1,3]dioxol-6-yl)methyl)-3,5-difluoroquinolin-2-amine (21 mg, 0.039 mmol) was added DCM (600 µl), water (190 µL), and then TFA (454 µL, 5.89 mmol). The mixture was stirred at room temperature for 3 h. The reaction was then directly concentrated under reduced pressure. The residue was purified by mass-triggered reverse phase HPLC (ACN/water gradient with 0.1% NH$_4$OH modifier) to afford (1S,2R,3aR,4S,6aR)-4-((2-amino-3,5-difluoroquinolin-7-yl)methyl)-2-(4-amino-5-fluoro-7H-pyrrolo[2,3-d]pyrimidin-7-yl)hexahydropentalene-1,6a(1H)-diol. MS: 485 (M+1). $^1$H NMR (600 MHz, DMSO) δ 8.69 (s, 2H), 8.29 (s, 1H), 7.98 (d, J=11.1 Hz, 1H), 7.87 (s, 1H), 7.68 (s, 2H), 7.19 (s, 1H), 7.06 (d, J=11.0 Hz, 1H), 4.84-4.77 (m, 1H), 3.76 (d, J=10.3 Hz, 1H), 2.79-2.66 (m, 2H), 2.49-2.42 (m, 1H), 2.16 (q, J=9.0 Hz, 1H), 1.82 (dd, J=12.2, 5.8 Hz, 1H), 1.78-1.69 (m, 2H), 1.69-1.63 (m, 1H), 1.63-1.54 (m, 1H), 1.48-1.41 (m, 1H).

Examples 31-34: Examples 31-34 in Table 11 were synthesized in an analogous fashion as described in example 30 by substituting 4-chloro-5-fluoro-7H-pyrrolo[2,3-d]pyrimidine with an appropriate nucleobase in step 1 and step 6 is replaced with step 3 in example 16, where an appropriate aryl-halide substitutes 7-bromo-3,5-difluoroquinolin-2-amine. The substituted reagents and starting material were commercially acquired, synthesized as reported above, or synthesized through known routes reported in the literature.

TABLE 11

| Ex | Structure | Name | MS |
|---|---|---|---|
| 31 | 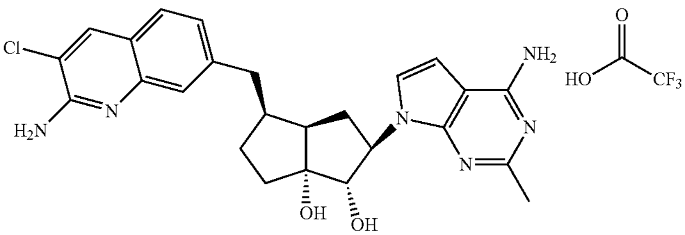 | (1S,2R,3aR,4S,6aR)-2-(4-amino-2-methyl-7H-pyrrolo[2,3-d]pyrimidin-7-yl)-4-((2-amino-3-chloroquinolin-7-yl)methyl)hexahydropentalene-1,6a(1H)-diol 2,2,2-trifluoroacetate | 479 (M + 1) |
| 32 | 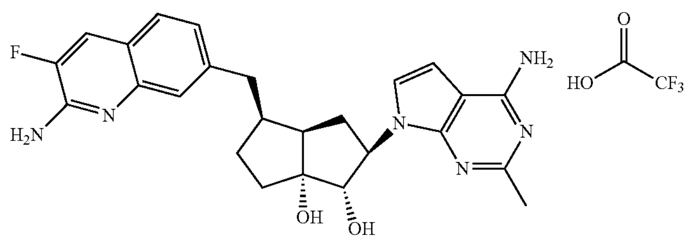 | (1S,2R,3aR,4S,6aR)-2-(4-amino-2-methyl-7H-pyrrolo[2,3-d]pyrimidin-7-yl)-4-((2-amino-3-fluoroquinolin-7-yl)methyl)hexahydropentalene-1,6a(1H)-diol 2,2,2-trifluoroacetate | 463 (M + 1) |
| 33 | 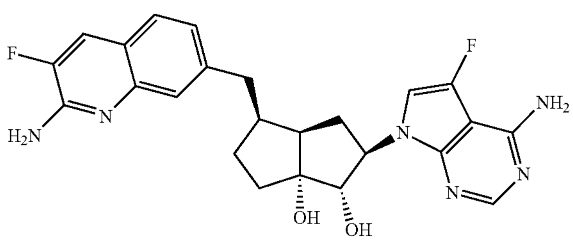 [SMILES: Nc1nc2cc(C[C@@H]3CC[C@@]4(O)[C@@H]3C[C@@H](n3cc(F)c5c(N)ncnc53)[C@@H]4O)ccc2cc1F] | (1S,2R,3aR,4S,6aR)-4-((2-amino-3-fluoroquinolin-7-yl)methyl)-2-(4-amino-5-fluoro-7H-pyrrolo[2,3-d]pyrimidin-7-yl)hexahydropentalene-1,6a(1H)-diol | 467 (M + 1) |
| 34 | 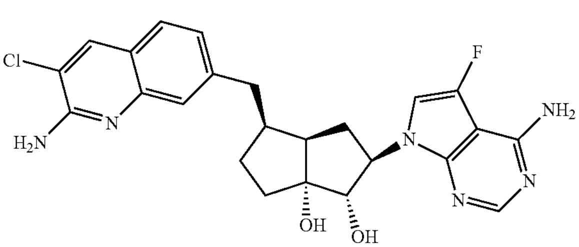 [SMILES: Nc1nc2cc(C[C@@H]3CC[C@@]4(O)[C@@H]3C[C@@H](n3cc(F)c5c(N)ncnc53)[C@@H]4O)ccc2cc1Cl] | (1S,2R,3aR,4S,6aR)-4-((2-amino-3-chloroquinolin-7-yl)methyl)-2-(4-amino-5-fluoro-7H-pyrrolo[2,3-d]pyrimidin-7-yl)hexahydropentalene-1,6a(1H)-diol | 483 (M + 1) |

Examples 35-42: Examples 35-42 in Table 12 were synthesized in an analogous fashion as described in example 30 by substituting 4-chloro-5-fluoro-7H-pyrrolo[2,3-d]pyrimidine with an appropriate nucleobase in step 1 and step 6 is replaced with step 1 in example 25, where an appropriate aryl-halide substitutes 7-bromo-3,5-difluoroquinolin-2-amine. The substituted reagents and starting material were commercially acquired, synthesized as reported above, or synthesized through known routes reported in the literature.

TABLE 12

| Ex | Structure | Name | MS |
|---|---|---|---|
| 35 | 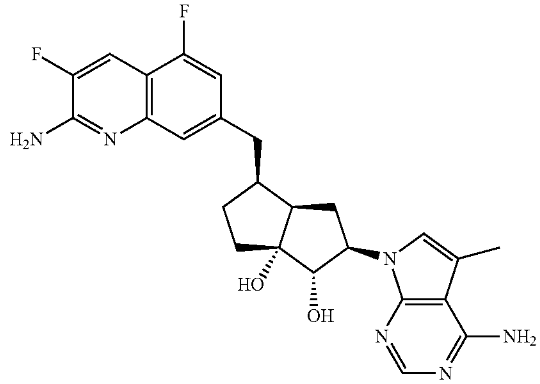 [SMILES: Cc1cn([C@@H]2C[C@@H]3[C@H](Cc4cc(F)c5cc(F)c(N)nc5c4)CC[C@]3(O)[C@H]2O)c2ncnc(N)c12] | (1S,2R,3aR,4S,6aR)-4-[(2-amino-3,5-difluoroquinolin-7-yl)methyl]-2-(4-amino-5-methyl-7H-pyrrolo[2,3-d]pyrimidin-7-yl)hexahydropentalene-1,6a(1H)-diol | 481 (M + 1) |
| 36 | 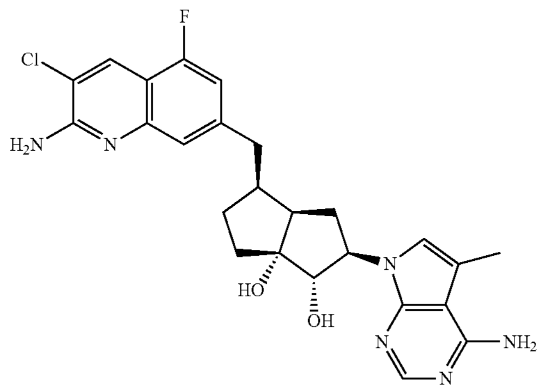 [SMILES: Cc1cn([C@@H]2C[C@@H]3[C@H](Cc4cc(F)c5cc(Cl)c(N)nc5c4)CC[C@]3(O)[C@H]2O)c2ncnc(N)c12] | (1S,2R,3aR,4S,6aR)-4-[(2-amino-3-chloro-5-fluoroquinolin-7-yl)methyl]-2-(4-amino-5-methyl-7H-pyrrolo[2,3-d]pyrimidin-7-yl)hexahydropentalene-1,6a(1H)-diol | 497 (M + 1) |
| 37 | 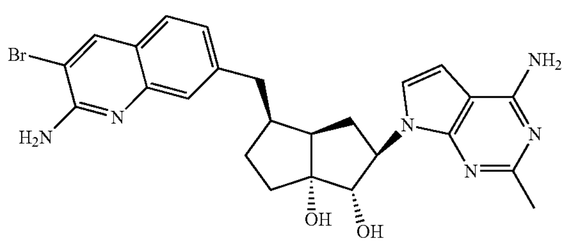 | (1S,2R,3aR,4S,6aR)-2-(4-amino-2-methyl-7H-pyrrolo[2,3-d]pyrimidin-7-yl)-4-((2-amino-3-bromoquinolin-7-yl)methyl)hexahydropentalene-1,6a(1H)-diol | 523/525 (M + 1/ M + 3) |
| 38 | 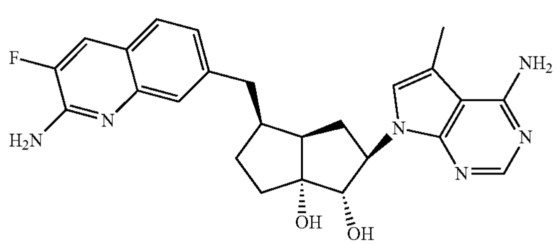 [SMILES: Cc1cn([C@@H]2C[C@@H]3[C@H](Cc4ccc5cc(F)c(N)nc5c4)CC[C@]3(O)[C@H]2O)c2ncnc(N)c12] | (1S,2R,3aR,4S,6aR)-4-((2-amino-3-fluoroquinolin-7-yl)methyl)-2-(4-amino-5-methyl-7H-pyrrolo[2,3-d]pyrimidin-7-yl)hexahydropentalene-1,6a(1H)-diol | 463 (M + 1) |
| 39 | 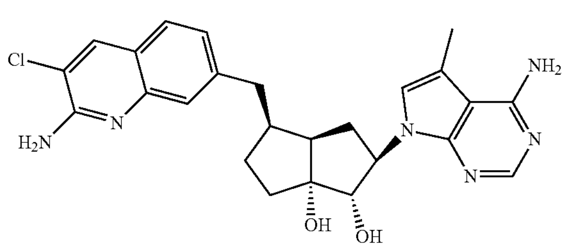 [SMILES: Cc1cn([C@@H]2C[C@@H]3[C@H](Cc4ccc5cc(Cl)c(N)nc5c4)CC[C@]3(O)[C@H]2O)c2ncnc(N)c12] | (1S,2R,3aR,4S,6aR)-4-((2-amino-3-chloroquinolin-7-yl)methyl)-2-(4-amino-5-methyl-7H-pyrrolo[2,3-d]pyrimidin-7-yl)hexahydropentalene-1,6a(1H)-diol | 479 (M + 1) |

TABLE 12-continued

| Ex | Structure | Name | MS |
|---|---|---|---|
| 40 | 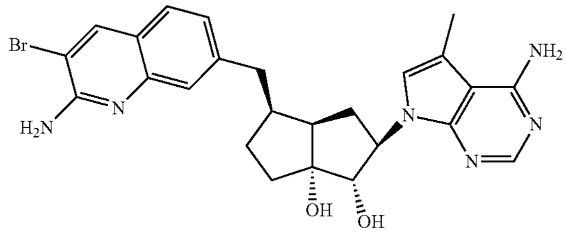 [SMILES: Cc1cn([C@@H]2C[C@@H]3[C@H](Cc4ccc5cc(Br)c(N)nc5c4)CC[C@]3(O)[C@H]2O)c2ncnc(N)c12] | (1S,2R,3aR,4S,6aR)-4-((2-amino-3-bromoquinolin-7-yl)methyl)-2-(4-amino-5-methyl-7H-pyrrolo[2,3-d]pyrimidin-7-yl)hexahydropentalene-1,6a(1H)-diol | 523/525 (M + 1/ M + 3) |
| 41 | | (1S,2R,3aR,4S,6aR)-4-((2-amino-3-bromoquinolin-7-yl)methyl)-2-(4-amino-7H-pyrrolo[2,3-d]pyrimidin-7-yl)hexahydropentalene-1,6a(1H)-diol 2,2,2-trifluoroacetate | 509/511 (M + 1/ M + 3) |
| 42 | 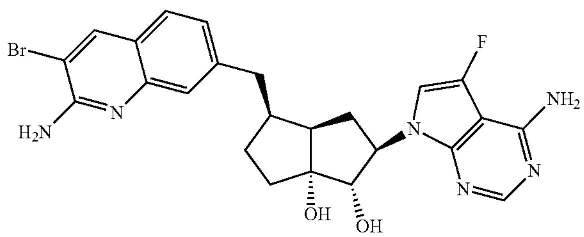 | (1S,2R,3aR,4S,6aR)-4-((2-amino-3-bromoquinolin-7-yl)methyl)-2-(4-amino-5-fluoro-7H-pyrrolo[2,3-d]pyrimidin-7-yl)hexahydropentalene-1,6a(1H)-diol | 527/529 (M + 1/ M + 3) |

Examples 43-44: Examples 43-44 in Table 13 were synthesized by applying the protocols as described in steps 6-8 of example 30 by substituting 7-bromo-3,5-difluoroquinolin-2-amine with an appropriate aryl-halide in step 6. The substituted reagents and starting material were commercially acquired, synthesized as reported above, or synthesized through known routes reported in the literature.

TABLE 13

| Ex | Structure | Name | MS |
|---|---|---|---|
| 43 | 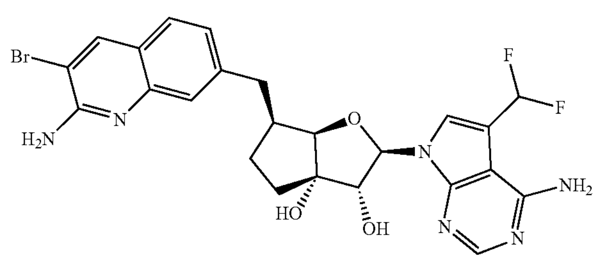 [SMILES: Nc1nc2cc(C[C@@H]3CC[C@@]4(O)[C@@H]3O[C@@H](n3cc(C(F)F)c5c(N)ncnc53)[C@@H]4O)ccc2cc1Br] | (2R,3R,3aS,6S,6aR)-6-[(2-amino-3-bromoquinolin-7-yl)methyl]-2-[4-amino-5-(difluoromethyl)-7H-pyrrolo[2,3-d]pyrimidin-7-yl]hexahydro-3aH-cyclopenta[b]furan-3,3a-diol | 561/563 (M + 1/ M + 3) |
| 44 | | (2R,3R,3aS,6S,6aR)-6-((2-amino-3-fluoroquinolin-7-yl)methyl)-2-(4-amino-5-fluoro-2-methyl-7H-pyrrolo[2,3-d]pyrimidin-7-yl)hexahydro-3aH-cyclopenta[b]furan-3,3a-diol 2,2,2-trifluoroacetate | 484 (M + 1) |

Example 45

(2R,3R,3aS,6S,6aR)-2(4-amino-2-fluoro-7H-pyrrolo[2,3-d]pyrimidin-7-yl)-6-((2-amino-3-fluoroquinolin-7-yl)methyl)hexahydro-3aH-cyclopenta[b]furan-3,3a-diol

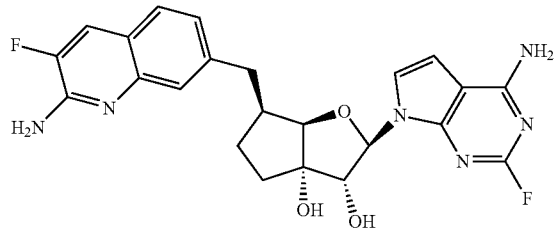

Step 1: To 2-fluoro-7H-pyrrolo[2,3-d]pyrimidin-4-amine (500 mg, 3.29 mmol) dissolved in DCM (8 mL) and acetonitrile (8 mL) was added di-tert-butyl dicarbonate (2.5 g, 12 mmol) and DMAP (80 mg, 0.66 mmol). The solution was stirred at room temperature for 1 h. The mixture was then concentrated under reduced pressure, and the residue was purified by column chromatography on silica (0-30% EtOAc/hexanes) to afford tert-butyl 4-[bis(tert-butoxycarbonyl)amino]-2-fluoro-7H-pyrrolo[2,3-d]pyrimidine-7-carboxylate. MS: 453 (M+1). $^1$H NMR (600 MHz, CDCl$_3$) δ 7.64 (d, 3=4.1 Hz, 1H), 6.48 (d, J=4.1 Hz, 1H), 1.69 (s, 9H), 1.44 (s, 18H).

Step 2: To a solution of tert-butyl 4-[bis(tert-butoxycarbonyl)amino]-2-fluoro-7H-pyrrolo[2,3-d]pyrimidine-7-carboxylate (1.35 g, 2.98 mmol) in MeOH (15 ml) was added TEA (4.15 mL, 29.8 mmol) at room temperature. The reaction was heated to 60° C. and stirred overnight. The mixture was cooled to room temperature and concentrated under reduced pressure. The residue was purified by column chromatography on silica (0-60% EtOAc/hexanes) to afford di-tert-butyl (2-fluoro-7H-pyrrolo[2,3-d]pyrimidin-4-yl)imidodicarbonate. MS: 353 (M+1). $^1$H NMR (600 MHz, CDCl$_3$) g 9.34 (s, 1H), 7.28 (dd, J=3.5, 2.3 Hz, 1H), 6.50 (dd, J=3.6, 2.0 Hz, 1H), 1.47 (s, 18H).

Step 3: To a vial containing (3R,3aS,6S,6aR)-6-((2-amino-3-fluoroquinolin-7-yl)methyl)hexahydro-3aH-cyclopenta[b]furan-2,3,3a-triol (100 mg, 0.299 mmol) dissolved in dry acetonitrile (5 mL) was added 1,1-(azodicarbonyl)dipiperidine (113 mg, 0.45 mmol) followed by tri-n-butylphosphine (120 µL, 0.48 mmol) at room temperature. The mixture was stirred for 1 h. In a separate vial containing di-tert-butyl (2-fluoro-7H-pyrrolo[2,3-d]pyrimidin-4-yl)imidodicarbonate (211 mg, 0.598 mmol) dissolved in dry acetonitrile (1 mL) was added DBU (90 µL, 0.60 mmol). The mixture was stirred for 30 minutes at room temperature. The mixture was then added to the mixture containing the pre-formed epoxide, and the reaction was stirred for 2.5 h at room temperature. The mixture was then filtered and purified by mass-triggered reverse phase HPLC (ACN/water with 0.10 NH$_4$OH modifier) to afford di-tert-butyl (7-{(2R,3R,3aS,6S,6aR)-6-[(2-amino-3-fluoroquinolin-7-yl)methyl]-3,3a-dihydroxyhexahydro-2H-cyclopenta[b]furan-2-yl}-2-fluoro-7H-pyrrolo[2,3-d]pyrimidin-4-yl)imidodicarbonate. MS: 669 (M+1).

Step 4: To di-tert-butyl(7-{(2R,3R,3aS,6S,6aR)-6-[(2-amino-3-fluoroquinolin-7-yl)methyl]-3,3a-dihydroxyhexahydro-2H-cyclopenta[b]furan-2-yl}-2-fluoro-7H-pyrrolo[2,3-d]pyrimidin-4-yl)imidodicarbonate (97 mg, 0.14 mmol) dissolved in DCM (3 mL) was added TFA (1.1 mL, 14.5 mmol). The mixture was stirred overnight at room temperature. The reaction was concentrated under reduced pressure. The residue was purified by mass-triggered reverse phase HPLC (ACN/water gradient with 0.1% NH$_4$OH modifier) to afford (2R,3R,3aS,6S,6aR)-2-(4-amino-2-fluoro-7H-pyrrolo[2,3-d]pyrimidin-7-yl)-6-((2-amino-3-fluoroquinolin-7-yl)methyl)hexahydro-3aH-cyclopenta[b]furan-3,3a-diol. MS: 469 (M+1). $^1$H NMR (600 MHz, DMSO) δ 7.75 (d, J=11.8 Hz, 1H), 7.59 (s, 2H), 7.54 (d, J=8.2 Hz, 1H), 7.40 (d, J=3.7 Hz, 11H), 7.30 (s, 1H), 7.09 (d, J=8.2 Hz, 1H), 6.78-6.62 (m, 3H), 5.72 (d, J=8.1 Hz, 1H), 5.26 (d, J=7.0 Hz, 1H), 5.08 (s, 1H), 4.09 (t, J=7.5 Hz, 1H), 3.96 (d, J=5.7 Hz, 1H), 2.82 (dd, J=13.6, 7.8 Hz, 1H), 2.62 (dd, J=13.6, 7.2 Hz, 1H), 2.28-2.20 (m, 1H), 1.92 (dd, J=12.7, 6.0 Hz, 1H), 1.76-1.64 (m, 2H), 1.55-1.48 (m, 1H).

Example 46: Example 45 in Table 14 was synthesized by applying the Mitsunobu protocol described in step 3 of the synthesis of example 45 followed by application of the TFA deprotection described in step 4 of example 45. Di-tert-butyl (2-fluoro-7H-pyrrolo[2,3-d]pyrimidin-4-yl)imidodicarbonate and (3R,3aS,6S,6aR)-6-((2-amino-3-fluoroquinolin-7-yl)methyl)hexahydro-3aH-cyclopenta[b]furan-2,3,3a-triol in the Mitsunobu sequence were substituted with an appropriate nucleobase and triol respectively. The substituted reagents and starting material were commercially acquired, synthesized as reported above, or synthesized through known routes reported in the literature.

TABLE 14

| Ex | Structure | Name | MS |
| --- | --- | --- | --- |
| 46 | 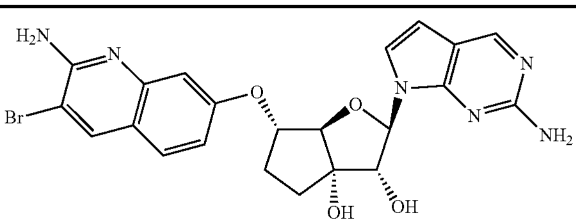 | (2R,3R,3aS,6S,6aR)-6-((2-amino-3-bromoquinolin-7-yl)oxy)-2-(2-amino-7H-pyrrolo[2,3-d]pyrimidin-7-yl)hexahydro-3aH-cyclopenta[b]furan-3,3a-diol dihydrochloride HCl HCl | 513/515 (M + 1/ M + 3) |

Examples 47-48: Examples 47-48 in Table 15 were synthesized in an analogous fashion as described with example 45 by substituting 2-fluoro-7H-pyrrolo[2,3-d]pyrimidin-4-amine with an appropriate nucleobase in step 1 and (3R,3aS,6S,6aR)-6-((2-amino-3-fluoroquinolin-7-yl)methyl)hexahydro-3aH-cyclopenta[b]furan-2,3,3a-triol with an appropriate triol in step 3. The substituted reagents and starting material were commercially acquired, synthesized as reported above, or synthesized through known routes reported in the literature.

TABLE 15

| Ex | Structure | Name | LCMS |
|----|-----------|------|------|
| 47 | 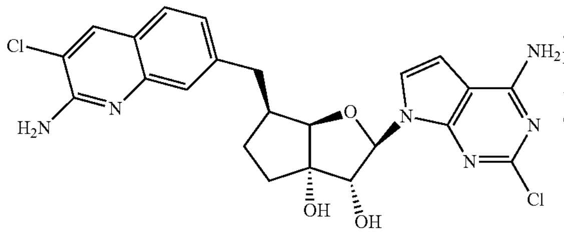 | (2R,3R,3aS,6S,6aR)-2-(4-amino-2-chloro-7H-pyrrolo[2,3-d]pyrimidin-7-yl)-6-[(2-amino-3-chloroquinolin-7-yl)methyl]hexahydro-3aH-cyclopenta[b]furan-3,3a-diol | 501 (M + 1) |
| 48 | 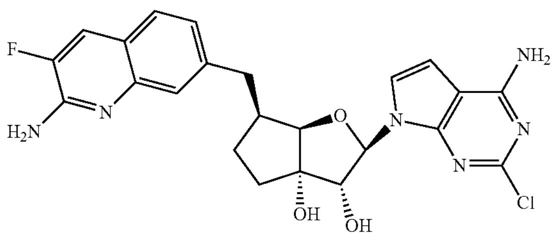 [SMILES: Nc1nc2cc(C[C@@H]3CC[C@@]4(O)[C@@H]3O[C@@H](n3ccc5c(N)nc(Cl)nc53)[C@@H]4O)ccc2cc1F] | (2R,3R,3aS,6S,6aR)-2-(4-amino-2-chloro-7H-pyrrolo[2,3-d]pyrimidin-7-yl)-6-[(2-amino-3-fluoroquinolin-7-yl)methyl]hexahydro-3aH-cyclopenta[b]furan-3,3a-diol | 485 (M + 1) |

Examples 49-66: Examples 49-66 in Table 16 were synthesized by applying the Mitsunobu protocol described in step 3 of the synthesis of example 45 followed by application of the aminolysis protocol described in step 7 of example 30. Di-tert-butyl (2-fluoro-7H-pyrrolo[2,3-d]pyrimidin-4-yl)imidodicarbonate and (3R,3aS,6S,6aR)-6-((2-amino-3-fluoroquinolin-7-yl)methyl)hexahydro-3aH-cyclopenta[b]furan-2,3,3a-triol in the Mitsunobu sequence were substituted with an appropriate nucleobase and triol respectively. The substituted reagents and starting material were commercially acquired, synthesized as reported above, or synthesized through known routes reported in the literature.

TABLE 16

| Ex | Structure | Name | MS |
|----|-----------|------|----|
| 49 | 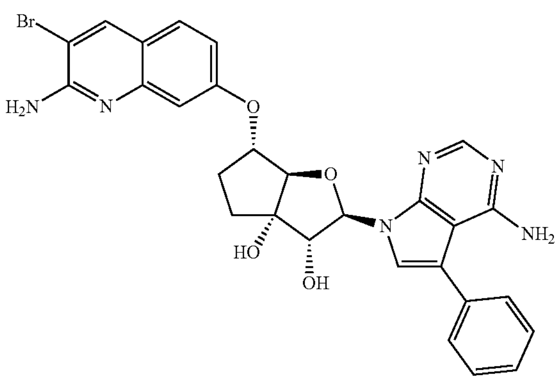 [SMILES: Nc1nc2cc(O[C@H]3CC[C@@]4(O)[C@@H]3O[C@@H](n3cc(-c5ccccc5)c5c(N)ncnc53)[C@@H]4O)ccc2cc1Br] | (2R,3R,3aS,6S,6aR)-6-[(2-amino-3-bromoquinolin-7-yl)oxy]-2-(4-amino-5-phenyl-7H-pyrrolo[2,3-d]pyrimidin-7-yl)hexahydro-3aH-cyclopenta[b]furan-3,3a-diol | 589/591 (M + 1/ M + 3) |
| 50 | 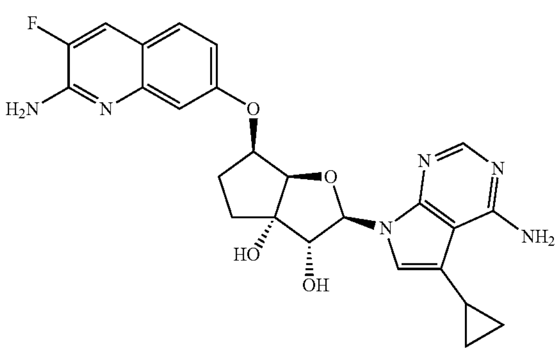 [SMILES: Nc1nc2cc(O[C@@H]3CC[C@@]4(O)[C@@H]3O[C@@H](n3cc(C5CC5)c5c(N)ncnc53)[C@@H]4O)ccc2cc1F] | (2R,3R,3aS,6S,6aR)-2-(4-amino-5-cyclopropyl-7H-pyrrolo[2,3-d]pyrimidin-7-yl)-6-[(2-amino-3-fluoroquinolin-7-yl)methylhexahydro-3aH-cyclopenta[b]furan-3,3a-diol | 491 (M + 1) |

TABLE 16-continued

| Ex | Structure | Name | MS |
|----|-----------|------|-----|
| 51 | 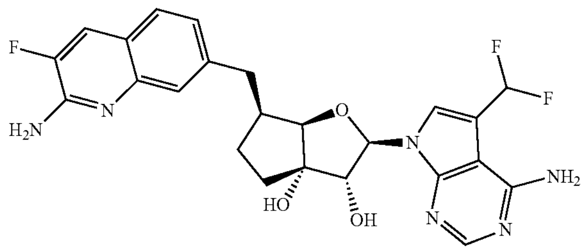 [SMILES: Nc1nc2cc(C[C@@H]3CC[C@@]4(O)[C@@H]3O[C@@H](n3cc(C(F)F)c5c(N)ncnc53)[C@@H]4O)ccc2cc1F] | (2R,3R,3aS,6S,6aR)-2-[4-amino-5-(difluoromethyl)-7H-pyrrolo[2,3-d]pyrimidin-7-yl]-6-[(2-amino-3-fluoroquinolin-7-yl)methyl]hexahydro-3aH-cyclopenta[b]furan-3,3a-diol | 501 (M + 1) |
| 52 | 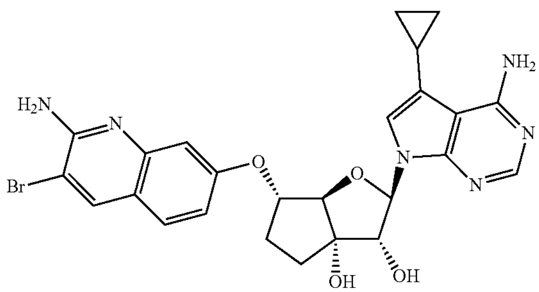 [SMILES: Nc1nc2cc(O[C@H]3CC[C@@]4(O)[C@@H]3O[C@@H](n3cc(C5CC5)c5c(N)ncnc53)[C@@H]4O)ccc2cc1Br] | (2R,3R,3aS,6S,6aR)-6-[(2-amino-3-bromoquinolin-7-yl)oxy]-2-(4-amino-5-cyclopropyl-7H-pyrrolo[2,3-d]pyrimidin-7-yl)hexahydro-3aH-cyclopenta[b]furan-3,3a-diol | 553/555 (M + 1/ M + 3) |
| 53 | 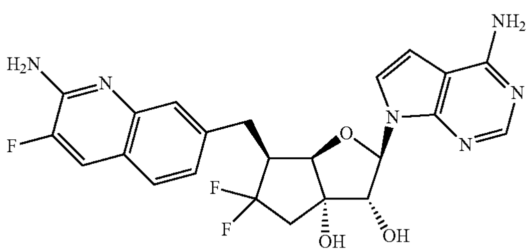 [SMILES: Nc1nc2cc(C[C@H]3[C@H]4O[C@@H](n5ccc6c(N)ncnc65)[C@H](O)[C@@]4(O)CC3(F)F)ccc2cc1F] | (2R,3R,3aS,6S,6aR)-6-[(2-amino-3-fluoroquinolin-7-yl)methyl]-2-(4-amino-7H-pyrrolo[2,3-d]pyrimidin-7-yl)-5,5-difluorohexahdro-3aH-cyclopenta[b]furan-3,3a-diol | 487 (M + 1) |
| 54 | 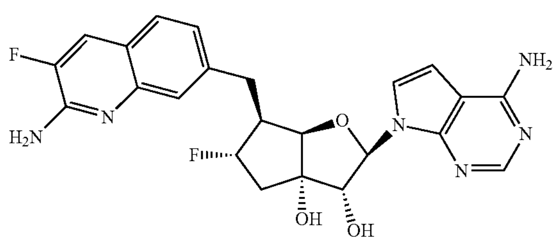 [SMILES: Nc1nc2cc(C[C@H]3[C@H]4O[C@@H](n5ccc6c(N)ncnc65)[C@H](O)[C@@]4(O)C[C@@H]3F)ccc2cc1F] | (2R,3R,3aS,5S,6S,6aR)-6-[(2-amino-3-fluoroquinolin-7-yl)methyl]-2-(4-amino-7H-pyrrolo[2,3-d]pyrimidin-7-yl)-5-fluorohexahydro-3aH-cyclopenta[b]furan-3,3a-diol | 469 (M + 1) |
| 55 | 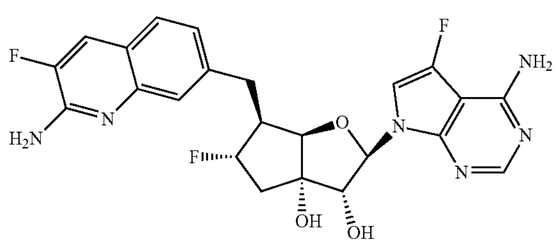 [SMILES: Nc1nc2cc(C[C@H]3[C@H]4O[C@@H](n5cc(F)c6c(N)ncnc65)[C@H](O)[C@@]4(O)C[C@@H]3F)ccc2cc1F] | (2R,3R,3aS,5S,6S,6aR)-2-(4-amino-5-fluoro-7H-pyrrolo[2,3-d]pyrimidin-7-yl)-6-[(2-amino-3-fluoroquinolin-7-yl)methyl]-5-fluorohexahydro-3aH-cyclopenta[b]furan-3,3a-diol,2,2,2-trifluoroethanol | 487 (M + 1) |
| 56 | 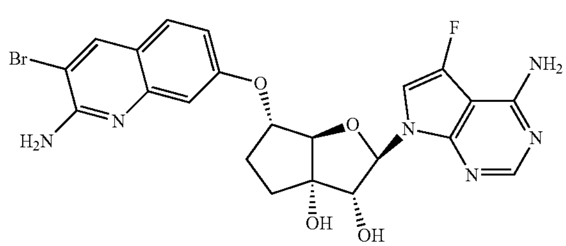 [SMILES: Nc1nc2cc(O[C@H]3CC[C@@]4(O)[C@@H]3O[C@@H](n3cc(F)c5c(N)ncnc53)[C@@H]4O)ccc2cc1Br] | (2R,3R,3aS,6S,6aR)-6-((2-amino-3-bromoquinolin-7-yl)oxy)-2-(4-amino-5-fluoro-7H-pyrrolo[2,3-d]pyrimidin-7-yl)hexahydro-3aH-cyclopenta[b]furan-3,3a-diol | 531/533 (M + 1/ M + 3) |

TABLE 16-continued

| Ex | Structure | Name | MS |
|---|---|---|---|
| 57 | 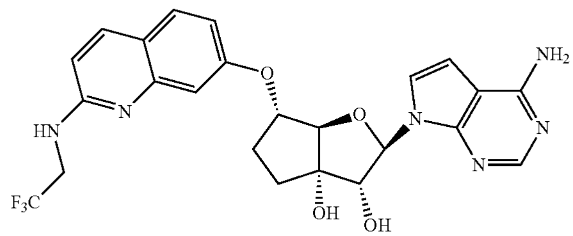 [SMILES: Nc1ncnc2c1ccn2[C@@H]1O[C@@H]2[C@@H](Oc3ccc4ccc(NCC(F)(F)F)nc4c3)CC[C@]2(O)[C@H]1O] | (2R,3R,3aS,6S,6aR)-2-(4-amino-7H-pyrrolo[2,3-d]pyrimidin-7-yl)-6-((2-((2,2,2-trifluoroethyl)amino)quinolin-7-yl)oxy)hexahydro-3aH-cyclopenta[b]furan-3,3a-diol | 517 (M + 1) |
| 58 | 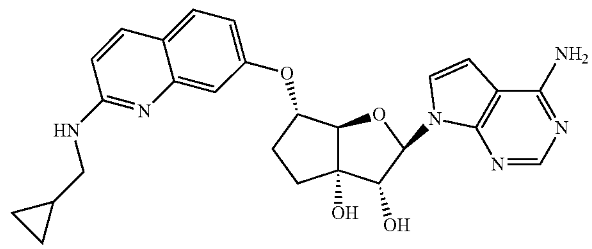 [SMILES: Nc1ncnc2c1ccn2[C@@H]1O[C@@H]2[C@@H](Oc3ccc4ccc(NCC5CC5)nc4c3)CC[C@]2(O)[C@H]1O] | (2R,3R,3aS,6S,6aR)-2-(4-amino-7H-pyrrolo[2,3-d]pyrimidin-7-yl)-6-((2-((cyclopropylmethyl)amino)quinolin-7-yl)oxy)hexahydro-3aH-cyclopenta[b]furan-3,3a-diol | 489 (M + 1) |
| 59 | 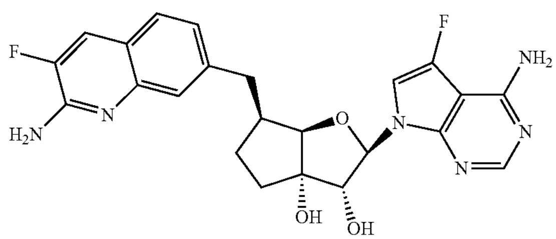 [SMILES: Nc1nc2cc(C[C@@H]3CC[C@@]4(O)[C@@H]3O[C@@H](n3cc(F)c5c(N)ncnc53)[C@@H]4O)ccc2cc1F] | (2R,3R,3aS,6S,6aR)-6-((2-amino-3-fluoroquinolin-7-yl)methyl)-2-(4-amino-5-fluoro-7H-pyrrolo[2,3-d]pyrimidin-7-yl)hexahydro-3aH-cyclopenta[b]furan-3,3a-diol | 469 (M + 1) |
| 60 | 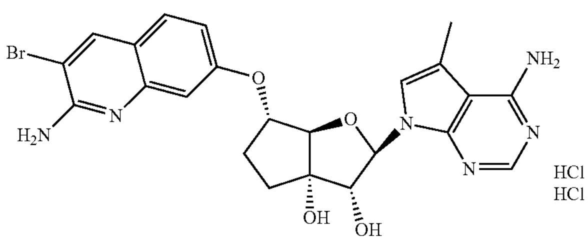 [SMILES: Cc1cn([C@@H]2O[C@@H]3[C@@H](Oc4ccc5cc(Br)c(N)nc5c4)CC[C@]3(O)[C@H]2O)c2ncnc(N)c12] | (2R,3R,3aS,6S,6aR)-6-((2-amino-3-bromoquinolin-7-yl)oxy)-2-(4-amino-5-methyl-7H-pyrrolo[2,3-d]pyrimidin-7-yl)hexahydro-3aH-cyclopenta[b]furan-3,3a-diol | 527/529 (M + 1/ M + 3) |
| 61 | 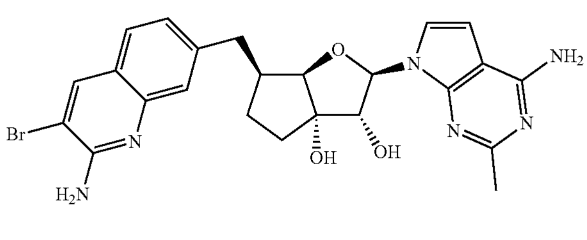 [SMILES: Cc1nc(N)c2ccn([C@@H]3O[C@@H]4[C@H](Cc5ccc6cc(Br)c(N)nc6c5)CC[C@]4(O)[C@H]3O)c2n1] | (2R,3R,3aS,6S,6aR)-2-(4-amino-2-methyl-7H-pyrrolo[2,3-d]pyrimidin-7-yl)-6-((2-amino-3-bromoquinolin-7-yl)methyl)hexahydro-3aH-cyclopenta[b]furan-3,3a-diol | 525/527 (M + 1/ M + 3) |
| 62 | 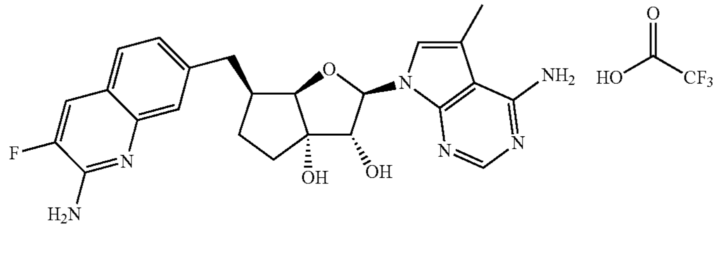 | (2R,3R,3aS,6S,6aR)-6-((2-amino-3-fluoroquinolin-7-yl)methyl)-2-(4-amino-5-methyl-7H-pyrrolo[2,3-d]pyrimidin-7-yl)hexahydro-3aH-cyclopenta[b]furan-3,3a-diol 2,2,2-trifluoroacetate | 465 (M + 1) |

TABLE 16-continued

| Ex | Structure | Name | MS |
|---|---|---|---|
| 63 | 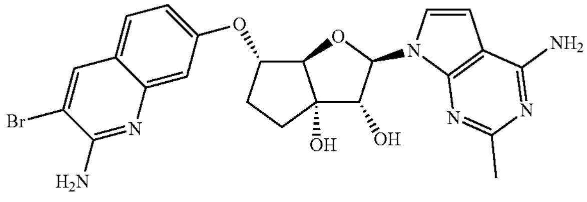 [SMILES: Cc1nc(N)c2ccn([C@@H]3O[C@@H]4[C@@H](Oc5ccc6cc(Br)c(N)nc6c5)CC[C@]4(O)[C@H]3O)c2n1] | (2R,3R,3aS,6S,6aR)-2-(4-amino-2-methyl-7H-pyrrolo[2,3-d]pyrimidin-7-yl)-6-((2-amino-3-bromoquinolin-7-yl)oxy)hexahydro-3aH-cyclopenta[b]furan-3,3a-diol | 527/529 (M + 1/ M + 3) |
| 64 | | (2R,3R,3aS,6S,6aR)-6-((2-amino-3-chloroquinolin-7-yl)oxy)-2-(4-amino-5-methyl-7H-pyrrolo[2,3-d]pyrimidin-7-yl)hexahydro-3aH-cyclopenta[b]furan-3,3a-diol 2,2,2-trifluoroacetate | 483 (M + 1) |
| 65 | | (2R,3R,3aS,6S,6aR)-6-((2-amino-3-fluoroquinolin-7-yl)oxy)-2-(4-amino-5-methyl-7H-pyrrolo[2,3-d]pyrimidin-7-yl)hexahydro-3aH-cyclopenta[b]furan-3,3a-diol 2,2,2-trifluoroacetate | 467 (M + 1) |
| 66 | 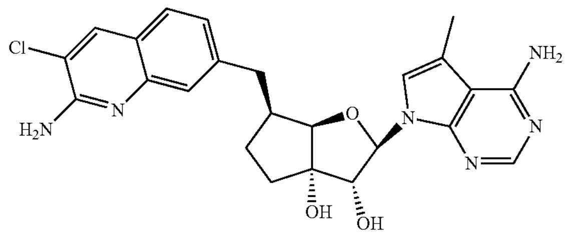 [SMILES: Cc1cn([C@@H]2O[C@@H]3[C@H](Cc4ccc5cc(Cl)c(N)nc5c4)CC[C@]3(O)[C@H]2O)c2ncnc(N)c12] | (2R,3R,3aS,6S,6aR)-6-((2-amino-3-chloroquinolin-7-yl)methyl)-2-(4-amino-5-methyl-7H-pyrrolo[2,3-d]pyrimidin-7-yl)hexahydro-3aH-cyclopenta[b]furan-3,3a-diol | 481 (M + 1) |

Examples 67-70: Examples 67-70 in Table 17 were synthesized by applying the Mitsunobu protocol described in step 3 of the synthesis of example 45 followed by application of the aminolysis protocol described in step 11 of example 10 & 11. Di-tert-butyl (2-fluoro-7H-pyrrolo[2,3-d]pyrimidin-4-yl)imidodicarbonate and (3R,3aS,6S,6aR)-6-((2-amino-3-fluoroquinolin-7-yl)methyl)hexahydro-3aH-cyclopenta[b]furan-2,3,3a-triol in the Mitsunobu sequence were substituted with an appropriate nucleobase and triol respectively. The substituted reagents and starting material were commercially acquired, synthesized as reported above, or synthesized through known routes reported in the literature.

TABLE 17

| Ex | Structure | Name | MS |
|---|---|---|---|
| 67 | 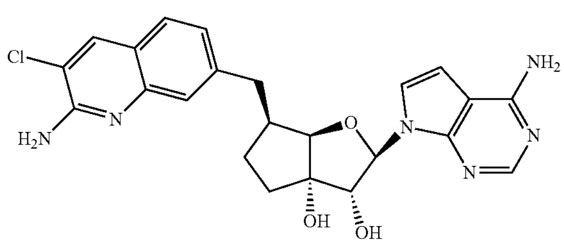 [SMILES: Nc1nc2cc(C[C@@H]3CC[C@@]4(O)[C@@H]3O[C@@H](n3ccc5c(N)ncnc53)[C@@H]4O)ccc2cc1Cl] | (2R,3R,3aS,6S,6aR)-6-((2-amino-3-chloroquinolin-7-yl)methyl)-2-(4-amino-7H-pyrrolo[2,3-d]pyrimidin-7-yl)hexahydro-3aH-cyclopenta[b]furan-3,3a-diol | 467 (M + 1) |

TABLE 17-continued

| Ex | Structure | Name | MS |
|---|---|---|---|
| 68 | 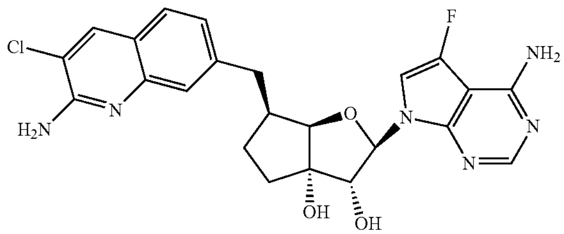 [SMILES: Nc1nc2cc(C[C@@H]3CC[C@@]4(O)[C@@H]3O[C@@H](n3cc(F)c5c(N)ncnc53)[C@@H]4O)ccc2cc1Cl] | (2R,3R,3aS,6S,6aR)-6-((2-amino-3-chloroquinolin-7-yl)methyl)-2-(4-amino-5-fluoro-7H-pyrrolo[2,3-d]pyrimidin-7-yl)hexahydro-3aH-cyclopenta[b]furan-3,3a-diol | 485 (M + 1) |
| 69 | | (2R,3R,3aS,6S,6aR)-6-((2-amino-3-bromoquinolin-7-yl)oxy)-2-(4-amino-5-ethyl-7H-pyrrolo[2,3-d]pyrimidin-7-yl)hexahydro-3aH-cyclopenta[b]furan-3,3a-diol | 541/543 (M + 1/M + 3) |
| 70 | | (2R,3R,3aS,6S,6aR)-6-((2-amino-3-bromoquinolin-7-yl)methyl)-2-(4-amino-5-methyl-7H-pyrrolo[2,3-d]pyrimidin-7-yl)hexahydro-3aH-cyclopenta[b]furan-3,3a-diol 2,2,2-trifluoroacetate | 525/527 (M + 1/M + 3) |

Examples 71-75: Examples 71-75 in Table 18 were synthesized by applying the Mitsunobu protocol described in step 3 of the synthesis of example 45 followed by application of the aminolysis protocol described in step 12 of intermediate 15. Di-tert-butyl (2-fluoro-7H-pyrrolo[2,3-d]pyrimidin-4-yl)imidodicarbonate and (3R,3aS,6S,6aR)-6-((2'-amino-3-fluoroquinolin-7-yl)methyl)hexahydro-3aH-cyclopenta[b]furan-2,3,3a-triol in the Mitsunobu sequence were substituted with an appropriate nucleobase and triol respectively. The substituted reagents and, starting material were commercially acquired, synthesized as reported above, or synthesized through known routes reported in the literature.

TABLE 18

| Ex | Structure | Name | MS |
|---|---|---|---|
| 71 | 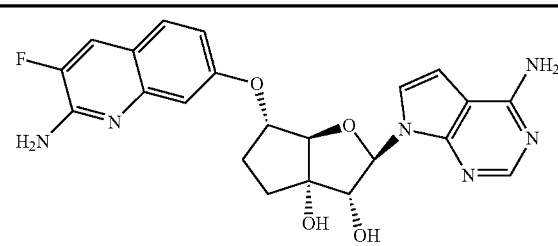 | (2R,3R,3aS,6S,6aR)-6-((2-amino-3-fluoroquinolin-7-yl)oxy)-2-(4-amino-7H-pyrrolo[2,3-d]pyrimidin-7-yl)hexahydro-3aH-cyclopenta[b]furan-3,3a-diol | 453 (M + 1) |
| 72 | 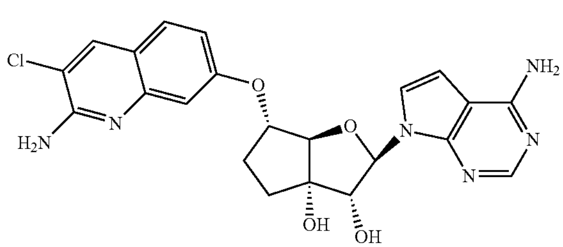 [SMILES: Nc1nc2cc(O[C@H]3CC[C@@]4(O)[C@@H]3O[C@@H](n3ccc5c(N)ncnc53)[C@@H]4O)ccc2cc1Cl] | (2R,3R,3aS,6S,6aR)-6-((2-amino-3-chloroquinolin-7-yl)oxy)-2-(4-amino-7H-pyrrolo[2,3-d]pyrimidin-7-yl)hexahydro-3aH-cyclopenta[b]furan-3,3a-diol | 469 (M + 1) |

TABLE 18-continued

| Ex | Structure | Name | MS |
|---|---|---|---|
| 73 | 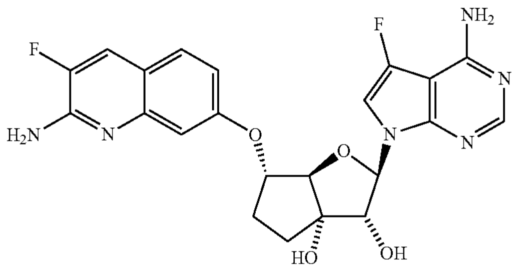 | (2R,3R,3aS,6S,6aR)-6-((2-amino-3-fluoroquinolin-7-yl)oxy)-2-(4-amino-5-fluoro-7H-pyrrolo[2,3-d]pyrimidin-7-yl)hexahydro-3aH-cyclopenta[b]furan-3,3a-diol | 471 (M + 1) |
| 74 | 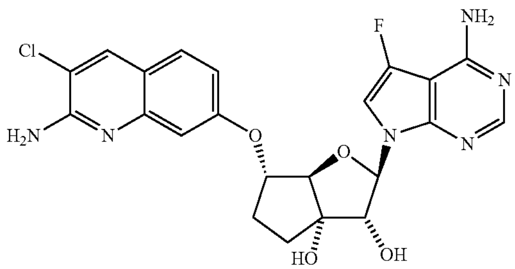 [SMILES: Nc1nc2cc(O[C@H]3CC[C@@]4(O)[C@@H]3O[C@@H](n3cc(F)c5c(N)ncnc53)[C@@H]4O)ccc2cc1Cl] | (2R,3R,3aS,6S,6aR)-6-((2-amino-3-chloroquinolin-7-yl)oxy)-2-(4-amino-5-fluoro-7H-pyrrolo[2,3-d]pyrimidin-7-yl)hexahydro-3aH-cyclopenta[b]furan-3,3a-diol | 487 (M + 1) |
| 75 | 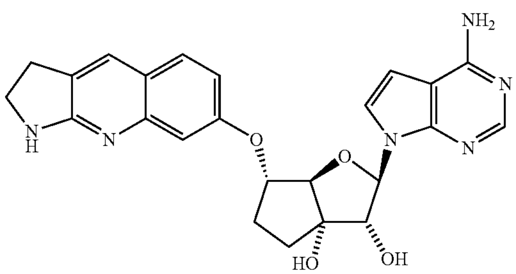 [SMILES: Nc1ncnc2c1ccn2[C@@H]1O[C@@H]2[C@@H](Oc3ccc4cc5c(nc4c3)NCC5)CC[C@]2(O)[C@H]1O] | (2R,3R,3aS,6S,6aR)-2-(4-amino-7H-pyrrolo[2,3-d]pyrimidin-7-yl)-6-((2,3-dihydro-1H-pyrrolo[2,3-b]quinolin-7-yl)oxy)hexahydro-3aH-cyclopenta[b]furan-3,3a-diol | 461 (M + 1) |

Example 76: Example 76 in Table 19 was synthesized by applying the Mitsunobu protocol in step 7 of the synthesis of example 14 followed by application of the aminolysis protocol described in step 12 of intermediate 15. 4-chloro-7H-pyrrolo[2,3-d]pyrimidine and (3R,4S,5R)-5-(2-(3-bromo-2-((4-methoxybenzyl)amino)quinolin-7-yl)ethyl)-4-methyltetrahydrofuran-2,3,4-triol in the Mitsunobu sequence were substituted with an appropriate nucleobase and triol respectively. The substituted reagents and starting material were commercially acquired, synthesized as reported above, or synthesized through known routes reported in the literature.

Examples 77-84: Examples 77-84 in Table 20 were synthesized by applying the Mitsunobu protocol described in step 3 of the synthesis of example 45. Di-tert-butyl (2-fluoro-7H-pyrrolo[2,3-d]pyrimidin-4-yl)imidodicarbonate and (3R,3aS,6S,6aR)-6-((2-amino-3-fluoroquinolin-7-yl)methyl)hexahydro-3aH-cyclopenta[b]furan-2,3,3a-triol in the Mitsunobu sequence were substituted with an appropriate nucleobase and triol respectively. The substituted reagents and starting material were commercially acquired, synthesized as reported above, or synthesized through known routes reported in the literature.

TABLE 19

| Ex | Structure | Name | MS |
|---|---|---|---|
| 76 | 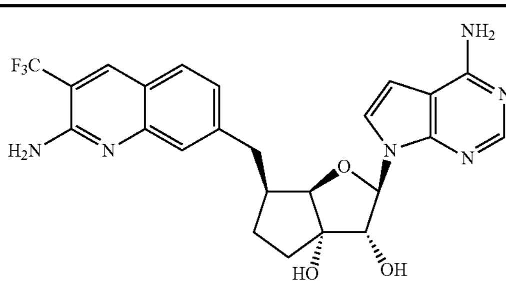 | (2R,3R,3aS,6S,6aR)-6-((2-amino-3-(trifluoromethyl)quinolin-7-yl)methyl)-2-(4-amino-7H-pyrrolo[2,3-d]pyrimidin-7-yl)hexahydro-3aH-cyclopenta[b]furan-3,3a-diol | 501 (M+) |

TABLE 20

| Ex | Structure | Name | MS |
|---|---|---|---|
| 77 | 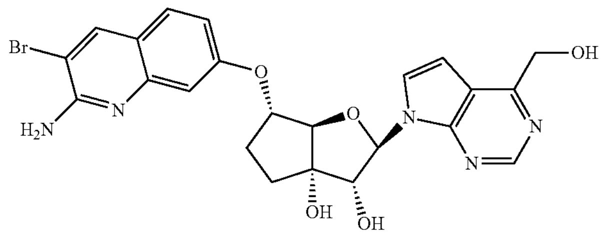 [SMILES: Nc1nc2cc(O[C@H]3CC[C@@]4(O)[C@@H]3O[C@@H](n3ccc5c(CO)ncnc53)[C@@H]4O)ccc2cc1Br] | (2R,3R,3aS,6S,6aR)-6-[(2-amino-3-bromoquinolin-7-yl)oxy]-2-[4-(hydroxymethyl)-7H-pyrrolo[2,3-d]pyrimidin-7-yl]hexahydro-3aH-cyclopenta[b]furan-3,3a-diol | 528/530 (M + 1/M + 3) |
| 78 | 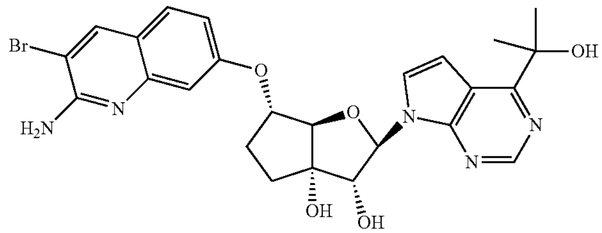 [SMILES: CC(C)(O)c1ncnc2c1ccn2[C@@H]1O[C@@H]2[C@@H](Oc3ccc4cc(Br)c(N)nc4c3)CC[C@]2(O)[C@H]1O] | (2R,3R,3aS,6S,6aR)-6-1(2-amino-3-bromoquinolin-7-yl)oxy]-2-[4-(2-hydroxypropan-2-yl)-7H-pyrrolo[2,3-d]pyrimidin-7-yl]hexahydro-3aH-cyclcopenta[b]furan-3,3a-diol | 556/558 (M + 1/M + 3) |
| 79 | 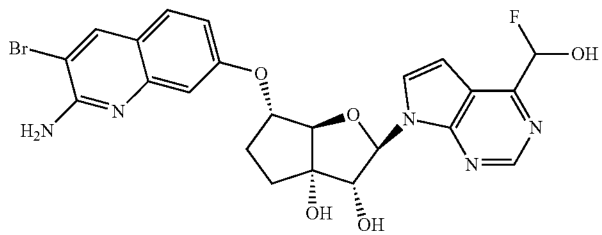 [SMILES: Nc1nc2cc(O[C@H]3CC[C@@]4(O)[C@@H]3O[C@@H](n3ccc5c(C(O)F)ncnc53)[C@@H]4O)ccc2cc1Br] | (2R,3R,3aS,6S,6aR)-6-((2-amino-3-bromoquinolin-7-yl)oxy)-2-(4-(difluoromethyl)-7H-pyrrolo[2,3-d]pyrimidin-7-yl)hexabodro-3aH-cyclopenta[b]furan-3,3a-diol | 548/550 (M + 1/M + 3) |
| 80 | | (2R,3R,3aS,6S,6aR)-6-((2-amino-3-bromoquinolin-7-yl)oxy)-2-(2,4-dimethyl-7H-pyrrolo[2,3-d]pyrimidin-7-yl)hexahydro-3aH-cyclopenta[b]furan-3,3a-diol 2,2,2-trifluoroacetate | 526/528 (M + 1/M + 3) |
| 81 | 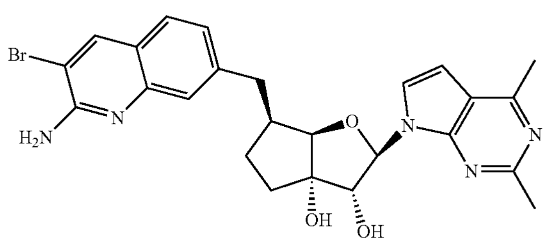 | (2R,3R,3aS,6S,6aR)-6-((2-ammo-3-bromoquinolin-7-yl)methyl)-2-(2,4-dimethyl-7H-pyrrolo[2,3-d]pyrimidin-7-yl)hexahydro-3aH-cyclcopenta[b]furan-3,3a-diol | 524/526 (M + 1/M + 3) |
| 82 | | (2R,3R,3aS,6S,6aR)-6-((2-amino-3-bromoquinolin-7-yl)oxy)-2-(4-amino-5-ethyl-7H-pyrrolo[2,3-d]pyrimidin-7-yl)hexahydro-3aH-cyclopenta[b]furan-3,3a-diol 2,2,2-trifluoroacetate | 526/528 (M + 1/M + 3) |

TABLE 20-continued

| Ex | Structure | Name | MS |
|---|---|---|---|
| 83 | 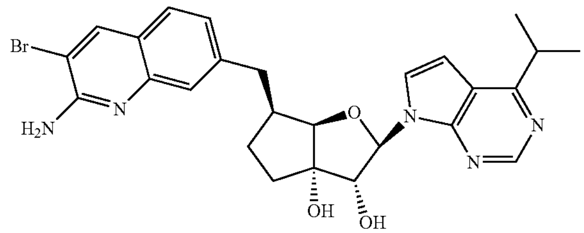 [SMILES: CC(C)c1ncnc2c1ccn2[C@@H]1O[C@@H]2[C@H](Cc3ccc4cc(Br)c(N)nc4c3)CC[C@]2(O)[C@H]1O] | (2R,3R,3aS,6S,6aR)-6-((2-amino-3-bromoquinolin-7-yl)methyl)-2-(4-isopropyl-7H-pyrrolo[2,3-d]pyrimidin-7-yl)hexahydro-3aH-cyclopenta[b]furan-3,3a-diol | 538/540 (M + 1/M + 3) |
| 84 | 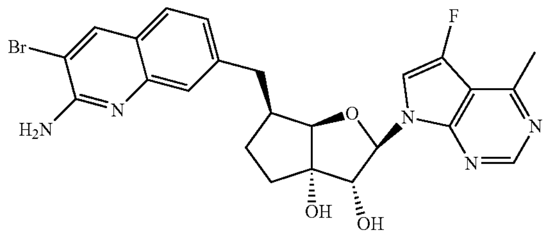 [SMILES: Cc1ncnc2c1c(F)cn2[C@@H]1O[C@@H]2[C@H](Cc3ccc4cc(Br)c(N)nc4c3)CC[C@]2(O)[C@H]1O] | (2R,3R,3aS,6S,6aR)-6-((2-amino-3-bromoquinolin-7-yl)methyl)-2-(5-fluoro-4-methyl-7H-pyrrolo[2,3-d]pyrimidin-7-yl)hexahydro-3aH-cyclopenta[b]furan-3,3a-diol | 528/530 (M + 1/M + 3) |

Examples 85-91: Examples 85-91 in Table 21 were synthesized by applying the Mitsunobu protocol described in step 7 of the synthesis of example 14. 4-chloro-7H-pyrrolo[2,3-d]pyrimidine and (3R,4S,5R)-5-(2-(3-bromo-2-((4-methoxybenzyl)amino)quinolin-7-yl)ethyl)-4-methyltetrahydrofuran-2,3,4-triol in the Mitsunobu sequence were substituted with an appropriate nucleobase and triol respectively. The substituted reagents and starting material were commercially acquired, synthesized as reported above, or synthesized through known routes reported in the literature.

TABLE 21

| Ex | Structure | Name | MS |
|---|---|---|---|
| 85 | 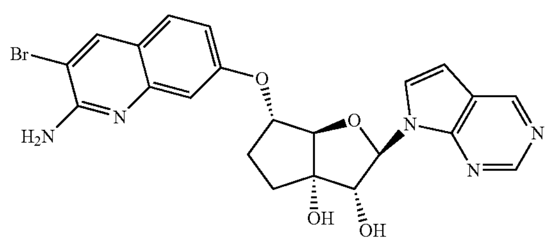 [SMILES: Nc1nc2cc(O[C@H]3CC[C@@]4(O)[C@@H]3O[C@@H](n3ccc5cncnc53)[C@@H]4O)ccc2cc1Br] | (2R,3R,3aS,6S,6aR)-6-((2-amino-3-bromoquinolin-7-yl)oxy)-2-(7H-pyrrolo[2,3-d]pyrimidin-7-yl)hexahydro-3aH-cyclopenta[b]furan-3,3a-diol | 498/500 (M + 1/M + 3) |
| 86 | 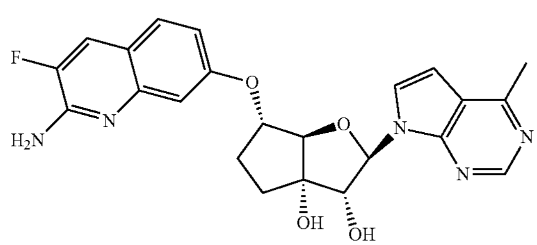 [SMILES: Cc1ncnc2c1ccn2[C@@H]1O[C@@H]2[C@@H](Oc3ccc4cc(F)c(N)nc4c3)CC[C@]2(O)[C@H]1O] | (2R,3R,3aS,6S,6aR)-6-((2-amino-3-fluoroquinolin-7-yl)oxy)-2-(4-methyl-7H-pyrrolo[2,3-d]pyrimidin-7-yl)hexahydro-3aH-cyclopenta[b]furan-3,3a-diol | 452 (M + 1) |
| 87 | 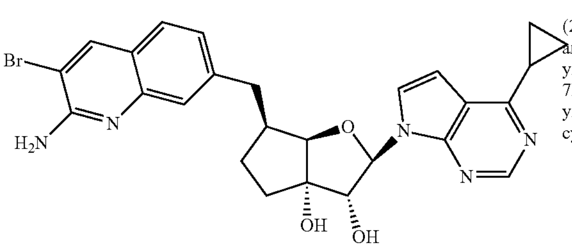 | (2R,3R,3aS,6S,6aR)-6-((2-amino-3-bromoquinolin-7-yl)methyl)-2-(4-cyclopropyl-7H-pyrrolo[2,3-d]pyrimidin-7-yl)hexahydro-3aH-cyclopenta[b]furan-3,3a-diol | 536/538 (M + 1/M + 3) |

TABLE 21-continued

| Ex | Structure | Name | MS |
|---|---|---|---|
| 88 | 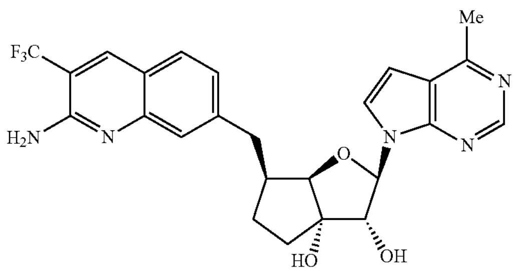 [SMILES: Cc1ncnc2c1ccn2[C@@H]1O[C@@H]2[C@H](Cc3ccc4cc(C(F)(F)F)c(N)nc4c3)CC[C@]2(O)[C@H]1O] | (2R,3R,3aS,6S,6aR)-6-((2-amino-3-(trifluoromethyl)quinolin-7-yl)methyl)-2-(4-methyl-7H-pyrrolo[2,3-d]pyrimidin-7-yl)hexahydro-3aH-cyclopenta[b]furan-3,3a-diol | 500 (M + 1) |
| 89 | 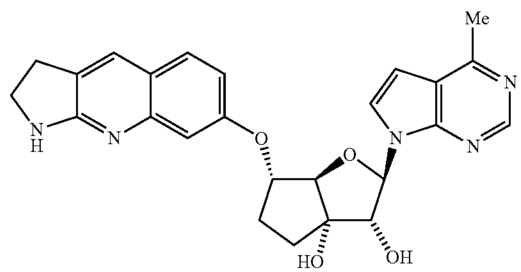 [SMILES: Cc1ncnc2c1ccn2[C@@H]1O[C@@H]2[C@@H](Oc3ccc4cc5c(nc4c3)NCC5)CC[C@]2(O)[C@H]1O] | (2R,3R,3aS,6S,6aR)-6-((2,3-dihydro-1H-pyrrolo[2,3-b]quinolin-7-yl)oxy)-2-(4-methyl-7H-pyrrolo[2,3-d]pyrimidin-7-yl)hexahydro-3aH-cyclopenta[b]furan-3,3a-diol | 460 (M + 1) |
| 90 | 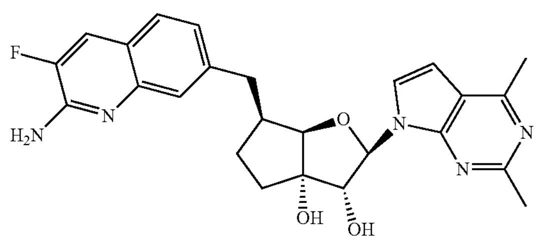 [SMILES: Cc1nc(C)c2ccn([C@@H]3O[C@@H]4[C@H](Cc5ccc6cc(F)c(N)nc6c5)CC[C@]4(O)[C@H]3O)c2n1] | (2R,3R,3aS,6S,6aR)-6-((2-amino-3-fluoroquinolin-7-yl)methyl)-2-(2,4-dimethyl-7H-pyrrolo[2,3-d]pyrimidin-7-yl)hexahydro-3aH-cyclopenta[b]furan-3,3a-diol | 464 (M + 1) |
| 91 | 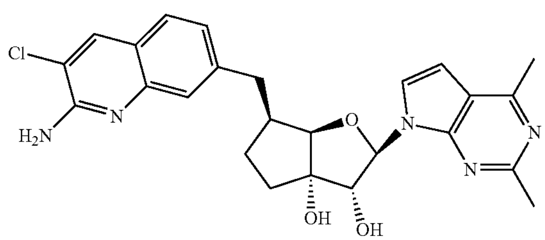 [SMILES: Cc1nc(C)c2ccn([C@@H]3O[C@@H]4[C@H](Cc5ccc6cc(Cl)c(N)nc6c5)CC[C@]4(O)[C@H]3O)c2n1] | (2R,3R,3aS,6S,6aR)-6-((2-amino-3-chloroquinolin-7-yl)methyl)-2-(2,4-dimethyl-7H-pyrrolo[2,3-d]pyrimidin-7-yl)hexahydro-3aH-cyclopenta[b]furan-3,3a-diol | 480 (M+ 1) |

Example 92

(2R,3R,3aS,6S,6aR)-6-((2-amino-3-bromoquinolin-7-yl)methyl-2-(4-(methylamino)-7H-pyrrolo[2,3-d]pyrimidin-7-yl)hexahydro-3aH-cyclopenta[b]furan-3,3a-diol

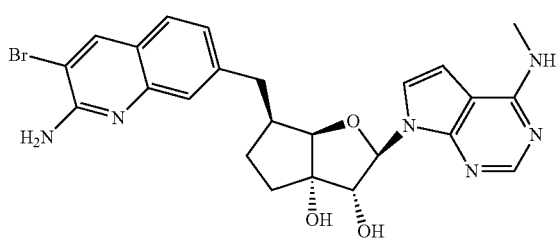 [SMILES: CNc1ncnc2c1ccn2[C@@H]1O[C@@H]2[C@H](Cc3ccc4cc(Br)c(N)nc4c3)CC[C@]2(O)[C@H]1O]

Step 1: To a vial containing (2R,3R,3aS,6S,6aR)-6-((3-bromo-2-((4-methoxybenzyl)amino)quinolin-7-yl)methyl)-2-(4-chloro-7H-pyrrolo[2,3-d]pyrimidin-7-yl)hexahydro-2H-cyclopenta[b]furan-3,3a-diol (102 ng, 0.157 mmol) dissolved in dioxane (3000 µl) was added methylamine (2.0 M in THF, 6.26 mL, 12.5 mmol) at room temperature. The mixture was sealed and heated at 70° C. for 6 h. The mixture was concentrated under reduced pressure to afford (2R,3R,3aS,6S,6aR)-6-((3-bromo-2-((4-methoxybenzyl)amino)quinolin-7-yl)methyl)-2-(4-(methylamino)-7H-pyrrolo[2,3-d]pyrimidin-7-yl)hexahydro-2H-cyclopenta[b]furan-3,3a-diol as a foam. MS: 645/647 (M+1/M+3).

Step 2: To (2R,3R,3aS,6aR)-6-((3-bromo-2-((4-methoxybenzyl)amino)quinolin-7-yl)methyl)-2-(4-(methylamino)-7H-pyrrolo[2,3-d]pyrimidin-7-yl)hexahydro-2H-cyclopenta[b]furan-3,3a-diol (101 mg, 0.156 mmol) dissolved in DCM (1304 µl) was added TFA (1300 µl, 16.87 mmol) at room temperature. The mixture was stirred for 5.5 h at 40° C. and then turned off the heat and let the reaction stir at room temperature overnight. The reaction was heated at 40° C. for 2 h. The mixture was concentrated under reduced pressure and purified by mass triggered reverse phase column chromatography (ACN:water with 0.1% NH₄OH modifier) to afford (2R,3R,3aS,6S,6aR)-6-((2-amino-3-bromoquinolin-7-yl)methyl)-2-(4-(methylamino)-7H-pyrrolo[2,3-d]pyrimidin-7-yl)hexahydro-2H-cyclopenta[b]furan-3,3a-diol as a solid. MS: 525/527 (M+1/M+3). 1H NMR (600 MHz, DMSO-d6) δ 8.31 (s, 1H), 8.19 (s, 1H), 7.55 (d, J=8.2 Hz, 2H), 7.45 (d, J=3.6 Hz, 1H), 7.28 (s, 1H), 7.09 (dd, J=8.2, 1.4 Hz, 1H), 6.67 (d, J=3.6 Hz, 1H), 6.57 (s, 2H), 5.90 (d, J=8.1 Hz, 1H), 5.25 (d, J=7.1 Hz, 1H), 5.07 (s, 1H), 4.15 (t, J=7.4 Hz, 1H), 3.96 (d, J=5.7 Hz, 1H), 2.99 (d, J=4.5 Hz, 3H), 2.86-2.79 (m, 1H), 2.66-2.58 (m, 1H), 2.29-2.22 (m, 1H), 1.98-1.91 (m, 1H), 1.78-1.65 (m, 2H), 1.58-1.49 (m, 1H).

Examples 93-97: Examples 93-97 in Table 22 were synthesized in an analogous fashion as described in steps 1-2 of Example 92 by substituting the (2R,3R,3aS,6S,6aR)-6-((3-bromo-2-((4-methoxybenzyl)amino)quinolin-7-yl)methyl)-2-(4-chloro-7H-pyrrolo[2,3-d]pyrimidin-7-yl)hexahydro-2H-cyclopenta[b]furan-3,3a-diol with an appropriate chloro nucleobase. The substituted reagents and starting material were commercially acquired, synthesized as reported above, or synthesized through known routes reported in the literature.

TABLE 22

| Ex | Structure | Name | MS |
|---|---|---|---|
| 93 | 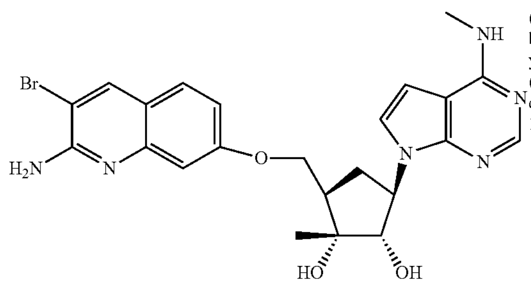 | (1R,2S,3R,5R)-5-(((2-amino-3-bromoquinolin-7-yl)oxy)methyl)-1-methyl-3-(4-(methylamino)-7H-pyrrolo[2,3-d]pyrimidin-7-yl)cyclopentane-1,2-diol | 513/515 (M + 1/M + 3) |
| 94 | 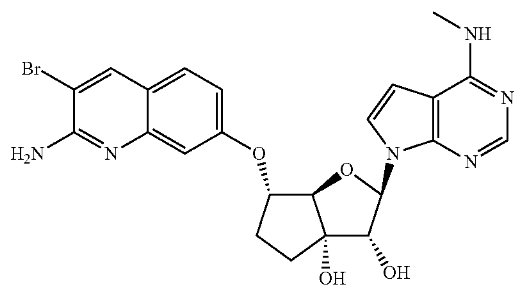 [SMILES: CNc1ncnc2c1ccn2[C@@H]1O[C@@H]2[C@@H](Oc3ccc4cc(Br)c(N)nc4c3)CC[C@]2(O)[C@H]1O] | (2R,3R,3aS,6S,6aR)-6-((2-amino-3-bromoquinolin-7-yl)oxy)-2-(4-(methylamino)-7H-pyrrolo[2,3-d]pyrimidin-7-yl)hexahydro-3aH-cyclopenta[b]furan-3,3a-diol | 527/529 (M + 1/M + 3) |
| 95 | 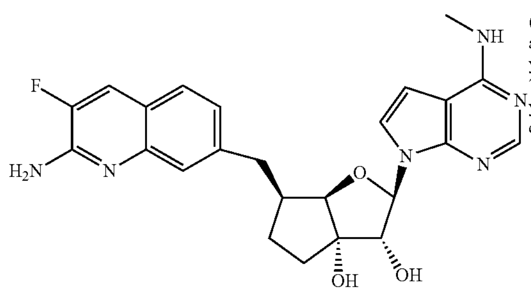 | (2R,3R,3aS,6S,6aR)-6-((2-amino-3-fluoroquinolin-7-yl)methyl)-2-(4-(methylamino)-7H-pyrrolo[2,3-d]pyrimidin-7-yl)hexahydro-3aH-cyclopenta[b]furan-3,3a-diol | 465 (M + 1) |
| 96 | 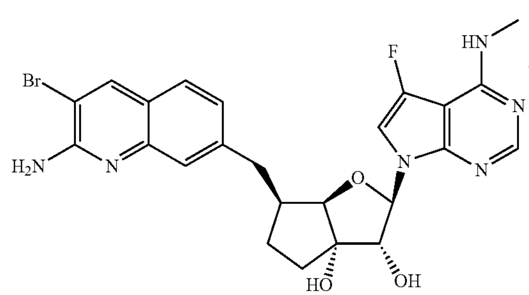 | (2R,3R,3aS,6S,6aR)-6-((2-amino-3-bromoquinolin-7-yl)methyl)-2-(5-fluoro-4-(methylamino)-7H-pyrrolo[2,3-d]pyrimidin-7-yl)hexahydro-3aH-cyclopenta[b]furan-3,3a-diol | 543/545 (M + 1/M + 3) |

TABLE 22-continued

| Ex | Structure | Name | MS |
|---|---|---|---|
| 97 | 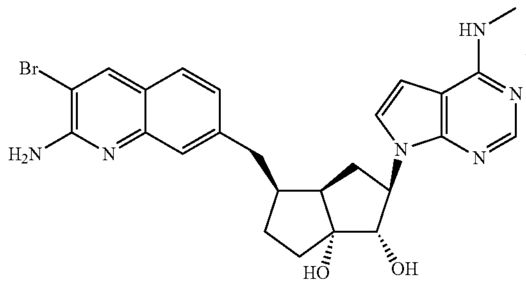 [SMILES: CNc1ncnc2c1ccn2[C@@H]1C[C@@H]2[C@H](Cc3ccc4cc(Br)c(N)nc4c3)CC[C@]2(O)[C@H]1O] | (1S,2R,3aR,4S,6aR)-4-((2-amino-3-bromoquinolin-7-yl)methyl)-2-(4-(methylamino)-7H-pyrrolo[2,3-d]pyrimidin-7-yl)hexahydropentalene-1,6a(1H)-diol | 523/525 (M + 1/M + 3) |

Example 98

(2R,3S,4R,5R)-5-(4-amino-7H-pyrrolo[2,3-d]pyrimidin-7-yl)-2-methyl-2-((quinolin-7-yloxy)methyl)tetrahydrofuran-3,4-diol

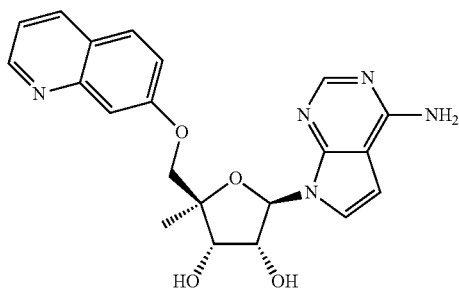 [SMILES: C[C@]1(COc2ccc3cccnc3c2)O[C@@H](n2ccc3c(N)ncnc32)[C@H](O)[C@@H]1O]

Step 1: To a solution of ((3aS,4R,6R,6aR)-6-(4-chloro-7H-pyrrolo[2,3-d]pyrimidin-7-yl)-2,2,4-trimethyltetrahydrofuro[3,4-d][1,3]dioxol-4-yl)methanol (400 mg, 1.18 mmol), quinolin-7-ol (205 mg, 1.41 mmol) and triphenylphosphine (1578 mg, 3.06 mmol) were stirred in anhydrous THF (12 mL) under nitrogen gas. DIAD (0.572 mL, 2.94 mmol) was added dropwise at 0° C. The mixture was stirred at room temperature overnight. The reaction mixture was filtered and washed with MeOH. The filtrate was concentrated under reduced pressure and purified by column chromatography on silica (EtOAc/PE 0-50% and then MeOH/DCM 0-5%) to afford 7-(((3aS,4R,6R,6aR)-6-(4-chloro-7H-pyrrolo[2,3-d]pyrimidin-7-yl)-2,2,4-trimethyltetrahydrofuro[3,4-d][1,3]dioxol-4-yl)methoxy)quinoline as a solid. Then, ammonia (28% in water) (I mL, 12.94 mmol) was added to a stirred solution of 7-(((3aS,4R,6R,6aR)-6-(4-chloro-7H-pyrrolo[2,3-d]pyrimidin-7-yl)-2,2,4-trimethyltetrahydrofuro[3,4-d][1,3]dioxol-4-yl)methoxy)quinoline (100 mg, 0.214 mmol) in dioxane (1 mL), and the mixture was stirred at 120° C. for 8.5 h. The reaction mixture was evaporated under reduced pressure and purified by reverse phase HPLC (ACN/Water) to afford 7-((3aR,4R,6R,6aS)-2,2,6-trimethyl-6-((quinolin-7-yloxy)methyl)tetrahydrofuro[3,4-d][1,3]dioxol-4-yl)-7H-pyrrolo[2,3-d]pyrimidin-4-amine as a solid. MS: 448 (M+1).

Step 2 To compound 7-((3aR,4R,6R,6aS)-2,2,6-trimethyl-6-((quinolin-7-yloxy)methyl)tetrahydrofuro[3,4-d][1,3]dioxol-4-yl)-7H-pyrrolo[2,3-d]pyrimidin-4-amine (11 mg, 0.025 mmol) was added premixed TFA (70 µl, 0.909 mmol)/water (150 µl) at 0° C. The resulting suspension was stirred at room temperature for 30 minutes. The reaction mixture was concentrated under reduced pressure. The residue was purified by reverse phase HPLC (MeCN/Water) to afford (2R,3S,4R,5R)-5-(4-amino-7H-pyrrolo[2,3-d]pyrimidin-7-yl)-2-methyl-2-((quinolin-7-yloxy)methyl)tetrahydrofuran-3,4-diol as a solid. MS: 408 (M+1). $^1$H NMR (400 MHz, Methanol-$d_4$) δ 8.79 (dd, J=4.5, 1.7 Hz, 1H), 8.32 (d, J=6.7 Hz, 1H), 8.10 (s, 1H), 7.91 (d, J=9.0 Hz, 1H), 7.48-7.37 (m, 51H), 6.62 (d, J=3.7 Hz, 1H), 6.30 (d, J=6.7 Hz, 1H), 4.45 (d, J=5.5 Hz, 1H), 4.32-4.21 (m, 2H), 1.53 (s, 3H).

Example 99: Example 99 in Table 23 was synthesized by following Steps 1-2 of Example 98 above starting from Intermediate 28.

TABLE 23

| Ex | Structure | Name | MS |
|---|---|---|---|
| 99 | 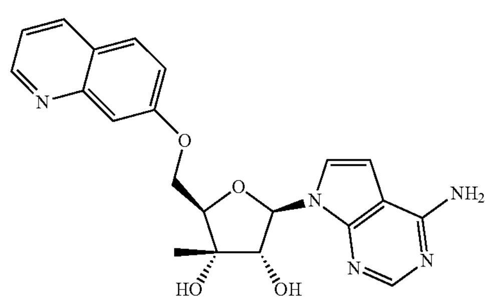 [SMILES: C[C@@]1(O)[C@@H](COc2ccc3cccnc3c2)O[C@@H](n2ccc3c(N)ncnc32)[C@@H]1O] | (2R,3S,4R,5R)-5-(4-amino-7H-pyrrolo[2,3-d]pyrimidin-7-yl)-3-methyl-2-((quinolin-7-yloxy)methyl)tetrahydrofuran-3,4-diol | 408 (M + 1) |

Example 100

(1S,2R,3R,5R)-3-(((2-amino-3-bromoquinolin-7-yl)oxy)methyl)-5-(4-amino-7H-pyrrolo[2,3-d]pyrimidin-7-yl)-3-methylcyclopentane-1,2-diol

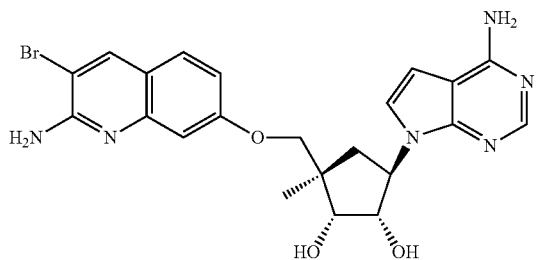 [SMILES: C[C@@]1(COc2ccc3cc(Br)c(N)nc3c2)C[C@@H](n2ccc3c(N)ncnc32)[C@H](O)[C@@H]1O]

Step 1: To a solution of lithium bis(trimethylsilyl)amide (73.9 mL, 73.9 mmol) at −70° C. was added a solution of (1S,4R)-methyl 4-((tert-butoxycarbonyl)amino)cyclopent-2-enecarboxylate (8 g, 33.2 mmol) in THF (8 mL) over 2 minutes at −70° C. The resulted solution was stirred at −70° C. for 30 minutes before iodomethane (3.67 mL, 59.0 mmol) was added for 5 minutes. The reaction was warmed to −25° C. and this temperature was maintained for 2 h. The resulting mixture was diluted with saturated aqueous NaHCO₃ (200 mL) and extracted with EtOAc (3×200 mL). The combined organic layers were washed with brine (200 mL), dried over anhydrous sodium sulfate, and filtered. The filtrate was concentrated under reduced pressure, and the residue was purified by column chromatography on silica (16.6% EtOAc/PE) to afford (1S,4R)-methyl 4-((tert-butoxycarbonyl)amino)-1-methylcyclopent-2-enecarboxylate as an oil. MS: 199 (M−56).

Step 2: To a stirred mixture of (1S,4R)-methyl 4-((tert-butoxycarbonyl)amino)-1-methylcyclopent-2-enecarboxylate (7.1 g, 27.8 mmol) in THF (100 mL) was added lithium tetrahydroborate (27.8 mL, 55.6 mmol) at 0° C. under an argon atmosphere. The resulting mixture was warmed to 25° C. and stirred for 16 h. The reaction mixture was quenched by MeOH (50 mL), diluted with saturated aqueous NH₄Cl (300 mL) and then extracted with EtOAc (3×200 mL). The combined organic layers were washed with brine (200 mL), dried over anhydrous sodium sulfate, and filtered. The filtrate was concentrated under reduced pressure and recrystallized from PE (100 mL). The solid was collected by filtration and dried under reduced pressure to afford tert-butyl ((1R,4S)-4-(hydroxymethyl)-4-methylcyclopent-2-en-1-yl)carbamate as a solid. MS: 228 (M+1).

Step 3: A mixture of tert-butyl ((1R,4S)-4-(hydroxymethyl)-4-methylcyclopent-2-en-1-yl)carbamate (7.84 g, 34.5 mmol) and HCl (4 M in dioxane, 80 mL) was stirred at 25° C. for 2 h. The solution was then concentrated under reduced pressure, and the residue was triturated with ether (200 mL). The solid was collected, washed with ether (100 mL), and dried to afford ((1S,4R)-4-amino-1-methylcyclopent-2-en-1-yl)methanol hydrochloride as a solid. MS: 128 (M+1).

Step 4: To a stirred mixture of ((1S,4R)-4-amino-1-methylcyclopent-2-en-1-Yl)methanol hydrochloride (5.5 g, 32.6 mmol) in 2-propanol (120 mL) were added 2-(4,6-dichloropyrimidin-5-yl)acetaldehyde (6.85 g, 35.9 mmol) and triethylamine (6.60 g, 65.2 mmol) at 25° C. under argon atmosphere. The resulting mixture was stirred at 82° C. for 16 h. The reaction mixture was quenched by water (250 mL) and extracted with ethyl acetate (3×200 mL). The combined organic layers were washed with brine (200 mL), dried over anhydrous sodium sulfate, and filtered. The filtrate was concentrated under reduced pressure, and the residue was purified by column chromatography on silica (25-32% EtOAc/PE) to afford ((1S,4R)-4-(4-chloro-7H-pyrrolo[2,3-d]pyrimidin-7-yl)-1-methylcyclopent-2-en-1-yl))methanol as a solid. MS: 264 (M+1).

Step 5: To a solution of ((1S,4R)-4-(4-chloro-7H-pyrrolo[2,3-d]pyrimidin-7-yl)-1-methylcyclopent-2-en-1-yl)methanol (300 mg, 1.138 mmol) in THF (5 mL) was added sodium phenolate (660 mg, 5.69 mmol) at 0° C. under an argon atmosphere. The reaction mixture was stirred at 66° C. for 12 h. The reaction mixture was quenched by saturated aqueous NH₄Cl (100 mL) and extracted with EtOAc (3×100 mL). The combined organic layers were washed with brine (100 mL), dried over anhydrous sodium sulfate, and filtered. The filtrate was concentrated under reduced pressure, and the residue was purified by column chromatography on silica (0-60% EtOAc/PE) to afford ((1S,4R)-1-methyl-4-(4-phenoxy-7H-pyrrolo[2,3-d]pyrimidin-7-yl)cyclopent-2-en-1-yl)methanol as a solid. MS: 322 (M+1).

Step 6: To a solution of ((1S,4R)-1-methyl-4-(4-phenoxy-7H-pyrrolo[2,3-d]pyrimidin-7-yl)cyclopent-2-en-1-yl)methanol (260 mg, 0.809 mmol) in DMF (1 mL) were added 1H-imidazole (116 mg 1.699 mmol) and tert-butylchlorodiphenylsilane (289 mg, 1.052 mmol) in one portion at 0° C. under an argon atmosphere. The reaction mixture was stirred at 25° C. for 1.5 h. The reaction mixture was quenched by saturated aqueous NH₄Cl (150 mL) and extracted with EtOAc (3×100 mL). The combined organic layers were washed with brine (100 mL), dried over anhydrous sodium sulfate, and filtered. The filtrate was concentrated under reduced pressure, and the residue was purified by column chromatography on silica (10-20% EtOAc/PE) to afford 7-((1R,4S)-4-(((tert-butyldiphenylsilyl)oxy)methyl)-4-methylcyclopent-2-en-1-yl)-4-phenoxy-7H-pyrrolo[2,3-d]pyrimidine as a solid. MS: 560 (M+1).

Step 7: To a stirred solution of 7-((1R,4S)-4-(((tert-butyldiphenylsilyl)oxy)methyl)-4-methylcyclopent-2-en-1-yl)-4-phenoxy-7H-pyrrolo[2,3-d]pyrimidine (260 mg, 0.464 mmol) in THF (4 mL) were added pyridine (4 mL, 49.5 mmol) and osmium(VIII) oxide (1.299 mL, 0.511 mmol) at 0° C. under argon atmosphere. The resulting mixture was stirred at the same temperature for 1 h. The reaction mixture was quenched by saturated aqueous Na₂S₂O₃ (25 mL) and extracted with EtOAc (5×20 mL). The combined organic layers were washed with brine (50 mL), dried over anhydrous sodium sulfate, and filtered. The filtrate was concentrated under reduced pressure. The residue was dissolved in tBuOH (3.00 mL), and water (3 mL) and hydrogen sodium sulfite (5.52 mg, 0.053 mmol) were added at 25° C. under air. The resulting mixture was stirred for 20 minutes. The reaction mixture was diluted with saturated aqueous NaHSO₃ (25 mL) and extracted with EtOAc (3×25 mL). The combined organic layers were washed with brine (50 mL), dried over anhydrous sodium sulfate, and filtered. The crude residue was purified by column chromatography on silica (0-70% EtOAc/PE) to afford (3R,5R)-3-(((tert-butyldiphenylsilyl)oxy)methyl)-3-methyl-5-(4-phenoxy-7H-pyrrolo[2,3-d]pyrimidin-7-yl)cyclopentane-1,2-diol as an oil. MS: 594 (M+1).

Step 8: To a stirred solution of (3R,5R)-3-(((tert-butyldiphenylsilyl)oxy)methyl)-3-methyl-5-(4-phenoxy-7H-pyrrolo[2,3-d]pyrimidin-7-yl)cyclopentane-1,2-diol (2.2 g, 3.71 mmol) in dry acetone (12 mL) were added 4-methylbenzenesulfonic acid (0.064 g, 0.371 mmol) and 2,2-dimethoxypropane (1.93 g, 18.5 mmol). The resulting mixture was stirred at 25° C. for 3 h. EtOAc (300 mL) and saturated aqueous NaHCO₃ (100 mL) were added to the solution, the organic layer was concentrated under reduced pressure, and the residue was purified by column chromatography on silica (0-30% EtOAc/PE) to afford 7-((3aS,4R,6R,6aR)-6-(((tert-butyldiphenylsilyl)oxy)methyl)-2,2,6-trimethyltetrahydro-3aH-cyclopenta[d][1,3]dioxol-4-yl)-4-phenoxy-7H-pyrrolo[2,3-d]pyrimidine as a foam. MS: 634 (M+1).

Step 9: To a stirred solution of 7-((3aS,4R,6R,6aR)-6-(((tert-butyldiphenylsilyl)oxy)methyl)-2,2,6-trimethyltetrahydro-3aH-cyclopenta[d][1,3]dioxol-4-yl)-4-phenoxy-7H-pyrrolo[2,3-d]pyrimidine (650 mg, 1.025 mmol) in THF (5 mL) was added tetrabutylammonium fluoride (1 M in THF, 3.08 mL, 3.08 mmol) at 25° C. The resulting mixture was stirred at 25° C. for 2 h. Saturated aqueous NaHCO₃(100 mL) and EtOAc (250 mL) were added to the solution, then the organic layer was concentrated under reduced pressure, and the residue was purified by column chromatography (0-70% EtOAc/PE) to afford ((3aR,4R,6R,6aS)-2,2,4-trimethyl-6-(4-phenoxy-7H-pyrrolo[2,3-d]pyrimidin-7-yl)tetrahydro-3aH-cyclopenta[d][1,3]dioxol-4-yl)methanol as a foam. MS: 396 (M+1).

Step 10: To a stirred mixture of ((3aR,4R,6R,6aS)-2,2,4-trimethyl-6-(4-phenoxy-7H-pyrrolo[2,3-d]pyrimidin-7-yl)tetrahydro-3aH-cyclopenta[d][1,3]dioxol-4-yl)methanol (270 mg, 0.683 mmol) in 1,4-dioxane (6 ml) were added 3-bromo-7-iodo-N-(4-methoxybenzyl)quinolin-2-amine (256 mg, 0.546 mmol), 1,10-phenanthroline (19.7 mg, 0.109 mmol), copper(I) iodide (10.4 mg, 0.055 mmol) and cesium carbonate (267 mg, 0.819 mmol). The resulting mixture was stirred at 110° C. for 18 h. The mixture was concentrated under reduced pressure, and the residue was purified by column chromatography on silica (0-30% EtOAc/PE) to afford 3-bromo-N-(4-methoxybenzyl)-7-(((3aR,4R,6R,6aS)-2,24-trimethyl-6-(4-phenoxy-7H-pyrrolo[2,3-d]pyrimidin-7-yl)tetrahydro-3aH-cyclopenta[d][1,3]dioxol-4-yl)methoxy)quinolin-2-amine as a solid. MS: 736/738 (M+₁/M+3).

Step 11: 3-bromo-N-(4-methoxybenzyl)-7-(((3aR,4R,6R,6aS)-2,2,4-trimethyl-6-(4-phenoxy-7-1 pyrrolo[2,3-d]pyrimidin-7-yl)tetrahydro-3aH-cyclopenta[d][1,3]dioxol-4-yl)methoxy)quinolin-2-amine (230 mg, 0.312 mmol) was dissolved in 2,2,2-trifluoroacetic acid (5 mL, 67.3 mmol), then the solution was stirred at 60° C. for 2 h. The solution was co-evaporated with toluene five times, to afford (1S,2R,3R,5R)-3-(((2-amino-3-bromoquinolin-7-yl)oxy)methyl)-3-methyl-5-(4-phenoxy-7H-pyrrolo[2,3-d]pyrimidin-7-yl)cyclopentane-1,2-diol. MS: 576/578 (M+1/M+3).

Step 12: To a solution of (1S,2R,3R,5R)-3-(((2-amino-3-bromoquinolin-7-yl)oxy)methyl)-3-methyl-5-(4-phenoxy-7H-pyrrolo[2,3-d]pyrimidin-7-yl)cyclopentane-1,2-diol (230 mg, 0.299 mmol) in 2-propanol (2 mL) was added ammonia in i-PrOH(NH₃/i-PrOH 5:1) (5 mL, 0.299 mmol) at −50° C., the resulting mixture was stirred at 130° C. for 64 h. The reaction mixture was concentrated under reduced pressure, and the residue was purified by prep-HPLC (ACN/water) to afford (1S,2R,3R,5R)-3-(((2-amino-3-bromoquinolin-7-yl)oxy)methyl)-5-(4-amino-7H-pyrrolo[2,3-d]pyrimidin-7-yl)-3-methylcyclopentane-1,2-diol as a solid. MS: 499/501 (M+1/M+3). 1H-NMR (400 MHz, DMSO-d6) δ 8.29 (s, 1H), 8.03 (s, 1H), 7.59 (d, J=9.2 Hz, 1H), 7.31 (d, J=3.6 Hz, 1H), 6.98-6.92 (m, 2H), 6.89 (br s, 2H), 6.55 (d, J=3.2 Hz, 1H), 6.51 (br s, 2H), 5.03-4.96 (m, 1H), 4.85 (d, J=6.8 Hz, 1H), 4.75 (d, J=4.8 Hz, 1H), 4.56-4.50 (m, 1H), 4.03 (d, J=9.2 Hz, 1H), 3.97-3.91 (m, 2H), 1.93 (d, J=9.6 Hz, 2H), 1.19 (s, 3H).

Example 101

(1S,2R,3R,5R)-5-(4-amino-7H-pyrrolo[2,3-d]pyrimidin-7-yl)-3-(((2-aminoquinolin-7-yl)oxy)methyl)-3-methylcyclopentane-1,2-diol

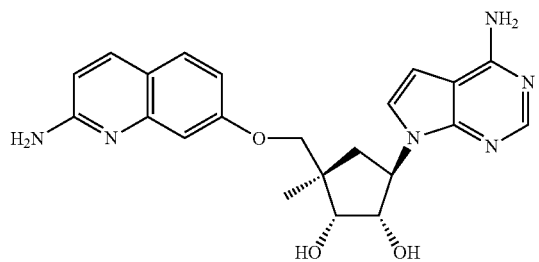 [SMILES: C[C@@]1(COc2ccc3ccc(N)nc3c2)C[C@@H](n2ccc3c(N)ncnc32)[C@H](O)[C@@H]1O]

Step 1: To a solution of (1S,2R,3R,5R)-3-(((2-amino-3-bromoquinolin-7-yl)oxy)methyl)-5-(4-amino-7H-pyrrolo[2,3-d]pyrimidin-7-yl)-3-methylcyclopentane-1,2-diol (26 mg, 0.052 mmol) in MeOH (3 mL) was added Pd/C (10%) (20 mg) at 25° C. The mixture was stirred under an atmosphere of hydrogen at 25° C. for 30 minutes, the mixture was filtered and the filtrate was purified by reverse phase flash column (ACN/water) to afford (1S,2R,3R,5R)-5-(4-amino-7H-pyrrolo[2,3-d]pyrimidin-7-yl)-3-(((2-aminoquinolin-7-yl)oxy)methyl)-3-methylcyclopentane-1,2-diol as a solid. MS: 421 (M+1). ¹H-NMR (300 MHz, DMSO-d6) δ 8.00 (s, 1H), 7.76 (d, J=9.0 Hz, 1H), 7.50 (d, J=8.7 Hz, 1H), 7.28 (d, J=3.6 Hz, 1H), 6.91-6.80 (m, 4H), 6.57-6.52 (m, 2H), 6.26 (br s, 2H), 5.01-4.92 (m, 1H), 4.82 (d, J=6.6 Hz, 1H), 4.71 (d, J=4.8 Hz, 1H), 4.53-4.46 (m, 1H), 3.98 (d, J=9.6 Hz, 1H), 3.91-3.89 (m, 2H), 1.91-1.88 (m, 2H), 1.16 (s, 3H).

Example 102

(1S,2R,5R)-3-(2-(2-amino-3-bromoquinolin-7-yl)ethyl-5-(4-amino-7H-pyrrolo[2,3-d]pyrimidin-7-yl)-3-(fluoromethyl)cyclopentane-1,2-diol

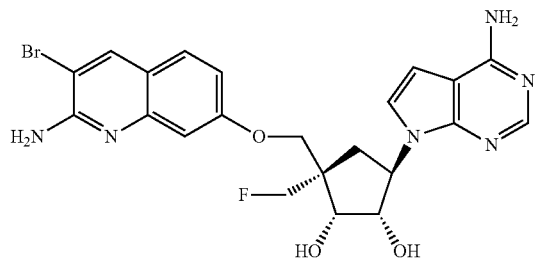 [SMILES: Nc1nc2cc(OC[C@]3(CF)C[C@@H](n4ccc5c(N)ncnc54)[C@H](O)[C@@H]3O)ccc2cc1Br]

Step 1: To a stirred mixture of (1R,2S,3R,5R)-3-(4-chloro-7H-pyrrolo[2,3-d]pyrimidin-7-yl)-5-(hydroxymethyl)cyclopentane-1,2-diol (4.0 g, 14.1 mmol) (azeotroped with toluene 3x) in pyridine (40 mL) was added 1-(chloro(4-methoxyphenyl)(phenyl)methyl)-3-methoxybenzene (5.25 g, 15.5 mmol) at room temperature under an argon atmosphere. The resulting mixture was stirred for about 3 h at room temperature. The reaction mixture was quenched by MeOH (25 mL). The mixture was azeotroped with toluene, and the residue was purified by column chromatography on silica (1-10% MeOH/DCM) to afford (1S,2R,3R,5R)-3-4 (bis(4-methoxyphenyl)(phenyl)methoxy)methyl)-5-(4- chloro-7H-pyrrolo[2,3-d]pyrimidin-7-yl)cyclopentane-1,2-diol as a solid. MS: 586 (M+1). ¹H-NMR (300 MHz, DMSO-d₆) δ 8.59 (s, 1H), 7.81 (d, J=3.6 Hz, 1H), 7.44-7.41 (m, 2H), 7.35-7.24 (m, 7H), 6.92-6.90 (m, 4H), 6.68 (d, J=3.6 Hz, 1H), 4.98-4.93 (m, 2H), 4.79 (d, J=3.6 Hz, 1H), 4.28-4.26 (m, 1H), 3.89-3.87 (m, 1H), 3.75 (s, 6H), 3.20-3.17 (m, 1H), 3.09-3.05 (m, 1H), 2.32-2.26 (m, 2H), 1.76-1.69 (m, 1H).

Step 2: To a stirred mixture of (1S,2R,3R,5R)-3-((bis(4-methoxyphenyl)(phenyl)methoxy)methyl)-5-(4-chloro-7H-pyrrolo[2,3-d]pyrimidin-7-yl)cyclopentane-1,2-diol (6.0 g, 10.2 mmol) (azeotroped with toluene 3×) in DMF (80 mL) was added sodium hydride (60% in mineral oil) (1.64 g, 41.0 mmol) at 0° C. under an argon atmosphere. The resulting mixture was stirred for about 30 minutes at 0° C., then tetrabutylammonium iodide (1.89 g, 5.12 mmol) and (bromomethyl)benzene (5.25 g, 30.7 mmol) were further added. The resulting mixture was warmed to room temperature and stirred for 3 h. The reaction mixture was quenched by saturated aqueous NH₄Cl (150 mL) and extracted with EtOAc (3×200 mL). The combined organic fractions were washed with brine (3×100 mL), dried over anhydrous sodium sulfate, and filtered. The filtrate was concentrated under reduced pressure, and the residue was purified by column chromatography on silica (0-50% EtOAc/PE) to afford 7-((1R,2S,3R,4R)-2,3-bis(benzyloxy)-4-((bis(4-methoxyphenyl)(phenyl)methoxy)methyl)cyclopentyl)-4-chloro-7H-pyrrolo[2,3-d]pyrimidine as a solid. MS: 766 (M+1). ¹H-NMR (300 MHz, DMSO-d₆) δ 8.46 (s, 1H), 7.75 (d, J=3.9 Hz, 1H), 7.38-7.08 (m, 17H), 6.91-6.84 (m, 6H), 6.61 (d, J=3.6 Hz, 1H), 5.20-5.10 (m, 1H), 4.61-4.48 (m, 2H), 4.39-4.35 (m, 1H), 4.27-4.19 (m, 2H), 3.93-3.91 (m, 1H), 3.71 (s, 6H), 3.15-3.11 (m, 2H), 2.50-2.40 (m, 1H), 2.30-2.20 (m, 1H), 1.82-1.72 (m, 1H).

Step 3: To a stirred solution of 7-((1R,2S,3R,4R)-2,3-bis(benzyloxy)-4-((bis(4-methoxyphenyl)(phenyl)methoxy)methyl)cyclopentyl)-4-chloro-7H-pyrrolo[2,3-d]pyrimidine (6.0 g, 7.83 mmol) in DCM (50 mL) were added water (1.411 g, 78 mmol) and 2,2-dichloroacetic acid (6% DCA in DCM) (9.09 g, 70.5 mmol) at room temperature under an argon atmosphere. The resulting mixture was stirred for 15 minutes at this temperature. Then triethylsilane (18.21 g, 157 mmol) was further added, the resulting mixture was stirred for 50 minutes at this temperature. The reaction mixture was quenched by pyridine (11.2 g, 141 mmol) at 0° C. and stirred for 15 minutes. The mixture was azeotroped with toluene and the residue was purified by column chromatography on silica (0-50% EtOAc/PE) to afford ((1R,2R,3S,4R)-2,3-bis(benzyloxy)-4-(4-chloro-7H-pyrrolo[2,3-d]pyrimidin-7-yl)cyclopentyl)methanol as a solid. MS: 464 (M+1). ¹H-NMR (300 MHz, DMSO-d₆) δ 8.56 (s, 1H), 7.86 (d, J=3.6 Hz, 1H), 7.39-7.27 (m, 5H), 7.15-7.11 (m, 3H), 6.94-6.91 (m, 2H), 6.66 (d, J=3.6 Hz, 1H), 5.36-5.14 (m, 1H), 4.86-4.84 (m, 1H), 4.67-4.52 (m, 2H), 4.45-4.41 (m, 1H), 4.35-4.30 (m, 1H), 4.29-4.25 (m, 1H), 4.03-3.97 (m, 1H), 3.49-3.47 (m, 2H), 2.31-2.27 (m, 2H), 1.74-1.68 (m, 1H).

Step 4: To a stirred solution of ((1R,2R,3S,4R)-2,3-bis(benzyloxy)-4-(4-chloro-7H-pyrrolo[2,3-d]pyrimidin-7-yl)cyclopentyl)nethanol (3.1 g, 6.68 mmol) in DCM (25 mL) was added Dess-Martin periodinane (5.67 g, 13.4 mmol) at 0° C. under an argon atmosphere. The resulting mixture was stirred for 15 minutes at 0° C., then the reaction mixture was warmed to room temperature and stirred for 1 h. The reaction mixture was quenched by saturated aqueous NaHCO₃ (20 mL) and extracted with EtOAc (3×100 mL). The combined organic fractions were washed with brine (3×40 mL), dried over anhydrous sodium sulfate, and filtered. The filtrate was concentrated under reduced pressure, and the residue was purified by column chromatography on silica (0-50% EtOAc/PE) to afford (1S,2R,3S,4R)-2,3-bis(benzyloxy)-4-(4-chloro-7H-pyrrolo[2,3-d]pyrimidin-7-yl)cyclopentanecarbaldehyde as a solid. MS: 462 (M+1). ¹H-NMR (400 MHz, DMSO-d₆) δ 9.79 (s, 1H), 8.57 (s, 1H), 7.85 (d, J=3.6 Hz, 1H), 7.43-7.33 (m, 5H), 7.18-7.13 (m, 3H), 6.96-6.93 (m, 2H), 6.70 (d, J=3.6 Hz, 1H), 5.35-5.28 (m, 1H), 4.75-4.64 (m, 2H), 4.51-4.49 (m, 2H), 4.35-4.23 (m, 2H), 3.32-3.28 (m, 1H), 2.49-2.33 (m, 2H).

Step 5: To a stirred solution of (1S,2R,3S,4R)-2,3-bis(benzyloxy)-4-(4-chloro-7H-pyrrolo[2,3-d]pyrimidin-7-yl)cyclopentanecarbaldehyde (2.4 g, 5.20 mmol) in dioxane (20 mL) were added potassium carbonate (18.8 mL, 37.7 mmol) and formaldehyde (1.01 mL, 5.20 mmol) at 25° C. under an argon atmosphere. The resulting mixture was stirred for 16 h at 25° C. The reaction mixture was quenched by adding HCl aqueous (1 M, 20 mL) to adjust pH=7 at 0° C. The mixture solvent was removed under reduced pressure. The residue was dissolved in ethanol (20 mL), then sodium borohydride (0.236 g, 6.23 mml) was added at 0° C. under an argon atmosphere. The reaction was stirred at 0° C. for about 2 h. The reaction mixture was quenched by HCl aqueous (1 M, 20 mL, to adjust pH=7) at 0° C., water (50 mL) was further added, and the mixture was extracted with EtOAc (3×100 mL). The combined organic fractions were washed with brine (3×50 mL), dried over anhydrous sodium sulfate, and filtered. The filtrate was concentrated under reduced pressure, and the residue was purified by column chromatography on silica (0-80% EtOAc/PE) to afford ((2R,3S,4R)-2,3-bis(benzyloxy)-4-(4-chloro-7H-pyrrolo[2,3-d]pyrimidin-7-yl)cyclopentane-1,1-diyl)dimethanol as a solid. MS: 494 (M+1). ¹H-NMR (300 MHz, DMSO-d₆) δ 8.54 (s, 1H), 7.83 (d, J=3.6 Hz, 1H), 7.38-7.29 (m, 5H), 7.12-7.08 (m, 3H), 6.91-6.88 (m, 2H), 6.64 (d, J=3.6 Hz, 1H), 5.29-5.19 (m, 1H), 4.89-4.85 (m, 1H), 4.73-4.69 (m, 1H), 4.61-4.59 (m, 1H), 4.55-4.49 (m, 1H), 4.48-4.46 (m, 1H), 4.39-4.35 (m, 1H), 4.31-4.27 (m, 1H), 4.09-4.07 (m, 1H), 3.61-3.51 (m, 4H), 2.08-2.00 (m, 1H), 1.71-1.63 (m, 1H).

Step 6: To a stirred solution of ((2R,3S,4R)-2,3-bis(benzyloxy)-4-(4-chloro-7H-pyrrolo[2,3-d]pyrimidin-7-yl)cyclopentane-1,1-diyl)dimethanol (1.2 g, 2.429 mmol) (azeotroped with toluene 3×) in DCM (30 mL) was added triethylamine (0.737 g, 7.29 mmol) at 0° C. under an argon atmosphere. (Chloro(4-methoxyphenyl)methylene)dibenzene (0.788 g, 2.55 mmol) was further added at this temperature, then the reaction mixture was warmed to room temperature and stirred for 2 h. The reaction mixture was quenched by saturated aqueous NH₄Cl (40 mL) and extracted with EtOAc (3×100 mL). The combined organic fractions were washed with brine (3×50 mL), dried over anhydrous sodium sulfate, and filtered. The filtrate was concentrated under reduced pressure, and the residue was purified by column chromatography on silica (0-80% EtOAc/PE) to afford a mixture ((1S,2R,3S,4R)-2,3-bis(benzyloxy)-4-(4-chloro-7H-pyrrolo[2,3-d]pyrimidin-7-yl)-1-(((4-methoxyphenyl)diphenylmethoxy)methyl)cyclopentyl)methanol and ((1R,2R,3S,4R)-2,3-bis(benzyloxy)-4-(4-chloro-7H-pyrrolo[2,3-d]pyrimidin-7-yl)-1-(((4-methoxyphenyl)diphenylmethoxy)methyl)cyclopentyl)methanol as a solid. MS: 766 (M+1). ¹H NMR of the mixture (two regioisomers) (400 MHz, DMSO-d₆) δ 8.57-8.52 (m, 1H), 7.82 (d, J=3.6 Hz, 1H), 7.43-7.24 (m, 15H), 7.13-7.06 (m, 5H), 6.88-6.84 (m, 4H), 6.66 (d, J=36 Hz, 1H), 5.14-5.08 (m, 2H), 4.96-4.40 (m, 4H), 4.2-4.12 (m, 2H), 3.77-3.74 (m, 5H), 3.39-3.36 (m, 1H), 3.21-3.19 (m, 1H), 2.09-2.00 (m, 1H), 1.86-1.80 (m, 1H).

Step 7: To a stirred mixture of ((1S,2R,3S,4R)-2,3-bis(benzyloxy)-4-(4-chloro-7H-pyrrolo[2,3-d]pyrimidin-7-yl)-1-(((4-methoxyphenyl)diphenylmethoxy)methyl)cyclopentyl)methanol (1.45 g, 0.473 mmol) and ((1R,2R,3S,4R)-2,3-bis(benzyloxy)-4-(4-chloro-7H-pyrrolo[2,3-d]pyrimidin-7-yl)-1-(((4-methoxyphenyl)diphenylmethoxy)methyl)cyclopentyl)methanol (1.45 g, 1.42 mmol) (azeotroped with toluene 3×) in DMF (15 mL) was added sodium hydride (60% in mineral oil) (0.227 g, 5.68 mmol) at 0° C. under an argon atmosphere. The resulting mixture was stirred for about 30 minutes at 0° C., then tetrabutylammonium iodide (0.262 g, 0.710 mmol) and (bromomethyl)benzene (0.728 g, 4.26 mmol) were further added. The resulting mixture was warmed to room temperature and stirred for 3 hours. The reaction mixture was quenched by saturated aqueous NH$_4$CJ (20 mL) and extracted with EtOAc (3×100 mL). The combined organic fractions were washed with brine (3×50 mL), dried over anhydrous sodium sulfate, and filtered. The filtrate was concentrated under reduced pressure, and the residue was purified by column chromatography on silica (0-80% EtOAc/PE) to afford a mixture 7-((1R,2S,3R,4S)-2,3-bis(benzyloxy)-4-((benzyloxy)methyl)-4-(((4-methoxyphenyl)diphenylmethoxy)methyl)cyclopentyl)-4-chloro-7H-pyrrolo[2,3-d]pyrimidine as a solid and 7-((1R,2S,3R,4R)-2,3-bis(benzyloxy)-4-((benzyloxy)methyl)-4-(((4-methoxyphenyl)diphenylmethoxy)methyl)cyclopentyl)-4-chloro-7H-pyrrolo[2,3-d]pyrimidine as a solid. MS: 856 (M+1).

Step 8: 7-((1R,2S,3R,4S)-2,3-bis(benzyloxy)-4-((benzyloxy)methyl)-4-(((4-methoxyphenyl)diphenylmethoxy)methyl)cyclopentyl)-4-chloro-7H-pyrrolo[2,3-d]pyrimidine (1.00 g, 0.292 mmol) and 7-((1R,2S,3R,4R)-2,3-bis(benzyloxy)-4-((benzyloxy)methyl)-4-(((4-methoxyphenyl)diphenylmethoxy)methyl)cyclopentyl)-4-chloro-7H-pyrrolo[2,3-d]pyrimidine (1.00 g, 0.876 mmol) was dissolved in AcOH (20 mL) and water (2.5 mL) at room temperature. Then the temperature was raised up to 40° C. and the reaction was stirred for about 4 h. The mixture (azeotroped with toluene 3×) was concentrated under reduced pressure, and the residue was purified by column chromatography on silica (0-80% EtOAc/PE) to afford a mixture of ((1R,2R,3S,4R)-2,3-bis(benzyloxy)-1-((benzyloxy)methyl)-4-(4-chloro-7H-pyrrolo[2,3-d]pyrimidin-7-yl)cyclopentyl)methanol as a solid and ((1S,2R,3S,4R)-2,3-bis(benzyloxy)-1-((benzyloxy)methyl)-4-(4-chloro-7H-pyrrolo[2,3-d]pyrimidin-7-yl)cyclopentyl)methanol as a solid. MS: 584 (M+1). $^1$H-NMR of the mixture of two regioisomers (300 MHz, DMSO-d$_6$) δ 8.51-8.49 (m, 1H), 7.78-7.66 (m, 1H), 7.37-7.26 (m, 10H), 7.11-7.07 (m, 3H), 6.89-6.86 (m, 2H), 6.59-6.54 (m, 1H), 5.26-5.16 (m, 1H), 4.74-4.24 (m, 8H), 4.09-4.07 (m, 1H), 3.66-3.50 (m, 4H), 2.08-1.97 (m, 1H), 1.79-1.71 (m, 1H).

Step 9: To a stirred mixture of ((1S,2R,3S,4R)-2,3-bis(benzyloxy)-1-((benzyloxy)methyl)-4-(4-chloro-7H-pyrrolo[2,3-d]pyrimidin-7-yl)cyclopentyl)methanol (500 mg, 0.642 mmol) and ((1R,2R,3S,4R)-2,3-bis(benzyloxy)-1-((benzyloxy)methyl)-4-(4-chloro-7H-pyrrolo[2,3-d]pyrimidin-7-yl)cyclopentyl)methanol (500 mg, 0.214 mmol) (azeotroped with toluene 3×) in DCM (10 mL) was added DAST (310 mg, 1.93 mmol) at 0° C. under an argon atmosphere. The resulting mixture was stirred for about 16 h at room temperature. The mixture was quenched by saturated aqueous NaHCO$_3$ (25 mL) and extracted with EtOAc (3×50 mL). The combined organic fractions were washed with brine (3×25 mL), dried over anhydrous sodium sulfate, and filtered. The filtrate was concentrated under reduced pressure, and the residue was purified by Prep-TLC (50% EtOAc/PE) to afford 7-((1R,2S,3R,4S)-2,3-bis(benzyloxy)-4-((benzyloxy)methyl)-4-(fluoromethyl)cyclopentyl)-4-chloro-7H-pyrrolo[2,3-d]pyrimidine as an oil. MS: 586 (M+1). $^1$H-NMR (400 MHz, DMSO-d$_6$) δ 8.51 (s, 1H), 7.74 (d, J=3.6 Hz, 1H), 7.39-7.33 (m, 10H), 7.15-7.06 (m, 3H), 6.90-6.87 (m, 2H), 6.61 (d, J=3.6 Hz, 1H), 5.30-5.20 (m, 1H), 4.80-4.75 (m, 2H), 4.63-4.57 (m, 5H), 4.52-4.48 (m, 1H), 4.33-4.29 (m, 1H), 4.15 (d, J=4.2 Hz, 1H), 3.63-3.61 (m, 2H), 2.10-1.89 (m, 2H).

Step 10: To a stirred mixture of 7-((1R,2S,3R,4S)-2,3-bis(benzyloxy)-4-((benzyloxy)methyl)-4-(fluoromethyl)cyclopentyl)-4-chloro-7H-pyrrolo[2,3-d]pyrimidine (395 mg, 0.674 mmol) (azeotroped with toluene 3×) in DCM (6 mL) was added trichloroborane (1 M in DCM) (6.74 mL, 6.74 mmol) at −80° C. under an argon atmosphere. The resulting mixture was stirred for about 60 minutes at −80° C. The reaction mixture was quenched with saturated aqueous NaHCO$_3$ (5 mL). The mixture was purified by reverse phase column chromatography (ACN/water with 5 mM NH$_4$HCO$_3$ modifier) to afford (1S,2R,3S,5R)-5-(4-chloro-7H-pyrrolo[2,3-d]pyrimidin-7-yl)-3-(fluoromethyl)-3-(hydroxymethyl)cyclopentane-1,2-diol as a solid. MS: 316 (M+1). $^1$H-NMR (300 MHz, DMSO-d$_6$) δ 8.63 (s, 1H), 7.92 (d, J=3.6 Hz, 1H), 6.71 (d, J=3.6 Hz, 1H), 5.18-5.04 (m, 2H), 4.94-4.92 (m, 2H), 4.73-4.34 (m, 3H), 3.90-3.87 (m, 1H), 3.55-3.45 (m, 2H), 2.04-1.96 (m, 1H), 1.70-1.62 (m, 1H).

Step 11: To a stirred mixture of (1S,2R,3S,5R)-5-(4-chloro-7H-pyrrolo[2,3-d]pyrimidin-7-yl)-3-(fluoromethyl)-3-(hydroxymethyl)cyclopentane-1,2-diol (178 mg, 0.564 mmol) (azeotroped with toluene 3×) in acetone (5 mL) was added 4-methylbenzenesulfonic acid (9.71 mg, 0.056 mmol) at 0° C. under an argon atmosphere. The resulting mixture was stirred for about 5 minutes at 0° C., then 2,2-dimethoxypropane (294 mg, 2.82 mmol) was added at this temperature. The resulting mixture was warmed to room temperature and stirred for 3 h. The reaction mixture was quenched by saturated aqueous NaHCO$_3$ (10 mL) and extracted with EtOAc (3×30 mL). The combined organic fractions were washed with brine (3×10 mL), dried over anhydrous sodium sulfate, and filtered. The filtrate was concentrated under reduced pressure, and the residue was purified by column chromatography on silica (0-80% EtOAc/PE) to afford ((3aR,4S,6R,6aS)-6-(4-chloro-7H-pyrrolo[2,3-d]pyrimidin-7-yl)-4-(fluoromethyl)-2,2-dimethyltetrahydro-3aH-cyclopenta[d][1,3]dioxol-4-yl)methanol as a solid. MS: 356 (M+1). $^1$H-NMR (400 MHz, DMSO-d$_6$) δ 8.67 (s, 1H), 8.01 (d, J=3.6 Hz, 1H), 6.75 (d, J=3.6 Hz, 1H), 5.29-5.23 (m, 1H), 5.18 (t, J=4.2 Hz, 1H), 5.04 (t, J=6.8 Hz, 1H), 4.68-4.60 (m, 2H), 4.56-4.48 (m, 1H), 3.53-3.45 (m, 2H), 2.24-2.15 (m, 2H), 1.50 (s, 3H), 1.24 (s, 3H).

Step 12: To a stirred solution of oxalyl dichloride (0.103 mL, 1.22 mmol) in anhydrous DCM (5 mL) was added (methylsulfinyl)methane (0.174 mL, 2.445 mmol) at −78° C. under an argon atmosphere, the mixture was stirred for 0.5 h at −78° C. Then, a solution of ((3aR,4S,6R,6aS)-6-(4-chloro-7H-pyrrolo[2,3-d]pyrimidin-7-yl)-4-(fluoromethyl)-2,2-dimethyltetrahydro-3aH-cyclopenta[d][1,3]dioxol-4-yl)methanol (145 mg, 0.408 mmol) in anhydrous DCM (3 mL) was added dropwise to the mixture at −78° C. The mixture was stirred for another 0.5 h at −78° C. Under this temperature, triethylamine (0.568 mL, 4.08 mmol) was further added to the reaction mixture, and the resulting mixture was stirred for 0.5 h at room temperature. The reaction was quenched with H$_2$O (10.0 mL) at 0° C. and extracted with DCM (20 mL). The combined organic layers were washed with saturated aqueous NaHCO$_3$ (10×3 mL), brine (10 mL), dried over anhydrous Na₂SO₄, and filtered. The filtrate was concentrated under reduced pressure to afford (3aR,4R,6R,6aS)-6-(4-chloro-7H-pyrrolo[2,3-d]pyrimidin-7-yl)-4-(fluoromethyl)-2,2-dimethyltetrahydro-3aH-cyclopenta[d][1,3]dioxole-4-carbaldehyde as an oil. MS: 354 (M+1).

Step 13: Bromo(methyl)triphenylphosphorane (367 mg, 1.03 mmol) was dissolved in THF (4 mL) at −30° C. under an argon atmosphere, then butyllithium (2.5 M in hexanes) (0.382 mL, 0.954 mmol) was added dropwise at this temperature. The reaction mixture was stirred at −10° C. for about 30 minutes. Then (3aR,4R,6R,6aS)-6-(4-chloro-7H-pyrrolo[2,3-d]pyrimidin-7-yl)-4-(fluoromethyl)-2,2-dimethyltetrahydro-3aH-cyclopenta[d][1,3]dioxole-4-carbaldehyde (130 mg, 0.367 mmol) in THF (2 mL) was added at −30° C. The reaction was stirred for about 1 h at room temperature. The reaction mixture was quenched by adding saturated aqueous NH₄Cl (10 mL) at −40° C. and extracted with EtOAc (3×30 mL). The combined organic fractions were washed with brine (3×10 mL), dried over anhydrous sodium sulfate, and filtered. The filtrate was concentrated under reduced pressure, and the residue was purified by Prep-TLC (2:1=PE:EtOAc) to afford 4-chloro-7-((3aS,4R,6S,6aR)-6-(fluoromethyl)-2,2-dimethyl-6-vinyltetrahydro-3aH-cyclopenta[d][1,3]dioxol-4-yl)-7H-pyrrolo[2,3-d]pyrimidine. MS: 352 (M+1). ¹H-NMR (300 MHz, DMSO-d₆): δ 8.67 (s, 1H), 8.00 (d, J=3.6 Hz, 1H), 6.73 (d, J=3.6 Hz, 1H), 6.06-5.96 (m, 1H), 5.31-5.08 (m, 4H), 4.79-4.77 (m, 1H), 4.65-4.58 (m, 1H), 4.49-4.42 (m, 1H), 2.49-2.44 (m, 2H), 1.48 (s, 3H), 1.24 (s, 3H).

Step 14: 4-chloro-7-((3aS,4R,6S,6aR)-6-(fluoromethyl)-2,2-dimethyl-6-vinyltetrahydro-3aH-cyclopenta[d][1,3]dioxol-4-yl)-7H-pyrrolo[2,3-d]pyrimidine (100 mg, 0.284 mmol) was dissolved in 5 mL dioxane and ammonia hydrate (28% in water)) (5 mL, 36.4 mmol) in a sealed tube. The reaction was stirred at 90° C. for about 16 h. The mixture was concentrated under reduced pressure, and the residue was purified by reverse phase column chromatography (ACN/water with 5 mM NH₄HCO₃ modifier) to afford 7-((3aS,4R,6S,6aR)-6-(fluoromethyl)-2,2-dimethyl-6-vinyltetrahydro-3aH-cyclopenta[d][1,3]dioxol-4-yl)-7H-pyrrolo[2,3-d]pyrimidin-4-amine as a solid. MS: 333 (M+1). ¹H NMR (300 MHz, DMSO-d₆): δ 8.07 (s, 1H), 7.36 (d, J=3.6 Hz, 1H), 6.99 (s, 2H), 6.58 (d, J=3.6 Hz, 1H), 6.07-5.98 (m, 1H), 5.26-5.17 (m, 3H), 5.08-5.04 (m, 1H), 4.77-4.74 (m, 1H), 4.68-4.52 (m, 1H), 4.49-4.42 (m, 1H), 2.39-2.35 (m, 2H), 1.48 (s, 3H), 1.25 (s, 3H).

Step 15: Under an argon atmosphere, 7-((3aS,4R,6S,6aR)-6-(fluoromethyl)-2,2-dimethyl-6-vinyltetrahydro-3aH-cyclopenta[d][1,3]dioxol-4-yl)-7H-pyrrolo[2,3-d]pyrimidin-4-amine (20 mg, 0.060 mmol) was dissolved in 9-BBN (0.5 M in THF 0.602 mL, 0.301 mmol) at room temperature, and the mixture was stirred for 1 h at 60° C. The mixture was cooled to 0° C., and a solution of K₃PO₄ (63.9 mg, 0.301 mmol) in 0.30 mL H₂O was added. The mixture was stirred for 0.5 h at room temperature. Then, a solution of 3-bromo-7-iodo-N-(4-methoxybenzyl)quinolin-2-amine (28.2 mg, 0.060 mmol) in 0.90 mL anhydrous THF and Pd(dppf)Cl₂ (7.37 mg, 9.03 μmol) were added to the mixture respectively. The resulting mixture was irradiated with microwave radiation at 70° C. for 3 h. The organic layer was separated and concentrated under reduced pressure. The crude product was purified by Prep-TLC (DCM/MeOH=15:1) to afford 7-(2-((3aR,6R,6aS)-6-(4-amino-7H-pyrrolo[2,3-d]pyrimidin-7-yl)-4-(fluoromethyl)-2,2-dimethyltetrahydro-3aH-cyclopenta[d][1,3]dioxol-4-yl)ethyl)-3-bromo-N-(4-methoxybenzyl)quinolin-2-amine as a solid. MS: 675/677 (M+1/M+3).

Step 16: Under an argon atmosphere, 7-(2-((3aR,6R,6aS)-6-(4-amino-7H-pyrrolo[2,3-d]pyrimidin-7-yl)-4-(fluoromethyl)-2,2-dimethyltetrahydro-3aH-cyclopenta[d][1,3]dioxol-4-yl)ethyl)-3-bromo-N-(4-methoxybenzyl)quinolin-2-amine (45 mg, 0.067 mmol) was dissolved in a solution of TFA in H₂O (2.0 mL, TFA/H₂O=1:1) at ambient temperature. The reaction mixture was stirred for 1 h at 50° C. The reaction mixture was azeotroped with toluene 3× to remove TFA. The crude product was purified by reverse phase column chromatography (ACN/water with 5 mM NH₄HCO₃ modifier). The product was further purified by Prep-HPLC (ACN/water with 6.3 mM NH₄HCO₃ modifier) afford desired product (1S,2R,5R)-3-(2-(2-amino-3-bromoquinolin-7-yl)ethyl)-5-(4-amino-7H-pyrrolo[2,3-d]pyrimidin-7-yl)-3-(fluoromethyl)cyclopentane-1,2-diol as a solid. MS: 515/517 (M+1/M+3). ¹H-NMR (300 MHz, DMSO-d₆) δ 8.34 (s, 1H), 8.04 (s, 1H), 7.60 (d, J=8.1 Hz, 1H), 7.36 (s, 1H), 7.28 (d, J=3.6 Hz, 1H), 7.17-7.14 (m, 1H), 6.92 (br s, 2H), 6.58-6.53 (m, 3H), 4.95-4.83 (m, 3H), 4.79-4.38 (m, 3H), 3.85 (t, J=4.2 Hz, 1H), 2.86-2.69 (m, 2H), 2.01-1.76 (m, 4H).

Example 103

(1R,2S,3R,5S)-5-(2-(2-amino-3-bromoquinolin-7-yl)ethyl)-3-(4-amino-7H-pyrrolo[2,3-d]pyrimidin-7-yl)-1-methylcyclopentane-1,2-diol

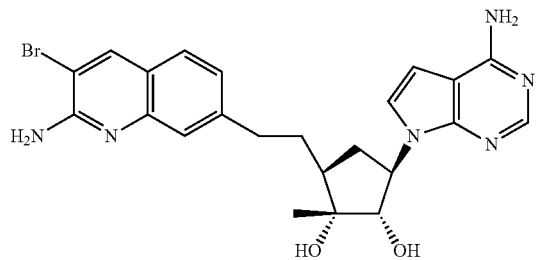 [SMILES: C[C@@]1(O)[C@@H](CCc2ccc3cc(Br)c(N)nc3c2)C[C@@H](n2ccc3c(N)ncnc32)[C@@H]1O]

Step 1: Under an argon atmosphere to a solution of oxalyl dichloride (1015 mg, 7.99 mmol) in anhydrous DCM (10 mL) was added DMSO (1249 mg, 15.99 mmol) at −78° C. The mixture was stirred for 0.5 h at −78° C. Then, a solution of ((3aR,4R,6R,6aS)-6-(4-chloro-7H-pyrrolo[2,3-d]pyrimidin-7-yl)-2,2,3a-trimethyltetrahydro-3aH-cyclopenta[d][1,3]dioxol-4-yl)methanol (900 mg, 2.66 mmol) in anhydrous DCM (10 mL) was added dropwise to the mixture at −78° C. The mixture was stirred for another 0.5 h at −78° C. Under this temperature, TEA (2.70 mg, 26.6 mmol) was added to the reaction mixture, and the resulting mixture was stirred for 0.5 h at −78° C. The reaction was quenched by H₂O (10 mL) at 0° C. The mixture was extracted with DCM (50 mL), washed with saturated aqueous NaHCO₃ (3×30 mL), brine (30 mL). The combined organic layers were dried over anhydrous Na₂SO₄ and filtered. The filtrate was concentrated under reduced pressure to afford the crude product (3aR,4S,6R,6aS)-6-(4-chloro-7H-pyrrolo[2,3-d]pyrimidin-7-yl)-2,2,3a-trimethyltetrahydro-3aH-cyclopenta[d][1,3]dioxole-4-carbaldehyde as a solid. MS: 336 (M+1).

Step 2: To a stirred solution of methyltriphenylphosphonium bromide (2.7 g, 7.50 mmol) in anhydrous THF (4.0 mL) was added n-BuLi (2.5 M in THF, 2.79 mL, 6.97 mmol) dropwise at −10° C. under an argon atmosphere. The reaction mixture was stirred for 0.5 h at room temperature. Then, a solution of (3aR,4S,6R,6aS)-6-(4-chloro-7H-pyrrolo[2,3- d]pyrimidin-7-yl)-2,2,3a-trimethyltetrahydro-3aH-cyclopenta[d][1,3]dioxole-4-carbaldehyde (900 mg, 2.68 mmol) in anhydrous THF (6.0 mL) was added to the mixture at −10° C. The reaction mixture was stirred for 1.5 h at room temperature. The reaction mixture was diluted with DCM (50 mL) and washed with water (50 mL) and brine (50 mL). The organic layer was dried over anhydrous sodium sulfate and filtered. The filtrate was concentrated under reduced pressure and purified by column chromatography on silica (EtOAc/PE 0-30%) to afford 4-chloro-7-((3aS,4R,6R,6aR)-2,2,6a-trimethyl-6-vinyltetrahydro-3aH-cyclopenta[d][1,3]dioxol-4-yl)-7H-pyrrolo[2,3-d]pyrimidine as a solid. MS: 334 (M+1).

Step 3: Into a sealed tube were added 4-chloro-7-((3aS,4R,6R,6aR)-2,2,6a-trimethyl-6-vinyltetrahydro-3aH-cyclopenta[d][1,3]dioxol-4-yl)-7H-pyrrolo[2,3-d]pyrimidine (800 mg, 2.40 mmol), 1,4-dioxane (12 mL) and $NH_3·H_2O$ (25%, 16 mL) at room temperature. The mixture was sealed tightly and then stirred at 90° C. for 16 h. Then the reaction mixture was concentrated under reduced pressure. The residue was purified by column chromatography on silica (0-10% MeOH/DCM) to afford 7-((3aS,4R,6R,6aR)-2,2,6a-trimethyl-6-vinyltetrahydro-3aH-cyclopenta[d][1,3]dioxol-4-yl)-7H-pyrrolo[2,3-d]pyrimidin-4-amine as a solid. MS: 315 (M+1).

Step 4: To a stirred solution of 7-((3aS,4R,6R,6aR)-2,2,6a-trimethyl-6-vinyltetrahydro-3aH-cyclopenta[d][1,3]dioxol-4-yl)-7H-pyrrolo[2,3-d]pyrimidin-4-amine (100 mg, 0.32 mmol) in anhydrous THF (0.5 mL) was added 9-BBN (0.5 M in THF, 3.18 mL, 1.59 mmol) dropwise at 0° C. under an argon atmosphere. The reaction solution was stirred at 50° C. for 1 h. To the reaction solution was added a solution of potassium phosphate tribasic (336 mg, 1.581 mmol) in water (1 mL) dropwise at 0° C. The reaction solution was stirred at room temperature for 0.5 h. A solution of 3-bromo-7-iodo-N-(4-methoxybenzyl)quinolin-2-amine (163 mg, 0.348 mmol) in THF (1 ml) and 1,1'-bis(diphenylphosphino)ferrocene-palladium(II)dichloride dichloromethane complex (25.8 mg, 0.032 mmol) were added at room temperature. The final reaction mixture was irradiated with microwave radiation at 70° C. for 2 h. The reaction mixture was cooled to room temperature, diluted with water (5 mL), and extracted with EtOAc (2×20 mL). The combined organic layers were dried over anhydrous sodium sulfate and filtered. The filtrate was concentrated under reduced pressure and purified by Combi-flash (Column: AQ-C18 Column, 80 g, 60 Å, 40-60 μm; Mobile Phase A: water, Mobile Phase B: MeCN; Flow rate: 50 mL/min; Gradient: 20% B to 90% B in 60 min (80% hold 5 min)) to afford 7-(2-((3aR,4S,6R,6aS)-6-(4-amino-7H-pyrrolo[2,3-d]pyrimidin-7-yl)-2,2,3a-trimethyltetrahydro-3aH-cyclopenta[d][1,3]dioxol-4-yl)ethyl)-3-bromo-N-(4-methoxybenzyl)quinolin-2-amine as a solid. MS: 657/659 (M+1/M+3).

Step 5: A solution of 7-(2-((3aR,4S,6R,6aS)-6-(4-amino-7H-pyrrolo[2,3-d]pyrimidin-7-yl)-2,2,3a-trimethyltetrahydro-3aH-cyclopenta[d][1,3]dioxol-4-yl)ethyl)-3-bromo-N-(4-methoxybenzyl)quinolin-2-amine (40 mg, 0.061 mmol) in TFA (2 mL, 26.0 mmol) was stirred at 60° C. for 1 h. TFA was removed under reduced pressure to obtain the crude product N-(7-(2-((1S,2R,3S,4R)-4-(4-amino-7H-pyrrolo[2,3-d]pyrimidin-7-yl)-2,3-dihydroxy-2-methylcyclopentyl)ethyl)-3-bromoquinolin-2-yl)-2,2,2-trifluoroacetamide as an oil. A mixture of N-(7-(2-((1S,2R,3S,4R)-4-(4-amino-7H-pyrrolo[2,3-d]pyrimidin-7-yl)-2,3-dihydroxy-2-methylcyclopentyl)ethyl)-3-bromoquinolin-2-yl)-2,2,2-trifluoroacetamide (40 mug, 0.067 mmol) and $K_2CO_3$ (28 mg, 0.202 mmol) in methanol (3 mL) was stirred at 60° C. for 1 h. The mixture was filtered and washed with MeOH (0.5 mL). The filtrate was concentrated under reduced pressure, and the residue was purified by reverse phase column chromatography (ACN/water) to afford (1R,2S,3R,5S)-5-(2-(2-amino-3-bromoquinolin-7-yl)ethyl)-3-(4-amino-7H-pyrrolo[2,3-d]pyrimidin-7-yl)-1-methylcyclopentane-1,2-diol as a solid. MS: 497/499 (M+1/M+3). $^1$H-NMR (400 MHz, DMSO-$d_6$) δ 8.32 (s, 1H), 8.03 (s, 1H), 7.58 (d, J=8.0 Hz, 1H), 7.32 (s, 1H), 7.25 (d, J=3.6 Hz, 1H), 7.11 (d, J=8.0 Hz. 1H), 6.87 (br s, 2H), 6.55-6.54 (m, 3H), 4.85 (d, J=6.8 Hz, 1H), 4.80-4.77 (m, 1H), 4.18 (s, 1H), 3.98-3.94 (m, 1H), 2.78-2.73 (m, 1H), 2.59-2.50 (m, 1H), 2.32-2.27 (m, 1H), 1.91-1.83 (m, 2H), 1.63-1.57 (m, 2H), 1.15 (s, 3H).

Example 104

(2R,3R,3aS,6S,6aR)-2-(4-amino-7H-pyrrolo[2,3-d]pyrimidin-7-yl)-6-((2-aminoquinolin-7-yl)oxy)hexahydro-2H-cyclopenta[b]furan-3,3a-diol

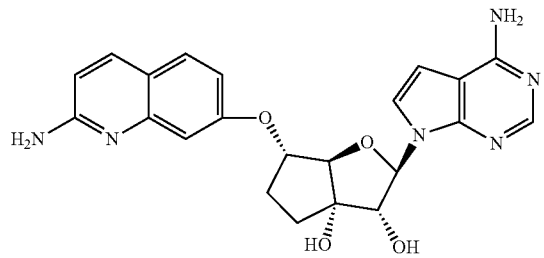 [SMILES: Nc1ccc2ccc(O[C@H]3CC[C@@]4(O)[C@@H]3O[C@@H](n3ccc5c(N)ncnc53)[C@@H]4O)cc2n1]

Step 1: To a solution of (2R,3R,3aS,6S,6aR)-6-((2-amino-3-bromoquinolin-7-yl)oxy)-2-(4-amino-7H-pyrrolo[2,3-d]pyrimidin-7-yl)hexahydro-2H-cyclopenta[b]furan-3,3a-diol (45 mg, 0.088 mmol) in MeOH (6 mL) was added dihydroxypalladium on carbon (18.5 mg, 0.026 mmol) at ambient temperature. The resulting mixture was stirred at 25° C. for 30 minutes under a hydrogen atmosphere (1.2 atm). Then the reaction mixture was filtered, and the filtrate was concentrated under reduced pressure, and the residue was purified by reverse phase HPLC (ACN/water modified with 0.05% TFA). The product-containing fractions were collected, and the pH value of the solution was adjusted to 7~8 with $NH_3·H_2O$ (25%). Then the solution was concentrated under reduced pressure and further purified by reverse phase column chromatography (ACN/water with 5 mM $NH_4HCO_3$ modifier) to afford (2R,3R,3aS,6S,6aR)-2-(4-amino-7H-pyrrolo[2,3-d]pyrimidin-7-yl)-6-((2-aminoquinolin-7-yl)oxy)hexahydro-2H-cyclopenta[b]furan-3,3a-diol as a solid. MS: 435 (+1). $^1$H-NMR (300 MHz, DMSO-$d_6$) δ 8.09 (s, 1H), 7.76 (d, J=9.0 Hz, 1H), 7.52-7.49 (m, 2H), 7.05 (br s, 2H), 6.80-6.75 (m, 2H), 6.66 (d, J=3.3 Hz, 1H), 6.55 (d, J=8.7 Hz, 1H), 6.30 (br s, 2H), 6.02 (d, J=8.4 Hz, 1H), 5.36 (d, J=7.2 Hz, 1H), 5.30 (s, 1H), 4.59 (d, J=4.5 Hz, 1H), 4.40 (t, J=7.8 Hz, 1H), 4.09-4.08 (m, 1H), 2.50-2.48 (m, 1H), 2.07-1.98 (m, 3H).

Example 105

(1R,2S,3R,5R)-5-(((2-aminoquinolin-7-yl)oxy)methyl)-1-methyl-3-(7H-pyrrolo[2,3-d]pyrimidin-7-yl)cyclopentane-1,2-diol

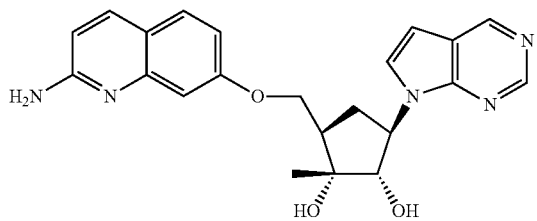 [SMILES: C[C@@]1(O)[C@@H](COc2ccc3ccc(N)nc3c2)C[C@@H](n2ccc3cncnc32)[C@@H]1O]

Step 1: To a solution of (1R,2S,3R,5R)-5-(((2-amino-3-bromoquinolin-7-yl)oxy)methyl)-3-(4-chloro-7H-pyrrolo[2,3-d]pyrimidin-7-yl)-1-methylcyclopentane-1,2-diol (20 mg, 0.039 mmol) in MeOH (4 mL) were added triethylamine (7.80 mg, 0.077 mmol) and anhydrous Pd/C (10 mg) (10% Pd/C) under an argon atmosphere. The resulting mixture was stirred at room temperature under a hydrogen atmosphere (~1 atm) for 4 h. The mixture was filtered, and the filtrate was concentrated under reduced pressure. The residue was purified by reverse phase HPLC (ACN/water with 10 mM NH$_4$HCO$_3$ modifier) to afford (1R,2S,3R,5R)-5-(((2-aminoquinolin-7-yl)oxy)methyl)-1-methyl-3-(7H-pyrrolo[2,3-d]pyrimidin-7-yl)cyclopentane-1,2-diol as a solid. MS: 406 (M+1). $^1$H-NMR (400 MHz, DMSO-d$_6$): δ 8.98 (s, 1H), 8.75 (s, 1H), 7.80-7.76 (m, 2H), 7.52 (d, J=8.8 Hz, 1H), 6.94 (d, J=2.4 Hz, 1H), 6.84 (dd, J=8.8, 2.4 Hz, 1H), 6.68 (d, J=3.6 Hz, 1H), 6.58 (d, J=8.8 Hz, 1H), 6.30 (br s, 2H), 5.14 (q, J=9.6 Hz, 1H), 4.95 (d, J=6.8 Hz, 1H), 4.48 (s, 1H), 4.23-4.10 (m, 3H), 2.48-2.37 (m, 2H), 1.80-1.73 (m, 1H), 1.26 (s, 3H).

Example 106

(1R,2S,3R,5R)-5-(((2-amino-3-methylquinolin-7-yl)oxy)methyl)-1-methyl-3-(4-methyl-7H-pyrrolo[2,3-d]pyrimidin-7-yl)cyclopentane-1,2-diol

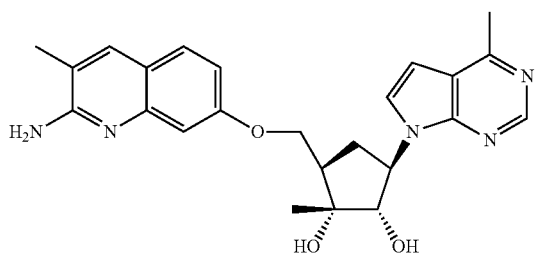 [SMILES: Cc1cc2ccc(OC[C@H]3C[C@@H](n4ccc5c(C)ncnc54)[C@H](O)[C@]3(C)O)cc2nc1N]

Step 1: To a mixture of (1R,2S,3R,5R)-5-(((2-amino-3-bromoquinolin-yl)oxy)methyl)-3-(4-chloro-7H-pyrrolo[2,3-d]pyrimidin-7-yl)-1-methylcyclopentane-1,2-diol (20 mg, 0.039 mmol) and Pd(PPh$_3$)$_4$ (4.45 mg, 3.86 μmol) in anhydrous THF (1 mL) was dropwise added trimethylaluminum (2 M in Toluene, 0.058 mL, 0.116 mmol) at room temperature under an argon atmosphere. The mixture was stirred at 100° C. for 2 h. After cooling down to ambient temperature, the mixture was cautiously poured into aqueous HCl (1 M, 10 ml). The mixture was partitioned between EtOAc (40 mL) and H$_2$O (10 mL). The water layer was concentrated under reduced pressure. The residue was purified by reverse phase HPLC (ACN/water with 10 mM NH$_4$HCO$_3$ modifier) to afford (1R,2S,3R,5R)-5-(((2-amino-3-methylquinolin-7-yl)oxy)methyl)-1-methyl-3-(4-methyl-7H-pyrrolo[2,3-d]pyrimidin-7-yl)cyclopentane-1,2-diol as a solid. MS: 434 (M+1). $^1$H-NMR (400 MHz, DMSO-d$_6$): δ 8.60 (s, 1H), 7.71 (d, J=3.6 Hz, 1H), 7.63 (s, 1H), 7.48 (d, J=8.4 Hz, 1H), 6.95 (d, J=2.0 Hz, 1H), 6.84 (dd, J=8.4, 2.0 Hz, 1H), 6.71 (d, J=3.6 Hz, 1H), 6.12 (br s, 2H), 5.10 (q, J=9.6 Hz, 1H), 4.91 (d, J=7.2 Hz, 1H), 4.45 (s, 1H), 4.21-4.09 (m, 3H), 2.64 (s, 3H), 2.46-2.37 (m, 2H), 2.17 (s, 3H), 1.79-1.72 (m, 1H), 1.26 (s, 3H).

Example 107

(2R,3R,3aS,6S,6aR)-6-((2-aminoquinolin-yl)methyl)-2-(4-methyl-7H-pyrrolo[2,3-d]pyrimidin-7-yl)hexahydro-2H-cyclopenta[b]furan-3,3a-diol

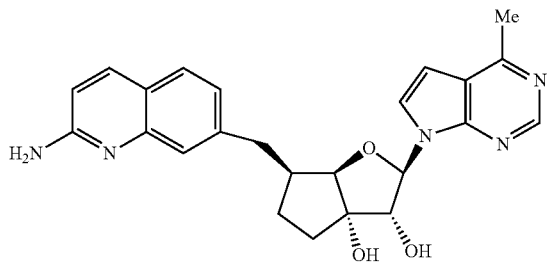 [SMILES: Cc1ncnc2c1ccn2[C@@H]1O[C@@H]2[C@H](Cc3ccc4ccc(N)nc4c3)CC[C@]2(O)[C@H]1O]

Step 1: To a solution of (2R,3R,3aS,6S,6aR)-6-((2-amino-3-bromoquinolin-7-yl)methyl)-2-(4-methyl-7H-pyrrolo[2,3-d]pyrimidin-7-yl)hexahydro-2H-cyclopenta[b]furan-3,3a-diol (20 mg, 0.039 mmol) in MeOH (5 mL) were added triethylamine (3.97 mg, 0.039 mmol) and anhydrous Pd/C (10 mg) (10% Pd/C) under an argon atmosphere. The resulting mixture was stirred at room temperature under hydrogen atmosphere (1.2 atm) for 30 minutes. The mixture was filtered, and the filtrate was concentrated under reduced pressure. The residue was purified by reverse phase HPLC (ACN/water with 10 mM NH$_4$HCO$_3$ modifier) to afford (2R,3R,3aS,6S,6aR)-6-((2-aminoquinolin-7-yl)methyl)-2-(4-methyl-7H-pyrrolo[2,3-d]pyrimidin-7-yl)hexahydro-2H-cyclopenta[b]furan-3,3a-diol as a solid. MS: 432 (M+1). $^1$H-NMR (400 MHz, DMSO-d$_6$): δ 8.69 (s, 1H), 7.87 (d, J=3.6 Hz, 1H), 7.79 (d, J=8.8 Hz, 1H), 7.48 (d, J=8.0 Hz, 1H), 7.22 (s, 1H), 7.00 (dd, J=8.0, 1.6 Hz, 1H), 6.82 (d, J=3.6 Hz, 1H), 6.66 (d, J=8.8 Hz, 1H), 6.31 (br s, 2H), 6.01 (d, J=8.0 Hz, 1H), 5.29 (d, J=7.2 Hz, 1H), 5.11 (s, 1H), 4.22 (t, J=7.6 Hz, 1H), 4.01 (d, J=5.6 Hz, 1H), 2.84-2.78 (m, 1H), 2.69 (s, 3H), 2.63-2.58 (m, 1H), 2.28-2.25 (m, 1H), 1.98-1.94 (m, 1H), 1.80-1.68 (m, 2H), 1.58-1.53 (m, 1H).

Example 108

(2R,3R,3aS,6S,6aR)-6-(2-amino-3-bromoquinolin-7-yl)methyl)-2-(4-amino-5-fluoro-7H-pyrrolo[2,3-d]pyrimidin-7-yl)hexahydro-2H-cyclopenta[b]furan-3,3a-diol

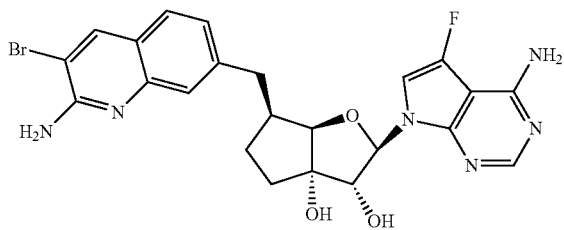 [SMILES: Nc1nc2cc(C[C@@H]3CC[C@@]4(O)[C@@H]3O[C@@H](n3cc(F)c5c(N)ncnc53)[C@@H]4O)ccc2cc1Br]

Step 1: To an oven-dried, argon cooled vial containing (3R,3aS,6aR)-6-((3-bromo-2-((4-methoxybenzyl)amino)quinolin 7-yl)methyl)hexahydro-211H-cyclopenta[b]furan-2,3,3a-triol (132.5 mg, 0.257 mmol) dissolved in dry acetonitrile (2.5 mL) was added 1,1'-(azodicarbonyl)dipiperidine (97 mg, 0.386 mmol) followed by tri-n-butylphosphine (103 μl, 0.411 mmol) at room temperature. The mixture was stirred for 1 h. In a separate oven-dried, argon cooled vial containing 4-chloro-5-fluoro-7H-pyrrolo[2,3-d]pyrimidine (88 mg, 0.514 mmol) dissolved in anhydrous acetonitrile (2.5 mL) was added DBU (78 μl, 0.514 mmol). The mixture was stirred at room temperature for 30 minutes, and this suspension was transferred to the first solution via syringe. The reaction was stirred at room temperature under argon for 7.5 h and then quenched with water and extracted with EtOAc (3×). The combined organics were then washed with brine, dried over sodium sulfate, filtered, and concentrated under reduced pressure. The residue was purified by column chromatography on silica (0-50% 3:1 EtOAc:EtOH in hexanes) to afford (2R,3R,3aS,6aR)-6-((3-bromo-2-((4-methoxybenzyl)amino)quinolin-7-yl)methyl)-2-(4-chloro-5-fluoro-7H-pyrrolo[2,3-d]pyrimidin-7-yl)hexahydro-2H-cyclopenta[b]furan-3,3a-diol as an oil. MS: 668 (M+1).

Step 2: To a vial containing (2R,3R,3aS,6aR)-6-((3-bromo-2-((4-m ethoxybenzyl)amino)quinolin-7-yl)methyl)-2-(4-chloro-5-fluoro-7H-pyrrolo[2,3-d]pyrimidin-7-yl) hexahydro-2H-cyclopenta[b]furan-3,3a-diol (138 mg, 0.206 mmol), was added ammonia (7 M in MeOH, 2.5 mL, 17.50 mmol). The vial was capped and heated at 140° C. in a microwave reactor for 5 h. The mixture was concentrated under reduced pressure, and the residue was purified by column chromatography on silica gel (0-70% 3:1 EtOAc:EtOH in hexanes) to afford (2R,3R,3aS,6aR)-2-(4-amino-5-fluoro-7H-pyrrolo[2,3-d]pyrimidin-7-yl)-6-((3-bromo-2-((4-methoxybenzyl)amino)quinolin-7-yl)methyl) hexahydro-2H-cyclopenta[b]furan-3,3a-diol as a solid. MS: 649 (M+1).

Step 3: To (2R,3R,3aS,6aR)-2-(4-amino-5-fluoro-7H-pyrrolo[2,3-d]pyrimidin-7-yl)-6-((3-bromo-2-((4-methoxybenzyl)amino)quinolin-7-yl)methyl)hexahydro-2H-cyclopenta[b]furan-3,3a-diol (68 mg, 0.105 mmol) dissolved in DCM (875 μl) was added TFA (348 μl, 4.516 mmol) at room temperature and stirred for 4 h. TFA (500 ul, 6.489 mmol) was added to the reaction mixture and stirred overnight at room temperature. The mixture was heated to 40° C. for 8 h. The reaction mixture was concentrated under reduced pressure and purified by mass trigged reverse phase HPLC (ACN/water with 0.1% NH$_4$OH modifier) to afford (2R,3R,3aS,6S,6aR)-6-((2-amino-3-bromoquinolin-7-yl)methyl)-2-(4-amino-5-fluoro-7H-pyrrolo[2,3-d]pyrimidin-7-yl)hexahydro-2H-cyclopenta[b]furan-3,3a-diol as a solid. MS: 668 (M+1). 1H NMR (600 MHz, DMSO-d6) δ 8.32 (s, 1H), 8.10 (s, 1H), 7.55 (d, J=8.3 Hz, 1H), 7.51 (d, J=1.7 Hz, 1H), 7.29 (s, 1H), 7.12-6.98 (m, 3H), 6.59 (s, 2H), 5.94 (dd, J=8.2, 1.5 Hz, 1H), 5.28 (d, J=7.0 Hz, 1H), 5.09 (s, 1H), 4.01 (t, J=7.5 Hz, 1H), 3.94 (d, J=5.8 Hz, 1H), 2.85-2.79 (m, 1H), 2.65-2.59 (m, 1H), 2.28-2.20 (m, 1H), 1.95-1.89 (m, 1H), 1.79-1.69 (m, 1H), 1.69-1.62 (m, 1H), 1.54-1.47 (m, 1H).

Example 109

(1S,2R,3S,5R)-3-(2-(2-amino-3-bromoquinolin-7-yl)ethyl)-3-methyl-5-(4-methyl-7H-pyrrolo[2,3-d]pyrimidin-7-yl)cyclopentane-1,2-diol

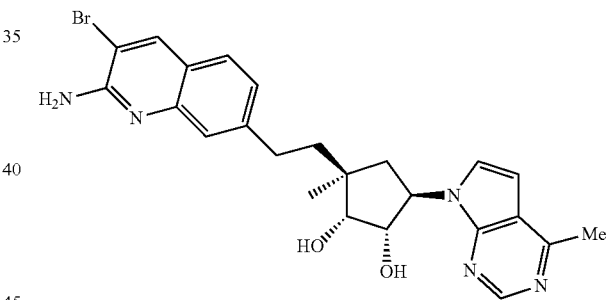

Step 1: In a microwave vial was added 4-chloro-7-((3a'R,4'R,6'R,6a'S)-4'-methyl-4'-vinyltetrahydro-4'H-spiro[cyclohexane-1,2'-cyclopenta[d][1,3]dioxol]-6'-yl)-7H-pyrrolo[2,3-d]pyrimidine (0.075 g, 0.2 mmol), solid supported Pd (0.077 g, 0.020 mmol), THF (1 mL), and dimethylzinc (2 M in PhMe, 0.5 mL, 1.0 mmol). The reaction mixture was stirred at room temperature overnight. The reaction was carefully quenched with IPA, then dropwise added MeOH. The reaction mixture was filtered through a plug of celite, washed with DCM/EtOAc, then concentrated under reduced pressure to afford 4-methyl-7-((3a'R,4'R,6'R,6a'S)-4'-methyl-4'-vinyltetrahydro-4'H-spiro[cyclohexane-1,2'-cyclopenta[d][1,3]dioxol]-6'-yl)-7H-pyrrolo[2,3-d]pyrimidine. MS: 354 (M+1).

Step 2: In a vial was added 4-methyl-7-((3a'R,4'R,6'R,6a'S)-4'-methyl-4'-vinyltetrahydro-3a'H-spiro[cyclohexane-1,2'-cyclopenta[d][1,3]dioxol]-6'-yl)-7H-pyrrolo[2,3-d]pyrimidine (70.7 mg, 0.2 mmol), THF (1 mL), and 9-BBN (0.5 M in THF, 1 mL, 0.500 mmol). The reaction mixture was heated to 50° C. for 2 h, then cooled to room temperature. Another portion of 9-BBN (0.5 M in THF, 1 mL, 0.5 mmol) was added and the reaction was heated to 50° C. overnight.

oxol]-6'-yl)-7H-pyrrolo[2,3-d]pyrimidine in step 2 was substituted with an appropriate exo olefin. The substituted reagents and starting material were commercially acquired, synthesized as reported above, or synthesized through known routes reported in the literature.

TABLE 24

| Ex | Structure | Name | MS |
|---|---|---|---|
| 110 | 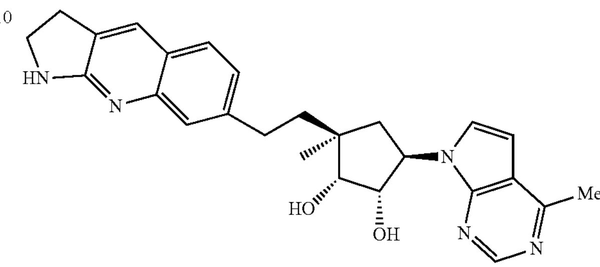 | (1S,2R,3S,5R)-3-(2-(2,3-dihydro-1H-pyrrolo[2,3-b]quinolin-7-yl)ethyl)-3-methyl-5-(4-methyl-7H-pyrrolo[2,3-d]pyrimidin-7-yl)cyclopentane-1,2-diol | 444 (M + 1) |

The reaction was cooled to room temperature and quenched with K₃PO₄ (2 M in water, 0.75 mL, 1.50 mmol) under an atmosphere of nitrogen gas. In a separate vial was added 3-bromo-N-(2,4-dimethoxybenzyl)-7-iodoquinolin-2-amine (100 mg, 0.20 mmol), 1,1'-Bis(diphenylphosphino)ferrocene]dichloropalladium(II) (16.3 mg, 0.020 mmol) in THF (0.5 mL). This suspension was added to the original reaction vessel, and the mixture was heated to 50° C. overnight. The reaction mixture was cooled to room temperature and diluted with EtOAc, DCM and water. The organic and aqueous layers were separated by passage through a phase separator, and the organic layer was concentrated under reduced pressure to afford 3-bromo-N-(2,4-dimethoxybenzyl)-7-(2-(((3a'R,4'S,6'R,6a'S)-4'-methyl-6'-(4-methyl-7H-pyrrolo[2,3-d]pyrimidin-7-yl)tetrahydro-4'H-spiro[cyclohexane-1,2'-cyclopenta[d][1,3]dioxol]-4'-yl)ethyl)quinolin-2-amine. MS: 726/728 (M+1/M+3).

Step 3: A solution of 3-bromo-N-(2,4-dimethoxybenzyl)-7-(2-(((3a'R,4'S,6'R,6a'S)-4'-methyl-6'-(4-methyl-7H-pyrrolo[2,3-d]pyrimidin-7-yl)tetrahydro-4'H-spiro[cyclohexane-1,2'-cyclopenta[d][1,3]dioxol]-4'-yl)ethyl)quinolin-2-amine (0.2 mmol) in THF (1 mL), water (0.3 mL, 16.7 mmol), and TFA (0.7 mL, 9.09 mmol) was stirred at room temperature overnight. The reaction mixture was then heated to 50° C. for 3 h. Another portion of TFA (1 mL, 13 mmol) was added at room temperature and the reaction mixture was heated to 50° C. for 3 h. The reaction mixture was concentrated under reduced pressure and purified by mass triggered reverse phase HPLC (ACN/water with 0,1% NH₄OH modifier) to afford (1S,2R,3S,5R)-3-(2-(2-amino-3-bromoquinolin-7-yl)ethyl)-3-methyl-5-(4-methyl-7H-pyrrolo[2,3-d]pyrimidin-7-yl)cyclopentane-1,2-diol as a solid. MS: 496/498 (M+1/M+3). ¹H-NMR (400 MHz, DMSO-d₆) δ 8.29 (s, 1H), 8.03 (s, 1H), 7.59 (d, J=9.2 Hz, 1H), 7.31 (d, J=3.6 Hz, 1H), 6.98-6.92 (m, 2H), 6.89 (br s, 2H), 6.55 (d, J=3.2 Hz, 1H), 6.51 (br s, 2H), 5.03-4.96 (m, 1H), 4.85 (d, J=6.8 Hz, 1H), 4.75 (d, J=4.8 Hz, 1H), 4.56-4.50 (m, 1H), 4.03 (d, J=9.2 Hz, 1H), 3.97-3.91 (m, 2H), 1.93 (d, J=9.6 Hz, 2H), 1.19 (s, 3H).

Example 110: Example 110 in Table 24 was Synthesized by using step 2 followed by step 1 & 3 of example 109. 4-methyl-7-((3a'R,4'R,6'R,6a'S)-4'-methyl-4'-vinyltetrahydro-3a'H-spiro[cyclohexane-1,2'-cyclopenta[d][1,3]di- Example 111

(1R,2S,3R,5R)-5-(((2-amino-3-bromoquinolin-7-yl)oxy)methyl)-3-(4-amino-7H-pyrrolo[2,3-d]pyrimidin-7-yl)-1,5-dimethylcyclopentane-1,2-diol

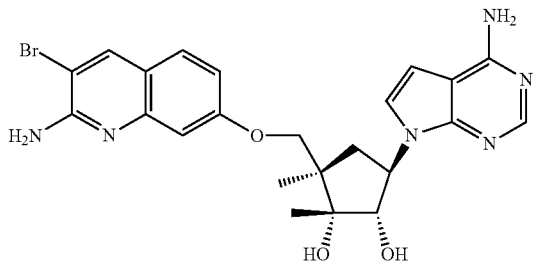 [SMILES: C[C@@]1(COc2ccc3cc(Br)c(N)nc3c2)C[C@@H](n2ccc3c(N)ncnc32)[C@H](O)[C@]1(C)O]

Step 1: A vial was charged with a mixture of 3-bromo-N-(4-methoxybenzyl)-7-(((3aR,4R,6R,6aS)-2,2,4-trimethyl-6-(4-phenoxy-7H-pyrrolo[2,3-d]pyrimidin-7-yl)tetrahydro-3aH-cyclopenta[d][1,3]dioxol-4-yl)methoxy)quinolin-2-amine (100 mg, 0.136 mmol) in 50% aqueous TFA (1 mL). The reaction mixture was stirred at room temperature for 1 h. The solvent was removed under reduced pressure, and the residue was purified by prep-TLC (DCM:MeOH=17:1) to afford (1S,2R,3R,5R)-3-(((3-bromo-2-((4-methoxybenzyl)amino)quinolin-7-yl)oxy)methyl)-3-methyl-5-(4-phenoxy-7H-pyrrolo[2,3-d]pyrimidin-7-yl)cyclopentane-1,2-diol as a solid. MS: 696/698 (M+1/M+3).

Step 2: To a stirred solution of (1S,2R,3R,5R)-3-(((3-bromo-2-((4-methoxybenzyl)amino)quinolin-7-yl)oxy)methyl)-3-methyl-5-(4-phenoxy-7H-pyrrolo[2,3-d]pyrimidin-7-yl)cyclopentane-1,2-diol (60 mg, 0.086 mmol), N-ethyl-N-isopropylpropan-2-aminium chloride (0.428 mg, 2.58 μmol) and (2R,4S)-4-isopropyl-2-methoxy-3-((R)-2-methyl-1-(1-methyl-1H-imidazol-2-yl)propyl)oxazolidine (49 mg, 0.172 mmol) in THF (0.2 mL) were added DIEA (0.045 mL, 0.258 mmol) and tert-butyldimethylsilyl trifluoromethanesulfonate (34.2 mg, 0.129 mmol) at 0° C. under an argon atmosphere. The resulting mixture was stirred at room temperature for 2 h. The reaction was quenched with 10 mL water and extracted with EtOAc (15 ml, ×3). The organic layer was dried over anhydrous sodium sulfate, filtered, and the filtrate was concentrated under reduced pressure. The residue was purified by prep-TLC (PE/EtOAc=3:1 to afford (1R,2R,4R,5S)-2-(((3-bromo-2-((4-methoxybenzyl)amino) quinolin-7-yl)oxy)methyl)-5-((tert-butyldimethylsilyl)oxy)-2-methyl-4-(4-phenoxy-7H-pyrrolo[2,3-d]pyrimidin-7-yl) cyclopentanol as an oil. MS: 810/812 (M+1/M+3). ¹H-NMR (300 MHz, Chloroform-d) δ 8.46 (s, 1H), 8.05 (s, 1H), 7.50-7.44 (m, 3H), 7.40-7.38 (m, 2H), 7.33-7.30 (m, 1H), 7.29-7.25 (m, 4H), 6.99-6.91 (m, 3H), 6.54 (d, J=3.6 Hz, 1H), 5.60-5.58 (m, 1H), 531-5.22 (m, 1H), 4.91-4.86 (m, 1H), 4.77 (s, 2H), 4.08-4.04 (m, 3H), 3.84 (s, 3H), 2.83-2.82 (m, 1H), 2.49-2.41 (m, 1H), 2.22-2.14 (m, 1H), 1.34 (s, 3H), 0.79 (s, 9H), −0.14 (s, 3H), −0.38 (s, 3H).

Step 3: To a stirred solution of (1R,2R,4R,5S)-2-(((3-bromo-2-((4-methoxybenzyl)amino)quinolin-7-yl)oxy) methyl)-5-((tert-butyldimethylsilyl)oxy)-2-methyl-4-(4-phenoxy-7H-pyrrolo[2,3-d]pyrimidin-7-yl)cyclopentanol (20 mg, 0.025 mmol) in DCM (0.5 mL) was added Dess-Martin Periodinane (20.92 mg, 0.049 mmol) in one portion at 0° C. under an argon atmosphere. The mixture was stirred at 0° C. for 2 h. The reaction was quenched with 5 mL saturated aqueous Na₂S₂O₃ and extracted with EtOAc (5 mL×3). The organic layer was dried over anhydrous sodium sulfate, filtered, and the filtrate was concentrated under reduced pressure to afford (2R,4R,5S)-2-(((3-bromo-2-((4-methoxybenzyl)amino)quinolin-7-yl)oxy)methyl)-5-((tert-butyldimethylsilyl)oxy)-2-methyl-4-(4-phenoxy-7H-pyrrolo[2,3-d]pyrimidin-7-yl)cyclopentanone. MS: 808/810 (M+1/M+3)

Step 4: A portion of cerium (III) chloride (37.0 mg, 0.150 mmol) was dried at 140° C. in vacuum for 1 h. The resulting powder was cooled under argon. Dry THF (0.25 mL) was added and then to the mixture was added methyllithium (1.6 M in ether, 0.094 mL, 0.150 mmol) at −78° C. The mixture was stirred at this temperature for 1 h. Then a cooled solution of (2R,4R,5S)-2-(((3-bromo-2-((4-methoxybenzyl) amino)quinolin-7-yl)oxy)methyl)-5-((tert-butyldimethylsilyl)oxy)-2-methyl-4-(4-phenoxy-7H-pyrrolo[2,3-d]pyrimidin-7-yl)cyclopentanone (20.22 mg, 0.025 mmol) in THF (0.25 mL) was rapidly added, and the resulting mixture was kept stirring at this temperature for 6 h. The reaction was quenched with saturated aqueous NH₄Cl (5 mL), and the mixture was extracted with EtOAc (5 mL×3). The organic layer was dried over anhydrous sodium sulfate, filtered, and the filtrate was concentrated under reduced pressure. The residue was purified by prep-TLC (PE/EA=4:1) to afford (1R,2R,4R,5S)-2-(((3-bromo-2-((4-methoxybenzyl)amino) quinolin-7-yl)oxy)methyl)-5-((tert-butyldimethylsilyl)oxy)-1,2-dimethyl-4-(4-phenoxy-7H-pyrrolo[2,3-d]pyrimidin-7-yl)cyclopentanol as an oil. MS: 824/826 (M+1/M+3). ¹H-NMR (400 MHz, Chloroform-d) δ 8.41 (s, 1H), 8.08 (s, 1H), 7.53 (d, J=8.8 Hz, 1H), 7.49-7.44 (m, 3H), 7.41-7.38 (m, 2H), 7.28-7.24 (m, 4H), 6.98-6.93 (m, 4H), 6.52 (d, J=3.2 Hz, 1H), 5.63-5.60 (m, 1H), 5.43-5.36 (m, 1H), 4.86 (d, J=8.8 Hz, 1H), 4.79 (s, 2H), 4.17 (d, J=9.2 Hz, 1H), 3.97 (d, J=9.2 Hz, 1H), 3.84 (s, 3H), 2.40-2.32 (m, 1H), 1.27 (s, 3H), 1.22 (s, 3H), 0.78 (s, 9H), 0.03 (s, 3H), −0.04 (s, 3H).

Step 5: To a stirred solution of (1R,2R,4R,5S)-2-(((3-bromo-2-((4-methoxybenzyl)amino)quinolin-7-yl)oxy) methyl)-5-((tert-butyldimethylsilyl)oxy)-1,2-dimethyl-4-(4-phenoxy-7H-pyrrolo[2,3-d]pyrimidin-7-yl)cyclopentanol (35 mg, 0.042 mmol) in THF (2 mL) was added TBAF (1 M in THF, 0.084 mL, 0.084 mmol) at 0° C. The mixture was stirred at room temperature for 3 h. The reaction mixture was quenched by saturated aqueous NH₄Cl (20 mL) and extracted with EtOAc (30 mL×3). The combined organic layers were washed with brine (20 mL), dried over anhydrous sodium sulfate, and filtered. The filtrate was concentrated under reduced pressure and purified by prep-TLC (PE:EA=1:1) to afford (1R,2S,3R,5R)-5-(((3-bromo-2-((4-methoxybenzyl)amino)quinolin-7-yl)oxy)methyl)-1,5-dimethyl-3-(4-phenoxy-7H-pyrrolo[2,3-d]pyrimidin-7-yl)cyclopentane-1,2-diol as a solid. MS: 710/712 (M+1/M+3). ¹H-NMR (400 MHz, DMSO-d₆) δ 8.31 (s, 1H), 8.24 (s, 1H), 7.67 (d, J=3.6 Hz, 1H), 7.60 (d, J=8.8 Hz, 1H), 7.49-7.45 (m, 2H), 7.35-7.25 (m, 5H), 7.15-7.12 (m, 1H), 7.07 (s, 1H), 6.94 (d, J=8.4 Hz, 1H), 6.88 (d, J=8.0 Hz, 2H), 6.52-6.51 (m, 1H), 5.19-5.14 (m, 1H), 4.99 (d, J=7.6 Hz, 1H), 4.67 (d, J=6.0 Hz, 2H), 4.56 (t, J=8.8 Hz, 1H), 4.38 (s, 1H), 4.14-4.11 (m, 1H), 3.96-3.94 (m, 1H), 3.71 (s, 3H), 2.17-2.11 (m, 1H), 2.05-2.02 (m, 1H), 1.19-1.16 (m, 6H).

Step 6: A solution of (1R,2S,3R,5R)-5-(((3-bromo-2-((4-methoxybenzyl)amino)quinolin-7-yl)oxy)methyl)-1,5-dimethyl-3-(4-phenoxy-7H-pyrrolo[2,3-d]pyrimidin-7-yl)cyclopentane-1,2-diol (17 mg, 0.024 mmol) in TFA (1 mL) was stirred at 50° C. for 3 h. The reaction was concentrated under reduced pressure, and the residue was purified by prep-TLC (DCM:MeOH=12:1) to afford (1R,2S,3R,5R)-5-(((2-amino-3-bromoquinolin-7-yl)oxy)methyl)-1,5-dimethyl-3-(4-phenoxy-7H-pyrrolo[2,3-d]pyrimidin-7-yl)cyclopentane-1,2-diol as a solid. MS: 590/592 (M+1/M+3). ¹H-NMR (400 MHz, DMSO-d₆) δ 8.29 (s, 1H), 8.21 (s, 1H), 7.66 (d, J=3.6 Hz, 1H), 7.60 (d, J=8.8 Hz, 1H), 7.50-7.45 (m, 2H), 7.31-7.28 (m, 1H), 7.26-7.24 (m, 21H), 7.03-7.02 (m, 1H), 6.96-6.94 (m, 1H), 6.54 (br s, 2H), 6.52 (d, J=3.6 Hz, 1H), 5.15 (q, J=9.6 Hz, 1H), 5.00 (d, J=7.2 Hz, 1H), 4.57-4.53 (m, 1H), 4.39 (s, 1H), 4.13 (d, J=9.6 Hz, 1H), 3.93 (d, J=9.6 Hz, 1H), 2.21-2.02 (m, 2H), 1.17-1.16 (m, 6H).

Step 7: (1R,2S,3R,5R)-5-(((2-amino-3-bromoquinolin-7-yl)oxy)methyl)-1,5-dimethyl-3-(4-phenoxy-7H-pyrrolo[2,3-d]pyrimidin-7-yl)cyclopentane-1,2-diol (13 mg, 0.022 mmol) was dissolved in NH₃ (liquid)/i-PrOH (v:v=5:1)) (10 mL) at ambient temperature in a sealed tube. Then the reaction mixture was stirred at 130° C. for 48 h. The reaction mixture was concentrated under reduced pressure and purified by reverse phase HPLC (ACN/water with 10 mmol NH₄HCO₃ modifier) to afford (1R,2S,3R,5R)-5-(((2-amino-3-bromoquinolin-7-yl)oxy)methyl)-3-(4-amino-7H-pyrrolo [2,3-d]pyrimidin-7-yl)-1,5-dimethylcyclopentane-1,2-diol as a solid. MS: 513/515 (M+1/M+3). ¹H-NMR (400 MHz, DMSO-d₆) δ 8.30 (s, 1H), 7.93 (s, 1H), 7.60 (d, J=8.8 Hz, 1H), 7.27 (d, J=3.2 Hz, 1H), 7.01 (s, 1H), 6.96-6.85 (m, 3H), 6.60-6.51 (m, 3H), 5.02-4.95 (m, 2H), 4.49 (d, J=8.8 Hz, 1H), 4.30 (s, 1H), 4.26 (d, J=9.2 Hz, 1H), 4.12 (d, J=9.2 Hz, 1H), 2.01-1.94 (m, 2H), 1.21 (s, 6H).

Examples 112 and 113

(2R,3R,3aS,6S,6aR)-6-((2-amino-3-chloroquinolin-7-v)oxy)-2-(4-methyl-7H-pyrrolo[2,3-d]pyrimidin-7-yl)hexahydro-2H-cyclopenta[b]furan-3,3a-diol &
(2R,3R,3aS,6S,6aR)-6-((2-aminoquinolin-7-yl)oxy)-2-(4-methyl 7H-pyrrolo[2,3-d]pyrimidin-7-yl)hexahydro-2H-cyclopenta[b]furan-3,3a-diol

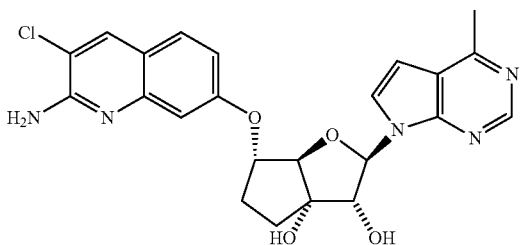

-continued

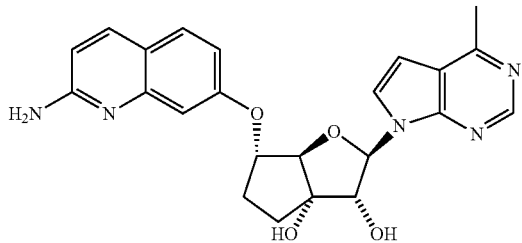

Step 1: To a stirred solution of (2R,3R,3aS,6S,6aR)-6-((2-amino-3-bromoquinolin-7-yl)oxy)-2-(4-methyl-7H-pyrrolo[2,3-d]pyrimidin-7-yl)hexahydro-2H-cyclopenta[b]furan-3,3a-diol (200 mg, 0.390 mmol) in EtOH (20 mL) were added monocopper(I) monocopper(III) monooxide (84 Mg, 0.586 mmol), tetramethylammonium chloride (428 mg, 3.90 mmol) and (S)-pyrrolidine-2-carboxylic acid (135 mg, 1.17 mmol) at ambient temperature. The mixture was stirred at 110° C. for overnight. The resulting mixture was concentrated under reduced pressure, and the residue was purified by reverse phase column chromatography (ACN/water with 5 mM NH$_4$HCO$_3$ modifier) to afford (2R,3R,3aS,6S,6aR)-6-((2-amino-3-chloroquinolin-7-yl)oxy)-2-(4-methyl-7H-pyrrolo[2,3-d]pyrimidin-7-yl)hexahydro-2H-cyclopenta[b]furan-3,3a-diol as a solid. MS: 468 (M+1). $^1$H-NMR (400 MHz, Methanol-d$_4$) δ 8.69 (s, 1H), 8.00 (s, 1H), 7.75 (d, J=3.6 Hz, 1H), 7.55 (d, J=8.8 Hz, 1H), 6.99-6.94 (m, 2H), 6.82 (d, J=3.6 Hz, 1H), 6.18 (d, J=8.0 Hz, 1H), 4.78 (d, J=4.8 Hz, 1H), 4.64 (d, J=8.0 Hz, 1H), 4.35-4.33 (m, 1H), 2.76 (s, 3H), 2.59-2.49 (m, 1H), 2.28-2.19 (m, 3H). $^1$H-NMR (400 MHz, DMSO-d$_6$) δ 8.70 (s, 1H), 8.09 (s, 1H), 7.96 (d, J=3.6 Hz, 1H), 7.57 (d, J=8.8 Hz, 1H), 6.88-6.84 (m, 3H), 6.62 (br s, 2H), 6.15 (d, J=8.4 Hz, 1H), 5.46 (d, J=7.2 Hz, 1H), 5.40 (s, 1H), 4.64 (d, J=5.6 Hz, 1H), 4.48 (t, J=7.6 Hz, 1H), 4.13-4.12 (m, 1H), 2.69 (s, 3H), 2.56-2.54 (m, 1H), 2.08-2.01 (m, 3H). Also, to afford (2R,3R,3aS,6S,6aR)-6-((2-aminoquinolin-7-yl)oxy)-2-(4-methyl-7H-pyrrolo[2,3-d]pyrimidin-7-yl)hexahydro-2H-cyclopenta[b]furan-3,3a-diol as a solid. MS: 434 (M+1). $^1$H-NMR (400 MHz, Methanol-d$_4$) δ 8.66 (s, 1H), 7.80 (d, J=8.8 Hz, 1H), 7.73 (d, J=3.6 Hz, 1H), 7.52 (d, J=8.8 Hz, 1H), 6.95 (d, J=2.0 Hz, 1H), 6.88 (dd, J=8.4, 2.4 Hz, 1H), 6.81 (d, J=3.6 Hz, 1H), 6.63 (d, J=8.4 Hz, 1H), 6.16 (d, J=8.0 Hz, 1H), 4.76 (d, J=5.2 Hz, 1H), 4.62 (d, J=8.0 Hz, 1H), 4.32 (s, 1H), 2.75 (s, 3H), 2.57-2.47 (m, 1H), 2.26-2.18 (m, 3H). $^1$H-NMR (400 MHz, DMSO-d$_6$) δ 8.69 (s, 1H), 7.95 (d, J=3.6 Hz, 1H), 7.76 (d, J=8.8 Hz, 1H), 7.51 (d, J=8.4 Hz, 1H), 6.84-6.76 (m, 3H), 6.55 (d, J=8.8 Hz, 1H), 6.30 (br s, 2H), 6.15 (d, J=8.4 Hz, 1H), 5.46 (d, J=7.2 Hz, 1H), 5.39 (s, 1H), 4.62 (d, J=5.2 Hz, 1H), 4.47 (t, J=7.6 Hz, 1H), 4.13 (s, 1H), 2.69 (s, 3H), 2.56-2.54 (m, 1H), 2.08-1.97 (m, 3H).

Example 114

(2R,3R,3aS,6S,6aR)-6-((2-amino-3-bromoquinolin-7-yl)oxy)-2-(2-amino-4-methyl-7H-pyrrolo[2,3-d]pyrimidin-7-yl)hexahydro-3aH-cyclopenta[b]furan-3,3a-diol

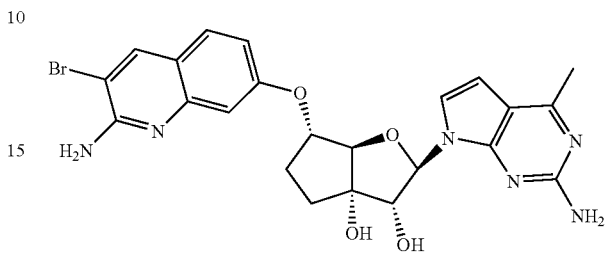

Step 1: To an oven-dried, argon cooled 2-5 mL microwave vial containing (3R,3aS,6S,6aR)-6-((2-amino-3-bromoquinolin-7-yl)oxy)hexahydro-3aH-cyclopenta[b]furan-2,3,3a-triol (0.086 g, 0.217 mmol) dissolved in anhydrous Acetonitrile (4.3 mL) was added 1,1'-(azodicarbonyl)dipiperidine (0.082 g, 0.325 mmol) followed by tri-n-butylphosphine (0.087 mL, 0.346 mmol) at room temperature. The mixture was stirred for 1 h, and then this solution was used directly without characterization because the product is unstable. In a separate oven-dried, argon cooled microwave vial containing di-tert-butyl (4-methyl-7H-pyrrolo[2,3-d]pyrimidin-2-yl)carbamate (0.151 g, 0.433 mol) dissolved in dry acetonitrile (1.0 mL) was added DBU (0.065 mL, 0.433 mmol). The mixture was stirred at room temperature for 30 min, and this suspension was transferred to the mixture described above via syringe. The combined reaction was stirred at room temperature under argon for 4 h. The reaction was quenched with water and extracted with EtOAc (3×), the organic layer washed with brine and dried with sodium sulfate, filtered, and concentrated under reduced pressure. The residue was purified by column chromatography (0-100% EtOAc/Hex) to afford di-tert-butyl (7-{(2R,3R,3aS,6S,6aR)-6-[(2-amino-3-bromoquinolin-7-yl)oxy]-3,3a-dihydroxyhexahydro-2H-cyclopenta[b]furan-2-yl}-4-methyl-7H-pyrrolo[2,3-d]pyrimidin-2-yl)imidodicarbonate. MS: 727/729 (M+1/M+3).

Step 2: To di-tert-butyl (7-{(2R,3R,3aS,6S,6aR)-6-[(2-amino-3-bromoquinolin-7-yl)oxy]-3,3a-dihydroxyhexahydro-2H-cyclopenta[b]furan-2-yl}-4-methyl-7H-pyrrolo[2,3-d]pyrimidin-2-yl)imidodicarbonate (0.04 g, 0.055 mmol) dissolved in DCM (1.10 mL) was added 2,2,2-trifluoroacetic acid (0.127 mL, 1.649 mmol). The mixture was stirred for 6 h at room temperature. The mixture was concentrated under reduced pressure and purified by mass triggered reverse phase HPLC (ACN/water modified with 0.1% NH$_4$OH) to afford (2R,3R,3aS,6S,6aR)-6-((2-amino-3-bromoquinolin-7-yl)oxy)-2-(2-amino-4-methy-7H-pyrrolo[2,3-d]pyrimidin-7-yl)hexahydro-3aH-cyclopenta[b]furan-3,3a-diol as a TFA salt, as a solid. MS: 527/529 (M+1/M+3). $^1$H NMR (499 MHz, DMSO-d$_6$) δ 9.55-9.19 (m, 3H), 9.15 (d, J=15.5 Hz, 1H), 8.42 (d, J=13.9 Hz, 1H), 8.05 (d, J=25.0 Hz, 1H), 7.29 (s, 1H), 7.27 (s, 2H), 6.21 (d, J=113.4 Hz, 2H), 4.79-4.46 (m, 2H), 4.42-4.24 (m, 2H), 3.85 (d, J=20.8 Hz, 1H), 3.52-3.38 (m, 1H), 3.20-3.10 (m, 1H), 2.98 (d, J=30.6 Hz, 3H), 1.90 (s, 1H), 1.80-1.63 (m, 1H).

Example 115

(2R,3R,3aS,6S,6aR)-6-((2-amino-3-(difluoromethyl)quinolin-7-yl)oxy)-2-(4-methyl-7H-pyrrolo[2,3-d]pyrimidin-7-yl)hexahydro-3aH-cyclopenta[b]furan-3,3a-diol

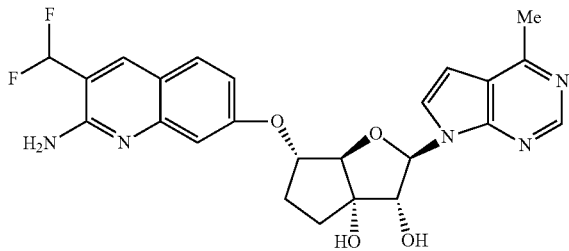 [SMILES: Cc1ncnc2c1ccn2[C@@H]1O[C@@H]2[C@@H](Oc3ccc4cc(C(F)F)c(N)nc4c3)CC[C@]2(O)[C@H]1O]

Step 1: To a stirred mixture of (3aR,4R,5aR,6R,8aR)-2,2-dimethyl-4-(4-methyl-7H-pyrrolo[2,3-d]pyrimidin-7-yl)hexahydrocyclopenta[2,3]furo[3,4-d][1,3]dioxol-6-ol (100 mg, 0.302 mmol) in DCM (1.5 mL) and pyridine (0.3 mL) was added trifluoromethanesulfonic anhydride (128 mg, 0.453 mmol) at 0° C. under an argon atmosphere. The resulting mixture was stirred for 1 h at 0° C. The reaction mixture was quenched by aqueous saturated NaHCO$_3$ (10 mL), extracted with EtOAc (25 mL×3). The combined organic layers were dried over anhydrous Na$_2$SO$_4$, filtered, and the filtrate was concentrated under reduced pressure. The residue was purified by column chromatography on silica (0-50% EtOAc/PE) to afford (3aR,4R,5aR,6R,8aR)-2,2-dimethyl-4-(4-methyl-7H-pyrrolo[2,3-d]pyrimidin-7-yl)hexahydrocyclopenta[2,3]furo[3,4-d][1,3]dioxol-6-yl trifluoromethanesulfonate as an oil. MS: 464 (M+1). $^1$H-NMR (300 MHz, DMSO-d$_6$) 8.76 (s, 1H), 7.85 (d, J=3.6 Hz, 1H), 6.90 (d, J=3.9 Hz, 1H), 6.30 (d, J=5.1 Hz, 1H), 5.34 (d, J=4.8 Hz, 1H), 4.91 (d, J=3.6 Hz, 1H), 4.54-4.52 (m, 1H), 2.71 (s, 3H), 2.65-2.50 (m, 1H), 2.45-2.13 (m, 3H), 1.59 (s, 3H), 1.40 (s, 3H).

Step 2: To a stirred mixture of (3aR,4R,5aR,6R,8aR)-2,2-dimethyl-4-(4-methyl-7H-pyrrolo[2,3-d]pyrimidin-7-yl)hexahydrocyclopenta[2,3]furo[3,4-d][1,3]dioxol-6-yl trifluoromethanesulfonate (100 mg, 0.216 mmol), 3-(difluoromethyl)-2-((4-methoxybenzyl)amino)quinolin-7-ol (71.3 mg, 0.216 mmol) in NMP (3 mL) was added Cs$_2$CO$_3$ (211 mg, 0.647 mmol) at 25° C. under an argon atmosphere. The resulting mixture was stirred at 25° C. for 2 h. The reaction mixture was diluted with water (50 mL), and extracted with DCM (50 mL×3). The combined organic layers were dried over anhydrous Na$_2$SO$_4$, filtered, and the filtrate was concentrated under reduced pressure. The residue was purified by reverse phase column chromatography (ACN/water with 5 mM NH$_4$HCO$_3$ modifier) to afford 3-(difluoromethyl)-7-(((3aR,4R,5aR,6S,8aR)-2,2-dimethyl-4-(4-methyl-7H-pyrrolo[2,3-d]pyrimidin-7-yl)hexahydrocyclopenta[2,3]furo[3,4-d][1,3]dioxol-6-yl)oxy)-N-(4-methoxybenzyl)quinolin-2-anine as a solid. MS: 644 (M+1). $^1$H-NMR (300 MHz, DMSO-d$_6$) δ 8.73 (s, 1H), 8.16 (s, 1H), 7.88 (d, J=3.6 Hz, 1H), 7.72 (d, J=8.7 Hz, 1H), 7.38-7.19 (m, 2H), 7.09-6.83 (m, 7H), 6.32 (d, J=4.8 Hz, 1H), 5.35 (d, J=5.1 Hz, 1H), 4.85-4.84 (m, 1H), 4.69-4.61 (m, 2H), 4.41-4.39 (m, 1H), 3.72 (s, 3H), 2.70 (s, 3H), 2.60-2.16 (m, 4H), 1.55 (s, 3H), 1.41 (s, 3H).

Step 3: To 3-(difluoromethyl)-7-(((3aR,4R,5aR,6S,8aR)-2,2-dimethyl-4-(4-methyl-7H-pyrrolo[2,3-d]pyrimidin-7-yl)hexahydrocyclopenta[2,3]furo[3,4-d][1,3]dioxol-6-yl)oxy)-N-(4-methoxybenzyl)quinolin-2-amine (100 mg, 0.155 mmol) was added TFA (5 mL) at 25° C. The resulting mixture was stirred for 1.5 h at 50° C. The reaction mixture was azeotroped with toluene five times (20 mL) to remove TFA. The residue was added to water (5 mL) and TFA (5 mL) at 25° C. The mixture was stirred for 16 h at 25° C. The mixture was azeotroped with toluene five times (20 mL) to remove TFA and water. The residue was purified by reverse phase column chromatography (ACN/water with 5 mM NH$_4$HCO$_3$ modifier) to afford (2R,3R,3aS,6S,6aR)-6-((2-amino-3-(difluoromethyl)quinolin-7-yl)oxy)-2-(4-methyl-7H-pyrrolo[2,3-d]pyrimidin-7-yl)hexahydro-2H-cyclopenta[b]furan-3,3a-diol as a solid. MS: 484 (M+1). $^1$H-NMR (300 MHz, DMSO-d$_6$) δ 8.70 (s, 1H), 8.14 (s, 1H), 7.96 (d, J=3.61 Hz, 1H), 7.70 (d, J=8.7 Hz, 1H), 7.27-6.84 (m, 4H), 6.45 (br s, 2H), 6.16 (d, J=8.4 Hz, 1H), 5.47 (d, J=7.2 Hz, 1H), 5.41 (s, 1H), 4.66 (d, J=5.4 Hz, 1H), 4.51-4.46 (m, 1H), 4.14 (s, 1H), 2.72 (s, 3H), 2.54-2.50 (m, 1H), 2.10-1.96 (m, 3H).

Example 116

(1S,2R,3R,5R)-3-(2-(2-amino-3-fluoroquinolin-7-yl)ethyl)-5-(4-amino-7H-pyrrolo[2,3-d]pyrimidin-7-yl)-3-methylcyclopentane-1,2-diol

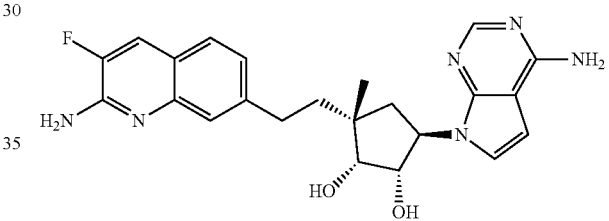

Step 1: Under argon protection, to a mixture of ((3aR,4R,6R,6aS)-6-(4-chloro-7H-pyrrolo[2,3-d]pyrimidin-7-yl)-2,2-dimethyltetrahydro-3aH-cyclopenta[d][1,3]dioxol-4-yl)methanol (1.0 g, 3.09 mmol) in anhydrous DCM (20 mL) was added Dess-Martin Periodinane (2.62 g, 6.18 mmol) at 0° C. The resulting mixture was stirred at room temperature for 1.5 h. The reaction mixture was quenched with saturated aqueous Na$_2$S$_2$O$_3$ (20 mL) at 0° C. and extracted with DCM (2×60 mL). The combined organic layers were washed with saturated aqueous NaHCO$_3$ (60 mL) and brine (60 mL) sequentially, dried over anhydrous Na$_2$SO$_4$, filtered, and the filtrate was concentrated under reduced pressure. The residue was purified by column chromatography on silica (0-33% EtOAc/PE) to afford (3aR,4S,6R,6aS)-6-(4-chloro-7H-pyrrolo[2,3-d]pyrimidin-7-yl)-2,2-dimethyltetrahydro-3aH-cyclopenta[d][1,3]dioxole-4-carbaldehyde as an oil. MS: 322 (M+1). $^1$H-NMR (400 MHz, DMSO-d$_6$) δ 9.75 (s, 1H), 8.65 (s, 1H), 7.92 (d, J=4.0 Hz, 1H), 6.73 (d, J=3.6 Hz, 1H), 5.22-5.16 (m, 1H), 5.11 (dd, J=6.8, 4.8 Hz, 1H), 4.97 (dd, J=7.2, 5.2 Hz, 1H), 3.19-3.14 (m, 1H), 2.54-2.46 (m, 2H), 1.51 (s, 3H), 1.27 (s, 3H).

Step 2: Compound (3aR,4R,6R,6aS)-6-(4-chloro-7H-pyrrolo[2,3-d]pyrimidin-7-yl)-2,2-dimethyl tetrahydro-3aH-cyclopenta[d][1,3]dioxole-4-carbaldehyde (1.9 g, 5.91 mmol) was dissolved in 1,4-dioxane (60 mL) at room temperature. Then, aqueous formaldehyde (37 wt % in water, 0.701 mL, 7.09 mmol) and aqueous potassium carbonate (2M, 14.76 mL, 29.5 mmol) were added at room temperature. The resultant mixture was stirred at room temperature for 16 h. The reaction mixture was neutralized with aqueous AcOH (50 w %) and then extracted with EtOAc (3×200 mL). The combined organic layers were washed with brine (50 mL), dried over anhydrous sodium sulfate, filtered, and the filtrate was concentrated under reduced pressure. The residue was dissolved in EtOH (60 mL) and treated with sodium tetrahydroborate (0.107 g, 2.83 mmol) at 0° C. The reaction mixture was stirred at 0° C. for 3 h. The mixture was then concentrated under reduced pressure. The resulting residue was diluted with water (50 mL). The pH of the mixture was adjusted to 7 with aqueous AcOH (50 wt %). Then the mixture was extracted with EtOAc (3×200 mL). The combined organic layers were washed with brine (50 mL), dried over anhydrous sodium sulfate, filtered, and the filtrate was concentrated under reduced pressure. The residue was purified by silica gel column chromatography (9:10:1 DCM/EtOAc/MeOH) to afford ((3aR,6R,6aS)-6-(4-chloro-7H-pyrrolo[2,3-d]pyrimidin-7-yl)-2,2-dimethyltetrahydro-3aH-cyclopenta[d][1,3]dioxole-4,4-diyl)dimethanol as a foam. MS: 354 (M+1). $^1$H-NMR (400 MHz, DMSO-$d_6$) δ 8.67 (s, 1H), 8.01 (d, J=3.6 Hz, 1H), 6.74 (d, J=3.6 Hz, 1H), 5.27-5.20 (m, 1H), 4.95 (t, J=6.4 Hz, 1H), 4.89 (t, J=5.2 Hz, 1H), 4.63 (d, J=7.2 Hz, 1H), 4.50 (t, J=5.6 Hz, 1H), 3.60-3.49 (m, 3H), 3.44-3.40 (m, 1H), 2.26-2.23 (m, 1H), 2.06-1.92 (m, 1H), 1.48 (s, 3H), 1.22 (s, 3H).

Step 3: To a solution of ((3aR,6R,6aS)-6-(4-chloro-7H-pyrrolo[2,3-d]pyrimidin-7-yl)-2,2-dimethyltetrahydro-3aH-cyclopenta[d][1,3]dioxole-4,4-diyl)dimethanol (2.5 g, 7.07 mmol) in DCM (26 mL) were added triethylamine (2.95 mL, 21.20 mmol) and TBDPS-Cl (3.63 mL, 14.13 mmol) at 0° C. under argon. The reaction mixture was then stirred at room temperature for 16 h. The resulting solution was concentrated under reduced pressure. The residue was purified by silica gel column chromatography (0-30% EtOAc/PE) to afford ((3aR,4S,6R,6aS)-4-(((tert-butyldiphenylsilyl)oxy)methyl)-6-(4-chloro-7H-pyrrolo[2,3-d]pyrimidin-7-yl)-2,2-dimethyltetrahydro-3aH-cyclopenta[d][1,3]dioxol-4-yl)methanol as a foam. MS: 592 (M+1). $^1$H-NMR (400 MHz, DMSO-$d_6$) δ 8.60 (s, 1H), 7.90 (d, J=3.6 Hz, 1H), 7.67-7.64 (m, 4H), 7.49-7.41 (m, 6H), 6.70 (d, J=3.6 Hz, 1H), 5.24-5.17 (m, 1H), 5.01 (t, J=6.8 Hz, 1H), 4.73 (d, J=7.2 Hz, 1H), 4.60 (br s, 1H), 3.77 (d, J=10.0 Hz, 1H), 3.70 (d, J=11.2 Hz, 1H), 3.62-3.58 (m, 2H), 2.29-2.24 (m, 1H), 2.20-2.14 (m, 1H), 1.47 (s, 3H), 1.22 (s, 3H), 1.05 (s, 9H). The column also afforded ((3aR,4R,6R,6aS)-4-(((tert-butyldiphenylsilyl)oxy)methyl)-6-(4-chloro-7H-pyrrolo[2,3-d]pyrimidin-7-yl)-2,2-dimethyltetrahydro-3aH-cyclopenta[d][1,3]dioxol-4-yl)methanol as a foam. MS: 592 (M+1). $^1$H NMR (400 MHz, DMSO-$d_6$) δ 8.49 (s, 1H), 7.80 (d, J=3.6 Hz, 1H), 7.53-7.51 (m, 4H), 7.29-7.24 (m, 6H), 6.56 (d, J=3.6 Hz, 1H), 5.04-4.99 (m, 1H), 4.87 (br s, 1H), 4.77 (t, J=6.4 Hz, 1H), 4.44 (d, J=6.4 Hz, 1H), 3.62 (d, J=10.0 Hz, 1H), 3.51 (d, J=10.4 Hz, 1H), 3.46 (d, J=10.4 Hz, 1H), 3.38 (d, J=10.4 Hz, 1H), 2.13-2.10 (m, 1H), 1.93-1.87 (m, 1H), 1.13 (s, 3H), 1.00 (s, 3H), 0.81 (s, 9H).

Step 4: To a stirred solution of ((3aR,4R,6R,6aS)-4-(((tert-butyldiphenylsilyl)oxy)methyl)-6-(4-chloro-7JH-pyrrolo[2,3-d]pyrimidin-7-yl)-2,2-dimethyltetrahydro-3aH-cyclopenta[d][1,3]dioxol-4-yl)methanol (1.7 g, 2.87 mmol) in toluene (50 mL) were added triphenylphosphine (3.01 g, 11.5 mmol), 1H-imidazole (782 mg, 11.5 mmol), and diiodine (1.46 g, 5.74 mmol) at room temperature under argon. Then the mixture was stirred at 120° C. for 3 h. The solvent was removed under reduced pressure, and the residue was purified by silica gel column chromatography (040% EtOAc/PE) to afford 7-((3aS,4R,6R,6aR)-6-(((tert-butyldiphenylsilyl)oxy)methyl)-6-(iodomethyl)-2,2-dimethyltetrahydro-3aH-cyclopenta[d][1,3]dioxol-4-yl)-4-chloro-7H-pyrrolo[2,3-d]pyrimidine as an oil. MS: 702 (M+1). $^1$H NMR (400 MHz, Methanol-$d_4$) δ 8.63 (s, 1H), 7.82-7.78 (m, 4H), 7.70 (d, J=3.6 Hz, 1H), 7.50-7.45 (m, 6H), 6.74 (d, J=3.6 Hz, 1H), 5.16-5.10 (m, 1H), 5.08-5.04 (m, 1H), 4.68 (d, J=7.2 Hz, 1H), 3.96 (d, J=11.2 Hz, 1H), 3.75 (t, J=10.0 Hz, 2H), 3.63 (d, J=11.2 Hz, 1H), 2.63-2.57 (m, 1H), 2.40-2.23 (m, 1H), 1.33 (s, 3H), 1.27 (s, 3H), 1.09 (s, 9H).

Step 5: To a stirred solution of 7-((3aS,4R,6R,6aR)-6-(((tert-butyldiphenylsilyl)oxy)methyl)-6-(iodomethyl)-2,2-dimethyltetrahydro-3aH-cyclopenta[d][1,3]dioxol-4-yl)-4-chloro-7H-pyrrolo[2,3-d]pyrimidine (1.6 g, 2.28 mmol) in 1,4-dioxane (40 mL) was added sodium phenolate (661 mg, 5.70 mmol) at room temperature under argon. The reaction mixture was stirred at 80° C. overnight. The reaction mixture was then directly purified by silica gel column chromatography (0-40% EtOAc/PE) to afford 7-((3aS,4R,6R,6aR)-6-(((tert-butyldiphenylsilyl)oxy)methyl)-6-(iodomethyl)-2,2-dimethyltetrahydro-3aH-cyclopenta[d][1,3]dioxol-4-yl)-4-phenoxy-7H-pyrrolo[2,3-d]pyrimidine as an oil. MS: 760 (M+1). $^1$H NMR (400 MHz, DMSO-$d_6$) δ 8.43 (s, 1H), 7.78-7.72 (m, 6H), 7.51-7.47 (m, 10H), 6.62 (d, J=3.6 Hz, 1H), 5.22-5.16 (m, 1H), 5.09 (t, J=6.4 Hz, 1H), 4.61 (d, J=6.8 Hz, 1H), 3.85 (d, J=11.2 Hz, 1H), 3.77-3.70 (m, 2H), 3.63 (d, J=11.2 Hz, 1H), 2.56-2.54 (m, 1H), 2.31-2.28 (m, 1H), 1.24 (s, 3H), 1.19 (s, 3H), 1.03 (s, 9H).

Step 6: To a stirred solution of 7-((3aS,4R,6R,6aR)-6-(((tert-butyldiphenylsilyl)oxy)methyl)-6-(iodomethyl)-2,2-dimethyltetrahydro-3aH-cyclopenta[d][1,3]dioxol-4-yl)-4-phenoxy-7H-pyrrolo[2,3-d]pyrimidine (1.6 g, 2.11 mmol) in EtOAc (20 mL) and ethanol (20 mL) was added dihydroxypalladium on carbon (20 wt %, 1600 mg, 2.28 mmol) at room temperature under nitrogen. The suspension was degassed under vacuum and purged with $H_2$ several times, then the mixture was stirred under 1-2 atm of $H_2$ at 25° C. for 30 min. The mixture was then filtered through a Celite pad, and the filtrate was concentrated under reduced pressure to afford 7-((3aS,4R,6S,6aR)-6-(((tert-butyldiphenylsilyl)oxy)methyl)-2,2,6-trimethyltetrahydro-3aH-cyclopenta[d][1,3]dioxol-4-yl)-4-phenoxy-7H-pyrrolo[2,3-d]pyrimidine as an oil. MS: 634 (M+1). $^1$H NMR (400 MHz, DMSO-$d_6$) δ 8.41 (s, 1H), 7.79 (d, J=2.7 Hz, 1H), 7.72-7.68 (m, 4H), 7.51-7.46 (m, 8H), 7.34-7.27 (m, 3H), 6.58 (d, J=2.7 Hz, 1H), 5.22-5.11 (m 1H), 5.06 (t, J=4.8 Hz, 1H), 4.52 (d, J=5.1 Hz, 1H), 3.71 (d, J=7.8 Hz, 1H), 3.61 (d, J=7.8 Hz, 1H), 2.50-2.44 (m, 1H), 2.15-2.02 (m, 1H), 1.30 (s, 3H), 1.29 (s, 3H), 1.20 (s, 3H), 1.03 (s, 9H).

Step 7: To a stirred solution of 7-((3aS,4R,6S,6aR)-6-(((tert-butyldiphenylsilyl)oxy)methyl)-2,2,6-trimethyltetrahydro-3aH-cyclopenta[d][1,3]dioxol-4-yl)-4-phenoxy-7H-pyrrolo[2,3-d]pyrimidine (1.1 g, 1.74 mmol) in THF (10 mL) was added tetrabutylammonium fluoride (1M in THF) (3.47 mL, 3.47 mmcl) at room temperature under argon. The reaction was stirred at 45° C. overnight. After completion, the solvent was removed under reduced pressure, and the residue was purified by silica gel column chromatography (0-40% EtOAc/PE) to afford ((3aR,4S,6R,6aS)-2,2,4-trimethyl-6-(4-phenoxy-7H-pyrrolo[2,3-d]pyrimidin-7-yl) tetrahydro-3aH-cyclopenta[d][1,3]dioxol-4-yl)methanol as a solid. MS: 396 (M+1). $^1$H-NMR (300 MHz, DMSO-$d_6$) δ 8.37 (s, 1H), 7.80 (d, J=3.9 Hz, 1H), 7.51-7.46 (m, 2H), 7.34-7.26 (m, 3H), 6.56 (d, J=3.6 Hz, 1H), 5.24-5.18 (m, 1H), 5.02 (t, J=6.3 Hz, 1H), 4.57 (t, J=4.8 Hz, 1H), 4.49 (d, J=7.2 Hz, 1H), 3.55-3.51 (m, 1H), 3.42-3.37 (m, 1H), 2.42-2.35 (m, 1H), 2.05-1.97 (m, 1H), 1.47 (s, 3H), 1.23 (s, 3H), 1.16 (s, 3H).

Step 8: To a stirred solution of ((3aR,4S,6R,6aS)-2,2,4-trimethyl-6-(4-phenoxy-7H-pyrrolo[2,3-d]pyrimidin-7-yl)tetrahydro-3aH-cyclopenta[d][1,3]dioxol-4-yl)methanol (520 mg, 1.315 mmol) in DCM (10 mL) was added Dess-Martin Periodinane (837 mg, 1.97 mmol) at room temperature under argon. The reaction was stirred at this temperature for 30 min. The resultant mixture was quenched with saturated aqueous $NaHCO_3$ (1M, 20 mL), and the mixture was extracted with DCM (3×30 mL). The combined organic layers were washed with brine (3×20 mL), dried over anhydrous sodium sulfate, and filtered. The filtrate was then concentrated under reduced pressure, and the resulting crude (3aR,4R,6R,6aS-2,2,4-trimethyl-6-(4-phenoxy-7H-pyrrolo[2,3-d]pyrimidin-7-yl)tetrahydro-3aH-cyclopenta[d][1,3]dioxole-4-carbaldehyde was used directly in the next step.

Step 9: To a stirred mixture of bromo(methyl)triphenylphosphorane (1.32 g, 3.68 mmol) in THF (20 mL) was added n-butyllithium (2.5M in hexane, 1.37 mL, 3.42 mmol) at −60° C. under argon. The reaction mixture was warmed to room temperature and kept for −30 minutes. Then crude (3aR,4R,6R,6aS)-2,2,4-trimethyl-6-(4-phenoxy-7H-pyrrolo[2,3-d]pyrimidin-7-yl)tetrahydro-3aH-cyclopenta[d][1,3]dioxole-4-carbaldehyde (1.315 mmol) in THF (5 mL) was added dropwise to the above solution at −40° C. under argon. The resultant mixture was stirred at room temperature for 3 h. The reaction was quenched with saturated aqueous $NH_4Cl$ (20 mL) at −40° C. and extracted with EtOAc (3×50 mL). The combined organic fractions were washed with brine (3×20 mL), dried over anhydrous sodium sulfate, and filtered. The filtrate was concentrated under reduced pressure, and the resulting residue was purified by silica gel column chromatography (0-40% EtOAc/PE) to afford 4-phenoxy-7-((3aS,4R,6S,6aR)-2,2,6-trimethyl-6-vinyltetrahydro-3aH-cyclopenta[d][1,3]dioxol-4-yl)-7H-pyrrolo[2,3-d]pyrimidine as a solid. MS: 392 (M+1). $^1$H-NMR (400 MHz, DMSO-$d_6$) δ 8.36 (s, 1H), 7.81 (d, J=3-6 Hz, 1H), 7.50-7.46 (m, 2H), 7.32-7.25 (m, 3H), 6.55 (d, J=3.6 Hz, 1H), 6.20-6.13 (m, 1H), 5.20-5.12 (m, 3H), 5.04 (dd, J=5.2, 7.2 Hz, 1H), 4.50 (d, J=7.2 Hz, 1H), 2.39-2.32 (m, 2H), 1.47 (s, 3H), 1.23 (s, 3H), 1.22 (s, 3H).

Step 10: 4-phenoxy-7-((3aS,4R,6S,6aR)-2,2,6-trimethyl-6-vinyltetrahydro-3aH-cyclopenta[d][1,3]dioxol-4-yl)-7H-pyrrolo[2,3-d]pyrimidine (272 mg, 0.695 mmol) was dissolved in 1,4-dioxane (15 mL) in a sealed tube, and then the mixture was treated with concentrated $NH_3·H_2O$ (28 wt %, 15 mL). The resultant mixture was heated at 120° C. for 16 h. The volatiles were removed under reduced pressure, and the residue was purified by prep TLC (1:1 PE:EtOAc) to afford 7-((3aS,4R,6S,6aR)-2,2,6-trimethyl-6-vinyltetrahydro-3aH-cyclopenta[d][1,3]dioxol-4-yl)-7H-pyrrolo[2,3-d]pyrimidin-4-amine as a solid. MS: 315 (M+1). $^1$H-NMR (400 MHz, DMSO-$d_6$) δ 8.06 (s, 1H), 7.38 (d, J=3.6 Hz, 1H), 6.97 (br s, 2H), 6.57 (d, J=3.6 Hz, 1H), 6.18-6.11 (m, 1H), 5.17-5.08 (m, 2H), 5.08-5.04 (m, 1H), 4.98 (dd, J=4.8, 7.2 Hz, 1H), 4.47 (d, J=6.8 Hz, 1H), 2.33-2.20 (m, 2H), 1.45 (s, 3H), 1.22 (s, 3H), 1.20 (s, 3H).

Step 11: To a 20 mL microwave tube charged with 7-((3aS,4R,6S,6aR)-2,2,6-trimethyl-6-vinyltetrahydro-3aH-cyclopenta[d][1,3]dioxol-4-yl)-7H-pyrrolo[2,3-d]pyrimidin-4-amine (174 mg, 0.553 mmol) was added 9-borabicyclo[3.3.1]nonane (0.5M in THF, 4.43 mL, 2.21 mmol) at room temperature under argon. The reaction mixture was heated at 60° C. for 1 h. The mixture was cooled to 0° C. after completion. To this mixture was added a solution of potassium phosphate (587 mg, 2.77 mmol) in water (1.3 mL) at 0° C. After stirring at room temperature for 30 min, Pd(dppf)$Cl_2$ (41 mg, 0.055 mmol) and a solution of 7-bromo-3-fluoroquinolin-2-amine (147 mg, 0.608 mmol) in THF (4 mL) were added. The final mixture was irradiated with microwave irradiation at 80° C. for 2 h. The reaction mixture was then diluted with water (20 nL) and the mixture was extracted with EtOAc (3×50 mL). The combined organic layers were washed with brine (3×20 mL), dried over anhydrous sodium sulfate, and filtered. The filtrate was concentrated under reduced pressure, and the residue was purified by prep-TLC (20:1 EtOAc:MeOH) to afford 7-(2-((3aR,4R,6R,6aS)-6-(4-amino-7H-pyrrolo[2,3-d]pyrimidin-7-yl)-2,2,4-trimethyltetrahydro-3aH-cyclopenta[d][1,3]dioxol-4-yl)ethyl)-3-fluoroquinolin-2-amine as a solid. MS: 477 (M+1). $^1$H-NMR (400 MHz. DMSO-$d_6$) δ 8.06 (s, 1H), 7.78 (d, J=11.6 Hz, 1H), 7.60 (d, J=8.4 Hz, 1H), 7.38-7.36 (m, 2H), 7.14 (d, J=8.4 Hz, 1H), 6.97 (br s, 2H), 6.71 (br s, 2H), 6.57 (d, J=3.6 Hz, 1H), 5.05-5.02 (m, 2H), 4.44 (d, J=4.0 Hz, 1H), 2.77-2.70 (m, 2H), 2.27-2.22 (m, 1H), 2.15-2.09 (m, 1H), 1.88-1.73 (m, 2H), 1.46 (s, 3H), 1.25 (s, 3H), 1.21 (s, 3H).

Step 12: 7-(2-((3aR,4R,6R,6aS)-6-(4-amino-7H-pyrrolo[2,3-d]pyrimidin-7-yl)-2,2,4-trimethyltetrahydro-4H-cyclopenta[d][1,3]dioxol-4-yl)ethyl)-3-fluoroquinolin-2-anine (129.4 mg, 0.272 mmol) in TFA (2.72 mL) and water (2.72 mL) was stirred for overnight at 40° C. The reaction mixture was then concentrated under reduced pressure, and the residue was purified by mass-triggered HPLC (ACN/water with 0.1% TFA modifier) to afford (1S,2R,3R,5R)-3-(2-(2-amino-3-fluoroquinolin-7-yl)ethyl)-5-(4-amino-7H-pyrrolo[2,3-d]pyrimidin-7-yl)-3-methylcyclopentane-1,2-diol, TFA salt, as an oil. MS: 437 (M+1). $^1$H NMR (DMSO-$d_6$) δ: 8.36 (s, 1H), 8.10 (d, J=11.2 Hz, 2H), 7.79-7.64 (m, 2H), 7.44 (s, 1H), 7.29 (d, J=8.1 Hz, 1H), 7.24 (s, 1H), 7.14 (s, 1H), 7.04 (s, 1H), 6.96 (d, J=3.6 Hz, 1H), 5.11-5.03 (m, 1H), 5.02-4.79 (m, 1H), 4.65-4.53 (m, 1H), 3.66 (d, J=4.2 Hz, 1H), 2.80 (td, J=12.7, 4.3 Hz, 1H), 2.67 (td, J=12.6, 4.3 Hz, 1H), 2.15 (dd, J=13.5, 10.4 Hz, 1H), 1.88 (td, J=12.9, 4.6 Hz, 1H), 1.67 (td, J=12.9, 4.6 Hz, 1H), 1.60 (dd, J=13.5, 8.9 Hz, 1H), 1.27 (s, 3H).

Example 117

(1R,2S,3R,5S)-5-(2-(2-amino-3-bromoquinolin-7-yl)ethyl)-3-(4-amino-7H-pyrrolo[2,3-d]pyrimidin-7-yl)-1,5-dimethylcyclopentane-1,2-diol

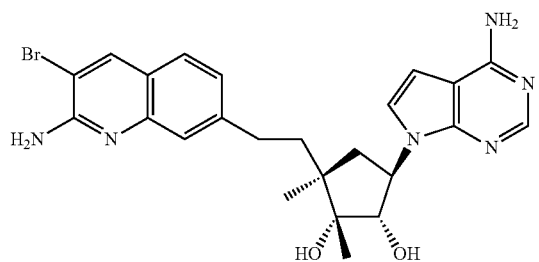 [SMILES: C[C@@]1(CCc2ccc3cc(Br)c(N)nc3c2)C[C@@H](n2ccc3c(N)ncnc32)[C@H](O)[C@]1(C)O]

Step 1: (1R,4S)-tert-butyl 5-methyl-3-oxo-2-azabicyclo[2.2.1]hept-5-ene-2-carboxylate (1 g, 4.48 mmol) was dissolved in 4 M HCl/MeOH (10 mL), and the reaction mixture was heated to reflux and stirred at this temperature for 2 h. The solvent was then removed under reduced pressure to give crude (1S,4R)-methyl 4-amino-2-methylcyclopent-2-enecarboxylate hydrochloride which was used directly in the next step.

Step 2: To a stirred solution of (1S,4R)-methyl 4-amino-2-methylcyclopent-2-enecarboxylate hydrochloride (859 mg, 4.48 mmol) in 5:1 Acetone:H$_2$O (12 mL) were added sodium bicarbonate (753 mg, 8.96 mmol) and di-tert-butyl dicarbonate (1076 mg, 4.93 mmol). The reaction mixture was stirred at 25° C. for 2 h. The reaction mixture was diluted with 100 mL of water and extracted with 100 mL EtOAc. The organic phase was then washed with 100 mL of brine, dried over anhydrous sodium sulfate, filtered, and the filtrate was concentrated under reduced pressure. The residue was purified by silica gel chromatography (3:1 PE/EtOAc) to give (1S,4R)-methyl 4-((tert-butoxy carbonyl)amino)-2-methylcyclopent-2-enecarboxylate as an oil. $^1$H NMR (400 MHz, Chloroform-d) δ 5.58-5.52 (m, 1H), 5.04 (s, 1H), 4.72 (s, 1H), 3.75 (s, 3H), 3.32-3.24 (m, 1H), 2.53 (dt, J=13.9, 8.5 Hz, 1H), 1.90 (dt, J=13.9, 3.2 Hz, 1H), 1.77 (q, J=1.3 Hz, 3H), 1.46 (s, 9H).

Step 3: To a stirred solution of (1S,4R)-methyl 4-((tert-butoxycarbonyl)amino)-2-methylcyclopent-2-enecarboxylate (4.3 g, 16.84 mmol) in THF (80 mL) was added IM lithium bis(trimethylsilyl)amide in THF (38.7 mL, 38.7 mmol, 1M) at −78° C., and the reaction mixture was stirred at −78° C. for 0.5 h. Then, iodomethane (2.63 g, 18.53 mmol) was added dropwise at −78° C. and the resulting mixture was stirred at −20° C. for 2 h. The reaction was quenched with saturated aqueous NH$_4$Cl (100 mL) and extracted with EtOAc (120 mL×3). The combined organic layers were dried over anhydrous sodium sulfate, filtered, and the filtrate was concentrated under reduced pressure. The residue was purified by silica gel column chromatography (20-25% EtOAc/PE) to afford (1S,4R)-methyl 4-((tert-butoxycarbonyl)amino)-1,2-dimethylcyclopent-2-enecarboxylate as an oil. $^1$H NMR (300 MHz, Chloroform-d) δ 5.49 (p, J=1.5 Hz, 1H), 5.03 (s, 1H), 4.69 (s, 1H), 3.72 (s, 3H), 2.21-2.15 (m, 2H), 1.69 (t, J=1.5 Hz, 3H), 1.46 (s, 9H), 1.31 (s, 3H).

Step 4: To a stirred solution of (1S,4R)-methyl 4-((tert-butoxycarbonyl)amino)-1,2-dimethylcyclopent-2-enecarboxylate (3.1 g, 11.5 mmol) in THF (50 mL) was added lithium borohydride (2M in THF, 11.5 mL, 23.02 mmol) dropwise at 0° C. Then, the reaction mixture was stirred at room temperature for 16 h. The mixture was quenched with water (100 mL) and extracted with EtOAc (100 mL×3). The combined organic layers were dried over anhydrous sodium sulfate, filtered, and the filtrate was concentrated under reduced pressure. The residue was purified by silica gel column chromatography (18-22% EtOAc/PE) to afford tert-butyl ((1R,4S)-4-(hydroxymethyl)-3,4-dimethylcyclopent-2-en-1-yl)carbamate as a solid. $^1$H NMR (400 MHz, Chloroform-d) δ 5.47 (s, 1H), 4.58 (d, J=8.7 Hz, 1H), 3.54 (d, J=10.5 Hz, 1H), 3.31 (d, J=10.5 Hz, 1H), 2.13 (dd, J=13.8, 8.7 Hz, 1H), 1.76 (dd, J=13.8, 3.0 Hz, 1H), 1.66 (d, J=1.5 Hz, 3H), 1.45 (s, 91H), 1.00 (s, 3H).

Step 5: To a stirred solution of tert-butyl ((1R,4S)-4-(hydroxymethyl)-3,4-dimethylcyclopent-2-en-1-yl)carbamate (550 mg, 2.279 mmol) in 1:1 tBuOH:H$_2$O (6 mL) was added 4-methylmorpholine 4-oxide (534 mg, 4.56 mmol) at room temperature. Then the mixture was cooled to 0° C. and 4% osmium(VIII) oxide in water (1.88 g, 0.296 mmol) was added at 0° C. The reaction mixture was stirred at 0° C. for 16 h. The reaction was quenched with 50 mL saturated aqueous sodium thiosulfate and extracted with 50 mL EtOAc. The organic layer was washed with 50 mL water and 50 mL brine, dried over anhydrous sodium sulfate, filtered, and the filtrate was concentrated under reduced pressure. The residue was purified by silica gel chromatography (1:1 PE/EtOAc) to give tert-butyl ((1R,2S,3R,4R)-2,3-dihydroxy-4-(hydroxymethyl)-3,4-dimethylcyclopentyl)carbamate as a solid. Then, tert-butyl ((1R,2S,3R,4R)-2,3-dihydroxy-4-(hydroxymethyl)-3,4-dimethylcyclopentyl)carbamate (530 ng, 1.93 mmol) was dissolved in HCl in MeOH (4M, 10 mL), and the reaction mixture was stirred at 25° C. for 2 h. The solvent was removed under reduced pressure to give crude product which was used directly in the next step. Then, to a stirred solution of (1R,2S,3R,5R)-3-amino-5-(hydroxymethyl)-1,5-dimethylcyclopentane-1,2-diol hydrochloride (402 mg, 1.9 mmol) in i-PrOH (6 mL) were added DIEA (0.664 mL, 3.80 mmol) and 4,6-dichloro-5-(2,2-diethoxyethyl)pyrimidine (554 mg, 2.09 mmol) at room temperature. The reaction mixture was heated to 100° C. and stirred at this temperature for 8 h. The solvent was then removed under reduced pressure, and the resulting crude residue was purified by silica gel column chromatography (eluting with EtOAc) to give (1R,2S,3R,5R)-3-((6-chloro-5-(2,2-diethoxyethyl)pyrimidin-4-yl)amino)-5-(hydroxymethyl)-1,5-dimethylcyclopentane-1,2-diol as an oil. MS: 404 (M+1).

Step 6: To a stirred solution of (1R,2S,3R,5R)-3-((6-chloro-5-(2,2-diethoxyethyl)pyrimidin-4-yl)amino)-5-(hydroxymethyl)-1,5-dimethylcyclopentane-1,2-diol (230 mg, 0.569 mmol) in dioxane (3 mL) was added HCl in water (4M, 0.285 mL, 1.139 mmol) at room temperature. The resulting mixture was warmed to 50° C. and stirred at this temperature for 15 min. The reaction mixture was quenched with 20 mL of saturated aqueous sodium bicarbonate and extracted with EtOAc (3×20 mL). The organic layers were combined, dried over anhydrous sodium sulfate, filtered, and the filtrate was concentrated under reduced pressure to give (1R,2S,3R,5R)-3-(4-chloro-7H-pyrrolo[2,3-d]pyrimidin-7-yl)-5-(hydroxymethyl)-1,5-dimethylcyclopentane-1,2-diol as a solid. MS: 312 (M+1).

Step 7: To a stirred solution of (1R,2S,3R,5R)-3-(4-chloro-7H-pyrrolo[2,3-d]pyrimidin-7-yl)-5-(hydroxymethyl)-1,5-dimethylcyclopentane-1,2-diol (540 mg, 1.73 mmol) in acetone (15 mL) were added 4-methylbenzenesulfonic acid (30 mg, 0.173 mmol) and 22-dimethoxypropane (1.80 gg, 17.3 mmol) at 0° C. The reaction mixture was stirred at 25° C. for 16 h. The mixture was concentrated under reduced pressure, and the residue was purified by silica gel column chromatography (54% EtOAc/PE) to afford ((3aR,4R,6R,6aS)-6-(4-chloro-7H-pyrrolo[2,3-d]pyrimidin-7-yl)-2,2,3a,4-tetramethyltetrahydro-3aH-cyclopenta[d][1,3]dioxol-4-yl)methanol as an oil. MS: 352 (M+1).

Step 8: To a stirred solution of oxalyl chloride (0.30 mL, 3.41 mmol) in DCM (8 mL) was added dropwise DMSO (0.484 mL, 6.82 mmol) at −78° C., and the resulting mixture was stirred at −78° C. for 0.5 h. Then ((3aR,4R,6R,6aS)-6-(4-chloro-7H-pyrrolo[2,3-d]pyrimidin-7-yl)-2,2,3a,4-tetramethyltetrahydro-3aH-cyclopenta[d][1,3]dioxol-4-yl)methanol (400 mg, 1.137 mmol) in DCM (3 mL) was added dropwise, and the reaction mixture kept stirring at −78° C. for another 0.5 h. Then, TEA (1.585 mL, 11.37 mmol) was added at −78° C., and the reaction mixture was warmed to room temperature and stirred at this temperature for 1 h. Then 100 mL of saturated aqueous ammonium chloride was added, and the mixture was extracted with EtOAc (2×100 mL). The combined organic layers were dried over anhydrous sodium sulfate, filtered, and the filtrate was concentrated under reduced pressure to give crude (3aR,4S,6R,6aS)-6-(4-chloro-7H-pyrrolo[2,3d]pyrimidin-7-yl)-2,2,3a,4-tetramethyltetrahydro-3aH-cyclopenta[d][1,3]dioxole-4-carbaldehyde, which was used directly in the next step.

Step 9: To a stirred solution of methyltriphenylphosphonium bromide (1.14 g, 3.18 mmol) in THF (8 mL) was added n-butyllithium (2.5M in hexane, 0.455 mL, 1.14 mmol) dropwise at −20° C. The resulting mixture was warmed to room temperature and stirred for 1 h. Then, a solution of (3aR,4S,6R,6aS)-6-(4-chloro-7H-pyrrolo[2,3-d]pyrimidin-7-yl)-2,2,3a,4-tetramethyltetrahydro-3aH-cyclopenta[d][1,3]dioxole-4-carbaldehyde (398 mg, 1.14 mmol) in THF (3 mL) was added dropwise at −20° C. The resulting mixture was then warmed to 25° C. and stirred for 2 h. The mixture was diluted with 100 mL of EtOAc and washed with 100 mL of water and 100 mL of brine. The organic layer was dried over anhydrous sodium sulfate, filtered, and the filtrate was concentrated under reduced pressure. The residue was purified by silica gel column chromatography (3:1 PE/EtOAc) to give 4-chloro-7-((3aS,4R,6R,6aR)-2,2,6,6a-tetramethyl-6-vinyltetrahydro-3aH-cyclopenta[d][1,3]dioxol-4-yl)-7H-pyrrolo[2,3-d]pyrimidine as an oil. MS: 348 (M+1).

Step 10: To a 25 mL sealed tube containing a solution of 4-chloro-7-((3aS,4R,6R,6aR)-2,2,6,6a-tetramethyl-6-vinyltetrahydro-3aH-cyclopenta[d][1,3]dioxol-4-yl)-7H-pyrrolo[2,3-d]pyrimidine (250 mg, 0.719 mmol) in dioxane (5 mL) was added 28 wt % NH$_3$ in H$_2$O (25 mL). The resulting mixture was heated to 90° C. and stirred for 16 h. The solvent was removed under reduced pressure to afford crude 7-((3aS,4R,6R,6aR)-2,2,6,6a-tetramethyl-6-vinyltetrahydro-3aH-cyclopenta[d][1,3]dioxol-4-yl)-7H-pyrrolo[2,3-d]pyrimidin-4-amine which was used directly in the next step.

Step 11: A 10 mL round bottom flask was charged with 7-((3aS,4R,6R,6aR)-2,2,6,6a-tetramethyl-6-vinyltetrahydro-3aH-cyclopenta[d][1,3]dioxol-4-yl)-7H-pyrrolo[2,3-d]pyrimidin-4-amine (70 mg, 0.213 mmol) and 9-BBN (0.5M in THF, 2.13 ml, 1.07 mmol) at room temperature under an argon atmosphere. The resulting mixture was heated to 50° C. and stirred for 1 h. To this crude reaction mixture was added a solution of potassium phosphate tribasic (226 ng, 1.07 mmol) in Water (0.2 mL) at 0° C., and the resulting mixture was heated to 50° C. and stirred for 0.5 h. Then, a solution of 3-bromo-7-iodo-N-(4-methoxybenzyl)quinolin-2-amine (110 mg, 0.234 mmol) in THF (0.2 mL) and [1,1'-bis(diphenylphosphino)ferrocene]dichloropalladium(II) (15.59 mg, 0.021 mmol) were added at room temperature, and the resulting mixture was heated to 50° C. and stirred for 1 h. The mixture was diluted with 30 mL EtOAc and washed with 30 mL water and 30 mL brine. The combined organic layers were dried over anhydrous sodium sulfate, filtered, and the filtrate was concentrated under reduced pressure. The residue was purified by prep-TLC (10% MeOH/DCM) to afford 7-(2-((3aR,6R,6aS)-6-(4-amino-7H-pyrrolo[2,3-d]pyrimidin-7-yl)-2,2,3a,4-tetramethyltetrahydro-3aH-cyclopenta[d][1,3]dioxol-4-yl)ethyl)-3-bromo-N-(4-methoxybenzyl)quinolin-2-amine as a solid. MS: 671/673 (M+0.1/M+3).

Step 12: A 10 mL round bottom flask was charged with 7-(2-((3aR,6R,6aS)-6-(4-amino-7H-pyrrolo[2,3-d]pyrimidin-7-yl)-12,23a,4-tetramethyltetrahydro-3aH-cyclopenta[d][1,3]dioxol-4-yl)ethyl)-3-bromo-N-(4-methoxybenzyl)quinolin-2-amine (80 mg, 0.119 mmol) and TFA (2 mL) at room temperature under an argon atmosphere. The resulting mixture was then heated to 50° C. and stirred for 40 minutes. The solvent was removed under reduced pressure. The resulting crude material was purified by reverse phase column chromatography (ACN/water with 5 mM to afford (1R,2S,3S)-5-(2-(2-amino-3-bromoquinolin-7H-yl)ethyl)-3-(4-amino-7H-pyrrolo[2,3-d]pyrimidin-7-yl)-1,5-dimethylcyclopentane-1,2-diol as a solid. MS: 511/513 (M+1/M+3). $^1$H-NMR (300 MHz, DMSO-d$_6$) δ 8.33 (s, 1H), 8.04 (s, 1H), 7.58 (d, J=8.4 Hz, 1H), 7.36 (s, 1H), 7.18-7.13 (m, 2H), 6.89 (br s, 2H), 6.54-6.53 (m, 3H), 4.90 (d, J=6.9 Hz, 1H), 4.81 (q, J=9.0 Hz, 1H), 4.41-4.36 (m, 1H), 4.09 (s, 1H), 2.68-2.65 (m, 2H), 2.08-1.90 (m, 3H), 1.66-1.63 (m, 1H), 1.09 (s, 6H).

Example 118

(1R,2S,3S,4R)-1-(2-(2-amino-3-bromoquinolin-7-yl)ethyl)-4-(4-amino-7H-pyrrolo[2,3-d]pyrimidin-7-yl)-2-methylcyclopentane-1,2,3-triol

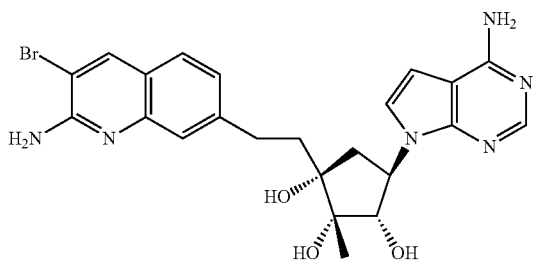 [SMILES: C[C@]1(O)[C@@H](O)[C@H](n2ccc3c(N)ncnc32)C[C@@]1(O)CCc1ccc2cc(Br)c(N)nc2c1]

Step 1: To a stirred solution of (1R,4S)-4-hydroxycyclopent-2-en-1-yl acetate (5.68 g, 40.0 mmol), 4-chloro-7H-pyrrolo[2,3-d]pyrimidine (9.20 g, 59.9 mmol), and triphenylphosphine (36.7 g, 140 mmol) in THF (80 mL) was added (E)-diisopropyl diazene-1,2-dicarboxylate (20.20 g, 100 mmol) under an argon atmosphere at 0° C. The resulting mixture was stirred at room temperature for 16 h. The solution was concentrated under reduced pressure, and the resulting residue was purified by column chromatography on silica (0-80% EtOAc/PE) to obtain (1R,4R)-4-(4-chloro-7H-pyrrolo[2,3-d]pyrimidin-7-yl)cyclopent-2-en-1-yl acetate as a solid. $^1$H NMR (300 MHz, DMSO-d$_6$) δ 8.66 (s, 1H), 7.66 (d, J=3.7 Hz, 1H), 6.69 (d, J=3.6 Hz, 1H), 6.32-6.19 (m, 2H), 6.09 (ddt, J=7.4, 4.9, 1.9 Hz, 1H), 6.03-5.92 (m 1H), 2.53-2.32 (m, 2H), 2.05 (s, 3H).

Step 2: To a stirred solution of (1R,4R)-4-(4-chloro-7H-pyrrolo[2,3-d]pyrimidin-7-yl)cyclopent-2-en-1-yl acetate (8.6 g, 31.0 mmol) in DCM (20 mL) was added ammonia in MeOH (200 mL, 7M, 1400 mmol), and the resulting mixture was stirred at room temperature for 16 h. The solution was concentrated under reduced pressure and the resulting residue was purified by column chromatography on silica (0-15% MeOH/DCM) to afford (1R,4R)-4-(4-chloro-7H-pyrrolo[2,3-d]pyrimidin-7-yl)cyclopent-2-enol as a solid. MS: 236 (M+1).

Step 3: To a solution of (1R,4R)-4-(4-chloro-7H-pyrrolo[2,3-d]pyrimidin-7-yl)cyclopent-2-enol (350 mg, 1.49 mmol) in anhydrous DCM (7 mL) was added Dess-Martin periodinane (945 mg, 2.23 mmol) at 0° C. under an argon atmosphere. The resulting mixture was stirred at 25° C. for 16 h. The reaction mixture was then cooled down to 0° C., quenched by saturated aqueous sodium bicarbonate (5 mL) and diluted with DCM (100 mL). The mixture solution was then filtered through Celite. The filtrate was concentrated under reduced pressure, and the resulting residue was purified by column chromatography on silica (20-35% EtOAc/PE) to afford (R)-4-(4-chloro-7H-pyrrolo[2,3-d]pyrimidin-7-yl)cyclopent-2-enone as a solid. MS: 234 (M+1).

Step 4: To a stirred solution of (R)-4-(4-chloro-7H-pyrrolo[2,3-d]pyrimidin-7-yl)cyclopent-2-enone (870 ng, 3.72 mmol) in DCM (3 mL) and pyridine (3 mL) was added a solution of diiodine (1.60 g 6.33 mmol) in DCM (3 mL) and pyridine (3 mL) at 0° C. The resulting mixture was stirred at room temperature for 16 h. Then, DCM (30 mL) and sodium thiosulfate solution (60 mL, 1 M) were added to the solution, and the organic layer was concentrated under reduced pressure. The resulting residue was purified by column chromatography on silica (0-80% EtOAc/PE) to afford (R)-4-(4-chloro-7H-pyrrolo[2,3-d]pyrimidin-7-yl)-2-iodocyclopent-2-enone as a solid. MS: 360 (M+1).

Step 5: To a stirred solution of (R)-4-(4-chloro-7H-pyrrolo[2,3-d]pyrimidin-7-yl)-2-iodocyclopent-2-enone (2.9 g, 8.07 mmol) in N-Methyl-2-pyrrolidinone (25 mL) were added copper(I) iodide (0.614 g, 3.23 mmol), triphenylarsine (0.99 g, 3.23 mmol), Dichlorobis(benzonitrile)palladium(II) (1.24 g, 3.23 mmol), and tetramethylstannane (14.4 g, 81 mmol). The resulting mixture was then stirred at 80° C. under an argon atmosphere for 2 h. The mixture was cooled and purified by column chromatography on silica (0-70% EtOAc/PE). The isolated material was then dissolved in DCM (100 mL) and washed with water (60 mL×4). The organic layer was concentrated under reduced pressure, and the resulting residue was washed with 30:1 PE/EtOAc (40 mL) and then filtered to afford (R)-4-(4-chloro-7H-pyrrolo[2,3-d]pyrimidin-7-yl)-2-methylcyclopent-2-enone as a solid. MS: 248 (M+1).

Step 6: To a mixture of (R)-4-(4-chloro-7H-pyrrolo[2,3-d]pyrimidin-7-yl)-2-methylcyclopent-2-enone (900 mg, 3.63 mmol) and NMO (851 mg, 7.27 mmol) in THF (90 mL), water (9.0 mL), and acetone (9.0 mL) was added osmium(VIII) oxide in $H_2O$ (9.25 mL, 4 wt %, 3.63 mmol) dropwise at room temperature (15° C.) under an argon atmosphere. The reaction mixture was then stirred for 15 h at room temperature. The reaction mixture was quenched with saturated sodium thiosulfate (60 mL) under argon and stirred for 20 minutes at 0° C. The resulting mixture was then diluted with EtOAc/$H_2O$ (600 mL/200 mL). The organic layer was separated and washed with $H_2O$ (200 mL) and brine (2×200 mL), dried over anhydrous sodium sulfate, filtered, and the filtrate was concentrated under reduced pressure. The resulting crude material was purified by column chromatography on silica (0-60% EtOAc/PE) to afford (2S,3S,4R)-4-(4-chloro-7H-pyrrolo[2,3-d]pyrimidin-7-yl)-2,3-dihydroxy-2-methylcyclopentanone as a solid. MS: 282 (M+1).

Step 7: To a mixture of (2S,3S,4R)-4-(4-chloro-7H-pyrrolo[2,3-d]pyrimidin-7-yl)-2,3-dihydroxy-2-methylcyclopentanone (500 mg, 1.78 mmol) and 4-methylbenzenesulfonic acid (61.1 mg, 0.355 mmol) in anhydrous acetone (25 mL) was added 2,2-dimethoxypropane (2.77 g, 26.6 mmol) dropwise at room temperature under argon. The reaction mixture was stirred for 15 h at 30° C. The reaction was then quenched with saturated sodium bicarbonate (20 mL) at 0° C. The resulting mixture was diluted with EtOAc/$H_2O$ (200 mL/30 mL), and the organic layer was separated, washed with brine (80 mL), dried over anhydrous sodium sulfate, filtered, and the filtrate was concentrated under reduced pressure. The resulting residue was purified by column chromatography on silica (0-25% EtOAc/PE) to afford (3aS,6R,6aS)-6-(4-chloro-7H-pyrrolo[2,3-d]pyrimidin-7-yl)-2,2,3a-trimethyldihydro-3aH-cyclopenta[d][1,3]dioxol-4(5H)-one as a solid. MS: 322 (M+1).

Step 8: Cerium(III) chloride (2.45 g, 9.95 mmol) was suspended in THF (15 mL) and stirred for 0.5 h at room temperature under argon. To a second flame-dried round-bottom flask was added ethynyltrimethylsilane (977 mg, 9.95 mmol) in anhydrous THF (10 mL). The TMS-acetylene solution and the flask containing the $CeCl_3$ were both cooled to −78° C. To the TMS-acetylene solution, n-BuLi (3.98 mL, 2.5 M in hexane, 9.95 mmol) was added dropwise by syringe. Both mixtures were stirred for 20 minutes and then the lithium TMS-acetylide solution was transferred via cannula into the rapidly-stirred $CeCl_3$ suspension. The mixture was stirred for 0.5 h at −78° C. (3 aS,6R,6aS)-6-(4-chloro-7H-pyrrolo[2,3-d]pyrimidin-7-yl)-2,2,3a-trimethyl-dihydro-3aH-cyclopenta[d][1,3]dioxol-4(5H)-one (400 mg, 1.243 mmol) was dissolved in anhydrous THF (15 mL), cooled to −78° C., and transferred via cannula into the flask containing the cerium acetylide salt. The resulting mixture was stirred for 2 h at −78° C. The reaction was quenched with saturated ammonium chloride (40 mL) at 0° C. and diluted with EtOAc/$H_2O$ (200 mL/80 mL). The organic layer was separated and washed with saturated sodium bicarbonate (100 mL) and brine (100 mL). The organic layer was then dried over anhydrous sodium sulfate, filtered, and the filtrate was concentrated under reduced pressure. The residue was purified by column chromatography (0-18% EtOAc/PE) to afford (3aS,4S,6R,6aS)-6-(4-chloro-7H-pyrrolo[2,3-d]pyrimidin-7-yl)-2,2,3a-trimethyl-4-((trimethylsilyl)ethynyl)tetrahydro-3aH-cyclopenta[d][1,3]dioxol-4-ol as a solid. MS: 420 (M+1).

Step 9: To a solution of (3aS,4S,6R,6aS)-6-(4-chloro-7H-pyrrolo[2,3-d]pyrimidin-7-yl)-2,2,3a-trimethyl-4-((trimethylsilyl)ethynyl)tetrahydro-3aH-cyclopenta[d][1,3]dioxol-4-ol (220 mg, 0.524 mmol) in anhydrous THF (5 mL) cooled to 0° C. was added TBAF (1.05 mL, 1 M in THE 1.048 mmol) dropwise under argon. The reaction mixture was stirred for 1 h at 0° C. Then, the solvent was removed under reduced pressure. The resulting residue was purified by column chromatography on silica (0-20% EtOAc/PE) to afford (3aS,4S,6R,6aS)-6-(4-chloro-7H-pyrrolo[2,3-d]pyrimidin-7-yl)-4-ethynyl-2,2,3a-trimethyltetrahydro-3aH-cyclopenta[d][1,3]dioxol-4-ol as a solid. MS: 348 (M+1).

Step 10: (3aS,4S,6R,6aS)-6-(4-chloro-7H-pyrrolo[2,3-d]pyrimidin-7-yl)-4-ethynyl-2,2,3a-trimethyltetrahydro-3aH-cyclopenta[d][1,3]dioxol-4-ol (170 mg, 0.489 mmol) was dissolved in $NH_3$ (15 mL, 20% in iPrOH) at −70° C. The reaction was stirred for 15 h at 90° C. in a sealed tube. Then, the solvent was removed under reduced pressure. The resulting residue was purified by column chromatography on silica (0-8% MeOH/DCM) to afford (3aS,4S,6R,6aS)-6-(4-amino-7H-pyrrolo[2,3-d]pyrimidin-7-yl)-4-ethynyl-2,2,3a-trimethyltetrahydro-3aH-cyclopenta[d][1,3]dioxol-4-ol as a solid. MS: 329 (M+1).

Step 11: A solution of (3aS,4S,6R,6aS)-6-(4-amino-7H-pyrrolo[2,3-d]pyrimidin-7-yl)-4-ethynyl-2,2,3a-trimethyltetrahydro-3aH-cyclopenta[d][1,3]dioxol-4-ol (150 mg, 0.457 mmol) in anhydrous MeOH (4 mL) was reduced under a hydrogen atmosphere using Lindlar Catalyst (22.5 mg, 10.57 μmol). The reaction mixture was stirred for 2.5 h at 30° C. The reaction mixture was then filtered through Celite, and the filtrate was concentrated under reduced pressure. The resulting residue was purified by chiral HPLC (EtOH/hexanes with 8 mM $NH_3$-MeOH modifier) to afford (3aS, 4S,6R,6aS)-6-(4-amino-7H-pyrrolo[2,3-d]pyrimidin-7-yl)-2,2,3a-trimethyl-4-vinyltetrahydro-3aH-cyclopenta[d][1,3]dioxol-4-ol as an oil. MS: 331 (M+1).

Step 12: Under an argon atmosphere, (3aS,4S,6R,6aS)-6-(4-amino-7H-pyrrolo[2,3-d]pyrimidin-7-yl)-2,2,3a-trimethyl-4-vinyltetrahydro-3aH-cyclopenta[d][1,3]dioxol-4-ol (70 mg, 0.212 mmol) was dissolved in 9-BBN solution (2.12 mL, 0.5 M in THF, 1.06 mmol) at room temperature, and the mixture was stirred for 1 h at 60° C. The reaction was then cooled to 0° C., and a solution of K₃PO₄ (183 mg, 1.059 mmol) in H₂O (2 mL) was added. The mixture was stirred for 0.5 h at room temperature. Then, a solution of 3-bromo-7-iodo-N-(4-methoxybenzyl)quinolin-2-amine (99 mg, 0.212 mmol) and Pd(dppf)Cl₂ (26.0 mg, 0.032 mmol) in anhydrous THF (2.5 mL) were added to the mixture. The resulting mixture was irradiated with microwave radiation at 70° (C for 2 h. The mixture was concentrated under reduced pressure, and the resulting residue was dissolved in EtOAc (100 mL) and then washed with 120 (30 mL) and brine (2×30 mL). The organic layer was dried over anhydrous sodium sulfate, filtered, and the filtrate was concentrated under reduced pressure. The resulting crude mixture was purified by column chromatography on silica (0-3% MeOH/DCM) to afford (3aS,4S,6R,6aS)-6-(4-amino-7H-pyrrolo[2,3-d]pyrimidin-7-yl)-4-(2-(3-bromo-2-((4-methoxybenzyl)amino)quinolin-7-yl)ethyl)-2,2,3a-trimethyltetrahydro-3aH-cyclopenta[d][1,3]dioxol-4-ol as a solid. MS: 673/675 (M+1/M+3).

Step 13: Under an argon atmosphere, (3aS,4S,6R,6aS)-6-(4-amino-7H-pyrrolo[2,3-d]pyrimidin-7-yl)-4-(2-(3-bromo-2-((4-methoxybenzyl)amino)quinolin-7-yl)ethyl)-2,2,3a-trimethyltetrahydro-3aH-cyclopenta[d][1,3]dioxol-4-ol (100 mg, 0.148 mmol) was dissolved in TFA (3.0 mL, 38.9 mmol) at room temperature. The reaction mixture was stirred for 4 h at 60° C. The mixture was then evaporated under reduced pressure. The resulting residue was co-evaporated with toluene (3×90 mL). This residue was then purified by reverse phase column chromatography (ACN/water). The product was further purified by reverse phase HPLC (ACN/water with 10 mM NH₄HCO₃ modifier) to afford (1R,2S,3S,4R)-1-(2-(2-amino-3-bromoquinolin-7-yl)ethyl)-4-(4-amino-7H-pyrrolo[2,3-d]pyrimidin-7-yl)-2-methylcyclopentane-1,2,3-triol as a solid. MS: 513/515 (M+1/M+3). ¹H-NMR (400 MHz, DMSO-d₆+10% D₂O) δ 8.66 (s, 1H), 8.36 (s, 1H), 7.75 (d, J=8.4 Hz, 1H), 7.62 (d, J=3.6 Hz, 1H), 7.50 (s, 1H), 7.33 (d, J=8.0 Hz, 1H), 7.00-6.97 (m, 1H), 5.06 (dd. J=9.6, 18.4 Hz, 1H), 4.06 (d, J=8.8 Hz, 1H), 2.96-2.77 (m, 2H), 2.23-2.12 (m, 2H), 1.98-1.81 (m, 2H), 1.38 (s, 3H).

Example 119

(1S,2R,3aR,4S,6aR)-4-((2-amino-3-bromoquinolin-7-yl)oxy)-2-(4-amino-7H-pyrrolo[2,3-d]pyrimidin-7-yl)hexahydropentalene-1,6a(1H)-diol 2,2,2-trifluoroacetate

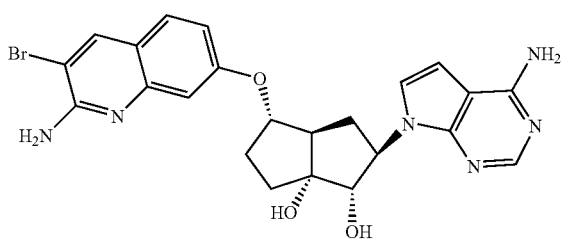

-continued

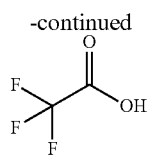

Step 1: To an oven-dried, argon-purged vial with (3aS,4R,5aR,6S,8aR)-4-(4-chloro-7H-pyrrolo[2,3-d]pyrimidin-7-yl)-2,2-dimethylhexahydro-5H-pentaleno[1,6a-d][1,3]dioxol-6-ol (141.4 mg, 0.404 mmol) was added 3-bromo-7-iodo-N-(4-methoxybenzyl)quinolin-2-amine (379 mg, 0.808 mmol), 1,10-phenanthroline (29.1 mg, 0.162 mmol), cuprous iodide (15.40 mg, 0.081 mmol), and cesium carbonate (395 mg, 1.213 mmol). The solids were dissolved in xylene (4 mL), and the reaction was heated to 140° C. for 18 h under argon. The reaction was then slowly cooled to room temperature. The reaction was filtered through Celite, and then concentrated under reduced pressure. The residue was purified by column chromatography on silica (20-35-800 EtOAc/hexanes) to afford 3-bromo-7-(((3aS,4R,5aR,6S,8aR)-4-(4-chloro-7H-pyrrolo[2,3-d]pyrimidin-7-yl)-2,2-dimethylhexahydro-3aH-pentaleno[1,6a-d][1,3]dioxol-6-yl)oxy)-N-(4-methoxybenzyl)quinolin-2-amine as a solid. MS: 690/692 (M+1/M+3).

Step 2: To a vial with 3-bromo-7-(((3aS,4R,5aR,6S,8aR)-4-(4-chloro-7H-pyrrolo[2,3-d]pyrimidin-7-yl)-2,2-dimethylhexahydro-3aH-pentaleno[1,6a-d][1,3]dioxol-6-yl)oxy)-N-(4-methoxybenzyl)quinolin-2-amine (37.4 mg, 0.054 mmol) was added ammonia (3.5 mL, 24.50 mmol, 7N in MeOH). The reaction was heated in the microwave at 140° C. for 5 h. The reaction was then concentrated under reduced pressure, and the resulting crude 7-(((3aS,4R,5aR,6S,8aR)-4-(4-amino-7H-pyrrolo[2,3-d]pyrimidin-7-yl)-2,2-dimethylhexahydro-3aH-pentaleno[1,6a-d][1,3]dioxol-6-yl)oxy)-3-bromo-N-(4-methoxybenzyl)quinolin-2-amine was carried directly to the next step.

Step 3: To a vial containing crude 7-(((3aS,4R,5aR,6S,8aR)-4-(4-amino-7H-pyrrolo[2,3-d]pyrimidin-7-yl)-2,2-dimethylhexahydro-3aH-pentaleno[1,6a-d][1,3]dioxol-6-yl)oxy)-3-bromo-N-(4-methoxybenzyl)quinolin-2-amine (25 mg, 0.037 mmol) was added DCM (0.5 mL), followed by TFA (0.4 mL, 5.19 mmol). The reaction was stirred at 40° C. for 75 minutes. Then, water (0.1 mL) was added, along with more DCM (0.1 mL), and the reaction was stirred at 40° C. for 2.5 h in total. Then, more DCM (0.2 mL), more TFA (0.3 mL), and more water (0.1 mL) were added, and the reaction was heated to 40° C. for another 2 h. Finally, anisole (100 μl, 0.915 mmol) was added, and the reaction was stirred at 40° C. for 1 h. The reaction was concentrated under reduced pressure, dissolved in DMSO, filtered, and submitted for mass-triggered reverse phase HPLC (MeCN/water with 0.1% TFA modifier) to afford (1S,2R,3aR,4S,6aR)-4-((2-amino-3-bromoquinolin-7-yl)oxy)-2-(4-amino-7H-pyrrolo[2,3-d]pyrimidin-7-yl)octahydropentalene-1,6a-diol as the TFA salt as a solid. MS: 511/513 (M+1/M+3). ¹H NMR (600 MHz, DMSO-d₆) δ 8.72 (s, 1H), 8.37 (s, 1H), 7.82 (d, J=3.6 Hz, 1H), 7.78 (d, J=8.9 Hz, 1H), 7.07 (dd, J=8.9, 2.0 Hz, 1H), 6.98-6.94 (m, 2H), 4.96-4.89 (m, 1H), 4.56 (d, J=4.2 Hz, 1H), 4.05 (d, J=10.5 Hz, 1H), 2.58-2.52 (m, 1H), 2.36-2.27 (m, 2H), 2.09-2.03 (m, 1H), 1.98-1.87 (m, 2H), 1.75-1.67 (m, 1H).

Example 120

(2R,3R,3aS,6S,6aR)-6-(2-amino-3-fluoroquinolin-7-yl)amino-2-(4-methyl-7H-pyrrolo[2,3-d]pyrimidin-7-yl)hexahydro-3aH-cyclopenta[b]furan-3,3a-diol

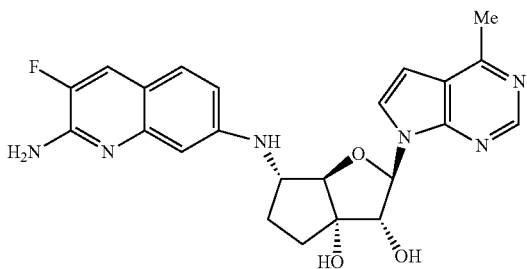 [SMILES: Cc1ncnc2c1ccn2[C@@H]1O[C@@H]2[C@@H](Nc3ccc4cc(F)c(N)nc4c3)CC[C@]2(O)[C@H]1O]

Step 1: To a mixture of (3aR,4R,5aR,6R,8aR)-2,2-dimethyl-4-(4-methyl-7H-pyrrolo[2,3-d]pyrimidin-7-yl)hexahydrocyclopenta[2,3]furo[3,4-d][1,3]dioxol-6-ol (200 mg, 0.604 mmol) and triphenylphosphine (317 mg, 1.21 mmol) in toluene (2.5 mL) was added isoindoline-1,3-dione (178 mg, 1.21 mmol) at room temperature. Then, the mixture was cooled to 0° C. and DIAD (0.235 ml, 1.21 mmol) was added dropwise. The resulting mixture was stirred for 1.5 h at 80° C. The reaction mixture was then concentrated under reduced pressure, and the resulting residue was purified by Prep-TLC (1:1 EtOAc:PE) to afford 2-((3aR,4R,5aR,6S,8aR)-2,2-dimethyl-4-(4-methyl-7H-pyrrolo[2,3-d]pyrimidin-7-yl)hexahydrocyclopenta[2,3]furo[3,4-d][1,3]dioxol-6-yl)isoindoline-1,3-dione as a solid. MS: 461 (M+1).

Step 2: To a stirred solution of 2-((3aR,4R,5aR,6S,8aR)-2,2-dimethyl-4-(4-methyl-7H-pyrrolo[2,3-d]pyrimidin-7-yl)hexahydrocyclopenta[2,3]furo[3,4-d][1,3]dioxol-6-yl)isoindoline-1,3-dione (220 mg, 0.478 mmol) in MeOH (1.5 mL) was added hydrazine hydrate (598 mg, 9.56 mmol). The resulting solution was stirred at room temperature for overnight. The reaction mixture was concentrated under reduced pressure, and the resulting solid was suspended in DCM (30 mL). The mixture was filtered, and the filtrate was concentrated under reduced pressure to afford (3aR,4R,5aR,6S,8aR)-2,2-dimethyl-4-(4-methyl-7H-pyrrolo[2,3-d]pyrimidin-7-yl)hexahydrocyclopenta[2,3]furo[3,4-d][1,3]dioxol-6-amine as an oil. MS: 331 (M+1).

Step 3: To a stirred solution of (3aR,4R,5aR,6S,8aR)-2,2-dimethyl-4-(4-methyl-7H-pyrrolo[2,3-d]pyrimidin-7-yl)hexahydrocyclopenta[2,3]furo[3,4-d][1,3]dioxol-6-anine (40 mg, 0.097 mmol) and 7-bromo-N-(2,4-dimethoxybenzyl)-3-fluoroquinolin-2-amine (41.7 mg, 0.107 mmol) in THF (0.5 mL) were added Xantphos Pd (3 (4.59 mg, 4.84 μmol) and sodium 2-methylpropan-2-olate (27.9 mg, 0.291 mmol). The resulting mixture was stirred at 50° C. for 16 h. The reaction was quenched with saturated aqueous ammonium chloride (25 mL) and extracted with EtOAc (3×40 mL). The combined organic layers were washed with brine (30 mL), dried over anhydrous sodium sulfate, and filtered. The filtrate was concentrated under reduced pressure, and the residue was purified by Prep-TLC (2:1 EtOAc:PE) to afford N2-(2,4-dimethoxybenzyl)-N7-((3aR,4R,5aR,6S,8aR)-2,2-dimethyl-4-(4-methyl-7H-pyrrolo[2,3-d]pyrimidin-7-yl)hexahydrocyclopenta[2,3]furo[3,4-d][1,3]dioxol-6-yl)-3-fluoroquinoline-2,7-diamine as a solid. MS: 641 (M+1).

Step 4: N2-(2,4-dimethoxybenzyl)-N7-((3aR,4R,5aR,6S,8aR)-2,2-dimethyl-4-(4-methyl-7H-pyrrolo[2,3-d]pyrimidin-7-yl)hexahydrocyclopenta[2,3]furo[3,4-d][1,3]dioxol-6-yl)-3-fluoroquinoline-2,7-diamine (58 mg 0.091 mmol) was dissolved in TFA (2 mL, 26.0 mmol). The resulting solution was stirred at 50° C. for overnight. The reaction mixture was then co-evaporated with toluene (2×5 mL) under reduced pressure. The resulting residue was purified by reverse phase column chromatography (ACN/water with 5 mM $NH_4HCO_3$ modifier). The product was further purified by prep-TLC (10:1 DCM/MeOH) followed by reverse phase column chromatography (ACN/water with 5 mM $NH_4HCO_3$ modifier) to afford (2R,3R,3aS,6S,6aR)-6-((2-amino-3-fluoroquinolin-7-yl)amino)-2-(4-methyl-7H-pyrrolo[2,3-d]pyrimidin-7-yl)hexahydro-2H-cyclopenta[b]furan-3,3a-diol as a solid. MS: 451 (M+1). $^1$H-NMR (300 MHz, DMSO-$d_6$) δ 8.69 (s, 1H), 7.92 (d, J=3.6 Hz, 1H), 7.53 (d, J=12.0 Hz, 1H), 7.32 (d, J=8.7 Hz, 1H), 6.83 (d, J=3.6 Hz, 1H), 6.69 (d, J=7.8 Hz, 1H), 6.42-6.36 (m, 3H), 6.8 (d, J=4.5 Hz, 1H), 6.11 (d, J=8.1 Hz, 1H), 5.38 (d, J=7.2 Hz, 1H), 5.23 (s, 1H), 4.42 (d, J=7.8 Hz, 1H), 3.96 (s, 1H), 3.55-3.53 (m, 1H), 2.69 (s, 3H), 2.50-2.49 (m, 1H), 2.07-2.02 (m, 2H), 1.94-1.90 (m, 1H).

Example 121

(2R,3R,3aS,6S,6aR)-6-((2-amino-3-fluoroquinolin-7-yl)methyl)-2-(4-amino-7H-pyrrolo[2,3-d]pyrimidin-7-yl)-6a-methylhexahydro-3aH-cyclopenta[b]furan-3,3a-diol

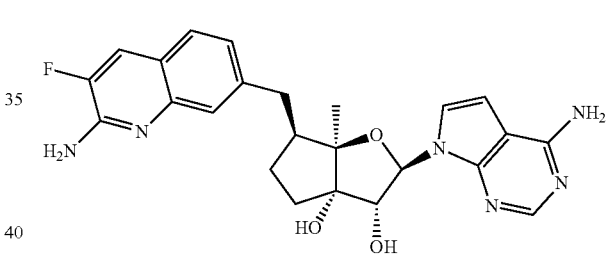

Step 1: To a solution of (S)-2-methyl-CBS-oxazaborolidine (1.788 g, 6.45 mmol) in THF (31 mL) was added borane-THF complex (6.45 mL, IM in THF, 6.45 mmol) dropwise at 0° C. The reaction was stirred for 30 minutes at 0° C. A solution of 2-methylcyclopent-2-enone (3.1 g, 32.2 mmol) in THF (25 mL) and borane-THF complex (22.57 mL, IM in THF, 22.57 mmol) were added simultaneously dropwise at 0° C. The reaction mixture was warmed slowly to room temperature and stirred for 1.5 h. The reaction mixture was carefully quenched by addition of 180 mL of water at 0° C. The mixture was stirred for 0.5 h at room temperature, and then extracted with DCM (200 mL). The organic extract was washed with saturated aqueous ammonium chloride (100 mL) and brine (100 mL), dried with anhydrous magnesium sulfate, filtered, and the filtrate was concentrated under reduced pressure to afford (R)-2-methylcyclopent-2-enol as an oil, which was used in the next step without further purification.

Step 2: To a stirred solution of (R)-2-methylcyclopent-2-enol (1 g, 10.19 mmol) in DCM (10 mL) were added DMAP (1.867 g, 15.28 mmol) and triethylamine (1.562 mL, 11.21 mmol) at 0° C. under an argon atmosphere. Then, acetic anhydride (2.08 g, 20.4 mmol) was added slowly. The mixture was stirred at 0° C. for 1 h. The mixture was quenched with $H_2O$ (50 mL) and extracted with DCM (60 mL×2). The combined organic layers were washed with brine (40 mL), dried over anhydrous sodium sulfate, and filtered. The filtrate was concentrated under reduced pressure. The resulting residue was purified by column chromatography on silica (0-15% EtOAc/PE) to afford (R)-2-methylcyclopent-2-en-1-yl acetate as an oil. Then, a solution of (R)-2-methylcyclopent-2-en-1-yl acetate (700 mg, 4.99 mmol) in THF (8 mL) was added to lithium diisopropylamide (3.99 mL, 2M in THF/heptane, 7.99 mmol) at −78° C. over 3 minutes. Then a solution of tert-butylchlorodimethylsilane (1.43 g, 9.49 mmol) in THF (2 mL) was added and the mixture was stirred at −78° C. for 20 minutes. The reaction mixture was warmed to room temperature and stirred for an additional 2 h. The solution was then heated at reflux overnight, cooled to 0° C. and treated with concentrated HCl (2 mL). The mixture was stirred at 0° C. for 1 h. The reaction mixture was then partitioned between diethyl ether (40 mL) and water (20 mL). The aqueous layer was extracted with diethyl ether (30 mL). The combined organic layers were dried with anhydrous sodium sulfate and filtered. The filtrate was then concentrated under reduced pressure, and the residue was purified by column chromatography on silica (0-30% EtOAc/PE) to afford (R)-2-(2-methylcyclopent-2-en-1-yl)acetic acid as an oil. $^1$H NMR (400 MHz, DMSO-$d_6$) δ 12.04 (s, 1H), 5.36-5.34 (m, 1H), 5.26 (s, 1H), 2.77-2.75 (In, 1H), 2.46-2.41 (m, 1H), 2.30-1.91 (m, 3H), 1.64 (s, 3H), 1.51-1.46 (m, 1H).

Step 3: To a solution of (R)-2-(2-methylcyclopent-2-en-1-yl)acetic acid (10 g, 71.3 mmol) in tert-butyl alcohol (100 mL) were added tetraoxotungsten(X)hydride (1.78 g, 7.13 mmol) and hydrogen peroxide (18.2 mL, 30% in water, 178 mmol). The resulting suspension was stirred at 80° C. for 30 minutes, and then the reaction mixture was cooled to 0° C. before it was quenched with saturated aqueous sodium thiosulfate (100 mL). The mixture was stirred for 1 h at room temperature and diluted with EtOAc (200 mL). The organic phases were separated, and the aqueous layer was extracted with EtOAc (4×100 mL). The combined organic phases were washed with brine (100 mL), dried over anhydrous sodium sulfate, filtered, and concentrated under reduced pressure. The residue was purified by column chromatography on silica (0-60% EtOAc/PE) to afford (3aR,6S,6aS)-6-hydroxy-6a-methylhexahydro-2H-cyclopenta[b]furan-2-one as an oil. $^1$H NMR (400 MHz, DMSO-$d_6$) δ 5.09 (d, J=4.4 Hz, 1H), 3.89-3.86 (m, 1H), 3.03-2.87 (m, 1H), 2.46-2.41 (m, 1H), 2.29-2.29 (m, 1H), 2.11-1.99 (m, 1H), 1.83-1.72 (m, 1H), 1.59-1.48 (m, 1H), 1.40-1.23 (m, 4H).

Step 4: To a stirred solution of (3aR,6S,6aS)-6-hydroxy-6a-methylhexahydro-2H-cyclopenta[b]furan-2-one (6 g, 38.4 mmol) in DMF (40 mL) were added 1H-imidazole (7.85 g, 115 mmol) and tert-butylchlorodiphenylsilane (12.7 g, 46.1 mmol) at 0° C. under an argon atmosphere. The resulting mixture was stirred at 25° C. for 16 h. The reaction mixture was then quenched with saturated aqueous Na$_2$CO$_3$ (100 mL) and extracted with EtOAc (200 mL×2). The combined organic layers were washed with water (2×100 mL), followed by brine (100 mL), dried over anhydrous sodium sulfate, and filtered. The filtrate was concentrated under reduced pressure and the resulting residue was purified by column chromatography on silica (0-15% EtOAc/ PE) to afford (3aR,6S,6aS)-6-((tert-butyldiphenylsilyl)oxy)-6a-methylhexahydro-2H-cyclopenta[b]furan-2-one as an oil. MS: 395 (M+1). $^1$H-NMR (400 MHz, DMSO-$d_6$) δ 7.65-7.60 (m, 4H), 7.56-7.37 (m, 6H), 4.11 (t, J=5.6 Hz, 1H), 2.97-2.88 (m, 1H), 2.57-2.51 (m, 1H), 2.28-2.23 (m, 1H), 2.05-1.96 (m, 1H), 1.61-1.48 (m, 1H), 1.46-1.39 (m, 4H), 1.32-1.19 (m, 1H), 1.04 (s, 9H).

Step 5: To a solution of (3aR,6S,6aS)-6-((tert-butyldiphenylsilyl)oxy)-6a-methylhexahydro-2H-cyclopenta[b]furan-2-one (13 g, 32.9 mmol) in THF (40 mL) was added chlorotrimethylsilane (179 g, 165 mmol) at −78° C. Lithium bis(trimethylsilyl)amide (49.4 mL, 1M in THF, 49.4 mmol) was added dropwise over 5 minutes. The resulting mixture was stirred at −78° C. for 30 minutes. A solution of phenyl hypochloroselenoite (7.57 g, 39.5 mmol) in THF (15 mL) was added to the reaction mixture, and the mixture was stirred at −78° C. for 2 h. The reaction mixture was then quenched with saturated aqueous ammonium chloride (100 mL) and extracted with EtOAc (150 mL×3). The combined organic layers were washed with brine (100 mL), dried over anhydrous sodium sulfate, and filtered. The filtrate was concentrated under reduced pressure to afford crude (3R, 3aS,6S,6aS)-6-((tert-butyldiphenylsilyl)oxy)-6a-methyl-3-(phenylselanyl)hexahydro-2H-cyclopenta[b]furan-2-one as an oil which was used directly in the next step.

Step 6: To a solution of crude (3R,3aS,6S,6aS)-6-((tert-butyldiphenylsilyl)oxy)-6a-methyl-3-(phenylselanyl)hexahydro-2H-cyclopenta[b]furan-2-one (18.08 g, 32.9 mmol) in DCM (250 mL) was added hydrogen peroxide (18.7 g, 30% in water, 165 mmol) at room temperature. The reaction mixture was stirred at room temperature for 1 h. The mixture was then concentrated under reduced pressure, and the resulting residue was purified by column chromatography on silica (1-20% EtOAc/PE) to afford (6S,6aS)-6-((tert-butyldiphenylsilyl)oxy)-6a-methyl-4,5,6,6a-tetrahydro-2H-cyclopenta[b]furan-2-one as an oil. MS: 410 (M+NH$_4$). $^1$H NMR (400 MHz, DMSO-$d_6$) δ 7.64-7.59 (m, 4H), 7.52-7.39 (m, 61H), 5.82-5.81 (m, 1H), 3.85 (t, J=8.8 Hz, 1H), 2.86-2.67 (m, 1H), 2.44-2.30 (m, 1H), 2.11-2.01 (m, 1H), 1.97-1.84 (m, 1H), 1.52 (s, 3H), 1.05 (s, 9H).

Step 7: A solution of (6S,6aS)-6-((tert-butyldiphenylsilyl)oxy)-6a-methyl-4,5,6,6a-tetrahydro-2H-cyclopenta[b]furan-2-one (8 g, 20.4 mmol) in MeCN (20 mL) was suspended in a solution of 2-hydroxypropane-1,2,3-tricarboxylic acid (7.83 g, 40.8 mmol) in water (15 mL). Then, potassium osmate(VI) dihydrate (0.375 g, 1.02 mmol) was added, followed by 4-methylmorpholine N-oxide (4.77 mL, 50 wt % in water, 22.4 mmol). The reaction mixture was stirred at room temperature for 16 h. To the reaction mixture was then added water (100 mL), and it was extracted with EtOAc (150 mL×3). The combined organic layers were washed with brine (100 mL), dried over anhydrous sodium sulfate, and filtered. The filtrate was concentrated under reduced pressure, and the resulting residue was purified by column chromatography on silica (1-50% EtOAc/PE) to afford (3R,3aS,6S,6aR)-6-((tert-butyldiphenylsilyl)oxy)-3,3a-dihydroxy-6a-methylhexahydro-2H-cyclopenta[b]furan-2-one as an oil. MS: 444 (M+NH$_4$). $^1$H-NMR (300 MHz, DMSO-$d_6$) δ 7.66-7.61 (m, 4H), 7.52-7.41 (m, 6H), 5.99 (d, J=7.2 Hz, 1H), 5.22 (s, 1H), 4.23 (t, J=7.5 Hz, 1H), 4.07 (d, J=7.2 Hz, 1H), 1.87-1.68 (m, 2H), 1.65-1.51 (m, 2H), 1.35 (s, 3H), 1.05 (s, 9H).

Step 8: To a stirred solution of (3R,3aS,6S,6aR)-6-((tert-butyldiphenylsilyl)oxy)-3,3a-dihydroxy-6a-methylhexahydro-2H-cyclopenta[b]furan-2-one (7 g, 16.4 mmol) and chlorobis(cyclooctene)iridium(I) dimer (0.147 g, 0.164 mmol) in DCM (13 mL) was added diethylsilane (2.17 g, 24.6 mmol) dropwise under an argon atmosphere at room temperature. The resulting solution was stirred at room temperature for 2 h. Solid tetrabutylammonium fluoride trihydrate (5.18 g, 16.4 mmol) was then added to the reaction mixture. The mixture was stirred at room temperature for 16 h. The reaction was then quenched with saturated aqueous sodium bicarbonate (100 mL) and extracted with DCM (3×100 mL). The combined organic layers were washed with brine (100 mL), dried over anhydrous sodium sulfate, and filtered. The filtrate was concentrated under reduced pressure and the resulting residue was purified by column chromatography on silica (1-50% EtOAc/PE) to afford (3R,3aS,6S,6aR)-6-((tert-butyldiphenylsilyl)oxy)-6a-methylhexahydro-2H-cyclopenta[b]furan-2,3,3a-triol as an oil. MS: 446 (M+NH$_4$).

Step 9: To a stirred solution of (3R,3aS,6S,6aR)-6-((tert-butyldiphenylsilyl)oxy)-6a-methylhexahydro-2H-cyclopenta[b]furan-2,3,3a-triol (5.5 g 12.8 mmol) in dry MeCN (260 mL) under the an argon atmosphere was added (E)-diazene-1,2-diylbis(piperidin-1-ylmethanone) (4.86 g, 19.3 mmol) at 0° C., followed by tributylphosphine (5.13 mL, 20.5 mmol) at 0° C. The resulting mixture was stirred at 35° C. for about 1 h. Separately, to a stirred solution of 4-chloro-7H-pyrrolo[2,3-d]pyrimidine (3.74 g, 24.4 mmol) in dry MeCN (25 mL) under an argon atmosphere was added DBU (3.48 mL, 23.1 mmol) at room temperature. The solution was stirred at room temperature for 30 minutes, and then this solution was transferred to the reaction mixture originally containing the triol by means of a syringe, and the resulting reaction was stirred at 35° C. for 1 h. The reaction mixture was quenched with saturated aqueous ammonium chloride (100 mL) and extracted with EtOAc (3×200 mL). The combined organic layers were washed with brine (200 mL), dried over anhydrous sodium sulfate, and filtered. The filtrate was concentrated under reduced pressure, and the residue was purified by reverse phase column chromatography (ACN/water with 5 mM NH$_4$HCO$_3$ modifier) to afford (2R,3R,3aS,6S,6aR)-6-((tert-butyldiphenylsilyl)oxy)-2-(4-chloro-7H-pyrrolo[2,3-d]pyrimidin-7-yl)-6a-methylhexahydro-2H-cyclopenta[b]furan-3,3a-diol as a solid. MS: 564 (M+1).

Step 10: To a solution of (2R,3R,3aS,6S,6aR)-6-((tert-butyldiphenylsilyl)oxy)-2-(4-chloro-7H-pyrrolo[2,3-d]pyrimidin-7-yl)-6a-methylhexahydro-2H-cyclopenta[b]furan-3,3a-diol (4 g, 7.09 mmol) in acetone (40 mL) were added 4-methylbenzenesulfonic acid (0.122 g, 0.709 mmol) and 2,2-dimethoxypropane (7.38 g, 70.9 mmol) at ambient temperature under argon. The mixture was stirred at room temperature for 16 h. The mixture was concentrated under reduced pressure, and the resulting residue was purified by column chromatography on silica (0-20% EtOAc/PE) to afford 7-((3aR,4R,5aR,6S,8aS)-6-((tert-butyldiphenylsilyl)oxy)-2,2,5a-trimethylhexahydrocyclopenta[2,3]furo[3,4-d][1,3]dioxol-4-yl)-4-chloro-7H-pyrrolo[2,3-d]pyrimidine as a solid. MS: 604 (M+1).

Step 11: To a solution of 7-((3aR,4R,5aR,6S,8aS)-6-((tert-butyldiphenylsilyl)oxy)-2,2,5a-trimethylhexahydrocyclopenta[2,3]furo[3,4-d][1,3]dioxol-4-yl)-4-chloro-7H-pyrrolo[2,3-d]pyrimidine (3.8 g, 6.29 mmol) in THF (20 mL) under an argon atmosphere was added tetrabutylammonium fluoride (12.6 mL, 1 M in THF, 12.6 mmol) at 0° C. The reaction mixture was then stirred at room temperature for 16 h and concentrated under reduced pressure. The resulting residue was purified by column chromatography on silica (0-50% EtOAc/PE). The product was further purified by PrepSFC (CHIRALPAK IF, 40% 8 mM NH$_3$ in MeOH in CO$_2$) to afford (3aR,4R,5aR,6S,8aS)-4-(4-chloro-7H-pyrrolo[2,3-d]pyrimidin-7-yl)-2,2,5a-trimethylhexahydrocyclopenta[2,3]furo[3,4-d][1,3]dioxol-6-ol as a solid. MS: 366 (M+1).

Step 12: Dess-Martin periodinane (696 mg, 1.640 mmol) was added portion wise to a stirred solution of (3aR,4R,5aR,6S,8aS)-4-(4-chloro-7H-pyrrolo[2,3-d]pyrimidin-7-yl)-2,2,5a-trimethylhexahydrocyclopenta[2,3]furo[3,4-d][1,3]dioxol-6-ol (400 mg, 1.093 mmol) in DCM (15 mL) at 0° C. The reaction mixture was then stirred at room temperature for 2 h. The reaction mixture was quenched with saturated aqueous sodium bicarbonate (100 mL) and extracted with EtOAc (100 mL×3). The combined organic layers were washed with brine (100 mL), dried over anhydrous sodium sulfate, and filtered. The filtrate was concentrated under reduced pressure, and the resulting residue was purified by column chromatography on silica (1-30% EtOAc/PE) to afford (3aR,4R,5aS,8aS)-4-(4-chloro-7H-pyrrolo[2,3-d]pyrimidin-7-yl)-2,2,5a-trimethyltetrahydrocyclopenta[2,3]furo[3,4-d][1,3]dioxol-6(5aH)-one as a solid. MS: 364 (M+1).

Step 13: To a mixture of Nysted Reagent (4.51 g, 20% in THF, 1.98 mmol) in anhydrous THF (20 mL) was added TiCl$_4$ (1.98 mL, IM in DCM, 1.98 mmol) dropwise at 0° C. under argon. The mixture was stirred at 0° C. for 5 minutes. Then, a solution of (3aR,4R,5aS,8aS)-4-(4-chloro-7H-pyrrolo[2,3-d]pyrimidin-7-yl)-2,2,5a-trimethyltetrahydrocyclopenta[2,3]furo[3,4-d][1,3]dioxol-6(5aH)-one (360 mg, 0.990 mmol) in anhydrous THF (10 mL) was added at 0° C. The resulting mixture was stirred at room temperature for 3 h. The reaction was then quenched with saturated sodium bicarbonate (100 mL) at 0° C. The resulting mixture was diluted with EtOAc (100 mL) at room temperature and extracted, and the aqueous layer was then re-extracted with EtOAc (100 mL×2). The combined organic layers were washed with H$_2$O (80 mL) and brine (80 mL), dried over anhydrous sodium sulfate, filtered, and the filtrate was concentrated under reduced pressure. The resulting residue was purified by column chromatography on silica (1-20% EtOAc/PE) to afford 4-chloro-7-((3aR,4R,5aR,8aS)-2,2,5a-trimethyl-6-methylenehexahydrocyclopenta[2,3]furo[3,4-d][1,3]dioxol-4-yl)-7H-pyrrolo[2,3-d]pyrimidine as a solid. MS: 362 (M+1).

Step 14: To a mixture of 4-chloro-7-((3aR,4R,5aR,8aS)-2,2,5a-trimethyl-6-methylenehexahydrocyclopenta[2,3]furo[3,4-d][1,3]dioxol-4-yl)-7H-pyrrolo[2,3-d]pyrimidine (240 mg, 0.663 mmol) in 1,4-dioxane (8 mL) was added ammonia hydrate (8 mL, 28 wt %, 0.663 mmol) at room temperature. The reaction mixture was then stirred at 90° C. for 15 hr in a sealed tube. The solvent was removed under reduced pressure, and the resulting residue was purified by column chromatography on silica (1-10% MeOH/DCM) to afford 7-((3aR,4R,5aR,8aS)-2,2,5a-trimethyl-6-methylenehexahydrocyclopenta[2,3]furo[3,4-d][1,3]dioxol-4-yl)-7H-pyrrolo[2,3-d]pyrimidin-4-amine as a solid. MS: 343 (M+1).

Step 15: 7-((3aR,4R,5aR,8aS)-2,2,5a-trimethyl-6-methylenehexahydrocyclopenta[2,3]furo[3,4-d][1,3]dioxol-4-yl)-7H-pyrrolo[2,3-d]pyrimidin-4-amine (200 mg, 0.584 mmol) was co-evaporated with THF (3 mL) three times. Then, 9-BBN solution (5.84 mL, 0.5M in THF, 2.92 mmol) was added at room temperature under argon. The reaction solution was stirred at 60° C. for 1 h. A solution of potassium phosphate (620 mg, 2.92 mmol) in Water (2.9 mL) was added dropwise at 0° C. under argon. The reaction solution was stirred at room temperature for 0.5 h. Then, 7-bromo-3-fluoroquinolin-2-amine (148 mg, 0.613 mmol) in THF (2.9 mL) and [1,1'-bis(diphenylphosphino)ferrocene]dichloropalladium(II) (42.7 mg, 0.058 mmol) were added at room temperature. The reaction was irradiated with microwave radiation at 80° C. for 2.5 h. The reaction mixture was then cooled to room temperature, diluted with water (20 mL), and extracted with EtOAc (3×50 mL). The combined organic layers were concentrated under reduced pressure, and the resulting residue was purified by reverse phase HP LC (ACN/water with 5 mM $NH_4HCO_3$ modifier) to afford 7-(((3aR,4R,5aR,6S,8aS)-4-(4-amino-7H-pyrrolo[2,3-d]pyrimidin-7-yl)-2,2,5a-trimethylhexahydrocyclopenta[2,3]furo[3,4-d][1,3]dioxol-6-yl)methyl)-3-fluoroquinolin-2-amine as a solid. MS: 505 (M+1).

Step 16: To a 40 mL vial containing a solution of 7-(((3aR,4R,5aR,6S,8aS)-4-(4-amino-7H-pyrrolo[2,3-d]pyrimidin-7-yl)-2,2,5a-trimethylhexahydrocyclopenta[2,3]furo[3,4-d][1,3]dioxol-6-yl)methyl)-3-fluoroquinolin-2-amine (130 mg, 0.258 mmol) in DCM (5 mL) was added water (1.2 mL), followed by TFA (4 mL, 51.9 mmol). The reaction was stirred at room temperature overnight. The reaction mixture was then concentrated under reduced pressure. The residue was dissolved in a mixture of DMSO/$NH_4OH$, filtered, and subjected to mass-triggered reverse phase HPLC (ACN/water with 0.1% $NH_4OH$ modifier) to afford (2R,3R,3aS,6S,6aR)-6-((2-amino-4-fluoroquinolin-7-yl)methyl)-2-(4-amino-7H-pyrrolo[2,3-d]pyrimidin-7-yl)-6a-methylhexahydro-3aH-cyclopenta[b]furan-3,3a-diol as a solid. MS: 465 (M+1). $^1$H NMR (600 MHz. DMSO-$d_6$) δ 8.09 (s, 1H), 7.74 (d, J=11.8 Hz, 1H), 7.54 (d, J=8.2 Hz, 1H), 7.44 (d, J=3.7 Hz, 1H), 7.28 (s, 1H), 7.07 (d, J=8.5 Hz, 1H), 7.04 (s, 2H), 6.69-6.63 (m, 3H), 5.85 (d, J=8.2 Hz, 1H), 5.34 (d, J=7.0 Hz, 1H), 4.84 (s, 1H), 4.15 (t, J=7.6 Hz, 1H), 2.84 (dd, J=13.5, 4.8 Hz, 1H), 2.57-2.51 (m, 1H), 1.89 (dd, J=11.7, 5.5 Hz, 1H), 1.87-1.80 (m, 1H), 1.64-1.55 (m, 1H), 1.52-1.40 (m, 2H), 1.17 (s, 3H).

Example 122

(2R,3R,3aS,6S,6aR)-6-((2-amino-3-chloroquinolin-7-yl)methyl)-2-(4-methyl-7H-pyrrolo[2,3-d]pyrimidin-7-yl)hexahydro-3aH-cyclopenta[b]furan-3,3a-diol

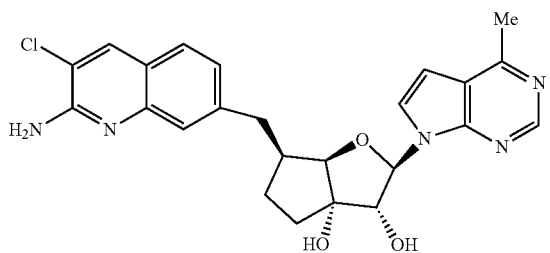 [SMILES: Cc1ncnc2c1ccn2[C@@H]1O[C@@H]2[C@H](Cc3ccc4cc(Cl)c(N)nc4c3)CC[C@]2(O)[C@H]1O]

Step 1: To a solution of (3aR,5aR,8aR)-4-methoxy-2,2-dimethyl-6-methylenehexahydrocyclopenta[2,3]furo[3,4-d][1,3]dioxole (123 mg, 0.544 mmol) in anhydrous THF (2 mL) was added 9-BBN solution (5.44 mL, 0.5M in THF, 2.72 mmol) dropwise at 0° C. under an argon atmosphere. The reaction mixture was then stirred at 52° C. for 1 h. The reaction mixture was cooled to room temperature. To the reaction mixture was added a solution of potassium phosphate tribasic (576 mg, 2.71 mmol) in water (0.2 mL) dropwise at 0° C. under argon. The reaction was stirred at room temperature for 0.5 h. 7-bromo-3-chloroquinolin-2-amine (140 mg, 0.543 mmol) in THF (0.3 mL) and 1,1'-bis(diphenylphosphino)ferrocene-palladium(II)dichloride dichloromethane complex (44.3 mg, 0.054 mmol) were added at room temperature. The reaction mixture was irradiated with microwave radiation at 70° C. for 2 h. The reaction was then cooled to room temperature, diluted with water (15 mL), and extracted with EtOAc (2×20 mL). The organic layer was dried over anhydrous sodium sulfate and filtered. The filtrate was concentrated under reduced pressure, and the resulting residue was purified by prep-TLC (eluted with 20% EtOAc/PE) to afford 3-chloro-7-(((3aR,4S,5aR,8aR)-4-methoxy-2,2-dimethylhexahydrocyclopenta[2,3]furo[3,4-d][1,3]dioxol-6-yl)methyl)quinolin-2-amine as a solid. MS: 405 (M+1).

Step 2: A solution of 3-chloro-7-(((3aR,4S,5aR,8aR)-4-methoxy-2,2-dimethylhexahydrocyclopenta[2,3]furo[3,4-d][1,3]dioxol-6-yl)methyl)quinolin-2-amine (100 mg, 0.247 mmol) in water (6 mL) and acetonitrile (9 mL) was added concentrated HCl (0.5 mL, 6.00 mmol) at room temperature. The solution was stirred at 90° C. for 1 h. The reaction solution was cooled to 0° C. and then sodium bicarbonate (500 mg) was added portion wise. The reaction mixture was concentrated under reduced pressure. The residue was purified by column chromatography on silica (0-10% MeOH/DCM) to afford (3R,3aS,6aR)-6-((2-amino-3-chloroquinolin-7-yl)methyl)hexahydro-2H-cyclopenta[b]furan-2,3,3a-triol as a solid. MS: 351 (M+1).

Step 3: To a stirred solution of (3R,3aS,6aR)-6-((2-amino-3-chloroquinolin-7-yl)methyl)hexahydro-2H-cyclopenta[b]furan-2,3,3a-triol (60 mg, 0.171 mmol) in dry MeCN (1 mL) under argon was added (E)-diazene-1,2-diylbis(piperidin-1-ylmethanone) (64.7 mg, 0.257 mmol) in MeCN (0.5 mL) dropwise at 0° C. This was followed by the addition of tributylphosphine (0.068 mL, 0.274 mmol) in MeCN (0.5 mL) dropwise at 0° C. The resulting solution was stirred at 30° C. for ~1 h. Separately, to a stirred solution of 4-methyl-7H-pyrrolo[2,3-d]pyrimidine (43.3 mg, 0.325 mmol) in dry DMF (1 mL) was added NaI (12.31 mg, 60% in mineral oil, 0.308 mmol) at room temperature. The suspension was stirred at room temperature for 30 minutes, then the suspension was transferred to the solution originally containing the triol via syringe. The resulting reaction mixture was stirred at room temperature for 1 h. The reaction was quenched with water (10 mL) and extracted with EtOAc (2×10 mL). The combined organic layers were dried over anhydrous sodium sulfate and filtered. The filtrate was concentrated under reduced pressure. The residue was purified by reverse phase column chromatography (ACN/water with 10 mM $NH_4HCO_3$ modifier) to afford (2R,3R,3aS,6S,6aR)-6-((2-amino-3-chloroquinolin-7-yl)methyl)-2-(4-methyl-7H-pyrrolo[2,3-d]pyrimidin-7-yl)hexahydro-2H-cyclopenta[b]furan-3,3a-diol as a solid. MS: 466 (M+1). $^1$H-NMR (400 MHz. DMSO-$d_6$) δ 8.69 (s, 1H), 8.12 (s, 1H), 7.88 (d, J=3.6 Hz, 1H), 7.54 (d, J=8.0 Hz, 1H), 7.28 (s, 1H), 7.08 (dd, J=8.4, 1.6 Hz, 1H), 6.82 (d, J=3.6 Hz, 1H), 6.64 (br s, 2H), 6.00 (d, J=8.4 Hz, 1H), 5.31 (d, J=6.8 Hz, 1H), 5.12 (s, 1H), 4.22 (t, J=8.0 Hz, 1H), 4.00 (d, J=6.0 Hz, 1H), 2.85-2.79 (m, 1H), 2.69 (s, 3H), 2.65-2.60 (m, 1H), 2.33-2.25 (m, 1H), 1.98-1.93 (m, 1H) 1.80-1.67 (m, 2H), 1.58-1.51 (m, 1H).

Example 123

(2R,3R,3aS,6S,6aR)-6-((2-amino-3-fluoroquinolin-7-yl)methyl)-2-(4-methyl-7H-pyrrolo[2,3-d]pyrimidin-7-yl)hexahydro-3aH-cyclopenta[b]furan-3,3a-diol

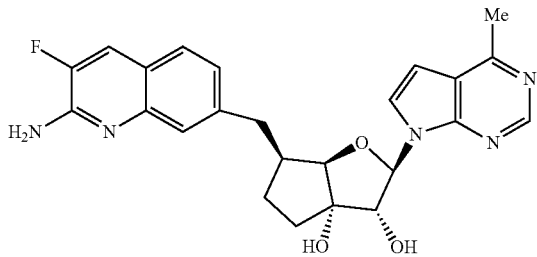 [SMILES: Cc1ncnc2c1ccn2[C@@H]1O[C@@H]2[C@H](Cc3ccc4cc(F)c(N)nc4c3)CC[C@]2(O)[C@H]1O]

Step 1: To a solution of (3aR,5aR,8aR)-4-methoxy-2,2-dimethyl-6-methylenehexahydrocyclopenta[2,3]furo[3,4-d][1,3]dioxole (245 mg, 1.08 mmol) in anhydrous THF (2.5 mL) was added 9-BBN solution (8.66 mL, 0.5M in THF, 4.33 mmol) dropwise at 0° C. under argon. The reaction solution was stirred at 55° C. for 1 h. To this reaction solution was added a solution of $K_3PO_4$ (1.15 g, 5.40 mmol) in water (2 mL) at 0° C. under argon. The reaction was stirred at room temperature for 0.5 h. Then, a solution of 7-bromo-3-fluoroquinolin-2-amine (273 mg, 1.13 mmol) in THF (2 mL) and Pd(dppf)Cl$_2$ (119 mg, 0.162 mmol) were added at room temperature. The reaction mixture was stirred at 75° C. for 1.5 h. The reaction was then concentrated under reduced pressure, and the residue was purified by preparative TLC (2:1 EtOAc/PE) to afford 3-fluoro-7-(((3aR,4S,5aR,8aR)-4-methoxy-2,2-dimethylhexahydrocyclopenta[2,3]furo[3,4-d][1,3]dioxol-6-yl)methyl)quinolin-2-amine as a solid. MS: 389 (M+1).

Step 2: A solution of 3-fluoro-7-(((3aR,4S,5aR,8aR)-4-methoxy-2,2-dimethylhexahydrocyclopenta[2,3]furo[3,4-d][1,3]dioxol-6-yl)methyl)quinolin-2-anine (300 mg, 0.772 mmol) in 0.4M aqueous HC in MeCN/H$_2$O (3:2) (6 mL, 2.400 mmol) was stirred at 90° C. for 1 h. The reaction solution was then cooled to 0° C. and quenched with saturated aqueous Na$_2$CO$_3$ (60 mL) and extracted with EtOAc (100 mL×3). The combined organic layers were washed with brine (60 mL), dried over anhydrous sodium sulfate, filtered, and the filtrate was concentrated under reduced pressure. The resulting residue was purified by column chromatography on silica (0-10% MeOH/DCM) to afford (3R,3aS,6aR)-6-((2-amino-3-fluoroquinolin-7-yl)methyl)hexahydro-2H-cyclopenta[b]furan-2,3,3a-triol as a solid. MS: 335 (M+1).

Step 3: To a stirred solution of (3R,3aS,6aR)-6-((2-amino-3-fluoroquinolin-7-yl)methyl)hexahydro-2H-cyclopenta[b]furan-2,3,3a-triol (0.067 g, 0.2 mmol) in dry MeCN (3 mL) was added tributylphosphine (0.077 g, 0.38 mmol), followed by (E)-diazene-1,2-diylbis(piperidin-1-ylmethanone) (0.091 g, 0.36 mmol) at room temperature. The reaction mixture was stirred at room temperature for 1 h. Separately, to a stirred solution of 4-methyl-7H-pyrrolo[2,3-d]pyrimidine (0.053 g, 0.400 mmol) in dry DMF (2 mL) was added NaH (0.024 g, 60% in mineral oil, 0.600 mmol) at 0° C. The suspension was stirred at room temperature for 30 minutes. The suspension was then transferred to the solution originally containing the triol via syringe. The resulting reaction was stirred at room temperature for 2 h. The reaction mixture was then quenched with saturated ammonium chloride (30 mL) and extracted with EtOAc (40 ml×3). The combined organic layers were washed with brine (40 mL), dried over anhydrous sodium sulfate, and filtered. The filtrate was concentrated under reduced pressure, and the resulting residue was purified by preparative TLC (1:1 DCM/MeOH). The product was further purified by reverse phase column chromatography (ACN/water with 5 mM NH$_4$HCO$_3$ modifier) to afford (2R,3R,3aS,6S,6aR)-6-((2-amino-3-fluoroquinolin-7-yl)methyl)-2-(4-methyl-7H-pyrrolo[2,3-d]pyrimidin-7-yl)hexahydro-2H-cyclopenta[b]furan-3,3a-diol as a solid. MS: 450 (M+1). $^1$H-NMR (400 MHz, DMSO-d$_6$) δ 8.69 (s, 1H), 7.87 (d, J=4.0 Hz, 1H), 7.74 (d, J=11.6 Hz, 1H), 7.52 (d, J=8.0 Hz, 1H), 7.28 (s, 1H), 7.07 (d, J=8.0 Hz, 1H), 6.82 (d, J=3.6 Hz, 1H), 6.66 (br s, 2H), 6.01 (d, J=8.0 Hz, 1H), 5.31 (d, J=7.2 Hz, 1H), 5.12 (s, 1H), 4.22 (d, J=7.6 Hz, 1H), 4.01 (d, J=6.0 Hz, 1H), 2.84-2.79 (m, 1H), 2.69 (s, 3H), 2.67-2.59 (m, 11H), 2.28-2.22 (m, 1H), 1.98-1.94 (m, 1H), 1.76-1.69 (m, 2H), 1.58-1.53 (m, 1H).

Example 124

(2R,3R,3aS,6S,6 aR)-6-((2-amino-3-fluoroquinolin-7-yl)methyl)-2-(4-amino-7H-pyrrolo[2,3-d]pyrimidin-7-yl)hexahydro-3aH-cyclopenta[b]furan-3,3a-diol

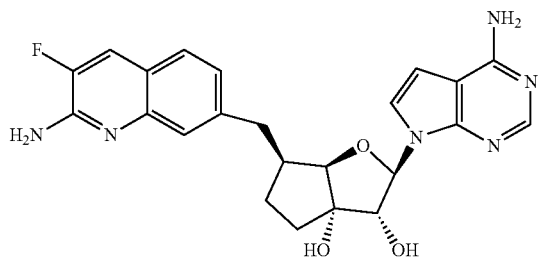

Step 1: To a stirred solution of (3R,3aS,6aR)-6-((2-amino-3-fluoroquinolin-7-yl)methyl)hexahydro-2H-cyclopenta[b]furan-2,3,3a-triol (0.100 g, 0.3 mmol) in dry MeCN (4.5 mL) was added tributylphosphine (0.115 g, 0.57 mmol), followed by (E)-diazene-1,2-diylbis(piperidin-1-ylmethanone) (0.136 g, 0.54 mmol) at room temperature. The reaction mixture was stirred at room temperature for 1 h. Separately, to a stirred solution of 4-chloro-7H-pyrrolo[2,3-d]pyrimidine (0.092 g, 0.60 mmol) in dry DMF (2 mL) was added sodium hydride (0.036 g, 60% in mineral oil, 0.90 mmol) at 0° C. The suspension was stirred at room temperature for 30 minutes. The suspension was then transferred to the solution originally containing the triol via syringe. The resulting reaction was stirred at room temperature for 2 h. The reaction mixture was quenched with saturated ammonium chloride (40 mL) and extracted with EtOAc (100 mL×3). The combined organic layers were washed with brine (40 mL), dried over anhydrous sodium sulfate, and filtered. The filtrate was concentrated under reduced pressure, and the resulting residue was purified by preparative TLC (1:1 PE/EtOAc) to afford (2R,3R,3aS,6aR)-6-((2-amino-3-fluoroquinolin-7-yl)methyl)-2-(4-chloro-7H-pyrrolo[2,3-d]pyrimidin-7-yl)hexahydro-2H-cyclopenta[b]furan-3,3a-diol as solid. MS: 470 (M+1).

Step 2: To a mixture of (2R,3R,3aS,6aR)-6-((2-amino-3-fluoroquinolin-7-yl)methyl)-2-(4-chloro-7H-pyrrolo[2,3-d]pyrimidin-7-yl)hexahydro-2H-cyclopenta[b]furan-3,3a-diol (70 mg, 0.149 mmol) in dioxane (8 mL) was added ammonia hydrate (8 mL, 28%, 0.050 mmol) in a sealed tube at room temperature. Then the reaction mixture was heated at 95° C. for 16 h. The reaction was concentrated under reduced pressure, and the residue was purified by preparative TLC (10:1 DCM/MeOH). The product was further purified by reverse phase column chromatography (ACN/water with 5 mM $NH_4HCO_3$ modifier) to afford (2R,3R,3aS,6S,6aR)-6-((2-amino-3-fluoroquinolin-7-yl)methyl)-2-(4-amino-7H-pyrrolo[2,3-d]pyrimidin-7-yl)hexahydro-2H-cyclopenta[b]furan-3,3a-diol as a solid. MS: 451 (M+1). $^1$H-NMR (400 MHz, DMSO-$d_6$) δ 8.09 (s, 1H), 7.74 (d, J=12.0 Hz, 1H), 7.53 (d, J=8.4 Hz, 1H), 7.44 (d, J=3.6 Hz, 1H), 7.29 (s, 1H), 7.09-7.05 (m, 3H), 6.68-6.66 (m, 3H), 5.88 (d, J=8.4 Hz, 1H), 5.25-5.20 (m, 1H), 5.07-5.05 (m, 1H), 4.13 (d, J=8.0 Hz, 1H), 3.95 (d, J=5.6 Hz, 1H), 2.84-2.79 (m, 1H), 2.67-2.58 (m, 1H), 2.29-2.13 (m, 1H), 1.96-1.92 (m, 1H), 1.74-1.68 (m, 2H), 1.57-1.49 (m, 1H).

Example 125

(2R,3R,3aS,6S,6aR)-6-((2-amino-3-methylquinolin-7-yl)methyl)-2-(4-amino-7H-pyrrolo[2,3-d]pyrimidin-7-yl)hexahydro-3aH-cyclopenta[b]furan-3,3a-diol

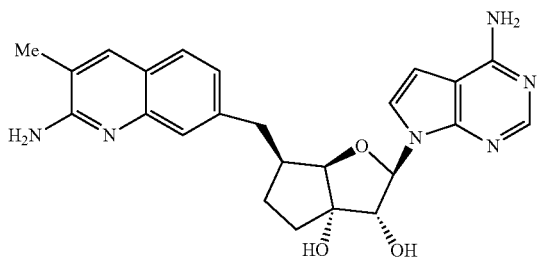 [SMILES: Cc1cc2ccc(C[C@@H]3CC[C@@]4(O)[C@@H]3O[C@@H](n3ccc5c(N)ncnc53)[C@@H]4O)cc2nc1N]

Step 1: Into a microwave tube were added (2R,3R,3aS,6S,6aR)-6-((2-amino-3-bromoquinolin-7-yl)methyl)-2-(4-amino-7H-pyrrolo[2,3-d]pyrimidin-7-yl)hexahydro-2H-cyclopenta[b]furan-3,3a-diol (40 mg, 0.078 mmol), 2,4,6-trimethyl-1,3,5,2,4,6-trioxatriborinane (19.6 mg, 0.156 mmol), $PdCl_2(dppf)$ (14.4 mg, 0.020 mmol), $K_2CO_3$ in water (0.96 mL, 2M, 1.92 mmol), and DMF (2 mL) at room temperature under argon. The reaction mixture was irradiated with microwave radiation for 1 h at 130° C. The reaction was then cooled to room temperature and concentrated under reduced pressure. The resulting residue was purified by reverse phase column chromatography (ACN/water with 5 mM $NH_4HCO_3$ modifier). The product was further purified by Prep-HPLC (ACN/water with 10 mM $NH_4HCO_3$ modifier) to afford (2R,3R,3aS,6S,6aR)-6-((2-amino-3-methylquinolin-7-yl)methyl)-2-(4-amino-7H-pyrrolo[2,3-d]pyrimidin-7-yl)hexahydro-2H-cyclopenta[b]furan-3,3a-diol as a solid. MS: 447 (M+1). $^1$H-NMR (400 MHz, DMSO-$d_6$) δ 8.10 (s, 1H), 7.65 (s, 1H), 7.47-7.45 (m, 2H), 7.25 (s, 1H), 7.06 (br s, 2H), 7.00 (dd, J=8.0, 1.2 Hz, 1H), 6.68 (d, J=4.0 Hz, 1H), 6.16 (br s, 2H), 5.90 (d, J=8.4 Hz, 1H), 5.25 (d, J=7.2 Hz, 1H), 5.07 (s, 1H), 4.14 (t, J=7.6 Hz, 1H), 3.97 (d, J=5.6 Hz, 1H), 2.84-2.79 (m, 1H), 2.63-2.58 (m, 1H), 2.28-2.22 (m, 1H), 2.19 (s, 3H), 1.95 (dd, J=12.0, 4.4 Hz, 1H), 1.75-1.70 (m, 2H), 1.56-1.51 (m, 1H).

Example 126

(1S,2R,3S,5R)-5-(4-amino-7H-pyrrolo[2,3-d]pyrimidin-7-yl)-3-(2-(2,3-dihydro-1H-pyrrolo[2,3-b]quinolin-7-yl)ethyl)-3-methylcyclopentane-1,2-diol

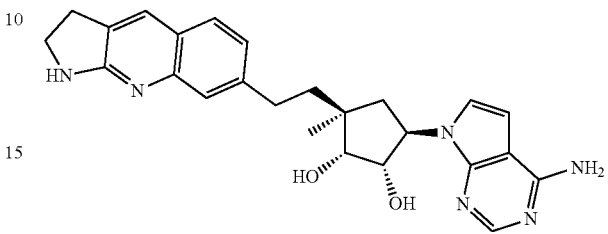

Step 1: To a solution of 7-((3a'R,4'R,6'R,6a'S)-4'-methyl-4'-vinyltetrahydro-4'H-spiro[cyclohexane-1,2'-cyclopenta[d][1,3]dioxol]-6'-yl)-7H-pyrrolo[2,3-d]pyrimidin-4-amine (223 mg, 0.63 mmol) in THF (1 mL) was added 9-BBN solution (3.16 mL, 0.5 M in THF, 1.58 mmol) under an atmosphere of nitrogen, and mixture was heated to 50° C. for a few hours, and then cooled to room temperature and quenched with $K_3PO_4$ (~3 mL, 2 M in water). The mixture was stirred for 15 mins, and the organic layer was separated from the aqueous layer. To a mixture of RuPhos-Pd-G3 (12.4 mg, 0.015 mmol) and tert-butyl 7-bromo-2,3-dihydro-1H-pyrrolo[2,3-b]quinoline-1-carboxylate (56.9 mg, 0.16 mmol) was added THF (0.4 mL) under an atmosphere of nitrogen. Next, one third of the aforementioned organic layer of 7-((3a'R,4'S,6'R,6a'S)-4'-(2-((1R,5R)-9-borabicyclo[3.3.1]nonan-9-yl)ethyl)-4'-methyltetrahydro-3aH-spiro[cyclohexane-1,2'-cyclopenta[d][1,3]dioxol]-6'-yl)-7H-pyrrolo[2,3-d]pyrimidin-4-amine solution (1.39 mL, 0.15 mmol) and $K_3PO_4$ (0.37 mL, 2 M in water, 0.74 mmol) was injected simultaneously. An additional rinse of the borane solution vial was added to the reaction vial with THF (0.3 mL). The resulting mixture was heated to 50° C. overnight, and then cooled to room temperature. The reaction mixture was diluted with DCM and water. The organic and aqueous layers were separated. The combined organic layers were concentrated under reduced pressure. The residue was re-dissolved in THF (0.5 mL), water (0.5 mL, 27.8 mol), and TFA (0.5 mL, 6.5 mol), and the resulting mixture was heated to 50° C. for a couple hours, and then cooled to room temperature, and concentrated under reduced pressure. The residue was purified by mass-triggered reverse phase HPLC (MeCN/$H_2O$ with 0.1% $NH_4OH$ modifier) to afford (1S,2R,3S,5R)-5-(4-amino-7H-pyrrolo[2,3-d]pyrimidin-7-yl)-3-(2-(2,3-dihydro-1H-pyrrolo[2,3-b]quinolin-7-yl)ethyl)-3-methylcyclopentane-1,2-diol as a solid. MS: 445 (M+1). $^1$H NMR (600 MHz, DMSO-$d_6$) δ 8.05 (s, 1H), 7.61 (s, 1H), 7.47 (d, J=8.1 Hz, 1H), 7.30-7.24 (m, 2H), 7.13 (s, 1H), 7.09-6.98 (m, 1H), 6.92 (s, 2H), 6.54 (d, J=3.5 Hz, 1H), 4.93-4.83 (m, 2H), 4.59 (d, J=5.5 Hz, 1H), 4.40 (q, J=6.2 Hz, 1H), 3.78 (t, J=5.8 Hz, 1H), 3.57 (t, J=7.8 Hz, 2H), 3.10 (t, J=7.5 Hz, 2H), 2.72 (td, J=12.9, 5.8 Hz, 1H), 2.62 (td, J=13.3, 12.9, 5.7 Hz, 1H), 1.88 (dd, J=12.8, 8.8 Hz, 1H), 1.84-1.70 (m, 3H), 1.11 (s, 3H).

Example 127

(2R,3R,3aS,6S,6aR)-6-((2-amino-3-bromoquinolin-7-yl)methyl)-2-(2-amino-4-methyl-7-pyrrolo[2,3-d]pyrimidin-7-yl)hexahydro-3aH-cyclopenta[b]furan-3,3a-diol

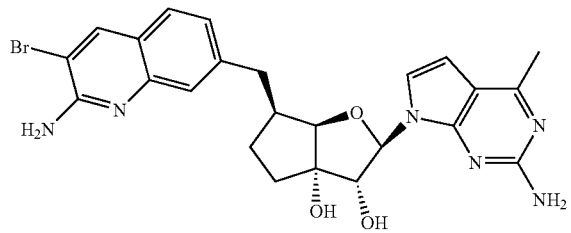 [SMILES: Cc1nc(N)nc2c1ccn2[C@@H]1O[C@@H]2[C@H](Cc3ccc4cc(Br)c(N)nc4c3)CC[C@]2(O)[C@H]1O]

Step 1: To an oven-dried, argon-cooled 2-5 mL microwave vial containing (3R,3aS,6S,6aR)-6-[(2-amino-3-bromoquinolin-7-yl)methyl]hexahydro-3aH-cyclopenta[b]furan-2,3,3a-triol (70 trig 0.177 mmol) dissolved in dry MeCN (3 mL) was added 1,1'-(azodicarbonyl)dipiperidine (67.0 mg, 0.266 mmol) followed by tri-n-butylphosphine (70.8 μl, 0.283 mmol) at room temperature. The mixture was stirred for 1 h. In a separate oven-dried, argon-cooled vial containing di-tert-butyl (4-methyl-7H-pyrrolo[2,3-d]pyrimidin-2-yl)imidodicarbonate (93 mg, 0.266 mmol) dissolved in anhydrous acetonitrile (1 mL) was added DBU (53.4 μl, 0.354 mmol). The mixture was stirred at room temperature for 30 minutes, and then this suspension was transferred to the mixture described above originally containing the triol via syringe. After 30 minutes at room temperature, the reaction was heated to 40° C. for 4 h. The mixture was then cooled to room temperature and quenched with water and extracted with EtOAc (3×). The combined organics were then washed with brine, dried over sodium sulfate, filtered, and concentrated under reduced pressure. The residue was purified by column chromatography on silica (0-100% EtOAc:hexanes) to afford di-tert-butyl (7-{(2R,3R,3aS,6S,6aR)-6-[(2-amino-3-bromoquinolin-7-yl)methyl]-3,3a-dihydroxyhexahydro-2H-cyclopenta[b]furan-2-yl}-4-methyl-7H-pyrrolo[2,3-d]pyrimidin-2-yl)imidodicarbonate as a solid. MS: 725/727 (M+1/M+3).

Step 2: To a solution of di-tert-butyl (7-{(2R,3R,3aS,6S,6aR)-6-[(2-amino-3-bromoquinolin-7-yl)methyl]-3,3a-dihydroxyhexahydro-2H-cyclopenta[b]furan-2-yl}-4-methyl-7H-pyrrolo[2,3-d]pyrimidin-2-yl)imidodicarbonate (39.8 mg, 0.055 mmol) in DCM (1.10 mL) was added TFA 20 equivalents), and the reaction was stirred for overnight at room temperature. The mixture was then concentrated under reduced pressure, and the residue was purified by mass triggered reverse phase HPLC (MeCN:H$_2$O gradient with 0.1% NH$_4$OH) to afford (2R,3R,3aS,6S,6aR)-6-((2-amino-3-bromoquinolin-7-yl)methyl)-2-(2-amino-4-methyl-7H-pyrrolo[2,3-d]pyrimidin-7-yl)hexahydro-3aH-cyclopenta[b]furan-3,3a-diol as a solid. MS: 525/527 (M+1/M+3). $^1$H NMR (600 MHz, DMSO-d$_6$) δ 8.31 (s, 1H), 7.55 (d, J=8.2 Hz, 1H), 7.32 (d, J=3.8 Hz, 1H), 7.28 (s, 1H), 7.09 (dd, J=8.2, 1.4 Hz, 1H), 6.55 (s, 2H), 6.51 (d, J=3.8 Hz, 1H), 6.18 (s, 2H), 5.82 (d, J=8.2 Hz, 1H), 5.27 (d, J=6.9 Hz, 1H), 5.03 (s, 1H), 4.08-4.03 (m, 1H), 3.91 (d, J=5.7 Hz, 1H), 2.83-2.78 (m, 1H), 2.64-2.59 (m, 1H), 2.45 (s, 3H), 2.28-2.21 (m, 1H), 1.97-1.93 (m, 1H), 1.72-1.67 (m, 2H), 1.57-1.49 (m, 1H).

Example 128

(2R,3R,3aS,6S,6aR)-6-((2-amino-3-(difluoromethyl)quinolin-7-yl)oxy)-2-(4-amino-7H-pyrrolo[2,3-d]pyrimidin-7-yl)hexahydro-3aH-cyclopenta[b]furan-3,3a-diol

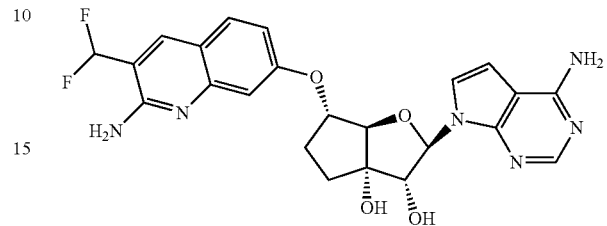

Step 1: To a stirred solution of (3R,3aS,6R,6aR)-6-(benzyloxy)hexahydro-2H-cyclopenta[b]furan-2,3,3a-triol (3.4 g, 12.8 mmol) in anhydrous MeCN (170 mL) was added tributylphosphine (5.10 mL, 20.4 mmol) in MeCN (70 mL) dropwise at 0° C. under argon. This was followed by the addition of (E)-diazene-1,2-diylbis(piperidin-1-ylmethanone) (4.83 g, 19.2 mmol) in MeCN (70 mL) dropwise at 0° C. under argon. The resulting mixture was stirred at 40° C. for 30 minutes. Separately, to a stirred solution of 4-chloro-7H-pyrrolo[2,3-d]pyrimidine (3.67 g, 23.88 mmol) in dry MeCN (35 mL) was added DBU (3.62 mL, 24.01 mmol) dropwise at 0° C. under argon. The resulting solution was stirred at 30° C. for 1 h. Then, this solution was transferred to the solution originally containing the triol via syringe over 1 minute. The resulting reaction was stirred at 39° C. for 2 h. The reaction was diluted with EtOAc (200 mL), washed with water (2×100 mL), and washed with brine (100 mL). The organic layer was dried over anhydrous sodium sulfate and filtered. The filtrate was concentrated under reduced pressure, and the residue was purified by reverse phase HPLC (ACN/water with 0.05% NH$_4$HCO$_3$) to afford (2R,3R,3aS,6R,6aR)-6-(benzyloxy)-2-(4-chloro-7H-pyrrolo[2,3-d]pyrimidin-7-yl)hexahydro-2H-cyclopenta[b]furan-3,3a-diol as a solid. MS: 402 (M+1).

Step 2: To a solution of (2R,3R,3aS,6R,6aR)-6-(benzyloxy)-2-(4-chloro-7H-pyrrolo[2,3-d]pyrimidin-7-yl)hexahydro-2H-cyclopenta[b]furan-3,3a-diol (8.6 g, 15.2 mmol, 71 wt %) in 2,2-dimethoxypropane (100 mL) was added 4-methylbenzenesulfonic acid (0.262 g, 1.52 mmol) at room temperature under argon. The mixture was stirred at 70° C. for 16 h. The reaction was then cooled to room temperature and quenched with saturated aqueous sodium bicarbonate (10 mL). The mixture was concentrated under reduced pressure, and the resulting residue was purified by column chromatography on silica (0-50% EtOAc/PE) to afford 7-((3aR,4R,5aR,6R,8aR)-6-(benzyloxy)-2,2-dimethylhexahydrocyclopenta[2,3]furo[3,4-d][1,3]dioxol-4-yl)-4-chloro-7H-pyrrolo[2,3-d]pyrimidine as an oil. MS: 442 (M+1).

Step 3: To a solution of 7-((3aR,4R,5aR,6R,8aR)-6-(benzyloxy)-2,2-dimethylhexahydrocyclopenta[2,3]furo[3,4-d][1,3]dioxol-4-yl)-4-chloro-7H-pyrrolo[2,3-d]pyrimidine (5 g, 10.75 mmol) in dioxane (60 mL) was added ammonium hydroxide (120 mL, 28%, 872 mmol) at room temperature. The mixture was sealed tightly and stirred at 90° C. for 16 h. The reaction mixture was concentrated under reduced pressure, and the resulting residue was purified by column chromatography on silica (0-10% MeOH/DCM) to afford 7-((3aR,4R,5aR,6R,8aR)-6-(benzyloxy)-2,2-dimethylhexahydrocyclopenta[2,3]furo[3,4-d][1,3]dioxol-4-yl)-7H-pyrrolo[2,3-d]pyrimidin-4-amine as a solid. MS: 423 (M+1).

Step 4: To a mixture of 7-((3aR,4R,5aR,6R,8aR)-6-(benzyloxy)-2,2-dimethylhexahydrocyclopenta[2,3]furo[3,4-d][1,3]dioxol-4-yl)-7H-pyrrolo[2,3-d]pyrimidin-4-amine (339 mg, 0.722 mmol) in MeOH (40 mL) was added palladium hydroxide on carbon (1.78 g, 20%, 50% in water, 2.53 mmol) at room temperature under argon. The suspension was degassed under vacuum and purged with H$_2$ several times. The reaction was stirred under 2 atm of H$_2$ at room temperature for 2 h. The mixture was filtered through a Celite pad, and the filtrate was concentrated under reduced pressure to afford (3aR,4R,5aR,6R,8aR)-4-(4-amino-7H-pyrrolo[2,3-d]pyrimidin-7-yl)-2,2-dimethylhexahydrocyclopenta[2,3]furo[3,4-d][1,3]dioxol-6-ol as a solid. MS: 333 (M+1).

Step 5: To a stirred mixture of (3aR,4R,5aR,6R,8aR)-4-(4-amino-7H-pyrrolo[2,3-d]pyrimidin-7-yl)-2,2-dimethylhexahydrocyclopenta[2,3]furo[3,4-d][1,3]dioxol-6-ol (170 mg, 0.512 mmol) in DCM (5 mL) and Pyridine (0.5 mL) was added trifluoromethanesulfonic anhydride (188 mg, 0.665 mmol) at 0° C. under argon. The resulting mixture was stirred for 2 h at 0° C. The reaction mixture was then quenched with saturated NaHCO$_3$(30 mL), extracted with EtOAc (30 mL×3), and the combined organic layers were dried over anhydrous sodium sulfate, filtered, and the filtrate was concentrated under reduced pressure. The resulting residue was purified by Prep-TLC (1:1 PE:EtOAc) to afford (3aR,4R,5aR,6R,8aR)-4-(4-amino-7H-pyrrolo[2,3-d]pyrimidin-7-yl)-2,2-dimethylhexahydrocyclopenta[2,3]furo[3,4-d][1,3]dioxol-6-yl trifluoromethanesulfonate as a solid. MS: 465 (M+1).

Step 6: To a stirred solution of (3aR,4R,5aR,6R,8aR)-4-(4-amino-7H-pyrrolo[2,3-d]pyrimidin-7-yl)-2,2-dimethylhexahydrocyclopenta[2,3]furo[3,4-d][1,3]dioxol-6-yl trifluoromethanesulfonate (90 mg, 0.194 mmol) and 2-amino-3-(difluoromethyl)quinolin-7-ol (44.8 mg, 0.213 mmol) in NMP (0.5 mL) was added Cs$_2$CO$_3$ (95 mg, 0.291 mmol) at 25° C. under argon. The resulting mixture was stirred for 2 h at 25° C. The reaction mixture was purified by reverse phase column chromatography (ACN/water with 5 mM NH$_4$HCO$_3$ modifier) to afford 7-(((3aR,4R,5aR,6S,8aR)-4-(4-amino-7H-pyrrolo[2,3-d]pyrimidin-7-yl)-2,2-dimethylhexahydrocyclopenta[2,3]furo[3,4-d][1,3]dioxol-6-yl)oxy)-3-(difluoromethyl)quinolin-2-amine as a solid. MS: 525 (M+1).

Step 7: To the vial charged with 7-(((3aR,4R,5aR,6S,8aR)-4-(4-amino-7H-pyrrolo[2,3-d]pyrimidin-7-yl)-2,2-dimethylhexahydrocyclopenta[2,3]furo[3,4-d][1,3]dioxol-6-yl)oxy)-3-(difluoromethyl)quinolin-2-amine (50 mg, 0.095 mmol) were added TFA (1 mL) and water (1 mL) at 25° C. The resulting mixture was stirred at 25° C. for 16 h. The reaction mixture was concentrated under reduced pressure, and the residue was purified by reverse phase column chromatography (ACN/water with 5 mM NH$_4$HCO$_3$ modifier) to afford (2R,3R,3aS,6S,6aR)-6-((2-amino-3-(difluoromethyl)quinolin-7-yl)oxy)-2-(4-amino-7H-pyrrolo[2,3-d]pyrimidin-7-yl)hexahydro-2H-1-cyclopenta[b]furan-3,3a-diol as a solid. MS: 485 (M+1). $^1$H-NMR (400 MHz, CD$_3$OD) δ 8.10-8.09 (m, 2H), 7.65 (d, J=8.8 Hz, 1H), 7.41 (d, J=3.6 Hz, 1H), 7.00-6.95 (m, 2H), 6.86-6.63 (m, 2H), 6.04 (d, J=8.4 Hz, 1H), 4.77 (d, J=4.8 Hz, 1H), 4.49 (d, J=8.4 Hz, 1H), 4.30 (s, 1H), 2.53-2.43 (m, 1H), 2.26-2.16 (m, 3H).

Example 129

(2R,3R,3aS,6R,6aR)-6-((2-amino-3-bromoquinolin-7-yl)oxy)-2-(4-methyl-7H-pyrrolo[2,3-d]pyrimidin-7-yl)hexahydro-3aH-cyclopenta[b]furan-3,3a-diol

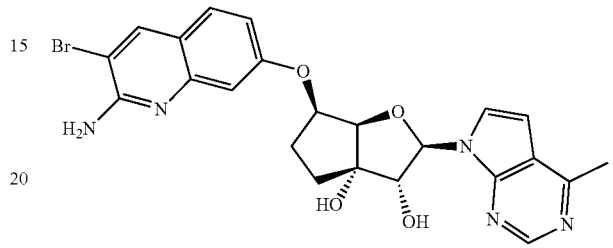

Step 1: To a vial charged with (3aR,4R,5aR,6R,8aR)-2,2-dimethyl-4-(4-methyl-7H-pyrrolo[2,3-d]pyrimidin-7-yl)hexahydrocyclopenta[2,3]furo[3,4-d][1,3]dioxol-6-ol (50 mg, 0.15 mmol), 3-bromo-N-(2,4-dimethoxybenzyl)-7-iodoquinolin-2-amine (113 mg, 0.23 mmol), 4-(pyrrolidin-1-yl)pyridine (26.8 ng, 0.181 mmol), copper iodide (2.87 mg, 0.015 mmol), potassium phosphate tribasic (128 mg, 0.60 mmol) was added toluene (754 µl), and the reaction was heated to 120° C. overnight. The reaction was filtered, concentrated under reduced pressure, and the residue was purified by column chromatography on silica (10-100% EtOAc/CH$_2$Cl$_2$) to afford 3-bromo-N-(2,4-dimethoxybenzyl)-7-(((3aR,4R,5aR,6R,8aR)-2,2-dimethyl-4-(4-methyl-7H-pyrrolo[2,3-d]pyrimidin-7-yl)hexahydrocyclopenta[2,3]furo[3,4-d][1,3]dioxol-6-yl)oxy)quinolin-2-amine as a solid. MS: 702/704 (M+1/M+3).

Step 2: To a solution of 3-bromo-N-(2,4-dimethoxybenzyl)-7-(((3aR,4R,5aR,6R,8aR)-2,2-dimethyl-4-(4-methyl-7H-pyrrolo[2,3-d]pyrimidin-7-yl)hexahydrocyclopenta[2,3]furo[3,4-d][1,3]dioxol-6-yl)oxy)quinolin-2-amine (64 mg, 0.091 mmol) in CH$_2$Cl$_2$(911 µl), was added TFA (1.40 mL, 18.2 mmol) and 1 drop of water. The reaction mixture was heated to 50° C. for 4 h. The solution was concentrated under reduced pressure, and the residue was purified by reverse phase HPLC (MeCN/water with 0.1% TFA modifier) to afford (2R,3R,3aS,6R,6aR)-6-((2-amino-3-bromoquinolin-7-yl)oxy)-2-(4-methyl-7H-pyrrolo[2,3-d]pyrimidin-7-yl)hexahydro-3aH-cyclopenta[b]furan-3,3a-diol as a solid. MS: 512/514 (M+1/i M+3). $^1$H NMR (500 MHz, DMSO-d$_6$) δ 8.63 (s, 1H), 8.24 (s, 1H), 7.78 (d, J=3.8 Hz, 1H), 7.51 (d, J=8.9 Hz, 1H), 6.94 (d, J=2.2 Hz, 1H), 6.86 (dd, J=8.8, 2.4 Hz, 1H), 6.77 (d, J=3.7 Hz, 1H), 6.54 (s, 2H), 6.14 (d, J=8.2 Hz, 1H), 5.46 (d, J=7.0 Hz, 1H), 5.39 (s, 1H), 4.84 (dt, J=8.8, 5.8 Hz, 1H), 4.41 (d, J=5.3 Hz, 1H), 4.33 (t, J=7.6 Hz, 1H), 2.64 (s, 3H), 2.25 (d, J=4.1 Hz, 1H), 2.22-2.12 (m, 1H), 2.11-2.03 (m, 1H), 1.73-1.64 (m, 1H).

Example 130

(2R,3R,3aS,6S,6aR)-6-((2-amino-3-bromoquinolin-7-yl)oxy)-2-(2-amino-5-fluoro-7H-pyrrolo[2,3-d]pyrimidin-7-yl)hexahydro-3aH-cyclopenta[b]furan-3,3a-diol

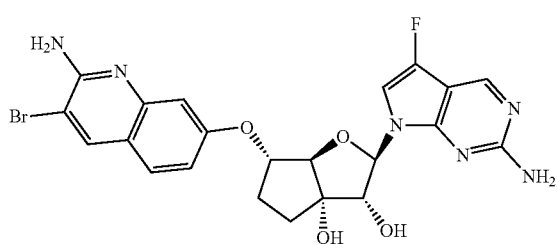 [SMILES: Nc1ncc2c(F)cn([C@@H]3O[C@@H]4[C@@H](Oc5ccc6cc(Br)c(N)nc6c5)CC[C@]4(O)[C@H]3O)c2n1]

Step 1: To a stirred slurry of 2-chloro-5-fluoro-7H-pyrrolo[2,3-d]pyrimidine (43.2 mg, 0.252 mmol) in THF (8.39 mL) was added pyridine (20.4 µl, 0.252 mmol), DIAD (103 µl, 0.529 mmol), and tri-n-butylphosphine (126 µl, 0.503 mmol). To the mixture was added (3R,3aS,6S,6aR)-6-((2-amino-3-bromoquinolin-7-yl)oxy)hexahydro-3aH-cyclopenta[b]furan-2,3,3a-triol (100 mg, 0.252 mmol) all at once. The mixture was left to stir for 2 h. The mixture was diluted with water and extracted with EtOAc (3×). The combined organics were washed with brine, dried over sodium sulfate, and concentrated under reduced pressure. The residue was purified by column chromatography on silica (0-20% MeOH/DCM) to afford (2R,3R,3aS,6S,6aR)-6-((2-amino-3-bromoquinolin-7-yl)oxy)-2-(2-chloro-5-fluoro-7H-pyrrolo[2,3-d]pyrimidin-7-yl)hexahydro-3aH-cyclopenta[b]furan-3,3a-diol. MS: 550/552 (M+1/M+3)

Step 2: A mixture of (2R,3R,3aS,6S,6aR)-6-((2-amino-3-bromoquinolin-7-yl)oxy)-2-(2-chloro-5-fluoro-7H-pyrrolo[2,3-d]pyrimidin-7-yl)hexahydro-3aH-cyclopenta[b]furan-3,3a-diol (55.1 mg, 0.1 mmol) in 1,4-Dioxane (1 mL) and ammonium hydroxide (1 mL, 7.19 mmol) was irradiated under microwave to 100° C. for 2 h. The mixture was concentrated under reduced pressure, and the residue was purified by column chromatography on silica (0-15% MeOH/DCM). The product was further purified by mass triggered reverse phase HPLC (MeCN/water with 0.1% TFA modifier) to afford (2R,3R,3aS,6S,6aR)-6-((2-amino-3-bromoquinolin-7-yl)oxy)-2-(2-amino-5-fluoro-7H-pyrrolo[2,3-d]pyrimidin-7-yl)hexahydro-3aH-cyclopenta[b]furan-3,3a-diol as a solid. MS: 531/533 (M+1/M+3). $^1$H NMR (500 MHz, DMSO-$d_6$) δ 8.68 (s, 1H), 8.63 (s, 1H), 7.74 (d, J=8.8 Hz, 1H), 7.59 (s, 1H), 7.25-6.72 (m, 5H), 5.99 (d, J=8.5 Hz, 1H), 4.63 (d, J=5.0 Hz, 1H), 4.23 (d, J=8.5 Hz, 2H), 4.03 (s, 2H), 2.13-1.90 (m, 3H).

Example 131

(2R,3R,3aS,6R,6aR)-6-((2-amino-3-chloroquinolin-7-yl)methyl)-2-(4-methyl-7H-pyrrolo[2,3-d]pyrimidin-7-yl)hexahydro-3aH-cyclopenta[b]furan-3,3a-diol

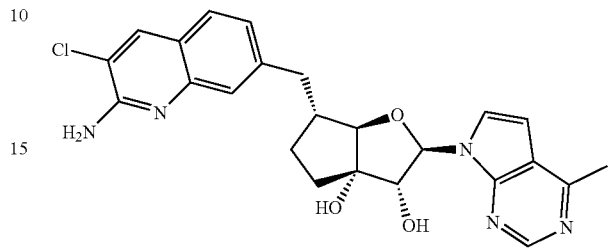

Step 1: To a mixture of chloro(1,5-cyclooctadiene)iridium (I) dimer (18.10 mg, 0.035 mmol) and DPPE (28.0 mg, 0.070 mmol) in CH$_2$Cl$_2$ (3.01 mL) was added 4,4,5,5-tetramethyl-1,3,2-dioxaborolane (281 µl, 1.76 mmol) under N$_2$. The mixture was degassed and backfilled three times with N$_2$. After stirring for 20 minutes at 25° C., 7-((3aR,4R,5aR,8aR)-2,2-dimethyl-6-methylenehexahydrocyclopenta[2,3]furo[3,4-d][1,3]dioxol-4-yl)-4-methyl-7H-pyrrolo[2,3-d]pyrimidine (230 mg, 0.703 mmol) in CH$_2$C$_2$(3.01 mL) was added to the mixture under N$_2$. The mixture was degassed and backfilled with N$_2$ three times and the resulting mixture was stirred at 25° C. for 15 h. The reaction was cooled to 0° C., quenched with 4 mL MeOH, concentrated under reduced pressure and the residue was purified by column chromatography on silica (10-100% EtOAc/DCM) to afford 7-((3aR,4R,5aR,8aR)-2,2-dimethyl-6-((4,4,5,5-tetramethyl-1,3,2-dioxaborolan-2-yl)methyl)hexahydrocyclopenta[2,3]furo[3,4-d][1,3]dioxol-4-yl)-4-methyl-7H-pyrrolo[2,3-d]pyrimidine as a resin. MS: 456 (M+1).

Step 2: To a vial charged with 7-bromo-3-chloroquinolin-2-amine (50.9 ng, 0.198 mmol), 7-((3aR,4R,5aR,8aR)-2,2-dimethyl-6-((4,4,5,5-tetramethyl-1,3,2-dioxaborolan-2-yl)methyl)hexahydrocyclopenta[2,3]furo[3,4-d][1,3]dioxol-4-yl)-4-methyl-7H-pyrrolo[2,3-d]pyrimidine (75 mg, 0.165 mmol), PdCl$_2$(dppf)-CH$_2$Cl$_2$Adduct (26.9 ng, 0.033 mmol) was added THF (2.75 mL), water (549 µl), and charged with thallium (1) ethoxide (35.0 µl, 0.49 mmol). The reaction was heated for 72 h at 65° C. The reaction was diluted with EtOAc, filtered, washed with brine, dried over sodium sulfate, filtered, and concentrated under reduced pressure. The residue was purified by column chromatography on silica (10-100% EtOAc/DCM) to afford 3-chloro-7-(((3aR,4R,5aR,8aR)-2,2-dimethyl-4-(4-methyl-7H-pyrrolo[2,3-d]pyrimidin-7-yl)hexahydrocyclopenta[2,3]furo[3,4-d][1,3]dioxol-6-yl)methyl)quinolin-2-amine which was used without further purification. MS: 506 (M+1).

Step 3: 3-chloro-7-(((3aR,4R,5aR,8aR)-2,2-dimethyl-4-(4-methyl-7H-pyrrolo[2,3-d]pyrimidin-7-yl)hexahydrocyclopenta[2,3]furo[3,4-d][1,3]dioxol-6-yl)methyl)quinolin-2-amine (10 mg, 0.012 mmol) was dissolved in CH$_2$Cl$_2$ (3 mL). A drop of water was added followed by TFA (0.457 mL, 5.93 mmol). The reaction was heated to 50° C. for 2 h and reaction was concentrated under reduced pressure and submitted for SFC resolution on (Whelk-O (R,R), 21×250 MeOH w/0.1% NH$_4$OH 35% modifier in CO$_2$) to afford (2R,3R,3aS,6R,6aR)-6-((2-amino-3-chloroquinolin-7-yl)methyl)-2-(4-methyl-7H-pyrrolo[2,3-d]pyrimidin-7-yl)

hexahydro-3aH-cyclopenta[b]furan-3,3a-diol as a solid MS: 466 (+1). $^1$H NMR (500 MHz, DMSO-d$_6$) δ 8.64 (s, 1H), 8.14 (s, 1H), 7.80 (d, J=3.8 Hz, 1H), 7.58 (d, J=8.2 Hz, 1H), 7.32 (s, 1H), 7.10 (d, J=8.1 Hz, 1H), 6.77 (d, J=3.7 Hz, 1H), 6.66 (s, 2H), 6.01 (d, J=8.1 Hz, 1H), 5.47 (s, 1H), 5.31 (s, 1H), 4.33 (d, J=8.1 Hz, 1H), 3.92 (m, 1H), 2.86 (dd, J=13.9, 8.2 Hz, 1H), 2.71 (dd, J=13.9, 8.2 Hz, 1H), 2.66 (s, 3H), 2.35 (m, 1H), 2.12-1.93 (m, 2H), 1.92-1.81 (m, 1H), 1.60 (m, 1H).

Example 132

(3aS,4S,5R)-1-(2-amino-3-bromoquinolin-7-yl)methyl)-5-(4-amino-7H-pyrrolo[2,3-d]pyrimidin-7-yl)tetrahydro-1H-cyclopenta[c]furan-3a,4(3H)-diol

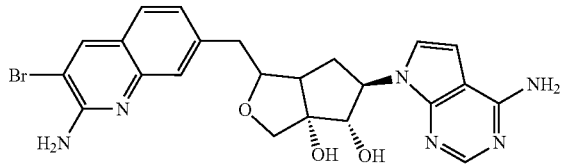 [SMILES: Nc1nc2cc(CC3OC[C@@]4(O)C3C[C@@H](n3ccc5c(N)ncnc53)[C@@H]4O)ccc2cc1Br]

Step 1: To a stirred solution of 3-bromo-7-iodo-N-(4-methoxybenzyl)quinolin-2-amine (3 g, 6.39 mmol) in THF (18.0 mL) was added allyltributylstannane (2.18 mL, 7.03 mmol) and Pd(PPh$_3$)$_4$ (0.739 g, 0.639 mmol) at room temperature under argon. The resulting mixture was heated to 95° C. and stirred for 6 h. The reaction was quenched by adding water (200 mL) and extracted by ethyl acetate (250 mL×2). The organic layer was washed with brine (200 mL), dried over sodium sulfate, filtered, and concentrated under reduced pressure. The residue was purified by column chromatography on silica (5-30% hexane/(3:1) mixture of ethyl acetate:ethanol) to afford 7-allyl-3-bromo-N-(4-methoxybenzyl)quinolin-2-amine as an oil. MS: 383/385 (M+1/M+3).

Step 2: Inside a round bottom flask equipped with a magnetic stir bar, 7-allyl-3-bromo-N-(4-methoxybenzyl)quinolin-2-amine (1 g, 2.61 mmol) was dissolved in DCM (52.2 mL). The flask was set in a dry ice-acetone bath and attached with an ozonator. Air was passed through ozonator and bubbled into the flask. The reaction was monitored every 5 minutes by LCMS, wherein the ozonator was stopped, and the reaction mixture was bubbled with air for 5 minutes before taking the aliquot. Upon complete consumption of starting material and observation of the corresponding ozonide mass, triphenylphosphane (1.369 g, 5.22 mmol) was added into the cold reaction and the reaction flask was taken out of the cold bath and stirred for another 30 minutes. The reaction was quenched with water (10 mL) extracted with DCM (10 mL), and the organic phase was washed with brine (10 mL). The organic layers were combined, dried over sodium sulfate, filtered, and concentrated under reduced pressure to afford 2-(3-bromo-2-((4-methoxybenzyl)amino)quinolin-7-yl)acetaldehyde which was used in next step without further purification.

Step 3: To a stirring solution of 2-(3-bromo-2-((4-methoxybenzyl)amino)quinolin-7-yl)acetaldehyde (5 g, 13.0 mmol) in THF (130 mL) was added vinylmagnesium bromide (20.8 mL, 1M in THF, 20.8 mmol) dropwise at 0° C. and stirred for 1 h. The reaction was quenched with saturated ammonium chloride solution (200 mL) and extracted with ethyl acetate (300 mL×2). The organic layer was washed with brine (200 mL), dried over sodium sulfate, filtered, and concentrated under reduced pressure. The residue was purified by column chromatography on silica (0-30% hexane/3:1 mixture of ethyl acetate:ethanol) to afford 1-(3-bromo-2-((4-methoxybenzyl)amino)quinolin-7-yl)but-3-en-2-ol. MS: 413/415 (M+1/M+3).

Step 4: The solution of 1-(3-bromo-2-((4-methoxybenzyl)amino)quinolin-7-yl)but-3-en-2-ol (1.5 g, 3.63 mmol) in anhydrous THF (36.3 mL) was cooled in an ice bath. Then, sodium hydride (363 mg, 9.08 mmol) was added under an atmosphere of nitrogen. After stirring for 15 minutes, a solution of 3-bromoprop-1-yne (0.61 mL, 5.44 mmol) in toluene was added dropwise. The resulting reaction mixture was warmed to room temperature slowly overnight. The reaction was quenched with a saturated aqueous solution of ammonium chloride, and the mixture was extracted with ethyl acetate. The organic phase was separated, dried over magnesium sulfate, and concentrated under reduced pressure. The residue was purified by column chromatography on silica (0-30% hexane/3:1 mixture of ethylacetate:ethanol) to afford 3-bromo-N-(4-methoxybenzyl)-7-(2-(prop-2-yn-1-yloxy)but-3-en-1-yl)quinolin-2-amine as a solid. MS: 451/453 (M+1/M+3).

Step 5: To a vial charged with dicobalt octacarbonyl (80 mg, 0.233 mmol) was added a solution of 3-bromo-N-(4-methoxybenzyl)-7-(2-(prop-2-yn-1-yloxy)but-3-en-1-yl)quinolin-2-amine (700 mg, 1.55 mmol) in toluene (15.5 mL) under argon atmosphere. The reaction was then heated to 100° C. in a CO Parr apparatus under ~70 psi CO for 20 hours. The reaction was cooled to room temperature, diluted with diethyl ether, passed through a Celite plug, and then concentrated under reduced pressure to afford crude 3-((3-bromo-2-((4-methoxy benzyl)amino)quinolin-7-yl)methyl)-3a,4-dihydro-1H-cyclopenta[c]furan-5(3H)-one, which was used as is in next step without further purification.

Step 6: A solution of 3-((3-bromo-2-((4-methoxybenzyl)amino)quinolin-7-yl)methyl)-3a,4-dihydro-1H-cyclopenta[c]furan-5(3H)-one (500 mg, 1.04 mmol) in THF (20 mL) and MeOH (10 mL) was cooled to −40° C. in a dry ice/acetonitrile bath. Cerium(III) chloride heptahydrate (389 mg, 1.04 mmol) was added. The mixture was stirred cold for 20 minutes. Then, sodium tetrahydroborate (79 mg, 2.09 mmol) was added. The reaction was then vigorously stirred cold for 40 minutes. The reaction was removed from the bath and after a few minutes was quenched by pouring into a separatory funnel containing ethyl acetate (100 mL) and 3:2:1 saturated ammonium chloride:water:brine (70 mL). After extraction, the aqueous layer was washed again with ethyl acetate (100 mL×2). The combined organics were dried over sodium sulfate, filtered, and concentrated under reduced pressure. The residue was purified by silica gel flash column chromatography (0-50% hexane/3:1 mixture of ethyl acetate:ethanol) to afford 3-((3-bromo-2-((4-methoxybenzyl)amino)quinolin-7-yl)methyl)-3,3a,4,5-tetrahydro-1H-cyclopenta[c]furan-5-ol. MS: 481/483 (M+1/M+3).

Step 7: To a solution of 3-((3-bromo-2-((4-methoxybenzyl)amino)quinolin-7-yl)methyl)-3,3a,4,5-tetrahydro-1H-cyclopenta[c]furan-5-ol (140 mg, 0.291 mmol) in DCM (20 mL) was added pyridine (0.071 mL, 0.872 mmol), N,N-dimethylpyridin-4-amine (71.1 mg, 0.582 mmol), and di-tert-butyl dicarbonate (127 mg, 0.582 mmol). The reaction was stirred at room temperature overnight. The reaction was poured into a separatory funnel containing saturated ammonium chloride solution and DCM. After extraction, the organic layer was dried over sodium sulfate, filtered, and concentrated under reduced pressure. The resulting crude was purified by column chromatography on silica (0-5-10%

EtOAc/hexanes) to afford 3-((3-bromo-2-((4-methoxybenzyl)amino)quinolin-7-yl)methyl)-3,3a,4,5-tetrahydro-1H-cyclopenta[c]furan-5-yl tert-butyl carbonate. MS: 581/583 (M+1/M+3).

Step 8: To a vial charged with N,N'-((1R,2R)-cyclohexane-1,2-diyl)bis(2-(diphenylphosphaneyl)benzamide) (3.56 mg, 5.16 μmol), tetrabutylammonium difluorotriphenylsilicate (9.28 mug, 0.017 mmol), 4-chloro-7H-pyrrolo[2,3-d]pyrimidine (5.28 mg, 0.034 mmol), and Pd$_2$dba$_3$ (1.575 mg, 1.720 μmol) was added anhydrous THF (1 mL). This mixture was stirred at room temperature for 15 minutes. Then, a solution of 3-((3-bromo-2-((4-methoxybenzyl)amino)quinolin-7-yl)methyl)-3,3a,4,5-tetrahydro-1H-cyclopenta[c]furan-5-yl tert-butyl carbonate (10 mg, 0.017 mmol) in anhydrous THF (1 mL) was added. The reaction was stirred under argon at room temperature overnight. The mixture was poured into a separatory funnel containing water (10 mL) and extracted with ethyl acetate (15 mL×2). The combined organics were dried over magnesium sulfate, filtered, and concentrated under reduced pressure. The residue was purified by column chromatography on silica (0-50% EtOAc/hexanes) to afford 3-bromo-7-((5-(4-chloro-7H-pyrrolo[2,3-d]pyrimidin-7-yl)-3,5,6,6a-tetrahydro-1H-cyclopenta[c]furan-1-yl)methyl)-N-(4-methoxybenzyl)quinolin-2-amine. MS: 616/618 (M+1/M 10+3).

Step 9: To a solution of 3-bromo-7-((5-(4-chloro-7H-pyrrolo[2,3-d]pyrimidin-7-yl)-3,5,6,6a-tetrahydro-1H-cyclopenta[c]furan-1-yl)methyl)-N-(4-methoxybenzyl)quinolin-2-amine (160 mg, 0.259 mmol) in THF (2 mL) and Water (1 mL) were added 4-methylmorpholine 4-oxide (60.8 mg, 0.519 mmol) and a solution of osmium(VIII) oxide (40 μl, 0.052 mmol). The mixture was stirred at room temperature overnight. The reaction was quenched with 40% aqueous sodium bisulfite solution (3 mL) and stirred for 15 minutes, and then extracted with chloroform containing 25% isopropyl acetate (5 mL×2). The combined organic layers were washed with water (3 mL) and then with brine (3 mL), dried over sodium sulfate, and filtered. The filtrate was concentrated under reduced pressure to afford 1-((3-bromo-2-((4-methoxybenzyl)amino)quinolin-7-yl)methyl)-5-(4-chloro-7H-pyrrolo[2,3-d]pyrimidin-7-yl)tetrahydro-1H-cyclopenta[c]furan-3a,4(3H)-diol, which was used in next step without further purification.

Step 10: To a solution of 1-((3-bromo-2-((4-methoxybenzyl)amino)quinolin-7-yl)methyl)-5-(4-chloro-7H-pyrrolo[2,3-d]pyrimidin-7-yl)tetrahydro-1H-cyclopenta[c]furan-3a,4(3H)-diol (16 mg, 0.025 mmol) in DCM (5 mL) was added 4-methylbenzenesulfonic acid-monohydrate (14.0 mg, 0.074 mmol) and 2,2-dimethoxypropane (30 μL, 0.244 mmol) under an argon atmosphere. The reaction was stirred at room temperature overnight. The reaction was poured into a separatory funnel containing saturated aqueous ammonium chloride (10 mL) and extracted with DCM (10 mL×2). The organic layers were combined, dried over sodium sulfate, filtered, and concentrated under reduced pressure to afford 3-bromo-7-((4-(4-chloro-7H-1-pyrrolo[2,3-d]pyrimidin-7-yl)-2,2-dimethyltetrahydro-5H,8H-furo[3',4':1,5]cyclopenta[1,2-d][1,3]dioxol-6-yl)methyl)-N-(4-methoxybenzyl)quinolin-2-amine, which was used in the next step without further purification.

Step 11: To a vial charged with 3-bromo-7-((4-(4-chloro-7H-pyrrolo[2,3-d]pyrimidin-7-yl)-2,2-dimethyltetrahydro-5H,8H-furo[3',4':1,5]cyclopenta[1,2-d][1,3]dioxol-6-yl)methyl)-N-(4-methoxybenzyl)quinolin-2-anine (16 mg, 0.023 mmol) was added ammonia (1 mL, 7M in MeOH, 7.00 mmol). The vial was sealed, and the reaction was heated in the microwave for 4 hours at 140° C. The reaction was then concentrated under reduced pressure, and the residue was purified by column chromatography on silica (10-60% hexane/3:1 mixture of ethyl acetate:ethanol). The product was further purified by SFC purification (MeOH w/0.1% NH$_4$OH, 35% modifier in CO$_2$) to afford 7-(((3aS,4R,8aS)-4-(4-amino-7H-pyrrolo[2,3-d]pyrimidin-7-yl)-2,2-dimethyltetrahydro-5H,8H-furo[3',4':1,5]cyclopenta[1,2-d][1,3]dioxol-6-yl)methyl)-3-bromo-N-(4-methoxybenzyl)quinolin-2-amine. MS: 671/673 (M+1/M+3).

Step 12: To a flask charged with 7-(((3aS,4R,8aS)-4-(4-amino-7H-pyrrolo[2,3-d]pyrimidin-7-yl)-2,2-dimethyltetrahydro-5H,8H-furo[3',4':1,5]cyclopenta[1,2-d][1,3]dioxol-6-yl)methyl)-3-bromo-N-(4-methoxybenzyl)quinolin-2-amine (2 mg, 2.16 μmol) was added TFA (121 μl, 1.57 mmol), and the reaction was stirred at 45° C. for 3 h. The crude was concentrated under reduced pressure, and the residue was purified by mass-triggered reverse phase HPLC (MeCN/water with 0.1% TFA modifier) to afford (3aS,4S,5R)-1-((2-amino-3-bromoquinolin-7-yl)methyl)-5-(4-amino-7H-pyrrolo[2,3-d]pyrimidin-7-yl)tetrahydro-1H-cyclopenta[c]furan-3a,4(3H)-diol as a solid as a TFA salt. MS: 511/513 (M+1/M+3). $^1$H NMR (499 MHz, DMSO-d$_6$) δ 8.31 (s, 1H), 8.00 (s, 1H), 7.57 (d, J=8.2 Hz, 1H), 7.36 (s, 1H), 7.25 (d, J=3.6 Hz, 1H), 7.14 (d, J=6.9 Hz, 1H), 6.89 (s, 2H), 6.56 (s, 2H), 6.50 (d, J=3.5 Hz, 1H), 5.02 (d, J=7.0 Hz, 1H), 4.99 (s, 1H), 4.92-4.80 (m, 1H), 4.24 (dd, J=10.5, 7.1 Hz, 1H), 4.00 (q, J=6.7 Hz, 1H), 3.76 (q, J=9.3 Hz, 2H), 3.05 (dd, J=13.5, 7.6 Hz, 1H), 2.91 (dd, J=13.3, 6.3 Hz, 1H), 2.28-2.19 (m, 1H), 1.99-1.87 (m, 1H), 1.59-1.44 (m, 1H).

Examples 133 and 134

(2R,3R,3aS,6S,6aR)-6-((2-amino-3-bromoquinolin-7-yl)methyl-2-(4-methyl-7H-pyrrolo[2,3-d]pyrimidin-7-yl)tetrahydrofuro[3,4-b]furan-3,3a(4H)-diol
and (2R,3R,3aS,6R,6aR)-6-((2-amino-3-bromoquinolin-7-yl)methyl)-2-(4-methyl-7H-pyrrolo[2,3-d]pyrimidin-7-yl)tetrahydrofuro[3,4-b]furan-3,3a(4H)-diol

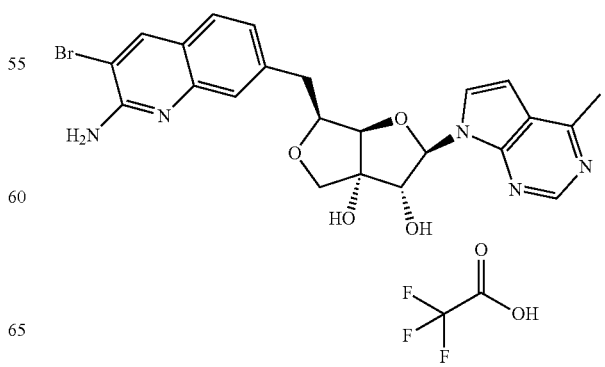

-continued

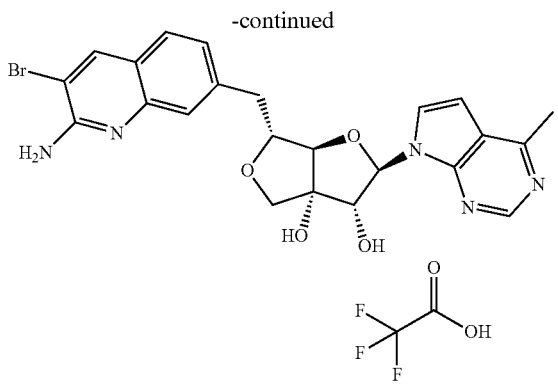

Step 1: DMP (61.6 g, 145 mmol) was added in portions to a solution of diacetone-D-glucose (25 g, 97 mmol) in DCM (300 mL) at 0° C. The reaction was then warmed to room temperature and stirred overnight. The reaction was then cooled to 0° C. and a saturated solution of sodium bicarbonate was added (100 mL) followed by a saturated solution of sodium sulfite (100 mL). The reaction was stirred for 30 minutes at room temperature, and the layers were separated. The aqueous layers were extracted with DCM (1×200 mL), the combined organic layers were then dried over sodium sulfate, filtered, and concentrated under reduced pressure to afford (3aR,5R,6aS)-5-((R)-2,2-dimethyl-1,3-dioxolan-4-yl)-2,2-dimethyldihydrofuro[2,3-d][1,3]dioxol-6(3aH)-one, which was used in the next step without further purification.

Step 2: A 500 mL 3-necked flask with stir bar, temperature probe, dropping funnel and septum was heated with a heat gun under vacuum, the glassware was cooled to room temperature and charged with (3aR,5R,6aS)-5-((R)-2,2-dimethyl-1,3-dioxolan-4-yl)-2,2-dimethyldihydrofuro[2,3-d][1,3]dioxol-6(3aH)-one (20 g, 77 mmol) and toluene (309 mL). The solution was cooled to 0° C. and vinylmagnesium chloride (58 mL, 1.6M, 93 mmol) was added dropwise at such a rate that the temperature did not exceed 5° C. After the addition was complete the reaction was warmed to room temperature and stirred for 3 h. The mixture was quenched with saturated aqueous ammonium chloride (250 mL) and then diluted with EtOAc (500 mL). The layers were separated, and the organic layer was washed with brine (2×250 mL), dried over sodium sulfate, filtered, and concentrated under reduced pressure to afford (3aR,5R,6R,6aR)-5-((R)-2,2-dimethyl-1,3-dioxolan-4-yl)-2,2-dimethyl-6-vinyltetrahydrofuro[2,3-d][1,3]dioxol-6-ol, which was used in the next step without further purification.

Step 3: A solution of (3aR,5R,6R,6aR)-5-((R)-2,2-dimethyl-1,3-dioxolan-4-yl)-2,2-dimethyl-6-vinyltetrahydrofuro[2,3-d][1,3]dioxol-6-ol (18.0 g, 62.8 mmol) in THF (165 mL) was cooled to 0° C. and sodium hydride (6.28 g, 157 mmol) was added in portions. The reaction was stirred for 30 minutes at 0° C. and then for 30 minutes at room temperature. Then TBAI (2.32 g, 6.28 mmol) was added followed by benzyl bromide (14.9 mL, 125 mmol), and the reaction was stirred at room temperature overnight. The mixture was cooled to 0° C. and quenched with a saturated ammonium chloride solution (200 mL). The mixture was diluted with EtOAc (200 mL) and the layers were separated. The combined organic layers were washed with brine (2×200 mL), dried over sodium sulfate, filtered, and concentrated under reduced pressure. The residue was purified by column chromatography on silica (0%-100% EtOAc/hexanes) to afford (3aR,5R,6R,6aR)-6-(benzyloxy)-5-((R)-2,2-dimethyl-1,3-dioxolan-4-yl)-2,2-dimethyl-6-vinyltetrahydrofuro[2,3-d][1,3]dioxole. $^1$H NMR (600 MHz, CDCl$_3$) δ 7.43 (d, J=7.5 Hz, 2H), 7.37-7.32 (m, 2H), 7.31-7.26 (m, 1H), 5.89 (dd, J=18.0, 11.4 Hz, 1H), 5.85 (d, J=3.6 Hz, 1H), 5.49 (d, J=11.4 Hz, 1H), 5.32 (d, J=18.0 Hz, 1H), 4.71 (d, J=11.4 Hz, 1H), 4.65 (d, J=3.6 Hz, 1H), 4.63 (d, J=11.4 Hz, 1H), 4.34 (d, J=5.7 Hz, 1H), 4.19 (dd, J=5.9 Hz, 1H), 4.01-3.94 (m, 2H), 1.64 (s, 3H), 1.45 (s, 3H), 1.41 (s, 3H), 1.36 (s, 3H).

Step 4: A solution of (3aR,5R,6R,6aR)-6-(benzyloxy)-5-((S)-2,2-dimethyl-1,3-dioxolan-4-yl)-2,2-dimethyl-6-vinyltetrahydrofuro[2,3-d][1,3]dioxole (1000 mg, 2.66 mmol) and pyridine (0,645 mL, 7.97 mmol) in DCM (20 mL) was cooled to −78° C. and a stream of ozone (Triogen ozonator, using compressed air) was passed through the solution for 10 minutes. The vessel was purged with air and warmed to room temperature. The reaction was cooled to −78° C. and ozone was passed through for another 10-15 minutes. The vessel was purged with air and warmed to 0° C. The crude was diluted with MeOH (20 mL) and sodium borohydride (502 mg, 13.3 mmol) was added at 0° C. The reaction was stirred at this temperature for 3 h. The reaction was quenched by the addition of NaOH solution (1M, 50 mL), stirred for 5 minutes and diluted with EtOAc (200 mL). The organic layer was washed with brine (3×50 mL), dried over sodium sulfate, filtered, and concentrated under reduced pressure to afford ((3aR,5R,6R,6aR)-6-(benzyloxy)-5-((S)-2,2-dimethyl-1,3-dioxolan-4-yl)-2,2-dimethyltetrahydrofuro[2,3-d][1,3]dioxol-6-yl)methanol, which was used in the next step without further purification.

Step 5: Sulfuric acid (0.348 mL, 5% v/v aqueous solution, 6.53 mmol) was added to a solution of (3aR,5R,6R,6aR)-6-(benzyloxy)-5-((R)-2,2-dimethyl-1,3-dioxolan-4-yl)-2,2-dimethyl-6vinyltetrahydrofuro[2,3-d][1,3]dioxole (6.15 g, 16.3 mmol) in MeCN (30 mL) at room temperature, and the reaction was stirred for 2 h. The reaction was made basic with a minimal amount of sodium hydroxide and then magnesium sulfate was added. The slurry was filtered and concentrated under reduced pressure to afford (R)-1-((3aR,5R,6R,6aR)-6-(benzyloxy)-6-(hydroxymethyl)-2,2-dimethyltetrahydrofuro[2,3-d][1,3]dioxol-5-yl)ethane-1,2-diol which was used crude without further purification.

Step 6: A solution of sodium periodate (277 mg, 1.30 mmol) in water was cooled to 0° C., then a solution of (R)-1-((3aR,5R,6R,6aR)-6-(benzyloxy)-6-(hydroxymethyl)-2,2-dimethyltetrahydrofuro[2,3-d][1,3]dioxol-5-yl)ethane-1,2-diol (315 mg, 0.925 mmol) in MeOH (2 mL) was added dropwise. The reaction was stirred for 1 h at 0° C. and then warmed to room temperature and stirred overnight. The reaction was cooled to 0° C., and ethylene glycol (1 mL, 17.9 mmol) was added. The reaction was stirred for 5 minutes, then saturated sodium sulfite (50 mL) was added, and the reaction was warmed to room temperature. The mixture was diluted with EtOAc (100 mL), and the organic layer was washed with brine (3×200 mL), dried over sodium sulfate, filtered, and concentrated under reduced pressure to afford (3aR,4aS,7aR,7bR)-7a-(benzyloxy)-2,2-dimethylhexahydrofuro[3',4':4,5]furo[2,3-d][1,3]dioxol-5-ol which was used without further purification.

Step 7: Potassium tert-butoxide (183 mg, 1.63 mmol) was added in portions to a suspension of methyltriphenylphosphonium bromide (611 mg, 1.71 mmol) in THF (4 mL) at room temperature. The reaction was stirred at room temperature for 3 h, then the solution was cooled to 0° C., a solution of (3aR,4aS,7aR,7bR)-7a-(benzyloxy)-2,2dimethylhexahydrofuro[3',4':4,5]furo[2,3-d][1,3]dioxol-5-ol (251 mg, 0.814 mmol) was added, and the reaction was stirred for 2 h. The mixture was quenched with saturated aqueous ammonium chloride (10 mL), and the mixture was extracted with EtOAc (1×50 mL). The combined organic layers were washed with brine (2×50 mL), dried over sodium sulfate, filtered, and concentrated under reduced pressure. The residue was purified by column chromatography on silica (0%-100% EtOAc/hexanes) to afford ((3aR,5R,6R,6aR)-6-(benzyloxy)-2,2-dimethyl-5-vinyltetrahydrofuro[2,3-d][1,3]dioxol-6-yl)methanol. $^1$H NMR (600 MHz, CDCl$_3$) δ 7.40 (d, J=7.3 Hz, 2H), 7.37-7.33 (m, 2H), 7.31-7.27 (In, 1H), 5.94 (ddd, J=17.2, 10.8, 5.3 Hz, 1H), 5.82 (d, J=3.9 Hz, 1H), 5.49 (dt, J=17.3, 16 Hz, 1H), 5.30 (dt, J=10.8, 1.5 Hz, 1H), 4.79 (d, J=11.1 Hz, 1H), 4.74 (d, J=11.1 Hz, 1H), 4.73-4.70 (m, 1H), 4.68 (d, J=3.9 Hz, 1H), 3.80 (d, J=12.1 Hz, 1H), 3.69 (d, J=12.1 Hz, 1H), 1.63 (s, 3H), 1.39 (s, 3H).

Step 8: To a vial charged with 3-bromo-N-(2,4-dimethoxybenzyl)-7-iodoquinolin-2-amine (1.62 g, 3.26 mmol), tris(dibenzylideneacetone)dipalladium(0) (75 mg, 0.08 mmol), sodium tert-butoxide (310 mg, 3.3 mmol) and bis(2-diphenylphosphinophenyl)ether (88 mg, 0.16 mmol) was added ((3aR,5R,6R,6aR)-6-(benzyloxy)-2,2-dimethyl-5-vinyltetrahydrofuro[2,3-d][1,3]dioxol-6-yl)methanol (500 mg, 1.63 mmol) in a solution in THF (8.16 mL). The reaction was heated to 65° C. overnight. The reaction was quenched with water and then extracted with DCM twice. The combined DCM layer were dried with Na$_2$SO$_4$ and concentrated under reduced pressure to afford 7-(((3aR,4aR,7aR,7bR)-7a-(benzyloxy)-2,2-dimethylhexahydrofuro[3',4':4,5]furo[2,3-d][1,3]dioxol-5-yl)methyl)-3-bromo-N-(2,4-dimethoxybenzyl)quinolin-2-amine. MS: 677/679 (M+1/M+3).

Step 9: Boron trichloride (0.79 mL, 0.79 mmol) was added to a solution of 7-(((3aR,4aR,7aR,7bR)-7a-(benzyloxy)-2,2-dimethylhexahydrofuro[3,4':4,5]furo[2,3-d][1,3]dioxol-5-yl)methyl)-3-bromo-N-(2,4-dimethoxybenzyl)quinolin-2-amine (107 mg, 0.16 mmol) in DCM (8 mL) at −78° C. The reaction was stirred for 15 minutes then warmed to 0° C. and stirred for 30 minutes. The reaction was quenched by the addition of T-F and saturated aqueous NaHCO$_3$ (4:1). All the solvent was evaporated under reduced pressure, and the crude was purified by mass-triggered reverse phase HPLC (MeCN/water with 0.1% NH$_4$OH modifier) to afford (3R,3aS,6aR)-6-((2-amino-3-bromoquinolin-7-yl)methyl)tetrahydrofuro[3,4-b]furan-2,3,3a(4H)-triol. MS: 397/399 (M+1/M+3).

Step 10: To a vial containing (3R,3aS,6S,6aR)-6-((2-amino-3-bromoquinolin-7-yl)methyl)tetrahydrofuro[3,4-b]furan-2,3,3a(4H)-triol (20 mg, 0.050 mmol) in anhydrous acetonitrile (750 μl) was added 1,1'-(azodicarbonyl)dipiperidine (19 mg, 0.076 mmol) followed by tri-n-butylphosphine (20 μl, 0.08 mmol) at room temperature. The mixture was stirred for 1 h. In a separate oven-dried vial containing 4-methyl-7H-pyrrolo[2,3-d]pyrimidine (13 mg, 0.10 mmol) dissolved in dry DMF (250 μl) was added NaH (4.0 mg, 0.10 mmol). This mixture was stirred for 30 minutes at room temperature and was then added to the mixture described before originally containing the triol. The final reaction mixture was then stirred at room temperature overnight. The reaction mixture was purified by Prep-HPLC (MeCN/water with 0.1% TFA modifier) directly to afford two isomers: (2R,3R,3aS,6S,6aR)-6-((2-amino-3-bromoquinolin-7-yl)methyl)-2-(4-methyl-7H-pyrrolo[2,3-d]pyrimidin-7-yl)tetrahydrofuro[3,4-b]furan-3,3a(4H)-diol as a TFA salt. MS: 512/514 (M+1/M+3). $^1$H NMR (600 MHz, DMSO-d$_6$) δ 8.96 (s, 1H), 8.80 (s, 1H), 8.00 (s, 1H), 7.77 (d, J=8.3 Hz, 1H), 7.55 (s, 1H), 7.41 (d, J=8.2 Hz, 1H), 7.07 (s, 1H), 6.25 (d, J=8.0 Hz, 1H), 4.37 (d, J=8.0 Hz, 1H), 4.32-4.30 (m, 1H), 4.14-4.08 (m, 1H), 3.99-3.95 (m, 1H), 3.42-3.36 (m, 1H), 3.08-3.03 (m, 2H), 2.82 (s, 3H) and (2R,3R,3aS,6R,6aR)-6-((2-amino-3-bromoquinolin-7-yl)methyl)-2-(4-methyl-7H-pyrrolo[2,3-d]pyrimidin-7-yl)tetrahydrofuro[3,4-b]furan-3,3a(4H)-diol as a TFA salt. (MS: 512/514 (M+1/M+3). $^1$H NMR (600 MHz, DMSO-d$_6$) δ 8.85 (s, 1H), 8.75 (s, 1H), 7.92 (s, 1H), 7.77 (d, J=8.1 Hz, 1H), 7.54 (s, 1H), 7.38 (d, J=7.8 Hz, 1H), 6.97 (s, 1H), 6.21 (d, J=7.6 Hz, 1H), 4.46 (d, J=7.6 Hz, 1H), 4.32-4.25 (m, 1H), 4.23-4.20 (m, 1H), 3.99-3.97 (m, 1H), 3.88-3.86 (m, 1H), 3.13-3.04 (m, 2H), 2.76 (s, 3H).

Example 135

(2R,3R,3aS,6S,6aR)-6-((2-amino-3-bromoquinolin-7-yl)methyl)-2-(4-amino-5-methyl-7H-pyrrolo[2,3-d]pyrimidin-7-yl)tetrahydrofuro[3,4-b]furan-3,3a(4H)-diol

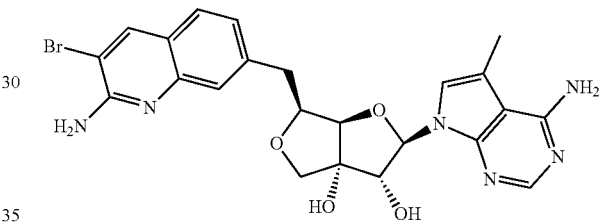

Step 1: Crude 7-(((3aR,4aR,7aR,7bR)-7a-(benzyloxy)-2,2-dimethylhexahydrofuro[3',4':4,5]furo[2,3-d][1,3]dioxol-5-yl)methyl)-3-bromo-N-(2,4-dimethoxybenzyl)quinolin-2-amine (1.1 g, 1.6 mmol) was purified by column chromatography on silica (0-40% EtOAc/hexanes) to afford 7-(((3aR,4aR,5S,7aR,7bR)-7a-(benzyloxy)-2,2-dimethylhexahydrofuro[3',4':4,5]furo[2,3-d][1,3]dioxol-5-yl)methyl)-3-bromo-N-(2,4-dimethoxybenzyl)quinolin-2-amine as a solid. MS: 677/679 (M+1/M+3). $^1$H NMR (600 MHz, CDCl$_3$) δ 8.03 (s, 1H), 7.65 (s, 1H), 7.44 (d, J=8.2 Hz, 1H), 7.40-7.27 (m, 6H), 7.18 (d, J=7.9 Hz, 1H), 6.52 (d, J=2.3 Hz, 1H), 6.47 (dd, J=8.3, 2.3 Hz, 1H), 6.06 (d, J=3.6 Hz, 1H), 5.85 (s, 1H), 4.76-4.73 (m, 2H), 4.70 (d, J=3.6 Hz, 1H), 4.53 (d, J=2.2 Hz, 1H), 4.49 (d, J=10.5 Hz, 1H), 4.27 (td, J=7.1, 2.2 Hz, 1H), 4.19-4.11 (m, 2H), 3.93 (d, J=10.3 Hz, 1H), 3.90 (s, 3H), 3.82 (s, 3H), 3.18-3.11 (m, 2H), 1.64 (s, 3H), 1.46 (s, 3H).

Step 2: Boron trichloride (5 mL, 5.1 mmol) was added to a solution of 7-(((3aR,4aR,5S,7aR,7bR)-7a-(benzyloxy)-2,2-dimethylhexahydrofuro[3',4':4,5]furo[2,3-d][1,3]dioxol-5-yl)methyl)-3-bromo-N-(2,4-dimethoxybenzyl)quinolin-2-amine (690 mg, 1.02 mmol) in DCM (20 mL) at −78° C. The reaction was stirred for 15 minutes then warmed to 0° C. and stirred for 30 minutes. The reaction was quenched by the addition of THF and saturated aqueous NaHCO$_3$ (8 mL:2 mL). The mixture was concentrated under reduced pressure, and the residue was purified by reverse phase HPLC (MeCN/water with 0.1% NH$_4$OH modifier) to afford (3R, 3aS,6S,6aR)-6-((2-amino-3-bromoquinolin-7-yl)methyl)tetrahydrofuro[3,4-b]furan-2,3,3a(4H)-triol. MS: 397/399 (M+1/M+3).

Step 3: To a vial containing (3R,3aS,6S,6aR)-6-((2-amino-3-bromoquinolin-7-yl)methyl)tetrahydrofuro[3,4-b]furan-2,3,3a(4H)-triol (20 mg, 0.05 mmol) in dry acetonitrile (750 µl) was added 1,1'-(azodicarbonyl)dipiperidine (19 mg, 0.076 mmol) followed by tri-n-butylphosphine (20 µl, 0.08 mmol) at room temperature. The mixture was stirred for 1 h. In a separate oven-dried vial containing 4-chloro-5-methyl-7H-pyrrolo[2,3-d]pyrimidine (17 mg, 0.1 mmol) in dry acetonitrile (250 µl) was added DBU (15 µl, 0.10 mmol). This mixture was stirred for 30 minutes at room temperature and was then added to the mixture described above originally containing the triol. The resulting mixture was stirred at room temperature overnight. The reaction was then purified by reverse phase HPLC (MeCN/water with 0.1% TFA modifier) directly to afford (2R,3R,3aS,6S,6aR)-6-((2-amino-3-bromoquinolin-7-yl)methyl)-2-(4-chloro-5-methyl-7H-pyrrolo[2,3-d]pyrimidin-7-yl)tetrahydrofuro[3,4-b]furan-3,3a(4H)-diol as a TFA salt, as a solid. MS: 546/548 (M+1/M+3).

Step 4: Ammonia in methanol (2 mL, 7M. 14 mmol) was added to a microwave vial with (2R,3R,3aS,6S,6aR)-6-((2-amino-3-bromoquinolin-7-yl)methyl)-2-(4-chloro-5-methyl-7H-pyrrolo[2,3-d]pyrimidin-7-yl)tetrahydrofuro[3,4-b]furan-3,3a(4H)-diol, TEA salt (16 mg, 0.029 mmol). The reaction mixture was heated at 145° C. for 5 hrs. The reaction mixture was concentrated under reduced pressure, and the residue was purified by mass-triggered reverse phase HPLC (MeCN/water with 0.1% NH₄OH modifier) to afford (2R,3R,3aS,6S,6aR)-6-((2-amino-3-bromoquinolin-7-yl)methyl)-2-(4-amino-5-methyl-7H-pyrrolo[2,3-d]pyrimidin-7-yl)tetrahydrofuro[3,4-b]furan-3,3a(4H)-diol as a solid. MS: 527/529 (M+1/M+3). $^1$H NMR (600 MHz, DMSO-d$_6$) δ 8.32 (s, 1H), 8.08 (s, 1H), 7.56 (d, J=8.3 Hz, 1H), 7.35 (s, 1H), 7.15-7.13 (m, 2H), 6.69 (s, 2H), 6.59 (s, 2H), 6.06 (d, J=8.2 Hz, 1H), 5.54 (d, J=6.7 Hz, 1H), 5.49 (s, 1H), 4.17-4.12 (m, 2H), 4.08-3.99 (m, 1H), 3.92 (d, J=9.0 Hz, 1H), 3.37-3.35 (m, 1H), 0.01-2.89 (m, 2H), 2.40 (s, 3H).

Example 136: Example 136 in Table 25 was synthesized in an analogous fashion as described in steps 1-4 of Example 135 by substituting 4-chloro-5-methyl-7H-pyrrolo[2,3-d]pyrimidine with an appropriate nucleobase. The substituted reagents and starting material were commercially acquired, synthesized as reported above or synthesized through known routes reported in the literature.

Example 137

(2R,3R,3aS,6S,6aR)-6-((2-amino-3-(difluoromethyl)quinolin-7-yl)methyl)-2-(4-amino-7H-pyrrolo[2,3-d]pyrimidin-7-yl)hexahydro-2H-cyclopenta[b]furan-3,3a-diol

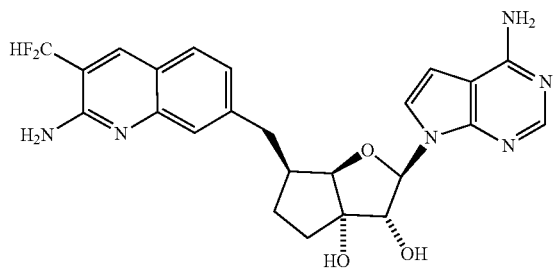

Step 1: A sealed tube was charged with (2R,3R,3aS,6aR)-2-(4-chloro-7H-pyrrolo[2,3-d]pyrimidin-7-yl)-6-methylenehexahydro-2H-cyclopenta[b]furan-3,3a-diol (200 mg, 0.650 mmol), 1,4-dioxane (3 mL) and concentrated ammonia hydrate (28 wt %, 3 mL) at room temperature. The mixture was sealed tightly and then stirred at 90° C. for 16 h. The reaction mixture was concentrated under reduced pressure, and the resulting residue was purified by column chromatography on silica (30% No MeOH/DCM) to afford (2R,3R,3aS,6aR)-2-(4-amino-7H-pyrrolo[2,3-d]pyrimidin-7-yl)-6-methylenehexahydro-2H-cyclopenta[b]furan-3,3a-diol as an oil. MS: 289 (M+1). $^1$H NMR (300 MHz. DMSO-d$_6$) δ 8.08 (s, 1H), 7.31 (d, J=3.9 Hz, 1H), 7.04 (br s, 2H), 6.63 (d, J=3.6 Hz, 1H), 6.06 (d, J=8.1 Hz, 1H), 5.37 (d, J=7.2 Hz, 1H), 5.25 (s, 1H), 5.10-5.06 (m, 2H), 4.31-4.23 (m, 2H), 2.65-2.61 (m, 1H), 2.50-2.40 (m, 1H), 2.07-2.02 (m, 1H), 1.72-1.61 (m, 1H).

Step 2: Compound (2R,3R,3a,6aR)-2-(4-amino-7H-pyrrolo[2,3-d]pyrimidin-7-yl)-6-methylenehexahydro-2H-cyclopenta[b]furan-3,3a-diol (60 mg, 0.208 mmol) was co-evaporated with THF three times (2 mL each). Then it was treated with 9-BBN (2289 µl, 0.5M in THF, 1.15 mmol) at room temperature under argon. The mixture was stirred at 50° C. for 1 h. To this reaction was then added a solution of K$_3$PO4 (220 mg, 1.04 mmol) in water (1 mL) at 0° C. and stirring continued at room temperature for 0.5 h. Then, a solution of 7-bromo-3-(difluoromethyl)quinolin-2-amine (56.6 mg, 0.207 mmol) in THF (3 mL) was added followed by PdCl$_2$(dppf) (15.2 mg, 0.021 mmol). The final reaction mixture was irradiated with microwave radiation at 70° C.

TABLE 25

| Ex | Structure | Name | MS |
|---|---|---|---|
| 136 | ![structure] | (2R,3R,3aS,6S,6aR)-6-((2-amino-3-bromoquinolin-7-yl)methyl)-2-(4-amino-7H-pyrrolo[2,3-d]pyrimidin-7-yl)tetrahydrofuro[3,4-b]furan-3,3a(4H)-diol | 513/515 (M + 1/M + 3) | for 2 h. The mixture was concentrated under reduced pressure, and the resulting residue was purified by reverse phase column chromatography (ACN/water with 5 mM NH₄HCO₃ modifier). The product was further purified by reverse phase HPLC (ACN/w-ater with 10 mM NH₄HCO₃ modifier) to afford (2R,3R,3aS,6S,6aR)-6-((2-amino-3-(difluoromethyl)quinolin-7-yl)methyl)-2-(4-amino-7H-pyrrolo[2,3-d]pyrimidin-7-yl)hexahydro-2H-cyclopenta[b]furan-3,3a-diol as a solid. MS: 483 (M+1). $^1$H-NMR (400 MHz, DMSO-d$_6$) δ 8.17 (s, 1H), 8.09 (s, 1H), 7.67 (d, J=8.4 Hz, 1H), 7.45 (d, J=3.6 Hz, 1H), 7.29 (s, 1H), 7.26-7.00 (m, 4H), 6.68 (d, J=3.6 Hz, 1H), 6.45 (br s, 2H), 5.89 (d, J=8.0 Hz, 1H), 5.26 (d, J=6.8 Hz, 1H), 5.08 (s, 1H), 4.13 (t, J=7.6 Hz, 1H), 3.96 (d, J=5.6 Hz, 1H), 2.84-2.81 (m, 1H), 2.66-2.65 (m, 1H), 2.30-2.23 (m, 1H), 1.97-1.93 (m, 1H), 1.71-1.68 (m, 2H), 1.58-1.51 (m, 1H).

PRMT5-MEP50 Enzyme Methylation Assay

PRMT5-MEP50 biochemical assay is a direct measurement of the methylation activity of the enzyme complex on a short peptide substrate derived from the N-terminus of 14 histone. Methylation experiment is performed with recombinant PRMT5-MEP50 protein complex. The assessment of inhibitory effect of small molecules is measured by the effectiveness of the compounds to inhibit this reaction ($EC_{50}$).

In this assay, the potency ($EC_{50}$) of each compound was determined from a twenty-point (1:2 serial dilution; top compound concentration of 100000 nM) titration curve using the following outlined procedure. To each well of a white ProxiPlus 384 well-plate, 100 nL of compound (1% DMSO in final assay volume of 10 μL) was dispensed, followed by the addition of 8 μL of 1× assay buffer (50 mM Bicine pH 8.0, 1 mM DTT, 0.004% Tween20, 0.01% BSA) containing 1.25 nM of Full-length (FL)-PRMT5-MEP50 enzyme complex (recombinant proteins from baculovirus-transfected Sf21 cells: FL-PRMT5; MW=73837 kDa and FL-MEP50; MW=38614) and 1 μL of 150 μM S-(5'-Adenosyl)-L-Methionine Chloride (SAM). Plates were sealed and placed in a 37° C. humidified chamber for a 60 minutes pre-incubation with compound. Subsequently, each reaction was initiated by the addition of 1 μL 1× assay buffer containing 750 nM biotinylated H4R3(Me1) peptide. The final reaction in each well of 10 μL consists of 1.0 nM PRMT5-MEP50, 75 nM biotinylated-peptide, and 15 μM SAM. Methylation reactions proceeded for 150 minutes in a sealed plate at 37° C. Reactions were immediately quenched by the addition of 1 μL of 5% formic acid. Plates were then frozen and shipped to SAMDI™ Tech Inc. to determine the percent conversion from H4R3(Me1) to H4R3(Me2). Dose-response curves were generated by plotting percent effect (% product conversion; Y-axis) vs. Log 10 compound concentrations (X-axis). $EC_{50}$ values were determined by non-linear regression according to models for either sigmoidal (4 parameters) or biphasic (7 parameters) dose-response curves.

PRMT5 Cell Target Engagement (TE) Assay

The PRMT5 TE assay is a biomarker assay for identifying compounds that inhibit symmetric dimethylation of arginine (SDMA) of PRMT5 substrates. The following substrates have been reported for PRMT5: Histone H2A and H4 R3, Histone H3 R2, Histone 1-13 R8, spliceosome Sm proteins, ribosomal protein RPS10, p53, FEN1, nucleoplasmin, nucleolin, EGFR and EBNA. The assay will focus on detecting symmetrically dimethylated nuclear proteins using high content imaging technology. Detection of the expression of symmetrically dimethylated nuclear proteins is through a mixture of primary rabbit monoclonal antibodies to SDMA (CST 13222) which in turn recognized by an Alexafluor 488 dye-conjugated anti-rabbit IgG secondary antibody. The IN Cell Analyzer 2200 or Opera-Phenix measures nuclear Alexafluor 488 fluorescent dye intensity that is directly related to the level of expression of symmetrically dimethylated nuclear proteins at the single cell level. Nuclear AF488 dye intensities are compared to the mean value for DMSO treated cells (MIN) to report percent of inhibition for each compound-treated well.

In this assay, the cell potency (EC50) of each compound was determined from a ten point (1:3 serial dilution; top compound concentration of 10000 nM) titration curve using the following outlined procedure. Each well of a BD falcon collagen coated black/clear bottom 384-well plate was seeded with 4000 MCF-7 cells in 30 pal media and allowed to attach for 5 hours. Media is ATCC-formulated Eagle's Minimum Essential Medium, Catalog No. 30-2003. The following components were added to the base medium: 0.01 mg/mL human recombinant insulin; fetal bovine serum to a final concentration of 10%. Additional 30 pal of media containing 2× compounds were added to each well. Cells were treated for 3 days in 37° C. CO$_2$ incubator. On day 3, cells were fixed with Cytofix, permeabilized with 0.4% Triton-X-100/Cytofix, and washed with D-PBS without Ca/Mg. Cells were blocked with Licor Odessey blocking reagent for 1 hour at room temperature, followed by incubation with anti-SDMA (1:1000) antibody at 4° C. overnight. 1° antibody was removed, followed by three washings with DPBS without Ca/Mg and 0.05% Tween20. Hoechst (5 μg/mL), Cell Mask deep stain (1:2000) and Alexa488-conjugated goat anti-rabbit IgG (2 μg/mL) was added for 1 hour at room temperature. A final washing step (three washes) was performed before sealing plate for imaging on in Cell Analyzer 2200 or Opera-Phenix. Images from analyzer were uploaded to Columbus for image analysis. $IC_{50}$ values were determined by 4 parameters robust fit of percent fluorescence units vs. (Log 10) compound concentrations.

Representative compounds of the present invention were tested using the assay protocol described in this example. Results are provided in Table 26 below.

TABLE 26

When only one $EC_{50}$ is shown, the data was fit to a 4 parameters single site sigmodal model. When two EC50s are shown, the data was fit to a 7 parameters biphasic model

| Ex. No. | Enzyme Methylation Assay ($EC_{50}$ or $EC_{50}$ 1, nM; $EC_{50}$ 2, nM) | TE Assay ($EC_{50}$, nM) |
| --- | --- | --- |
| 1 | 0.5; 56 | 18.0 |
| 2 | 0.5 | 0.7 |
| 3 | 0.8; 193 | 20.0 |
| 4 | 2.4; 288 | 186.0 |
| 5 | 0.8 | 19.0 |
| 6 | 0.6 | 1.2 |
| 7 | 0.7 | 4.8 |
| 8 | 0.5 | 0.5 |
| 9 | 0.3 | 1.3 |
| 10 | 0.5; 22 | 6.4 |
| 11 | 0.9; 501 | 131.0 |
| 12 | 33; 20890 | 10000.0 |
| 13 | 0.5; 89 | 14.0 |
| 14 | 1.3; 182 | 17.0 |
| 15 | 0.8 | 0.5 |
| 16 | 0.4 | 0.9 |
| 17 | 0.3 | 0.9 |
| 18 | 0.4; 228.5 | 10.6 |
| 19 | 0.4 | 1.1 |
| 20 | 0.5 | 18.6 |
| 21 | 0.8 | 0.5 |

TABLE 26-continued

When only one $EC_{50}$ is shown, the data was fit to a 4 parameters single site sigmodal model. When two EC50s are shown, the data was fit to a 7 parameters biphasic model

| Ex. No. | Enzyme Methylation Assay ($EC_{50}$ or $EC_{50}$ 1, nM; $EC_{50}$ 2, nM) | TE Assay ($EC_{50}$, nM) |
|---|---|---|
| 22 | 1.0 | 30.0 |
| 23 | 0.4 | 1.5 |
| 24 | 0.4 | 1.3 |
| 25 | 11.0; 8913.0 | 258.2 |
| 26 | 1.1 | 4.0 |
| 27 | 0.4 | 2.8 |
| 28 | 0.8 | 13.0 |
| 29 | 0.3 | 1.7 |
| 30 | 0.7 | 0.8 |
| 31 | 0.4 | 0.8 |
| 32 | 0.4 | 0.8 |
| 33 | 0.6 | 0.4 |
| 34 | 0.3 | 0.3 |
| 35 | 0.5 | 0.8 |
| 36 | 0.5 | 1.4 |
| 37 | 0.3 | 0.6 |
| 38 | 0.3 | 0.6 |
| 39 | 0.3 | 0.3 |
| 40 | 0.4 | 0.7 |
| 41 | 0.7 | 2.9 |
| 42 | 0.3 | 0.3 |
| 43 | 0.4 | 1.0 |
| 44 | 0.4 | 8.8 |
| 45 | 0.3 | 1.2 |
| 46 | 0.5 | 16.8 |
| 47 | 0.2 | 1.4 |
| 48 | 0.5 | 1.7 |
| 49 | 0.5 | 13.0 |
| 50 | 0.3 | 0.7 |
| 51 | 1.2 | 2.8 |
| 52 | 0.5 | 75.5 |
| 53 | 0.3 | 4.5 |
| 54 | 0.3 | 8.1 |
| 55 | 0.5; 190.5 | 3.9 |
| 56 | 0.2 | 1.2 |
| 57 | 0.7; 142.9 | 2.1 |
| 58 | 0.4 | 1.0 |
| 59 | 0.6 | 4.6 |
| 60 | 0.4 | 1.5 |
| 61 | 0.5 | 3.2 |
| 62 | 0.5 | 3.7 |
| 63 | 0.4 | 5.6 |
| 64 | 0.3 | 16.2 |
| 65 | 0.2; 199.5 | 178.6 |
| 66 | 0.3 | 0.9 |
| 67 | 0.8 | 1.2 |
| 68 | 0.5 | 1.1 |
| 69 | 1.1 | 103.0 |
| 70 | 0.4 | 1.0 |
| 71 | 1.6 | 9.0 |
| 72 | 0.9 | 1.2 |
| 73 | 0.4 | 2.0 |
| 74 | 0.3 | 1.0 |
| 75 | 0.7 | 5.0 |
| 76 | 0.9 | 8.6 |
| 77 | 2.0; 242.7 | 185.7 |
| 78 | 13.3; 1.19 | 5993.0 |
| 79 | 2.9 | 52.5 |
| 80 | 2.9 | 97.0 |
| 81 | 0.7 | 3.9 |
| 82 | 0.7; 75.9 | 87.2 |
| 83 | 1.2 | 41.1 |
| 84 | 0.6 | 7.5 |
| 85 | 1.2; 245.5 | 32.4 |
| 86 | 0.5; 63.8 | 37.5 |
| 87 | 0.5 | 22.9 |
| 88 | 0.2 | 25.3 |
| 89 | 1.3 | 4.4 |
| 90 | 0.9 | 42.2 |
| 91 | 0.4 | 6.3 |
| 92 | 0.5 | 9.9 |
| 93 | 0.5; 109.6 | 3.5 |
| 94 | 0.8 | 5.3 |
| 95 | 2.8 | 47.0 |
| 96 | 0.8 | 11.1 |
| 97 | 0.4 | 1.3 |
| 98 | 3.4; 2570.0 | 271.7 |
| 99 | 1.7, 1884.0 | 202.4 |
| 100 | 0.6; 32.0 | 7.4 |
| 101 | 0.3 | 1.0 |
| 102 | 0.3 | 2.0 |
| 103 | 0.4; 40.7 | 12.4 |
| 104 | 3.8 | 7.0 |
| 105 | 0.3; 21.9 | 0.9 |
| 106 | 0.3 | 0.5 |
| 107 | 0.2 | 0.5 |
| 108 | 0.2 | 0.9 |
| 109 | 0.7 | 5.9 |
| 110 | 0.9 | 39.6 |
| 111 | 30.6; 2661.0 | 2330.0 |
| 112 | 0.6 | 4.0 |
| 113 | 1.1 | 1.8 |
| 114 | 1.4 | 4.4 |
| 115 | 0.4; 255.1 | 13.6 |
| 116 | 2.4; 660.7 | 53.7 |
| 117 | 1.0 | 8.5 |
| 118 | 3.2; 1585.0 | 103.4 |
| 119 | 1.0; 116.1 | 180.0 |
| 120 | 0.6 | 2.0 |
| 121 | 0.4 | 1.0 |
| 122 | 0.6 | 2.5 |
| 123 | 1.0 | 13.1 |
| 124 | 0.3 | 2.3 |
| 125 | 0.8 | 0.7 |
| 126 | 0.6 | 2.9 |
| 127 | 0.7 | 0.8 |
| 128 | 0.7 | 15.5 |
| 129 | 33.9; 31620.0 | 10000.0 |
| 130 | 0.6 | 134.9 |
| 131 | 0.6 | 21.3 |
| 132 | 3.9; 3311.0 | 236.3 |
| 133 | 0.8 | 2.7 |
| 134 | 3.5 | 35.8 |
| 135 | 0.4 | 0.6 |
| 136 | 0.5 | 0.4 |
| 137 | 0.5 | 0.8 |

What is claimed is:

1. A compound of formula I,

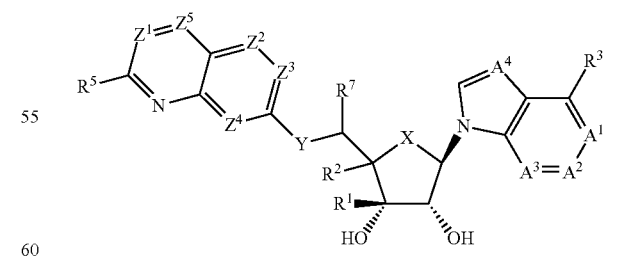

(I)

or a pharmaceutically acceptable salt thereof, wherein
X is $CH_2$ or O;
Y is $CH_2$, NH, or O;
$Z^1$ is $CR^4$ or N;
$Z^2$, $Z^3$, $Z^4$, and $Z^5$ are independently selected from N and $CR^9$;

A¹ is CH or N;
A² is CR 10 or N
A³ is CH or N;
A⁴ is CR⁸ or N;
  R¹ and R⁷ taken together to form a five membered carbon ring optionally substituted with 1-3 halogens or a five membered heterocycloalkyl ring comprising one O atom;
  R² is H, OH, CH₃, CHF₂, or F;
  R³ is H, halogen, NH₂, NHCH₃, CN, OH, OCH₃, C₁₋₄alkyl optionally substituted with 1-3 halogen or OH, or C₃₋₅cycloalkyl optionally substituted with 1-3 halogens or OH;
  R⁵ is H, NH₂, or NHR⁶; and R⁴, when present, is H, halogen, CH₃, CHF₂, or CF₃; or
  R⁴ and R⁵ taken together with the carbon atoms to which they are attached, join to form a 5 membered heterocycloalkyl comprising one N atom, wherein the heterocycloalkyl is optionally substituted with one to four substituents independently selected from halogen, CH₃, CF₃, and CF₂H;
  R⁶, when present, is CH₃, C₂H₅, CH₂CH₂CH₃, CH (CH₃)₂, CH₂CHF₂, CH₂CF₃, or CH₂-cyclopropyl;
  R⁸, when present, is H, halogen, C₁₋₄alkyl optionally substituted with 1-3 halogens, C₃₋₅cycloalkyl optionally substituted with 1-3 halogens, or aryl optionally substituted with 1-3 halogens;
each R⁹, when present, is independently selected from H and halogen; and
R¹⁰, when present, is H, C₁₋₆alkyl, NH₂, or halogen.

2. A compound of claim 1, thereof, of formula Ib:

(Ib)

or a pharmaceutically acceptable salt thereof, wherein
X is CH₂ or O;
Y is CH₂, NH, or O;
W is CR¹¹R¹¹ or O;
72, Z³, Z⁴, and Z⁵ are independently selected from N and CR⁹;
A² is CR¹⁰ or N;
R² is H, OH, CH₃, CHF₂, or F;
R³ is H, halogen, OH, NH₂, NHCH₃, CN, OCH₃, C₁₋₄alkyl optionally substituted with 1-3 halogen or OH, or C₃₋₅cycloalkyl optionally substituted with 1-3 halogens or OH;
R⁴ is H, halogen, CH₃, CHF₂, or CF₃;
R⁵ is H, NH₂, or NHR⁶;
R⁸ is H, halogen, C₁₋₄alkyl optionally substituted with 1-3 halogens, C₃₋₅cycloalkyl optionally substituted with 1-3 halogens, or aryl optionally substituted with 1-3 halogens;

each R⁹, when present, is independently selected from H and halogen;
R¹⁰, when present, is H, C₁₋₆alkyl, NH₂, or halogen; and
each R¹¹, when present, is independently selected from H and halogen.

3. A compound of claim 2, or a pharmaceutically acceptable salt thereof, wherein R⁴ is H, F, Cl, Br, CF₃, CHF₂, or CH₃.

4. A compound of claim 2, or a pharmaceutically acceptable salt thereof, wherein each R⁹, when present, is independently selected from F, Cl and H.

5. A compound of claim 2, or a pharmaceutically acceptable salt thereof, wherein A² is N, CH, CNH₂, CF, CCl or C (CH₃).

6. A compound of claim 2, or a pharmaceutically acceptable salt thereof, wherein R³ is NH₂, Cl, OCH₃, CH₂OH, CHF₂, C (CH₃)₂OH, CH₂CH₃, CH (CH₃)₂, cyclopropyl, NHCH₃, or CH₃.

7. A compound of claim 2, or a pharmaceutically acceptable salt thereof, wherein R⁸ is H, CH₃, CH₂CH₃, cyclopropyl, CHF₂, or F.

8. A compound of claim 2, or a pharmaceutically acceptable salt thereof, wherein R⁵ is NH₂, NHCH₂CF₃ or NCH₂cyclopropyl.

9. A compound of claim 2, or a pharmaceutically acceptable salt thereof, wherein W is O, CHF, CF₂, or CH₂.

10. A compound of claim 1 of formula Ic:

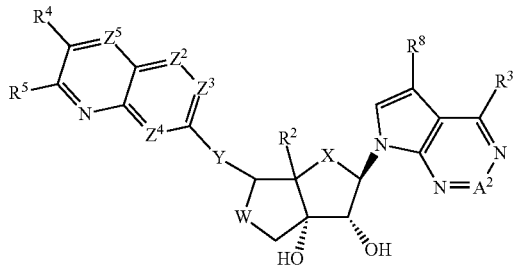

Ic or a pharmaceutically acceptable salt thereof, wherein
X is CH₂ or O;
Y is CH₂, NH, or O;
W is CH₂ or O;
R² is H, halogen, OH, CH₃, NH₂, NHCH₃, CH₂OH, CH₂F, or CHF₂;
R³ is H, halogen, CH₃, C₂H₅, cyclopropyl, NH₂, NHCH₃, CN, CF₃, OH, OCH₃ or CHF₂, CH₂OH, C (CH₃)₂OH CH₂CH₃ or CH (CH₃)₂;
R⁴ is H, halogen, CH₃, CHF₂, or CF₃;
R⁵ is H, NH₂, or NHR⁶; or
R⁴ and R⁵ taken together with the carbon atoms to which they are attached, join to form a 5 membered heterocycloalkyl comprising one N atom, wherein the heterocycloalkyl is optionally substituted with one to four substituents independently selected from halogen, CH₃, CF₃, and CF₂H;
R⁶, when present, is CH₃, C₂H₅, CH₂CH₂CH₃, CH (CH₃)₂, CH₂CHF₂, CH₂CF₃, or CH₂-cyclopropyl; and
R⁸ is H, C₁₋₄alkyl, or halogen.

11. A compound of claim 10, or a pharmaceutically acceptable salt thereof, wherein R² is H.

12. A compound of claim 10, or a pharmaceutically acceptable salt thereof, wherein R³ is CH₃, Cl, OCH₃, CH₂OH, C (CH₃)₂OH, CHF₂, CH₂CH₃, CH (CH₃)₂, cyclopropyl or NH₂.

13. A compound of claim 11, or a pharmaceutically acceptable salt thereof, wherein $R^4$ is H, Cl, F, $CH_3$, $CHF_2$, $CF_3$ or Br.

14. A compound of claim 10, or a pharmaceutically acceptable salt thereof, wherein $R^5$ is $NH_2$, $NHCH_2CF_3$ or $NHCH_2$cyclopropyl.

15. A compound of claim 10, or a pharmaceutically acceptable salt thereof, wherein $R^8$ is H.

16. A compound of claim 1, or a pharmaceutically acceptable salt thereof,
which is:
(2R,3R,3aS,6S,6aR)-6-((2-amino-3-bromoquinolin-7-yl)oxy)-2-(4-chloro-7H-pyrrolo[2,3-d] pyrimidin-7-yl) hexahydro-2H-cyclopenta[b] furan-3,3a-diol,
(2R,3R,3aS,6S,6aR)-6-((2-amino-3-bromoquinolin-7-yl)oxy)-2-(4-amino-7H-pyrrolo[2,3-d] pyrimidin-7-yl) hexahydro-2H-cyclopenta[b] furan-3,3a-diol,
(2R,3R,3aS,6S,6aR)-6-((2-amino-3-bromoquinolin-7-yl)oxy)-2-(4-methyl-7H-pyrrolo[2,3-d] pyrimidin-7-yl) hexahydro-2H-cyclopenta[b] furan-3,3a-diol,
(2R,3R,3aS,6S,6aR)-6-((2-amino-3-bromoquinolin-7-yl)methyl)-2-(4-methyl-7H-pyrrolo[2,3-d] pyrimidin-7-yl) hexahydro-2H-cyclopenta[b] furan-3,3a-diol,
(2R,3R,3aS,6S,6aR)-6-((2-amino-3-bromoquinolin-7-yl)methyl)-2-(4-amino-7H-pyrrolo[2,3-d] pyrimidin-7-yl) hexahydro-2H-cyclopenta[b] furan-3,3a-diol,
(1S,2R,3aR,4S,6aR)-4-((2-amino-3-fluoroquinolin-7-yl)methyl)-2-(4-methyl-7H-pyrrolo[2,3-d] pyrimidin-7-yl) hexahydropentalene-1,6a (1H)-diol,
(1S,2R,3aR,4S,6aR)-4-((2-amino-3-chloroquinolin-7-yl)methyl)-2-(4-methyl-7H-pyrrolo[2,3-d] pyrimidin-7-yl) hexahydropentalene-1,6a (1H)-diol,
(1S,2R,3aR,4R,6aR)-4-((2-amino-3-fluoroquinolin-7-yl)methyl)-2-(4-methyl-7H-pyrrolo[2,3-d] pyrimidin-7-yl) hexahydropentalene-1,6a (1H)-diol,
(1S,2R,3aR,4S,6aR)-4-((2-amino-3-bromoquinolin-7-yl)methyl)-2-(4-methyl-7H-pyrrolo[2,3-d] pyrimidin-7-yl) hexahydropentalene-1,6a (1H)-diol,
(2R,3R,3aS,6S,6aR)-6-[(2-amino-3,8-difluoroquinolin-7-yl)methyl]-2-(4-amino-7H-pyrrolo[2,3-d] pyrimidin-7-yl) hexahydro-3aH-cyclopenta[b] furan-3,3a-diol,
(2R,3R,3aS,6S,6aR)-6-[(2-amino-3-chloro-5-fluoroquinolin-7-yl)methyl]-2-(4-amino-7H-pyrrolo[2,3-d] pyrimidin-7-yl) hexahydro-3aH-cyclopenta[b] furan-3,3a-diol,
(2R,3R,3aS,6S,6aR)-6-[(2-amino-3-chloro-8-fluoroquinolin-7-yl)methyl]-2-(4-methyl-7H-pyrrolo[2,3-d] pyrimidin-7-yl) hexahydro-3aH-cyclopenta[b] furan-3,3a-diol,
(2R,3R,3aS,6S,6aR)-6-((2-amino-3-(difluoromethyl) quinolin-7-yl)methyl)-2-(4-methyl-7H-pyrrolo[2,3-d] pyrimidin-7-yl) hexahydro-3aH-cyclopenta[b] furan-3,3a-diol,
(2R,3R,3aS,6S,6aR)-6-((2-amino-3,5-difluoroquinolin-7-yl)methyl)-2-(4-amino-5-fluoro-7H-pyrrolo[2,3-d] pyrimidin-7-yl) hexahydro-3aH-cyclopenta[b] furan-3,3a-diol,
(2R,3R,3aS,6S,6aR)-6-((6-amino-7-fluoro-1,5-naphthyridin-3-yl)methyl)-2-(4-methyl-7H-pyrrolo[2,3-d] pyrimidin-7-yl) hexahydro-3aH-cyclopenta[b] furan-3,3a-diol,
(2R,3R,3aS,6S,6aR)-6-((2-amino-3-chloro-8-fluoroquinolin-7-yl)methyl)-2-(4-amino-7H-pyrrolo[2,3-d] pyrimidin-7-yl) hexahydro-3aH-cyclopenta[b] furan-3,3a-diol,
(2R,3R,3aS,6S,6aR)-6-[(2-amino-3,6-difluoroquinolin-7-yl)methyl]-2-(4-amino-7H-pyrrolo[2,3-d] pyrimidin-7-yl) hexahydro-3aH-cyclopenta[b] furan-3,3a-diol,
(2R,3R,3aS,6S,6aR)-6-((7-amino-6-chloro-1,8-naphthyridin-2-yl)methyl)-2-(4-amino-7H-pyrrolo[2,3-d] pyrimidin-7-yl) hexahydro-3aH-cyclopenta[b] furan-3, 3a-diol,
(2R,3R,3aS,6S,6aR)-6-[(2-amino-3,5-difluoroquinolin-7-yl)methyl]-2-(4-amino-7H-pyrrolo[2,3-d] pyrimidin-7-yl) hexahydro-3aH-cyclopenta[b] furan-3,3a-diol,
(1S,2R,3aR,4S,6aR)-2-(4-amino-2-methyl-7H-pyrrolo[2,3-d] pyrimidin-7-yl)-4-((2-amino-3-chloroquinolin-7-yl)methyl) hexahydropentalene-1,6a (1H)-diol,
(1S,2R,3aR,4S,6aR)-2-(4-amino-2-methyl-7H-pyrrolo[2,3-d] pyrimidin-7-yl)-4-((2-amino-3-fluoroquinolin-7-yl)methyl) hexahydropentalene-1,6a (1H)-diol,
(1S,2R,3aR,4S,6aR)-4-((2-amino-3-fluoroquinolin-7-yl)methyl)-2-(4-amino-5-fluoro-7H-pyrrolo[2,3-d] pyrimidin-7-yl) hexahydropentalene-1,6a (1H)-diol,
(1S,2R,3aR,4S,6aR)-4-((2-amino-3-chloroquinolin-7-yl)methyl)-2-(4-amino-5-fluoro-7H-pyrrolo[2,3-d] pyrimidin-7-yl) hexahydropentalene-1,6a (1H)-diol,
(1S,2R,3aR,4S,6aR)-4-[(2-amino-3,5-difluoroquinolin-7-yl)methyl]-2-(4-amino-5-methyl-7H-pyrrolo[2,3-d] pyrimidin-7-yl) hexahydropentalene-1,6a (1H)-diol,
(1S,2R,3aR,4S,6aR)-4-[(2-amino-3-chloro-5-fluoroquinolin-7-yl)methyl]-2-(4-amino-5-methyl-7H-pyrrolo[2,3-d] pyrimidin-7-yl) hexahydropentalene-1,6a (1H)-diol,
(1S,2R,3aR,4S,6aR)-2-(4-amino-2-methyl-7H-pyrrolo[2,3-d] pyrimidin-7-yl)-4-((2-amino-3-bromoquinolin-7-yl)methyl) hexahydropentalene-1,6a (1H)-diol,
(1S,2R,3aR,4S,6aR)-4-((2-amino-3-fluoroquinolin-7-yl)methyl)-2-(4-amino-5-methyl-7H-pyrrolo[2,3-d] pyrimidin-7-yl) hexahydropentalene-1,6a (1H)-diol,
(1S,2R,3aR,4S,6aR)-4-((2-amino-3-chloroquinolin-7-yl)methyl)-2-(4-amino-5-methyl-7H-pyrrolo[2,3-d] pyrimidin-7-yl) hexahydropentalene-1,6a (1H)-diol,
(1S,2R,3aR,4S,6aR)-4-((2-amino-3-bromoquinolin-7-yl)methyl)-2-(4-amino-5-methyl-7H-pyrrolo[2,3-d] pyrimidin-7-yl) hexahydropentalene-1,6a (1H)-diol,
(1S,2R,3aR,4S,6aR)-4-((2-amino-3-bromoquinolin-7-yl)methyl)-2-(4-amino-7H-pyrrolo[2,3-d] pyrimidin-7-yl) hexahydropentalene-1,6a (1H)-diol,
(1S,2R,3aR,4S,6aR)-4-((2-amino-3-bromoquinolin-7-yl)methyl)-2-(4-amino-5-fluoro-7H-pyrrolo[2,3-d] pyrimidin-7-yl) hexahydropentalene-1,6a (1H)-diol,
(2R,3R,3aS,6S,6aR)-6-[(2-amino-3-bromoquinolin-7-yl)methyl]-2-[4-amino-5-(difluoromethyl)-7H-pyrrolo[2,3-d] pyrimidin-7-yl] hexahydro-3aH-cyclopenta[b] furan-3,3a-diol,
(2R,3R,3aS,6S,6aR)-6-((2-amino-3-fluoroquinolin-7-yl)methyl)-2-(4-amino-5-fluoro-2-methyl-7H-pyrrolo[2,3-d] pyrimidin-7-yl) hexahydro-3aH-cyclopenta[b] furan-3,3a-diol,
(2R,3R,3aS,6S,6aR)-2-(4-amino-2-fluoro-7H-pyrrolo[2,3-d] pyrimidin-7-yl)-6-((2-amino-3-fluoroquinolin-7-yl)methyl) hexahydro-3aH-cyclopenta[b] furan-3a-diol,
(2R,3R,3aS,6S,6aR)-6-((2-amino-3-bromoquinolin-7-yl)oxy)-2-(2-amino-7H-pyrrolo[2,3-d] pyrimidin-7-yl) hexahydro-3aH-cyclopenta[b] furan-3,3a-diol dihydrochloride,
(2R,3R,3aS,6S,6aR)-2-(4-amino-2-chloro-7H-pyrrolo[2,3-d] pyrimidin-7-yl)-6-[(2-amino-3-chloroquinolin-7-yl)methyl] hexahydro-3aH-cyclopenta[b] furan-3,3a-diol, (2R,3R,3aS,6S,6aR)-2-(4-amino-2-chloro-7H-pyrrolo[2,3-d] pyrimidin-7-yl)-6-[(2-amino-3-fluoroquinolin-7-yl)methyl] hexahydro-3aH-cyclopenta[b] furan-3,3a-diol, (2R,3R,3aS,6S,6aR)-6-[(2-amino-3-bromoquinolin-7-yl) oxy]-2-(4-amino-5-phenyl-7H-pyrrolo[2,3-d] pyrimidin-7-yl) hexahydro-3aH-cyclopenta[b] furan-3,3a-diol, (2R,3R,3aS,6S,6aR)-2-(4-amino-5-cyclopropyl-7H-pyrrolo[2,3-d] pyrimidin-7-yl)-6-[(2-amino-3-fluoroquinolin-7-yl)methyl] hexahydro-3aH-cyclopenta[b] furan-3,3a-diol, (2R,3R,3aS,6S,6aR)-2-[4-amino-5-(difluoromethyl)-7H-pyrrolo[2,3-d] pyrimidin-7-yl]-6-[(2-amino-3-fluoroquinolin-7-yl)methyl] hexahydro-3aH-cyclopenta[b] furan-3,3a-diol, (2R,3R,3aS,6S,6aR)-6-[(2-amino-3-bromoquinolin-7-yl) oxy]-2-(4-amino-5-cyclopropyl-7H-pyrrolo[2,3-d] pyrimidin-7-yl) hexahydro-3aH-cyclopenta[b] furan-3,3a-diol, (2R,3R,3aS,6S,6aR)-6-[(2-amino-3-fluoroquinolin-7-yl) methyl]-2-(4-amino-7H-pyrrolo[2,3-d] pyrimidin-7-yl)-5,5-difluorohexahydro-3aH-cyclopenta[b] furan-3,3a-diol, (2R,3R,3aS,5S,6S,6aR)-6-[(2-amino-3-fluoroquinolin-7-yl)methyl]-2-(4-amino-7H-pyrrolo[2,3-d] pyrimidin-7-yl)-5-fluorohexahydro-3aH-cyclopenta[b] furan-3,3a-diol, (2R,3R,3aS,5S,6S,6aR)-2-(4-amino-5-fluoro-7H-pyrrolo[2,3-d] pyrimidin-7-yl)-6-[(2-amino-3-fluoroquinolin-7-yl)methyl]-5-fluorohexahydro-3aH-cyclopenta[b] furan-3,3a-diol, (2R,3R,3aS,6S,6aR)-6-((2-amino-3-bromoquinolin-7-yl) oxy)-2-(4-amino-5-fluoro-7H-pyrrolo[2,3-d] pyrimidin-7-yl) hexahydro-3aH-cyclopenta[b] furan-3,3a-diol, (2R,3R,3aS,6S,6aR)-2-(4-amino-7H-pyrrolo[2,3-d] pyrimidin-7-yl)-6-((2-((2,2,2-trifluoroethyl)amino) quinolin-7-yl) oxy) hexahydro-3aH-cyclopenta[b] furan-3,3a-diol, (2R,3R,3aS,6S,6aR)-2-(4-amino-7H-pyrrolo[2,3-d] pyrimidin-7-yl)-6-((2-((cyclopropylmethyl)amino) quinolin-7-yl) oxy) hexahydro-3aH-cyclopenta[b] furan-3,3a-diol, (2R,3R,3aS,6S,6aR)-6-((2-amino-3-fluoroquinolin-7-yl) methyl)-2-(4-amino-5-fluoro-7H-pyrrolo[2,3-d] pyrimidin-7-yl) hexahydro-3aH-cyclopenta[b] furan-3,3a-diol, (2R,3R,3aS,6S,6aR)-6-((2-amino-3-bromoquinolin-7-yl) oxy)-2-(4-amino-5-methyl-7H-pyrrolo[2,3-d] pyrimidin-7-yl) hexahydro-3aH-cyclopenta[b] furan-3,3a-diol, (2R,3R,3aS,6S,6aR)-2-(4-amino-2-methyl-7H-pyrrolo[2,3-d] pyrimidin-7-yl)-6-((2-amino-3-bromoquinolin-7-yl)methyl) hexahydro-3aH-cyclopenta[b] furan-3,3a-diol, (2R,3R,3aS,6S,6aR)-6-((2-amino-3-fluoroquinolin-7-yl) methyl)-2-(4-amino-5-methyl-7H-pyrrolo[2,3-d] pyrimidin-7-yl) hexahydro-3aH-cyclopenta[b] furan-3,3a-diol, (2R,3R,3aS,6S,6aR)-2-(4-amino-2-methyl-7H-pyrrolo[2,3-d] pyrimidin-7-yl)-6-((2-amino-3-bromoquinolin-7-yl) oxy) hexahydro-3aH-cyclopenta[b] furan-3,3a-diol, (2R,3R,3aS,6S,6aR)-6-((2-amino-3-chloroquinolin-7-yl) oxy)-2-(4-amino-5-methyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-fluoroquinolin-7-yl) oxy)-2-(4-amino-5-methyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-chloroquinolin-7-yl) methyl)-2-(4-amino-5-methyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-chloroquinolin-7-yl) methyl)-2-(4-amino-7H-pyrrolo[2,3-d] pyrimidin-7-yl) hexahydro-3aH-cyclopenta[b] furan-3,3a-diol, (2R,3R,3aS,6S,6aR)-6-((2-amino-3-chloroquinolin-7-yl) methyl)-2-(4-amino-5-fluoro-7H-pyrrolo[2,3-d] pyrimidin-7-yl) hexahydro-3aH-cyclopenta[b] furan-3,3a-diol, (2R,3R,3aS,6S,6aR)-6-((2-amino-3-bromoquinolin-7-yl) oxy)-2-(4-amino-5-ethyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-bromoquinolin-7-yl) methyl)-2-(4-amino-5-methyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-fluoroquinolin-7-yl) oxy)-2-(4-amino-7H-pyrrolo[2,3-d] pyrimidin-7-yl) hexahydro-3aH-cyclopenta[b] furan-3,3a-diol, (2R,3R,3aS,6S,6aR)-6-((2-amino-3-chloroquinolin-7-yl) oxy)-2-(4-amino-7H-pyrrolo[2,3-d] pyrimidin-7-yl) hexahydro-3aH-cyclopenta[b] furan-3,3a-diol, (2R,3R,3aS,6S,6aR)-6-((2-amino-3-fluoroquinolin-7-yl) oxy)-2-(4-amino-5-fluoro-7H-pyrrolo[2,3-d] pyrimidin-7-yl) hexahydro-3aH-cyclopenta[b] furan-3,3a-diol, (2R,3R,3aS,6S,6aR)-6-((2-amino-3-chloroquinolin-7-yl) oxy)-2-(4-amino-5-fluoro-7H-pyrrolo[2,3-d] pyrimidin-7-yl) hexahydro-3aH-cyclopenta[b] furan-3,3a-diol, (2R,3R,3aS,6S,6aR)-2-(4-amino-7H-pyrrolo[2,3-d] pyrimidin-7-yl)-6-((2,3-dihydro-1H-pyrrolo[2,3-b] quinolin-7-yl) oxy) hexahydro-3aH-cyclopenta[b] furan-3,3a-diol, (2R,3R,3aS,6S,6aR)-6-((2-amino-3-(trifluoromethyl) quinolin-7-yl)methyl)-2-(4-amino-7H-pyrrolo[2,3-d] pyrimidin-7-yl) hexahydro-3aH-cyclopenta[b] furan-3,3a-diol, (2R,3R,3aS,6S,6aR)-6-[(2-amino-3-bromoquinolin-7-yl) oxy]-2-[4-(hydroxymethyl)-7H-pyrrolo[2,3-d] pyrimidin-7-yl] hexahydro-3aH-cyclopenta[b] furan-3,3a-diol, (2R,3R,3aS,6S,6aR)-6-[(2-amino-3-bromoquinolin-7-yl) oxy]-2-[4-(2-hydroxypropan-2-yl)-7H-pyrrolo[2,3-d] pyrimidin-7-yl] hexahydro-3aH-cyclopenta[b] furan-3,3a-diol, (2R,3R,3aS,6S,6aR)-6-((2-amino-3-bromoquinolin-7-yl) oxy)-2-(4-(difluoromethyl)-7H-pyrrolo[2,3-d] pyrimidin-7-yl) hexahydro-3aH-cyclopenta[b] furan-3,3a-diol, (2R,3R,3aS,6S,6aR)-6-((2-amino-3-bromoquinolin-7-yl) oxy)-2-(2,4-dimethyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-bromoquinolin-7-yl) methyl)-2-(2,4-dimethyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-bromoquinolin-7-yl) oxy)-2-(4-amino-5-ethyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-bromoquinolin-7-yl) methyl)-2-(4-isopropyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-bromoquinolin-7-yl) methyl)-2-(5-fluoro-4-methyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-bromoquinolin-7-yl) oxy)-2-(7H-pyrrolo[2,3-d] pyrimidin-7-yl) hexahydro-3aH-cyclopenta[b] furan-3,3a-diol, (2R,3R,3aS,6S,6aR)-6-((2-amino-3-fluoroquinolin-7-yl) oxy)-2-(4-methyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-bromoquinolin-7-yl) methyl)-2-(4-cyclopropyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-(trifluoromethyl) quinolin-7-yl)methyl)-2-(4-methyl-7H-pyrrolo[2,3-d] pyrimidin-7-yl) hexahydro-3aH-cyclopenta[b] furan-3,3a-diol, (2R,3R,3aS,6S,6aR)-6-((2,3-dihydro-1H-pyrrolo[2,3-b] quinolin-7-yl) oxy)-2-(4-methyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-fluoroquinolin-7-yl) methyl)-2-(2,4-dimethyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-chloroquinolin-7-yl) methyl)-2-(2,4-dimethyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-bromoquinolin-7-yl) methyl)-2-(4-(methylamino)-7H-pyrrolo[2,3-d] pyrimidin-7-yl) hexahydro-3aH-cyclopenta[b] furan-3,3a-diol, (2R,3R,3aS,6S,6aR)-6-((2-amino-3-bromoquinolin-7-yl) oxy)-2-(4-(methylamino)-7H-pyrrolo[2,3-d] pyrimidin-7-yl) hexahydro-3aH-cyclopenta[b] furan-3,3a-diol, (2R,3R,3aS,6S,6aR)-6-((2-amino-3-fluoroquinolin-7-yl) methyl)-2-(4-(methylamino)-7H-pyrrolo[2,3-d] pyrimidin-7-yl) hexahydro-3aH-cyclopenta[b] furan-3,3a-diol, (2R,3R,3aS,6S,6aR)-6-((2-amino-3-bromoquinolin-7-yl) methyl)-2-(5-fluoro-4-(methylamino)-7H-pyrrolo[2,3-d] pyrimidin-7-yl) hexahydro-3aH-cyclopenta[b] furan-3,3a-diol, (1S,2R,3aR,4S,6aR)-4-((2-amino-3-bromoquinolin-7-yl) methyl)-2-(4-(methylamino)-7H-pyrrolo[2,3-d] pyrimidin-7-yl) hexahydropentalene-1,6a (1H)-diol, (2R,3R,3aS,6S,6aR)-2-(4-amino-7H-pyrrolo[2,3-d] pyrimidin-7-yl)-6-((2-aminoquinolin-7-yl) oxy) hexahydro-2H-cyclopenta[b] furan-3,3a-diol, (2R,3R,3aS,6S,6aR)-6-((2-aminoquinolin-7-yl)methyl)-2-(4-methyl-7H-pyrrolo[2,3-d] pyrimidin-7-yl) hexahydro-2H-cyclopenta[b] furan-3,3a-diol, (2R,3R,3aS,6S,6aR)-6-((2-amino-3-bromoquinolin-7-yl) methyl)-2-(4-amino-5-fluoro-7H-pyrrolo[2,3-d] pyrimidin-7-yl) hexahydro-2H-cyclopenta[b] furan-3,3a-diol, (2R,3R,3aS,6S,6aR)-6-((2-amino-3-chloroquinolin-7-yl) oxy)-2-(4-methyl-7H-pyrrolo[2,3-d] pyrimidin-7-yl) hexahydro-2H-cyclopenta[b] furan-3,3a-diol, (2R,3R,3aS,6S,6aR)-6-((2-aminoquinolin-7-yl) oxy)-2-(4-methyl-7H-pyrrolo[2,3-d] pyrimidin-7-yl) hexahydro-2H-cyclopenta[b] furan-3,3a-diol, (2R,3R,3aS,6S,6aR)-6-((2-amino-3-bromoquinolin-7-yl) oxy)-2-(2-amino-4-methyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-(difluoromethyl) quinolin-7-yl) oxy)-2-(4-methyl-7H-pyrrolo[2,3-d] pyrimidin-7-yl) hexahydro-3aH-cyclopenta[b] furan-3,3a-diol, (1S,2R,3aR,4S,6aR)-4-((2-amino-3-bromoquinolin-7-yl) oxy)-2-(4-amino-7H-pyrrolo[2,3-d] pyrimidin-7-yl) hexahydropentalene-1,6a (1H)-diol, (2R,3R,3aS,6S,6aR)-6-((2-amino-3-fluoroquinolin-7-yl) amino)-2-(4-methyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-fluoroquinolin-7-yl) methyl)-2-(4-amino-7H-pyrrolo[2,3-d] pyrimidin-7-yl)-6a-methylhexahydro-3aH-cyclopenta[b] furan-3,3a-diol, (2R,3R,3aS,6S,6aR)-6-((2-amino-3-chloroquinolin-7-yl) methyl)-2-(4-methyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-fluoroquinolin-7-yl) methyl)-2-(4-methyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-fluoroquinolin-7-yl) methyl)-2-(4-amino-7H-pyrrolo[2,3-d] pyrimidin-7-yl) hexahydro-3aH-cyclopenta[b] furan-3,3a-diol, (2R,3R,3aS,6S,6aR)-6-((2-amino-3-methylquinolin-7-yl) methyl)-2-(4-amino-7H-pyrrolo[2,3-d] pyrimidin-7-yl) hexahydro-3aH-cyclopenta[b] furan-3,3a-diol, (2R,3R,3aS,6S,6aR)-6-((2-amino-3-bromoquinolin-7-yl) methyl)-2-(2-amino-4-methyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-(difluoromethyl) quinolin-7-yl) oxy)-2-(4-amino-7H-pyrrolo[2,3-d] pyrimidin-7-yl) hexahydro-3aH-cyclopenta[b] furan-3,3a-diol, (2R,3R,3aS,6R,6aR)-6-((2-amino-3-bromoquinolin-7-yl) oxy)-2-(4-methyl-7H-pyrrolo[2,3-d] pyrimidin-7-yl) hexahydro-3aH-cyclopenta[b] furan-3,3a-diol, (2R,3R,3aS,6S,6aR)-6-((2-amino-3-bromoquinolin-7-yl) oxy)-2-(2-amino-5-fluoro-7H-pyrrolo[2,3-d] pyrimidin-7-yl) hexahydro-3aH-cyclopenta[b] furan-3,3a-diol, (2R,3R,3aS,6R,6aR)-6-((2-amino-3-chloroquinolin-7-yl) methyl)-2-(4-methyl-7H-pyrrolo[2,3-d] pyrimidin-7-yl) hexahydro-3aH-cyclopenta[b] furan-3,3a-diol, (3aS,4S,5R)-1-((2-amino-3-bromoquinolin-7-yl)methyl)-5-(4-amino-7H-pyrrolo[2,3-d] pyrimidin-7-yl) tetrahydro-1H-cyclopenta[c] furan-3a,4 (3H)-diol, (2R,3R,3aS,6S,6aR)-6-((2-amino-3-bromoquinolin-7-yl) methyl)-2-(4-methyl-7H-pyrrolo[2,3-d] pyrimidin-7-yl) tetrahydrofuro[3,4-b] furan-3,3a (4H)-diol, (2R,3R,3aS,6R,6aR)-6-((2-amino-3-bromoquinolin-7-yl) methyl)-2-(4-methyl-7H-pyrrolo[2,3-d] pyrimidin-7-yl) tetrahydrofuro[3,4-b] furan-3,3a (4H)-diol, (2R,3R,3aS,6S,6aR)-6-((2-amino-3-bromoquinolin-7-yl) methyl)-2-(4-amino-5-methyl-7H-pyrrolo[2,3-d] pyrimidin-7-yl) tetrahydrofuro[3,4-b] furan-3,3a (4H)-diol, (2R,3R,3aS,6S,6aR)-6-((2-amino-3-bromoquinolin-7-yl) methyl)-2-(4-amino-7H-pyrrolo[2,3-d] pyrimidin-7-yl) tetrahydrofuro[3,4-b] furan-3,3a (4H)-diol, or (2R,3R,3aS,6S,6aR)-6-((2-amino-3-(difluoromethyl) quinolin-7-yl)methyl)-2-(4-amino-7H-pyrrolo[2,3-d] pyrimidin-7-yl) hexahydro-2H-cyclopenta[b] furan-3, 3a-diol.

17. A composition for treating cancer comprising a compound of claim 1, or a pharmaceutically acceptable salt thereof, and a pharmaceutically carrier.

18. A method for treating cancer comprising administering to a patient in need thereof a compound of claim 1, or a pharmaceutically acceptable salt thereof.

19. A compound of formula Ia,

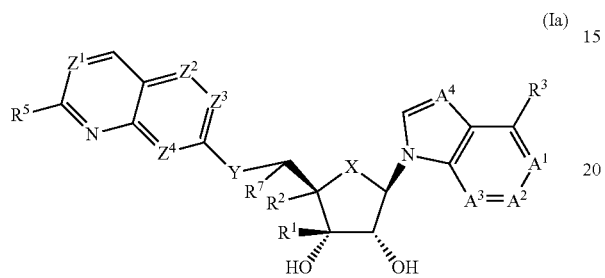

(Ia)

or a pharmaceutically acceptable salt thereof, wherein
X is $CH_2$ or O;
Y is $CH_2$, NH, or O;
$Z^1$ is $CR^4$ or N;
$Z^2$ is CH or N;
$Z^3$ is CH or N;
$Z^4$ is CH or N;
$A^1$ is CH or N;
$A^2$ is CH, N, $CNH_2$ or $CCH_3$;
$A^3$ is CH or N;
$A^4$ is $CR^8$ or N;
$R^1$ and $R^7$ taken together to form a five membered ring;
$R^2$ is H, OH, $CH_3$, $CHF_2$, or F;
$R^3$ is H, halogen, $CH_3$, $C_2H_5$, cyclopropyl, $NH_2$, $NHCH_3$, CN, $CF_3$, OH, $OCH_3$, or $CHF_2$;
$R^4$, when present, is H, halogen, $CH_3$, $CHF_2$, or $CF_3$; and
$R^5$ is H, $NH_2$, or $NHR^6$; or
$R^4$ and $R^5$ taken together with the carbon atoms to which they are attached, join to form a 5 membered heterocycloalkyl comprising one N atom, wherein the heterocycloalkyl is optionally substituted with one to four substituents independently selected from halogen, $CH_3$, $CF_3$, and $CF_2H$;
$R^6$, when present, is $CH_3$, $C_2H_5$, $CH_2CH_2CH_3$, $CH(CH_3)_2$, $CH_2CHF_2$, $CH_2CF_3$, or $CH_2$-cyclopropyl; and
$R^8$, when present, is H, $C_{1-4}$alkyl, or halogen.

20. A compound, or a pharmaceutically acceptable salt thereof,
which is:
(2R,3S,4R,5R)-2-(2-(2-amino-3-bromoquinolin-7-yl) ethyl)-5-(4-amino-7H-pyrrolo[2,3-d] pyrimidin-7-yl)-2,3-dimethyltetrahydrofuran-3,4-diol,
(2R,3S,4R,5R)-2-(((2-amino-3-bromoquinolin-7-yl) oxy) methyl)-5-(4-methoxy-7H-pyrrolo[2,3-d] pyrimidin-7-yl)-2-methyltetrahydrofuran-3,4-diol,
(2R,3S,4R,5R)-2-(((2-amino-3-bromoquinolin-7-yl) oxy) methyl)-5-(4-amino-7H-pyrrolo[2,3-d] pyrimidin-7-yl)-2-methyltetrahydrofuran-3,4-diol,
(1S,2R,3S,5R)-3-[2-(2-amino-3-bromo-7-quinolinyl) ethyl]-5-(4-amino-7H-pyrrolo[2,3-d] pyrimidin-7-yl)-3-methyl-1,2-cyclopentanediol,
(1R,2S,3R,5R)-5-(((2-amino-3-bromoquinolin-7-yl) oxy) methyl)-1-methyl-3-(4-(methylamino)-7H-pyrrolo[2,3-d] pyrimidin-7-yl)cyclopentane-1,2-diol,
(2R,3S,4R,5R)-5-(4-amino-7H-pyrrolo[2,3-d] pyrimidin-7-yl)-2-methyl-2-((quinolin-7-yloxy) methyl) tetrahydrofuran-3,4-diol,
(1S,2R,3R,5R)-3-(((2-amino-3-bromoquinolin-7-yl) oxy) methyl)-5-(4-amino-7H-pyrrolo[2,3-d] pyrimidin-7-yl)-3-methylcyclopentane-1,2-diol,
(1S,2R,3R,5R)-5-(4-amino-7H-pyrrolo[2,3-d] pyrimidin-7-yl)-3-(((2-aminoquinolin-7-yl) oxy) methyl)-3-methylcyclopentane-1,2-diol,
(1S,2R,5R)-3-(2-(2-amino-3-bromoquinolin-7-yl) ethyl)-5-(4-amino-7H-pyrrolo[2,3-d] pyrimidin-7-yl)-3-(fluoromethyl)cyclopentane-1,2-diol,
(1R,2S,3R,5R)-5-(((2-aminoquinolin-7-yl) oxy) methyl)-1-methyl-3-(7H-pyrrolo[2,3-d] pyrimidin-7-yl)cyclopentane-1,2-diol,
(1S,2R,3S,5R)-3-(2-(2,3-dihydro-1H-pyrrolo[2,3-b] quinolin-7-yl)ethyl)-3-methyl-5-(4-methyl-7H-pyrrolo[2,3-d] pyrimidin-7-yl)cyclopentane-1,2-diol,
(1S,2R,3R,5R)-3-(2-(2-amino-3-fluoroquinolin-7-yl) ethyl)-5-(4-amino-7H-pyrrolo[2,3-d] pyrimidin-7-yl)-3-methylcyclopentane-1,2-diol,
(1R,2S,3R,5S)-5-(2-(2-amino-3-bromoquinolin-7-yl) ethyl)-3-(4-amino-7H-pyrrolo[2,3-d] pyrimidin-7-yl)-1,5-dimethylcyclopentane-1,2-diol,
(1R,2S,3S,4R)-1-(2-(2-amino-3-bromoquinolin-7-yl) ethyl)-4-(4-amino-7H-pyrrolo[2,3-d] pyrimidin-7-yl)-2-methylcyclopentane-1,2,3-triol,
(1R,2S,3R,5R)-5-(((2-amino-3-bromoquinolin-7-yl) oxy) methyl)-3-(4-amino-7H-pyrrolo[2,3-d] pyrimidin-7-yl)-1,5-dimethylcyclopentane-1,2-diol, or
(1S,2R,3S,5R)-5-(4-amino-7H-pyrrolo[2,3-d] pyrimidin-7-yl)-3-(2-(2,3-dihydro-1H-pyrrolo[2,3-b] quinolin-7-yl)ethyl)-3-methylcyclopentane-1,2-diol.

\* \* \* \* \*

UNITED STATES PATENT AND TRADEMARK OFFICE
CERTIFICATE OF CORRECTION

| | | |
|---|---|---|
| PATENT NO. | : 12,173,026 B2 | Page 1 of 1 |
| APPLICATION NO. | : 17/266521 | |
| DATED | : December 24, 2024 | |
| INVENTOR(S) | : Michelle Machacek et al. | |

It is certified that error appears in the above-identified patent and that said Letters Patent is hereby corrected as shown below:

In the Specification

Column 265, Line 53:
Delete "72" and replace with "$Z^2$".

Signed and Sealed this
Eleventh Day of March, 2025

Coke Morgan Stewart
*Acting Director of the United States Patent and Trademark Office*